(12) United States Patent
Alexander et al.

(10) Patent No.: US 11,098,061 B2
(45) Date of Patent: Aug. 24, 2021

(54) MK2 INHIBITORS AND USES THEREOF

(71) Applicant: Celgene CAR LLC, Pembroke (BM)

(72) Inventors: Matthew David Alexander, San Diego, CA (US); Joseph John McDonald, Sudbury, MA (US); Yike Ni, Lexington, MA (US); Deqiang Niu, Lexington, MA (US); Russell C. Petter, Stow, MA (US); Lixin Qiao, Andover, MA (US); Juswinder Singh, Southborough, MA (US); Tao Wang, Sudbury, MA (US); Zhendong Zhu, Westborough, MA (US)

(73) Assignee: Celgene CAR LLC, Pembroke (BM)

( * ) Notice: Subject to any disclaimer, the term of this patent is extended or adjusted under 35 U.S.C. 154(b) by 0 days.

(21) Appl. No.: 16/194,577

(22) Filed: Nov. 19, 2018

(65) Prior Publication Data
US 2019/0135835 A1 May 9, 2019

Related U.S. Application Data

(62) Division of application No. 14/760,697, filed as application No. PCT/US2014/011501 on Jan. 14, 2014, now Pat. No. 10,138,256.

(60) Provisional application No. 61/794,310, filed on Mar. 15, 2013.

(51) Int. Cl.
| | |
|---|---|
| C07D 487/04 | (2006.01) |
| C07D 519/00 | (2006.01) |
| C07D 213/74 | (2006.01) |
| C07D 213/75 | (2006.01) |
| C07D 401/04 | (2006.01) |
| C07D 401/12 | (2006.01) |
| C07D 413/04 | (2006.01) |
| C07D 413/12 | (2006.01) |
| C07D 471/04 | (2006.01) |
| C07D 471/14 | (2006.01) |
| C07D 471/20 | (2006.01) |
| C07D 487/10 | (2006.01) |
| C07D 495/04 | (2006.01) |
| C07D 495/14 | (2006.01) |
| A61K 47/64 | (2017.01) |
| C12N 9/12 | (2006.01) |
| C12N 9/96 | (2006.01) |
| C12N 9/99 | (2006.01) |
| G01N 33/573 | (2006.01) |

(52) U.S. Cl.
CPC ............ *C07D 519/00* (2013.01); *A61K 47/64* (2017.08); *C07D 213/74* (2013.01); *C07D 213/75* (2013.01); *C07D 401/04* (2013.01); *C07D 401/12* (2013.01); *C07D 413/04* (2013.01); *C07D 413/12* (2013.01); *C07D 471/04* (2013.01); *C07D 471/14* (2013.01); *C07D 471/20* (2013.01); *C07D 487/04* (2013.01); *C07D 487/10* (2013.01); *C07D 495/04* (2013.01); *C07D 495/14* (2013.01); *C12N 9/12* (2013.01); *C12N 9/96* (2013.01); *C12N 9/99* (2013.01); *G01N 33/573* (2013.01); *C12Y 207/11001* (2013.01); *G01N 2333/91205* (2013.01); *G01N 2458/00* (2013.01); *G01N 2500/04* (2013.01); *G01N 2500/20* (2013.01)

(58) Field of Classification Search
CPC .. C07D 487/04; C07D 487/10; C07D 519/00; C07D 473/00; C07D 498/04; C07D 213/74; C07D 213/75; C07D 401/04; C07D 401/12; A61K 31/499; A61K 31/4985
USPC ........................................... 544/349; 514/249
See application file for complete search history.

(56) References Cited

U.S. PATENT DOCUMENTS

| | | | |
|---|---|---|---|
| 7,167,802 B2 | 1/2007 | Parris et al. | |
| 9,458,175 B2 | 10/2016 | Alexander et al. | |
| 10,138,256 B2 | 11/2018 | Alexander et al. | |
| 2004/0091872 A1 | 5/2004 | Parris et al. | |
| 2004/0152739 A1 | 8/2004 | Hanau et al. | |
| 2004/0209897 A1 | 10/2004 | Vernier et al. | |
| 2010/0029610 A1 | 2/2010 | Singh et al. | |

(Continued)

FOREIGN PATENT DOCUMENTS

| | | |
|---|---|---|
| WO | WO-2004/058762 A1 | 7/2004 |
| WO | WO-2008/025512 A1 | 3/2008 |

(Continued)

OTHER PUBLICATIONS

Anderson, D.R. et al., Benzothiophene inhibitors of MK2. Part 1: Structure-activity relationships, assessments of selectivity and cellular potency, Bioorganic & Medicinal Chemistry Letters, 19: 4878-4881 (2009).

(Continued)

*Primary Examiner* — Jeffrey H Murray
(74) *Attorney, Agent, or Firm* — Choate, Hall & Stewart LLP; Kristen C. Buteau; Nicholas J. Pace

(57) ABSTRACT

The present invention provides compounds of formula V:

(Continued)

or pharmaceutically acceptable salts thereof, useful as inhibitors of MK2 kinases, compositions thereof, and methods of using the same.

14 Claims, 3 Drawing Sheets

Specification includes a Sequence Listing.

(56) References Cited

U.S. PATENT DOCUMENTS

| | | |
|---|---|---|
| 2010/0069360 A1 | 3/2010 | Revesz et al. |
| 2011/0223207 A1 | 9/2011 | Mickle et al. |
| 2011/0281322 A1 | 11/2011 | Honigberg et al. |
| 2012/0245175 A1 | 9/2012 | Barf et al. |
| 2013/0137708 A1 | 5/2013 | Garske et al. |
| 2014/0018343 A1 | 1/2014 | Romero et al. |
| 2015/0376208 A1 | 12/2015 | Alexander et al. |
| 2016/0075720 A1 | 3/2016 | Alexander et al. |
| 2017/0114073 A1 | 4/2017 | Alexander et al. |

FOREIGN PATENT DOCUMENTS

| | | |
|---|---|---|
| WO | WO-2009/010488 A1 | 1/2009 |
| WO | WO-2010/028236 A1 | 3/2010 |
| WO | WO-2014/149164 A1 | 9/2014 |
| WO | WO-2016/044463 A2 | 3/2016 |

OTHER PUBLICATIONS

Anderson, D.R. et al., Benzothiophene inhibitors of MK2. Part 2: Improvements in kinase selectivity and cell potency, Bioorganic & Medicinal Chemistry Letters, 19: 4882-4884 (2009).
Anderson, D.R. et al., Pyrrolopyridine Inhibitors of Mitogen-Activated Protein Kinase-Activated Protein Kinase 2 (MK-2), J. Med. Chem., 50(11): 2647-2654 (2007).
Apsel, B. et al., Targeted polypharmacology: discovery of dual inhibitors of tyrosine and phosphoinositide kinases, Nature Chemical Biology, 4(11): 691-699 (2008).
Barf, T. and Kaptein, A., Irreversible Protein Kinase Inhibitors: Balacing the Benefits and Risks, Journal of Medicinal Chemistry, 55: 6243-6262 (2012).
Barf, T. et al., Structure-based lead identification of ATP-competitive MK2 inhibitors, Bioorganic & Medicinal Chemistry Letters, 21(12): 3818-3822 (2011).
Ben-Levy, R. et al., Nuclear export of the stress-activated protein kinase p38 mediated by its substrate MAPKAP kinase-2, Current Biology, 8(19): 1049-1057 (1998).
Caffrey, D.R. et al., Prediction of specificity-determining residues for small-molecule kinase inhibitors, BMC Bioinformatics, 9(491): 1-15 (2008).
Crisp, G.T., Conjugate addition of amino acid side chains to alkynones and alkynoic acid derivatives, Tetrahedron, 54(3-4): 637-648 (1998).
Crisp, G.T., Conjugate addition of amino acid side chains to dyes containing alkynone, alkynoic ester and alkynoic amide linker arms, Tetrahedron, 54(3-4): 649-666 (1998).
Downey, C.D. et al., One-pot synthesis of (Z)-_-sulfonyl enoates from ethyl propiolate, Tetrahedron Letters, 53(43): pp. 5763-5765 (2012).
Goldberg, D.R. et al., Pyrazinoindolone inhibitors of MAPKAP-K2, Bioorganic & Medicinal Chemistry, 18: 938-941 (2008).
International Search Report for PCT/US14/11501, 6 pages (dated Jul. 3, 2014).
International Search Report for PCT/US2015/050495, 2 pages (dated Dec. 11, 2015).

Kaptein, A. et al., Discovery of selective and orally available spiro-3-piperidyl ATP-competitive MK2 inhibitors, Bioorganic & Medicinal Chemistry Letters, 21: 3823-3827 (2011).
Knight, Z.A. et al., Targeting the cancer kinome through polypharmacology, Nature Reviews, Cancer, 10: 130-137 (2010).
Kopper, F. et al., The MAPK-activated protein kinase 2 mediates gemcitabine sensitivity in pancreatic cancer cells, Cell Cycle, 13(6): 1-6 (2014).
Kosugi, T. et al., Mitogen-Activated Protein Kinase-Activated Protein Kinase 2 (MAPKAP-K2) as an Antiinflammatory Target: Discovery and in Vivo Activity of Selective Pyrazolo[1,5-a]pyrimidine Inhibitors Using a Focused Library and Structure-Based Optimization Approach, Journal of Medicinal Chemistry, 55: 6700-6715 (2012).
Leproult, et al., Cysteine Mapping in Conformationally Distinct Kinase Nucleotide Binding Sites: Application to the Design of Selective Covalent Inhibitors, J. Med. Chem., 54: 1347-1355 (2011).
Mansour, F.R. et al., Separation methods for captopril in pharmaceuticals and biological fluids, Journal of Separation Science, 35(10-11): 1213-1226 (2012).
Mola, L. et al., Nucleophile-catalyzed additions to activated triple bonds. Protection of lactams, imides, and nucleosides with MocVinyl and related groups, Journal of Organic Chemistry, 78(12) : 5832-5842 (2013).
Mourey, R.J. et al., A Benzothiophene Inhibitor of Mitogen-Activated Protein Kinase-Activated Protein Kinase 2 Inhibits Tumor Necrosis Factor α Production and Has Oral Anti-Inflammatory Efficacy in Acute and Chronic Models of Inflammation, The Journal of Pharmacology and Experimental Therapeutics, 333(2): 797-807 (2010).
Natesan, S. et al., Binding Affinity Prediction for Ligans and Receptors Forming Tautomers and Ionization Species: Inhibition of Mitogen-Activated Protein Kinase-Activated Protein Kinase 2 (MK2), Journal of Medicinal Chemistry, 55(5): 2035-2047 (2012).
O'Donnell, J.S. et al., Cesium (Z)-2-carbomethoxyethenethiolate: a reagent for the preparation of (Z)-2-carbomethoxyethenyl thioethers including selected cysteine and homocysteine derivatives, European Journal of Organic Chemistry, 2009(4): 547-553 (2009).
Oubrie, A. et al., Novel ATP competitive MK2 inhibitors with potent biochemical and cell-based activity throughout the series, Bioorganic & Medicinal Chemistry Letters, 22: 613-618 (2012).
Revesz, L. et al., In vivo and in vitro SAR of tetracyclic MAPKAP-K2 (MK2) inhibitors. Part I, Bioorganic & Medicinal Chemistry Letters, 20: 4715-4718 (2010).
Revesz, L. et al., In vivo and in vitro SAR of tetracyclic MAPKAP-K2 (MK2) inhibitors. Part II, Bioorganic & Medicinal Chemistry Letters, 20: 4719-4723 (2010).
Schlapbach, A. et al., Pyrrolo-pyrimidones: A novel class of MK2 inhibitors with potent cellular activity, Bioorganic & Medicinal Chemistry Letters, 18: 6142-6146 (2008).
Schwan, A.L. et al., Diastereoselective alkylations of a protected cysteinesulfenate, Journal of Organic Chemistry, 74(17): 6851-6854 (2009).
Serafimova, I.M. et al., Reversible targeting of noncatalytic cysteines with chemically tuned electrophiles, Nature Chemical Biology, 8(5):471-476 (2012).
Shiu, H.-Y. et al., Electron-deficient alkynes as cleavable reagents for the modification of cysteine-containing peptides in aqueous medium, Chemistry—A European Journal, 15(15): 3839-3850 (2009).
Singh, J. et al., The resurgence of covalent drugs, Nature Review, Drug Discovery, 10: 307-317 (2011).
Written Opinion for PCT/US14/11501, 50 pages (dated Jul. 3, 2014).
Written Opinion for PCT/US2015/050495, 7 pages (dated Dec. 11, 2015).
Zheng, C. et al., MAPK-activated Protein Kinase-2 (MK2)-mediated Formation and Phosphorylation-regulated Dissociation of the Signal Complex Consisting of p38, MK2, Akt, and Hsp27, Journal of Biological Chemistry, 281(48): 37215-37226 (2006).

SEQUENCE LISTING

<160> NUMBER OF SEQ ID NOS: 3

<210> SEQ ID NO 1
<211> LENGTH: 400
<212> TYPE: PRT
<213> ORGANISM: Homo sapiens

<400> SEQUENCE: 1

```
Met Leu Ser Asn Ser Gln Gly Gln Ser Pro Val Pro Phe Pro Ala
1               5                   10                  15

Pro Ala Pro Pro Gln Pro Pro Thr Pro Ala Leu Pro His Pro Pro
                20                  25                  30

Ala Gln Pro Pro Pro Pro Pro Gln Gln Phe Pro Gln Phe His Val
                35                  40                  45

Lys Ser Gly Leu Gln Ile Lys Lys Asn Ala Ile Ile Asp Asp Tyr Lys
    50                  55                  60

Val Thr Ser Gln Val Leu Gly Leu Gly Ile Asn Gly Lys Val Leu Gln
65                  70                  75                  80

Ile Phe Asn Lys Arg Thr Gln Glu Lys Phe Ala Leu Lys Met Leu Gln
                85                  90                  95

Asp Cys Pro Lys Ala Arg Arg Glu Val Glu Leu His Trp Arg Ala Ser
                100                 105                 110

Gln Cys Pro His Ile Val Arg Ile Val Asp Val Tyr Glu Asn Leu Tyr
                115                 120                 125

Ala Gly Arg Lys Cys Leu Leu Ile Val Met Glu Cys Leu Asp Gly Gly
        130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
                180                 185                 190

Leu Tyr Thr Ser Lys Arg Pro Asn Ala Ile Leu Lys Leu Thr Asp Phe
            195                 200                 205

Gly Phe Ala Lys Glu Thr Thr Ser His Asn Ser Leu Thr Thr Pro Cys
210                 215                 220

Tyr Thr Pro Tyr Tyr Val Ala Pro Glu Val Leu Gly Pro Glu Lys Tyr
225                 230                 235                 240

Asp Lys Ser Cys Asp Met Trp Ser Leu Gly Val Ile Met Tyr Ile Leu
                245                 250                 255

Leu Cys Gly Tyr Pro Pro Phe Tyr Ser Asn His Gly Leu Ala Ile Ser
            260                 265                 270

Pro Gly Met Lys Thr Arg Ile Arg Met Gly Gln Tyr Glu Phe Pro Asn
            275                 280                 285

Pro Glu Trp Ser Glu Val Ser Glu Val Lys Met Leu Ile Arg Asn
            290                 295                 300
```

```
Leu Leu Lys Thr Glu Pro Thr Gln Arg Met Thr Ile Thr Glu Phe Met
305                 310                 315                 320

Asn His Pro Trp Ile Met Gln Ser Thr Lys Val Pro Gln Thr Pro Leu
                325                 330                 335

His Thr Ser Arg Val Leu Lys Glu Asp Lys Glu Arg Trp Glu Asp Val
                340                 345                 350

Lys Glu Glu Met Thr Ser Ala Leu Ala Thr Met Arg Val Asp Tyr Glu
                355                 360                 365

Gln Ile Lys Ile Lys Lys Ile Glu Asp Ala Ser Asn Pro Leu Leu Leu
                370                 375                 380

Lys Arg Arg Lys Lys Ala Arg Ala Leu Glu Ala Ala Leu Ala His
385                 390                 395                 400

<210> SEQ ID NO 2
<211> LENGTH: 28
<212> TYPE: PRT
<213> ORGANISM: Homo sapiens

<400> SEQUENCE: 2

Asn Leu Tyr Ala Gly Arg Lys Cys Leu Leu Ile Val Met Glu Cys Leu
1               5                   10                  15

Asp Gly Gly Glu Leu Phe Ser Arg Ile Gln Asp Arg
                20                  25

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 3

Cys Cys Xaa Xaa Cys Cys
1               5
```

MK2 INHIBITORS AND USES THEREOF

CROSS-REFERENCE TO RELATED APPLICATIONS

The present application is a divisional of U.S. Ser. No. 14/760,697 (now U.S. Pat. No. 10,138,256), which is a national phase application under 35 U.S.C. § 371 of PCT International Application No. PCT/US2014/011501, filed Jan. 14, 2014, which claims priority to U.S. provisional application No. 61/794,310, filed Mar. 15, 2013, the entirety of each of which is hereby incorporated by reference.

TECHNICAL FIELD OF THE INVENTION

The present invention relates to compounds useful as inhibitors of MK2 kinases. The invention also provides pharmaceutically acceptable compositions comprising compounds of the present invention and methods of using said compositions in the treatment of various disorders.

SEQUENCE LISTING

In accordance with 37 CFR 1.52(e)(5), the present specification makes reference to a Sequence Listing submitted electronically in the form of a text file (entitled "Sequence_Listing.txt," created on Sep. 16, 2015, 4.21 KB in size). The entire contents of the Sequence Listing are herein incorporated by reference, with the intention that, upon publication (including issuance), this incorporated sequence listing will be inserted in the published document immediately before the claims.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNFa), interleukin 6 (Il-6) and interferon gamma (IFNg), that are involved in many acute and chronic inflammatory diseases, e.g. theumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-quadrature. (see Deak et al., EMBO. 17:4426-4441 (1998); Shi et al., Biol. Chem. 383:1519-1536 (2002); Staklatvala., Curr. Opin. Pharmacol. 4:372-377 (2004), and Shiroto et al., J. Mol. Cardiol. 38:93-97 (2005)).

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of MK2. Such compounds have general formula I, II, II-e, III, III-d, IV, IV-b, V, and VI:

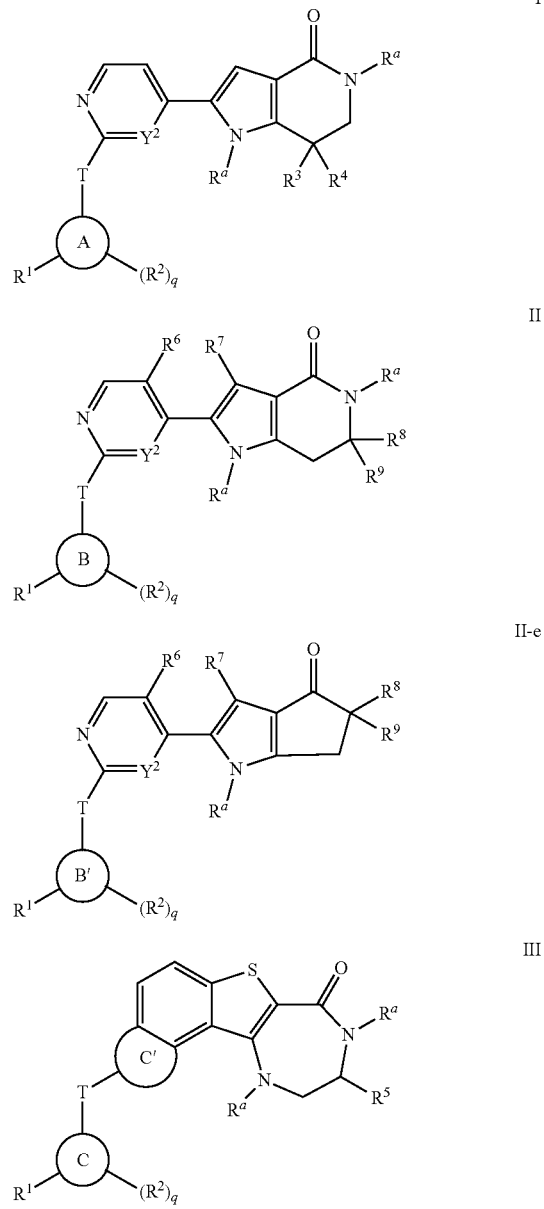

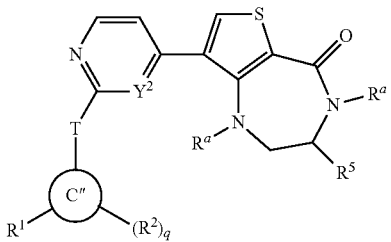

III-d

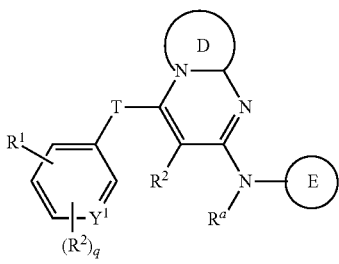

IV

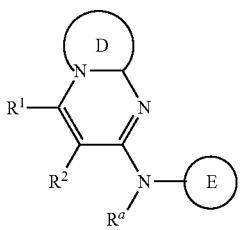

IV-b

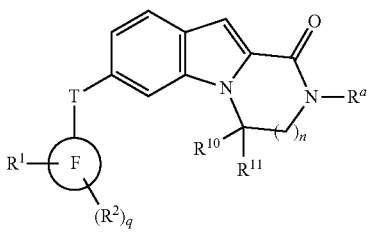

V

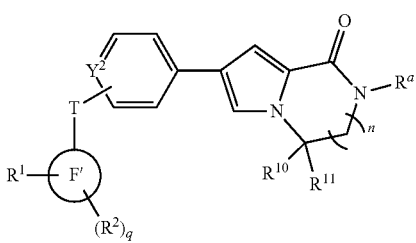

V-c

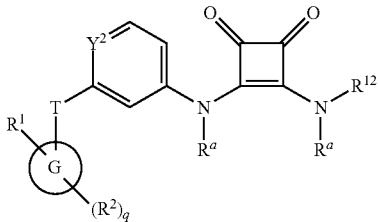

VI or a pharmaceutically acceptable salt thereof, wherein each of Ring A, Ring B, Ring B', Ring C, Ring C', Ring C'', Ring D, Ring E, Ring F, Ring F', Ring G, $R^1$, $R^2$, $R^3$, $R^4$, $R^5$, $R^6$, $R^7$, $R^8$, $R^9$, $R^{10}$, $R^{11}$, $R^{12}$, $R^a$, $Y^1$, $Y^2$, T, and q, with respect to the formulae above, is as defined and described in embodiments herein. In certain embodiments, $R^1$ is a warhead group.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF CERTAIN EMBODIMENTS

Figure 1:
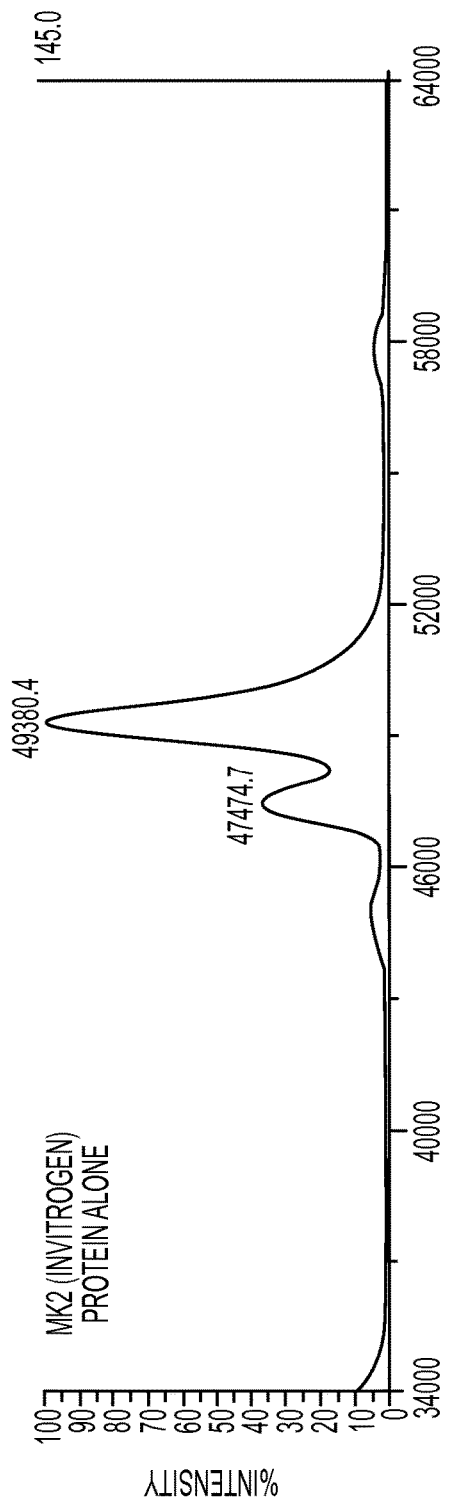
FIG. 1. Covalent Modification Assessment via Mass Modification Assay.
Figure 1:
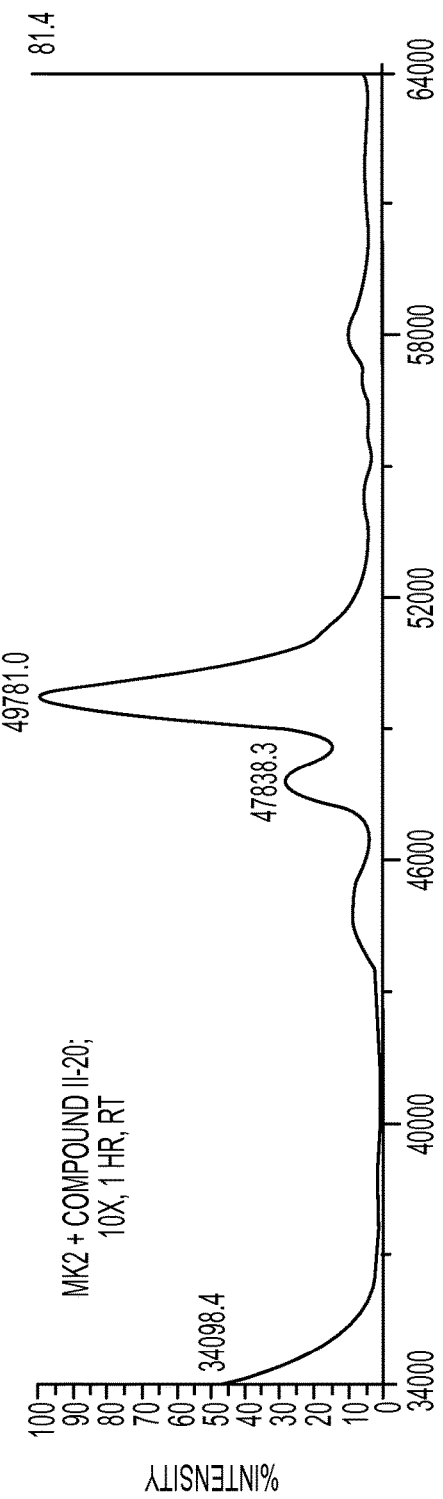

1. General Description of Compounds of the Invention

In certain embodiments, the present invention provides irreversible inhibitors of MK2 and conjugates thereof. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

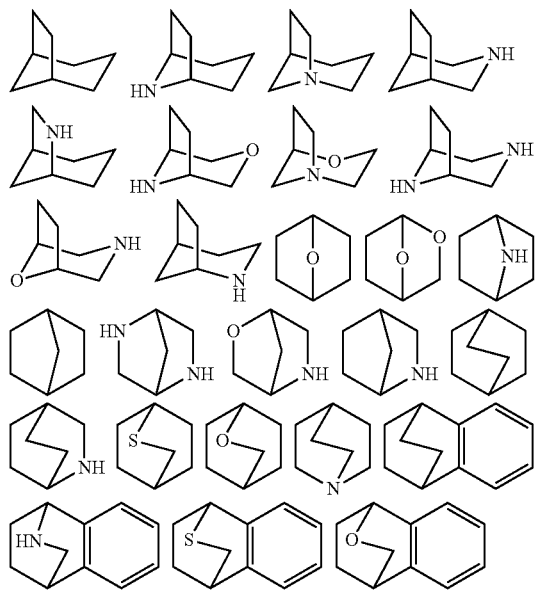

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

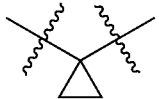

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Exemplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g., 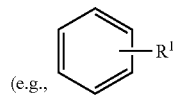

refers to at least

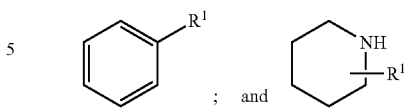

; and refers to at least

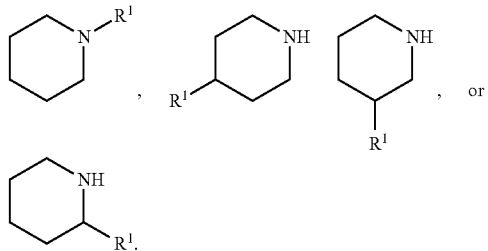

, or

[structure with NH and $R^1$].

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR$_2$; —C(S)NR°$_2$; —C(S)SR°; —SC(S)SRO, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^{\bullet}$, -(haloR$^{\bullet}$), —$(CH_2)_{0-2}OH$, —$(CH_2)_{0-2}OR^{\bullet}$, —$(CH_2)_{0-2}CH(OR^{\bullet})_2$; —$O(haloR^{\bullet})$, —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)$C(O)OR^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^{\bullet}$, -(haloR$^{\bullet}$), —OH, —OR$^{\bullet}$, —O(haloR$^{\bullet}$), —CN, —C(O)OH, —C(O)OR$^{\bullet}$, —$NH_2$, —NHR$^{\bullet}$, —NR$^{\bullet}_2$, or —$NO_2$, wherein each R° is unsubstituted or where preceded by "halo" is substituted only with one or more halogens, and is independently $C_{1-4}$ aliphatic, —$CH_2Ph$, —$O(CH_2)_{0l}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^{\dagger}$, —NR$^{\dagger}_2$, —C(O)R$^{\dagger}$, —C(O)OR$^{\dagger}$, —C(O)C(O)R$^{\dagger}$, —C(O)CH$_2$C(O)R$^{\dagger}$, —S(O)$_2$R$^{\dagger}$, —S(O)$_2$NR$^{\dagger}_2$, —C(S)NR$^{\dagger}_2$, —C(NH)NR$^{\dagger}_2$, or —N(R$^{\dagger}$)S(O)$_2$R$^{\dagger}$; wherein each R$^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^{\dagger}$ are independently halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —$NH_2$, —NHR$^{\bullet}$, —NR$^{\bullet}_2$, or —$NO_2$, wherein each R$^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+($C_{1-4}$-alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "irreversible" or "irreversible inhibitor" refers to an inhibitor (i.e. a compound) that is able to be covalently bonded to a kinase in a substantially non-reversible manner. That is, whereas a reversible inhibitor is able to bind to (but is generally unable to form a covalent bond with) a kinase, and therefore can become dissociated from the a kinase, an irreversible inhibitor will remain substantially bound to a kinase once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to a kinase once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with a kinase, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. It will be appreciated that the -L-Y group, as defined and described herein, provides such warhead groups for covalently, and irreversibly, inhibiting the protein. In certain instances, a "pro-warhead group" can be used in place of a warhead group. Such pro-warhead groups convert to a warhead group in vivo or in vitro.

As used herein, the term "inhibitor" is defined as a compound that binds to and/or inhibits a kinase with measurable affinity. In certain embodiments, an inhibitor has an $IC_{50}$ and/or binding constant of less about 50 µM, less than about 1 µM, less than about 500 nM, less than about 100 nM, less than about 10 nM, or less than about 1 nM. In certain embodiments, an inhibitor has an $IC_{50} \leq 100$ nM; in certain embodiments, an inhibitor has an $IC_{50}$ of 101-500 nM; in certain embodiments, an inhibitor has an $IC_{50}$ of 501-999 nM; in certain embodiments, an inhibitor has an $IC_{50}$ of $\geq 1000$ nM. In certain embodiments, an inhibitor has an $EC_{50} \leq 100$ nM; in certain embodiments, an inhibitor has an $EC_{50}$ of 101-500 nM; in certain embodiments, an inhibitor has an $EC_{50}$ of 501-999 nM; in certain embodiments, an inhibitor has an $EC_{50}$ of $\geq 1000$ nM.

The terms "measurable affinity" and "measurably inhibit," as used herein, means a measurable change in a kinase activity between a sample comprising a compound of the present invention, or composition thereof, and a kinase, and an equivalent sample comprising a kinase, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Embodiments

As described herein, the present invention provides irreversible inhibitors of MK2 kinase. The compounds of the invention comprise a warhead group, designated as $R^1$, as described herein. Without wishing to be bound by any particular theory, it is believed that such $R^1$ groups, i.e. warhead groups, are particularly suitable for covalently binding to a key cysteine residue in the binding domain of MK2 kinase. One of ordinary skill in the art will appreciate that MK2 kinase, and mutants thereof, have a cysteine residue in the binding domain. Without wishing to be bound by any particular theory, it is believed that proximity of a warhead group to the cysteine of interest facilitates covalent modification of that cysteine by the warhead group.

The cysteine residues of interest can also be described by an identifying portion of the Target's amino acid sequence which includes the cysteine of interest. Thus, in certain embodiments, Cys140 of MK2 is characterized in that Cys140 is the cysteine embedded in the amino acid sequence of MK2:

```
SEQ ID NO. 1:
MLSNSQGQSPPVPFPAPAPPPQPPTPALPHPPAQPPPPPPQQFPQFHVKS

GLQIKKNAIIDDYKVTSQVLGLGINGKVLQIFNKRTQEKFALKMLQDCPK

ARREVELHWRASQCPHIVRIVDVYENLYAGRKCLLIVMECLDGGELFSRI

QDRGDQAFTEREASEIMKSIGEAIQYLHSINIAHRDVKPENLLYTSKRPN

AILKLTDFGFAKETTSHNSLTTPCYTPYYVAPEVLGPEKYDKSCDMWSLG

VIMYILLCGYPPFYSNHGLAISPGMKTRIRMGQYEFPNPEWSEVSEEVKM

LIRNLLKTEPTQRMTITEFMNHPWIMQSTKVPQTPLHTSRVLKEDKERWE

DVKEEMTSALATMRVDYEQIKIKKIEDASNPLLLKRRKKARALEAAALA

H.
```

Cys140 is more clearly provided in the abbreviated amino acid sequence below:

```
SEQ ID NO. 2:
NLYAGRKCLLIVMEC(140)LDGGELFSRIQDR.
```

In both SEQ ID NOS. 1 and 2, Cysteine 140 is highlighted in bold with underlining.

In some embodiments, compounds of the present invention include a warhead group characterized in that provided compounds covalently modify Cys140 of MK2.

In certain embodiments, compounds of the present invention include a warhead group characterized in that a compound covalently modifies a target of Cys140 of MK2, thereby irreversibly inhibiting the kinase.

Thus, in some embodiments, the $R^1$ warhead group is characterized in that the -L-Y moiety, as defined and described below, is capable of covalently binding to a cysteine residue thereby irreversibly inhibiting the enzyme. In some embodiments, the cysteine residue is Cys140 of MK2. One of ordinary skill in the art will recognize that a variety of warhead groups, as defined herein, are suitable for such covalent bonding. Such $R^1$ groups include, but are not limited to, those described herein and depicted infra.

According to one aspect, the present invention provides a compound of formula I,

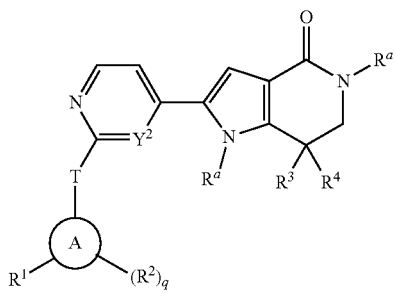

I or a pharmaceutically acceptable salt thereof, wherein:
Ring A is an optionally substituted group selected from

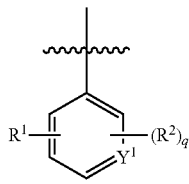

or a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;
$Y^1$ is $CR^2$ or N;
$Y^2$ is $CR'$ or N;
each $R'$ is independently hydrogen, halo, or an optionally substituted group selected from $C_1$a aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
$R^1$ is a warhead group;
q is 0-6;
each $R^2$ is independently —R, halogen, —OR, —SR, —CN, —NO$_2$, —SO$_2$NR, —SO$_2$R, —SOR, —C(O)R, —CO$_2$R, —C(O)N(R)$_2$, —NRC(O)R, —NRC(O)OR, —NRC(O)N(R)$_2$, —NRSO$_2$R, or —N(R)$_2$;
each R is independently hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or
two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;
$R^3$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
$R^4$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
or $R^3$ and $R^4$ are taken together with the carbon atom to which they are attached to form a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
each $R^a$ is independently hydrogen or an optionally substituted $C_{1-6}$ aliphatic group; and
T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.
In certain embodiments, $R^1$ is a warhead group, wherein when Ring A is a 5 or 6-membered ring, then $R^1$ is attached to an atom next to an atom adjacent to where T is attached (i.e., in the case where Ring A is phenyl, $R^1$ is attached at the meta position), or $R^1$ is attached to an atom adjacent to where T is attached (i.e., in the case where Ring A is phenyl, $R^1$ is attached at the ortho position).

In some embodiments, Ring A is

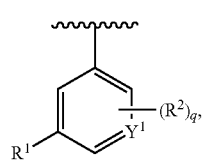

wherein each of $R^1$, $Y^1$, $R^2$, and q is as defined above and described herein. In certain embodiments, Ring A is

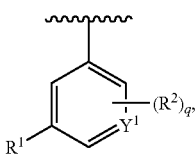

wherein $Y^1$ is CH (i.e., Ring A is phenyl). In some embodiments, $Y^1$ is N.

In certain embodiments, Ring A is an optionally substituted 3-8 membered saturated or partially unsaturated carbocyclic ring, an optionally substituted 4-7 membered heterocylic ring having 1-2 heteroatoms independently selected from nitrogen, oxygen, or sulfur, an optionally substituted 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur.

In various embodiments, Ring A is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, Ring A is

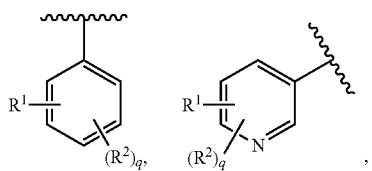

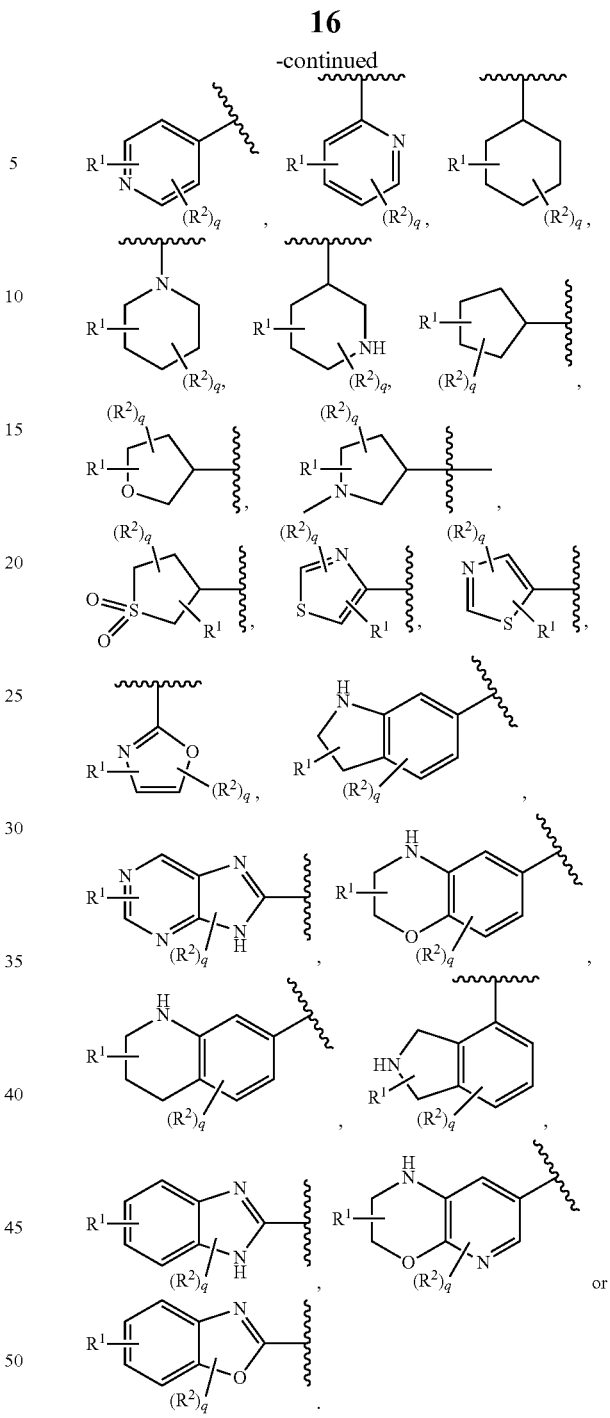

In some embodiments, Ring A is selected from those depicted in Table 1, below.

In certain embodiments, $Y^1$ is $CR^2$ wherein $R^2$ is hydrogen.

In certain embodiments, $Y^1$ is $CR^2$ wherein $R^2$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^1$ is $CR^2$ wherein $R^2$ is an optionally substituted $C_{1-6}$ aliphatic. In certain embodiments, $Y^1$ is $CR^2$ wherein $R^2$ is an optionally substituted phenyl. In certain embodiments, $Y^1$ is $CR^2$ wherein $R^2$ is an optionally substituted 3-8 membered saturated or partially unsaturated carbocyclic ring. In certain embodiments, $Y^1$ is $CR^2$ wherein $R^2$ is an optionally substituted 4-7 membered heterocylic ring having 1-2 heteroatoms independently selected from nitrogen, oxygen, or sulfur. In certain embodiments, $Y^1$ is $CR^2$ wherein $R^2$ is an optionally substituted 5-6 membered monocyclic heteroaryl ring having 1-4 heteroatoms independently selected from nitrogen, oxygen, or sulfur.

In certain embodiments, $Y^1$ is $CR^2$ wherein $R^2$ is —$CF_3$.

In certain embodiments, $Y^2$ is N. In certain embodiments, $Y^2$ is CR'.

In certain embodiments, $Y^2$ is CR' wherein R' is hydrogen.

In certain embodiments, $Y^2$ is CR' wherein R is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^2$ is CR' wherein R' is an optionally substituted $C_{1-6}$ aliphatic. In certain embodiments, $Y^2$ is CR' wherein R' is an optionally substituted phenyl. In certain embodiments, $Y^2$ is CR' wherein R' is an optionally substituted 3-8 membered saturated or partially unsaturated carbocyclic ring. In certain embodiments, $Y^2$ is CR' wherein R' is an optionally substituted 4-7 membered heterocylic ring having 1-2 heteroatoms independently selected from nitrogen, oxygen, or sulfur. In certain embodiments, $Y^2$ is CR' wherein R' is an optionally substituted 5-6 membered monocyclic heteroaryl ring having 1-4 heteroatoms independently selected from nitrogen, oxygen, or sulfur.

In certain embodiments, each $R^2$ is independently hydrogen.

In certain embodiments, each $R^2$ is independently —R.

In certain embodiments, each $R^2$ is independently halogen, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$.

In certain embodiments, each $R^2$ is independently cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, or pyrrolinyl.

In certain embodiments, each $R^2$ is independently

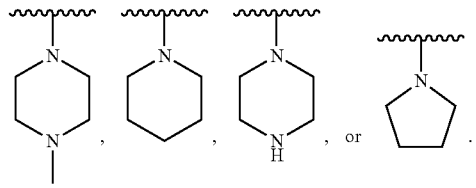

In certain embodiments, each $R^2$ is independently

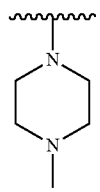

In certain embodiments, each $R^2$ is independently —$CH_3$, —F, —$CF_3$, —$OCH_3$, —$OCF_3$, —$OCH_2CH_2NMe_2$, —$OCH_2CH_2NH_2$, or —$OCH_2CH_2OCH_3$.

In certain embodiments, each $R^2$ is independently —$CH_3$, —F, —$CF_3$, —$OCH_3$, —$OCF_3$, —$OCH_2CH_2NMe_2$, or —$OCH_2CH_2OCH_3$.

In some embodiments, each $R^2$ is independently selected from those depicted in Table 1, below.

In certain embodiments, $R^3$ is an optionally substituted group selected from $C_1$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur. In some embodiments, $R^3$ is selected from those depicted in Table 1, below.

In certain embodiments, $R^4$ is an optionally substituted group selected from $C_1$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur. In some embodiments, $R^4$ is selected from those depicted in Table 1, below.

In certain embodiments, $R^3$ and $R^4$ are taken together with the carbon atom to which they are attached to form a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $R^3$ and $R^4$ are taken together with the carbon atom to which they are attached to form a 3-8 membered saturated or partially unsaturated carbocyclic ring. In certain embodiments, $R^3$ and $R^4$ are taken together with the carbon atom to which they are attached to form a 4-7 membered heterocyclic ring having 1-2 heteroatoms independently selected from nitrogen, oxygen, or sulfur. In certain embodiments, $R^3$ and $R^4$ are taken together with the carbon atom to which they are attached to form a 5-6 membered monocyclic heteroaryl ring having 1-4 heteroatoms independently selected from nitrogen, oxygen, or sulfur.

In certain embodiments, $R^3$ and $R^4$ are taken together with the carbon atom to which they are attached to form a spiro cyclopropyl, cyclobutyl, cyclopentyl, cyclohexyl, cycloheptyl, adamantyl, cyclooctyl, fluorenyl, indanyl, tetrahydronaphthyl, decahydroquinolinyl, 2H,6H-1,5,2-dithiazinyl, dihydrofuro [2,3-b] tetrahydrofuran, imidazolidinyl, imidazolinyl, indolinyl, 3H-indolyl, isoindolinyl, isochromanyl, isoindolinyl, morpholinyl, octahydroisoquinolinyl, oxazolidinyl, oxazolidinyl, piperazinyl, piperidinyl, pyranyl, pyrazolidinyl, pyrazolinyl, pyrazolyl, pyridazinyl, pyridooxazole, pyridoimidazole, pyridothiazole, pyrrolidinyl, pyrrolinyl, 2H-pyrrolyl, 4H-quinolizinyl, quinuclidinyl, tetrahydrofuranyl, tetrahydroisoquinolinyl, tetrahydroquinolinyl, 6H-1,2,5-thiadiazinyl, or xanthenyl.

In certain embodiments, $R^3$ and $R^4$ are taken together with the carbon atom to which they are attached to form:

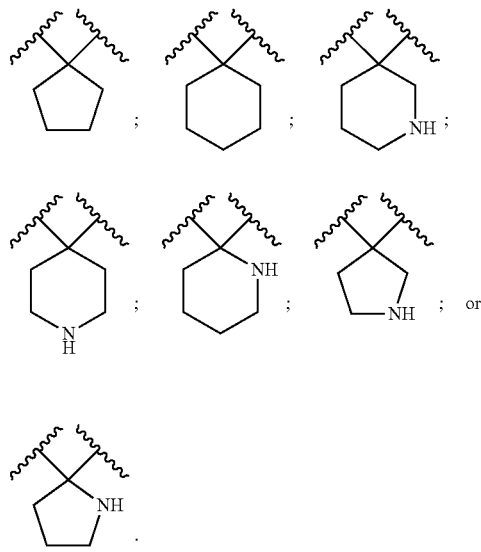

In certain embodiments, $R^3$ and $R^4$ are taken together with the carbon atom to which they are attached to form:

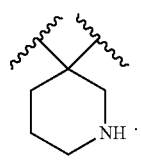

In some embodiments, the ring formed by $R^3$ and $R^4$ is selected from those depicted in Table 1, below.

In certain embodiments, each $R^a$ is independently hydrogen. In certain embodiments, each $R^a$ is independently an optionally substituted $C_{1-6}$ aliphatic group. In some embodiments, each $R^a$ is selected from those depicted in Table 1, below.

In various embodiments, T is a covalent bond.

In various embodiments, T is —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In various embodiments, T is —N(R)—, —C(O)N(R)—, or —N(R)C(O)—. In some embodiments, T is selected from those depicted in Table 1, below.

In various embodiments, the invention provides a compound of formula I-a:

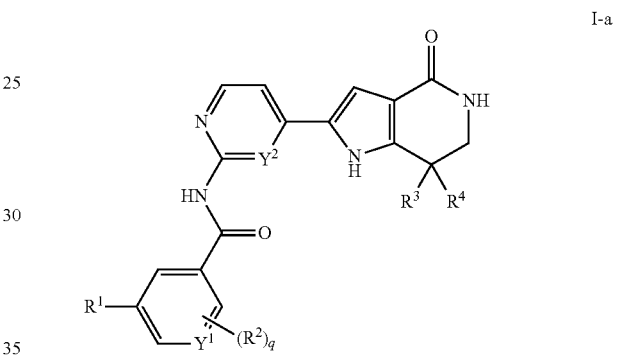

I-a or a pharmaceutically acceptable salt thereof, wherein each of $R^1$, $R^2$, $R^3$, $R^4$, $Y^1$, $Y^2$, and q is as defined above and described in embodiments, classes and subclasses above and herein, singly or in combination.

In various embodiments, the invention provides a compound of formula I-aa:

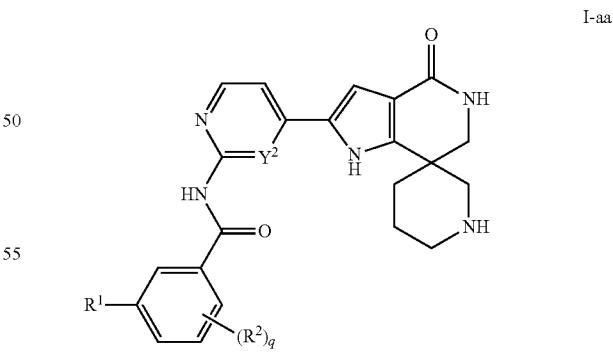

I-aa or a pharmaceutically acceptable salt thereof, wherein each of $R^1$, $R^2$, $Y^2$, and q is as defined above and described in embodiments, classes and subclasses above and herein, singly or in combination.

In various embodiments, the invention provides a compound of formula I-b:

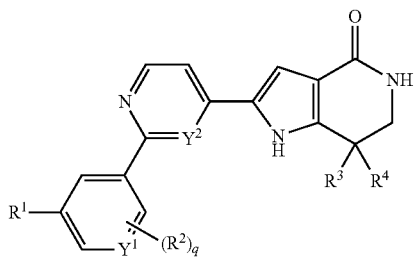

I-b or a pharmaceutically acceptable salt thereof, wherein each of $R^1$, $R^2$, $R^3$, $R^4$, $Y^1$, $Y^2$, and q is as defined above and described in embodiments, classes and subclasses above and herein, singly or in combination.

In various embodiments, the invention provides a compound of formula I-bb:

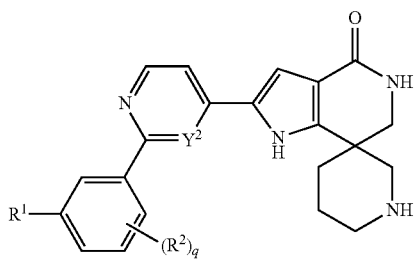

I-bb or a pharmaceutically acceptable salt thereof, wherein each of $R^1$, $R^2$, $Y^2$, and q is as defined above and described in embodiments, classes and subclasses above and herein, singly or in combination.

In various embodiments, the invention provides a compound of formula I-c:

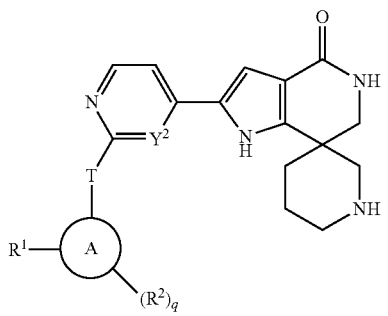

I-c or a pharmaceutically acceptable salt thereof, wherein each of Ring A, $R^1$, $R^2$, $Y^2$, T, and q is as defined above and described in embodiments, classes and subclasses above and herein, singly or in combination, and wherein Ring A is

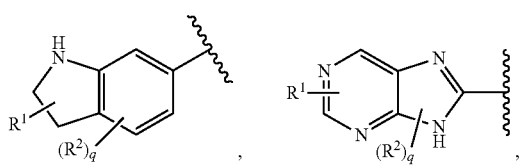

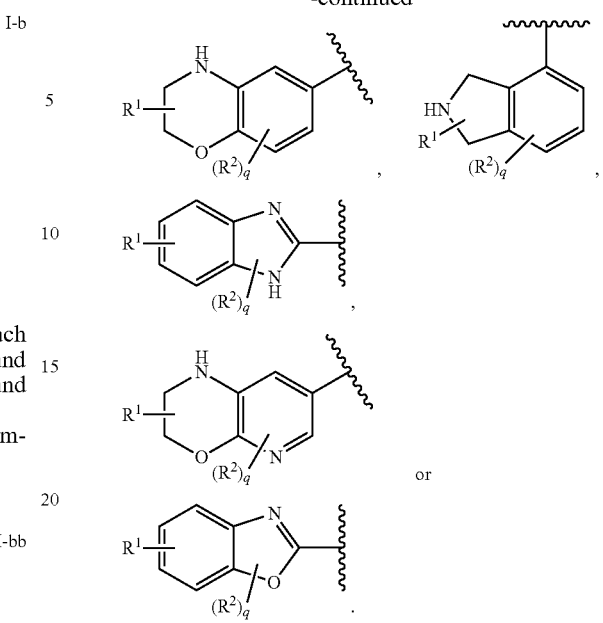

In certain embodiments, the invention provides a compound selected from those depicted in Table 1, below:

TABLE 1

Examplary Compounds of Formula I

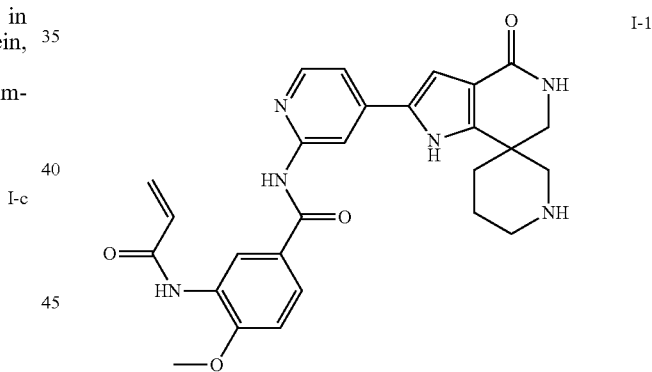

I-1

(rac)

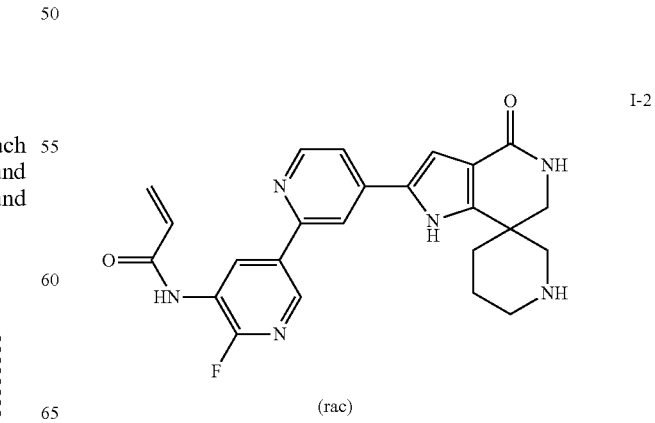

I-2

(rac)

TABLE 1-continued
Examplary Compounds of Formula I
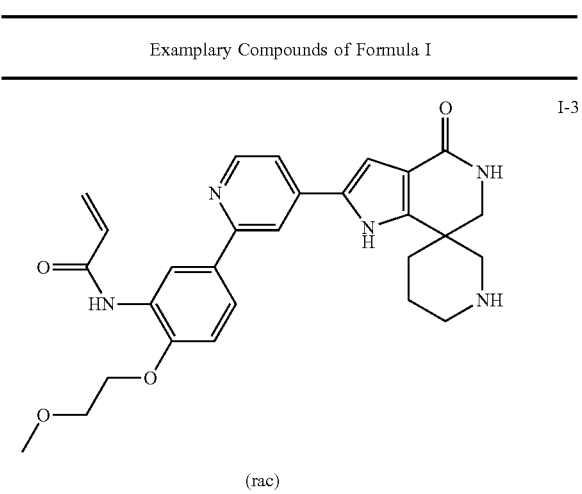
I-3 (rac)
I-4 (rac)
I-5 (rac)
I-6 (rac)
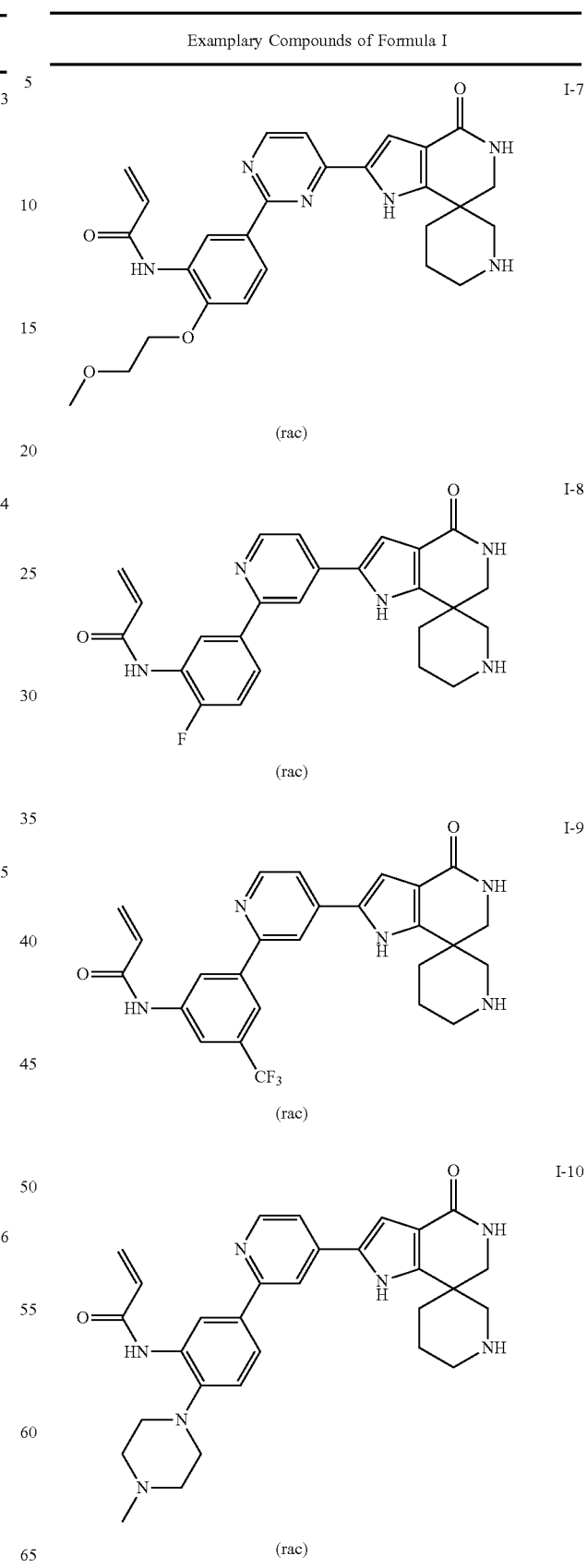
I-7 (rac)
I-8 (rac)
I-9 (rac)
I-10 (rac)

TABLE 1-continued
Examplary Compounds of Formula I
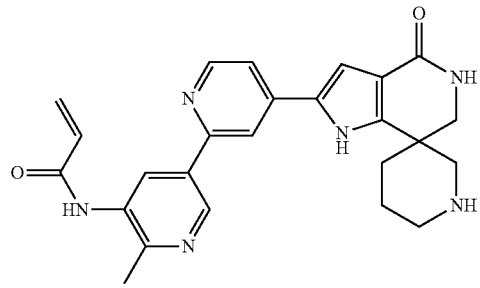
I-11
(rac)
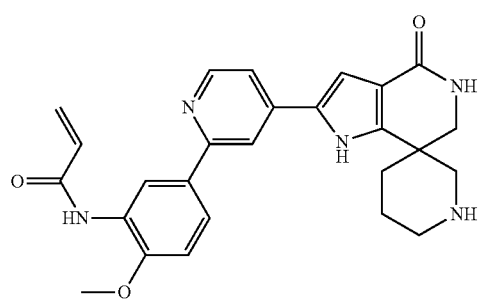
I-12
(rac)
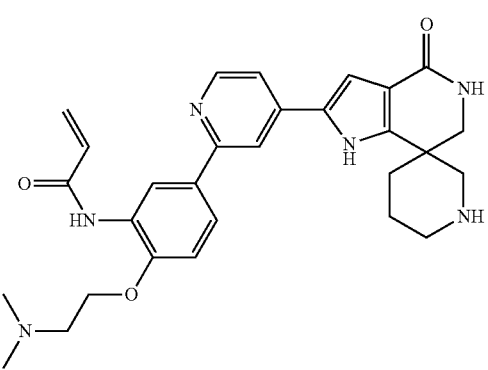
I-13
(rac)
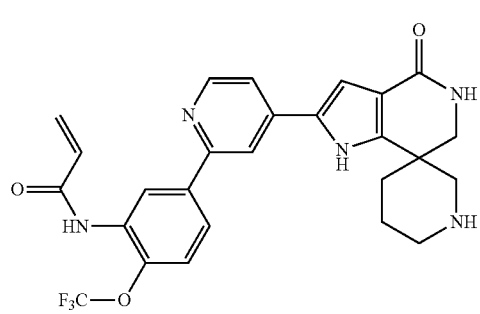
I-14
(rac)
TABLE 1-continued
Examplary Compounds of Formula I
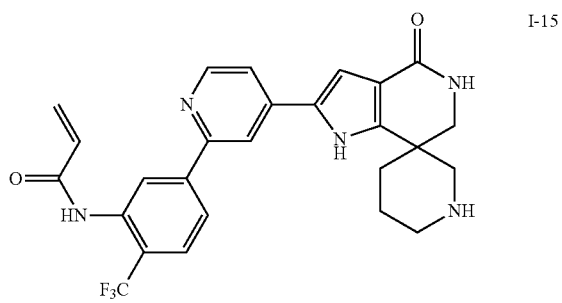
I-15
(rac)
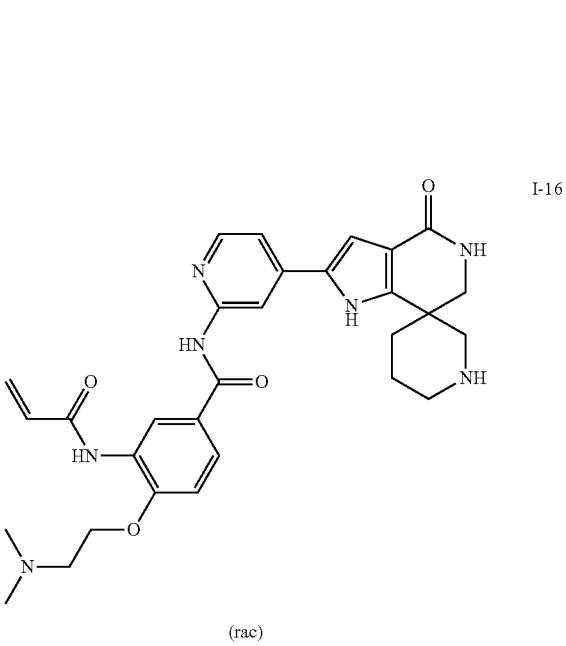
I-16
(rac)
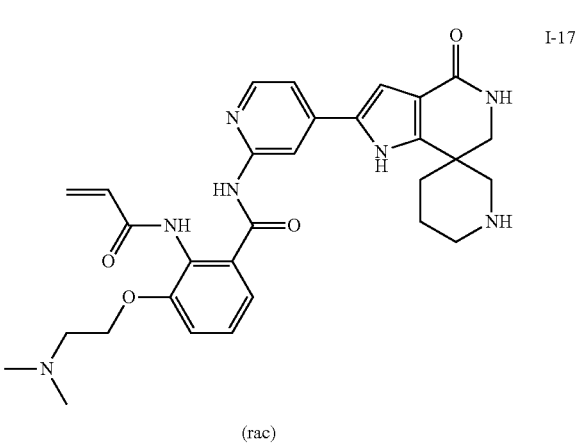
I-17
(rac)

TABLE 1-continued
Examplary Compounds of Formula I
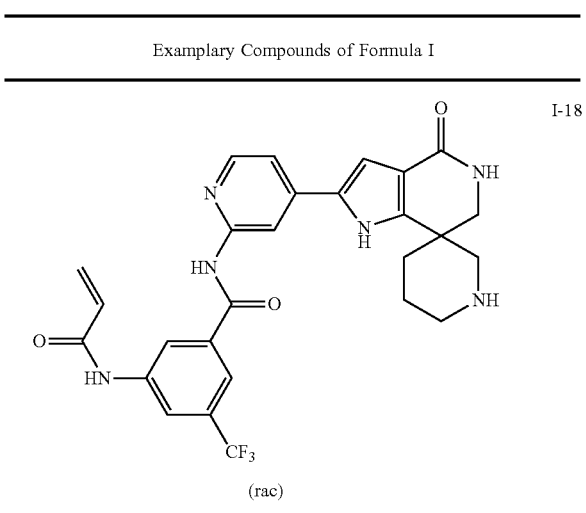
I-18
(rac)
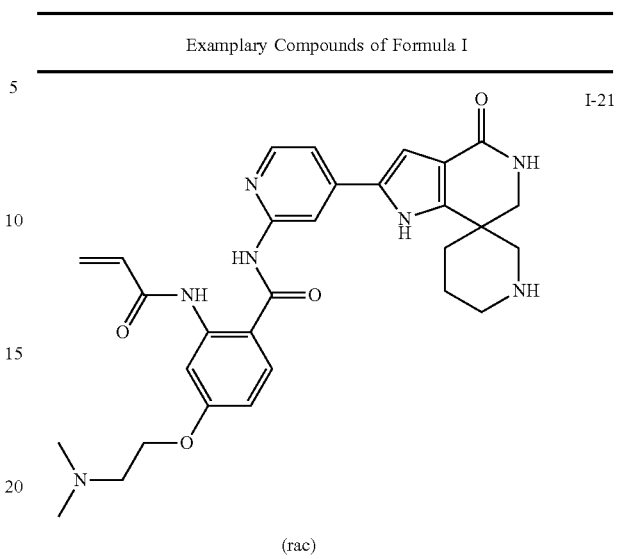
I-21
(rac)
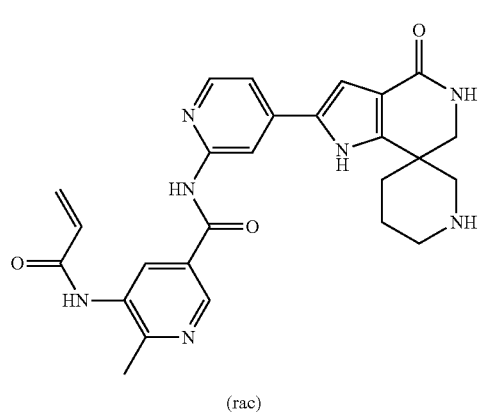 [SMILES: C=CC(=O)Nc1cc(C(=O)Nc2cc(-c3cc4c([nH]3)C3(CCCNC3)CNC4=O)ccn2)cnc1C]
I-19
(rac)
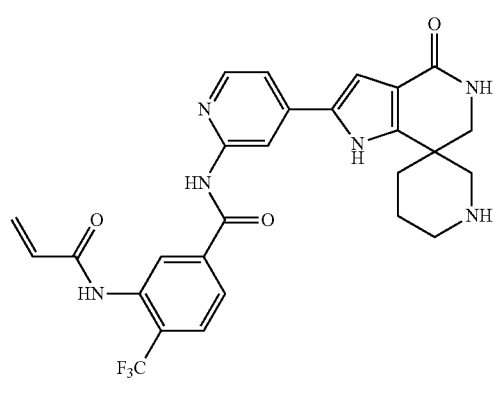
I-22
(rac)
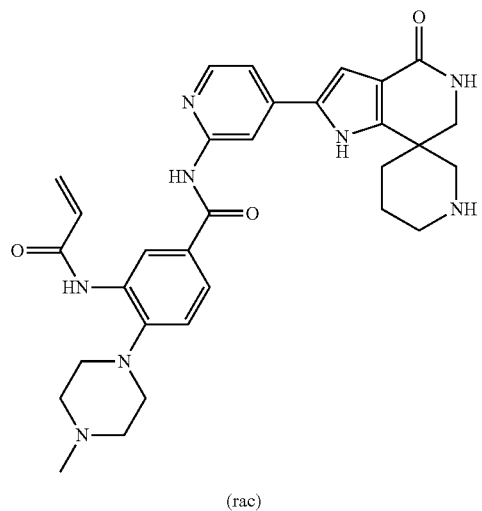 [SMILES: C=CC(=O)Nc1cc(C(=O)Nc2cc(-c3cc4c([nH]3)C3(CCCNC3)CNC4=O)ccn2)ccc1N1CCN(C)CC1]
I-20
(rac)
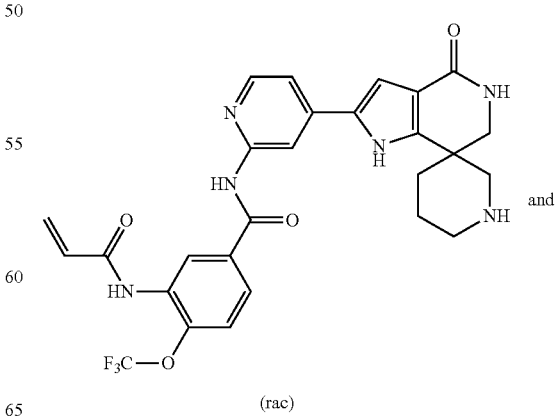
I-23
and
(rac)

TABLE 1-continued

Examplary Compounds of Formula I

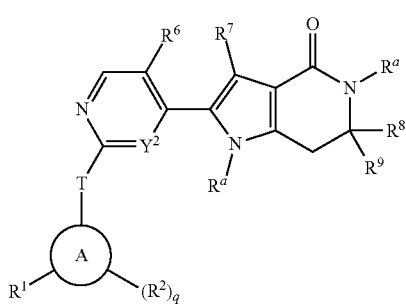

I-24

(rac)

In some embodiments, the present invention provides a compound depicted in Table 1, above, or a pharmaceutically acceptable salt thereof.

Where a compound is designated as racemic, each of its enantiomers and/or diastereomers is also envisaged and encompassed by such structure.

According to another aspect, the present invention provides a compound of formula II:

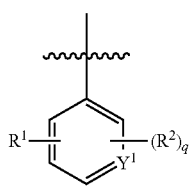

II or a pharmaceutically acceptable salt thereof, wherein:
Ring B is an optionally substituted group selected from or a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;

$Y^1$ is $CR^2$ or N;

$Y^2$ is $CR'$ or N;

each R' is independently hydrogen, halo, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^1$ is a warhead group;

q is 0-6;

each $R^2$ is independently —R, halogen, —OR, —SR, —CN, —NO$_2$, —SO$_2$NR, —SO$_2$R, —SOR, —C(O)R, —CO$_2$R, —C(O)N(R)$_2$, —NRC(O)R, —NRC(O)OR, —NRC(O)N(R)$_2$, —NRSO$_2$R, or —N(R)$_2$;

each R is independently hydrogen or an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocyclic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

$R^6$ is hydrogen, an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^7$ is hydrogen, an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or $R^6$ and $R^7$ are taken together to form a $C_{2-6}$ alkylene;

$R^8$ is hydrogen, an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^9$ is hydrogen, an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or $R^8$ and $R^9$ are taken together with the carbon atom to which they are attached to form a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

each $R^a$ is independently hydrogen or an optionally substituted $C_{1-6}$ aliphatic group; and T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—;

provided that when $Y^1$ is CH; $Y^2$ is CH; each of $R^6$, $R^7$, $R^8$, $R^9$, and $R^a$ is hydrogen; and T is a covalent bond, then at least one of $(R^2)_q$ is other than hydrogen.

In certain embodiments, $R^1$ is a warhead group, wherein when Ring B is a 5 or 6-membered ring, then $R^1$ is attached to an atom next to an atom adjacent to where T is attached (i.e., in the case where Ring B is phenyl, $R^1$ is attached at the meta position), or $R^1$ is attached to an atom adjacent to where T is attached (i.e., in the case where Ring B is phenyl, $R^1$ is attached at the ortho position).

In some embodiments, Ring B is

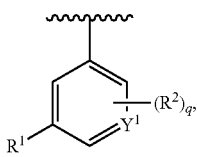

wherein each of $R^1$, $R^2$, $Y^1$, and q is as defined above and described herein. In certain embodiments, Ring B is

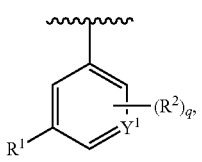

wherein $Y^1$ is CH (i.e., Ring B is phenyl). In some embodiments $Y^1$ is N.

In certain embodiments, Ring B is an optionally substituted 3-8 membered saturated or partially unsaturated carbocyclic ring, an optionally substituted 4-7 membered heterocylic ring having 1-2 heteroatoms independently selected from nitrogen, oxygen, or sulfur, an optionally substituted 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur.

In various embodiments, Ring B is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, $Y^1$ is $CR^2$ wherein $R^2$ is hydrogen.

In certain embodiments, $Y^1$ is $CR^2$ wherein $R^2$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^1$ is $CR^2$ wherein $R^2$ is an optionally substituted $C_{1-6}$ aliphatic. In certain embodiments, $Y^1$ is $CR^2$ wherein $R^2$ is an optionally substituted phenyl. In certain embodiments, $Y^1$ is $CR^2$ wherein $R^2$ is an optionally substituted 3-8 membered saturated or partially unsaturated carbocyclic ring. In certain embodiments, $Y^1$ is $CR^2$ wherein $R^2$ is an optionally substituted 4-7 membered heterocylic ring having 1-2 heteroatoms independently selected from nitrogen, oxygen, or sulfur. In certain embodiments, $Y^1$ is $CR^2$ wherein $R^2$ is an optionally substituted 5-6 membered monocyclic heteroaryl ring having 1-4 heteroatoms independently selected from nitrogen, oxygen, or sulfur.

In certain embodiments, $Y^1$ is $CR^2$ wherein $R^2$ is halo. In certain embodiments, $R^2$ is F.

In certain embodiments, Ring B is

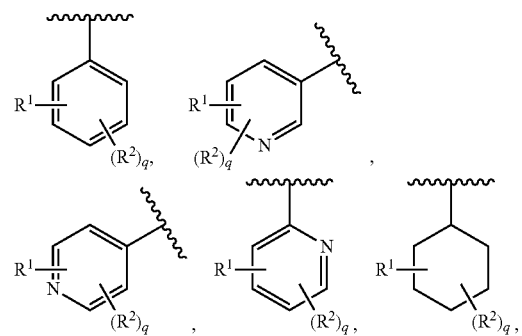

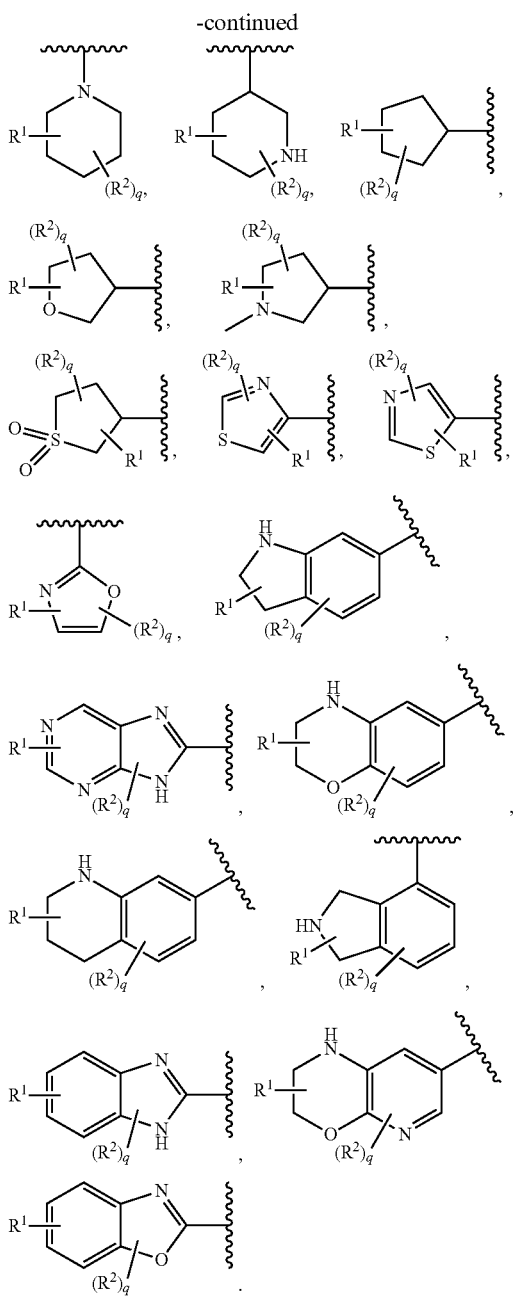

In certain embodiments, Ring B is

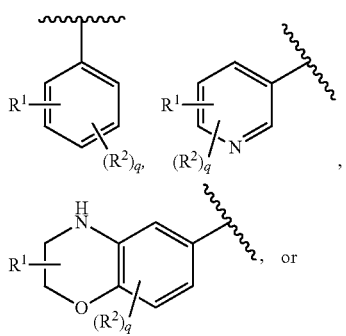

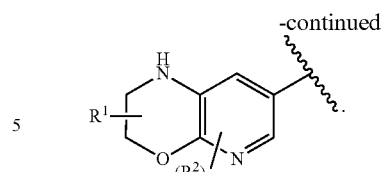

In certain embodiments, Ring B is

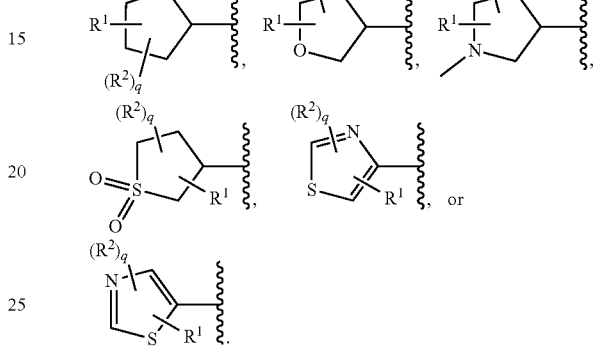

In some embodiments, Ring B is selected from those depicted in Table 2, below.

In certain embodiments, $Y^2$ is N. In certain embodiments, $Y^2$ is CR'.

In certain embodiments, $Y^2$ is CR' wherein R' is hydrogen.

In certain embodiments, $Y^2$ is CR' wherein R' is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^2$ is CR' wherein R' is an optionally substituted $C_1$ 6 aliphatic. In certain embodiments, $Y^2$ is CR' wherein R' is an optionally substituted phenyl. In certain embodiments, $Y^2$ is CR' wherein R' is an optionally substituted 3-8 membered saturated or partially unsaturated carbocyclic ring. In certain embodiments, $Y^2$ is CR' wherein R' is an optionally substituted 4-7 membered heterocylic ring having 1-2 heteroatoms independently selected from nitrogen, oxygen, or sulfur. In certain embodiments, $Y^2$ is CR' wherein R' is an optionally substituted 5-6 membered monocyclic heteroaryl ring having 1-4 heteroatoms independently selected from nitrogen, oxygen, or sulfur.

In certain embodiments, each $R^2$ is independently hydrogen.

In certain embodiments, each $R^2$ is independently —R.

In certain embodiments, each $R^2$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, or pyrrolinyl.

In certain embodiments, each $R^2$ is independently

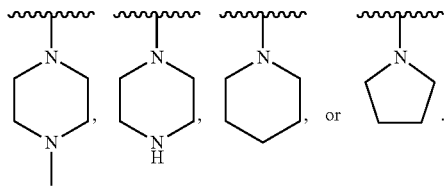

In certain embodiments, each $R^2$ is independently

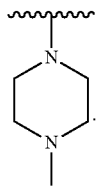

In certain embodiments, each $R^2$ is independently —$CH_3$, —F, —$CF_3$, —$OCH_3$, —$OCF_3$, —$OCH_2CH_2NMe_2$, —$OCH_2CH_2NH_2$, or —$OCH_2CH_2OCH_3$. In certain embodiment, each $R^2$ is selected from those depicted in Table 2, below.

In various embodiments, $R^6$ is hydrogen. In various embodiments, $R^6$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^6$ is an optionally substituted $C_{1-6}$ aliphatic. In various embodiments, $R^6$ is an optionally substituted phenyl. In various embodiments, $R^6$ is an optionally substituted 3-8 membered saturated or partially unsaturated carbocyclic ring. In various embodiments, $R^6$ is an optionally substituted a 4-7 membered heterocylic ring having 1-2 heteroatoms independently selected from nitrogen, oxygen, or sulfur. In various embodiments, $R^6$ is an optionally substituted 5-6 membered monocyclic heteroaryl ring having 1-4 heteroatoms independently selected from nitrogen, oxygen, or sulfur. In some embodiments, $R^6$ is selected from those depicted in Table 2, below.

In various embodiments, $R^7$ is hydrogen. In various embodiments, $R^7$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^7$ is an optionally substituted $C_{1-6}$ aliphatic. In various embodiments, $R^7$ is an optionally substituted phenyl. In various embodiments, $R^7$ is an optionally substituted 3-8 membered saturated or partially unsaturated carbocyclic ring. In various embodiments, $R^7$ is an optionally substituted a 4-7 membered heterocylic ring having 1-2 heteroatoms independently selected from nitrogen, oxygen, or sulfur. In various embodiments, $R^7$ is an optionally substituted 5-6 membered monocyclic heteroaryl ring having 1-4 heteroatoms independently selected from nitrogen, oxygen, or sulfur. In some embodiments, $R^7$ is selected from those depicted in Table 2, below.

In various embodiments, $R^6$ and $R^7$ are taken together to form a $C_{2-6}$ alkylene.

In various embodiments, $R^6$ and $R^7$ are taken together to form a $C_2$ alkylene.

In various embodiments, $R^6$ and $R^7$ are taken together to form a $C_3$ alkylene.

In various embodiments, $R^8$ is hydrogen. In various embodiments, $R^8$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^8$ is an optionally substituted $C_{1-6}$ aliphatic. In various embodiments, $R^8$ is an optionally substituted phenyl. In various embodiments, $R^8$ is an optionally substituted 3-8 membered saturated or partially unsaturated carbocyclic ring. In various embodiments, $R^8$ is an optionally substituted 4-7 membered heterocylic ring having 1-2 heteroatoms independently selected from nitrogen, oxygen, or sulfur. In various embodiments, $R^8$ is an optionally substituted 5-6 membered monocyclic heteroaryl ring having 1-4 heteroatoms independently selected from nitrogen, oxygen, or sulfur. In some embodiments, $R^8$ is selected from those depicted in Table 2, below.

In various embodiments, $R^9$ is hydrogen. In various embodiments, $R^9$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^9$ is an optionally substituted $C_{1-6}$ aliphatic. In various embodiments, $R^9$ is an optionally substituted phenyl. In various embodiments, $R^9$ is an optionally substituted 3-8 membered saturated or partially unsaturated carbocyclic ring. In various embodiments, $R^9$ is an optionally substituted 4-7 membered heterocylic ring having 1-2 heteroatoms independently selected from nitrogen, oxygen, or sulfur. In various embodiments, $R^9$ is an optionally substituted 5-6 membered monocyclic heteroaryl ring having 1-4 heteroatoms independently selected from nitrogen, oxygen, or sulfur. In some embodiments, $R^9$ is selected from those depicted in Table 2, below.

In various embodiments, $R^8$ and $R^9$ are taken together with the carbon atom to which they are attached to form a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^8$ and $R^9$ are taken together with the carbon atom to which they are attached to form a 3-8 membered saturated or partially unsaturated carbocyclic ring. In various embodiments, $R^8$ and $R^9$ are taken together with the carbon atom to which they are attached to form a 4-7 membered heterocylic ring having 1-2 heteroatoms independently selected from nitrogen, oxygen, or sulfur. In various embodiments, $R^8$ and $R^9$ are taken together with the carbon atom to which they are attached to form a 5-6 membered monocyclic heteroaryl ring having 1-4 heteroatoms independently selected from nitrogen, oxygen, or sulfur.

In various embodiments, $R^8$ and $R^9$ are taken together with the carbon atom to which they are attached to form a 3 membered saturated or partially unsaturated carbocyclic ring. In various embodiments, $R^8$ and $R^9$ are taken together with the carbon atom to which they are attached to form a 4 membered saturated or partially unsaturated carbocyclic ring. In various embodiments, $R^8$ and $R^9$ are taken together with the carbon atom to which they are attached to form a 5 membered saturated or partially unsaturated carbocyclic ring. In various embodiments, $R^8$ and $R^9$ are taken together with the carbon atom to which they are attached to form a 6 membered saturated or partially unsaturated carbocyclic ring. In various embodiments, $R^8$ and $R^9$ are taken together with the carbon atom to which they are attached to form a 7 membered saturated or partially unsaturated carbocyclic ring.

In various embodiments, $R^8$ and $R^9$ are taken together with the carbon atom to which they are attached to form a cyclopropyl, cyclobutyl, cyclopentyl, cyclohexyl, or cycloheptyl.

In various embodiments, each $R^a$ is independently hydrogen. In various embodiments, each $R^a$ is independently an optionally substituted $C_{1-6}$ aliphatic group.

In various embodiments, T is a covalent bond.

In various embodiments, T is —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In various embodiments, T is —O—, —N(R)—, —C(O)N(R)—, or —N(R)C(O)—. In some embodiments, T is selected from those depicted in Table 2, below.

In various embodiments, the invention provides a compound of II-a:

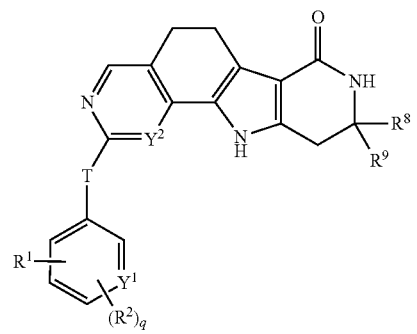

II-a or a pharmaceutically acceptable salt thereof, wherein each of $R^1$, $R^2$, $R^8$, $R^9$, $Y^1$, $Y^2$, T, and q is as defined above and described in embodiments, classes and subclasses above and herein, singly or in combination.

In various embodiments, the invention provides a compound of II-b:

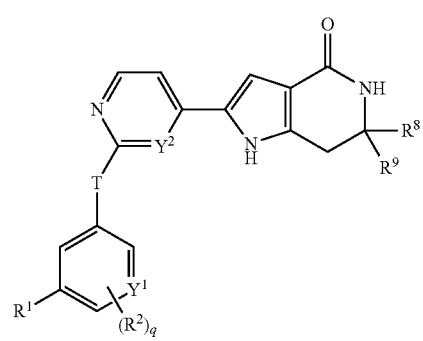

II-b or a pharmaceutically acceptable salt thereof, wherein each of $R^1$, $R^2$, $R^8$, $R^9$, $Y^1$, $Y^2$, T, and q is as defined above and described in embodiments, classes and subclasses above and herein, singly or in combination.

In various embodiments, the invention provides a compound of II-c:

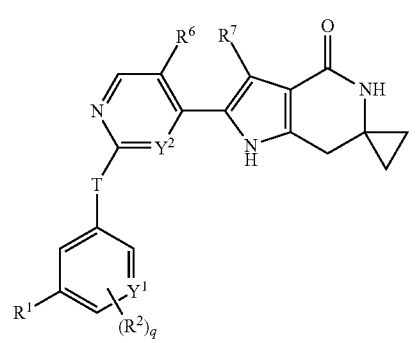

II-c or a pharmaceutically acceptable salt thereof, wherein each of $R^1$, $R^2$, $R^6$, $R^7$, $Y^1$, $Y^2$, T, and q is as defined above and described in embodiments, classes and subclasses above and herein, singly or in combination.

In various embodiments, the invention provides a compound of II-d:

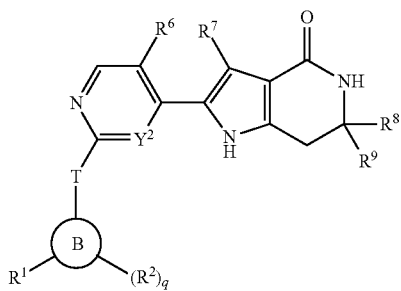

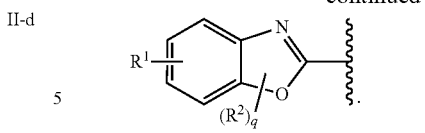

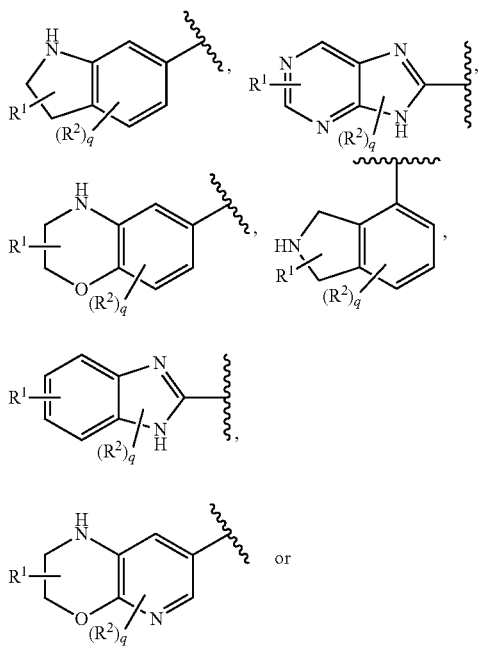

or a pharmaceutically acceptable salt thereof, wherein each of $R^1$, $R^2$, $R^6$, $R^7$, $R^8$, $R^9$, $Y^2$, T, and q is as defined above and described in embodiments, classes and subclasses above and herein, singly or in combination, and Ring B is In various embodiments, the invention provides a compound of II-d:

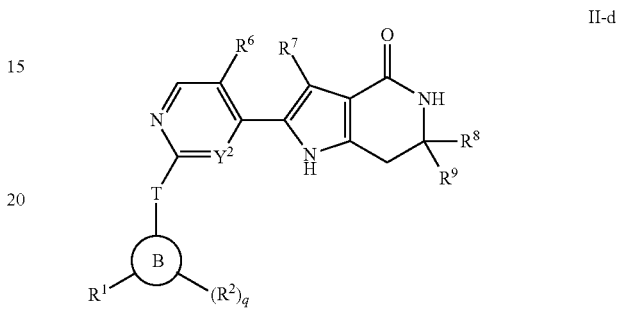

II-d or a pharmaceutically acceptable salt thereof, wherein each of $R^1$, $R^2$, $R^6$, $R^7$, $R^8$, $R^9$, $Y^2$, T, and q is as defined above and described in embodiments, classes and subclasses above and herein, singly or in combination, and Ring B is

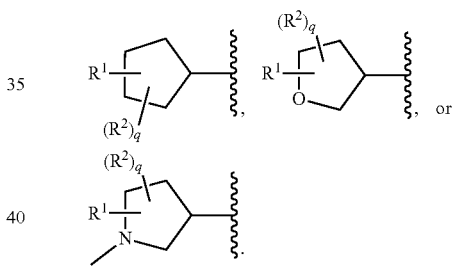

In certain embodiments, the invention provides a compound selected from those depicted in Table 2:

TABLE 2

Exemplary Compounds of Formula II

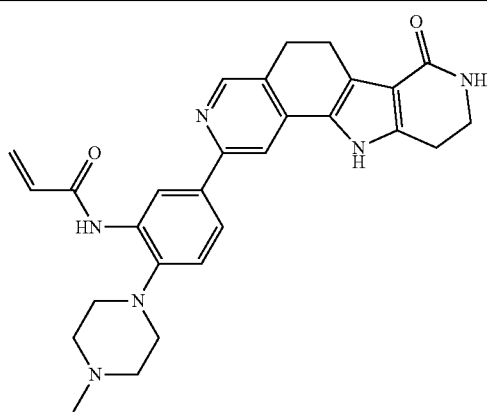

II-1

TABLE 2-continued
Exemplary Compounds of Formula II
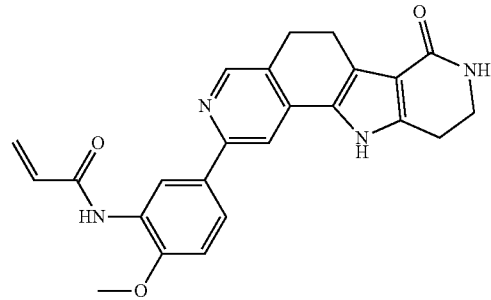 [SMILES: C=CC(=O)Nc1cc(-c2cc3c(cn2)CCc2c-3[nH]c3c2C(=O)NCC3)ccc1OC]
II-2
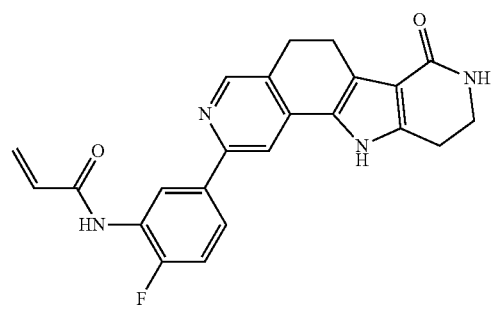 [SMILES: C=CC(=O)Nc1cc(-c2cc3c(cn2)CCc2c-3[nH]c3c2C(=O)NCC3)ccc1F]
II-3
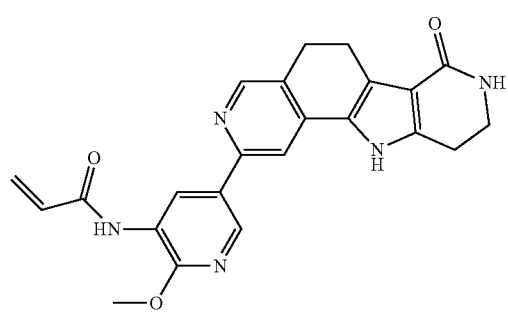 [SMILES: C=CC(=O)Nc1cc(-c2cc3c(cn2)CCc2c-3[nH]c3c2C(=O)NCC3)cnc1OC]
II-4
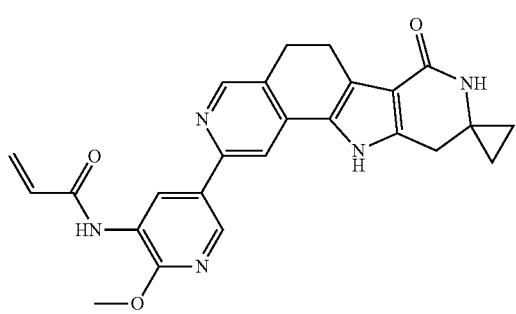 [SMILES: C=CC(=O)Nc1cc(-c2cc3c(cn2)CCc2c-3[nH]c3c2C(=O)NC2(CC2)C3)cnc1OC]
II-5
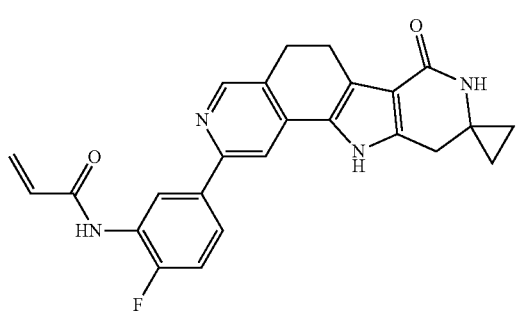 [SMILES: C=CC(=O)Nc1cc(-c2cc3c(cn2)CCc2c-3[nH]c3c2C(=O)NC2(CC2)C3)ccc1F]
II-6

TABLE 2-continued
Exemplary Compounds of Formula II
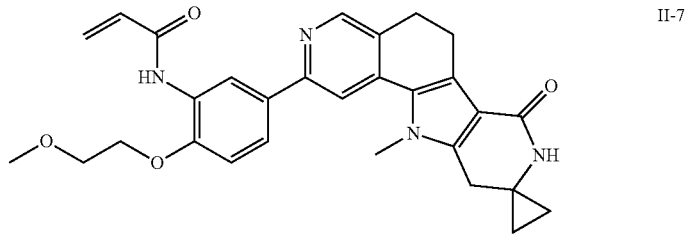
II-7
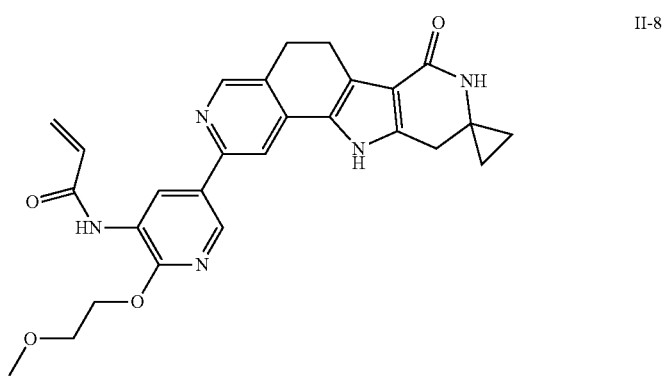
II-8
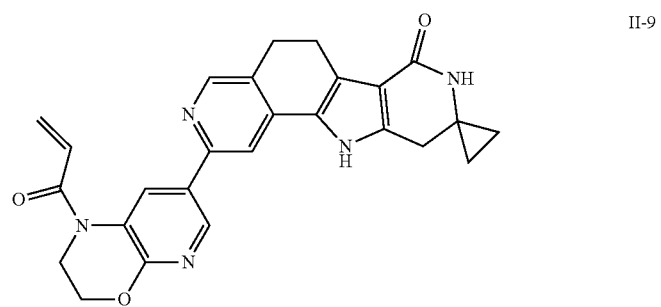
II-9
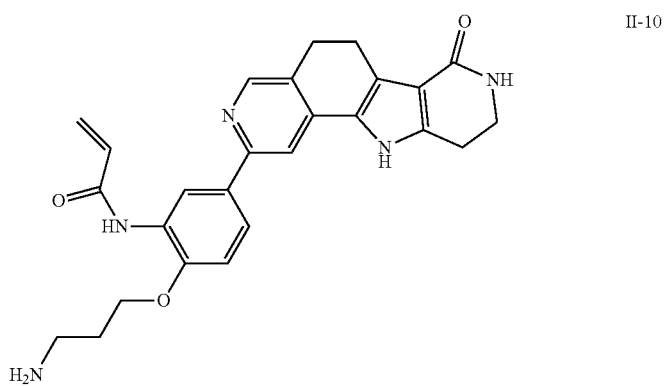
II-10

TABLE 2-continued
Exemplary Compounds of Formula II
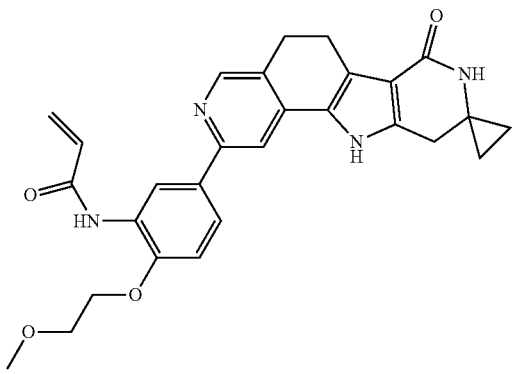 [SMILES: C=CC(=O)Nc1cc(-c2cc3c(cn2)CCc2c-3[nH]c3c2C(=O)NC2(CC2)C3)ccc1OCCOC]
II-11
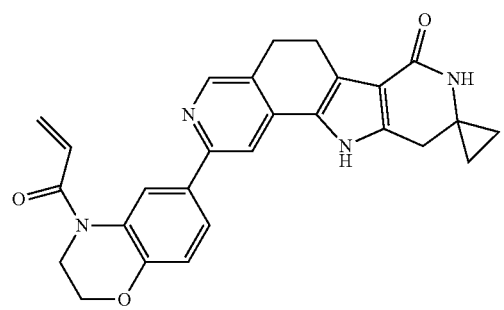 [SMILES: C=CC(=O)N1CCOc2ccc(-c3cc4c(cn3)CCc3c-4[nH]c4c3C(=O)NC3(CC3)C4)cc21]
II-12
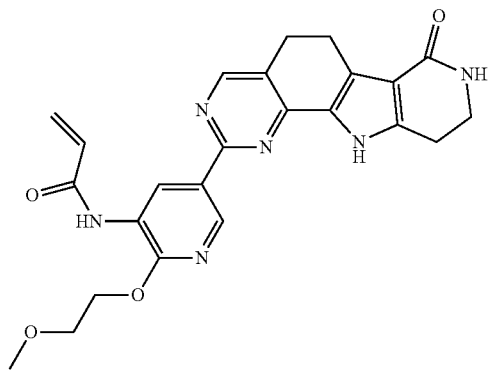
II-13
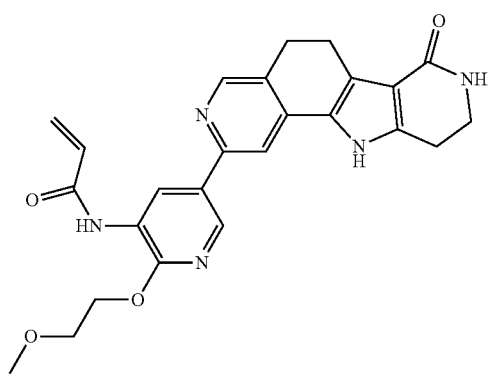
II-14

TABLE 2-continued
Exemplary Compounds of Formula II
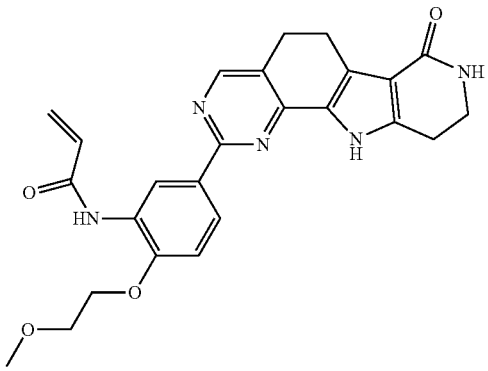 [SMILES: C=CC(=O)Nc1cc(-c2ncc3c(n2)-c2[nH]c4c(c2CC3)C(=O)NCC4)cnc1OCCOC]
II-15
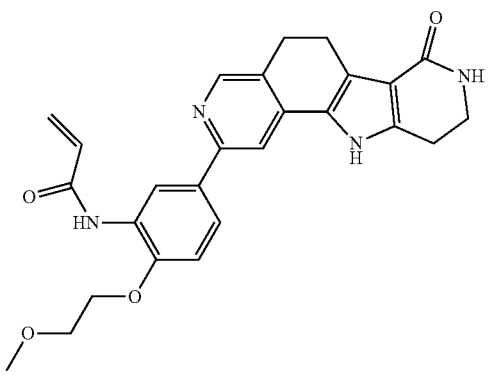 [SMILES: C=CC(=O)Nc1cc(-c2cc3c(cn2)CCc2c-3[nH]c3c2C(=O)NCC3)ccc1OCCOC]
II-16
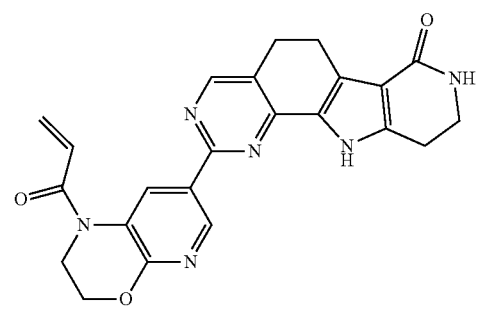
II-17
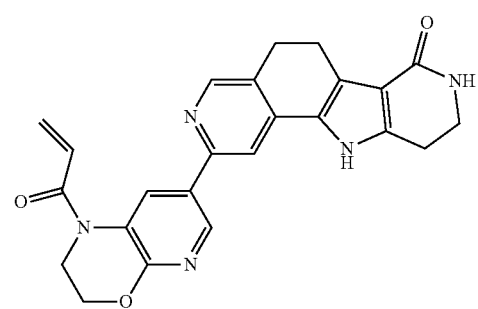 [SMILES: C=CC(=O)N1CCOc2ncc(-c3cc4c(cn3)CCc3c-4[nH]c4c3C(=O)NCC4)cc21]
II-18

TABLE 2-continued
Exemplary Compounds of Formula II
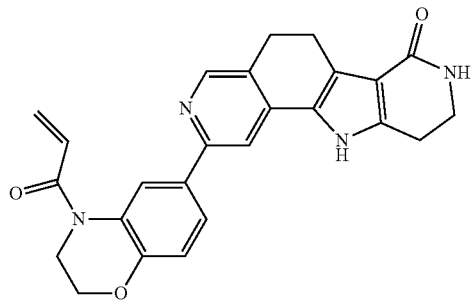
II-20
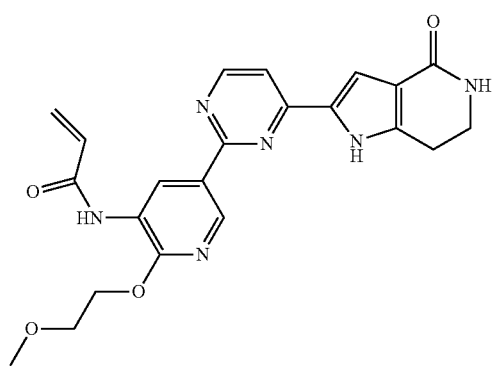 [SMILES: C=CC(=O)Nc1cc(-c2nccc(-c3cc4c([nH]3)CCNC4=O)n2)cnc1OCCOC]
II-21
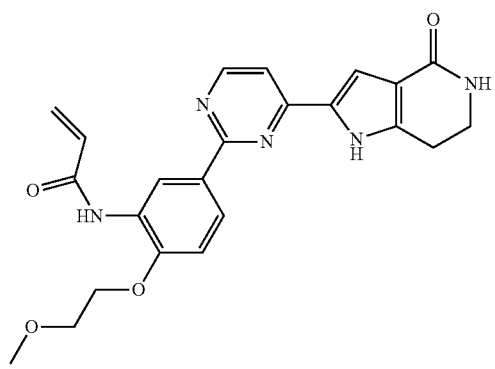 [SMILES: C=CC(=O)Nc1cc(-c2nccc(-c3cc4c([nH]3)CCNC4=O)n2)ccc1OCCOC]
II-22
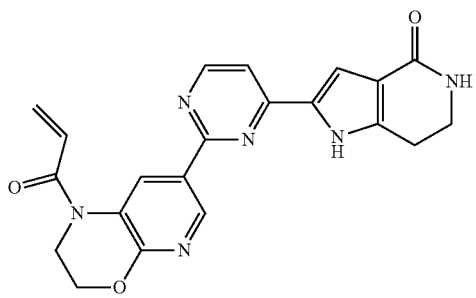 [SMILES: C=CC(=O)N1CCOc2ccc(-c3nccc(-c4cc5c([nH]4)CCNC5=O)n3)cc21]
II-23

TABLE 2-continued
Exemplary Compounds of Formula II
II-24
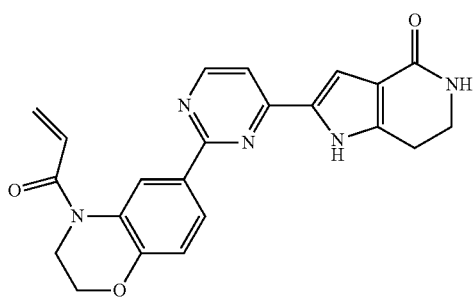
II-25
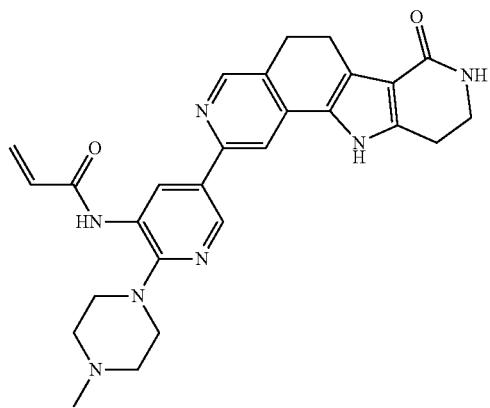 [SMILES: C=CC(=O)Nc1cc(-c2cc3c(cn2)CCc2c-3[nH]c3c2C(=O)NCC3)cnc1N1CCN(C)CC1]
II-26
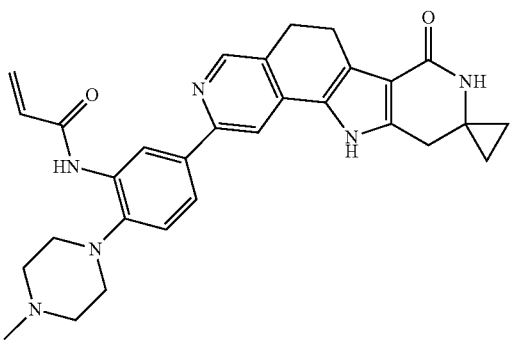 [SMILES: C=CC(=O)Nc1cc(-c2cc3c(cn2)CCc2c-3[nH]c3c2C(=O)NC2(CC2)C3)ccc1N1CCN(C)CC1]
II-27
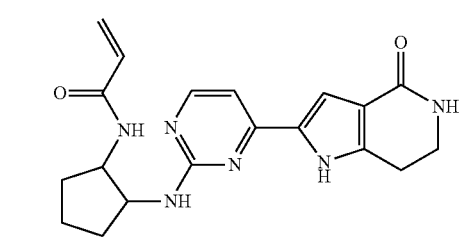 [SMILES: C=CC(=O)NC1COCC1Nc1nccc(-c2cc3c([nH]2)CCNC3=O)n1]
II-28

TABLE 2-continued

Exemplary Compounds of Formula II

| | |
|---|---|
| (structure) | II-29 |
| (structure) | II-30 |
| (structure) | II-31 |
| (structure) | II-32 |
| (structure) | II-33 |
| (structure) | II-34 |

TABLE 2-continued
Exemplary Compounds of Formula II
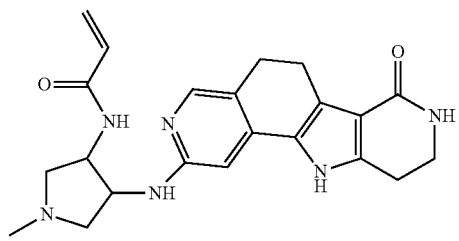 [SMILES: C=CC(=O)NC1CN(C)CC1Nc1cc2c(cn1)CCc1c-2[nH]c2c1C(=O)NCC2]
II-35
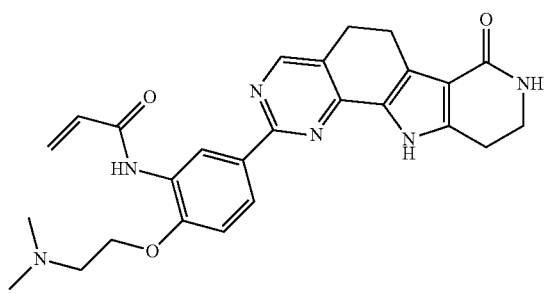 [SMILES: C=CC(=O)Nc1cc(-c2ncc3c(n2)-c2[nH]c4c(c2CC3)C(=O)NCC4)ccc1OCCN(C)C]
II-36
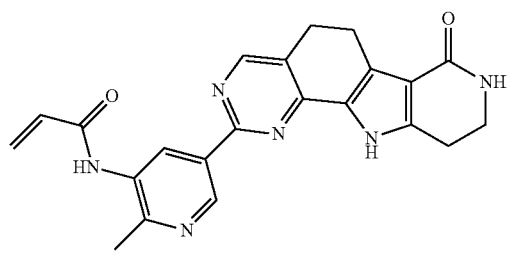 [SMILES: C=CC(=O)Nc1cc(-c2ncc3c(n2)-c2[nH]c4c(c2CC3)C(=O)NCC4)cnc1C]
II-37
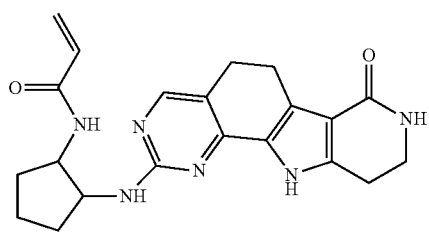 [SMILES: C=CC(=O)NC1CCCC1Nc1ncc2c(n1)-c1[nH]c3c(c1CC2)C(=O)NCC3]
II-38
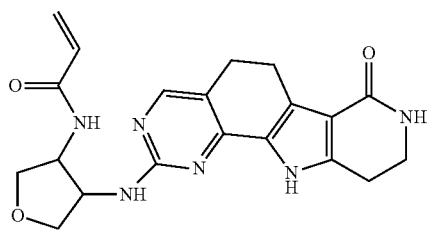
II-39
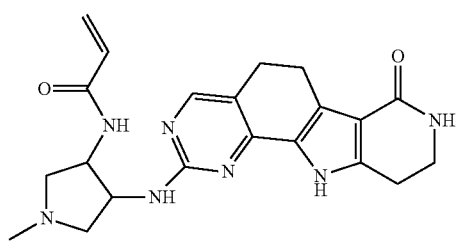 [SMILES: C=CC(=O)NC1CN(C)CC1Nc1ncc2c(n1)-c1[nH]c3c(c1CC2)C(=O)NCC3]
II-40

TABLE 2-continued
Exemplary Compounds of Formula II
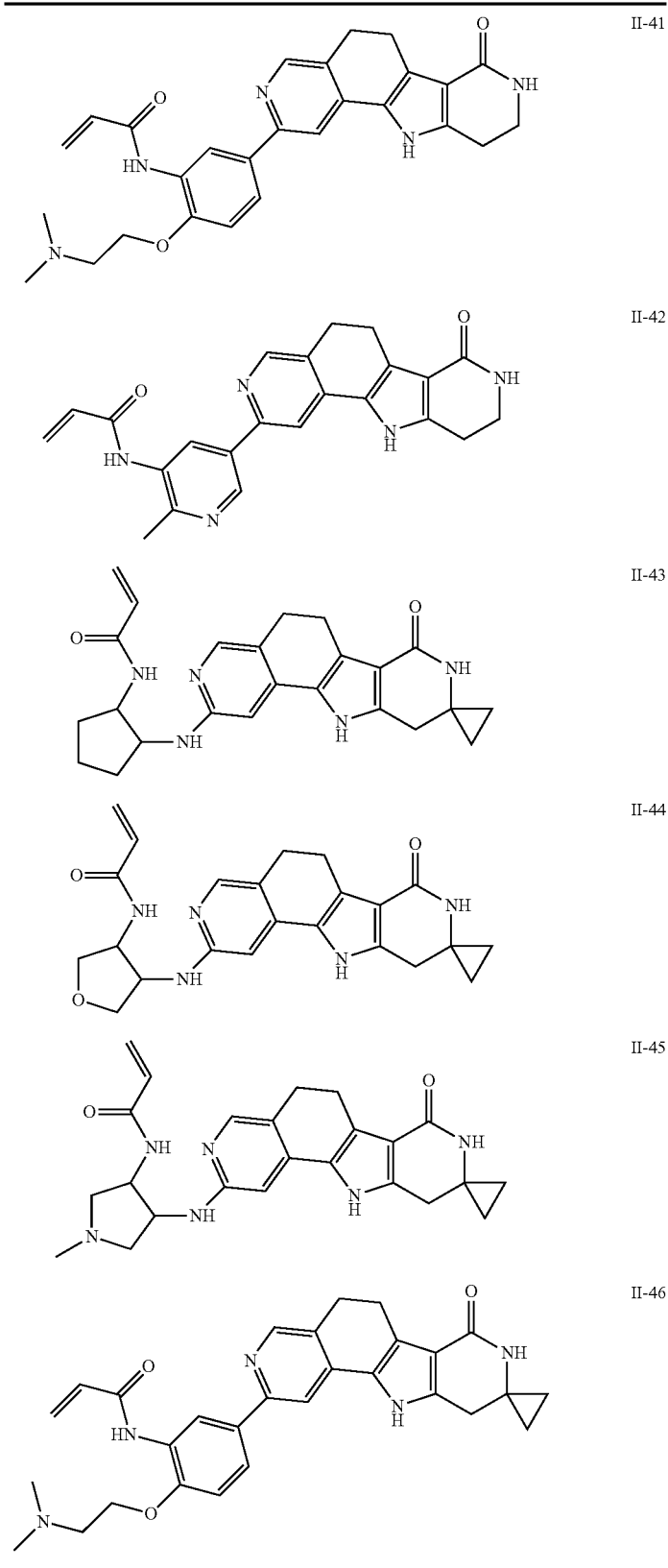
II-41
II-42
II-43
II-44
II-45
II-46
and TABLE 2-continued Exemplary Compounds of Formula II

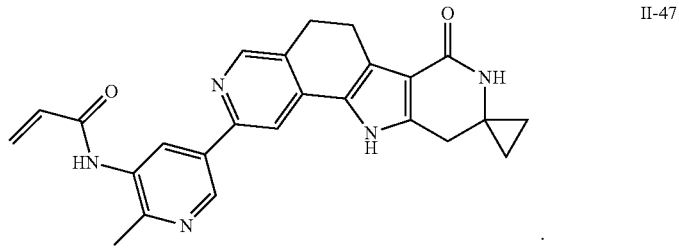

II-47

In some embodiments, the present invention provides a compound depicted in Table 2, above, or a pharmaceutically acceptable salt thereof.

According to another aspect, the present invention provides a compound of formula II-e:

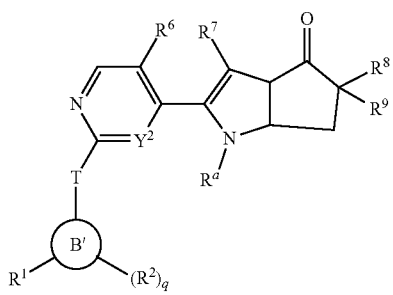

II-e or a pharmaceutically acceptable salt thereof, wherein:
Ring B' is

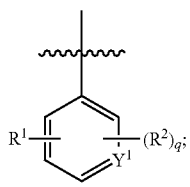

or an optionally substituted group selected from a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur; or
$Y^1$ is $CR^2$ or N;
$Y^2$ is CR' or N;
each R' is independently hydrogen, halo, or an optionally substituted group selected from $C_1$a aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
$R^1$ is a warhead group;
q is 0-6;
each $R^2$ is independently —R, halogen, —OR, —SR, —CN, —$NO_2$, —$SO_2$NR, —$SO_2$R, —SOR, —C(O)R, —$CO_2$R, —C(O)N(R)$_2$, —NRC(O)R, —NRC(O)OR, —NRC(O)N(R)$_2$, —NRSO$_2$R, or —N(R)$_2$;
each R is independently hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or
two R groups on the same nitrogen are taken together with the nitrogen atom to which they are attached to form a 4-7 membered heterocyclic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;
$R^6$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
$R^7$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
or $R^6$ and $R^7$ are taken together to form a $C_{2-6}$ alkylene or $C_{2-6}$ alkenylene;
$R^8$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
$R^9$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
or $R^8$ and $R^9$ are taken together with the carbon atom to which they are attached to form a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
each $R^a$ is independently hydrogen or an optionally substituted $C_{1-6}$ aliphatic group; and
T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In certain embodiments, $R^1$ is a warhead group, wherein when Ring B' is a 5 or 6-membered ring, then $R^1$ is attached to an atom next to an atom adjacent to where T is attached (i.e., in the case where Ring B' is phenyl, $R^1$ is attached at the meta position), or $R^1$ is attached to an atom adjacent to where T is attached (i.e., in the case where Ring B' is phenyl, $R^1$ is attached at the ortho position).

In certain embodiments, Ring B' is

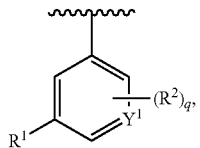

wherein each of $R^1$, $R^2$, Y, and q is as defined above and described herein. In various embodiments, Ring B' is

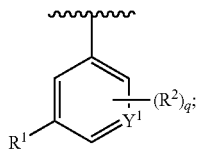

wherein $Y^1$ is CH. In some embodiments, $Y^1$ is N.

In various embodiments, Ring B' is a 5-6 membered monocyclic heteroaryl ring having 1-4 heteroatoms independently selected from nitrogen, oxygen, or sulfur an optionally substituted 4-7 membered saturated or partially unsaturated heterocyclic ring having 1-3 heteroatoms independently selected from nitrogen, oxygen, or sulfur a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur.

In various embodiments, Ring B' is a 3-8 membered saturated or partially unsaturated carbocyclic ring.

In various embodiments, Ring B' is a 5-6 membered monocyclic heteroaryl ring having 1-4 heteroatoms independently selected from nitrogen, oxygen, or sulfur.

In various embodiments, Ring B' is a 4-7 membered saturated or partially unsaturated heterocyclic ring having 1-3 heteroatoms independently selected from nitrogen, oxygen, or sulfur.

In various embodiments, Ring B' is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, Ring B' is

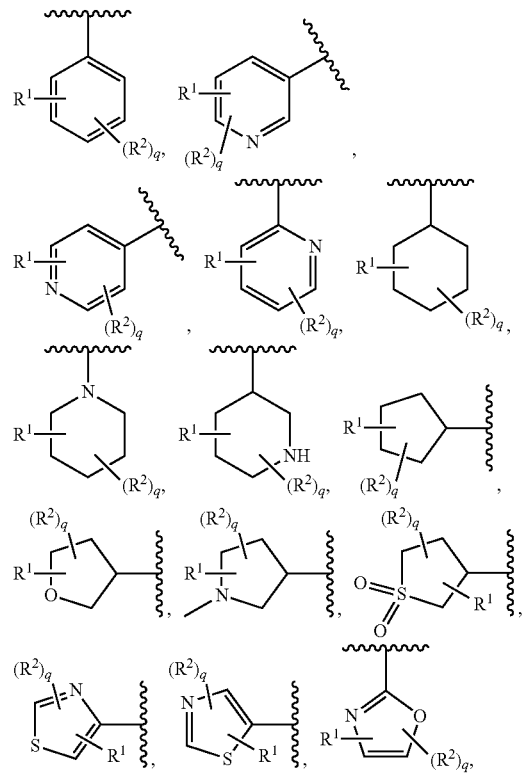

In certain embodiments, each $R^2$ is independently hydrogen.

In certain embodiments, each $R^2$ is independently —R.

In certain embodiments, each $R^2$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, or pyrrolinyl.

In certain embodiments, each $R^2$ is independently

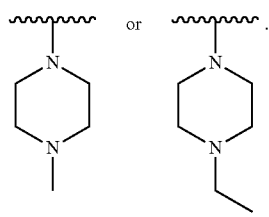

In certain embodiments, each $R^2$ is independently —CH$_3$, —F, —CF$_3$, —OCH$_3$, —OCF$_3$, —OCH$_2$CH$_2$NMe$_2$, —OCH$_2$CH$_2$NH$_2$, or —OCH$_2$CH$_2$OCH$_3$. In certain embodiments, each $R^2$ is —F, —CF$_3$, —OCH$_3$, —OCH$_2$CH$_2$CH$_2$NH$_2$, or —OCH$_2$CH$_2$OCH$_3$.

In various embodiments, $R^6$ is hydrogen. In various embodiments, $R^6$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected

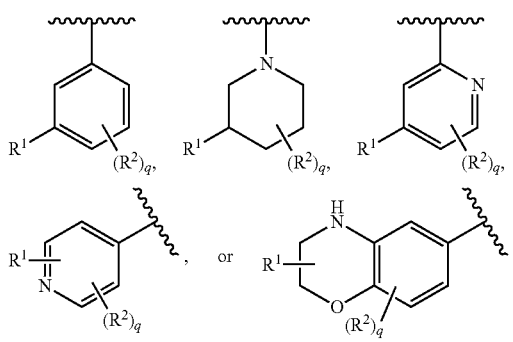

In various embodiments, Ring B' is

In some embodiments, Ring B' is selected from those depicted in Table 3, below.

In certain embodiments, $Y^2$ is CR' wherein R' is hydrogen.

In certain embodiments, $Y^2$ is CR' wherein R' is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^2$ is CR' wherein R' is an optionally substituted $C_{1-6}$ aliphatic. In certain embodiments, $Y^2$ is CR' wherein R' is an optionally substituted phenyl. In certain embodiments, $Y^2$ is CR' wherein R' is an optionally substituted 3-8 membered saturated or partially unsaturated carbocyclic ring. In certain embodiments, $Y^2$ is CR' wherein R' is an optionally substituted 4-7 membered heterocylic ring having 1-2 heteroatoms independently selected from nitrogen, oxygen, or sulfur. In certain embodiments, $Y^2$ is CR' wherein R' is an optionally substituted 5-6 membered monocyclic heteroaryl ring having 1-4 heteroatoms independently selected from nitrogen, oxygen, or sulfur.

from nitrogen, oxygen, or sulfur, or a 5-6 membered monocyclic heteroaryl ring having 1-4 heteroatoms independently selected from nitrogen, oxygen, or sulfur.

In various embodiments, $R^6$ is an optionally substituted $C_{1-6}$ aliphatic. In various embodiments, $R^6$ is an optionally substituted phenyl. In various embodiments, $R^6$ is an optionally substituted 3-8 membered saturated or partially unsaturated carbocyclic ring. In various embodiments, $R^6$ is an optionally substituted a 4-7 membered heterocylic ring having 1-2 heteroatoms independently selected from nitrogen, oxygen, or sulfur. In various embodiments, $R^6$ is an optionally substituted 5-6 membered monocyclic heteroaryl ring having 1-4 heteroatoms independently selected from nitrogen, oxygen, or sulfur. In some embodiments, $R^6$ is selected from those depicted in Table 3, below.

In various embodiments, $R^7$ is hydrogen. In various embodiments, $R^7$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^7$ is an optionally substituted $C_1$ aliphatic. In various embodiments, $R^7$ is an optionally substituted phenyl. In various embodiments, $R^7$ is an optionally substituted 3-8 membered saturated or partially unsaturated carbocyclic ring. In various embodiments, $R^7$ is an optionally substituted a 4-7 membered heterocylic ring having 1-2 heteroatoms independently selected from nitrogen, oxygen, or sulfur. In various embodiments, $R^7$ is an optionally substituted 5-6 membered monocyclic heteroaryl ring having 1-4 heteroatoms independently selected from nitrogen, oxygen, or sulfur. In some embodiments, $R^7$ is selected from those depicted in Table 3, below.

In various embodiments, $R^6$ and $R^7$ are taken together to form a $C_{2-6}$ alkylene.

In various embodiments, $R^6$ and $R^7$ are taken together to form a $C_2$ alkylene.

In various embodiments, $R^6$ and $R^7$ are taken together to form a $C_3$ alkylene.

In various embodiments, $R^6$ and $R^7$ are taken together to form a $C_{2-6}$ alkenylene.

In various embodiments, $R^6$ and $R^7$ are taken together to form a $C_2$ alkenylene.

In various embodiments, $R^6$ and $R^7$ are taken together to form a $C_3$ alkenylene.

In various embodiments, $R^8$ is hydrogen. In various embodiments, $R^8$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^8$ is an optionally substituted $C_{1-6}$ aliphatic. In various embodiments, $R^8$ is an optionally substituted phenyl. In various embodiments, $R^8$ is an optionally substituted 3-8 membered saturated or partially unsaturated carbocyclic ring. In various embodiments, $R^8$ is an optionally substituted 4-7 membered heterocylic ring having 1-2 heteroatoms independently selected from nitrogen, oxygen, or sulfur. In various embodiments, $R^8$ is an optionally substituted 5-6 membered monocyclic heteroaryl ring having 1-4 heteroatoms independently selected from nitrogen, oxygen, or sulfur. In some embodiments, $R^8$ is selected from those depicted in Table 3, below.

In various embodiments, $R^9$ is hydrogen. In various embodiments, $R^9$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^9$ is an optionally substituted $C_{15}$ aliphatic. In various embodiments, $R^9$ is an optionally substituted phenyl. In various embodiments, $R^9$ is an optionally substituted 3-8 membered saturated or partially unsaturated carbocyclic ring. In various embodiments, $R^9$ is an optionally substituted 4-7 membered heterocylic ring having 1-2 heteroatoms independently selected from nitrogen, oxygen, or sulfur. In various embodiments, $R^9$ is an optionally substituted 5-6 membered monocyclic heteroaryl ring having 1-4 heteroatoms independently selected from nitrogen, oxygen, or sulfur. In some embodiments, $R^9$ is selected from those depicted in Table 3, below.

In various embodiments, $R^8$ and $R^9$ are taken together with the carbon atom to which they are attached to form a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In various embodiments, $R^8$ and $R^9$ are taken together with the carbon atom to which they are attached to form a 3-8 membered saturated or partially unsaturated carbocyclic ring. In various embodiments, $R^8$ and $R^9$ are taken together with the carbon atom to which they are attached to form a 4-7 membered heterocylic ring having 1-2 heteroatoms independently selected from nitrogen, oxygen, or sulfur. In various embodiments, $R^8$ and $R^9$ are taken together with the carbon atom to which they are attached to form a 5-6 membered monocyclic heteroaryl ring having 1-4 heteroatoms independently selected from nitrogen, oxygen, or sulfur.

In various embodiments, $R^8$ and $R^9$ are taken together with the carbon atom to which they are attached to form a 3 membered saturated or partially unsaturated carbocyclic ring. In various embodiments, $R^8$ and $R^9$ are taken together with the carbon atom to which they are attached to form a 4 membered saturated or partially unsaturated carbocyclic ring. In various embodiments, $R^8$ and $R^9$ are taken together with the carbon atom to which they are attached to form a 5 membered saturated or partially unsaturated carbocyclic ring. In various embodiments, $R^8$ and $R^9$ are taken together with the carbon atom to which they are attached to form a 6 membered saturated or partially unsaturated carbocyclic ring. In various embodiments, $R^8$ and $R^9$ are taken together with the carbon atom to which they are attached to form a 7 membered saturated or partially unsaturated carbocyclic ring.

In various embodiments, $R^8$ and $R^9$ are taken together with the carbon atom to which they are attached to form a cyclopropyl, cyclobutyl, cyclopentyl, cyclohexyl, or cycloheptyl.

In various embodiments, each $R^a$ is independently hydrogen. In various embodiments, each $R^a$ is independently an optionally substituted $C_{1-6}$ aliphatic group.

In various embodiments, T is a covalent bond.

In various embodiments, T is —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In various embodiments, T is —O—, —N(R)—, —C(O)N(R)—, or —N(R)C(O)—. In some embodiments, T is selected from those depicted in Table 3, below.

In various embodiments, the invention provides a compound of formula II-e, wherein the moiety

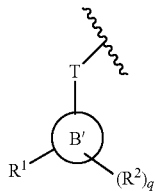

is selected from any one of the following structures:

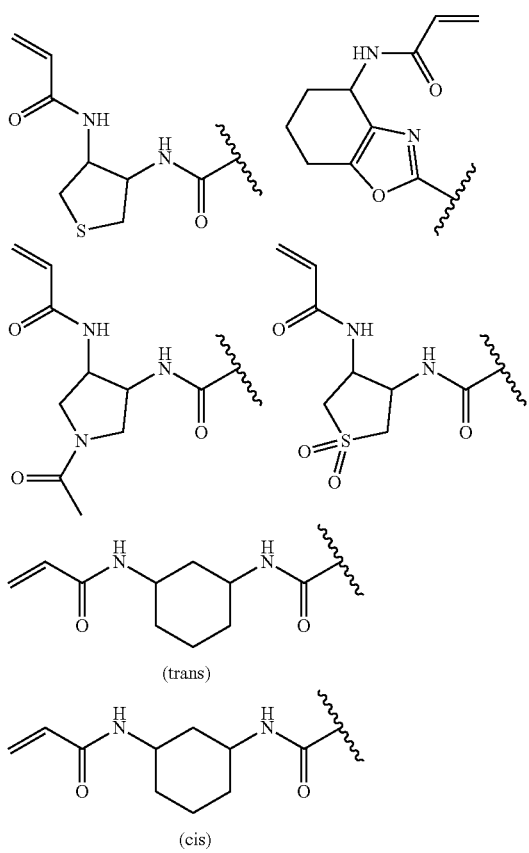

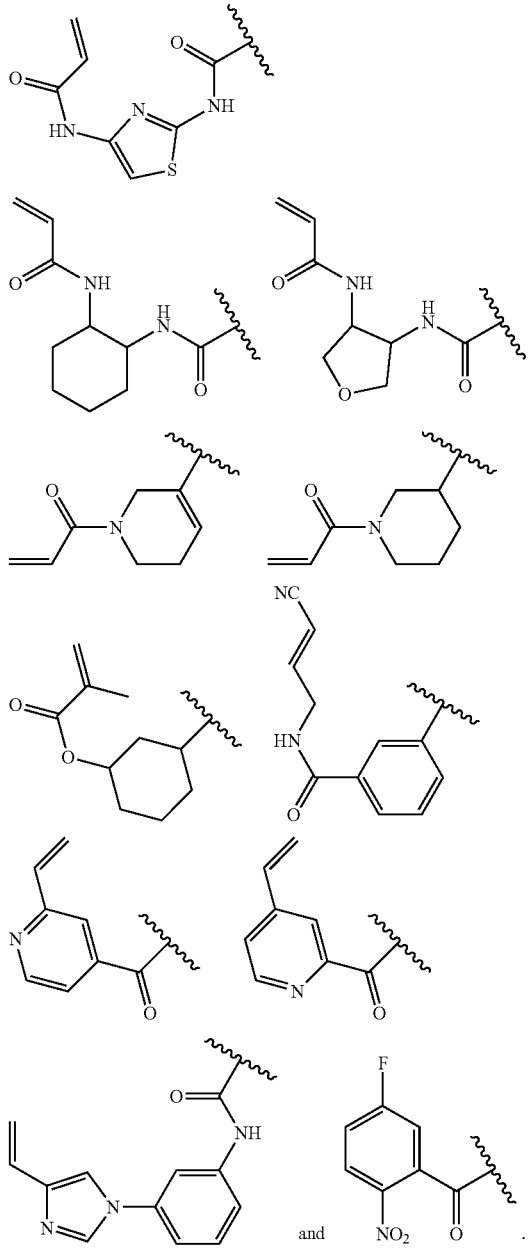

In various embodiments, the invention provides a compound of II-ee:

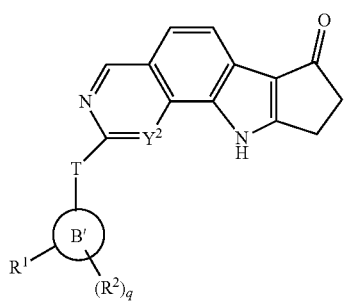

II-ee or a pharmaceutically acceptable salt thereof, wherein each of $R^1$, $R^2$, $Y^2$, T, and q is as defined above and described in embodiments, classes and subclasses above and herein, singly or in combination.

In certain embodiments, the invention provides a compound selected from those depicted in Table 3, below:

TABLE 3

Exemplary Compounds of Formula II-e

II-e-1

II-e-2

II-e-3

II-e-4

II-e-5

II-e-6

TABLE 3-continued
Exemplary Compounds of Formula II-e
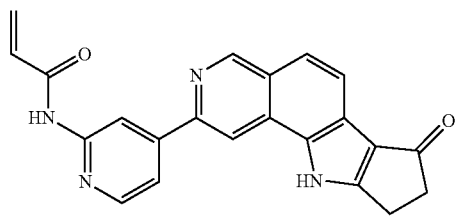 [SMILES: C=CC(=O)Nc1cc(-c2cc3c(ccc4c5c([nH]c43)CCC5=O)cn2)ccn1]
II-e-7
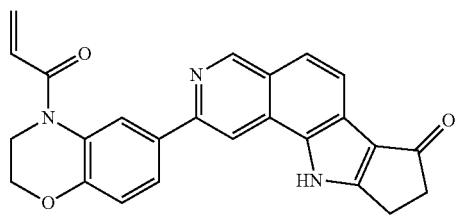 [SMILES: C=CC(=O)N1CCOc2ccc(-c3cc4c(ccc5c6c([nH]c54)CCC6=O)cn3)cc21]
II-e-8
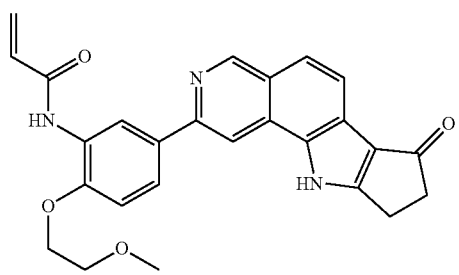 [SMILES: C=CC(=O)Nc1cc(-c2cc3c(ccc4c5c([nH]c43)CCC5=O)cn2)ccc1OCCOC]
II-e-9
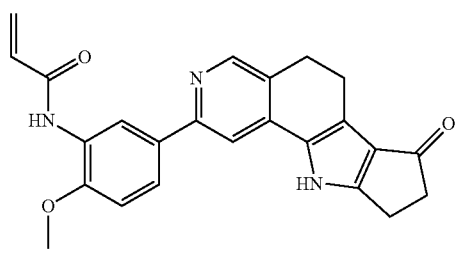 [SMILES: C=CC(=O)Nc1cc(-c2cc3c(cn2)CCc2c-3[nH]c3c2C(=O)CC3)ccc1OC]
II-e-10
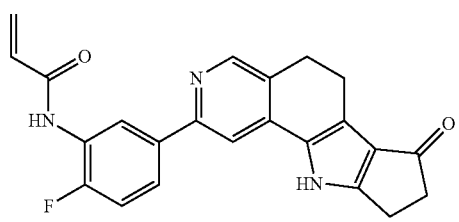 [SMILES: C=CC(=O)Nc1cc(-c2cc3c(cn2)CCc2c-3[nH]c3c2C(=O)CC3)ccc1F]
II-e-11
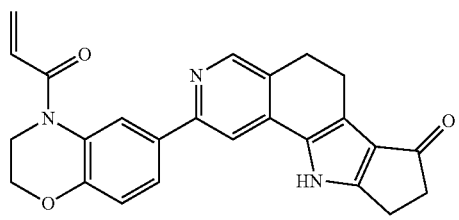 [SMILES: C=CC(=O)N1CCOc2ccc(-c3cc4c(cn3)CCc3c-4[nH]c4c3C(=O)CC4)cc21]
II-e-12

TABLE 3-continued

Exemplary Compounds of Formula II-e

| | |
|---|---|
| (structure) | II-e-13 |
| (structure) | II-e-14 |
| (structure) | II-e-15 |
| (structure) | II-e-17 |
| (structure) | II-e-19 |
| (structure) | II-e-20 |
| (structure) | II-e-21 |

TABLE 3-continued

Exemplary Compounds of Formula II-e

II-e-22

II-e-23

In some embodiments, the present invention provides a compound depicted in Table 3, above, or a pharmaceutically acceptable salt thereof.

According to another aspect, the present invention provides a compound of formula III.

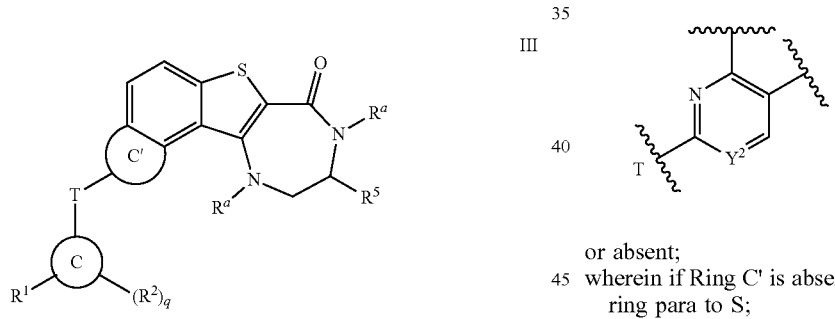

III or a pharmaceutically acceptable salt thereof, wherein:
Ring C is an optionally substituted group selected from

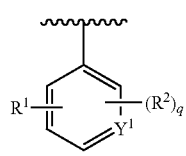

or a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxy- gen, or sulfur, or a 7-10 membered bicyclic saturated or partially unsaturated heterocyclic ring having 1-5 heteroatoms independently selected from nitrogen, oxygen, or sulfur; or Ring C' is

[structure]

or absent;
wherein if Ring C' is absent, then T is attached to the benzo ring para to S;
$Y^1$ is $CR^2$ or N;
$Y^2$ is CR' or N;
each R' is independently hydrogen, halo, or an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
$R^1$ is a warhead group;
q is 0-6;
each $R^2$ is independently —R, halogen, —OR, —SR, —CN, —NO$_2$, —SO$_2$NR, —SO$_2$R, —SOR, —C(O)R, —CO$_2$R, —C(O)N(R)$_2$, —NRC(O)R, —NRC(O)OR, —NRC(O)N(R)$_2$, —NRSO$_2$R, or —N(R)$_2$;
each R is independently hydrogen or an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

$R^5$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

each $R^a$ is independently hydrogen or an optionally substituted $C_{1-6}$ aliphatic group; and T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —SO₂—, —SO₂N(R)—, —N(R)SO₂—, or —N(R)SO₂N(R)—.

In certain embodiments, $R^1$ is a warhead group, wherein when Ring C is a 5 or 6-membered ring, then $R^1$ is attached to an atom next to an atom adjacent to where T is attached (i.e., in the case where Ring C is phenyl, $R^1$ is attached at the meta position), or $R^1$ is attached to an atom adjacent to where T is attached (i.e., in the case where Ring C is phenyl, $R^1$ is attached at the ortho position).

In certain embodiments, Ring C is

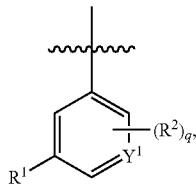

wherein $Y^1$ is CH (i.e., phenyl). In some embodiments, $Y^1$ is N.

In certain embodiments, Ring C is an optionally substituted 3-8 membered saturated or partially unsaturated carbocyclic ring, an optionally substituted 4-7 membered heterocylic ring having 1-2 heteroatoms independently selected from nitrogen, oxygen, or sulfur, an optionally substituted 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocylic ring having 1-5 heteroatoms independently selected from nitrogen, oxygen, or sulfur.

In various embodiments, Ring C is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, $Y^1$ is N. In certain embodiments, $Y^1$ is $CR^2$.

In certain embodiments, $Y^1$ is $CR^2$ wherein $R^2$ is hydrogen.

In certain embodiments, $Y^1$ is $CR^2$ wherein $R^2$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^1$ is $CR^2$ wherein $R^2$ is an optionally substituted $C_{1-6}$ aliphatic. In certain embodiments, $Y^1$ is $CR^2$ wherein $R^2$ is an optionally substituted phenyl. In certain embodiments, $Y^1$ is $CR^2$ wherein $R^2$ is an optionally substituted 3-8 membered saturated or partially unsaturated carbocyclic ring. In certain embodiments, $Y^1$ is $CR^2$ wherein $R^2$ is an optionally substituted 4-7 membered heterocylic ring having 1-2 heteroatoms independently selected from nitrogen, oxygen, or sulfur. In certain embodiments, $Y^1$ is $CR^2$ wherein $R^2$ is an optionally substituted 5-6 membered monocyclic heteroaryl ring having 1-4 heteroatoms independently selected from nitrogen, oxygen, or sulfur.

In certain embodiments, Ring C is

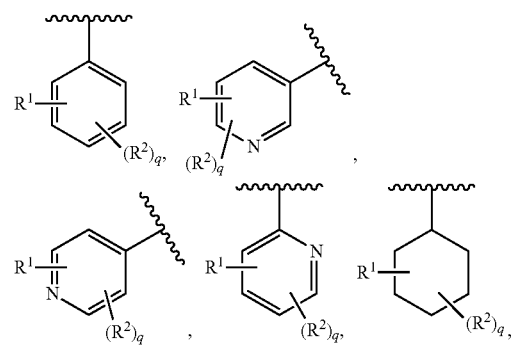

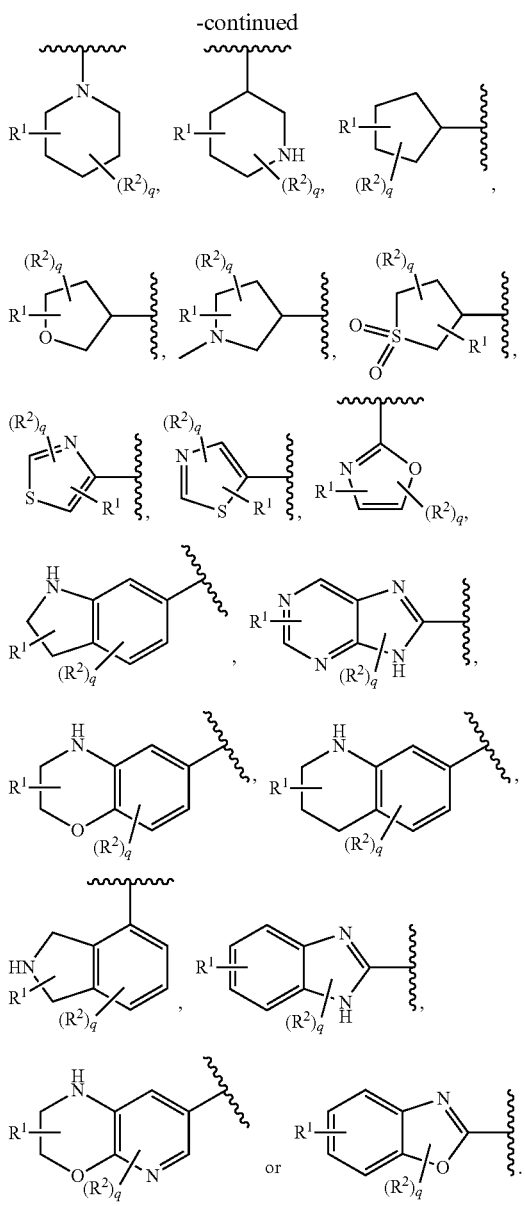

In certain embodiments, Ring C is

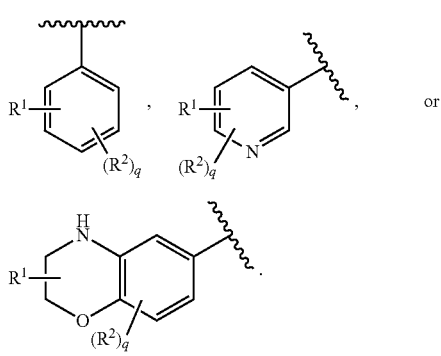

In some embodiments, Ring C is selected from those depicted in Table 4, below.

In certain embodiments, Ring C' is

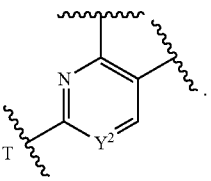

In certain embodiments, $Y^2$ is N. In certain embodiments, $Y^2$ is CR'.

In certain embodiments, $Y^2$ is CR' wherein R' is hydrogen.

In certain embodiments, $Y^2$ is CR' wherein R' is an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^2$ is CR' wherein R' is an optionally substituted $C_{1-6}$ aliphatic. In certain embodiments, $Y^2$ is CR' wherein R' is an optionally substituted phenyl. In certain embodiments, $Y^2$ is CR' wherein R' is an optionally substituted 3-8 membered saturated or partially unsaturated carbocyclic ring. In certain embodiments, $Y^2$ is CR' wherein R' is an optionally substituted 4-7 membered heterocylic ring having 1-2 heteroatoms independently selected from nitrogen, oxygen, or sulfur. In certain embodiments, $Y^2$ is CR' wherein R' is an optionally substituted 5-6 membered monocyclic heteroaryl ring having 1-4 heteroatoms independently selected from nitrogen, oxygen, or sulfur.

In certain embodiments, Ring C' is absent.

In certain embodiments, each $R^2$ is independently hydrogen.

In certain embodiments, each $R^2$ is independently —R.

In certain embodiments, each $R^2$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, or pyrrolinyl.

In certain embodiments, each $R^2$ is independently

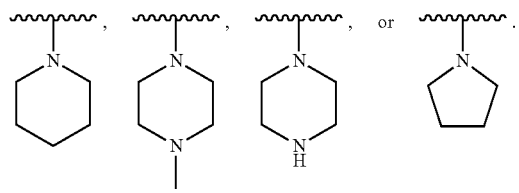

In certain embodiments, each $R^2$ is independently -$CH_3$, -F, -$CF_3$, -$OCH_3$, -$OCF_3$, -$OCH_2CH_2NMe_2$, -$OCH_2CH_2NH_2$, or -$OCH_2CH_2OCH_3$.

In certain embodiments, each $R^2$ is independently -F, -$CH_3$, -$CF_3$, -$OCH_3$, or -$OCH_2CH_2OCH_3$. In some embodiments, each $R^2$ is selected from those depicted in Table 4, below.

In certain embodiments, $R^5$ is hydrogen.

In certain embodiments, $R^5$ is an optionally substituted group selected from $C_1$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $R^5$ is an optionally substituted $C_{1-6}$ aliphatic. In certain embodiments, $R^5$ is an optionally substituted phenyl. In certain embodiments, $R^5$ is an optionally substituted a 3-8 membered saturated or partially unsaturated carbocyclic ring. In certain embodiments, $R^5$ is an optionally substituted a 4-7 membered heterocyclic ring having 1-2 heteroatoms independently selected from nitrogen, oxygen, or sulfur. In certain embodiments, $R^5$ is an optionally substituted a 5-6 membered monocyclic heteroaryl ring having 1-4 heteroatoms independently selected from nitrogen, oxygen, or sulfur.

In certain embodiments, $R^5$ is methyl. In some embodiments, $R^5$ is selected from those depicted in Table 4, below.

In various embodiments, each $R^a$ is independently hydrogen. In various embodiments, each $R^a$ is independently an optionally substituted $C_{1-6}$ aliphatic group. In some embodiments, $R^a$ is selected from those depicted in Table 4, below.

In various embodiments, T is a covalent bond.

In various embodiments, T is -O-, -S-, -N(R)-, -C(O)-, -OC(O)-, -C(O)O-, -C(O)N(R)-, -N(R)C(O)-, -N(R)C(O)N(R)-, -S(O)-, -$SO_2$-, -$SO_2$N(R)-, -N(R)$SO_2$-, or -N(R)$SO_2$N(R)-.

In various embodiments, T is -O-, -N(R)-, -C(O)N(R)-, or -N(R)C(O)-. In some embodiments, T is selected from those depicted in Table 4, below.

In various embodiments, the invention provides a compound of formula III, wherein the moiety

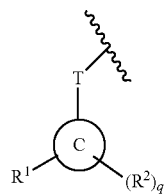

is selected from any one of the following structures:

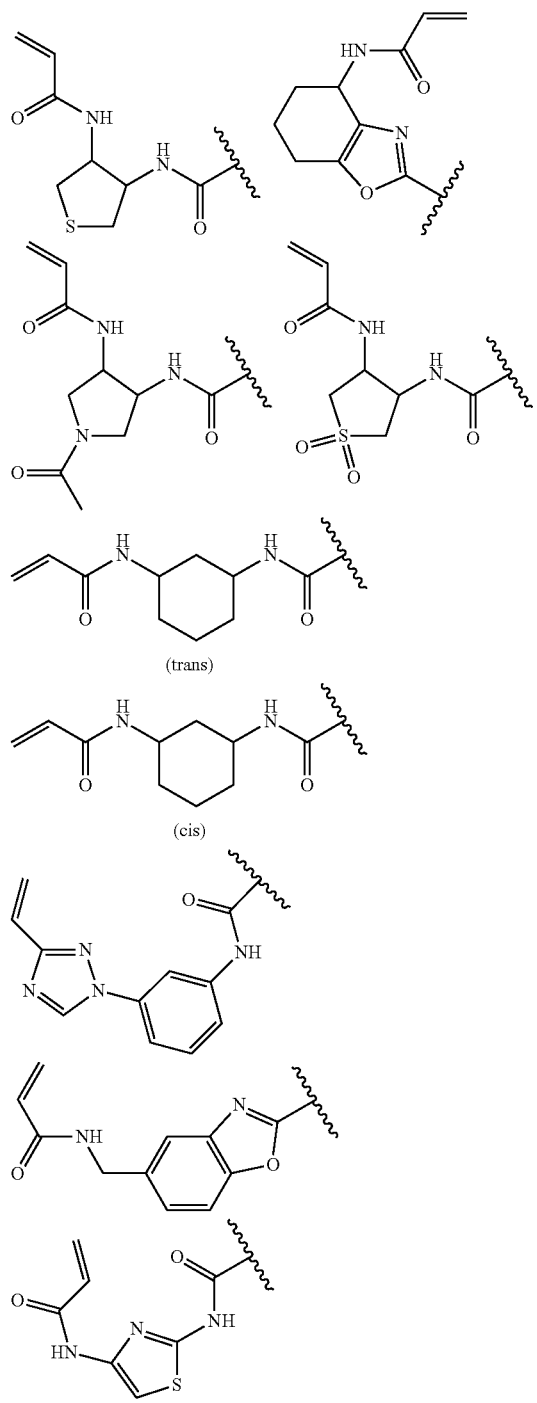

-continued

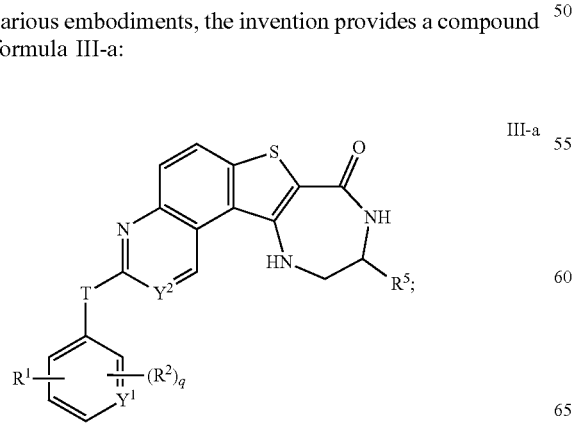

In various embodiments, the invention provides a compound of formula III-a:

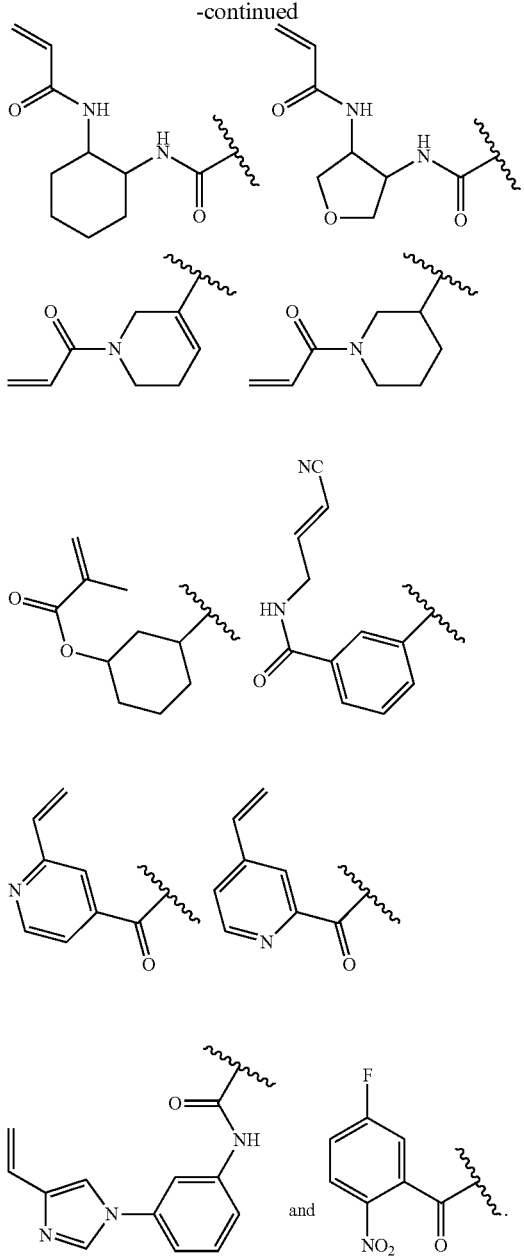

or a pharmaceutically acceptable salt thereof, wherein each of $R^1$, $R^2$, $R^5$, $Y^1$, $Y^2$, T, and q is as defined above and described in embodiments, classes and subclasses above and herein, singly or in combination.

In various embodiments, the invention provides a compound of formula III-aa:

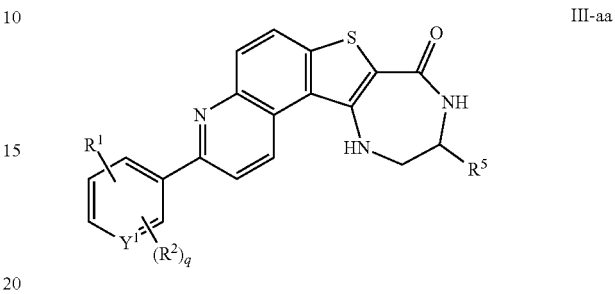

or a pharmaceutically acceptable salt thereof, wherein each of $R^1$, $R^2$, $R^5$, $Y^1$, and q is as defined above and described in embodiments, classes and subclasses above and herein, singly or in combination.

In various embodiments, the invention provides a compound of formula III-b:

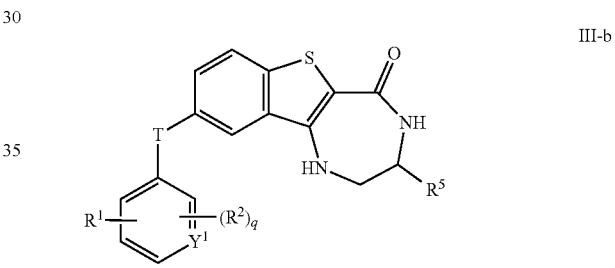

or a pharmaceutically acceptable salt thereof, wherein each of $R^1$, $R^2$, $R^5$, $Y^1$, $Y^2$, T, and q is as defined above and described in embodiments, classes and subclasses above and herein, singly or in combination.

In various embodiments, the invention provides a compound of formula III-bb:

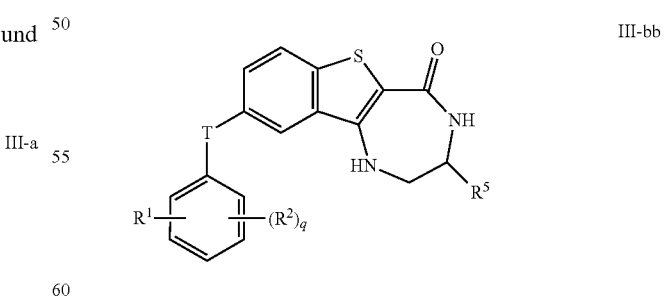

or a pharmaceutically acceptable salt thereof, wherein each of $R^1$, $R^2$, $R^5$, T, and q is as defined above and described in embodiments, classes and subclasses above and herein, singly or in combination.

In various embodiments, the invention provides a compound of formula III-c:

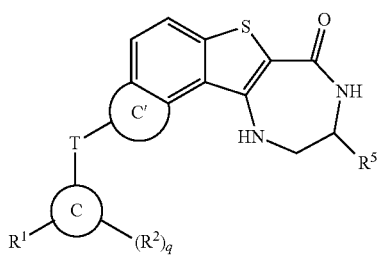

or a pharmaceutically acceptable salt thereof, wherein each of Ring C', $R^1$, $R^2$, $R^5$, T, and q is as defined above and described in embodiments, classes and subclasses above and herein, singly or in combination, wherein:
Ring C is

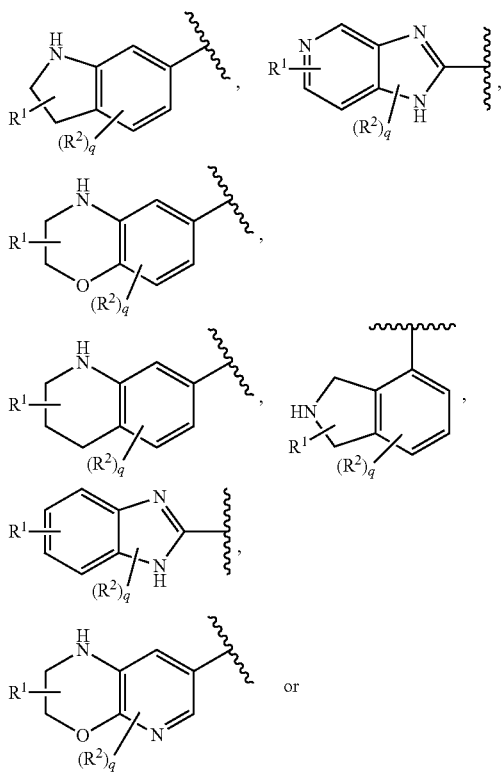

or

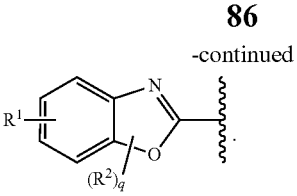

In various embodiments, the invention provides a compound of formula III-c:

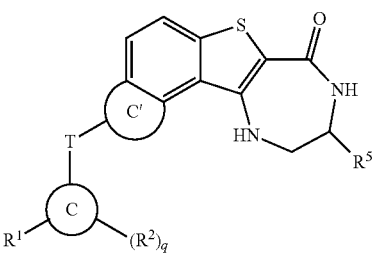

or a pharmaceutically acceptable salt thereof, wherein each of Ring C', $R^1$, $R^2$, $R^5$, T, and q is as defined above and described in embodiments, classes and subclasses above and herein, singly or in combination, wherein:
Ring C is

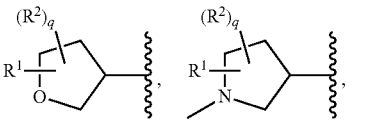

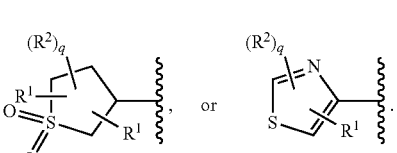

In certain embodiments, the invention provides a compound selected from those depicted in Table 4:

TABLE 4

Exemplary Compounds of Formula III

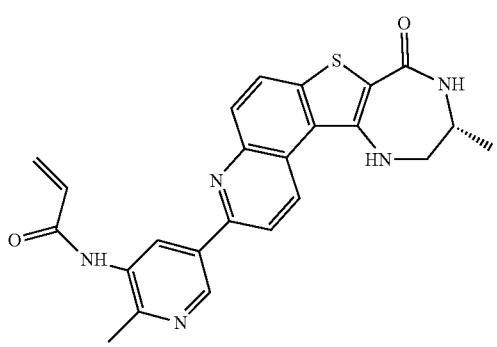 [SMILES: C=CC(=O)Nc1cc(-c2ccc3c(ccc4sc5c(c43)NC[C@@H](C)NC5=O)n2)cnc1C]

III-1

TABLE 4-continued
Exemplary Compounds of Formula III
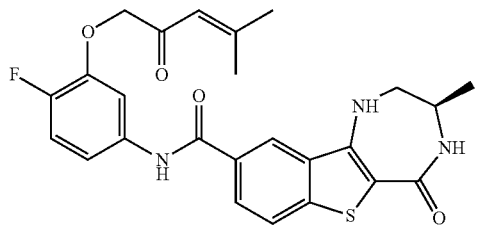 [SMILES: CC(C)=CC(=O)COc1cc(NC(=O)c2ccc3sc4c(c3c2)NC[C@@H](C)NC4=O)ccc1F]
III-2
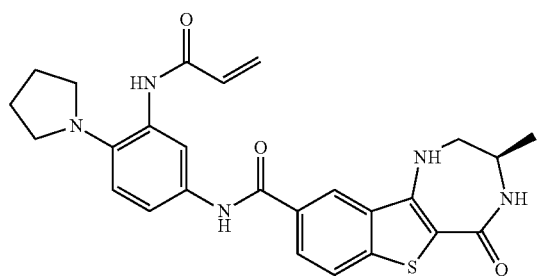 [SMILES: C=CC(=O)Nc1cc(NC(=O)c2ccc3sc4c(c3c2)NC[C@@H](C)NC4=O)ccc1N1CCCC1]
III-3
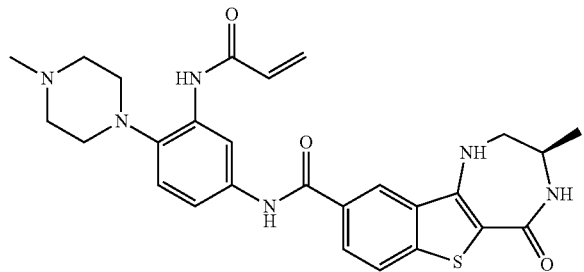
III-4
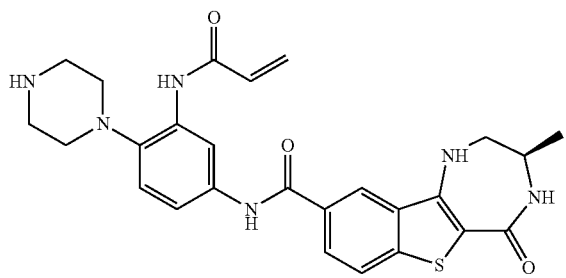 [SMILES: C=CC(=O)Nc1cc(NC(=O)c2ccc3sc4c(c3c2)NC[C@@H](C)NC4=O)ccc1N1CCNCC1]
III-5
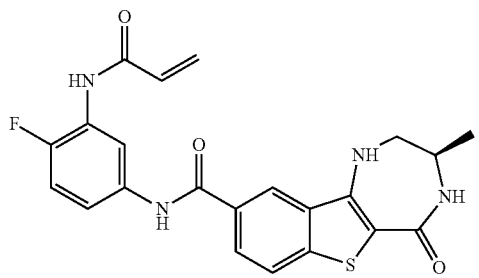 [SMILES: C=CC(=O)Nc1cc(NC(=O)c2ccc3sc4c(c3c2)NC[C@@H](C)NC4=O)ccc1F]
III-6

TABLE 4-continued
Exemplary Compounds of Formula III
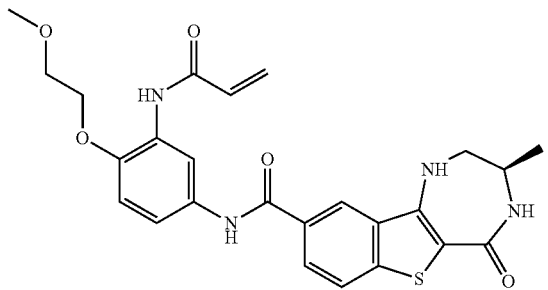
III-7
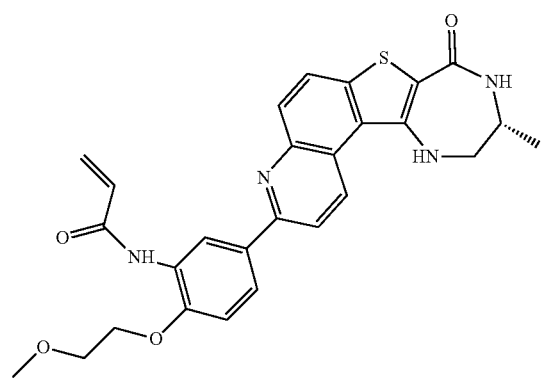
III-8
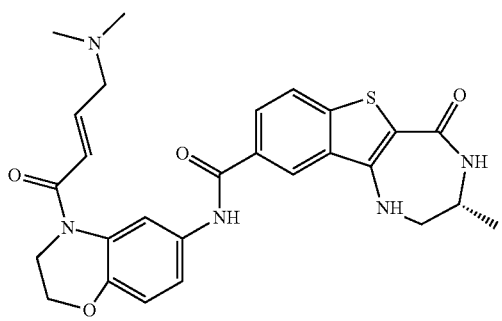 [SMILES: C[C@@H]1CNc2c(sc3ccc(C(=O)Nc4ccc5c(c4)N(C(=O)/C=C/CN(C)C)CCO5)cc23)C(=O)N1]
III-9
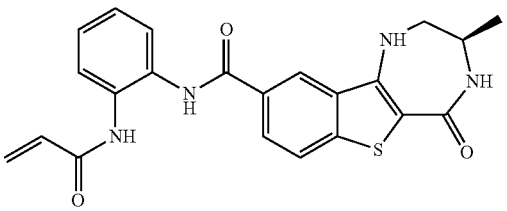 [SMILES: C=CC(=O)Nc1ccccc1NC(=O)c1ccc2sc3c(c2c1)NC[C@@H](C)NC3=O]
III-10
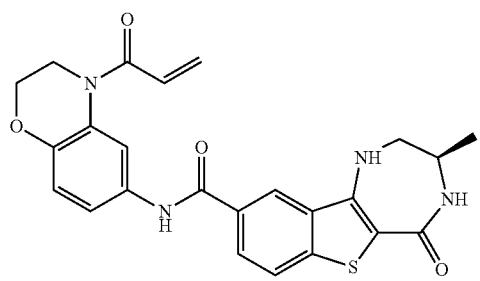 [SMILES: C=CC(=O)N1CCOc2ccc(NC(=O)c3ccc4sc5c(c4c3)NC[C@@H](C)NC5=O)cc21]
III-11

TABLE 4-continued
Exemplary Compounds of Formula III
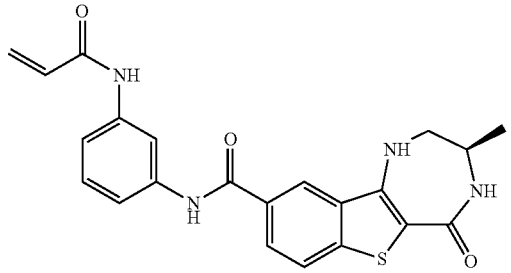 [SMILES: C=CC(=O)Nc1cccc(NC(=O)c2ccc3sc4c(c3c2)NC[C@@H](C)NC4=O)c1]
III-12
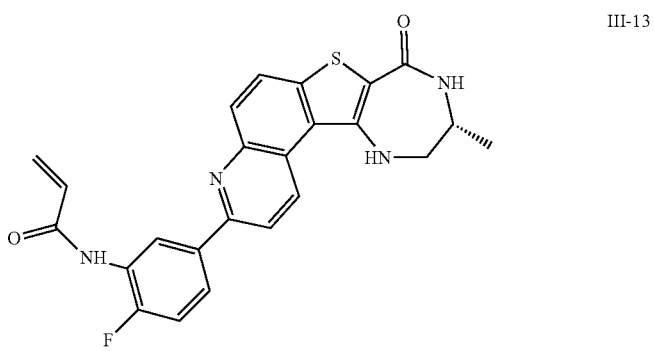
III-13
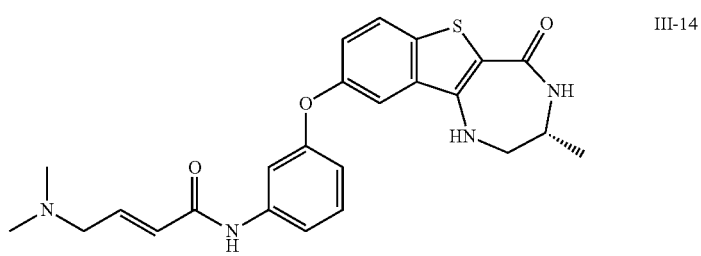
III-14
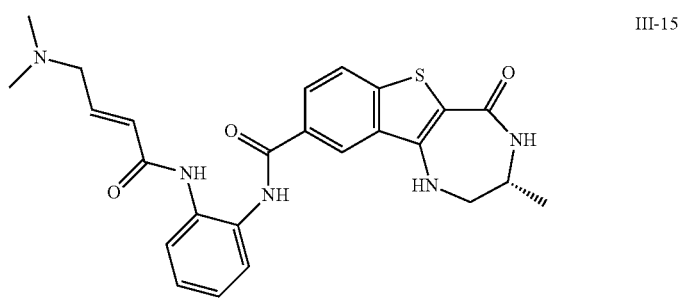
III-15
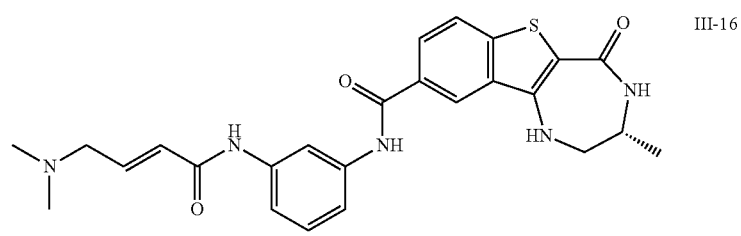
III-16

TABLE 4-continued
Exemplary Compounds of Formula III
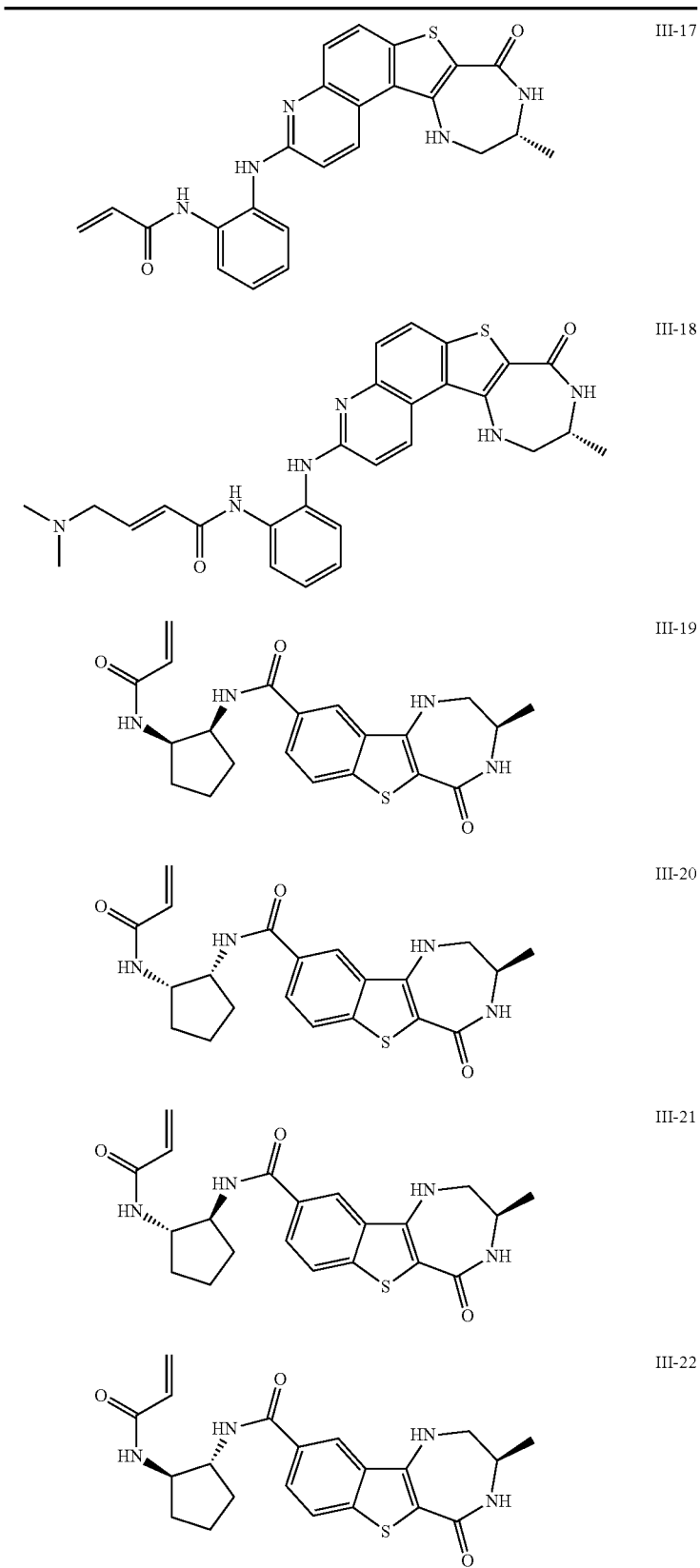
III-17
III-18
III-19
III-20
III-21
III-22

TABLE 4-continued
Exemplary Compounds of Formula III
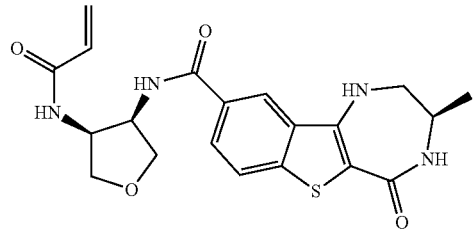 [SMILES: C=CC(=O)N[C@@H]1COC[C@@H]1NC(=O)c1ccc2sc3c(c2c1)NC[C@@H](C)NC3=O]
III-23
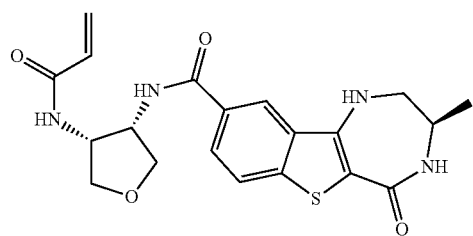 [SMILES: C=CC(=O)N[C@H]1COC[C@H]1NC(=O)c1ccc2sc3c(c2c1)NC[C@@H](C)NC3=O]
III-24
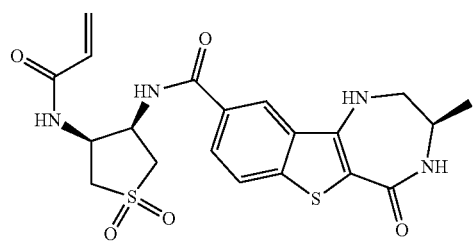 [SMILES: C=CC(=O)N[C@@H]1CS(=O)(=O)C[C@@H]1NC(=O)c1ccc2sc3c(c2c1)NC[C@@H](C)NC3=O]
III-25
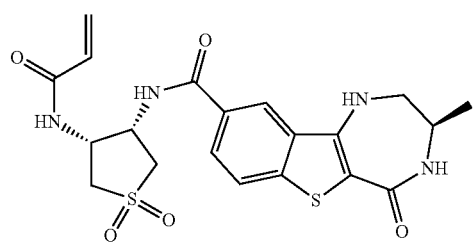 [SMILES: C=CC(=O)N[C@H]1CS(=O)(=O)C[C@H]1NC(=O)c1ccc2sc3c(c2c1)NC[C@@H](C)NC3=O]
III-26
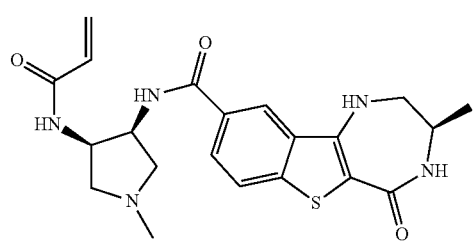 [SMILES: C=CC(=O)N[C@@H]1CN(C)C[C@@H]1NC(=O)c1ccc2sc3c(c2c1)NC[C@@H](C)NC3=O]
III-27
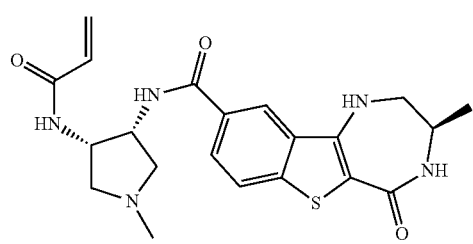
III-28

TABLE 4-continued
Exemplary Compounds of Formula III
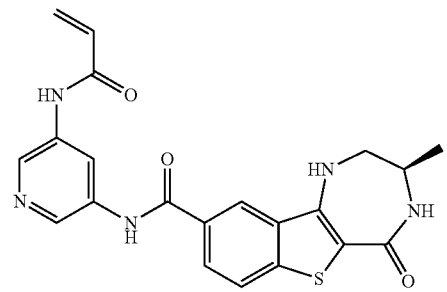 [SMILES: C=CC(=O)Nc1cncc(NC(=O)c2ccc3sc4c(c3c2)NC[C@@H](C)NC4=O)c1]
III-29
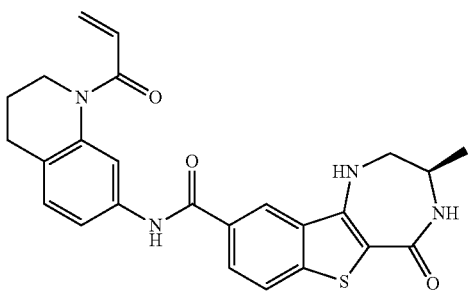 [SMILES: C=CC(=O)N1CCCc2ccc(NC(=O)c3ccc4sc5c(c4c3)NC[C@@H](C)NC5=O)cc21]
III-30
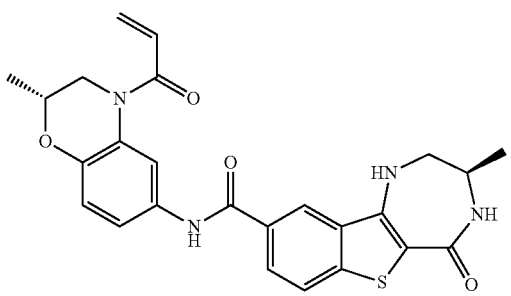
III-31
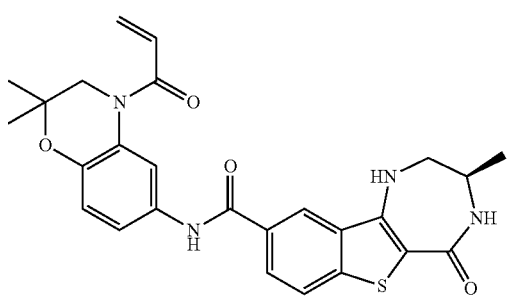
III-32
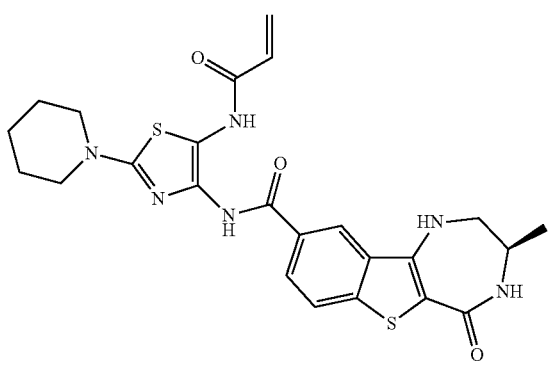 [SMILES: C=CC(=O)Nc1sc(N2CCCCC2)nc1NC(=O)c1ccc2sc3c(c2c1)NC[C@@H](C)NC3=O]
III-33

TABLE 4-continued
Exemplary Compounds of Formula III
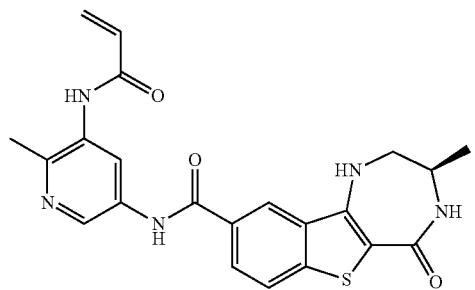
III-34
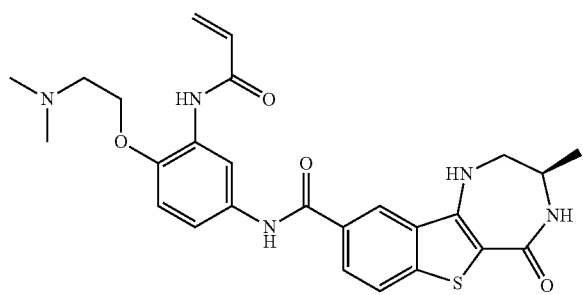
III-35
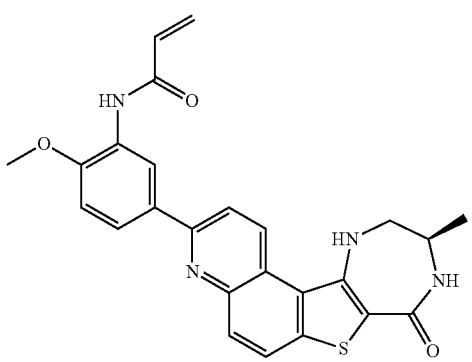
III-36
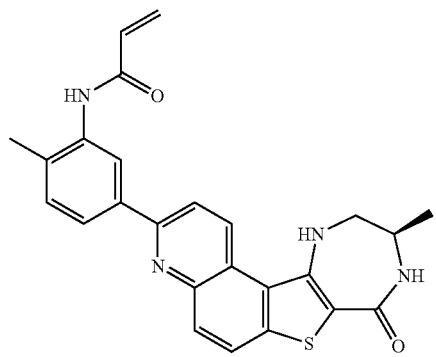
III-37

TABLE 4-continued
Exemplary Compounds of Formula III
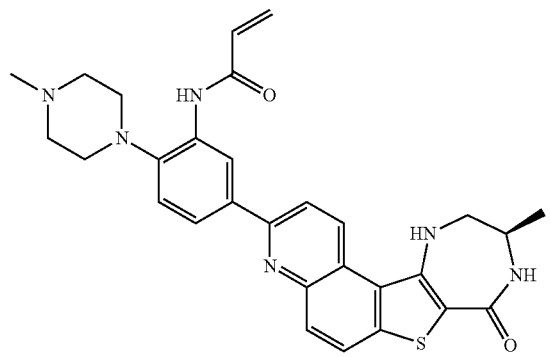
III-38
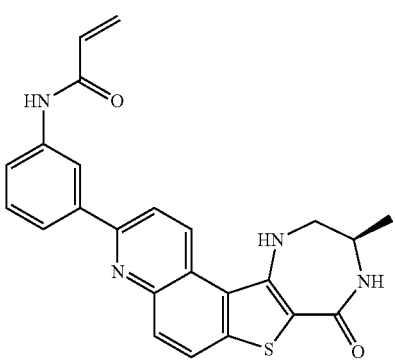 [SMILES: C=CC(=O)Nc1cccc(-c2ccc3c(ccc4sc5c(c43)NC[C@@H](C)NC5=O)n2)c1]
III-39
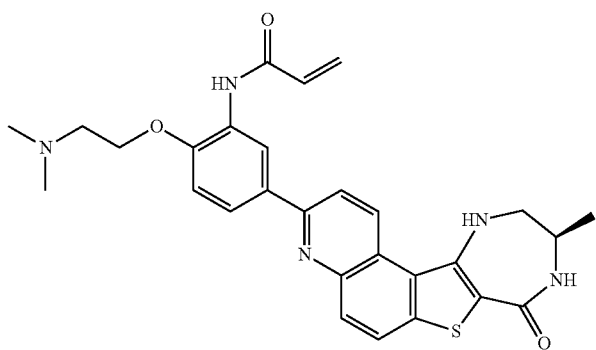
III-40
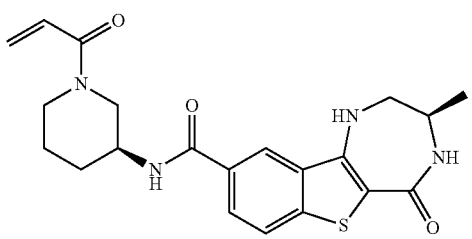 [SMILES: C=CC(=O)N1CCC[C@H](NC(=O)c2ccc3sc4c(c3c2)NC[C@@H](C)NC4=O)C1]
III-41
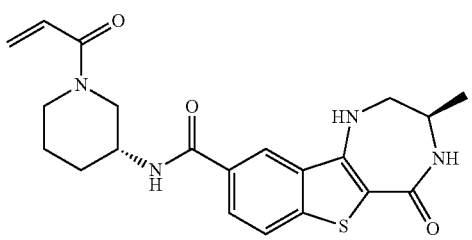
III-42

TABLE 4-continued
Exemplary Compounds of Formula III
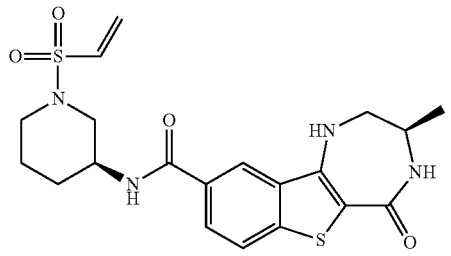 [SMILES: C=CS(=O)(=O)N1CCC[C@H](NC(=O)c2ccc3sc4c(c3c2)NC[C@@H](C)NC4=O)C1]
III-43
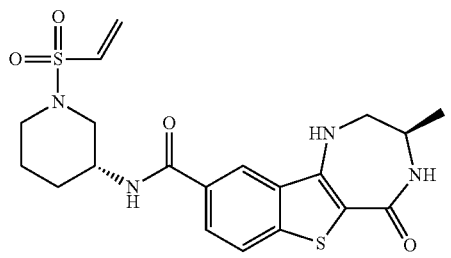
III-44
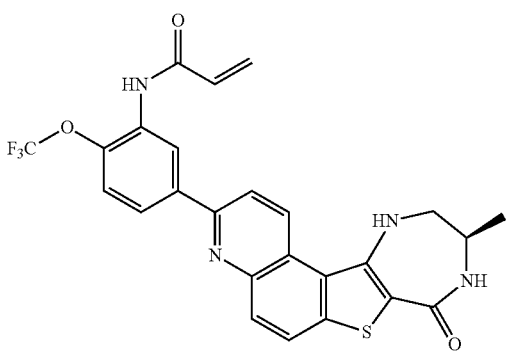 [SMILES: C=CC(=O)Nc1cc(-c2ccc3c(ccc4sc5c(c43)NC[C@@H](C)NC5=O)n2)ccc1OC(F)(F)F]
III-45
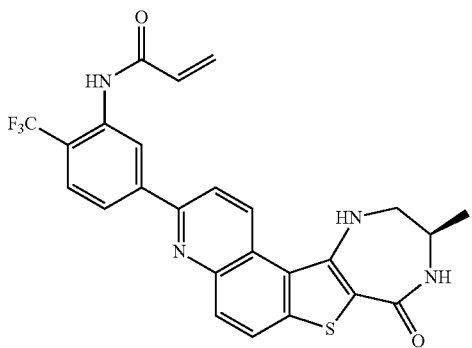 [SMILES: C=CC(=O)Nc1cc(-c2ccc3c(ccc4sc5c(c43)NC[C@@H](C)NC5=O)n2)ccc1C(F)(F)F]
III-46
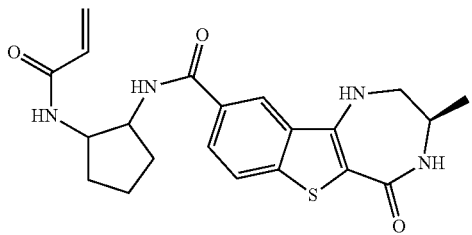 [SMILES: C=CC(=O)NC1CCCC1NC(=O)c1ccc2sc3c(c2c1)NC[C@@H](C)NC3=O]
III-47

TABLE 4-continued
Exemplary Compounds of Formula III
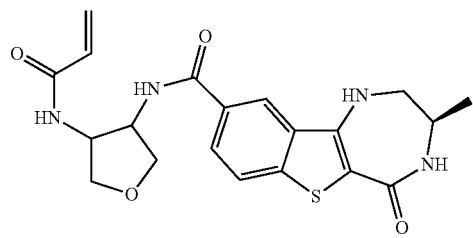 [SMILES: C=CC(=O)NC1COCC1NC(=O)c1ccc2sc3c(c2c1)NC[C@@H](C)NC3=O]
III-48
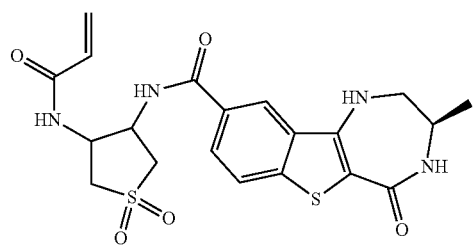 [SMILES: C=CC(=O)NC1CS(=O)(=O)CC1NC(=O)c1ccc2sc3c(c2c1)NC[C@@H](C)NC3=O]
III-49
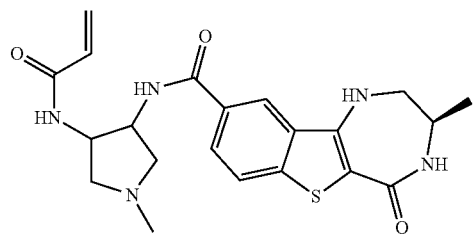 [SMILES: C=CC(=O)NC1CN(C)CC1NC(=O)c1ccc2sc3c(c2c1)NC[C@@H](C)NC3=O]
III-50
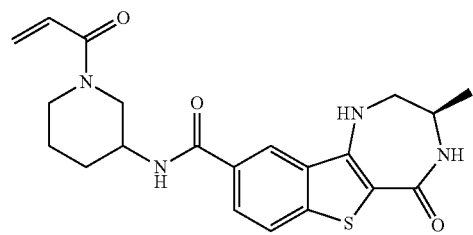 [SMILES: C=CC(=O)N1CCCC(NC(=O)c2ccc3sc4c(c3c2)NC[C@@H](C)NC4=O)C1]
III-51
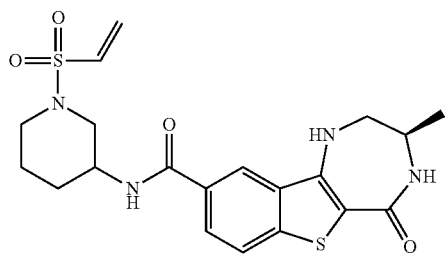 [SMILES: C=CS(=O)(=O)N1CCCC(NC(=O)c2ccc3sc4c(c3c2)NC[C@@H](C)NC4=O)C1]
III-52
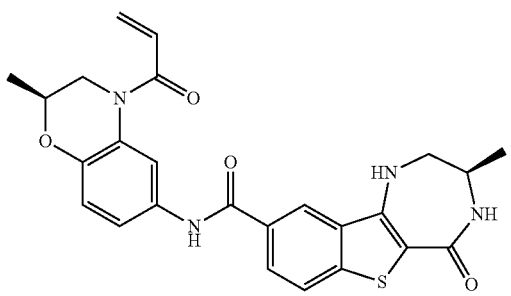
III-53

TABLE 4-continued

Exemplary Compounds of Formula III

| | |
|---|---|
| (structure) | III-54 |
| (structure) | III-55 |
| (structure) | III-56 |
| (structure) | III-57 |
| (structure) | III-58 |
| (structure) | III-59 |

TABLE 4-continued
Exemplary Compounds of Formula III
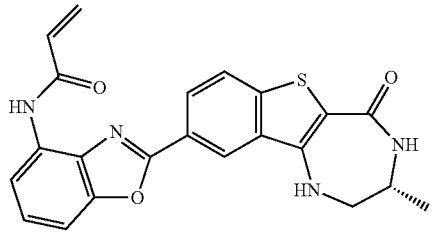 [SMILES: C=CC(=O)Nc1cccc2oc(-c3ccc4sc5c(c4c3)NC[C@@H](C)NC5=O)nc12]
III-61
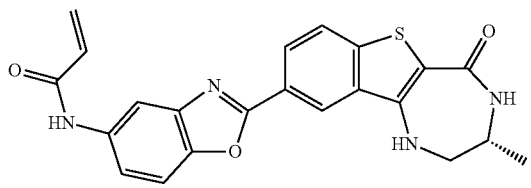 [SMILES: C=CC(=O)Nc1ccc2oc(-c3ccc4sc5c(c4c3)NC[C@@H](C)NC5=O)nc2c1]
III-62
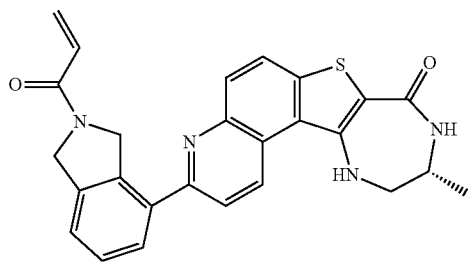 [SMILES: C=CC(=O)N1Cc2cccc(-c3ccc4c(ccc5sc6c(c54)NC[C@@H](C)NC6=O)n3)c2C1]
III-63
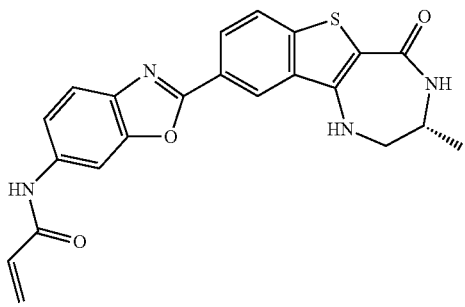 [SMILES: C=CC(=O)Nc1ccc2nc(-c3ccc4sc5c(c4c3)NC[C@@H](C)NC5=O)oc2c1]
III-64
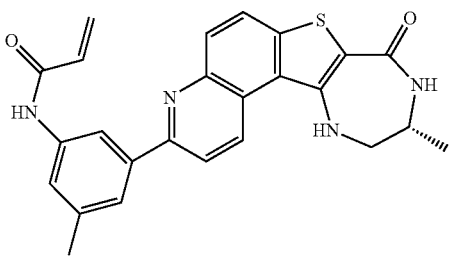 [SMILES: C=CC(=O)Nc1cc(C)cc(-c2ccc3c(ccc4sc5c(c43)NC[C@@H](C)NC5=O)n2)c1]
III-65
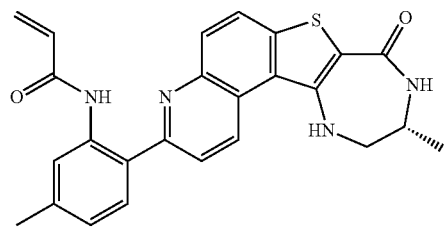
III-66

TABLE 4-continued
Exemplary Compounds of Formula III
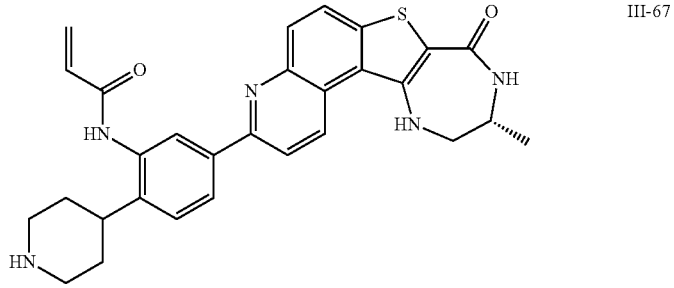 III-67
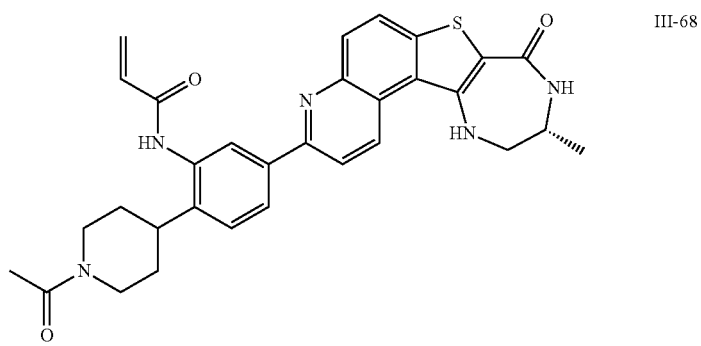 III-68
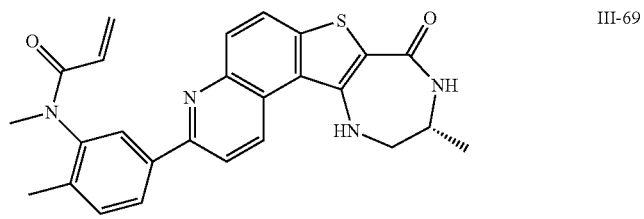 III-69
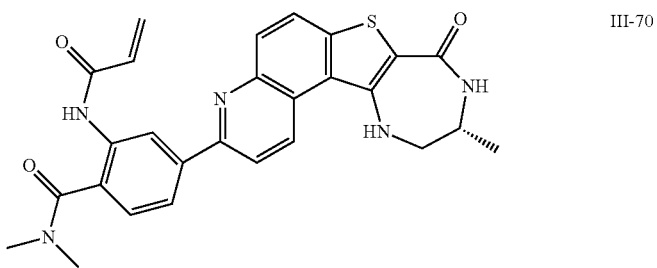 III-70
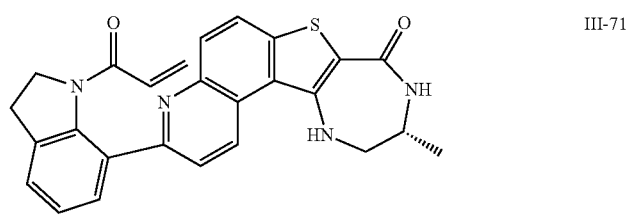 III-71

TABLE 4-continued

Exemplary Compounds of Formula III

III-72

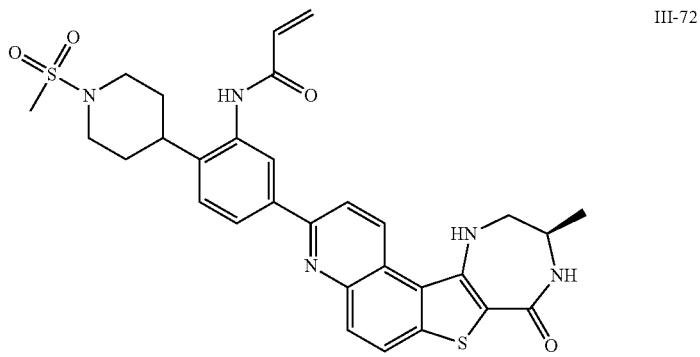

III-73

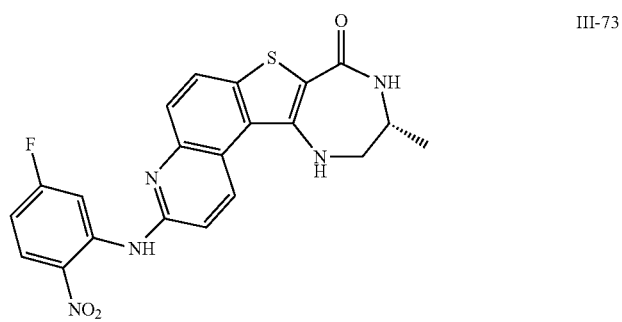

and

III-74

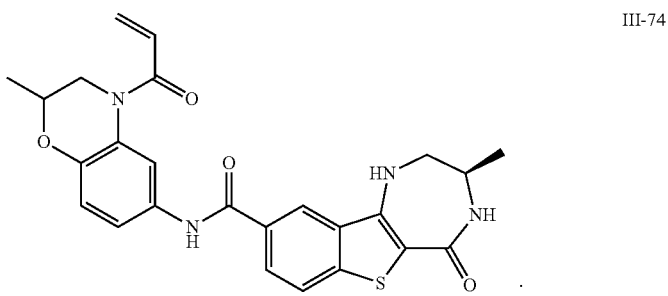

In some embodiments, the present invention provides a compound depicted in Table 4, above, or a pharmaceutically acceptable salt thereof.

In certain aspects, the invention provides a compound of formula III-d:

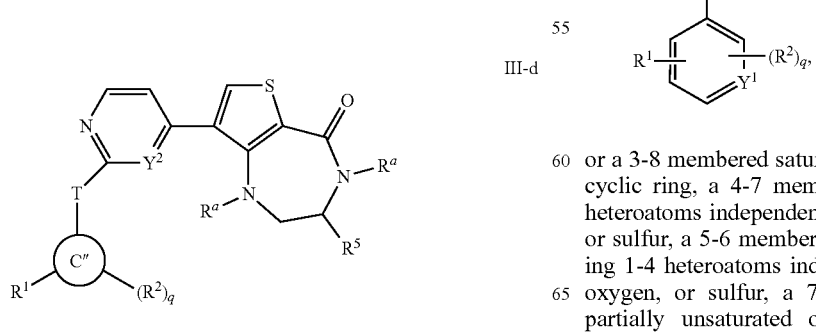

III-d or a pharmaceutically acceptable salt thereof, wherein:

Ring C" is an optionally substituted group selected from

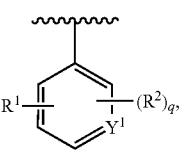

or a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;

$Y^1$ is $CR^2$ or N;

$Y^2$ is CR' or N;

each R' is independently hydrogen, halo, or an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^1$ is a warhead group;

q is 0-6;

each $R^2$ is independently —R, halogen, —OR, —SR, —CN, —$NO_2$, —$SO_2$NR, —$SO_2$R, —SOR, —C(O)R, —$CO_2$R, —C(O)N(R)$_2$, —NRC(O)R, —NRC(O)OR, —NRC(O)N(R)$_2$, —NRSO$_2$R, or —N(R)$_2$;

each R is independently hydrogen or an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocyclic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

$R^5$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

each $R^a$ is independently hydrogen or an optionally substituted $C_{1-6}$ aliphatic group; and T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —$SO_2$—, —$SO_2$N(R)—, —N(R)$SO_2$—, or —N(R)$SO_2$N(R)—.

In certain embodiments, $R^1$ is a warhead group, wherein when Ring C" is a 5 or 6-membered ring, then $R^1$ is attached to an atom next to an atom adjacent to where T is attached (i.e., in the case where Ring C" is phenyl, $R^1$ is attached at the meta position), or $R^1$ is attached to an atom adjacent to where T is attached (i.e., in the case where Ring C' is phenyl, $R^1$ is attached at the ortho position).

In certain embodiments, Ring C" is

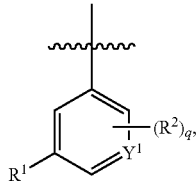

wherein $Y^1$ is CH (i.e., phenyl). In some embodiments, $Y^1$ is N.

In certain embodiments, Ring C'" is an optionally substituted 3-8 membered saturated or partially unsaturated carbocyclic ring, an optionally substituted 4-7 membered heterocylic ring having 1-2 heteroatoms independently selected from nitrogen, oxygen, or sulfur, an optionally substituted 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur.

In various embodiments, Ring C'" is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, $Y^1$ is $CR^2$ wherein $CR^2$ is hydrogen.

In certain embodiments, $Y^1$ is $CR^2$ wherein $R^2$ is an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^1$ is $CR^2$ wherein $R^2$ is an optionally substituted $C_{1-6}$ aliphatic. In certain embodiments, $Y^1$ is $CR^2$ wherein $R^2$ is an optionally substituted phenyl. In certain embodiments, $Y^1$ is $CR^2$ wherein $R^2$ is an optionally substituted 3-8 membered saturated or partially unsaturated carbocyclic ring. In certain embodiments, $Y^1$ is $CR^2$ wherein $R^2$ is an optionally substituted 4-7 membered heterocyclic ring having 1-2 heteroatoms independently selected from nitrogen, oxygen, or sulfur. In certain embodiments, $Y^1$ is $CR^2$ wherein $R^2$ is an optionally substituted 5-6 membered monocyclic heteroaryl ring having 1-4 heteroatoms independently selected from nitrogen, oxygen, or sulfur.

In certain embodiments, Ring C" is

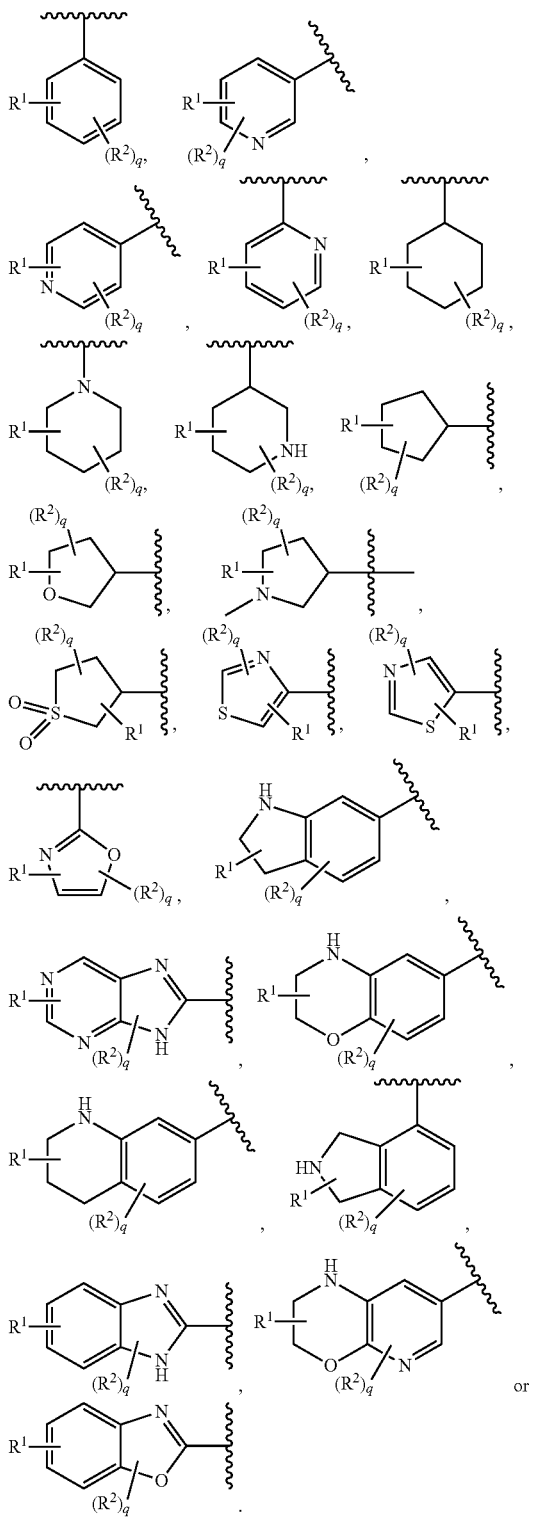

In certain embodiments, Ring C" is

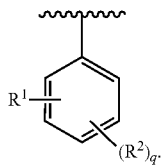

In some embodiments, Ring C" is selected from those depicted in Table 5, below.

In certain embodiments, $Y^2$ is N. In certain embodiments, $Y^2$ is CR'.

In certain embodiments, $Y^2$ is CR' wherein R' is hydrogen.

In certain embodiments, $Y^2$ is CR' wherein R' is an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $Y^2$ is CR' wherein R' is an optionally substituted $C_1$ 6 aliphatic. In certain embodiments, $Y^2$ is CR' wherein R' is an optionally substituted phenyl. In certain embodiments, $Y^2$ is CR' wherein R' is an optionally substituted 3-8 membered saturated or partially unsaturated carbocyclic ring. In certain embodiments, $Y^2$ is CR' wherein R' is an optionally substituted 4-7 membered heterocylic ring having 1-2 heteroatoms independently selected from nitrogen, oxygen, or sulfur. In certain embodiments, $Y^2$ is CR' wherein R' is an optionally substituted 5-6 membered monocyclic heteroaryl ring having 1-4 heteroatoms independently selected from nitrogen, oxygen, or sulfur.

In certain embodiments, each $R^2$ is independently hydrogen.

In certain embodiments, each $R^2$ is independently —R.

In certain embodiments, each $R^2$ is independently cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, or pyrrolinyl.

In certain embodiments, each $R^2$ is independently

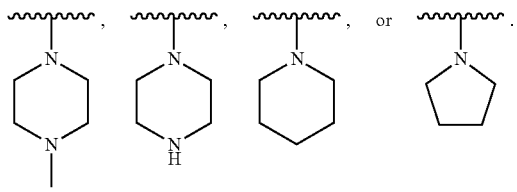

In certain embodiments, each $R^2$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently —CH$_3$, —F, —CF$_3$, —OCH$_3$, —OCF$_3$, —OCH$_2$CH$_2$NMe$_2$, —OCH$_2$CH$_2$NH$_2$, or —OCH$_2$CH$_2$OCH$_3$. In certain embodiments, each $R^2$ is independently —F, —CF$_3$, —OCH$_3$, or —OCH$_2$CH$_2$OCH$_3$. In some embodiments, each $R^2$ is selected from those depicted in Table 5, below.

In certain embodiments, $R^5$ is hydrogen.

In certain embodiments, $R^5$ is an optionally substituted group selected from C$_1$aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $R^5$ is an optionally substituted C$_{1-6}$ aliphatic. In certain embodiments, $R^5$ is an optionally substituted phenyl. In certain embodiments, $R^5$ is an optionally substituted a 3-8 membered saturated or partially unsaturated carbocyclic ring. In certain embodiments, $R^5$ is an optionally substituted a 4-7 membered heterocyclic ring having 1-2 heteroatoms independently selected from nitrogen, oxygen, or sulfur. In certain embodiments, $R^5$ is an optionally substituted a 5-6 membered monocyclic heteroaryl ring having 1-4 heteroatoms independently selected from nitrogen, oxygen, or sulfur.

In certain embodiments, $R^5$ is methyl. In some embodiments, $R^5$ is selected from those depicted in Table 5, below.

In various embodiments, each $R^a$ is independently hydrogen. In various embodiments, each $R^a$ is independently an optionally substituted C$_{1-6}$ aliphatic group.

In various embodiments, T is a covalent bond.

In various embodiments, T is —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In various embodiments, T is —O—, —N(R)—, —C(O)N(R)—, or —N(R)C(O)—. In some embodiments, T is selected from those depicted in Table 5, below.

In certain embodiments, the invention provides a compound selected from those depicted in Table 5:

TABLE 5

Exemplary Compounds of Formula III-d

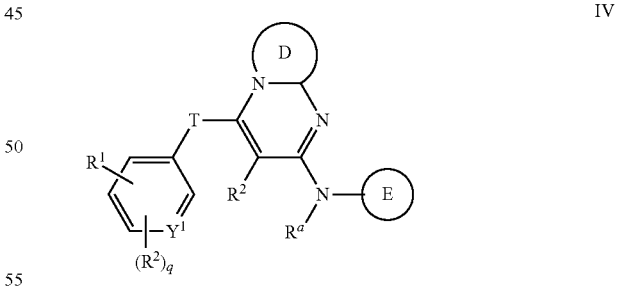

III-d-1

In some embodiments, the present invention provides a compound depicted in Table 5, above, or a pharmaceutically acceptable salt thereof.

According to another aspect, the present invention provides a compound of formula IV:

IV or a pharmaceutically acceptable salt thereof, wherein:
Ring D is an optionally substituted group selected from a fused 5-6 membered monocyclic heteroaryl ring having 0-2 additional heteroatoms independently selected from nitrogen, oxygen, or sulfur, and a fused 4-7 membered saturated or partially unsaturated heterocyclic ring having 1-3 additional heteroatoms independently selected from nitrogen, oxygen, or sulfur;
Ring E is an optionally substituted group selected from phenyl, a 3-8 membered saturated or partially unsaturated carbocyclic ring which is optionally bridged, a 5-6 membered monocyclic heteroaryl ring having 1-4 heteroatoms independently selected from nitrogen, oxygen, or sulfur, and a 4-7 membered saturated or partially unsaturated heterocyclic ring having 1-3 heteroatoms independently selected from nitrogen, oxygen, or sulfur;

$Y^1$ is $CR^2$ or N;

each R' is independently hydrogen, halo, or an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^1$ is a warhead;

q is 0-6;

each $R^2$ is independently —R, halogen, —OR, —SR, —CN, —NO$_2$, —SO$_2$NR, —SO$_2$R, —SOR, —C(O)R, —CO$_2$R, —C(O)N(R)$_2$, —NRC(O)R, —NRC(O)OR, —NRC(O)N(R)$_2$, —NRSO$_2$R, or —N(R)$_2$;

each R is independently hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

each $R^a$ is independently hydrogen or an optionally substituted $C_{1-6}$ aliphatic group; and T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In certain embodiments, $R^1$ is a warhead, wherein $R^1$ is in an ortho or meta position. In some embodiments, $R^1$ is a warhead, wherein $R^1$ is in an ortho position. In some embodiments, $R^1$ is a warhead, wherein $R^1$ is in a meta position.

In certain embodiments, Ring D is an optionally substituted fused 5-6 membered monocyclic heteroaryl ring having 0-2 additional heteroatoms independently selected from nitrogen, oxygen, or sulfur.

In certain embodiments, Ring D is an optionally substituted fused 4-7 membered saturated or partially unsaturated heterocyclic ring having 1-3 additional heteroatoms independently selected from nitrogen, oxygen, or sulfur.

In certain embodiments, Ring D is an optionally substituted fused imidazolidinyl, imidazolinyl, imidazolyl, isoxazolyl, morpholinyl, pyrimidinyl, piperazinyl, piperidinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, or quinoxalinyl.

In certain embodiments, Ring D is

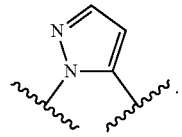 [SMILES: *c1ccnn1*]

In some embodiments, Ring D is selected from those depicted in Table 6, below.

In various embodiments, Ring E is an optionally substituted phenyl.

In various embodiments, Ring E is an optionally substituted a 3-8 membered saturated or partially unsaturated carbocyclic ring.

In various embodiments, Ring E is an optionally substituted 5-6 membered monocyclic heteroaryl ring having 1-4 heteroatoms independently selected from nitrogen, oxygen, or sulfur.

In various embodiments, Ring E is an optionally substituted 4-7 membered saturated or partially unsaturated heterocyclic ring having 1-3 heteroatoms independently selected from nitrogen, oxygen, or sulfur.

In various embodiments, Ring E is an optionally substituted cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, Ring E is

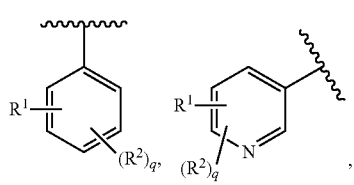

-continued

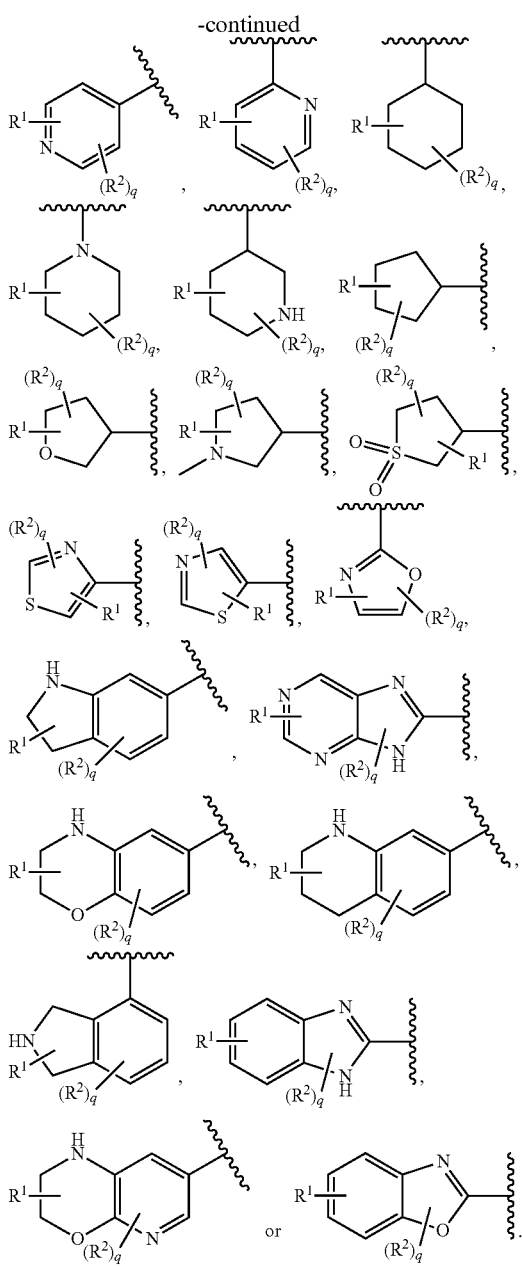

In various embodiments, Ring E is

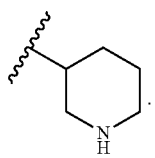 [SMILES: *C1CCCNC1]

In some embodiments, Ring E is selected from those depicted in Table 6, below.

In various embodiments, $Y^1$ is $CR^2$. In various embodiments, $Y^1$ is N. In various embodiments, $Y^1$ is CH.

In certain embodiments, each $R^2$ is independently hydrogen.

In certain embodiments, each $R^2$ is independently —R.

In certain embodiments, each $R^2$ is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, or pyrrolinyl.

In certain embodiments, each $R^2$ is independently

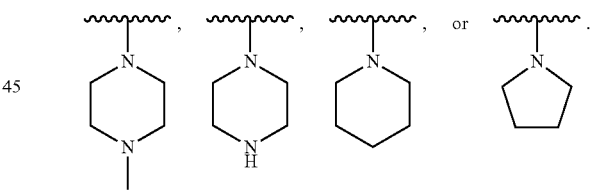

In certain embodiments, each $R^2$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently —CH$_3$, —F, —CF$_3$, —OCH$_3$, —OCF$_3$, —OCH$_2$CH$_2$NMe$_2$, —OCH$_2$CH$_2$NH$_2$, or —OCH$_2$CH$_2$OCH$_3$. In certain embodiments, each $R^2$ is independently OCH$_3$ or —OCH$_2$CH$_3$. In some embodiments, each $R^2$ is selected from those depicted in Table 6, below.

In various embodiments, each $R^a$ is independently hydrogen. In various embodiments, each $R^a$ is independently an optionally substituted $C_{1-6}$ aliphatic group. In some embodiments, $R^a$ is selected from those depicted in Table 6, below.

In various embodiments, T is a covalent bond.

In various embodiments, T is —O—, —S—, —N(R)—, —C(O)—, —OC(O)—, —C(O)O—, —C(O)N(R)—, —N(R)C(O)—, —N(R)C(O)N(R)—, —S(O)—, —SO₂—, —SO₂N(R)—, —N(R)SO₂—, or —N(R)SO₂N(R)—.

In various embodiments, T is —O—, —N(R)—, —C(O)N(R)—, or —N(R)C(O)—. In some embodiments, T is selected from those depicted in Table 6, below.

In various embodiments, the invention provides a compound of formula IV-a:

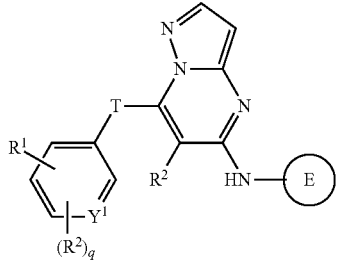

IV-a or a pharmaceutically acceptable salt thereof, wherein each of Ring E, R¹, R², Y¹, T, and q is as defined above and described in embodiments, classes and subclasses above and herein, singly or in combination.

In certain embodiments, the invention provides a compound selected from those depicted in Table 6:

TABLE 6

Exemplary Compounds of Formula IV

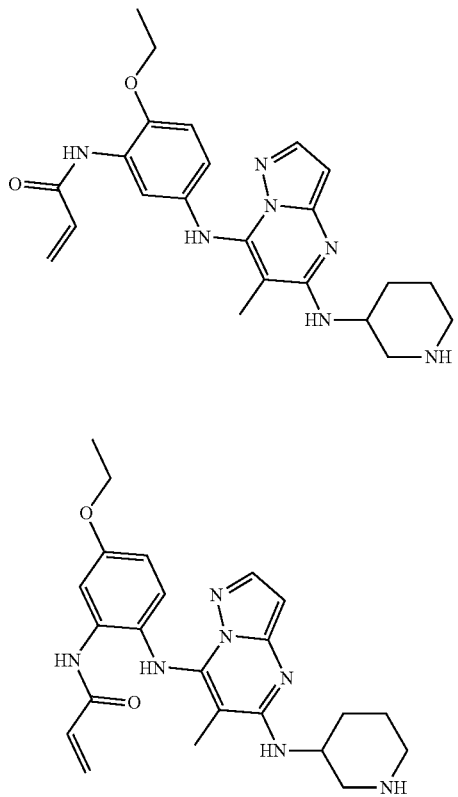

IV-1

IV-2

TABLE 6-continued

Exemplary Compounds of Formula IV

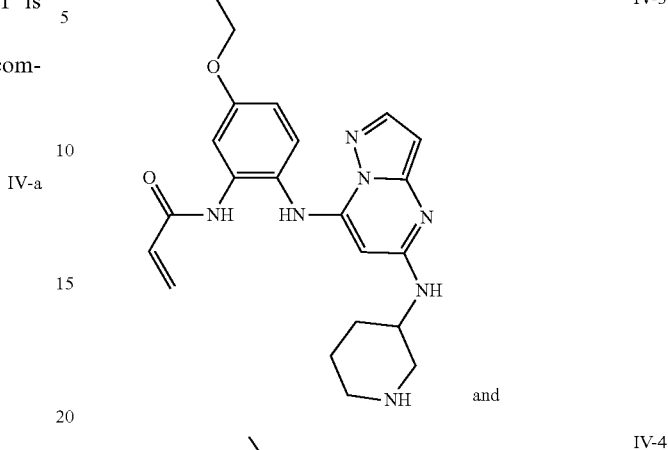

IV-3 and

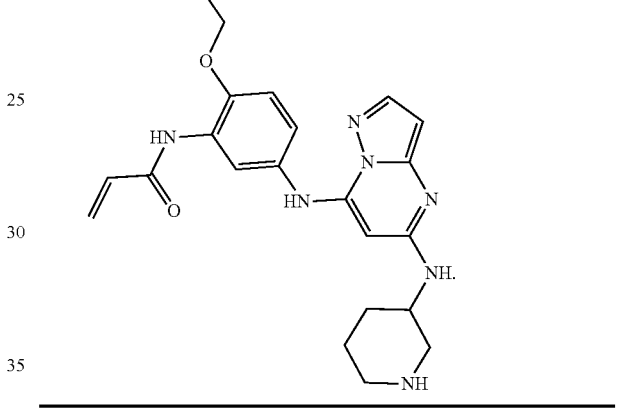

IV-4

In some embodiments, the present invention provides a compound depicted in Table 6, above, or a pharmaceutically acceptable salt thereof.

In certain aspects, the invention provides a compound of formula IV-b:

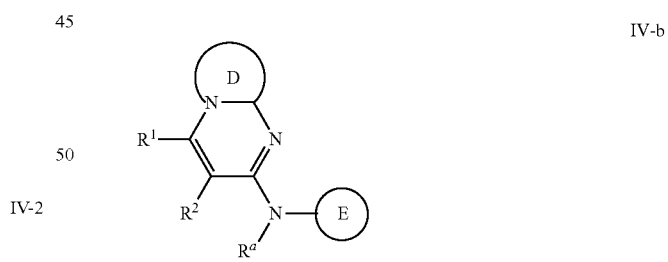

IV-b or a pharmaceutically acceptable salt thereof, wherein:
Ring D is an optionally substituted group selected from a fused 5-6 membered monocyclic heteroaryl ring having 0-2 additional heteroatoms independently selected from nitrogen, oxygen, or sulfur, and a fused 4-7 membered saturated or partially unsaturated heterocyclic ring having 1-3 additional heteroatoms independently selected from nitrogen, oxygen, or sulfur;
Ring E is an optionally substituted group selected from phenyl, a 3-8 membered saturated or partially unsaturated carbocyclic ring, a 5-6 membered monocyclic heteroaryl ring having 1-4 heteroatoms independently selected from nitrogen, oxygen, or sulfur, and a 4-7 membered saturated or partially unsaturated heterocyclic ring having 1-3 heteroatoms independently selected from nitrogen, oxygen, or sulfur;

$R^1$ is a warhead group;

each $R^2$ is independently —R, halogen, —OR, —SR, —CN, —NO₂, —SO₂NR, —SO₂R, —SOR, —C(O)R, —CO₂R, —C(O)N(R)₂, —NRC(O)R, —NRC(O)OR, —NRC(O)N(R)₂, —NRSO₂R, or —N(R)₂;

each R is independently hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur; and each $R^a$ is independently hydrogen or an optionally substituted $C_{1-6}$ aliphatic group.

In certain embodiments, Ring D is an optionally substituted fused 5-6 membered monocyclic heteroaryl ring having 0-2 additional heteroatoms independently selected from nitrogen, oxygen, or sulfur.

In certain embodiments, Ring D is an optionally substituted fused 4-7 membered saturated or partially unsaturated heterocyclic ring having 1-3 additional heteroatoms independently selected from nitrogen, oxygen, or sulfur.

In certain embodiments, Ring D is an optionally substituted fused imidazolidinyl, imidazolinyl, imidazolyl, isoxazolyl, morpholinyl, pyrimidinyl, piperazinyl, piperidinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, or quinoxalinyl.

In certain embodiments, Ring D is

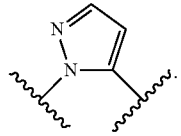 [SMILES: *c1ccnn1*]

In some embodiments, Ring D is selected from those depicted in Table 7, below.

In various embodiments, Ring E is an optionally substituted phenyl.

In various embodiments, Ring E is an optionally substituted a 3-8 membered saturated or partially unsaturated carbocyclic ring.

In various embodiments, Ring E is an optionally substituted 5-6 membered monocyclic heteroaryl ring having 1-4 heteroatoms independently selected from nitrogen, oxygen, or sulfur.

In various embodiments, Ring E is an optionally substituted 4-7 membered saturated or partially unsaturated heterocyclic ring having 1-3 heteroatoms independently selected from nitrogen, oxygen, or sulfur.

In various embodiments, Ring E is an optionally substituted cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In various embodiments, Ring E is

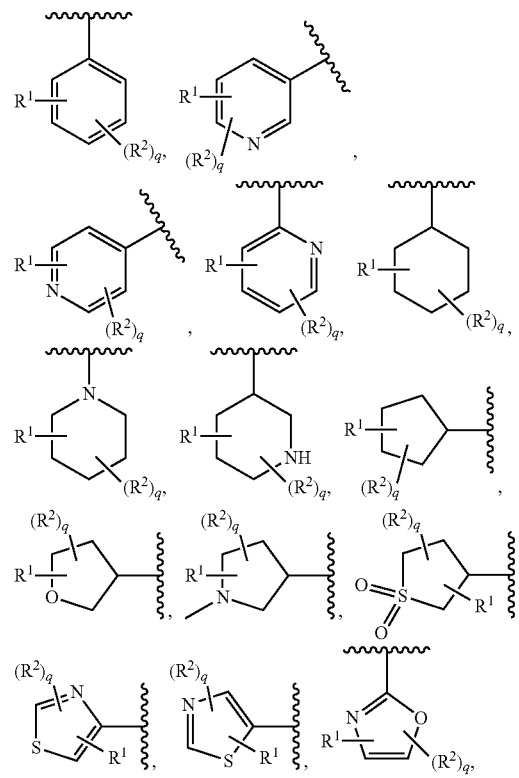

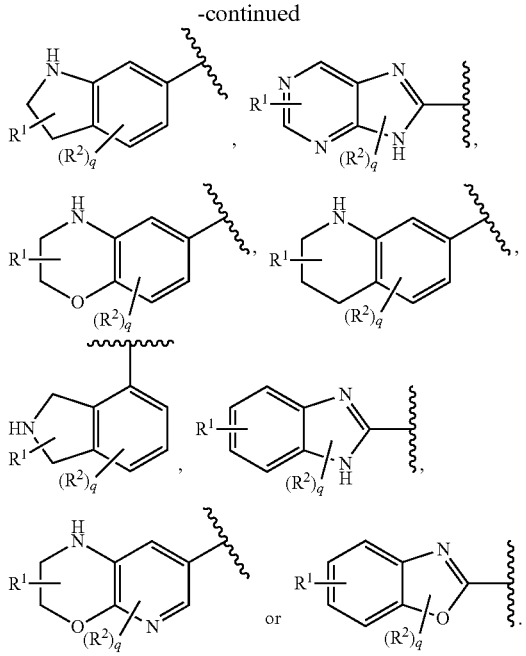

In various embodiments, Ring E is

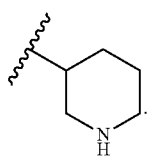

In some embodiments, Ring E is selected from those depicted in Table 7, below.

In certain embodiments, $R^2$ is hydrogen.

In certain embodiments, $R^2$ is —R.

In certain embodiments, $R^2$ is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, $R^2$ is piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, or pyrrolinyl.

In certain embodiments, $R^2$ is halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^2$ is independently —CH$_3$, —F, —CF$_3$, —OCH$_3$, —OCF$_3$, —OCH$_2$CH$_2$NMe$_2$, —OCH$_2$CH$_2$NH$_2$, or —OCH$_2$CH$_2$OCH$_3$. In certain embodiments, $R^2$ is —F, —CH$_3$, —CF$_3$, —OCH$_3$, —OCH$_2$CH$_2$CH$_2$NH$_2$, or —OCH$_2$CH$_2$OCH$_3$. In certain embodiments, $R^2$ is —CH$_3$. In some embodiments, each $R^2$ is selected from those depicted in Table 7, below.

In various embodiments, each $R^a$ is independently hydrogen. In various embodiments, each $R^a$ is independently an optionally substituted $C_{1-6}$ aliphatic group. In some embodiments, $R^a$ is selected from those depicted in Table 7, below.

In certain embodiments, the invention provides a compound selected from those depicted in Table 7.

TABLE 7

Exemplary Compounds of Formula IV-b

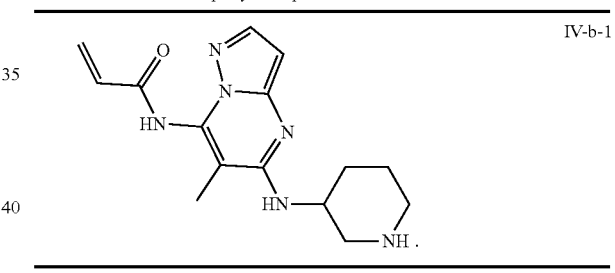

IV-b-1

In some embodiments, the present invention provides a compound of formula IV-b depicted in Table 7, above, or a pharmaceutically acceptable salt thereof.

In certain aspects, the invention provides a compound of formula V:

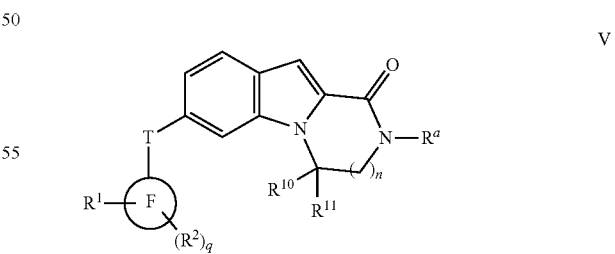

V or a pharmaceutically acceptable salt thereof, wherein:
Ring F is an optionally substituted group selected from phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;

$R^1$ is a warhead group;

q is 0-6;

each $R^2$ is independently —R, halogen, —OR, —SR, —CN, —NO$_2$, —SO$_2$NR, —SO$_2$R, —SOR, —C(O)R, —CO$_2$R, —C(O)N(R)$_2$, —NRC(O)R, —NRC(O)OR, —NRC(O)N(R)$_2$, —NRSO$_2$R, or —N(R)$_2$;

each R is independently hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

$R^{10}$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^{11}$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

or $R^{10}$ and $R^{11}$ are taken together with the carbon atom to which they are attached to form a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

n is 1 or 2;

each $R^a$ is independently hydrogen or an optionally substituted $C_{1-6}$ aliphatic group; and T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In certain embodiments, $R^1$ is a warhead group, wherein when Ring F is a 5 or 6-membered ring, then $R^1$ is attached to an atom next to an atom adjacent to where T is attached (i.e., in the case where Ring F is phenyl, $R^1$ is attached at the meta position), or $R^1$ is attached to an atom adjacent to where T is attached (i.e., in the case where Ring F is phenyl, $R^1$ is attached at the ortho position).

In various embodiments, Ring F is an optionally substituted phenyl. In various embodiments, Ring F is an optionally substituted 3-8 membered saturated or partially unsaturated carbocyclic ring. In various embodiments, Ring F is an optionally substituted 4-7 membered heterocylic ring having 1-2 heteroatoms independently selected from nitrogen, oxygen, or sulfur. In various embodiments, Ring F is an optionally substituted 5-6 membered monocyclic heteroaryl ring having 1-4 heteroatoms independently selected from nitrogen, oxygen, or sulfur.

In certain embodiments, Ring F is a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur.

In various embodiments, Ring F is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, Ring F is an optionally substituted group selected from phenyl, cyclohexyl, piperidinyl, and oxazolyl.

In certain embodiments, Ring F is substituted as defined herein.

In certain embodiments, Ring F is

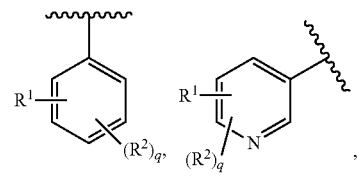

,

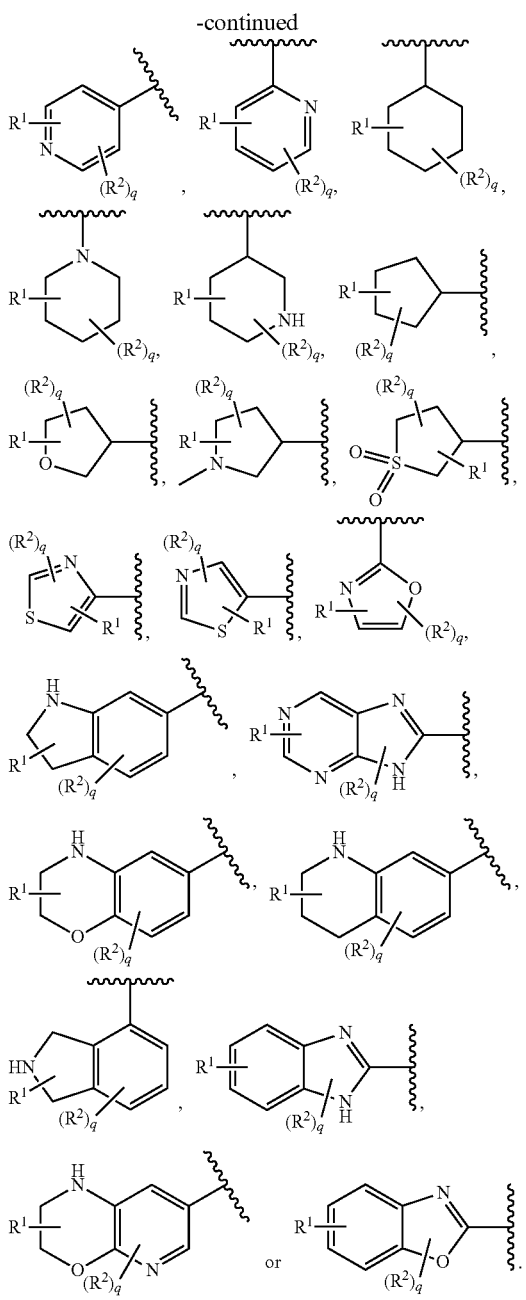
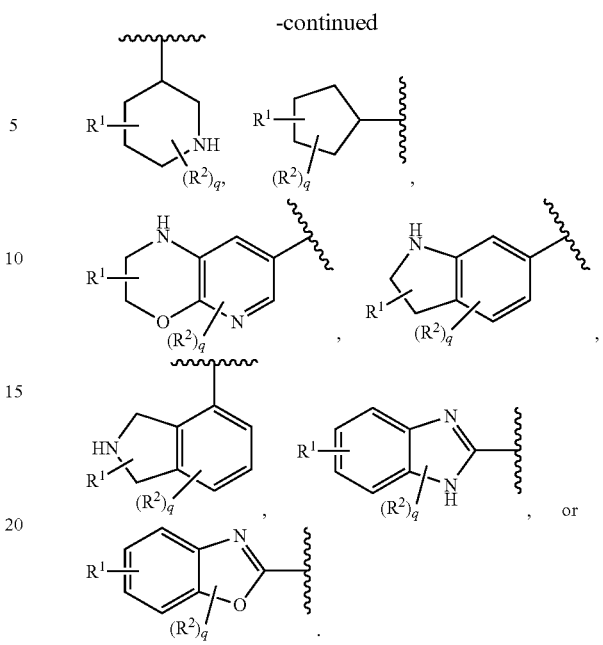

Exemplary Ring F groups are set forth below:

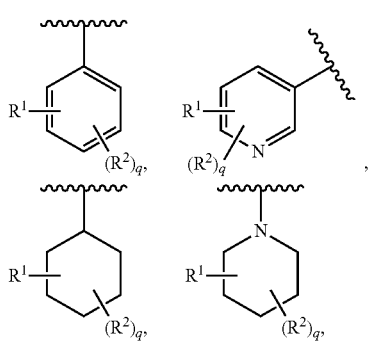

In some embodiments, Ring F is selected from those depicted in Table 8, below.

In certain embodiments, each $R^2$ is hydrogen.

In certain embodiments, each $R^2$ is independently —R.

In certain embodiments, each $R^2$ is independently methyl, ethyl, propyl, i-propyl, straight chain or branched butyl, straight chain or branched pentyl, or straight chain or branched hexyl. In various embodiments, each $R^2$ is independently F, Cl, Br, or I.

In certain embodiments, each $R^2$ is independently cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently

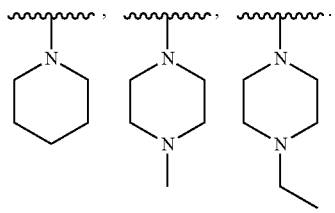

In certain embodiments, each $R^2$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently —CH$_3$, —F, —CF$_3$, —OCH$_3$, —OCF$_3$, —OCH$_2$CH$_2$NMe$_2$, —OCH$_2$CH$_2$NH$_2$, or —OCH$_2$CH$_2$OCH$_3$. In certain embodiments, $R^2$ is OCH$_3$.

In certain embodiments, $R^{10}$ is hydrogen. In certain embodiments, $R^{10}$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur. In some embodiments, each $R^2$ is independently selected from those depicted in Table 8, below.

In certain embodiments, $R^{10}$ is an optionally substituted $C_{1-6}$ aliphatic. In certain embodiments, $R^{10}$ is an optionally substituted phenyl. In certain embodiments, $R^{10}$ is an optionally substituted 3-8 membered saturated or partially unsaturated carbocyclic ring. In certain embodiments, $R^{10}$ is an optionally substituted 4-7 membered heterocylic ring having 1-2 heteroatoms independently selected from nitrogen, oxygen, or sulfur. In certain embodiments, $R^{10}$ is an optionally substituted 5-6 membered monocyclic heteroaryl ring having 1-4 heteroatoms independently selected from nitrogen, oxygen, or sulfur. In some embodiments, $R^{10}$ is selected from those depicted in Table 8, below.

In certain embodiments, $R^{11}$ is hydrogen. In certain embodiments, $R^{11}$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $R^{11}$ is an optionally substituted $C_{1-6}$ aliphatic. In certain embodiments, $R^{11}$ is an optionally substituted phenyl. In certain embodiments, $R^{11}$ is an optionally substituted 3-8 membered saturated or partially unsaturated carbocyclic ring. In certain embodiments, $R^{11}$ is an optionally substituted 4-7 membered heterocylic ring having 1-2 heteroatoms independently selected from nitrogen, oxygen, or sulfur. In certain embodiments, $R^{11}$ is an optionally substituted 5-6 membered monocyclic heteroaryl ring having 1-4 heteroatoms independently selected from nitrogen, oxygen, or sulfur. In some embodiments, $R^{11}$ is selected from those depicted in Table 8, below.

In various embodiments, $R^{10}$ and $R^{11}$ are taken together with the carbon atom to which they are attached to form a 3-8 membered saturated or partially unsaturated carbocyclic ring.

In various embodiments, $R^{10}$ and $R^{11}$ are taken together with the carbon atom to which they are attached to form a 4-7 membered heterocylic ring having 1-2 heteroatoms independently selected from nitrogen, oxygen, or sulfur.

In various embodiments, $R^{10}$ and $R^{11}$ are taken together with the carbon atom to which they are attached to form a 5-6 membered monocyclic heteroaryl ring having 1-4 heteroatoms independently selected from nitrogen, oxygen, or sulfur.

In various embodiments, $R^{10}$ and $R^{11}$ are taken together with the carbon atom to which they are attached to form a cyclopropyl, cyclobutyl, cyclopentyl, or cyclohexyl.

In various embodiments, $R^{10}$ and $R^{11}$ are taken together with the carbon atom to which they are attached to form cyclobutyl.

In various embodiments, each $R^a$ is independently hydrogen. In various embodiments, each $R^a$ is independently an optionally substituted $C_{1-6}$ aliphatic group. In some embodiments, each $R^a$ is independently selected from those depicted in Table 8, below.

In various embodiments, T is a covalent bond.

In various embodiments, T is —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In various embodiments, T is —N(R)—, —C(O)—, —C(O)N(R)—, or —N(R)C(O)—. In some embodiments, T is selected from those depicted in Table 8, below.

In various embodiments, the invention provides a compound of formula V, wherein the moiety

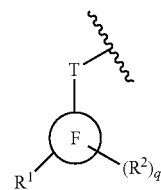

is selected from any one of the following structures:

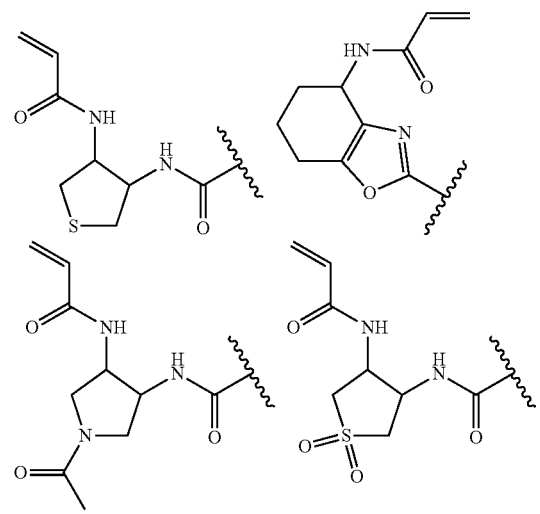

137
-continued

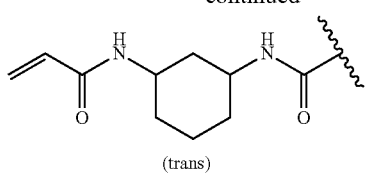
(trans)

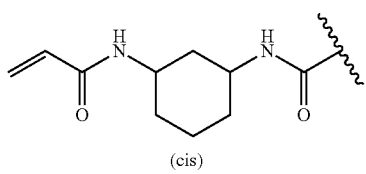
(cis)

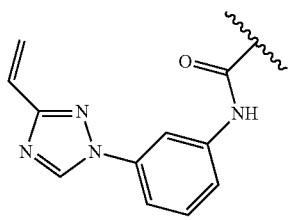

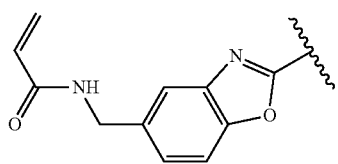

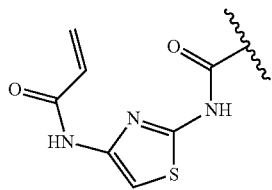

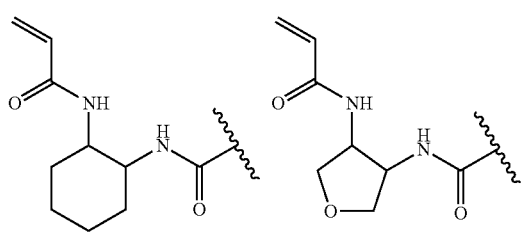

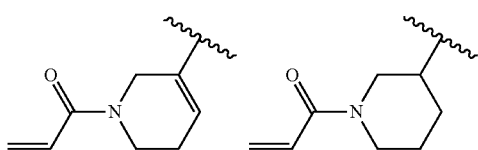

138
-continued

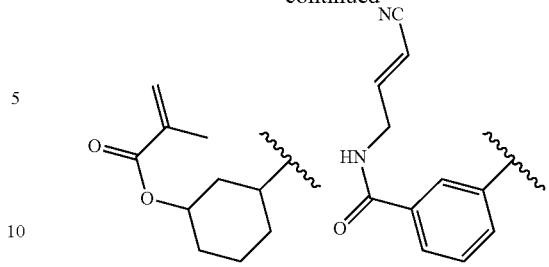

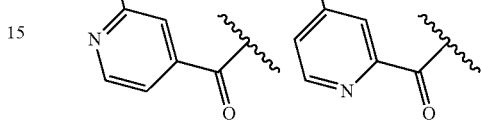

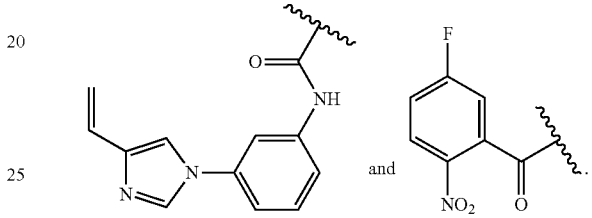

and

In various embodiments, the invention provides a compound of formula V-a:

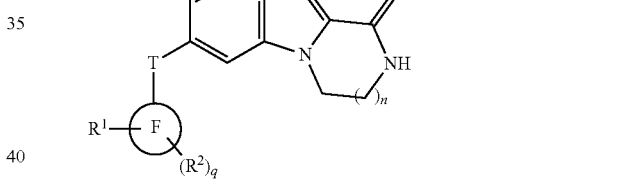

V-a or a pharmaceutically acceptable salt thereof, wherein each of Ring F, $R^1$, $R^2$, T, and q is as defined above and described in embodiments, classes and subclasses above and herein, singly or in combination.

In various embodiments, the invention provides a compound of formula V-b:

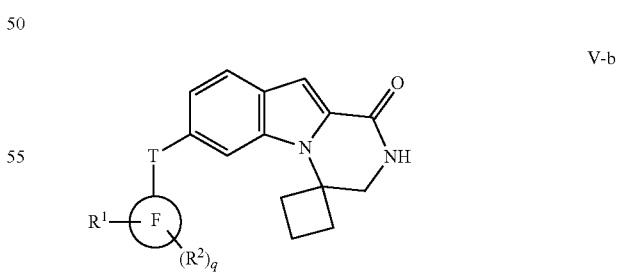

V-b or a pharmaceutically acceptable salt thereof, wherein each of Ring F, $R^1$, $R^2$, T, and q is as defined above and described in embodiments, classes and subclasses above and herein, singly or in combination.

In certain embodiments, the invention provides a compound selected from those depicted in Table 8:

TABLE 8
Exemplary Compounds of Formula V
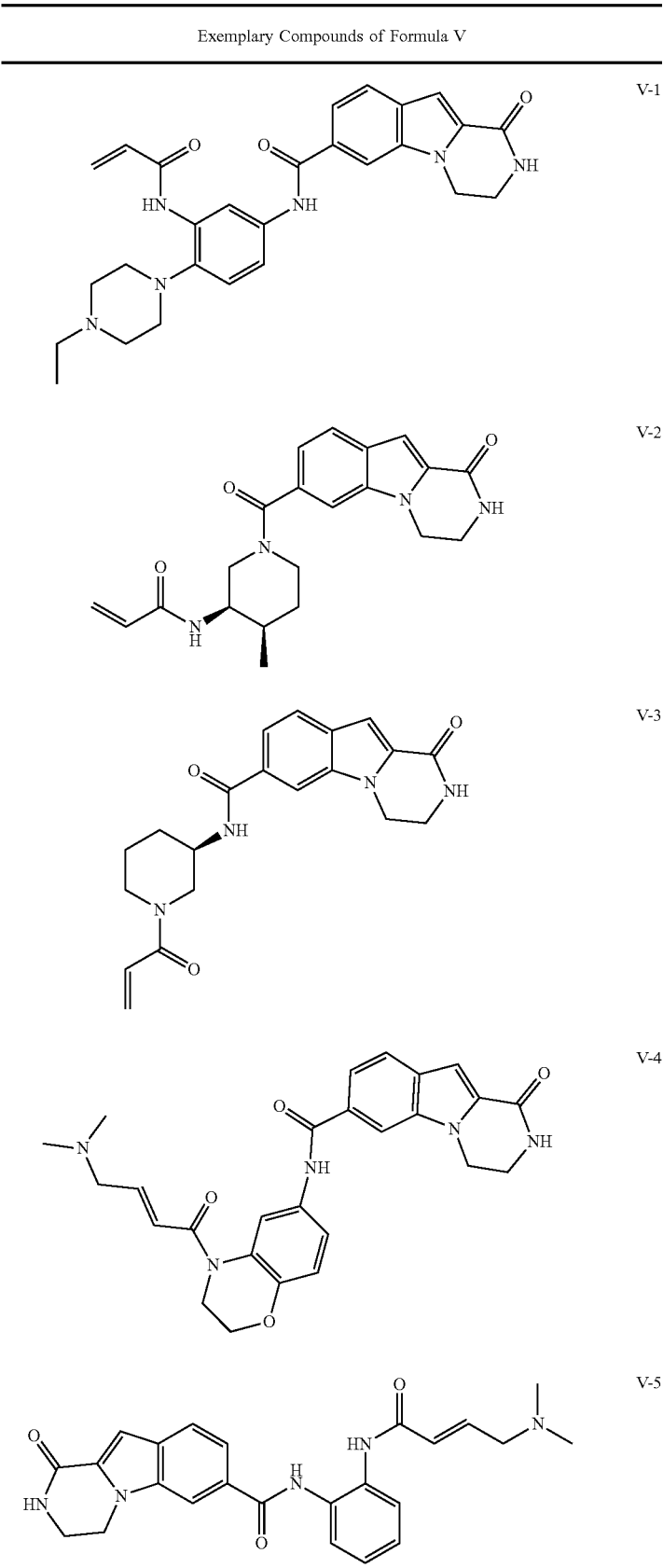

TABLE 8-continued
Exemplary Compounds of Formula V
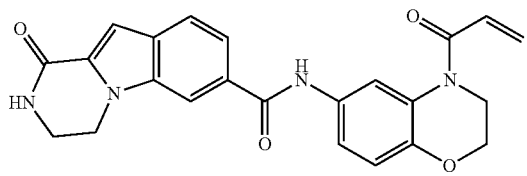 [SMILES: C=CC(=O)N1CCOc2ccc(NC(=O)c3ccc4cc5n(c4c3)CCNC5=O)cc21]
V-6
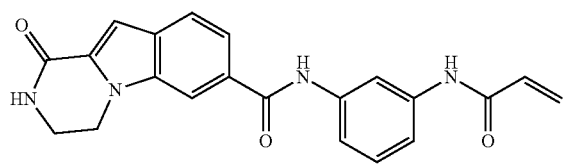 [SMILES: C=CC(=O)Nc1cccc(NC(=O)c2ccc3cc4n(c3c2)CCNC4=O)c1]
V-7
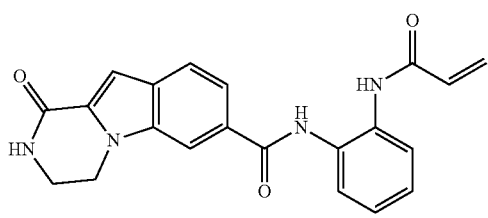 [SMILES: C=CC(=O)Nc1ccccc1NC(=O)c1ccc2cc3n(c2c1)CCNC3=O]
V-8
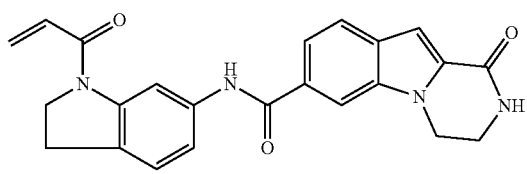 [SMILES: C=CC(=O)N1CCc2ccc(NC(=O)c3ccc4cc5n(c4c3)CCNC5=O)cc21]
V-9
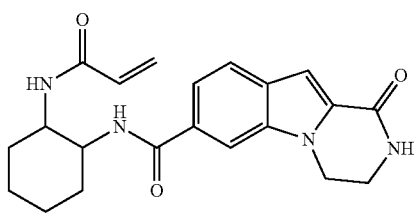 [SMILES: C=CC(=O)NC1CCCCC1NC(=O)c1ccc2cc3n(c2c1)CCNC3=O]
V-10
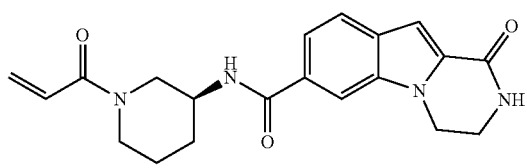 [SMILES: C=CC(=O)N1CCC[C@H](NC(=O)c2ccc3cc4n(c3c2)CCNC4=O)C1]
V-11
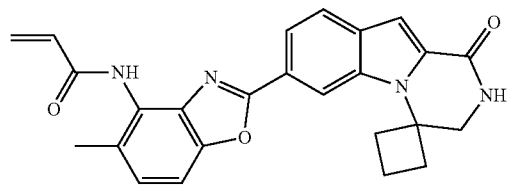 [SMILES: C=CC(=O)Nc1c(C)ccc2oc(-c3ccc4cc5n(c4c3)C3(CCC3)CNC5=O)nc12]
V-12

143 144
TABLE 8-continued
Exemplary Compounds of Formula V
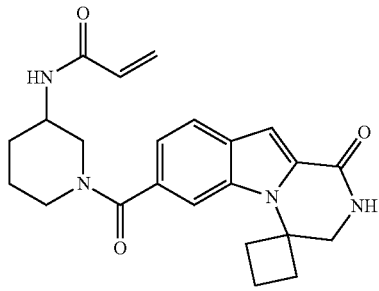 [SMILES: C=CC(=O)NC1CCCN(C(=O)c2ccc3cc4n(c3c2)C2(CCC2)CNC4=O)C1]
V-13
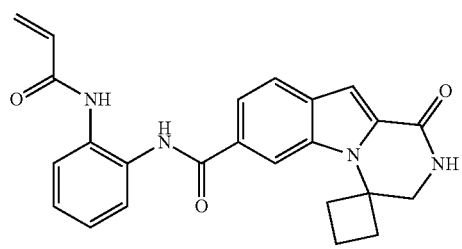 [SMILES: C=CC(=O)Nc1ccccc1NC(=O)c1ccc2cc3n(c2c1)C1(CCC1)CNC3=O]
V-14
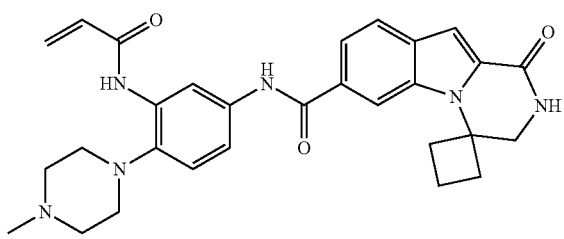 [SMILES: C=CC(=O)Nc1cc(NC(=O)c2ccc3cc4n(c3c2)C2(CCC2)CNC4=O)ccc1N1CCN(C)CC1]
V-15
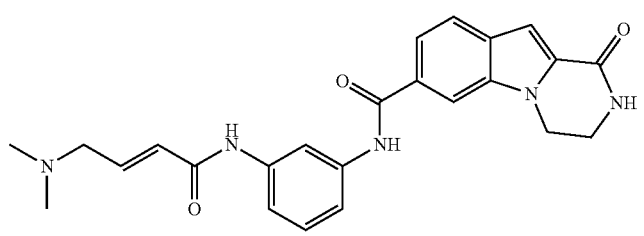 [SMILES: CN(C)C/C=C/C(=O)Nc1cccc(NC(=O)c2ccc3cc4n(c3c2)CCNC4=O)c1]
V-16
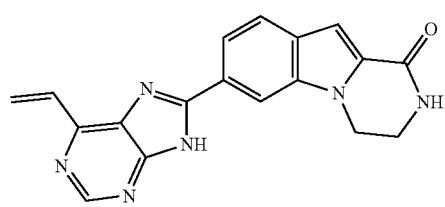 [SMILES: C=Cc1ncnc2[nH]c(-c3ccc4cc5n(c4c3)CCNC5=O)nc12]
V-17
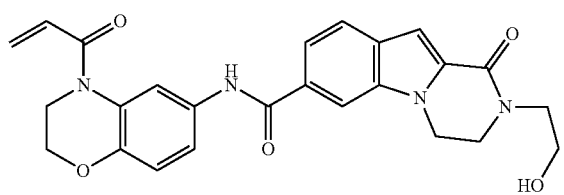 [SMILES: C=CC(=O)N1CCOc2ccc(NC(=O)c3ccc4cc5n(c4c3)CCN(CCO)C5=O)cc21]
V-18

TABLE 8-continued
Exemplary Compounds of Formula V
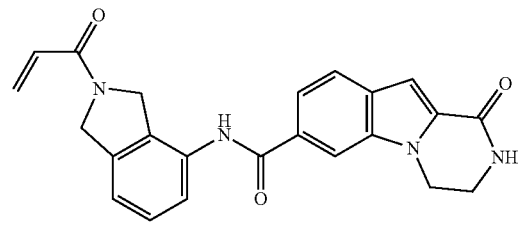 [SMILES: C=CC(=O)N1Cc2cccc(NC(=O)c3ccc4cc5n(c4c3)CCNC5=O)c2C1]
V-19
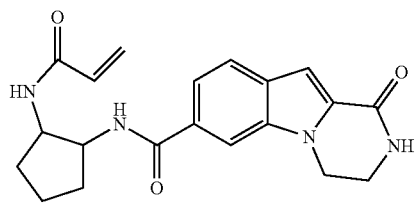 [SMILES: C=CC(=O)NC1CCCC1NC(=O)c1ccc2cc3n(c2c1)CCNC3=O]
V-20
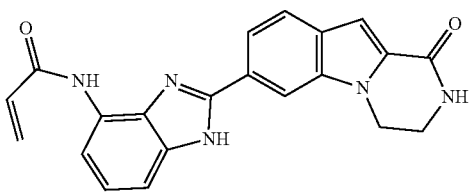 [SMILES: C=CC(=O)Nc1cccc2[nH]c(-c3ccc4cc5n(c4c3)CCNC5=O)nc12]
V-21
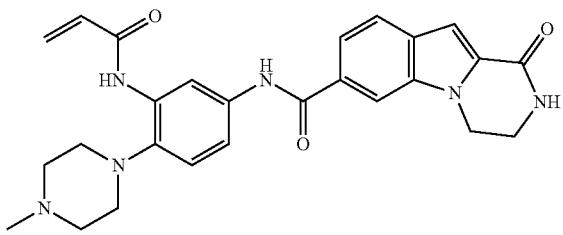 [SMILES: C=CC(=O)Nc1cc(NC(=O)c2ccc3cc4n(c3c2)CCNC4=O)ccc1N1CCN(C)CC1]
V-22
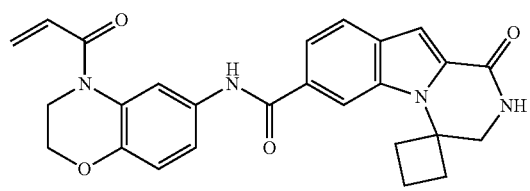 [SMILES: C=CC(=O)N1CCOc2ccc(NC(=O)c3ccc4cc5n(c4c3)C3(CCC3)CNC5=O)cc21]
V-23
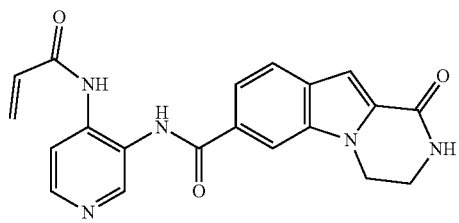 [SMILES: C=CC(=O)Nc1ccncc1NC(=O)c1ccc2cc3n(c2c1)CCNC3=O]
V-24
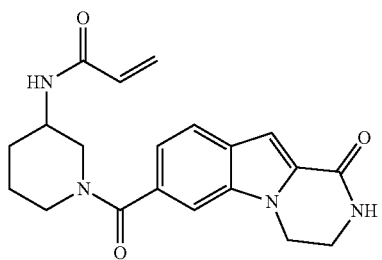 [SMILES: C=CC(=O)NC1CCCN(C(=O)c2ccc3cc4n(c3c2)CCNC4=O)C1]
V-25

TABLE 8-continued
Exemplary Compounds of Formula V
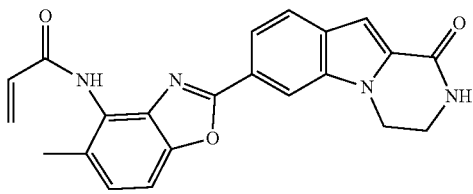 [SMILES: C=CC(=O)Nc1c(C)ccc2oc(-c3ccc4cc5n(c4c3)CCNC5=O)nc12] V-26
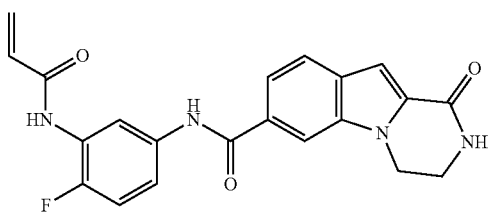 [SMILES: C=CC(=O)Nc1cc(NC(=O)c2ccc3cc4n(c3c2)CCNC4=O)ccc1F] V-27
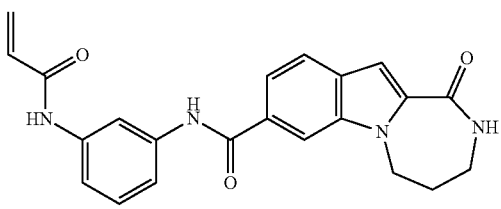 [SMILES: C=CC(=O)Nc1cccc(NC(=O)c2ccc3cc4n(c3c2)CCCNC4=O)c1] V-28
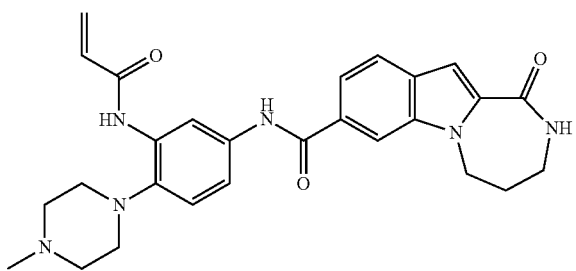 [SMILES: C=CC(=O)Nc1cc(NC(=O)c2ccc3cc4n(c3c2)CCCNC4=O)ccc1N1CCN(C)CC1] V-29
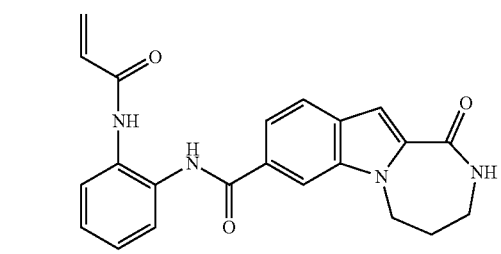 [SMILES: C=CC(=O)Nc1ccccc1NC(=O)c1ccc2cc3n(c2c1)CCCNC3=O] V-30
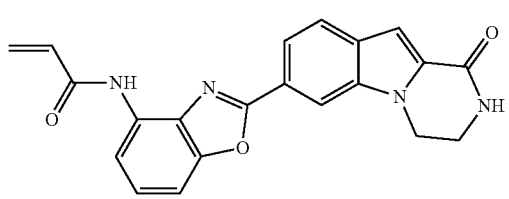 [SMILES: C=CC(=O)Nc1cccc2oc(-c3ccc4cc5n(c4c3)CCNC5=O)nc12] V-31

TABLE 8-continued
Exemplary Compounds of Formula V
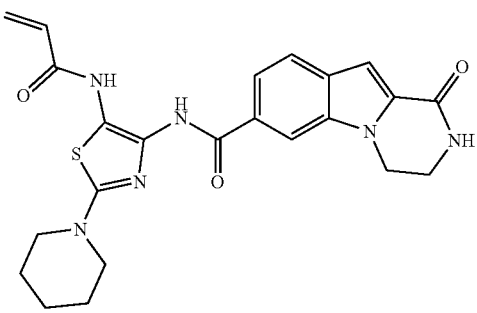 [SMILES: C=CC(=O)Nc1sc(N2CCCCC2)nc1NC(=O)c1ccc2cc3n(c2c1)CCNC3=O]
V-32
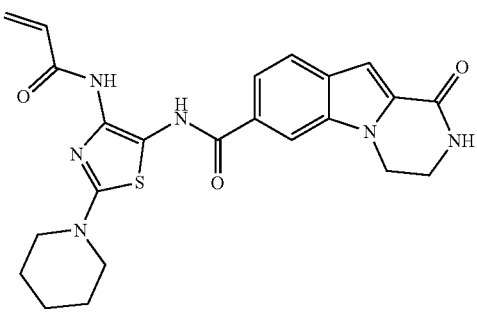 [SMILES: C=CC(=O)Nc1nc(N2CCCCC2)sc1NC(=O)c1ccc2cc3n(c2c1)CCNC3=O]
V-33
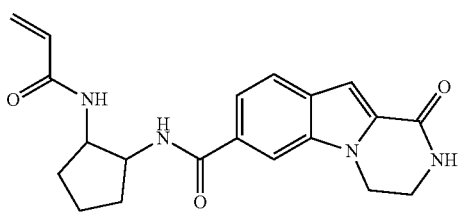 [SMILES: C=CC(=O)NC1CCCC1NC(=O)c1ccc2cc3n(c2c1)CCNC3=O]
V-34
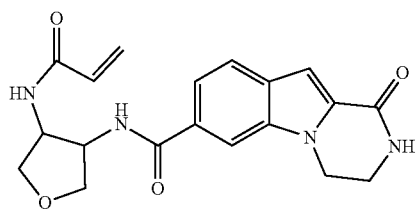 [SMILES: C=CC(=O)NC1COCC1NC(=O)c1ccc2cc3n(c2c1)CCNC3=O]
V-35
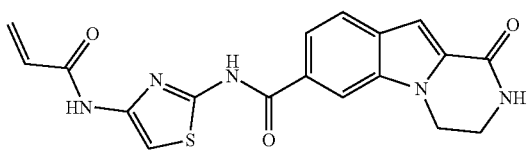 [SMILES: C=CC(=O)Nc1csc(NC(=O)c2ccc3cc4n(c3c2)CCNC4=O)n1]
V-36
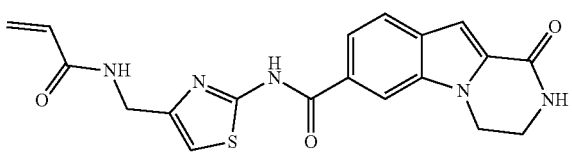 [SMILES: C=CC(=O)NCc1csc(NC(=O)c2ccc3cc4n(c3c2)CCNC4=O)n1]
V-37
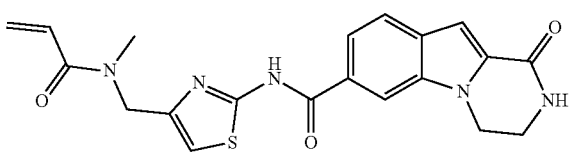 [SMILES: C=CC(=O)N(C)Cc1csc(NC(=O)c2ccc3cc4n(c3c2)CCNC4=O)n1]
V-38

TABLE 8-continued
Exemplary Compounds of Formula V
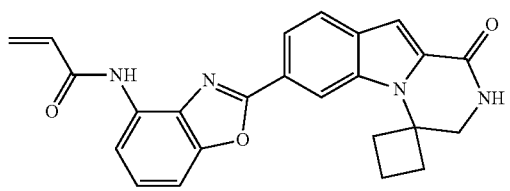 [SMILES: C=CC(=O)Nc1cccc2oc(-c3ccc4cc5n(c4c3)C3(CCC3)CNC5=O)nc12]
V-39
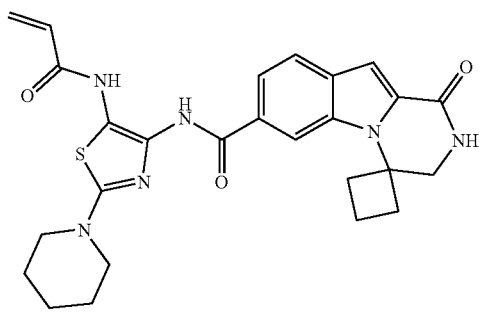 [SMILES: C=CC(=O)Nc1sc(N2CCCCC2)nc1NC(=O)c1ccc2cc3n(c2c1)C1(CCC1)CNC3=O]
V-40
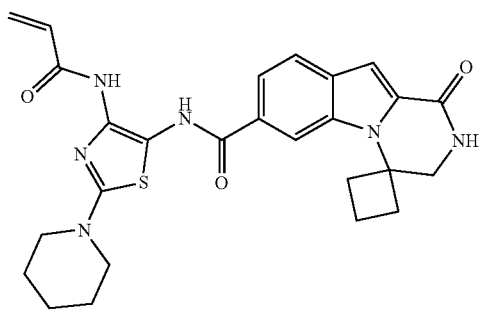 [SMILES: C=CC(=O)Nc1nc(N2CCCCC2)sc1NC(=O)c1ccc2cc3n(c2c1)C1(CCC1)CNC3=O]
V-41
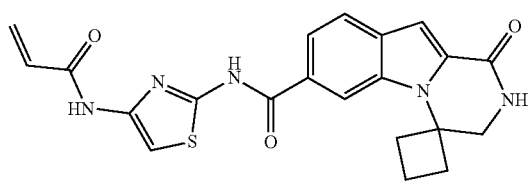 [SMILES: C=CC(=O)Nc1csc(NC(=O)c2ccc3cc4n(c3c2)C2(CCC2)CNC4=O)n1]
V-42
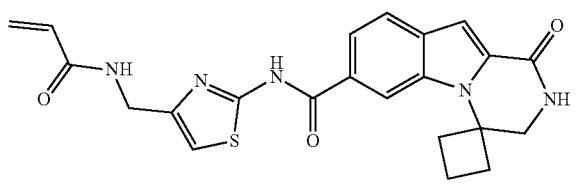 [SMILES: C=CC(=O)NCc1csc(NC(=O)c2ccc3cc4n(c3c2)C2(CCC2)CNC4=O)n1]
V-43
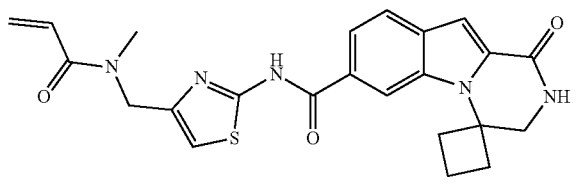 [SMILES: C=CC(=O)N(C)Cc1csc(NC(=O)c2ccc3cc4n(c3c2)C2(CCC2)CNC4=O)n1]
V-44
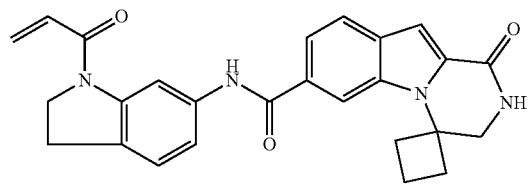 [SMILES: C=CC(=O)N1CCc2ccc(NC(=O)c3ccc4cc5n(c4c3)C3(CCC3)CNC5=O)cc21]
V-45

TABLE 8-continued
Exemplary Compounds of Formula V
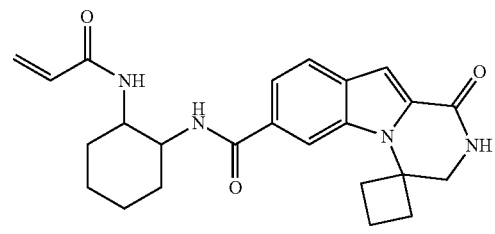
V-46
(cis)
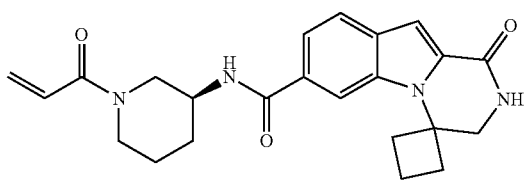 [SMILES: C=CC(=O)N1CCC[C@H](NC(=O)c2ccc3cc4n(c3c2)C2(CCC2)CNC4=O)C1]
V-47
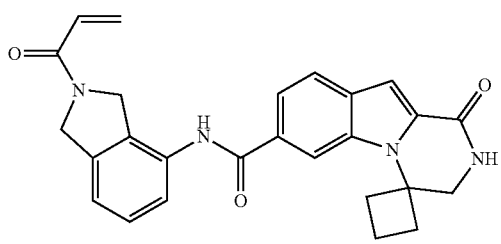 [SMILES: C=CC(=O)N1Cc2cccc(NC(=O)c3ccc4cc5n(c4c3)C3(CCC3)CNC5=O)c2C1]
V-48
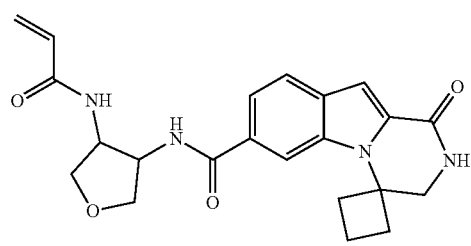 [SMILES: C=CC(=O)NC1COCC1NC(=O)c1ccc2cc3n(c2c1)C1(CCC1)CNC3=O]
V-49
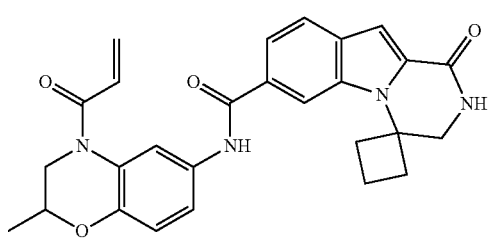 [SMILES: C=CC(=O)N1CC(C)Oc2ccc(NC(=O)c3ccc4cc5n(c4c3)C3(CCC3)CNC5=O)cc21]
V-50
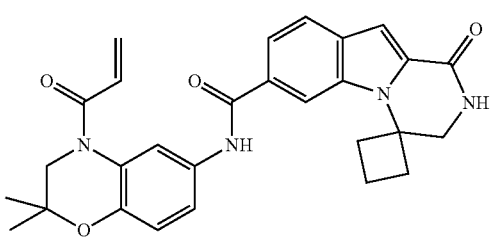 [SMILES: C=CC(=O)N1CC(C)(C)Oc2ccc(NC(=O)c3ccc4cc5n(c4c3)C3(CCC3)CNC5=O)cc21]
V-51
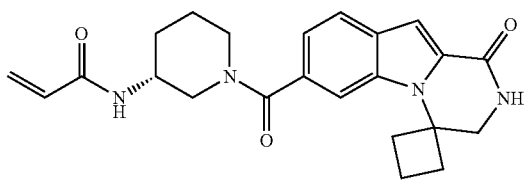 [SMILES: C=CC(=O)N[C@@H]1CCCN(C(=O)c2ccc3cc4n(c3c2)C2(CCC2)CNC4=O)C1]
V-52

TABLE 8-continued
Exemplary Compounds of Formula V
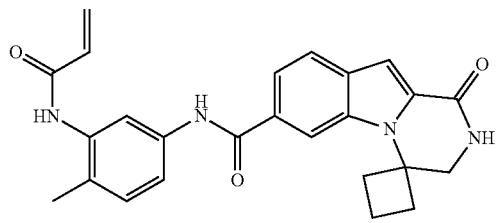 [SMILES: C=CC(=O)Nc1cc(NC(=O)c2ccc3cc4n(c3c2)C2(CCC2)CNC4=O)ccc1C]
V-53
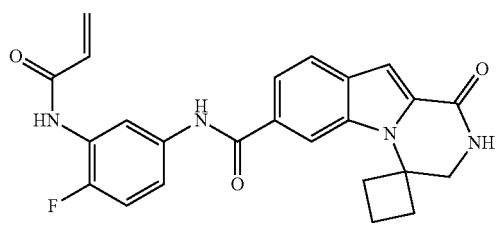 [SMILES: C=CC(=O)Nc1cc(NC(=O)c2ccc3cc4n(c3c2)C2(CCC2)CNC4=O)ccc1F]
V-54
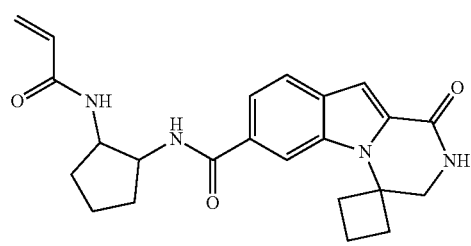
V-55
(cis)
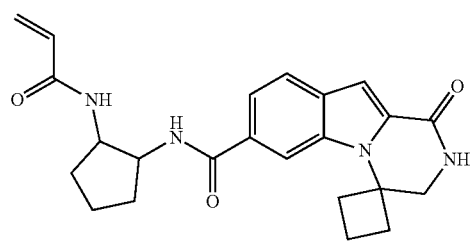
V-56
(trans)
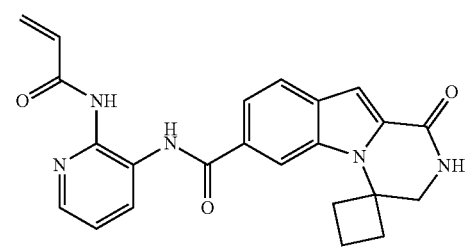
V-57
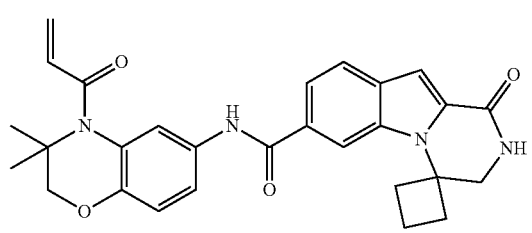 [SMILES: C=CC(=O)N1c2cc(NC(=O)c3ccc4cc5n(c4c3)C3(CCC3)CNC5=O)ccc2OCC1(C)C]
V-58

157
TABLE 8-continued
Exemplary Compounds of Formula V
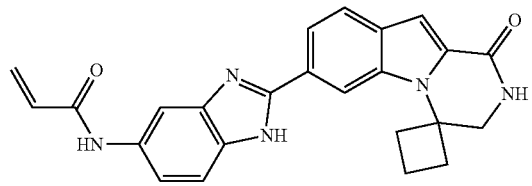 [SMILES: C=CC(=O)Nc1ccc2[nH]c(-c3ccc4cc5n(c4c3)C3(CCC3)CNC5=O)nc2c1]
V-59
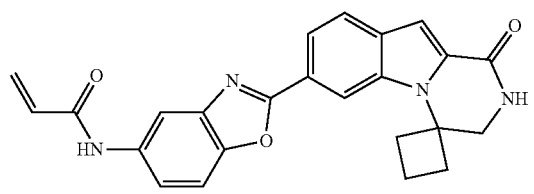 [SMILES: C=CC(=O)Nc1ccc2oc(-c3ccc4cc5n(c4c3)C3(CCC3)CNC5=O)nc2c1]
V-60
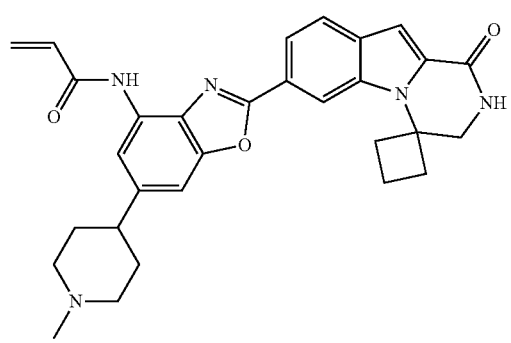 [SMILES: C=CC(=O)Nc1cc(C2CCN(C)CC2)cc2oc(-c3ccc4cc5n(c4c3)C3(CCC3)CNC5=O)nc12]
V-61
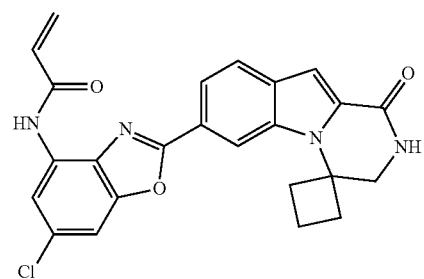 [SMILES: C=CC(=O)Nc1cc(Cl)cc2oc(-c3ccc4cc5n(c4c3)C3(CCC3)CNC5=O)nc12]
V-62
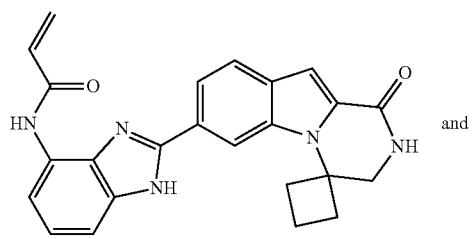 [SMILES: C=CC(=O)Nc1cccc2[nH]c(-c3ccc4cc5n(c4c3)C3(CCC3)CNC5=O)nc12]
V-63
and
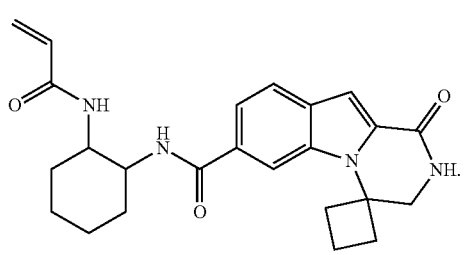
V-64
(trans)

In some embodiments, the present invention provides a compound of formula V depicted in Table 8, above, or a pharmaceutically acceptable salt thereof.

Where a compound is designated as racemic, each of its enantiomers and/or diastereomers is also envisaged and encompassed by such structure.

In certain aspects, the invention provides a compound of formula V-c:

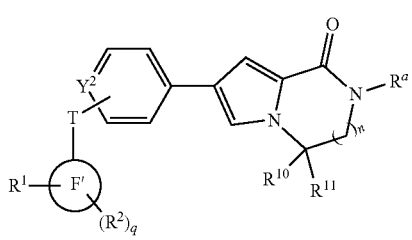

V-c or a pharmaceutically acceptable salt thereof, wherein:

Ring F' is an optionally substituted group selected from phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;

$R^1$ is a warhead group;

q is 0-6;

each $R^2$ is independently —R, halogen, —OR, —SR, —CN, —NO$_2$, —SO$_2$NR, —SO$_2$R, —SOR, —C(O)R, —CO$_2$R, —C(O)N(R)$_2$, —NRC(O)R, —NRC(O)OR, —NRC(O)N(R)$_2$, —NRSO$_2$R, or —N(R)$_2$;

each R is independently hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

$Y^2$ is CR' or N;

each R' is independently hydrogen, halo, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^{10}$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^{11}$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

or $R^{10}$ and $R^{11}$ are taken together with the carbon atom to which they are attached to form a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

n is 1 or 2;

each $R^a$ is independently hydrogen or an optionally substituted $C_{1-6}$ aliphatic group; and T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In certain embodiments, $R^1$ is a warhead group, wherein when Ring F' is a 5 or 6-membered ring, then $R^1$ is attached to an atom next to an atom adjacent to where T is attached (i.e., in the case where Ring F' is phenyl, $R^1$ is attached at the meta position), or $R^1$ is attached to an atom adjacent to where T is attached (i.e., in the case where Ring F' is phenyl, $R^1$ is attached at the ortho position).

In various embodiments, Ring F is an optionally substituted phenyl. In various embodiments, Ring F is an optionally substituted 3-8 membered saturated or partially unsaturated carbocyclic ring. In various embodiments, Ring F is an optionally substituted 4-7 membered heterocyclic ring having 1-2 heteroatoms independently selected from nitrogen, oxygen, or sulfur. In various embodiments, Ring F is an optionally substituted 5-6 membered monocyclic heteroaryl ring having 1-4 heteroatoms independently selected from nitrogen, oxygen, or sulfur.

In certain embodiments, Ring F is a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur.

In various embodiments, Ring F is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, Ring F is an optionally substituted group selected from phenyl, cyclohexyl, piperidinyl, and oxazolyl.

In certain embodiments, Ring F is substituted as defined herein.

In certain embodiments, Ring F is

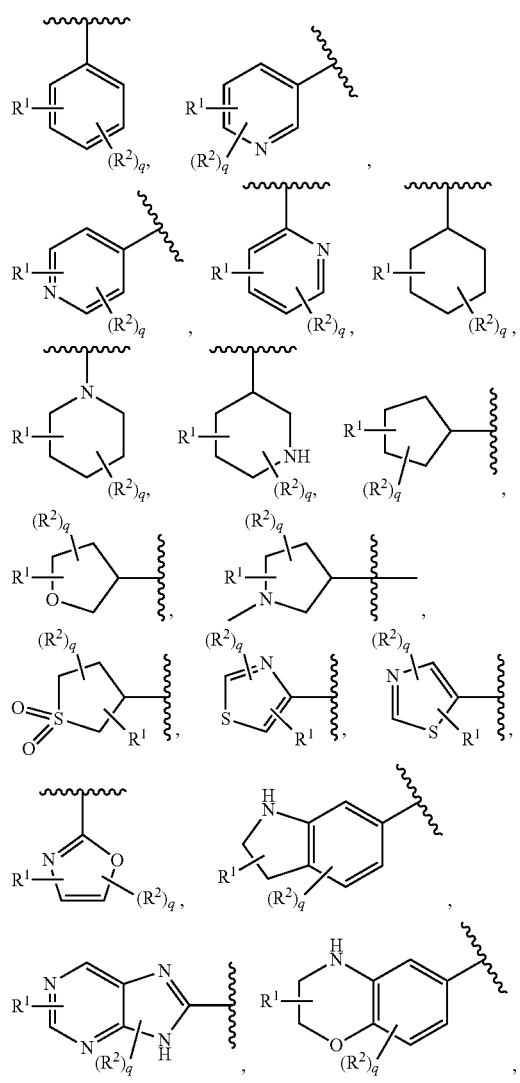

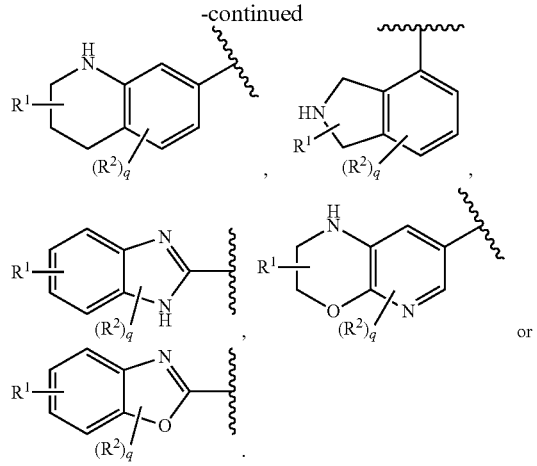

Exemplary Ring F groups are set forth below:

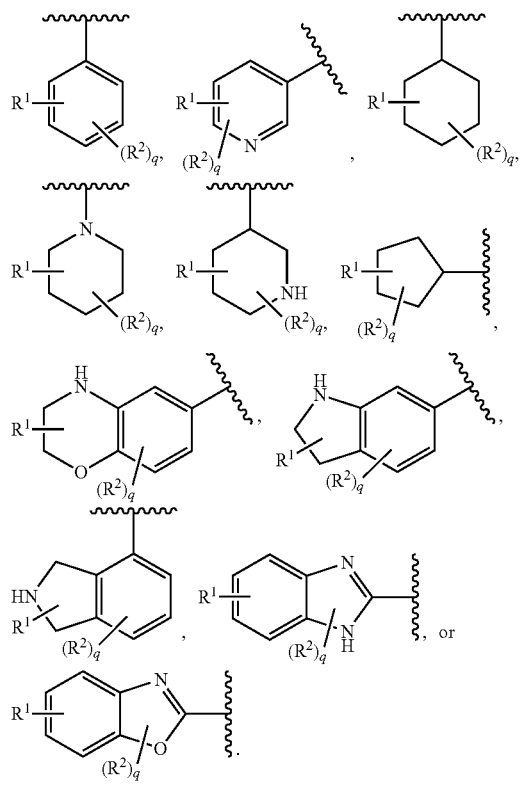

In some embodiments, Ring F is selected from those depicted in Table 9, below.

In certain embodiments, each $R^2$ is hydrogen.

In certain embodiments, each $R^2$ is independently —R.

In certain embodiments, each $R^2$ is independently methyl, ethyl, propyl, i-propyl, straight chain or branched butyl, straight chain or branched pentyl, or straight chain or branched hexyl. In various embodiments, each $R^2$ is independently F, Cl, Br, or I.

In certain embodiments, each $R^2$ is independently cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently

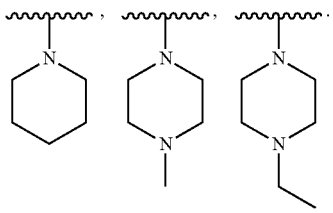

In certain embodiments, each $R^2$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently —CH$_3$, —F, —CF$_3$, —OCH$_3$, —OCF$_3$, —OCH$_2$CH$_2$NMe$_2$, —OCH$_2$CH$_2$NH$_2$, or —OCH$_2$CH$_2$OCH$_3$. In certain embodiments, $R^2$ is OCH$_3$. In some embodiments, each $R^2$ is independently selected from those depicted in Table 9, below.

In certain embodiments, $Y^2$ is N. In certain embodiments, $Y^2$ is CR' and R' is independently hydrogen, halo, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $R^{10}$ is hydrogen. In certain embodiments, $R^{10}$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $R^{10}$ is an optionally substituted $C_{1-6}$ aliphatic. In certain embodiments, $R^{10}$ is an optionally substituted phenyl. In certain embodiments, $R^{10}$ is an optionally substituted 3-8 membered saturated or partially unsaturated carbocyclic ring. In certain embodiments, $R^{10}$ is an optionally substituted 4-7 membered heterocyclic ring having 1-2 heteroatoms independently selected from nitrogen, oxygen, or sulfur. In certain embodiments, $R^{10}$ is an optionally substituted 5-6 membered monocyclic heteroaryl ring having 1-4 heteroatoms independently selected from nitrogen, oxygen, or sulfur. In some embodiments, $R^{10}$ is selected from those depicted in Table 9, below.

In certain embodiments, $R^{11}$ is hydrogen. In certain embodiments, $R^{11}$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $R^{11}$ is an optionally substituted $C_{1-6}$ aliphatic. In certain embodiments, $R^{11}$ is an optionally substituted phenyl. In certain embodiments, $R^{11}$ is an optionally substituted 3-8 membered saturated or partially unsaturated carbocyclic ring. In certain embodiments, $R^{11}$ is an optionally substituted 4-7 membered heterocyclic ring having 1-2 heteroatoms independently selected from nitrogen, oxygen, or sulfur. In certain embodiments, $R^{11}$ is an optionally substituted 5-6 membered monocyclic heteroaryl ring having 1-4 heteroatoms independently selected from nitrogen, oxygen, or sulfur. In some embodiments, $R^{11}$ is selected from those depicted in Table 9, below.

In various embodiments, $R^{10}$ and $R^{11}$ are taken together with the carbon atom to which they are attached to form a 3-8 membered saturated or partially unsaturated carbocyclic ring.

In various embodiments, $R^{10}$ and $R^{11}$ are taken together with the carbon atom to which they are attached to form a 4-7 membered heterocyclic ring having 1-2 heteroatoms independently selected from nitrogen, oxygen, or sulfur.

In various embodiments, $R^{10}$ and $R^{11}$ are taken together with the carbon atom to which they are attached to form a 5-6 membered monocyclic heteroaryl ring having 1-4 heteroatoms independently selected from nitrogen, oxygen, or sulfur.

In various embodiments, $R^{10}$ and $R^{11}$ are taken together with the carbon atom to which they are attached to form a cyclopropyl, cyclobutyl, cyclopentyl, or cyclohexyl.

In various embodiments, $R^{10}$ and $R^{11}$ are taken together with the carbon atom to which they are attached to form cyclobutyl.

In various embodiments, each $R^a$ is independently hydrogen. In various embodiments, each $R^a$ is independently an optionally substituted $C_{1-6}$ aliphatic group. In some embodiments, each $R^a$ is independently selected from those depicted in Table 9, below.

In various embodiments, T is a covalent bond.

In various embodiments, T is —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In various embodiments, T is —N(R)—, —C(O)—, —C(O)N(R)—, or —N(R)C(O)—. In some embodiments, T is selected from those depicted in Table 9, below.

In various embodiments, the invention provides a compound of formula V-cc:

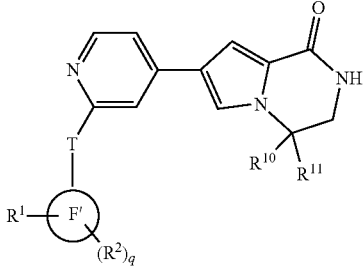

V-cc or a pharmaceutically acceptable salt thereof, wherein each of Ring F', $R^1$, $R^2$, $R^{10}$, $R^{11}$, T, and q is as defined above and described in embodiments, classes and subclasses above and herein, singly or in combination.

In certain embodiments, the invention provides a compound selected from those depicted in Table 9:

TABLE 9

Exemplary Compounds of Formula V-c

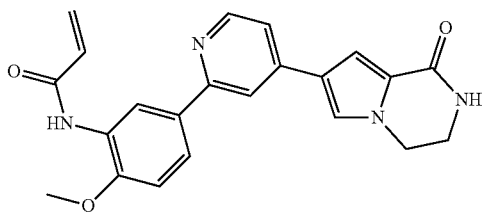 [SMILES: C=CC(=O)Nc1cc(-c2cc(-c3cc4n(c3)CCNC4=O)ccn2)ccc1OC]

V-c-1

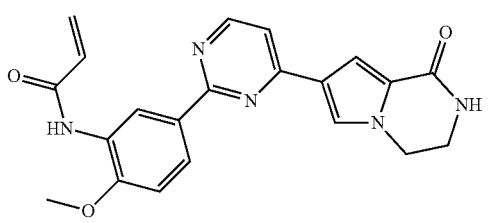

V-c-2 and

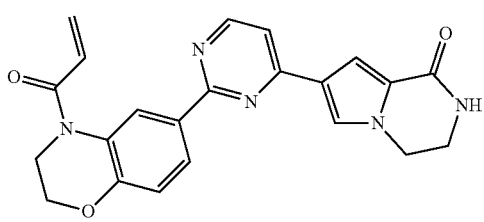 [SMILES: C=CC(=O)N1CCOc2ccc(-c3nccc(-c4cc5n(c4)CCNC5=O)n3)cc21]

V-c-3

In some embodiments, the present invention provides a compound depicted in Table 9, above, or a pharmaceutically acceptable salt thereof.

In certain aspects, the invention provides a compound of formula VI:

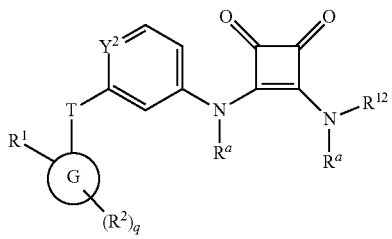

VI or a pharmaceutically acceptable salt thereof, wherein:

Ring G is an optionally substituted group selected from phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;

or Ring G is absent, and $R^1$ is attached to T;

$Y^2$ is CR' or N;

each R' is independently hydrogen, halo, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^1$ is a warhead group;

q is 0-6;

each $R^2$ is independently —R, halogen, —OR, —SR, —CN, —$NO_2$, —$SO_2NR$, —$SO_2R$, —SOR, —C(O)R, —$CO_2R$, —$C(O)N(R)_2$, —NRC(O)R, —NRC(O)OR, —NRC(O)N$(R)_2$, —$NRSO_2R$, or —$N(R)_2$;

each R is independently hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

$R^{12}$ is hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

each $R^a$ is independently hydrogen or an optionally substituted $C_{1-6}$ aliphatic group; and T is a covalent bond, —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In certain embodiments, $R^1$ is a warhead group, wherein when ring G is a 5 or 6-membered ring, then $R^1$ is attached to an atom next to an atom adjacent to where T is attached (i.e., in the case where Ring G is phenyl, $R^1$ is attached at the meta position), or $R^1$ is attached to an atom adjacent to where T is attached (i.e., in the case where Ring G is phenyl, $R^1$ is attached at the ortho position).

In various embodiments, Ring G is an optionally substituted phenyl. In various embodiments, Ring G is an optionally substituted 3-8 membered saturated or partially unsaturated carbocyclic ring. In various embodiments, Ring G is an optionally substituted 4-7 membered heterocylic ring having 1-2 heteroatoms independently selected from nitrogen, oxygen, or sulfur. In various embodiments, Ring G is an optionally substituted 5-6 membered monocyclic heteroaryl ring having 1-4 heteroatoms independently selected from nitrogen, oxygen, or sulfur.

In various embodiments, Ring G is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, Ring G is an optionally substituted group selected from phenyl, cyclohexyl, piperidinyl, and oxazolyl.

In certain embodiments, Ring G is substituted as defined herein.

Exemplary Ring G groups are set forth below:

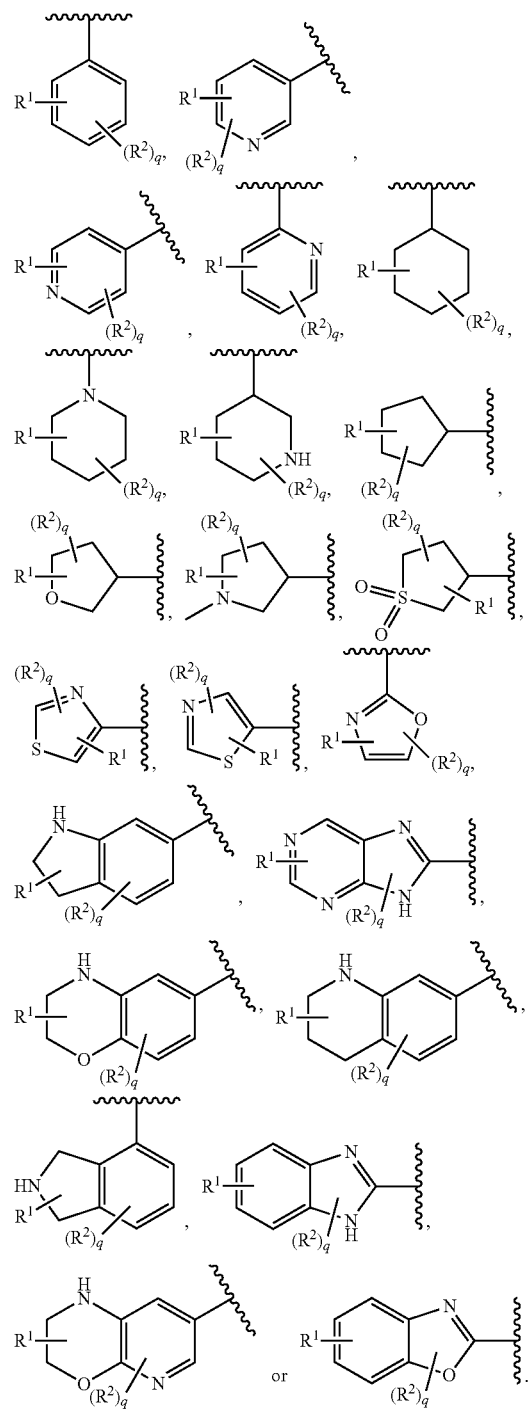

Exemplary Ring G groups are set forth below:

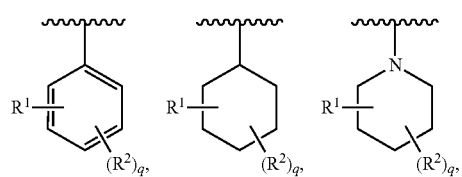

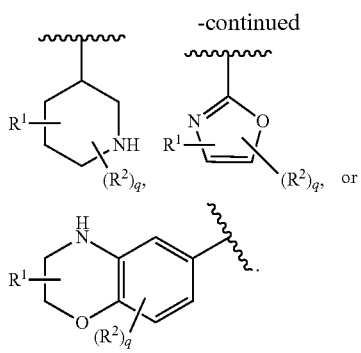

In some embodiments, Ring G is selected from those depicted in Table 10, below.

In certain embodiments, Ring G is absent.

In certain embodiments, each $R^2$ is hydrogen.

In certain embodiments, each $R^2$ is independently —R.

In certain embodiments, each $R^2$ is independently cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each $R^2$ is independently piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, or pyrrolinyl.

In certain embodiments, each $R^2$ is independently methyl, ethyl, propyl, i-propyl, straight chain or branched butyl, straight chain or branched pentyl, or straight chain or branched hexyl.

In certain embodiments, each $R^2$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^2$ is independently —CH$_3$, —F, —CF$_3$, —OCH$_3$, —OCF$_3$, —OCH$_2$CH$_2$NMe$_2$, —OCH$_2$CH$_2$NH$_2$, or —OCH$_2$CH$_2$OCH$_3$. In certain embodiments, each $R^2$ is independently —F, —CF$_3$, —OCH$_3$, —OCH$_2$CH$_2$CH$_2$NH$_2$, or —OCH$_2$CH$_2$OCH$_3$. In some embodiments, each $R^2$ is independently selected from those depicted in Table 10, below.

In certain embodiments, $R^{12}$ is hydrogen.

In certain embodiments, $R^{12}$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, $R^{12}$ is an optionally substituted $C_{1-6}$ aliphatic. In certain embodiments, $R^{12}$ is an optionally substituted phenyl. In certain embodiments, $R^{12}$ is an optionally substituted 3-8 membered saturated or partially unsaturated carbocyclic ring. In certain embodiments, $R^{12}$ is an optionally substituted 4-7 membered heterocylic ring having 1-2 heteroatoms independently selected from nitrogen, oxygen, or sulfur. In certain embodiments, $R^{12}$ is an optionally substituted 5-6 membered monocyclic heteroaryl ring having 1-4 heteroatoms independently selected from nitrogen, oxygen, or sulfur.

In certain embodiments, $R^{12}$ is an optionally substituted methyl, ethyl, propyl, i-propyl, straight chain or branched butyl, straight chain or branched pentyl, or straight chain or branched hexyl.

In certain embodiments, $R^{12}$ is

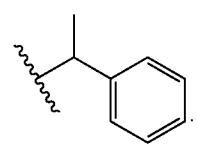 [SMILES: *C(C)c1ccccc1]

In some embodiments, $R^{12}$ is selected from those depicted in Table 10, below.

In various embodiments, each $R^a$ is independently hydrogen. In various embodiments, each $R^a$ is independently an optionally substituted $C_{1-6}$ aliphatic group. In some embodiments, each $R^a$ is independently selected from those depicted in Table 10, below.

In various embodiments, T is a covalent bond.

In various embodiments, T is —O—, —S—, —N(R)—, —C(O)—, —OC(O)—, —C(O)O—, —C(O)N(R)—, —N(R)C(O)—, —N(R)C(O)N(R)—, —S(O)—, —SO$_2$—, —SO$_2$N(R)—, —N(R)SO$_2$—, or —N(R)SO$_2$N(R)—.

In various embodiments, T is —N(R)—, —C(O)N(R)—, or —N(R)C(O)—. In some embodiments, T is selected from those depicted in Table 10, below.

In various embodiments, the invention provides a compound of formula VI-a:

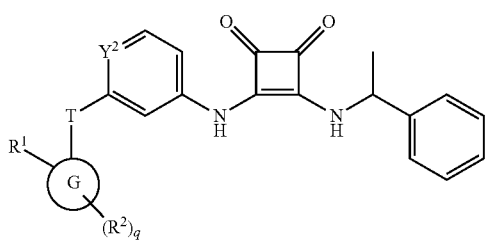

VI-a or a pharmaceutically acceptable salt thereof, wherein each of Ring G, $R^1$, $R^2$, $Y^2$, T, and q is as defined above and described in embodiments, classes and subclasses above and herein, singly or in combination.

In various embodiments, the invention provides a compound of formula VI-b:

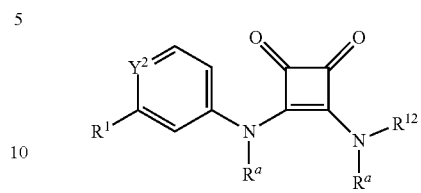

VI-b or a pharmaceutically acceptable salt thereof, wherein each of Ring G, $R^1$, $R^{12}$, $Y^2$, T, and q is as defined above and described in embodiments, classes and subclasses above and herein, singly or in combination.

In certain embodiments, the invention provides a compound selected from those depicted in Table 10:

TABLE 10

Exemplary Compounds of Formula VI

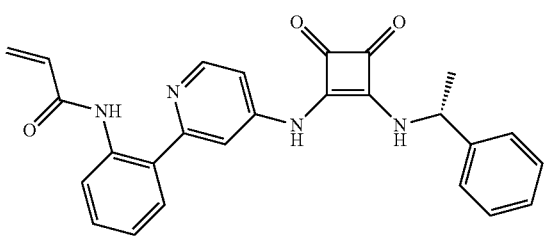 [SMILES: C=CC(=O)Nc1ccccc1-c1cc(Nc2c(N[C@H](C)c3ccccc3)c(=O)c2=O)ccn1]

VI-1

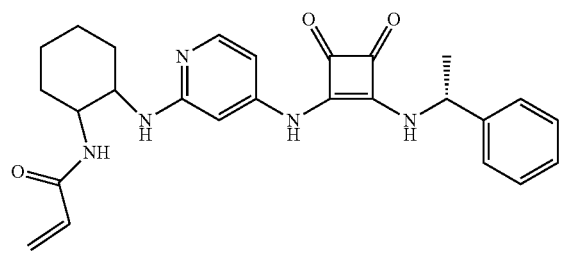 [SMILES: C=CC(=O)NC1CCCCC1Nc1cc(Nc2c(N[C@H](C)c3ccccc3)c(=O)c2=O)ccn1]

VI-2

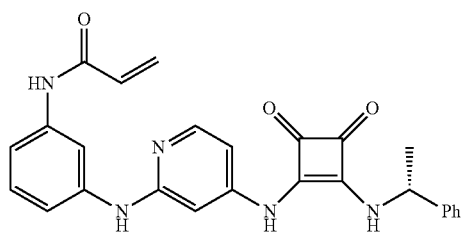 [SMILES: C=CC(=O)Nc1cccc(Nc2cc(Nc3c(N[C@H](C)c4ccccc4)c(=O)c3=O)ccn2)c1]

VI-3

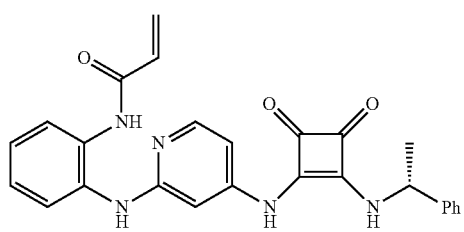 [SMILES: C=CC(=O)Nc1ccccc1Nc1cc(Nc2c(N[C@H](C)c3ccccc3)c(=O)c2=O)ccn1]

VI-4

TABLE 10-continued
Exemplary Compounds of Formula VI
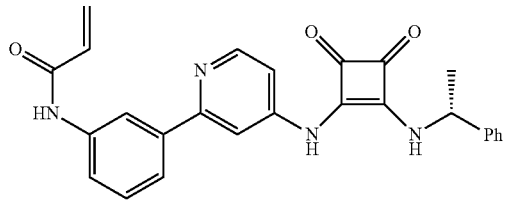 [SMILES: C=CC(=O)Nc1cccc(-c2cc(Nc3c(N[C@H](C)c4ccccc4)c(=O)c3=O)ccn2)c1]
VI-5
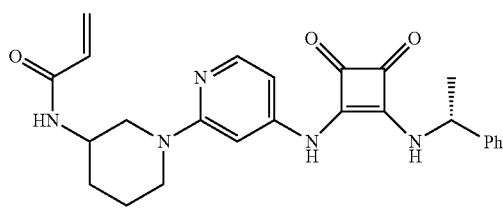 [SMILES: C=CC(=O)NC1CCCN(c2cc(Nc3c(N[C@H](C)c4ccccc4)c(=O)c3=O)ccn2)C1]
VI-6
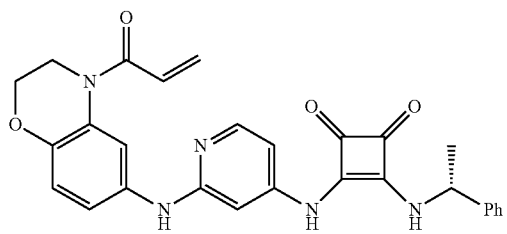 [SMILES: C=CC(=O)N1CCOc2ccc(Nc3cc(Nc4c(N[C@H](C)c5ccccc5)c(=O)c4=O)ccn3)cc21]
VI-7
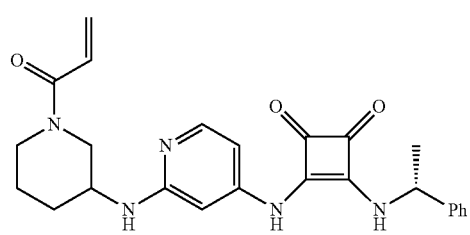 [SMILES: C=CC(=O)N1CCCC(Nc2cc(Nc3c(N[C@H](C)c4ccccc4)c(=O)c3=O)ccn2)C1]
VI-8
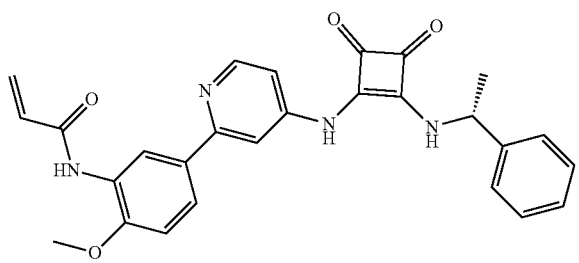
VI-9
and
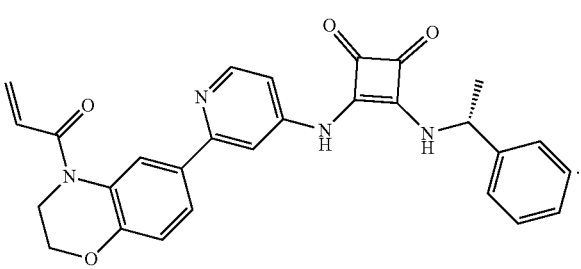 [SMILES: C=CC(=O)N1CCOc2ccc(-c3cc(Nc4c(N[C@H](C)c5ccccc5)c(=O)c4=O)ccn3)cc21]
VI-10

In some embodiments, the present invention provides a compound depicted in Table 10, above, or a pharmaceutically acceptable salt thereof.

In certain embodiments, the invention provides a compound selected from

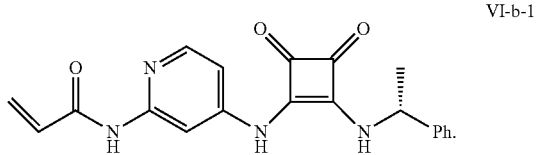 [SMILES: C=CC(=O)Nc1cc(Nc2c(N[C@H](C)c3ccccc3)c(=O)c2=O)ccn1]

VI-b-1

As defined generally above, the $R^1$ group of formulae I, II, II-e, III, III-d, IV, IV-b, V, and VI is a warhead group. In certain embodiments, $R^1$ is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and each $R^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, NO$_2$, or CN.

In certain embodiments, L is a covalent bond.

In certain embodiments, L is a bivalent $C_{1-8}$ saturated or unsaturated, straight or branched, hydrocarbon chain. In certain embodiments, L is —CH$_2$—.

In certain embodiments, L is a covalent bond, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—.

In certain embodiments, L is a bivalent $C_{1-8}$ hydrocarbon chain wherein at least one methylene unit of L is replaced by —C(O)—. In certain embodiments, L is a bivalent $C_{1-8}$ hydrocarbon chain wherein at least two methylene units of L are replaced by —C(O)—. In some embodiments, L is —C(O)CH$_2$CH$_2$C(O)—, —C(O)CH$_2$NHC(O)—, —C(O)CH$_2$NHC(O)CH$_2$CH$_2$C(O)—, or —C(O)CH$_2$CH$_2$CH$_2$NHC(O)CH$_2$CH$_2$C(O)—.

In certain embodiments, L is a bivalent $C_{1-8}$ hydrocarbon chain wherein at least one methylene unit of L is replaced by —S(O)$_2$—. In certain embodiments, L is a bivalent $C_{1-8}$ hydrocarbon chain wherein at least one methylene unit of L is replaced by —S(O)$_2$— and at least one methylene unit of L is replaced by —C(O)—. In certain embodiments, L is a bivalent $C_{1-8}$ hydrocarbon chain wherein at least one methylene unit of L is replaced by —S(O)$_2$— and at least two methylene units of L are replaced by —C(O)—. In some embodiments, L is —S(O)$_2$CH$_2$CH$_2$NHC(O)CH$_2$CH$_2$C(O)— or —S(O)$_2$CH$_2$CH$_2$NHC(O)—.

In some embodiments, L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—.

In certain embodiments, L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—.

In some embodiments, L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

As described above, in certain embodiments, L is a bivalent $C_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes —CH$_2$C(=CH$_2$)CH$_2$—. Thus, in some embodiments, L is a bivalent $C_{2-8}$ straight or branched, hydrocarbon chain wherein L has at least one alkylidenyl double bond. Exemplary L groups include —NHC(O)C(=CH$_2$)CH$_2$—.

In certain embodiments, L is a bivalent $C_{2-8}$ straight or branched, hydrocarbon chain wherein L has at least one double bond and at least one methylene unit of L is replaced by —C(O)—. In certain embodiments, L is —C(O)CH=CH(CH$_3$)—, —C(O)CH=CHCH$_2$NH(CH$_3$)—, —C(O)CH=CH(CH$_3$)—, —C(O)CH=CH—, —CH$_2$C(O)CH=CH—, —CH$_2$C(O)CH=CH(CH$_3$)—, —CH$_2$CH$_2$C(O)CH=CH—, —CH$_2$CH$_2$C(O)CH=CHCH$_2$—, —CH$_2$CH$_2$C(O)CH=CHCH$_2$NH(CH$_3$)—, or —CH$_2$CH$_2$C(O)CH=CH(CH$_3$)—, or —CH(CH$_3$)OC(O)CH=CH—.

In certain embodiments, L is a bivalent $C_{2-8}$ straight or branched, hydrocarbon chain wherein L has at least one double bond and at least one methylene unit of L is replaced by —OC(O)—.

In some embodiments, L is a bivalent $C_{2-8}$ straight or branched, hydrocarbon chain wherein L has at least one double bond and at least one methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—. In some embodiments, L is —CH$_2$OC(O)CH=CHCH$_2$—, —CH$_2$—OC(O)CH=CH—, or —CH(CH=CH$_2$)OC(O)CH=CH—.

In certain embodiments, L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH₂CH₂NRC(O)—, or —CH₂NRC(O)cyclopropylene-, wherein each R is independently hydrogen or optionally substituted C₁₋₆ aliphatic.

In certain embodiments, L is —NHC(O)CH═CH—, —NHC(O)CH═CHCH₂N(CH₃)—, —NHC(O)CH═CHCH₂O—, —CH₂NHC(O)CH═CH—, —NHSO₂CH═CH—, —NHSO₂CH═CHCH₂—, —NHC(O)(C═N₂)C(O)—, —NHC(O)CH═CHCH₂N(CH₃)—, —NHSO₂CH═CH—, —NHSO₂CH═CHCH₂—, —NHC(O)CH═CHCH₂O—, —NHC(O)C(═CH₂)CH₂—, —CH₂NHC(O)—, —CH₂NHC(O)CH═CH—, —CH₂CH₂NHC(O)—, or —CH₂NHC(O)cyclopropylene-.

In some embodiments, L is a bivalent C₂₋₈ straight or branched, hydrocarbon chain wherein L has at least one triple bond. In certain embodiments, L is a bivalent C₂₋₈ straight or branched, hydrocarbon chain wherein L has at least one triple bond and one or two additional methylene units of L are optionally and independently replaced by —NRC(O)—, —C(O)NR—, —S—, —S(O)—, —SO₂—, —C(═S)—, —C(═NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —OC(O)—, or —O—.

Exemplary L groups include —C≡C—, —C≡CCH₂N(isopropyl)-, —NHC(O)C≡CCH₂CH₂—, —CH₂—C≡C—CH₂—, —C≡CCH₂O—, —CH₂C(O)C≡C—, —C(O)C≡C—, or —CH₂OC(═O)C≡C—.

In certain embodiments, L is a bivalent C₂₋₈ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO₂—, or —SO₂N(R)—. Exemplary L groups include —NHC(O)-cyclopropylene-SO₂— and —NHC(O)— cyclopropylene-.

As defined generally above, Y is hydrogen, C₁₋₆ aliphatic optionally substituted with oxo, halogen, NO₂, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 Rᵉ groups, each Rᵉ is independently selected from -Q-Z, oxo, NO₂, halogen, CN, a suitable leaving group, or C₁₋₆ aliphatic, wherein Q is a covalent bond or a bivalent C₁₋₆ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO₂—, —N(R)C(O)—, —C(O)N(R)—, —N(R)SO₂—, or —SO₂N(R)—; and, Z is hydrogen or C₁₋₆ aliphatic optionally substituted with oxo, halogen, NO₂, or CN.

In certain embodiments, Y is hydrogen.

In certain embodiments, Y is C₁₋₆ aliphatic optionally substituted with oxo, halogen, NO₂, or CN. In some embodiments, Y is C₂₋₆ alkenyl optionally substituted with oxo, halogen, NO₂, or CN. In other embodiments, Y is C₂₋₆ alkynyl optionally substituted with oxo, halogen, NO₂, or CN. In some embodiments, Y is C₂₋₆ alkenyl. In other embodiments, Y is C₂₋₄ alkynyl.

In other embodiments, Y is C₁₋₆ alkyl substituted with oxo, halogen, NO₂, or CN. Such Y groups include —CH₂F, —CH₂Cl, —CH₂CN, and —CH₂NO₂.

In certain embodiments, Y is a saturated 3-6 membered monocyclic ring having 0-3 heteroatoms independently selected from nitrogen, oxygen, or sulfur, wherein Y is substituted with 1-4 Rᵉ groups, wherein each Rᵉ is as defined above and described herein.

In some embodiments, Y is a saturated 3-4 membered heterocyclic ring having 1 heteroatom selected from oxygen or nitrogen wherein said ring is substituted with 1-2 Rᵉ groups, wherein each Rᵉ is as defined above and described herein. Exemplary such rings are epoxide and oxetane rings, wherein each ring is substituted with 1-2 Rᵉ groups, wherein each Rᵉ is as defined above and described herein.

In other embodiments, Y is a saturated 5-6 membered heterocyclic ring having 1-2 heteroatom selected from oxygen or nitrogen wherein said ring is substituted with 1-4 Rᵉ groups, wherein each Rᵉ is as defined above and described herein. Such rings include piperidine and pyrrolidine, wherein each ring is substituted with 1-4 Rᵉ groups, wherein each Rᵉ is as defined above and described herein. In certain embodiments, Y is

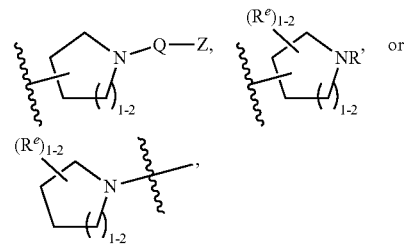

wherein each R, Q, Z, and Rᵉ is as defined above and described herein. In certain embodiments, Y is piperazine.

In some embodiments, Y is a saturated 3-6 membered carbocyclic ring, wherein said ring is substituted with 1-4 Rᵉ groups, wherein each Rᵉ is as defined above and described herein. In certain embodiments, Y is cyclopropyl, cyclobutyl, cyclopentyl, or cyclohexyl, wherein each ring is substituted with 1-4 Rᵉ groups, wherein each Rᵉ is as defined above and described herein. In certain embodiments, Y is

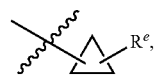

wherein R is as defined above and described herein. In certain embodiments, Y is cyclopropyl optionally substituted with halogen, CN or NO₂.

In certain embodiments, Y is a partially unsaturated 3-6 membered monocyclic ring having 0-3 heteroatoms independently selected from nitrogen, oxygen, or sulfur, wherein said ring is substituted with 1-4 Rᵉ groups, wherein each Rᵉ is as defined above and described herein.

In some embodiments, Y is a partially unsaturated 3-6 membered carbocyclic ring, wherein said ring is substituted with 1-4 Rᵉ groups, wherein each Rᵉ is as defined above and described herein. In some embodiments, Y is cyclopropenyl, cyclobutenyl, cyclopentenyl, or cyclohexenyl wherein each ring is substituted with 1-4 Rᵉ groups, wherein each Rᵉ is as defined above and described herein. In certain embodiments, Y is

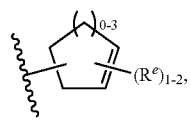

wherein each Rᵉ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein. In certain embodiments, Y is selected from:

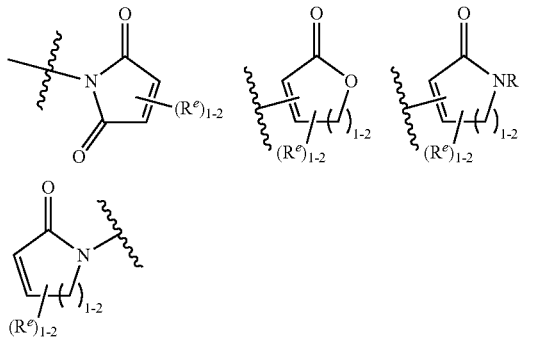

wherein each R and $R^e$ is as defined above and described herein.

In certain embodiments, Y is a 6-membered aromatic ring having 0-2 nitrogens wherein said ring is substituted with 1-4 $R^e$ groups, wherein each $R^e$ group is as defined above and described herein. In certain embodiments, Y is phenyl, pyridyl, or pyrimidinyl, wherein each ring is substituted with 1-4 $R^e$ groups, wherein each $R^e$ is as defined above and described herein.

In some embodiments, Y is selected from:

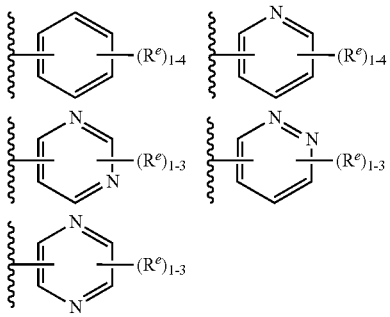

wherein each $R^e$ is as defined above and described herein.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above and described herein. In certain embodiments, Y is selected from:

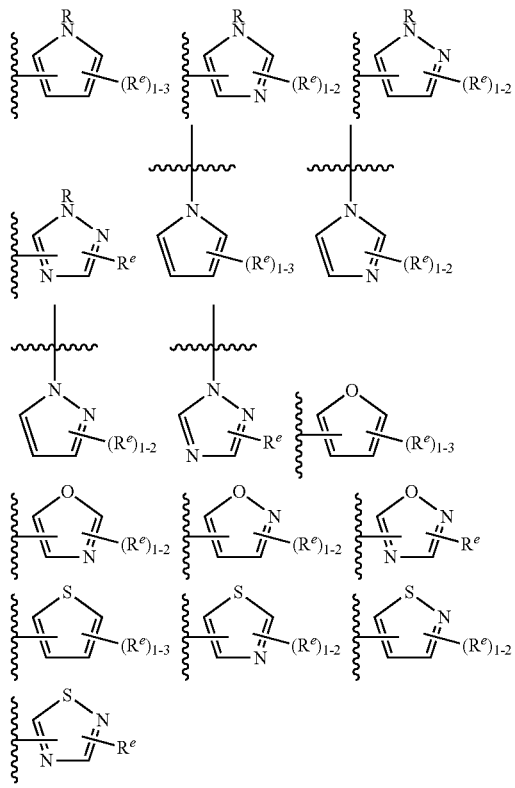

wherein each R and $R^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above and described herein. Exemplary such bicyclic rings include 2,3-dihydrobenzo[d]isothiazole, wherein said ring is substituted with 1-4 $R^e$ groups, wherein $R^e$ is as defined above and described herein.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —SO$_2$—. In other embodiments, Q is a bivalent C$_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —SO$_2$—. In certain embodiments, the Z moiety of the R$^e$ group is hydrogen. In some embodiments, -Q-Z is —NHC(O)CH=CH$_2$ or —C(O)CH=CH$_2$.

In certain embodiments, each R$^e$ is independently selected from oxo, NO$_2$, CN, fluoro, chloro, —NHC(O)CH=CH$_2$, —C(O)CH=CH$_2$, —CH$_2$CH=CH$_2$, —C≡CH, —C(O)OCH$_2$Cl, —C(O)OCH$_2$F, —C(O)OCH$_2$CN, —C(O)CH$_2$Cl, —C(O)CH$_2$F, —C(O)CH$_2$CN, or —CH$_2$C(O)CH$_3$.

In certain embodiments, R$^e$ is a suitable leaving group, is a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyloxy, and diazonium moieties. Examples of suitable leaving groups include chloro, iodo, bromo, fluoro, acetoxy, methanesulfonyloxy (mesyloxy), tosyloxy, triflyloxy, nitrophenylsulfonyloxy (nosyloxy), and bromo-phenylsulfonyloxy (brosyloxy).

In certain embodiments, the following embodiments and combinations of -L-Y apply:

(a) L is a bivalent C$_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen or C$_{1-6}$ aliphatic optionally substituted with oxo, halogen, NO$_2$, or CN; or (b) L is a bivalent C$_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or (c) L is a bivalent C$_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or (d) L is a bivalent C$_{2-8}$ straight or branched, hydrocarbon chain wherein L has at least one double bond and at least one methylene unit of L is replaced by —C(O)—; and Y is hydrogen or C$_{1-6}$ aliphatic optionally substituted with oxo, halogen, NO$_2$, or CN; or (e) L is a bivalent C$_{2-8}$ straight or branched, hydrocarbon chain wherein L has at least one double bond and at least one methylene unit of L is replaced by —OC(O)—; and Y is hydrogen or C$_{1-6}$ aliphatic optionally substituted with oxo, halogen, NO$_2$, or CN; or (f) L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene-; wherein R is H or optionally substituted C$_{1-6}$ aliphatic; and Y is hydrogen or C$_{1-6}$ aliphatic optionally substituted with oxo, halogen, NO$_2$, or CN; or (g) L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)—, —NHC(O)(C=N$_2$)C(O)—, —NHC(O)CH=CHCH$_2$N(CH$_3$)—, —NHSO$_2$CH=CH—, —NHSO$_2$CH=CHCH$_2$—, —NHC(O)CH=CHCH$_2$O—, —NHC(O)C(=CH$_2$)CH$_2$—, —CH$_2$NHC(O)—, —CH$_2$NHC(O)CH=CH—, —CH$_2$CH$_2$NHC(O)—, or —CH$_2$NHC(O)cyclopropylene-; and Y is hydrogen or C$_{1-6}$ aliphatic optionally substituted with oxo, halogen, NO$_2$, or CN; or (h) L is a bivalent C$_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or (i) is a bivalent C$_{2-8}$ straight or branched, hydrocarbon chain wherein L has at least one triple bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, or —C(O)O—, and Y is hydrogen or C$_{1-6}$ aliphatic optionally substituted with oxo, halogen, NO$_2$, or CN; or (j) L is —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$OC(=O)C≡C—; and Y is hydrogen or C$_{1-6}$ aliphatic optionally substituted with oxo, halogen, NO$_2$, or CN; or (k) L is a bivalent C$_{2-8}$ straight or branched, hydrocarbon chain wherein one methylene unit of L is replaced by cyclopropylene and one or two additional methylene units of L are independently replaced by —NRC(O)—, —C(O)NR—, —N(R)SO$_2$—, —SO$_2$N(R)—, —S—, —S(O)—, —SO$_2$—, —OC(O)—, or —C(O)O—; and Y is hydrogen or C$_{1-6}$ aliphatic optionally substituted with oxo, halogen, NO$_2$, or CN; or (l) L is a covalent bond and Y is selected from:
(i) C$_{1-6}$ alkyl substituted with oxo, halogen, NO$_2$, or CN;
(ii) C$_{2-6}$ alkenyl optionally substituted with oxo, halogen, NO$_2$, or CN; or
(iii) C$_{2-6}$ alkynyl optionally substituted with oxo, halogen, NO$_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or

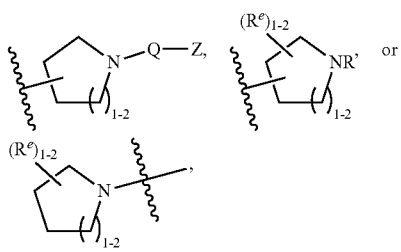

(vi)

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or

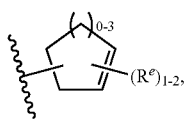

(x)

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or

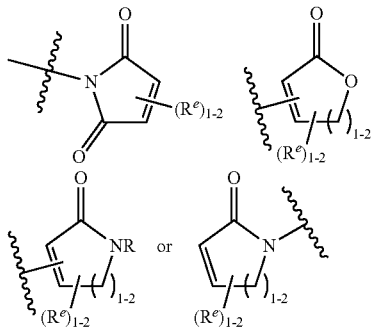

(xii)

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or

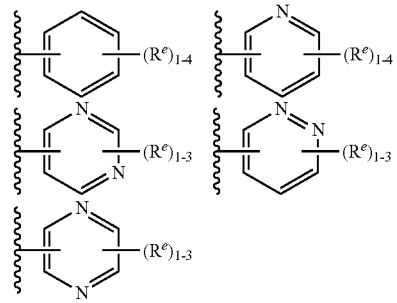

(xiv)

wherein each $R^e$ is as defined above and described herein; or
(xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or

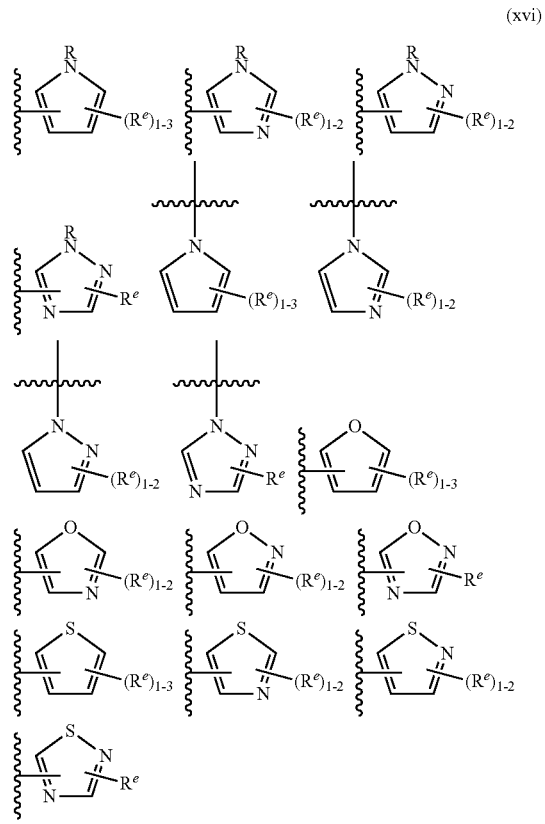

(xvi)

wherein each R and $R^e$ is as defined above and described herein; or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;
(m) L is —C(O)— and Y is selected from:
(i) $C_{1-6}$ alkyl substituted with oxo, halogen, $NO_2$, or CN; or
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

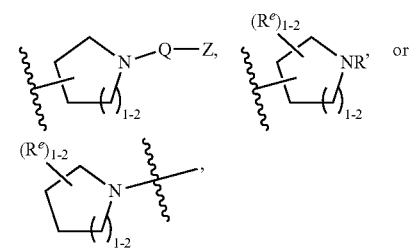

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or (x)

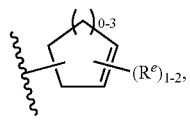

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

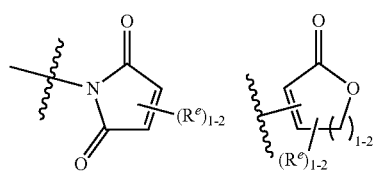

-continued

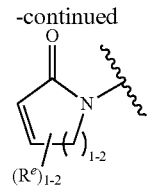

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or (xiv)

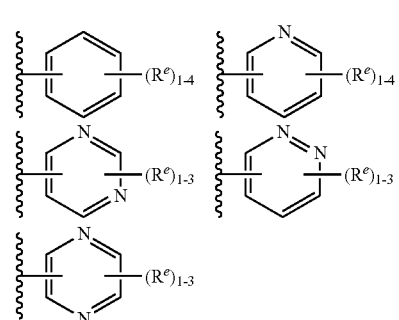

wherein each $R^e$ is as defined above and described herein; or
(xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

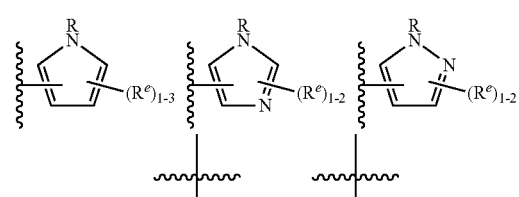

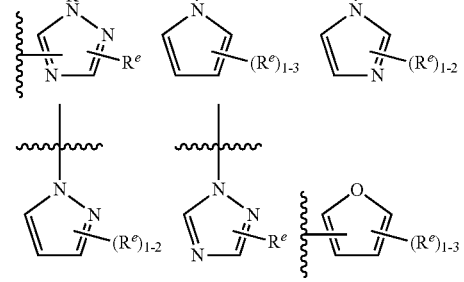

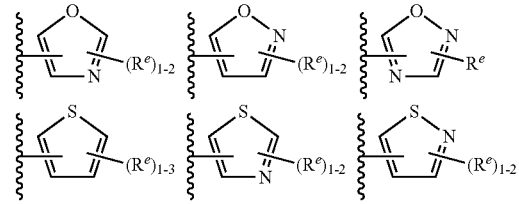

-continued

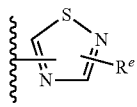

wherein each R and R$^e$ is as defined above and described herein; or
(xvii) an 8-10 membered bicyclic, saturated, partially unsaturated, or aryl ring having 0-3 heteroatoms independently selected from nitrogen, oxygen, or sulfur, wherein said ring is substituted with 1-4 R$^e$ groups, wherein R$^e$ is as defined above and described herein;
(n) L is —N(R)C(O)— and Y is selected from:
(i) $C_{1-6}$ alkyl substituted with oxo, halogen, $NO_2$, or CN; or
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or
(v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or (vi)

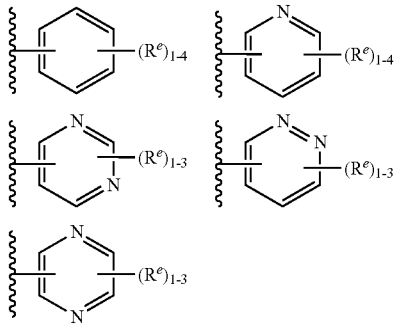

wherein each R, Q, Z, and R$^e$ is as defined above and described herein; or
(vii) a saturated 3-6 membered carbocyclic ring, wherein said ring is substituted with 1-4 R$^e$ groups, wherein each R$^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein; or
(ix) a partially unsaturated 3-6 membered carbocyclic ring, wherein said ring is substituted with 1-4 R$^e$ groups, wherein each R$^e$ is as defined above and described herein; or (x)

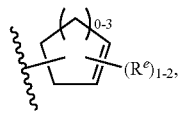

wherein each R$^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 R$^e$ groups, wherein each R$^e$ is as defined above and described herein; or (xii)

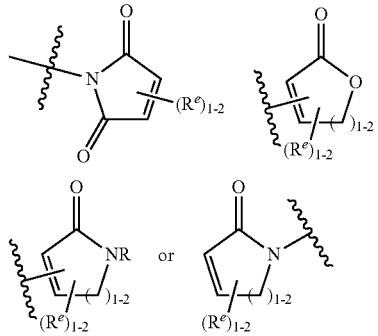

wherein each R and R$^e$ is as defined above and described herein; or
(xiii) a 6-membered aromatic ring having 0-2 nitrogens wherein said ring is substituted with 1-4 R$^e$ groups, wherein each R$^e$ group is as defined above and described herein; or (xiv)

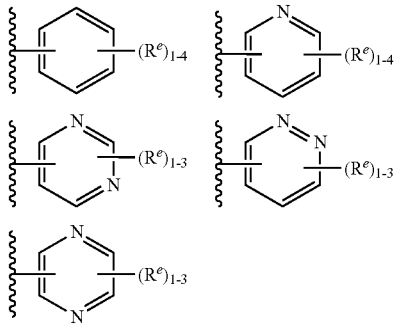

wherein each R$^e$ is as defined above and described herein; or
(xv) a 5-membered heteroaryl ring having 1-3 heteroatoms independently selected from nitrogen, oxygen, or sulfur, wherein said ring is substituted with 1-3 R$^e$ groups, wherein each R$^e$ group is as defined above and described herein; or (xvi)

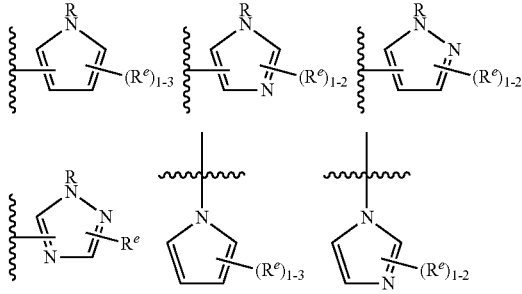

-continued

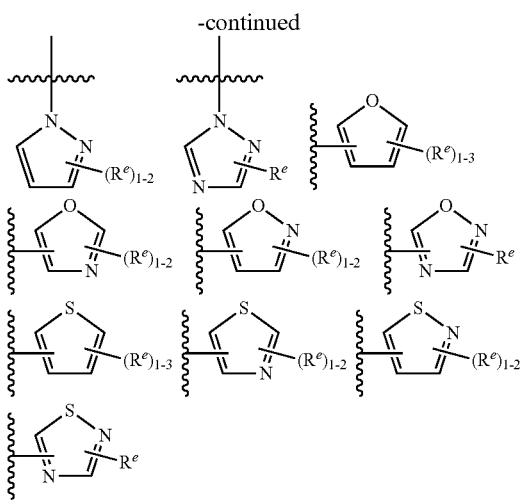

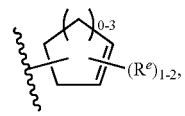

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(o) L is a bivalent $C_{1-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

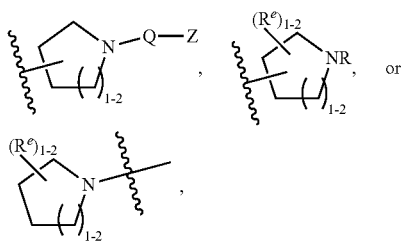

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

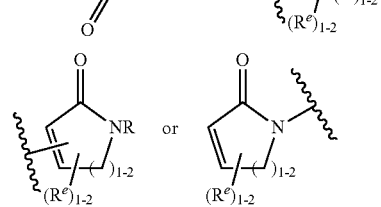

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

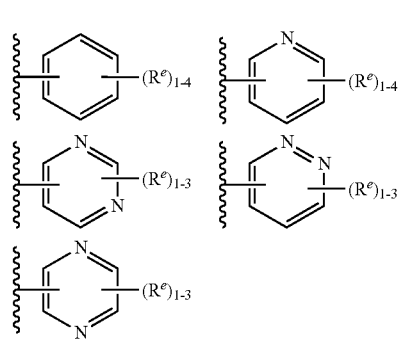

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

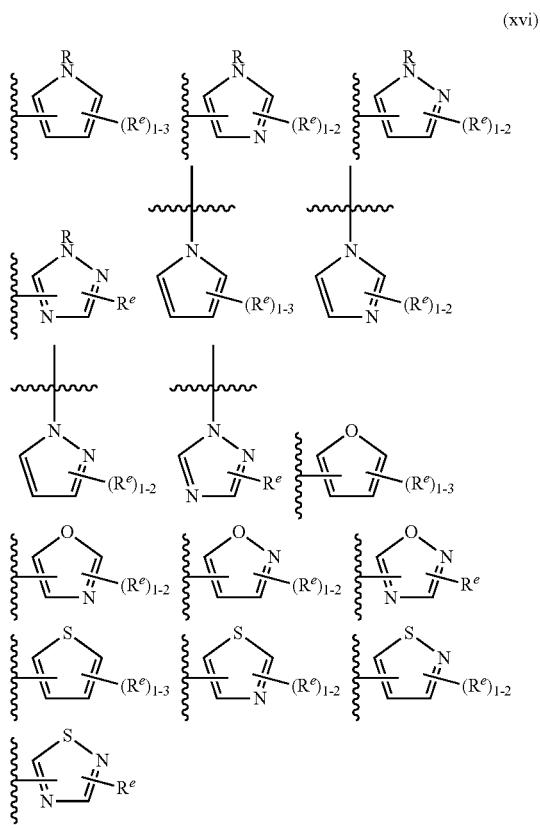

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(p) L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—; and Y is selected from:

(i) C$_{1-6}$ alkyl substituted with oxo, halogen, NO$_2$, or CN; or
(ii) C$_{2-6}$ alkenyl optionally substituted with oxo, halogen, NO$_2$, or CN; or
(iii) C$_{2-6}$ alkynyl optionally substituted with oxo, halogen, NO$_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

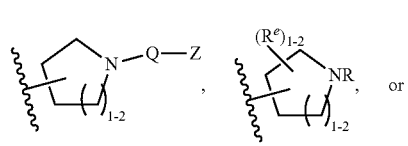

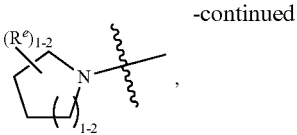

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or (x)

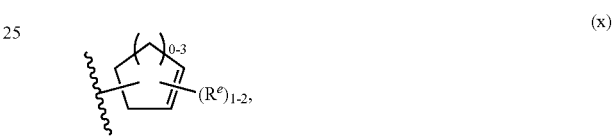

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

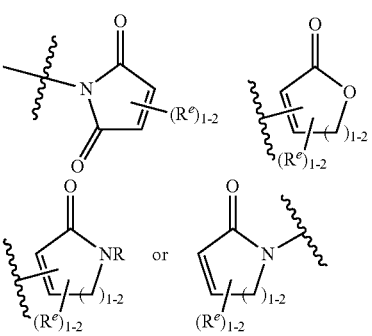

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

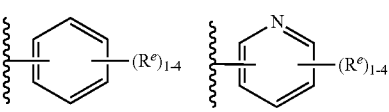

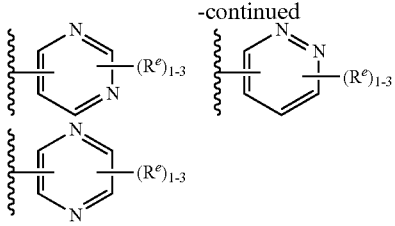

wherein each $R^e$ is as defined above and described herein; or
(xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

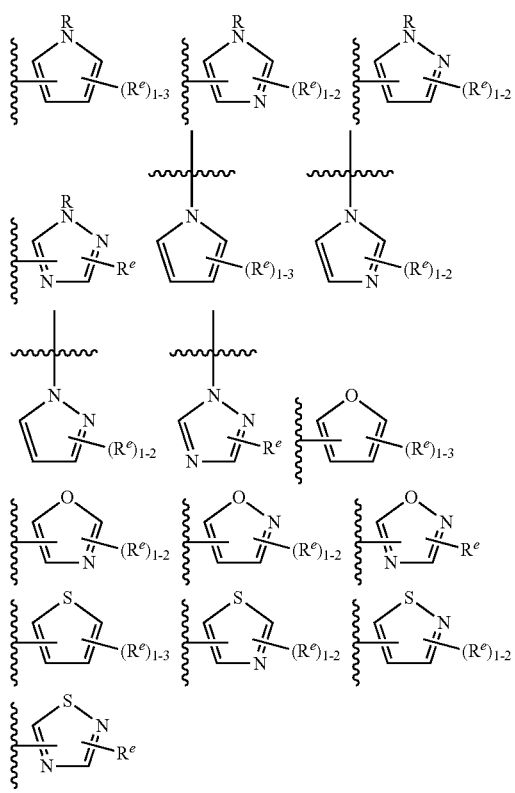

wherein each R and $R^e$ is as defined above and described herein; or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.
(q) L is a bivalent $C_{2-8}$ straight or branched, hydrocarbon chain wherein two or three methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen or $C_{1-6}$ aliphatic optionally substituted with oxo, halogen, NO$_2$, or CN.
(r) L-Y is "pro-warhead" that is converted in vitro or in vivo to an irreversible warhead. In certain embodiments, L-Y is

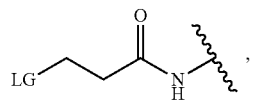

wherein LG is a leaving group as understood by one of ordinary skill in the art. In certain embodiments, L-Y is

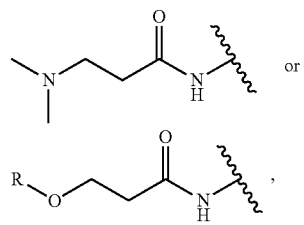

wherein R is as defined and described above and herein. In certain embodiments, the "pro-warhead" is converted to a warhead group (e.g., an acrylamide group) according to the following:

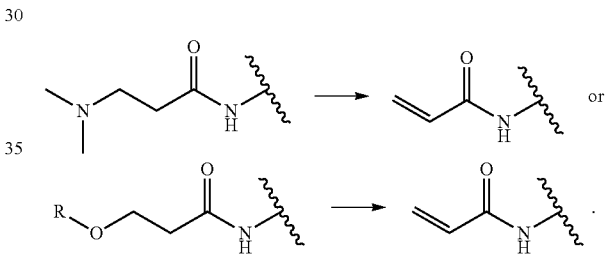

Such "pro-warheads" are applicable to any α,β unsaturated system, e.g.,

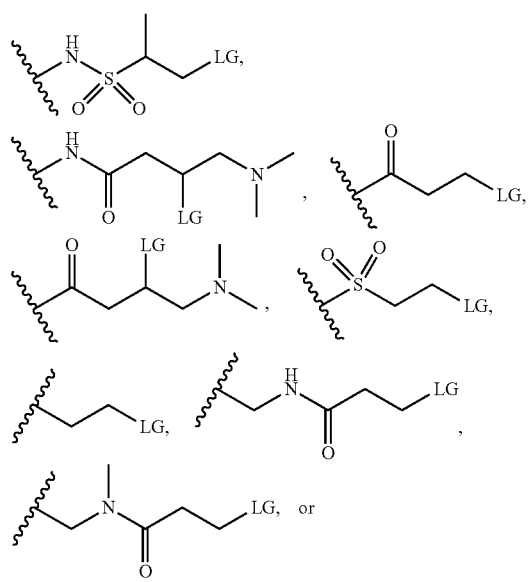

-continued

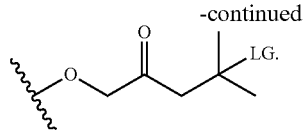

In certain embodiments, $R^1$ is -L-Y, wherein:

L is a covalent bond or a bivalent $C_{1-8}$ saturated or unsaturated, straight or branched, hydrocarbon chain, wherein one, two, or three methylene units of L are optionally and independently replaced by —N(R)C(O)—, —N(R)SO₂—, —O—, —C(O)—, or —SO₂—; and Y is hydrogen, or $C_{1-6}$ aliphatic optionally substituted with oxo, halogen, $N(R)_2$, $NO_2$, or CN.

In certain embodiments, the Y group of an $R^1$ warhead group is selected from those set forth in Table 11, below, wherein each wavy line indicates the point of attachment to the rest of the molecule.

TABLE 11

| Exemplary Y groups: | |
|---|---|
| 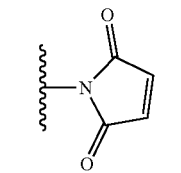 [SMILES: *N1C(=O)C=CC1=O] | a |
| 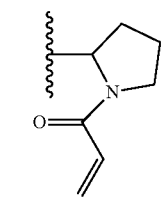 [SMILES: *C1CCCN1C(=O)C=C] | b |
| 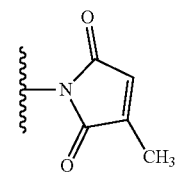 [SMILES: *N1C(=O)C=C(C)C1=O] | c |
| 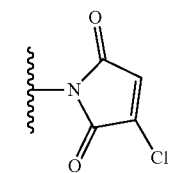 [SMILES: *N1C(=O)C=C(Cl)C1=O] | d |
| 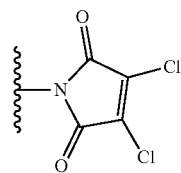 [SMILES: *N1C(=O)C(Cl)=C(Cl)C1=O] | e |
| 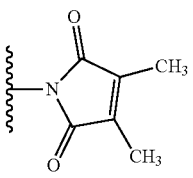 [SMILES: *N1C(=O)C(C)=C(C)C1=O] | f |

TABLE 11-continued

| Exemplary Y groups: | |
|---|---|
| 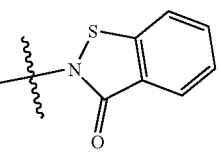 | g |
| 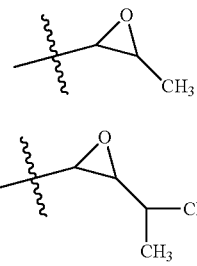 | h |
| 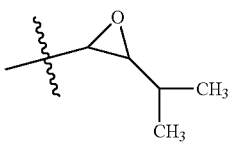 [SMILES: *C1OC1C(C)C] | i |
| 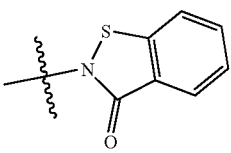 [SMILES: *n1sc2ccccc2c1=O] | j |
| 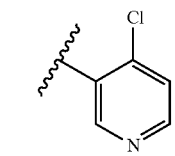 | k |
| 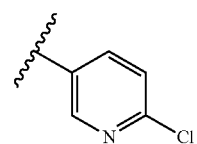 [SMILES: *c1ccc(Cl)nc1] | l |
| 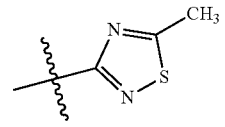 [SMILES: *c1nsc(C)n1] | m |
| 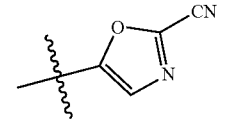 [SMILES: *c1cnc(C#N)o1] | n |
| 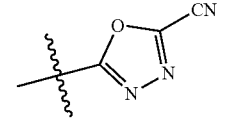 [SMILES: *c1nnc(C#N)o1] | o |
| 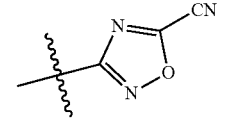 [SMILES: *c1noc(C#N)n1] | p |
| 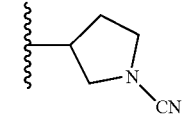 [SMILES: *C1CCN(C#N)C1] | q |

TABLE 11-continued
Exemplary Y groups:
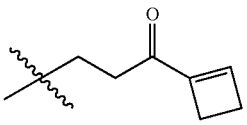 [SMILES: *CCC(=O)C1=CCC1] r
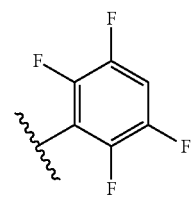 s
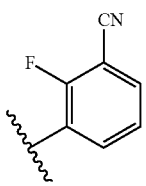 [SMILES: *c1cccc(C#N)c1F] t
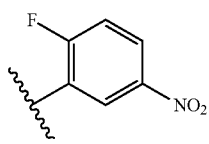 [SMILES: *c1cc([N+](=O)[O-])ccc1F] u
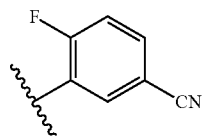 [SMILES: *c1cc(C#N)ccc1F] v
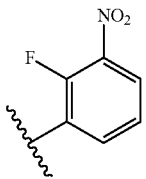 [SMILES: *c1cccc([N+](=O)[O-])c1F] w
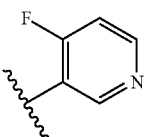 x
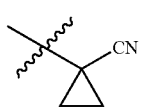 [SMILES: *C1(C#N)CC1] y
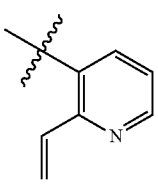 [SMILES: *c1cccnc1C=C] z
TABLE 11-continued
Exemplary Y groups:
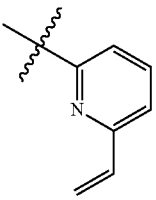 [SMILES: *c1cccc(C=C)n1] aa
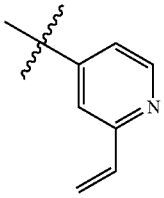 [SMILES: *c1ccnc(C=C)c1] bb
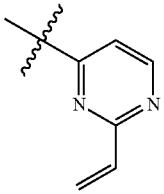 [SMILES: *c1ccnc(C=C)n1] cc
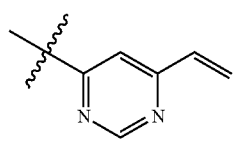 [SMILES: *c1cc(C=C)ncn1] dd
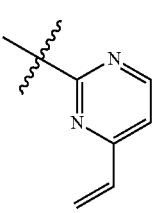 [SMILES: *c1nccc(C=C)n1] ee
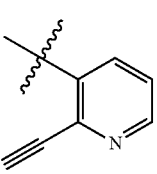 [SMILES: *c1cccnc1C#C] ff
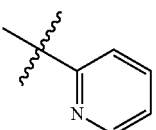 gg
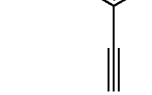 
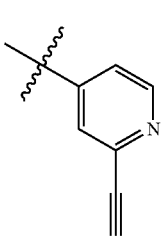 [SMILES: *c1ccnc(C#C)c1] hh TABLE 11-continued
Exemplary Y groups:
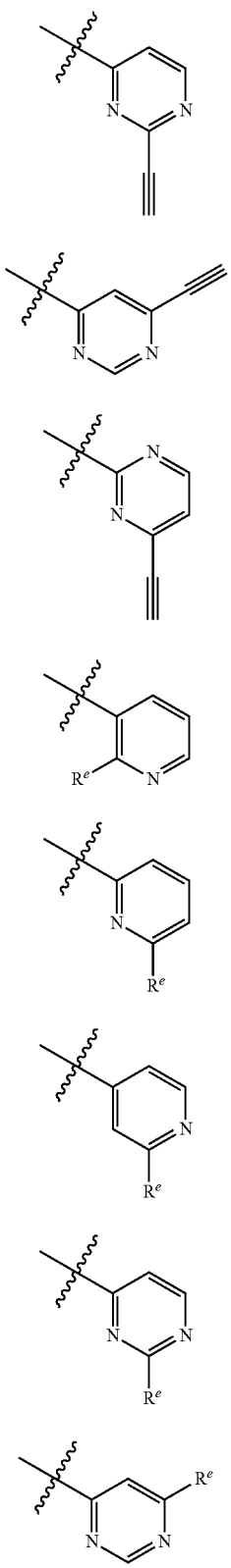
ii
jj
kk
ll
mm
nn
oo
pp
TABLE 11-continued
Exemplary Y groups:
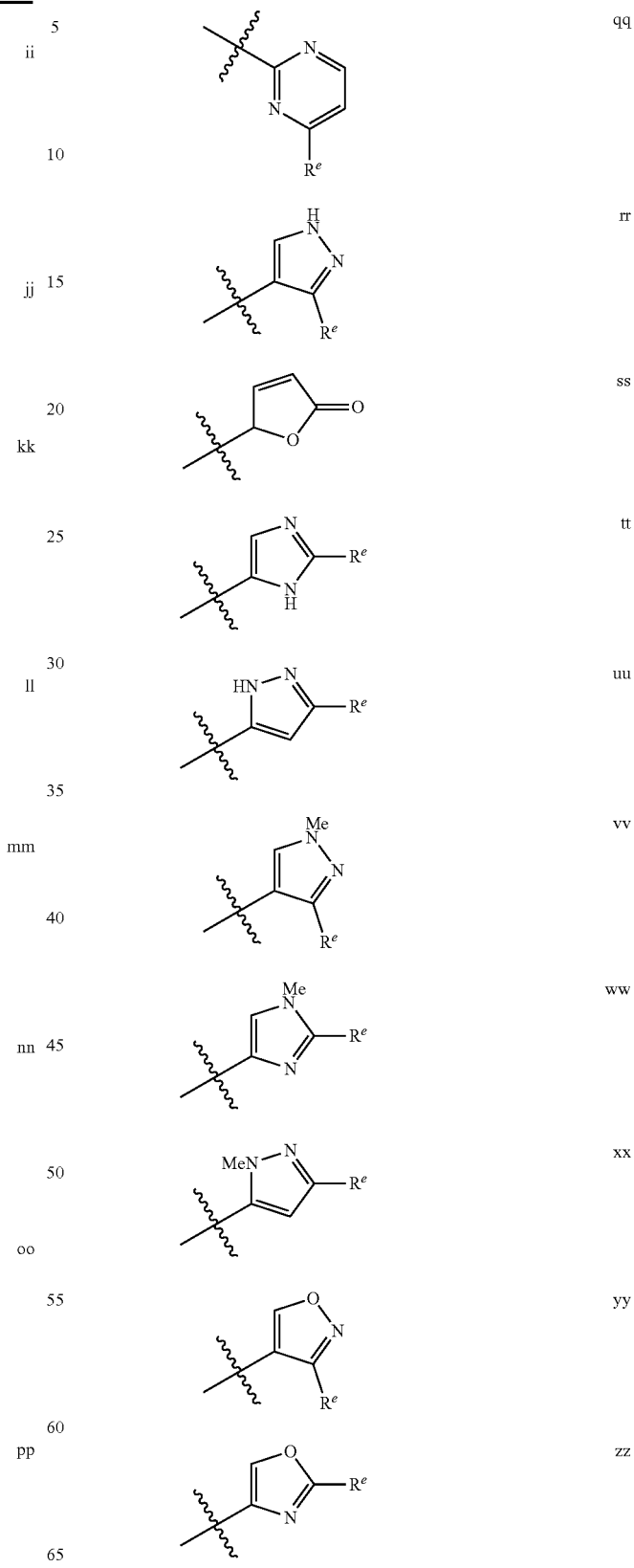
qq
rr
ss
tt
uu
vv
ww
xx
yy
zz TABLE 11-continued
Exemplary Y groups:
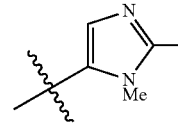 aaa
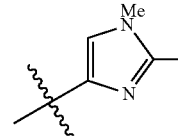 bbb
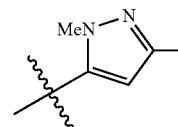 ccc
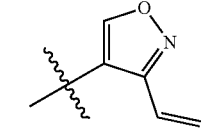 [SMILES: *c1conc1C=C] ddd
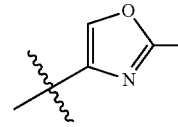 eee
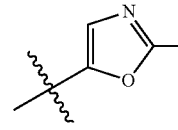 fff
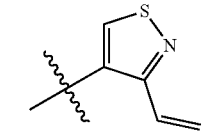 ggg
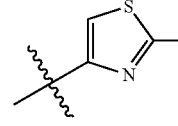 hhh
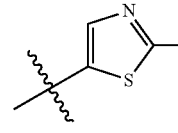 iii
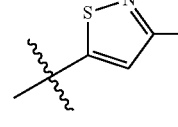 jjj
TABLE 11-continued
Exemplary Y groups:
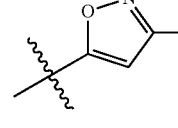 kkk
lll
mmm
nnn
ooo
ppp
qqq
rrr
sss
ttt
uuu TABLE 11-continued
Exemplary Y groups:
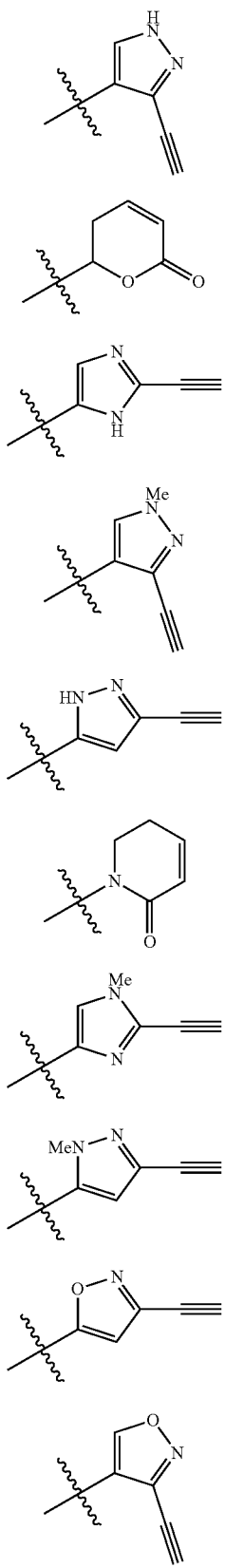
vvv
qqq
www
xxx
yyy
zzz
aaaa
bbbb
cccc
dddd
TABLE 11-continued
Exemplary Y groups:
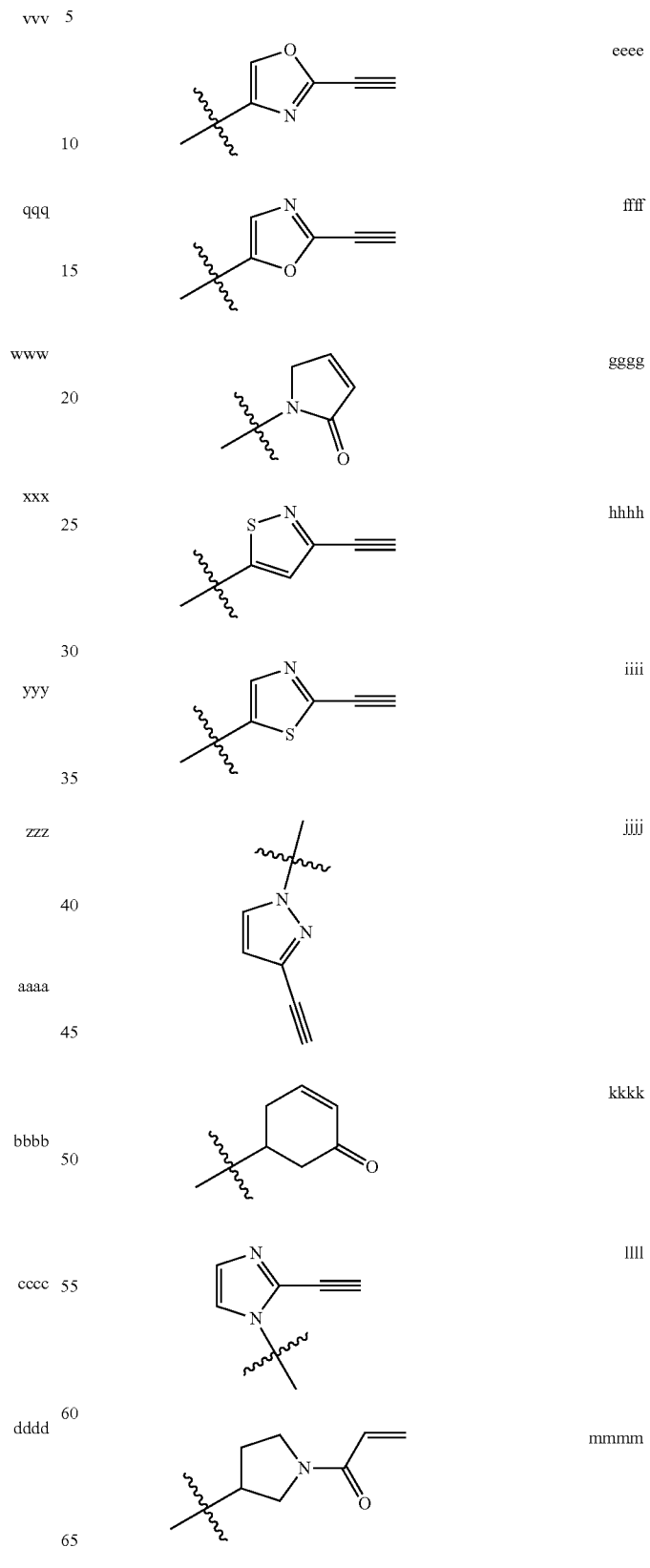
eeee
ffff
gggg
hhhh
iiii
jjjj
kkkk
llll
mmmm TABLE 11-continued Exemplary Y groups:

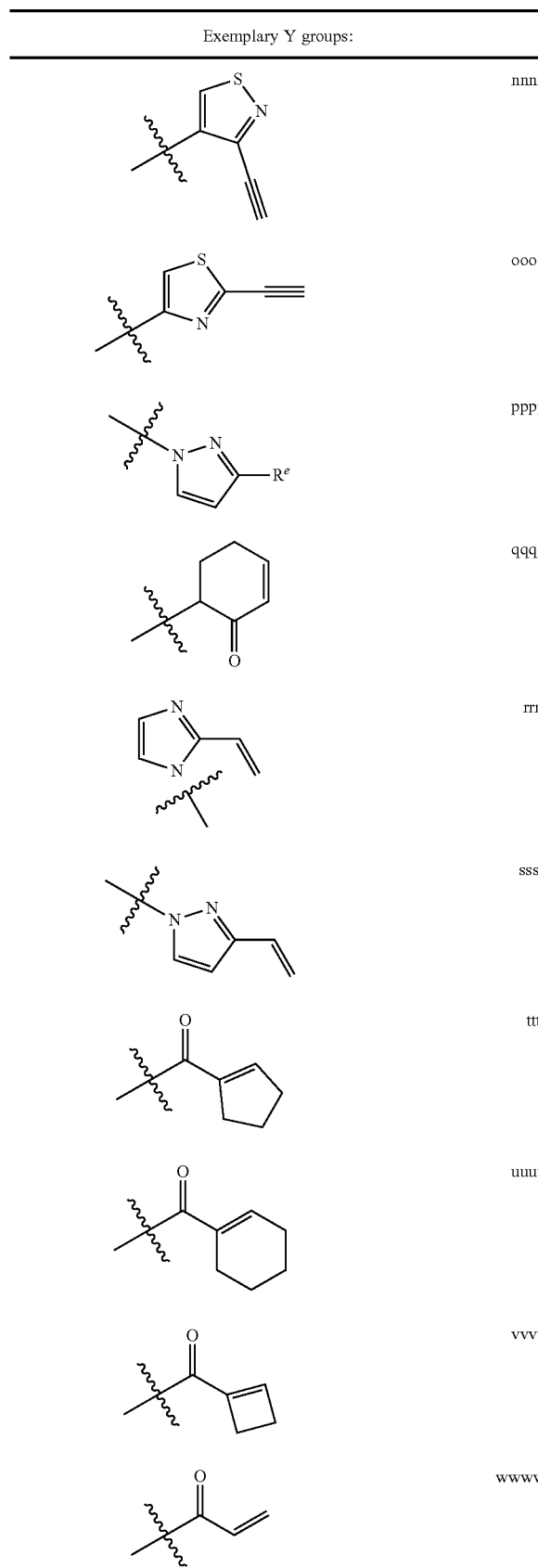
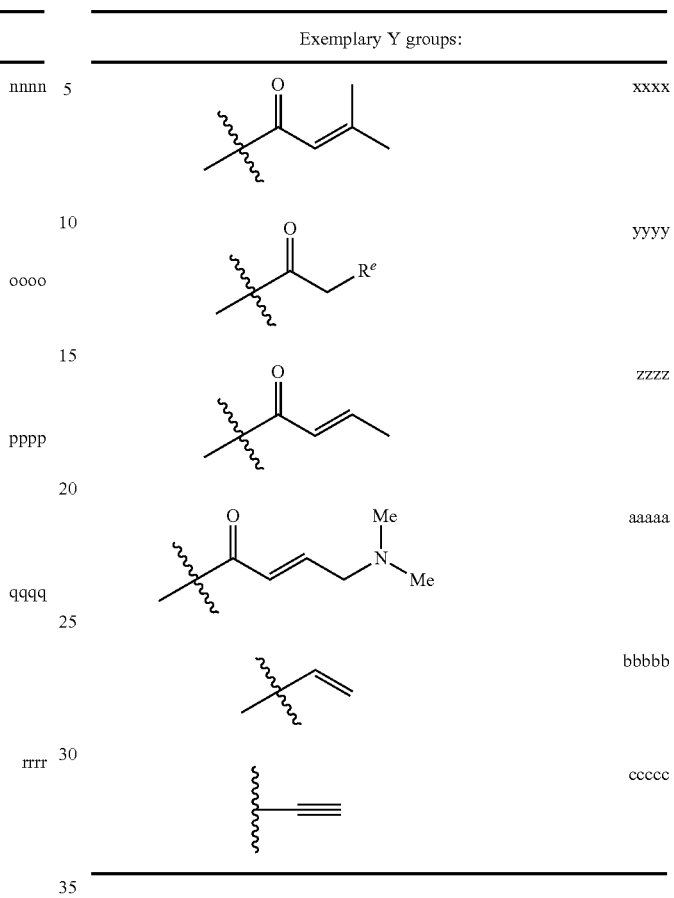

wherein each $R^e$ is independently a suitable leaving group, $NO_2$, CN, or oxo.

In certain embodiments, $R^1$ is —C≡CH, C≡CCH₂NH (isopropyl), —NHC(O)C≡CCH₂CH₃, —CH₂—C≡C—CH₃, —C≡CCH₂OH, —CH₂C(O)C≡CH, —C(O)C≡CH, or —CH₂OC(=O)C≡CH. In some embodiments, $R^1$ is selected from —NHC(O)CH=CH₂, —NHC(O)CH=CHCH₂N(CH₃)₂, or —CH₂NHC(O)CH=CH₂.

In some embodiments, $R^1$ is 6-12 atoms long. In certain embodiments, $R^1$ is 6-9 atoms long. In certain embodiments, $R^1$ is 10-12 atoms long. In certain embodiments, $R^1$ is at least 8 atoms long.

In certain embodiments, $R^1$ is —C(O)CH₂CH₂C(O)CH=C(CH₃)₂, —C(O)CH₂CH₂C(O)CH=CH(cyclopropyl), —C(O)CH₂CH₂C(O)CH=CHCH₃, —C(O)CH₂CH₂C(O)CH=CHCH₂CH₃, or —C(O)CH₂CH₂C(O)C(=CH₂)CH₃. In certain embodiments, $R^1$ is —C(O)CH₂NHC(O)CH=CH₂, —C(O)CH₂NHC(O)CH₂CH₂C(O)CH=CHCH₃, or —C(O)CH₂NHC(O)CH₂CH₂C(O)C(=CH₂)CH₃. In certain embodiments, $R^1$ is —S(O)₂CH₂CH₂NHC(O)CH₂CH₂C(O)CH=C(CH₃)₂, S(O)₂CH₂CH₂NHC(O)CH₂CH₂C(O)CH=CHCH₃, or S(O)₂CH₂CH₂NHC(O)CH₂CH₂C(O)CH=CH₂. In certain embodiments, $R^1$ is —C(O)(CH₂)₃NHC(O)CH₂CH₂C(O)CH=CHCH₃ or —C(O)(CH₂)₃NHC(O)CH₂CH₂C(O)CH=CH₂.

In certain embodiments, $R^1$ is selected from those set forth in Table 12, below, wherein each wavy line indicates the point of attachment to the rest of the molecule.

TABLE 12
Exemplary R¹ Groups
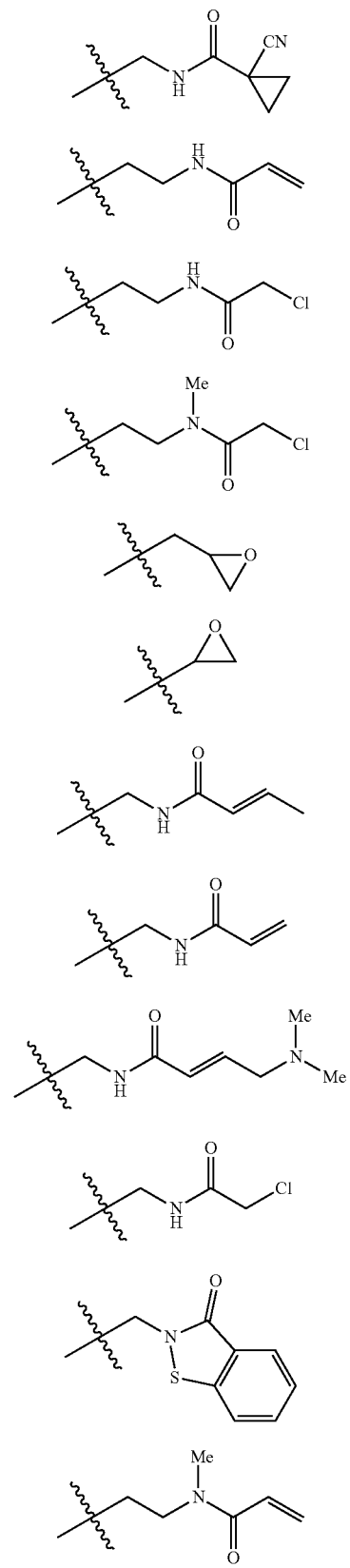
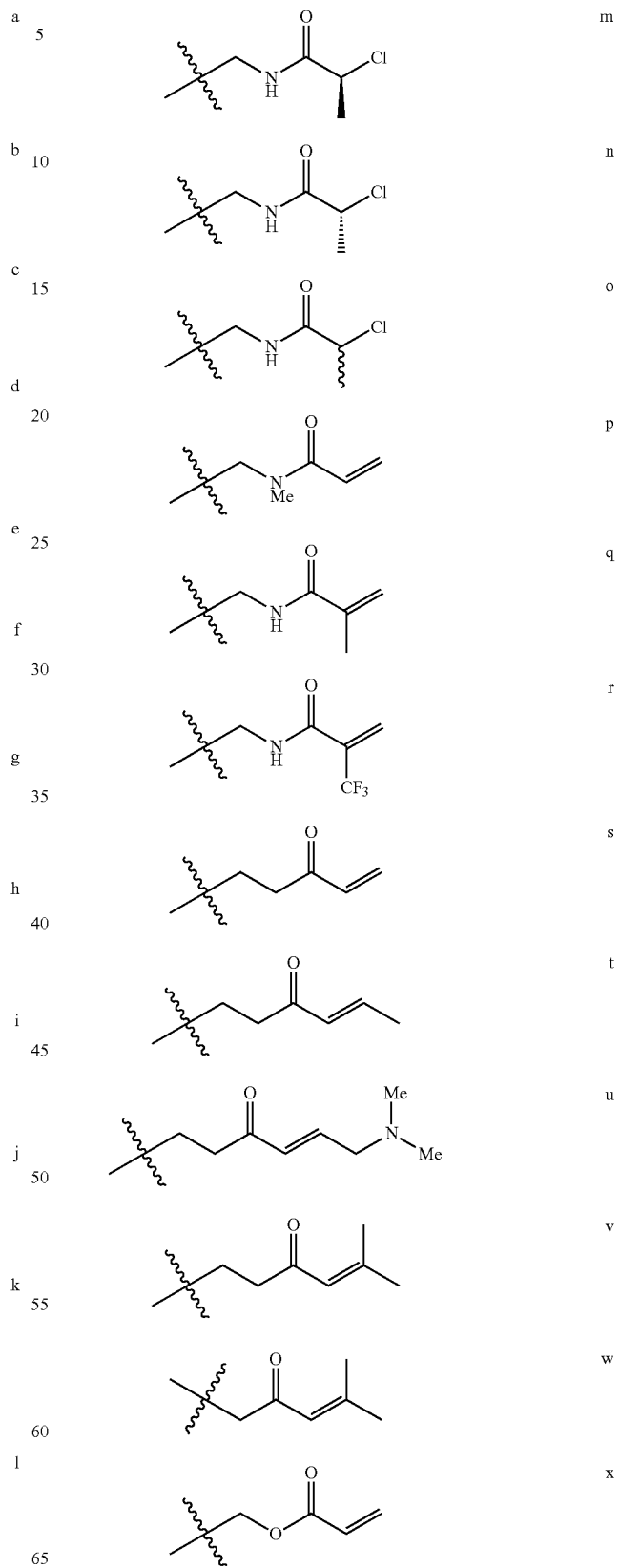

TABLE 12-continued

Exemplary R¹ Groups

| | |
|---|---|
| (structure) | y |
| (structure) | z |
| (structure) | aa |
| (structure) | bb |
| (structure) | cc |
| (structure) | dd |
| (structure) | ee |
| (structure) | ff |
| (structure) | gg |
| (structure) | hh |
| (structure) | ii |
| (structure) | jj |
| (structure) | kk |
| (structure) | ll |
| (structure) | mm |
| (structure) | nn |
| (structure) | oo |
| (structure) | pp |

TABLE 12-continued

Exemplary R¹ Groups

| | |
|---|---|
| (pyrimidine with ethynyl) | qq |
| (pyridine with Rᵉ) | rr |
| (pyridine with Rᵉ) | ss |
| (pyridine with Rᵉ) | tt |
| (pyrimidine with Rᵉ) | uu |
| (pyrimidine with Rᵉ) | vv |
| (pyrimidine with Rᵉ) | ww |
| (pyrazole with Rᵉ) | xx |
| (furanone) | yy |
| (imidazole with Rᵉ) | zz |
| (pyrazole with Rᵉ) | aaa |
| (N-Me pyrazole with Rᵉ) | bbb |
| (N-Me imidazole with Rᵉ) | ccc |
| (N-Me imidazole with Rᵉ) | ddd |
| (N-Me pyrazole with Rᵉ) | eee |
| (isoxazole with Rᵉ) | fff |
| (oxazole with Rᵉ) | ggg |
| (oxazole with Rᵉ) | hhh |
| (isoxazole with Rᵉ) | iii |

TABLE 12-continued
Exemplary R¹ Groups
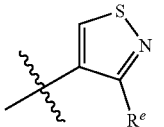 jjj
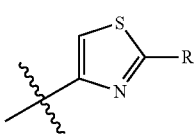 kkk
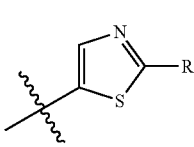 lll
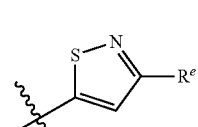 mmm
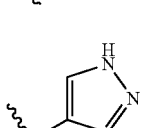 nnn
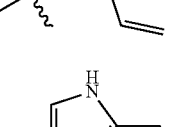 ooo
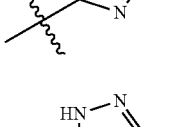 ppp
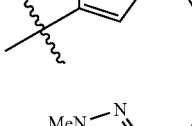 qqq
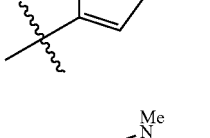 rrr
TABLE 12-continued
Exemplary R¹ Groups
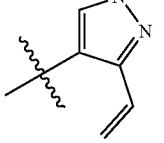 sss
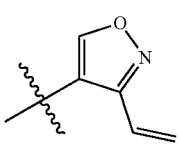 ttt
 uuu
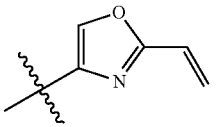 [SMILES: *c1coc(C=C)n1] vvv
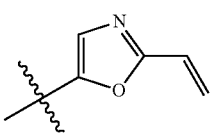 [SMILES: *c1cnc(C=C)o1] www
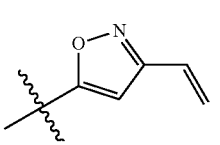 [SMILES: *c1cc(C=C)no1] xxx
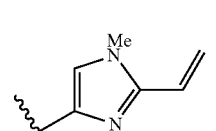 yyy
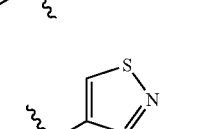 zzz
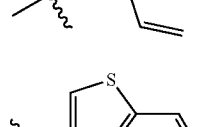 aaaa
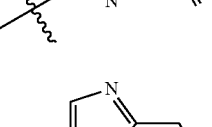 bbbb TABLE 12-continued
Exemplary R¹ Groups
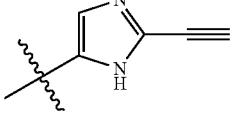 cccc
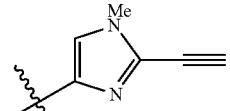 dddd
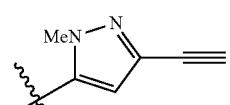 eeee
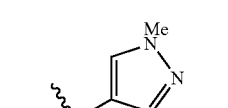 ffff
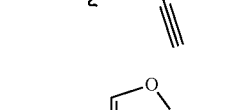 gggg
 hhhh
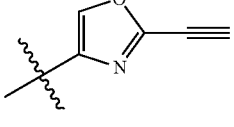 iiii
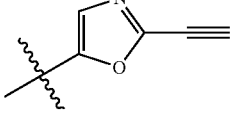 jjjj
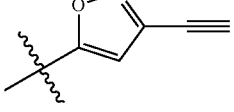 kkkk
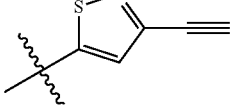 llll
TABLE 12-continued
Exemplary R¹ Groups
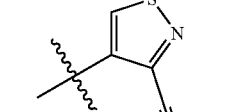 mmmm
 nnnn
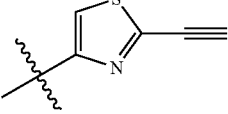 oooo
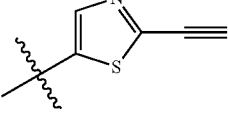 pppp
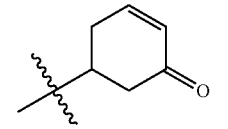 [SMILES: *C1CC=CC(=O)C1] qqqq
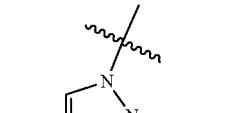 rrrr
 ssss
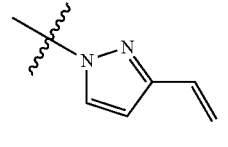 [SMILES: *n1ccc(C=C)n1] tttt
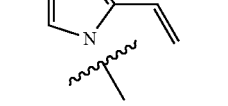 uuuu
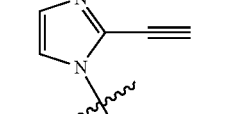 vvvv TABLE 12-continued Exemplary R¹ Groups

| | |
|---|---|
| (structure) | wwww |
| (structure) | xxxx |
| (structure) | yyyy |
| (structure) | zzzz |
| (structure) | aaaaa |
| (structure) | bbbbb |
| (structure) | ccccc |
| (structure) | ddddd |
| (structure) | eeeee |
| (structure) | fffff |
| (structure) | ggggg |
| (structure) | hhhhh |
| (structure) | iiiii |
| (structure) | jjjjj |
| (structure) | kkkkk |
| (structure) | lllll |
| (structure) | mmmmm |
| (structure) | nnnnn |
| (structure) | ooooo |
| (structure) | ppppp |
| (structure) | qqqqq |
| (structure) | rrrrr |

TABLE 12-continued

| Exemplary R¹ Groups | |
|---|---|
| [structure] | sssss |
| [structure] | ttttt |
| [structure] | uuuuu |
| [structure] | vvvvv |
| [structure] | wwwww |
| [structure] | xxxxx |
| [structure] | yyyyy |
| [structure] | zzzzz |
| [structure] | aaaaaa |
| [structure] | bbbbbb |
| [structure] | cccccc |
| [structure] | dddddd |
| [structure] | eeeeee |
| [structure] | ffffff |
| [structure] | gggggg |
| [structure] | hhhhhh |
| [structure] | iiiiii |
| [structure] | jjjjjj |
| [structure] | kkkkkk |
| [structure] | llllll |
| [structure] | mmmmmm |
| [structure] | nnnnnn |
| [structure] | oooooo |
| [structure] | pppppp |

TABLE 12-continued

Exemplary R¹ Groups

| | |
|---|---|
| (structure) | qqqqqq |
| (structure) | rrrrrr |
| (structure) | ssssss |
| (structure) | tttttt |
| (structure) | uuuuuu |
| (structure) | vvvvvv |
| (structure) | wwwwww |
| (structure) | xxxxxx |
| (structure) | yyyyyy |
| (structure) | zzzzzz |
| (structure) | aaaaaaa |
| (structure) | bbbbbbb |
| (structure) | ccccccc |
| (structure) | ddddddd |
| (structure) | eeeeeee |
| (structure) | fffffff |
| (structure) | ggggggg |
| (structure) | hhhhhhh |
| (structure) | iiiiiii |
| (structure) | jjjjjjj |
| (structure) | kkkkkkk |

TABLE 12-continued

Exemplary R¹ Groups

| Structure | Label |
|---|---|
| (structure) | lllllll |
| (structure) | mmmmmmm |
| (structure) | nnnnnnn |
| (structure) | ooooooo |
| (structure) | ppppppp |
| (structure) | qqqqqqq |
| (structure) | rrrrrrr |
| (structure) | sssssss |
| (structure) | ttttttt |
| (structure) | uuuuuuu |
| (structure) | vvvvvvv |
| (structure) | wwwwwww |
| (structure) | xxxxxxx |
| (structure) | yyyyyyy |
| (structure) | zzzzzzz |
| (structure) | aaaaaaaa |
| (structure) | bbbbbbbb |
| (structure) | cccccccc |
| (structure) | dddddddd |
| (structure) | eeeeeeee |
| (structure) | ffffffff |
| (structure) | gggggggg |

TABLE 12-continued
| Exemplary R¹ Groups | |
|---|---|
| 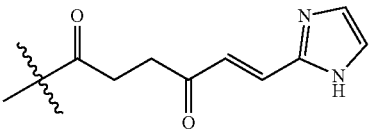 [SMILES: *C(=O)CCC(=O)/C=C/c1ncc[nH]1] | hhhhhhhh |
| 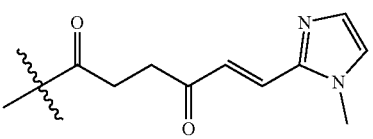 [SMILES: *C(=O)CCC(=O)/C=C/c1nccn1C] | iiiiiiii |
| 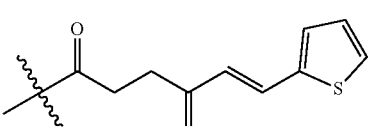 | jjjjjjjj |
| 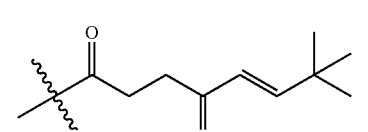 | kkkkkkkk |
| 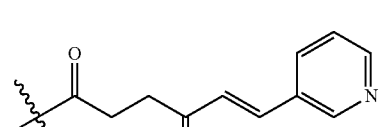 | llllllll |
| 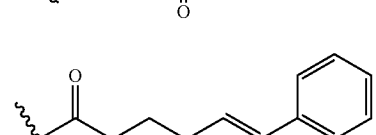 | mmmmmmmm |
|  | nnnnnnnn |
| 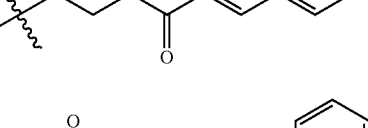 | oooooooo |
| 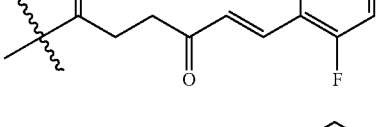 | pppppppp |
| 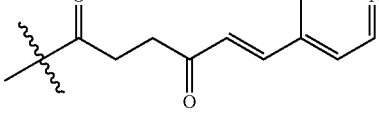 | qqqqqqqq |
TABLE 12-continued
| Exemplary R¹ Groups | |
|---|---|
| 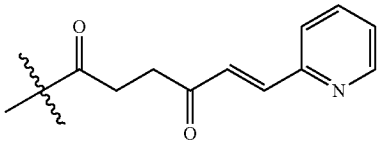 [SMILES: *C(=O)CCC(=O)/C=C/c1ccccn1] | rrrrrrrr |
| 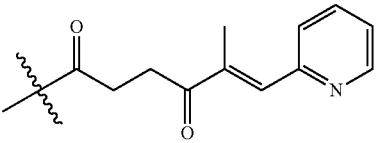 [SMILES: *C(=O)CCC(=O)/C(C)=C/c1ccccn1] | ssssssss |
| 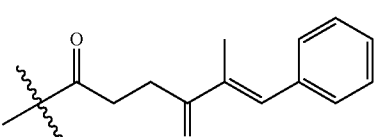 | tttttttt |
| 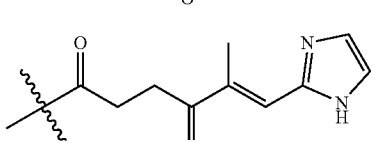 | uuuuuuuu |
| 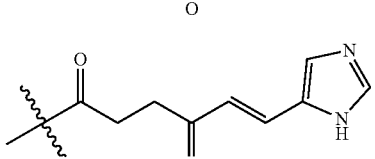 | vvvvvvvv |
| 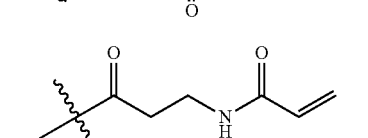 | wwwwwwww |
| 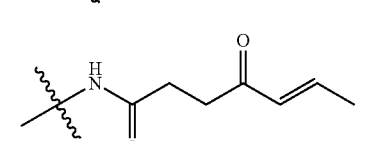 | xxxxxxxx |
| 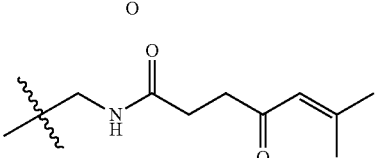 | yyyyyyyy |
| 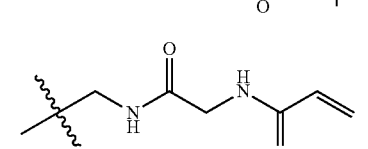 | zzzzzzzz |
| 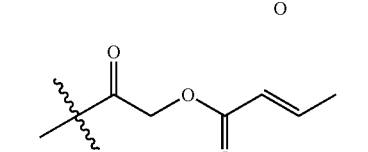 | aaaaaaaaa |
| 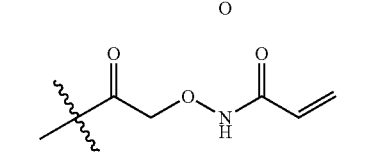 | bbbbbbbbb |

TABLE 12-continued

Exemplary R¹ Groups wherein each R^e is independently a suitable leaving group, NO₂, CN, or oxo.

In certain embodiments, R¹ is selected from:

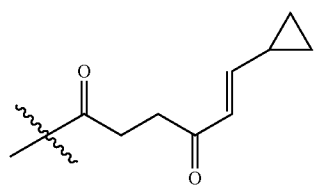
zzzzzz
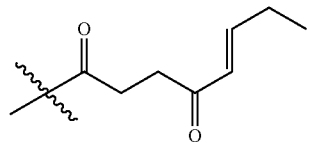
aaaaaaa
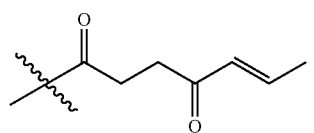
bbbbbbb
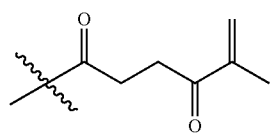
ccccccc
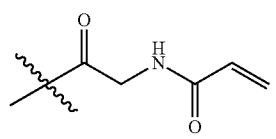
ddddddd
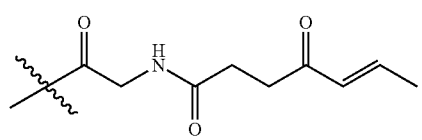
eeeeeee
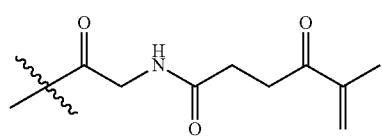
fffffff
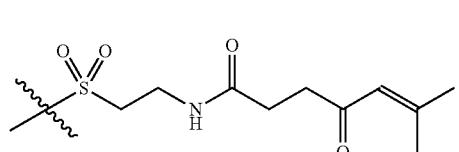
hhhhhhh
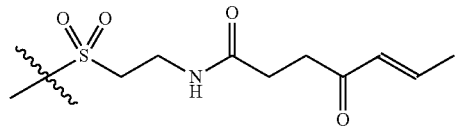
iiiiiii
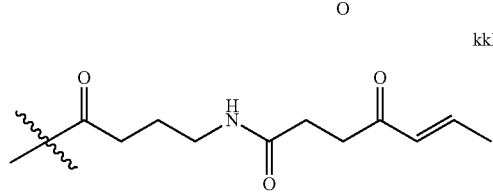
kkkkkkk
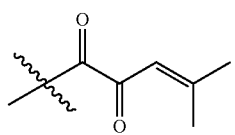
mmmmmmm
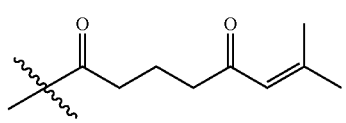
nnnnnnn
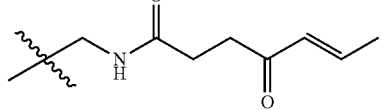
ppppppp
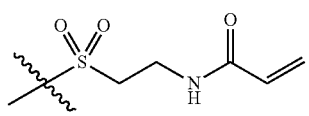
qqqqqqq
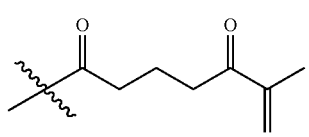
rrrrrrr
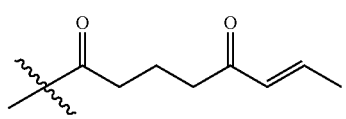
sssssss
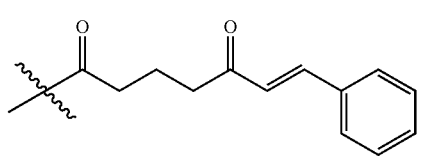
ttttttt
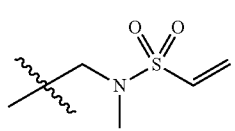
uuuuuuu
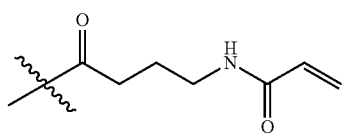
vvvvvvv
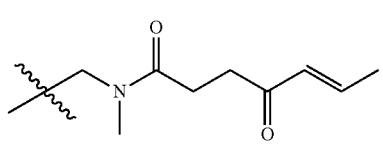
wwwwwww
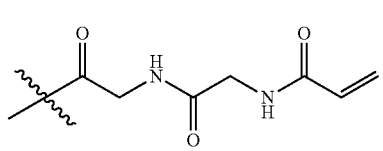
xxxxxxx

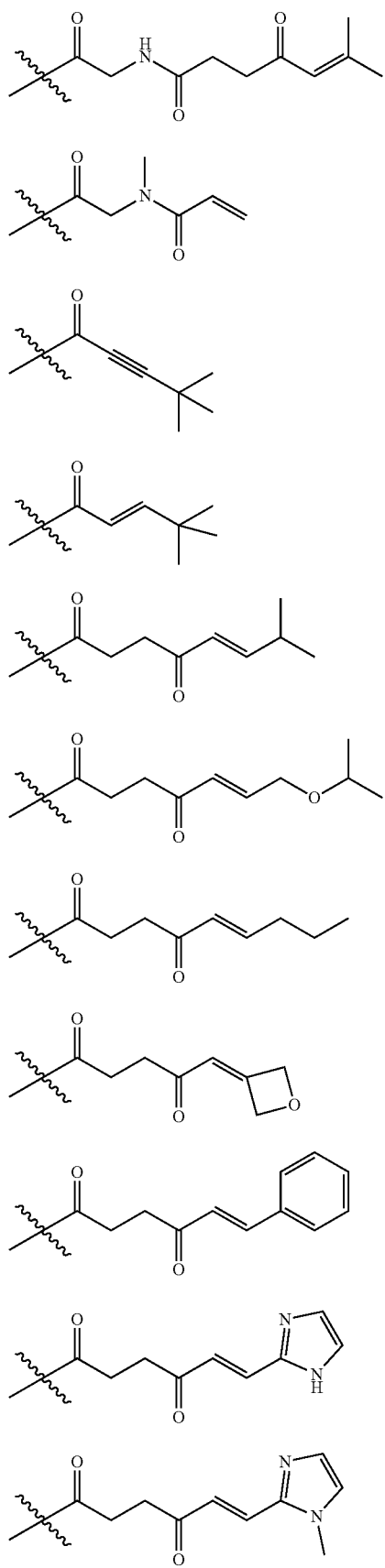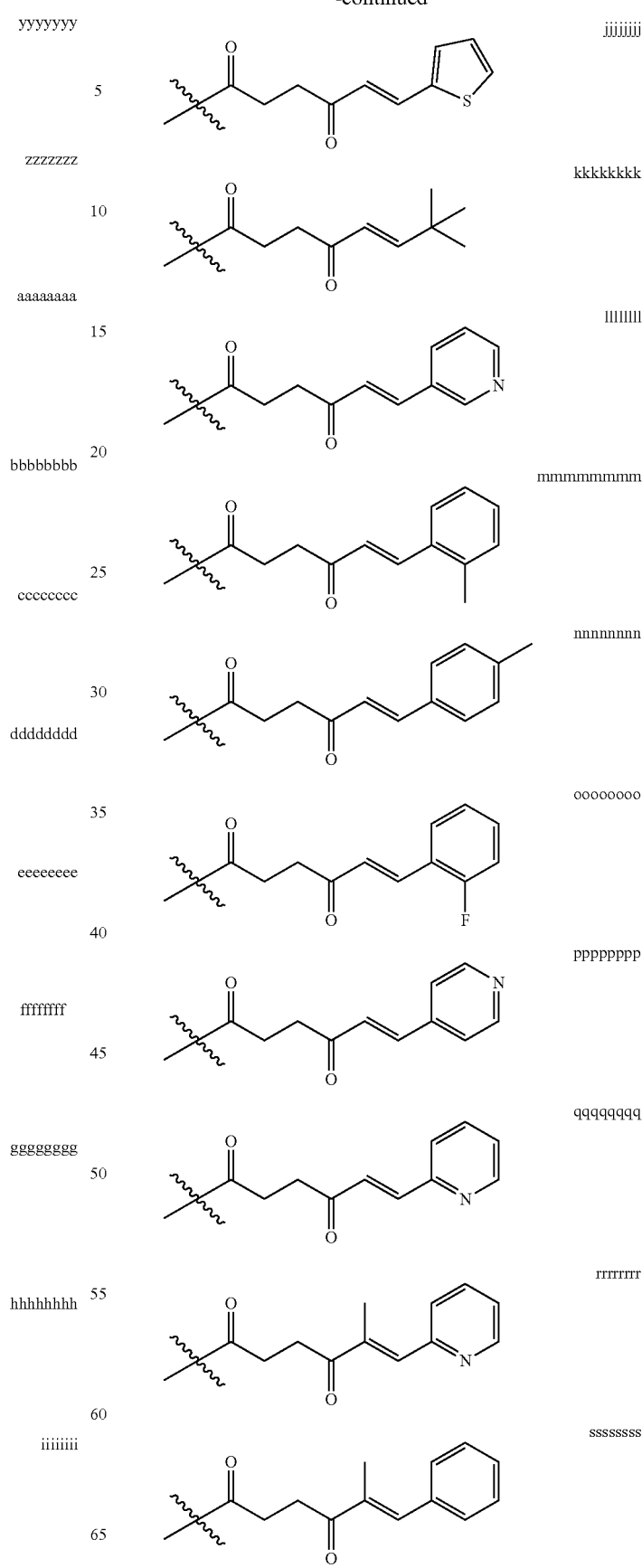

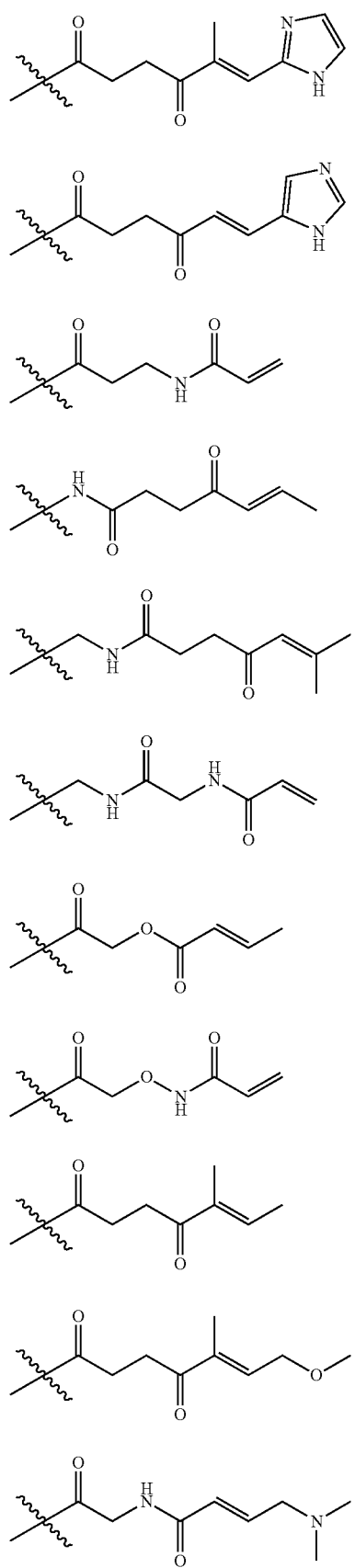
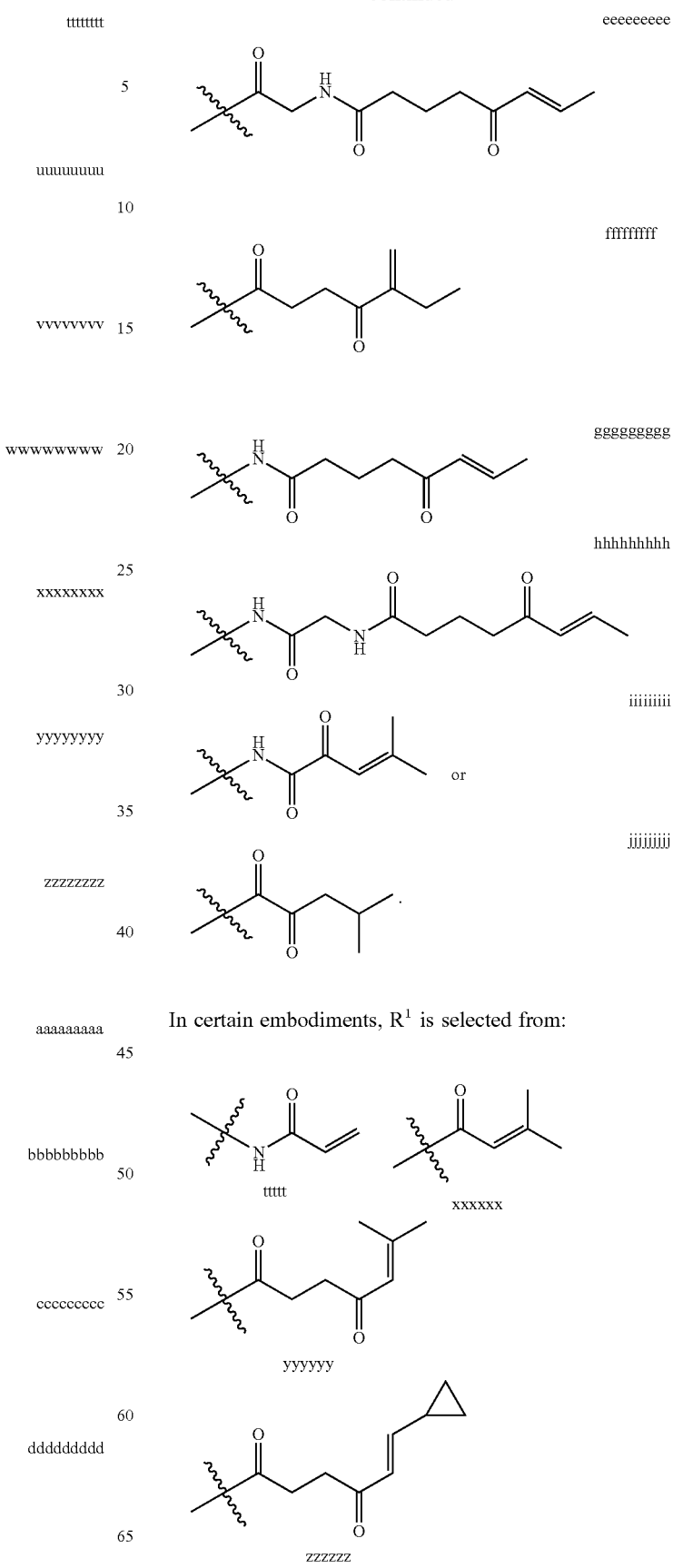
In certain embodiments, R¹ is selected from:

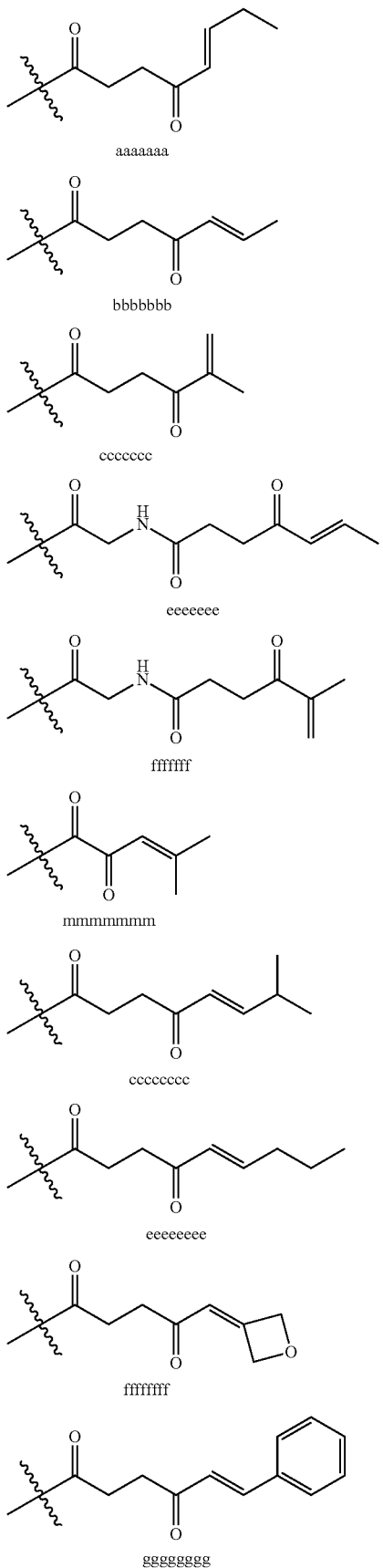
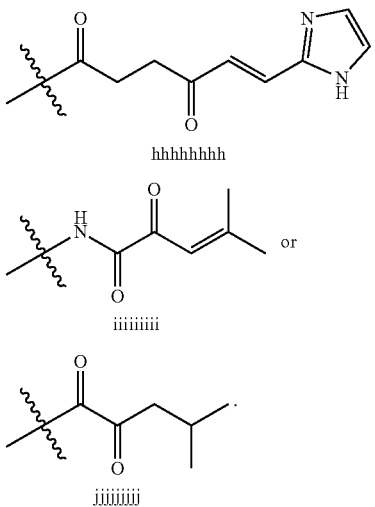
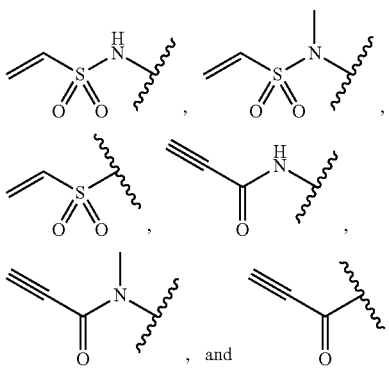
In certain embodiments, R¹ is selected from:
In certain embodiments, R¹ is selected from:
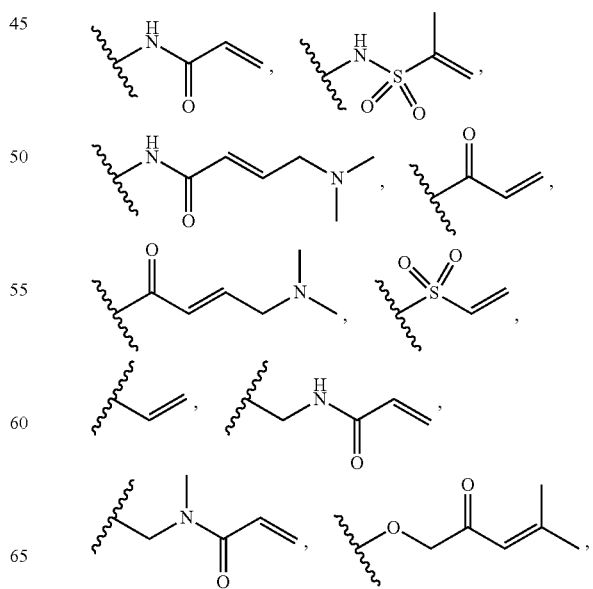

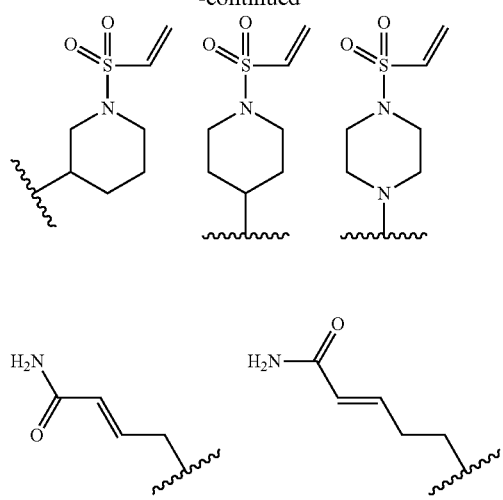

In certain embodiments, the present invention provides a conjugate comprising MK2 kinase having a cysteine residue, Cys140, wherein the CysX is covalently, and irreversibly, bonded to an inhibitor, such that inhibition of the kinase is maintained.

In certain embodiments, the present invention provides a conjugate of the formula A:

Cys140-modifier-inhibitor moiety    A wherein:

the Cys140 is Cys140 of MK2;

the modifier is a bivalent group resulting from covalent bonding of a warhead group with the Cys140 of MK2 kinase;

the warhead group is a functional group capable of covalently binding to Cys140; and the inhibitor moiety is a moiety that binds in the active site of the MK2 kinase.

In certain embodiments, the inhibitor moiety of conjugate A is of formula I-i:

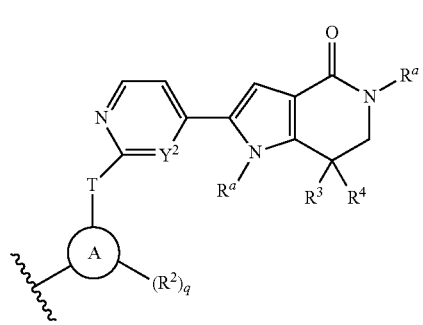

wherein the wavy bond indicates the point of attachment to Cys140 of conjugate A via the modifier, and wherein each of Ring A, $R^2$, $R^3$, $R^4$, $R^a$, $Y^2$, T, and q, of formula I-i is as defined for formula I above and as defined and described in embodiments herein.

In certain embodiments, the inhibitor moiety of conjugate A is of formula II-i:

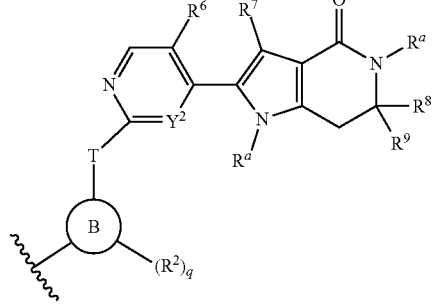

wherein the wavy bond indicates the point of attachment to Cys140 of conjugate A via the modifier, and wherein each of Ring B, $R^2$, $R^6$, $R^7$, $R^8$, $R^9$, $R^a$, $Y^2$, T and q of formula II-i is as defined for formula II above and as defined and described in embodiments herein.

In certain embodiments, the inhibitor moiety of conjugate A is of formula II-e-i:

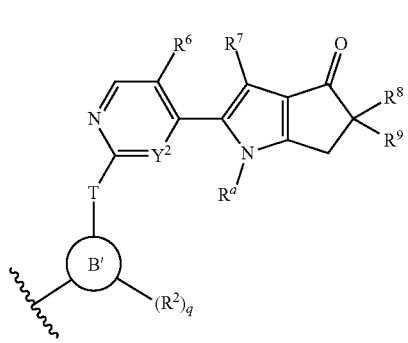

wherein the wavy bond indicates the point of attachment to Cys140 of conjugate A via the modifier, and wherein each of Ring B', $R^2$, $R^6$, $R^7$, $R^8$, $R^9$, $R^a$, $Y^2$, T and q of formula II-e-i is as defined for formula II-e above and as defined and described in embodiments herein.

In certain embodiments, the inhibitor moiety of conjugate A is of formula III-i:

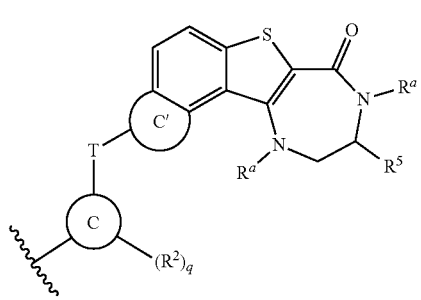

wherein the wavy bond indicates the point of attachment to Cys140 of conjugate A via the modifier, and wherein each of Ring C, Ring C', $R^2$, $R^5$, $R^a$, T, and q, of formula III-i is as defined for formula III above and as defined and described in embodiments herein.

In certain embodiments, the inhibitor moiety of conjugate A is of formula III-d-i:

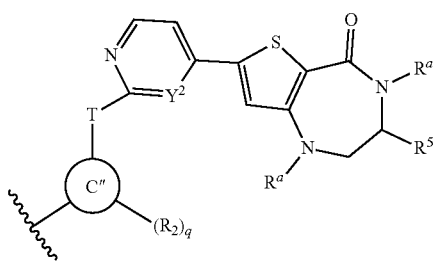

III-d-i wherein the wavy bond indicates the point of attachment to Cys140 of conjugate A via the modifier, and wherein each of Ring C'', $R^2$, $R^5$, $R^a$, $Y^2$, T, and q, of formula III-d-i is as defined for formula III-d above and as defined and described in embodiments herein.

In certain embodiments, the inhibitor moiety of conjugate A is of formula IV-i:

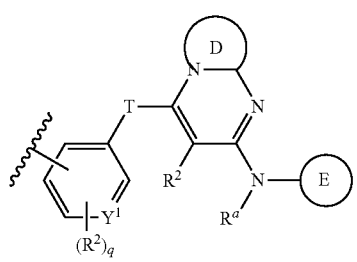

IV-i wherein the wavy bond indicates the point of attachment to Cys140 of conjugate A via the modifier, and wherein each of Ring D, Ring E, $R^2$, $R^a$, $Y^1$, T and q of formula IV-i is as defined for formula IV above and as defined and described in embodiments herein.

In certain embodiments, the inhibitor moiety of conjugate A is of formula IV-b-i:

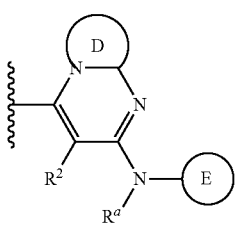

IV-b-i wherein the wavy bond indicates the point of attachment to Cys140 of conjugate A via the modifier, and wherein each of Ring D, Ring E, $R^2$, T and q of formula IV-b-i is as defined for formula IV-b above and as defined and described in embodiments herein.

In certain embodiments, the inhibitor moiety of conjugate A is of formula V-i:

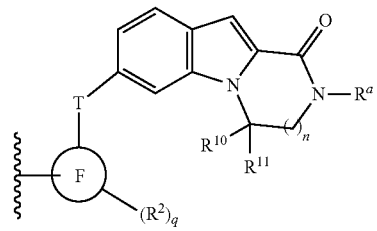

V-i wherein the wavy bond indicates the point of attachment to Cys140 of conjugate A via the modifier, and wherein each of Ring F, $R^2$, $R^{10}$, $R^{11}$, $R^a$, T, n, and q of formula V-i is as defined for formula V above and as defined and described in embodiments herein.

In certain embodiments, the inhibitor moiety of conjugate A is of formula V-c-i:

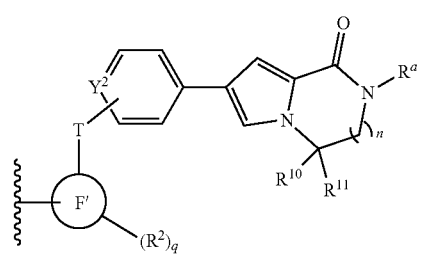

V-c-i wherein the wavy bond indicates the point of attachment to Cys140 of conjugate A via the modifier, and wherein each of Ring F', $R^2$, $R^{10}$, $R^{11}$, $R^a$, $Y^2$, T, n, and q of formula V-c-i is as defined for formula V-c above and as defined and described in embodiments herein.

In certain embodiments, the inhibitor moiety of conjugate A is of formula VI-i:

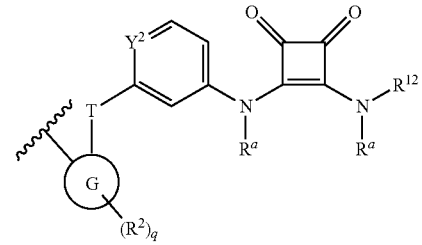

VI-i wherein the wavy bond indicates the point of attachment to Cys140 of conjugate A via the modifier, and wherein each of Ring G, $R^2$, $R^{12}$, $R^a$, $Y^2$, T and q of formula VI-i is as defined for formula VI above and as defined and described in embodiments herein.

In certain embodiments, the present invention provides a conjugate of any of formulae below:

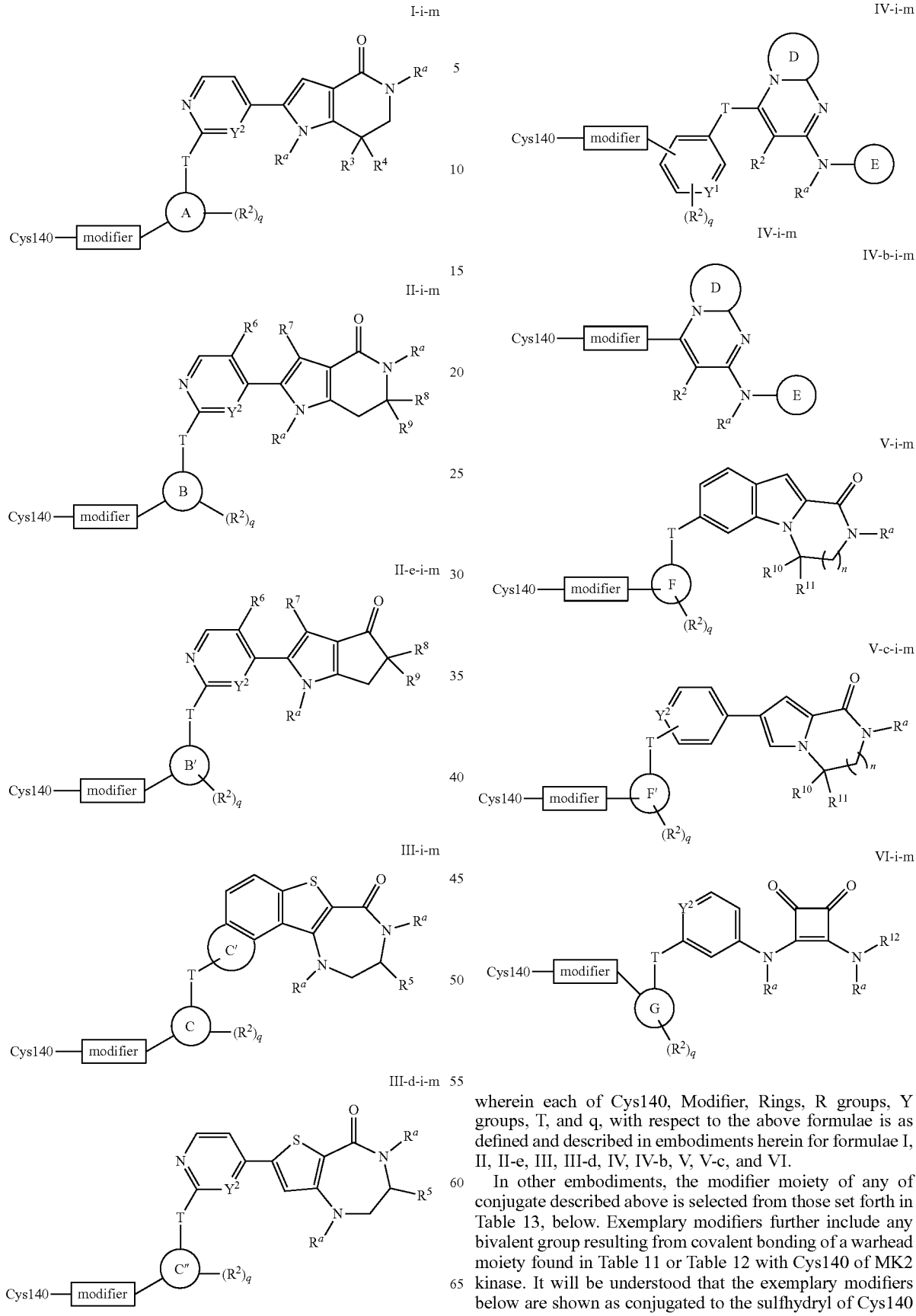

wherein each of Cys140, Modifier, Rings, R groups, Y groups, T, and q, with respect to the above formulae is as defined and described in embodiments herein for formulae I, II, II-e, III, III-d, IV, IV-b, V, V-c, and VI.

In other embodiments, the modifier moiety of any of conjugate described above is selected from those set forth in Table 13, below. Exemplary modifiers further include any bivalent group resulting from covalent bonding of a warhead moiety found in Table 11 or Table 12 with Cys140 of MK2 kinase. It will be understood that the exemplary modifiers below are shown as conjugated to the sulfhydryl of Cys140 of MK2 kinase.

TABLE 13
Exemplary Modifiers Conjugated to Cys140:
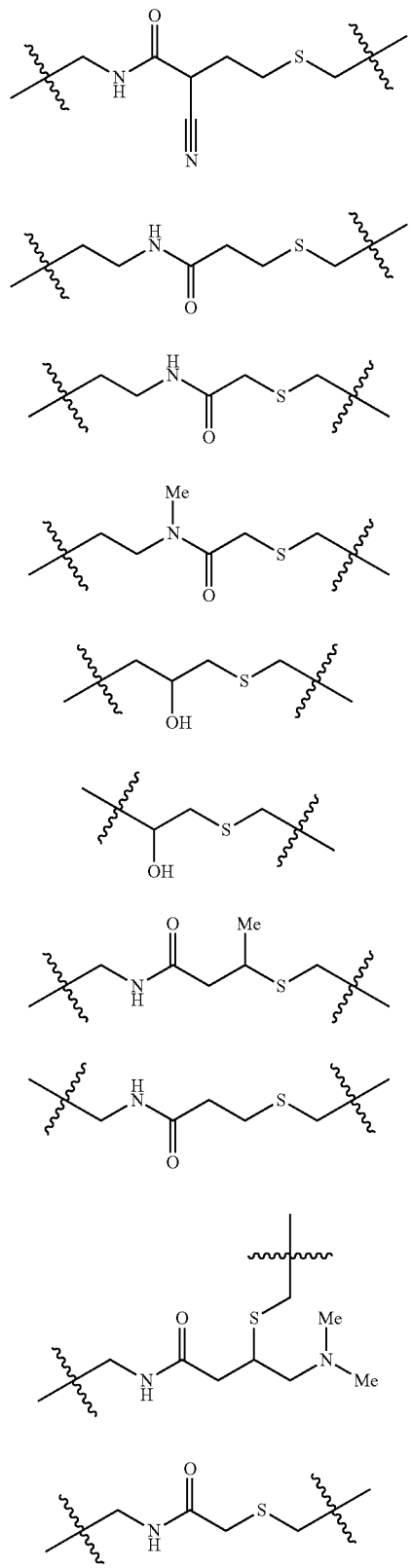
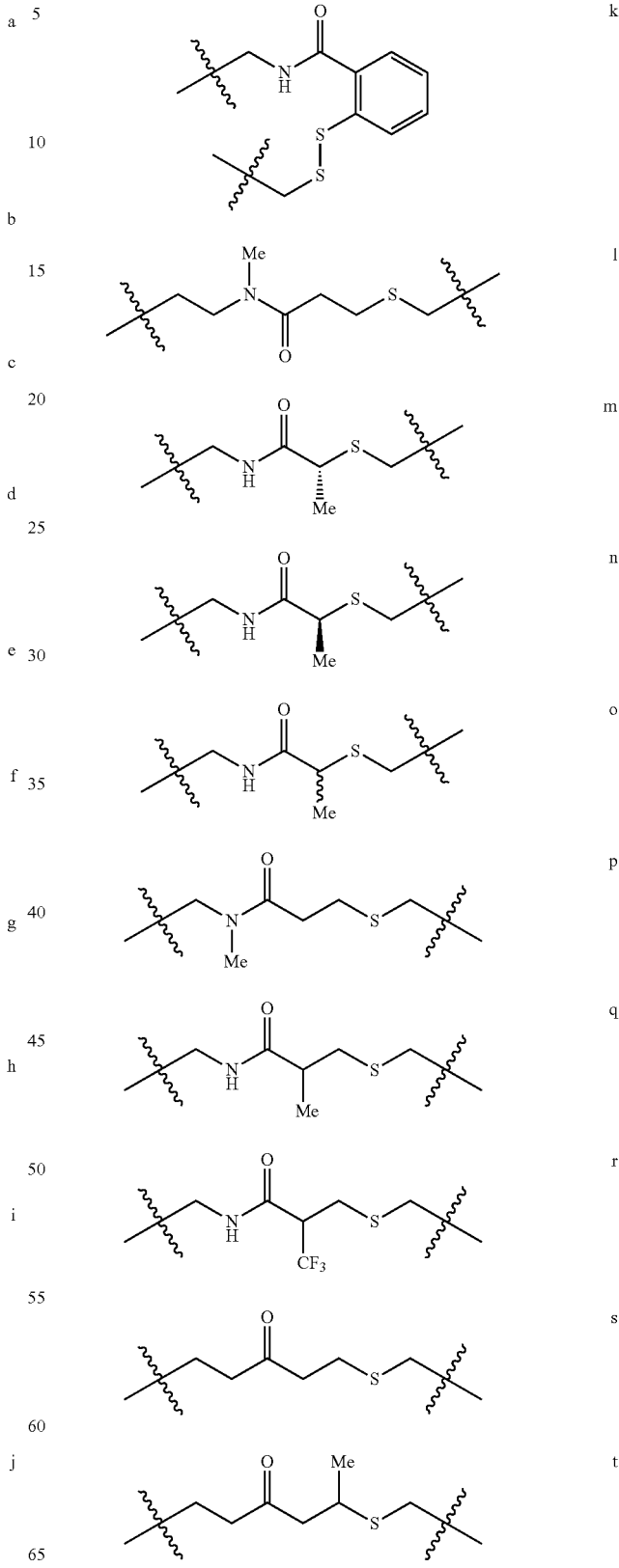

TABLE 13-continued

Exemplary Modifiers Conjugated to Cys140:

TABLE 13-continued
Exemplary Modifiers Conjugated to Cys140:
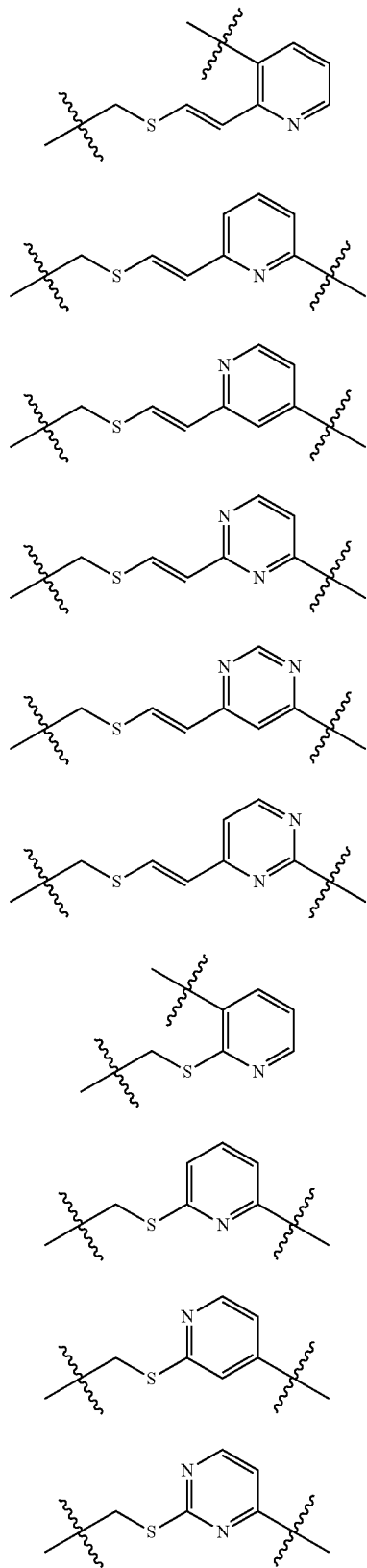
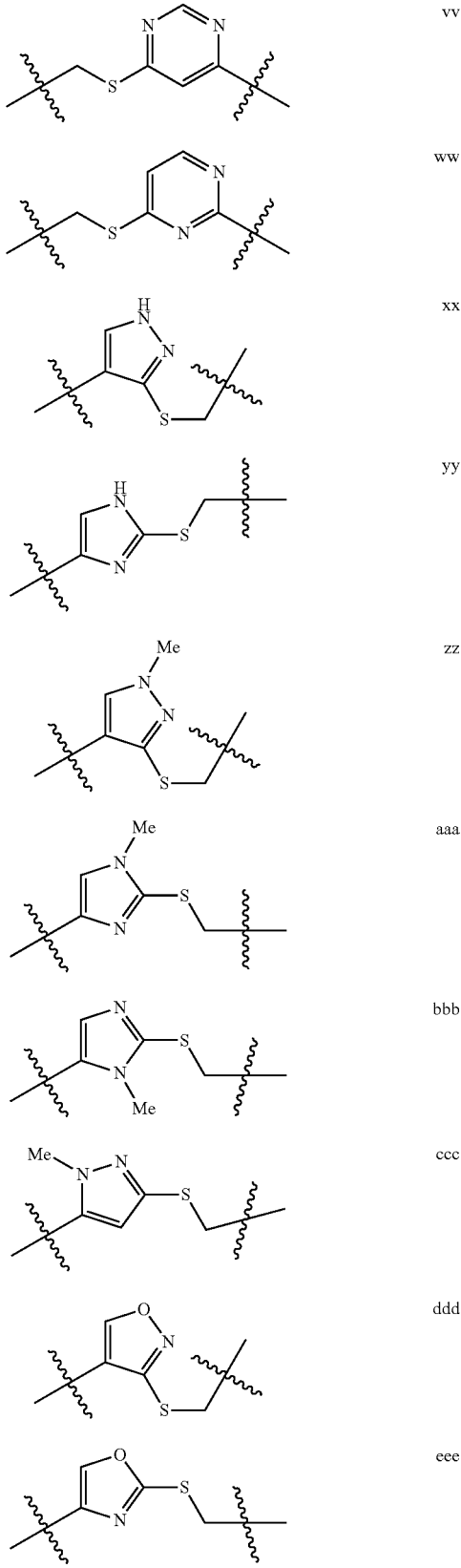

TABLE 13-continued
Exemplary Modifiers Conjugated to Cys140:
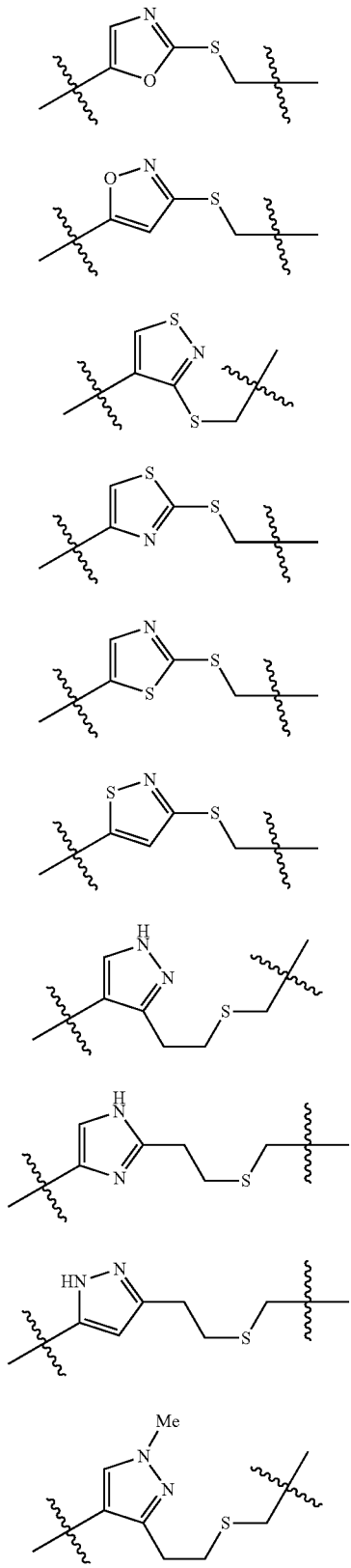
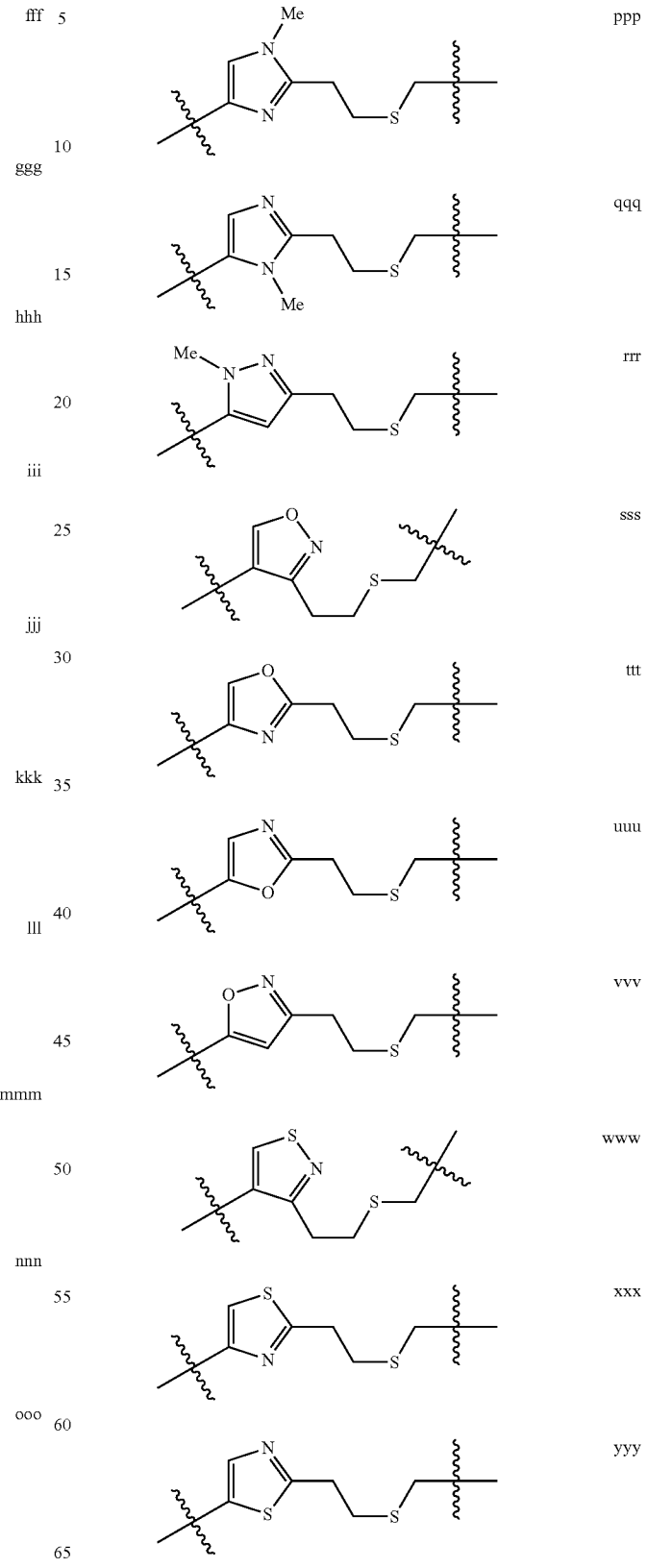

TABLE 13-continued
Exemplary Modifiers Conjugated to Cys140:
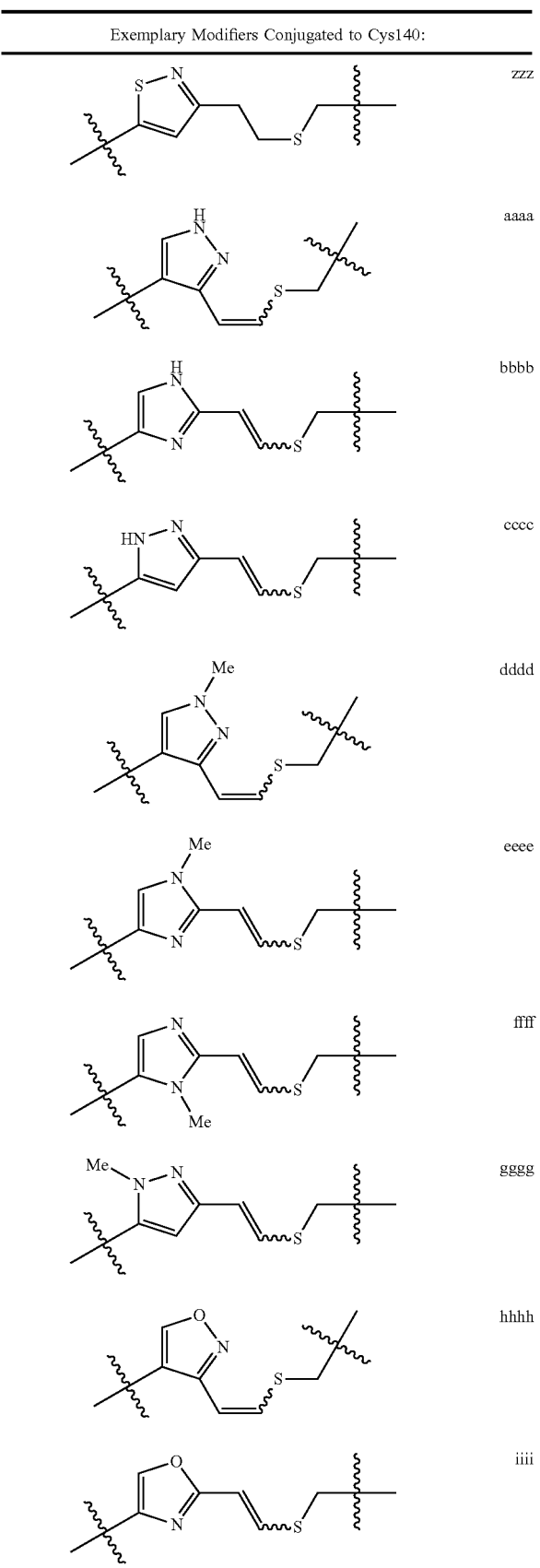
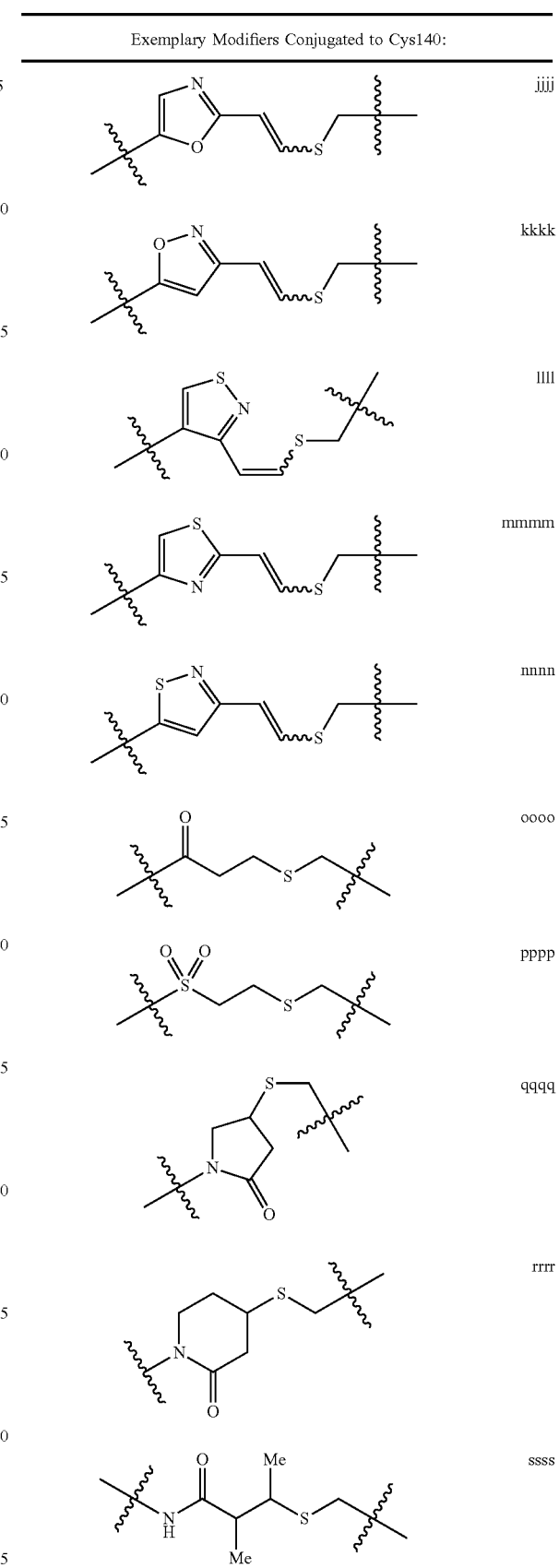

TABLE 13-continued

Exemplary Modifiers Conjugated to Cys140:

tttt uuuu vvvv wwww xxxx yyyy zzzz aaaaa bbbbb ccccc ddddd eeeee

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit MK2, or a mutant thereof, in a biological sample or in a patient. In certain embodiments, the amount of compound in compositions of this invention is such that is effective to measurably inhibit MK2, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of MK2, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrastemal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes.

Examples of kinases that are inhibited by the compounds and compositions described herein and against which the methods described herein are useful MK2, or a mutant thereof.

The activity of a compound utilized in this invention as an inhibitor of a MK2 kinase, or a mutant thereof, may be assayed in vitro, in vivo or in a cell line. In vitro assays include assays that determine inhibition of either the phosphorylation activity and/or the subsequent functional consequences, or ATPase activity of activated MK2 kinase, or a mutant thereof. Alternate in vitro assays quantitate the ability of the test compound to bind to MK2. Inhibitor binding may be measured by radiolabeling the test compound prior to binding, isolating the test compound/MK2 complex and determining the amount of radiolabel bound. Alternatively, inhibitor binding may be determined by running a competition experiment where test compounds are incubated with MK2 kinase bound to known radioligands. Detailed conditions for assaying a compound utilized in this invention as an inhibitor of MK2, or a mutant thereof, are set forth in the Examples below.

Without wishing to be bound by any particular theory, it is believed that a provided compound comprising a warhead moiety is more effective at inhibiting MK2 or a mutant thereof, as compared to a corresponding compound wherein the $R^1$ moiety of any of the formulae herein is instead a non-warhead group or is completely absent (i.e., is hydrogen). For example, a compound of any of the formulae herein is more effective at inhibition of MK2, or a mutant thereof, as compared to a corresponding compound wherein the $R^1$ moiety of any of the formulae herein is instead a non-warhead moiety or is absent.

A provided compound comprising a warhead moiety, as disclosed above, is more potent with respect to an $IC_{50}$ against MK2, or a mutant thereof, than a corresponding compound wherein the $R^1$ moiety of any of the formulae herein is instead a non-warhead moiety or is absent. Such comparative potency can be determined by standard time-dependent assay methods, such as those described in detail in the Examples section, infra. In certain embodiments, a compound of any of the formulae herein is measurably more potent than a corresponding compound of any of the formulae herein wherein the $R^1$ moiety is a non-warhead moiety or is absent. In some embodiments, a compound of any of the formulae herein is measurably more potent, wherein such potency is observed after about 1 minute, about 2 minutes, about 5 minutes, about 10 minutes, about 20 minutes, about 30 minutes, about 1 hour, about 2 hours, about 3 hours, about 4 hours, about 8 hours, about 12 hours, about 16 hours, about 24 hours, or about 48 hours, than a corresponding compound of any of the formulae herein wherein the $R^1$ moiety of formula is a non-warhead moiety or is absent. In some embodiments, a compound of any of the formulae herein is any of about 1.5 times, about 2 times, about 5 times, about 10 times, about 20 times, about 25 times, about 50 times, about 100 times, or even about 1000 times more potent than a corresponding compound of any of the formulae herein wherein the $R^1$ moiety is a non-warhead moiety or is absent.

MK2 Kinase

MAP kinase-activated protein kinase 2 is an enzyme that in humans is encoded by the MAPKAPK2 gene. This gene encodes a member of the Ser/Thr protein kinase family. This kinase is regulated through direct phosphorylation by p38 MAP kinase. In conjunction with p38 MAP kinase, this kinase is known to be involved in many cellular processes including stress and inflammatory responses, nuclear export, gene expression regulation and cell proliferation. Heat shock protein HSP27 was shown to be one of the substrates of this kinase in vivo. Two transcript variants encoding two different isoforms have been found for this gene.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS. MK2 is located in the nucleus of the cell and upon binding and phosphorylation by p38, the MK2 NES becomes functional and both kinases are co-transported out of the nucleus to the cytoplasm. Interestingly, transport of the MK2/p38 complex does not require catalytically active MK2, as the active site mutant, Asp207Ala, is still transported to the cytoplasm. Phosphorylation of human MK2 by p38 on residues T222, S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

The term "MK2-mediated disease" or "MK2-mediated condition", as used herein, means any disease or other deleterious condition in which MK2 protein kinase is known or suspected to play a role. Such conditions include, without limitation, inflammatory disorders, arthritis, ischemia/reperfusion Disorders related to MK2 kinase that are treated by the compounds of any of the formulae presented herein include autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, lymphoma and the like.

In some embodiments, the methods described herein are used to treat a patient in need thereof suffering from an autoimmune disorder, chronic and/or acute inflammatory disorder and/or auto-inflammatory disorder. Exemplary disorders include: colitis, multiple sclerosis, arthritis, rheumatoid arthritis, osteoarthritis, juvenile arthritis, psoriatic arthritis, cryopyrin associated periodic syndromes, Muckle-Wells Syndrome, Familial Cold Auto-inflammatory Syndrome, neonatal-onset multisystem inflammatory disease, TNF receptor associated periodic synderome, acute pancreatitis, chronic pancreatitis, atherosclerosis, inflammatory bowel disease, Crohn's disease, gout, ankylosing spondylitis, hepatic fibrosis, idiopathic pulmonary fibrosis, nephropathy, sarcoidosis, scleroderma, anaphylaxis, ulcerative colitis, Diabetes mellitus type 1, Diabetes mellitus type 2, diabetic retinopathy, Still's disease, multiple sclerosis, vasculitis, sarcoidosis, pulmonary inflammation, acute respiratory distress syndrome, wet and dry age-related macular degeneration, autoimmune hemolytic syndromes, autoimmune hepatitis, autoimmune neuropathy, autoimmune ovarian failure, autoimmune orchitis, autoimmune thrombocytopenia, reactive arthritis, ankylosing spondylitis, silicone implant associated autoimmune disease, Sjogren's syndrome, Familial Mediterranean Fever, systemic lupus erythematosus, vasculitis syndromes (such as, for example, giant cell arteritis, Behcet's disease & Wegener's granulomatosis), Vitiligo, secondary hematologic manifestation of autoimmune diseases (such as, for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (including, for example, Meniere's disease), Goodpasture's syndrome, Graves' disease, HW-related autoimmune syndromes and Gullain-Barre disease.

Exemplary inflammatory disorders include sepsis, septic shock, endotoxic shock, exotoxin-induced toxic shock, gram negative sepsis, toxic shock syndrome, glomerulonephritis, peritonitis, interstitial cystitis, psoriasis, atopic dermatitis, hyperoxia-induced inflammations, asthma, chronic obstructive pulmonary disease (COPD), vasculitis, graft vs. host reaction (i.e., graft vs. host disease), allograft rejections (e.g., acute allograft rejection, and chronic allograft rejection), early transplantation rejection (e.g., acute allograft rejection), reperfusion injury, acute pain, chronic pain, neuropathic pain, Fibromyalgia, pancreatitis, chronic infections, meningitis, encephalitis, myocarditis, gingivitis, post surgical trauma, tissue injury, traumatic brain injury, hepatitis, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

Exemplary fibrotic diseases and/or metabolic disorders include obesity, steroid-resistance, glucose intolerance, metabolic syndrome.

In some embodiments, the methods described herein can be used to treat a patient in need thereof and suffering from neoplasia. Exemplary conditions include angiogenesis, multiple myeloma, leukemia, B cell lymphoma, T cell lymphoma, mast cell tumors, lymphoma, Hodgkin's disease, cancer of the bone, mouth/pharynx, esophagus, larynx, stomach, intestine, colon, rectum, lung, liver, pancreas, nerve, brain, head and neck, throat, ovary, uterus, prostate, testis, bladder, kidney, breast, gall bladder, cervix, thyroid, prostate, including squamous cell carcinoma; leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma myeloma, and Burkett's lymphoma; acute and chronic myelogenous leukemia, myelodysplastic syndrome and promyelocytic leukemia; fibrosarcoma, rhabdomyosarcoma; astrocytoma, neuroblastoma, glioma and schwannomas; melanoma, seminoma, teratocarcinoma, osteosarcoma, xenoderoma pigmentosum, keratoctanthoma, thyroid follicular cancer and Kaposi's sarcoma, non-small cell lung carcinoma, small cell lung carcinoma, melanoma, skin cancer, teratoma, rhabdomyosarcoma, glioma, metastatic and bone disorders.

In some embodiments, the disease is a cardiovascular or cerebrovascular disease, and exemplary disorders include atherosclerosis, restenosis of an atherosclerotic coronary artery, acute coronary syndrome, myocardial infarction, cardiac-allograft vasculopathy and stroke; central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

As used herein, the term "clinical drug resistance" refers to the loss of susceptibility of a drug target to drug treatment as a consequence of mutations in the drug target.

As used herein, the term "resistance" refers to changes in the wild-type nucleic acid sequence coding a target protein, and/or the protein sequence of the target, which changes decrease or abolish the inhibitory effect of the inhibitor on the target protein.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting MK2 kinase, or a mutant thereof, activity in a biological sample comprising the step of contacting said biological sample with a compound of this invention, or a composition comprising said compound. In certain embodiments, the invention relates to a method of irreversibly inhibiting MK2 kinase, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of MK2, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting MK2 kinase, or a mutant thereof, activity in a patient comprising the step of administering to said patient a compound of the present invention, or a composition comprising said compound. According to certain embodiments, the invention relates to a method of irreversibly inhibiting MK2 kinase, or a mutant thereof, activity in a patient comprising the step of administering to said patient a compound of the present invention, or a composition comprising said compound. In other embodiments, the present invention provides a method for treating a disorder mediated by MK2 kinase, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

5. Probe Compounds

In certain aspects, a compound of the present invention is tethered to a detectable moiety to form a probe compound.

In one aspect, a probe compound of the invention comprises an irreversible protein kinase inhibitor of any formulae as described herein, a detectable moiety, and a tethering moiety that attaches the inhibitor to the detectable moiety.

In some embodiments, such probe compounds of the present invention comprise a provided compound of any formulae as described herein, tethered to a detectable moiety, $R^P$, by a bivalent tethering moiety, $-T^P-$. The tethering moiety is attached to a compound of the invention via $R^1$. One of ordinary skill in the art will appreciate that when a tethering moiety is attached to $R^1$, $R^1$ is a bivalent warhead group denoted as $R^{1'}$. In certain embodiments, a provided probe compound is selected from any of following formulae:

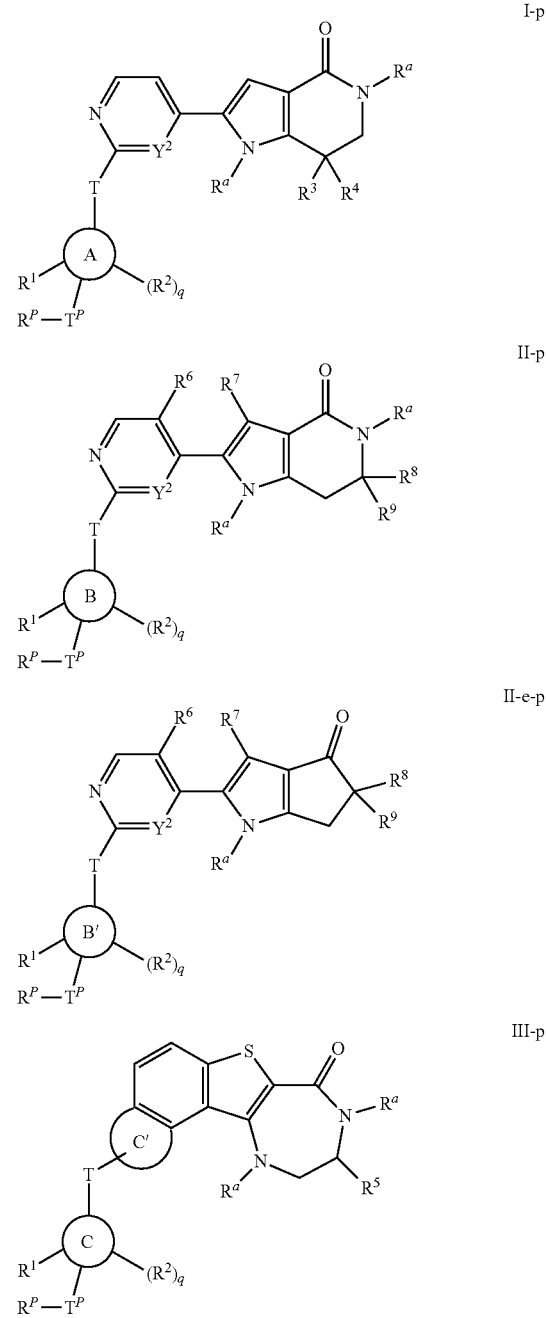

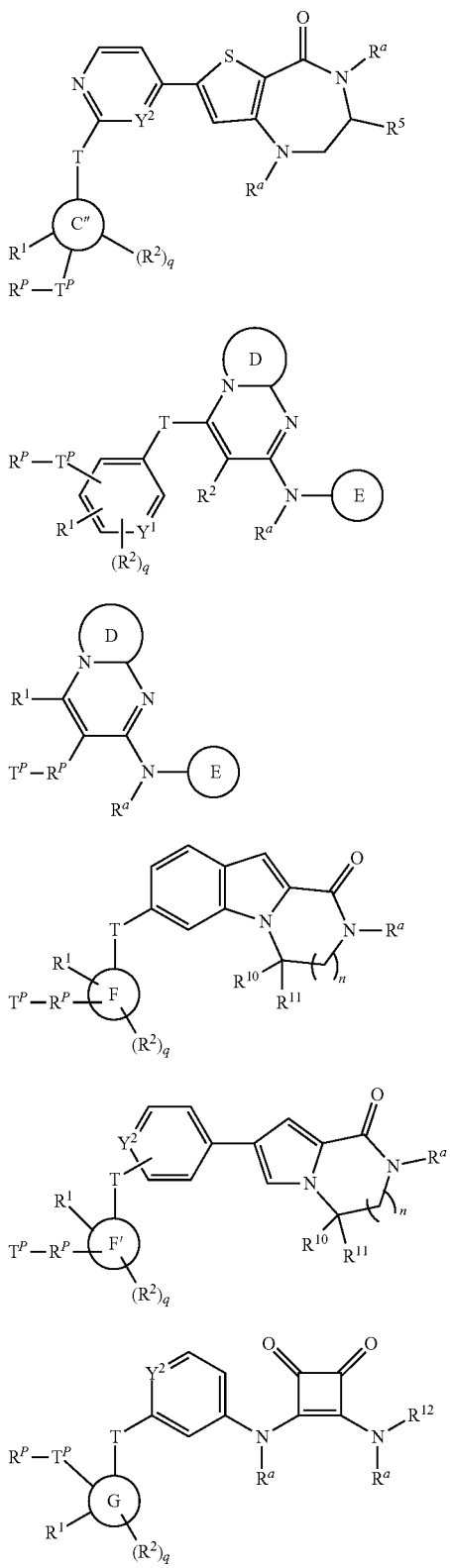

wherein each of Ring A, Ring B, Ring B', Ring C, Ring C', Ring C", Ring D, Ring E, Ring F, Ring F', Ring G, $R^1$, $R^2$, $R^3$, $R^4$, $R^5$, $R^6$, $R^7$, $R^8$, $R^9$, $R^{10}$, $R^{11}$, $R^a$, $Y^1$, $Y^2$, T, and q, with respect to the formulae above, is as defined and described in embodiments herein, $T^P$ is a bivalent tethering moiety; and $R^P$ is a detectable moiety.

In some embodiments, $R^P$ is a detectable moiety selected from a primary label or a secondary label. In certain embodiments, $R^P$ is a detectable moiety selected from a fluorescent label (e.g., a fluorescent dye or a fluorophore), a mass-tag, a chemiluminescent group, a chromophore, an electron dense group, or an energy transfer agent.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}P$, $^{33}P$, $^{35}S$, $^{14}C$, $^{123}I$, $^{124}I$, $^{125}I$, or 131I), mass-tags are stable isotopes (e.g., $^{13}C$, $^{2}H$, $^{17}O$, $^{18}O$, $^{15}N$, $^{19}F$, and $^{127}I$), positron emitting isotopes (e.g., $^{11}C$, $^{18}F$, $^{13}N$, $^{124}I$, and $^{15}O$), and fluorescent labels, which are signal generating reporter groups which can be detected without further modifications. Detectable moieties are analyzed by methods. Exemplary methods are fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate includes streptavidin-enzyme conjugates. For antigen labels, secondary intermediates include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromo-sulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), F1ASH-CCXXCC ("CCXXCC" disclosed as SEQ ID NO: 3), Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1, 3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) are also used as mass-tags. Stable isotopes (e.g., $^{13}C$, $^{2}H$, $^{17}O$, $^{18}O$, and $^{15}N$) are also used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a linkage with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety is attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties are directly attached to a provided compound or via a tethering moiety, such as a bivalent saturated or unsaturated hydrocarbon chain.

In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a click ready inhibitor moiety is provided and reacted with a click ready -T-R$^t$ moiety. As used herein, "click ready" refers to a moiety containing an azide or alkyne for use in a click chemistry reaction. In some embodiments, the click ready inhibitor moiety comprises an azide. In certain embodiments, the click ready -T-R$^t$ moiety comprises a strained cyclooctyne for use in a copper-free click chemistry reaction (for example, using methods described in Baskin et al., Proc. Natl. Acad. Sci. USA 2007, 104, 16793-16797).

In some embodiments, the detectable moiety, R$^P$, is selected from a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In some embodiments, R$^P$ is biotin or an analog thereof. In certain embodiments, R$^P$ is biotin. In certain other embodiments, R$^P$ is biotin sulfoxide.

In another embodiment, R$^P$ is a fluorophore. In a further embodiment, the fluorophore is selected from Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), F1ASH-CCXXCC ("CCXXCC" disclosed as SEQ ID NO: 3), Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, or SuperGlo GFP.

As described generally above, a provided probe compound comprises a tethering moiety, -T$^P$-, that attaches the irreversible inhibitor to the detectable moiety. As used herein, the term "tether" or "tethering moiety" refers to any bivalent chemical spacer. Exemplary tethers are a covalent bond, a polymer, a water soluble polymer, optionally substituted alkyl, optionally substituted heteroalkyl, optionally substituted heterocycloalkyl, optionally substituted cycloalkyl, optionally substituted heterocyclyl, optionally substituted heterocycloalkylalkyl, optionally substituted heterocycloalkylalkenyl, optionally substituted aryl, optionally substituted heteroaryl, optionally substituted heterocycloalkylalkenylalkyl, an optionally substituted amide moiety, an ether moiety, an ketone moiety, an ester moiety, an optionally substituted carbamate moiety, an optionally substituted hydrazone moiety, an optionally substituted hydrazine moiety, an optionally substituted oxime moiety, a disulfide moiety, an optionally substituted imine moiety, an optionally substituted sulfonamide moiety, a sulfone moiety, a sulfoxide moiety, a thioether moiety, or any combination thereof.

In some embodiments, the tethering moiety, -T$^P$-, is selected from a covalent bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the tethering moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole, isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the tethering moiety is optionally substituted with halogen, —CN, —OH, —NO$_2$, alkyl, S(O), and S(O)$_2$. In other embodiments, the water soluble polymer is a PEG group.

In other embodiments, the tethering moiety provides sufficient spatial separation between the detectable moiety and the protein kinase inhibitor moiety. In further embodiments, the tethering moiety is stable. In yet a further embodiment, the tethering moiety does not substantially affect the response of the detectable moiety. In other embodiments, the tethering moiety provides chemical stability to the probe compound. In further embodiments, the tethering moiety provides sufficient solubility to the probe compound.

In some embodiments, a tethering moiety, -T$^P$-, such as a water soluble polymer is coupled at one end to a provided irreversible inhibitor and to a detectable moiety, R$^t$, at the other end. In other embodiments, a water soluble polymer is coupled via a functional group or substituent of the provided irreversible inhibitor. In further embodiments, a water soluble polymer is coupled via a functional group or substituent of the reporter moiety.

In some embodiments, examples of hydrophilic polymers, for use in tethering moiety -$T^P$-, include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof, terpolymers thereof, mixtures thereof, and derivatives of the foregoing. In other embodiments, a water soluble polymer is any structural form. Exemplary forms are linear, forked or branched. In further embodiments, multifunctional polymer derivatives include, but are not limited to, linear polymers having two termini, each terminus being bonded to a functional group which is the same or different.

In some embodiments, a water polymer comprises a poly(ethylene glycol) moiety. In further embodiments, the molecular weight of the polymer is of a wide range. Exemplary ranges are between about 100 Da and about 100,000 Da or more. In yet further embodiments, the molecular weight of the polymer is between about 100 Da and about 100,000 Da, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly(ethylene glycol) molecule is a branched polymer. In further embodiments, the molecular weight of the branched chain PEG is between about 1,000 Da and about 100,000 Da. Exemplary ranges are about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of a branched chain PEG is between about 1,000 Da and about 50,000 Da. In some embodiments, the molecular weight of a branched chain PEG is between about 1,000 Da and about 40,000 Da. In some embodiments, the molecular weight of a branched chain PEG is between about 5,000 Da and about 40,000 Da. In some embodiments, the molecular weight of a branched chain PEG is between about 5,000 Da and about 20,000 Da. The foregoing list for substantially water soluble backbones is by no means exhaustive and is merely illustrative, and in some embodiments, polymeric materials having the qualities described above are suitable for use in methods and compositions described herein.

One of ordinary skill in the art will appreciate that when -$T^P$-$R^P$ is attached to a compound of the formulae herein.

In certain embodiments, the tethering moiety, -$T^P$-, has one of the following structures:

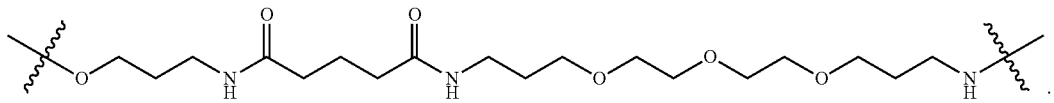 [SMILES: *NCCCOCCOCCOCCCNC(=O)CCCC(=O)NCCCO*]

In some embodiments, the tethering moiety, -$T^P$-, has the following structure:

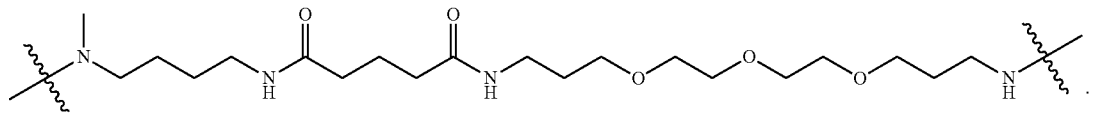 [SMILES: *NCCCOCCOCCOCCCNC(=O)CCCC(=O)NCCCCN(*)C]

In other embodiments, the tethering moiety, -$T^P$-, has the following structure:

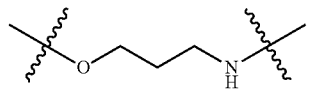

In certain other embodiments, the tethering moiety, -T$^P$-, has the following structure:

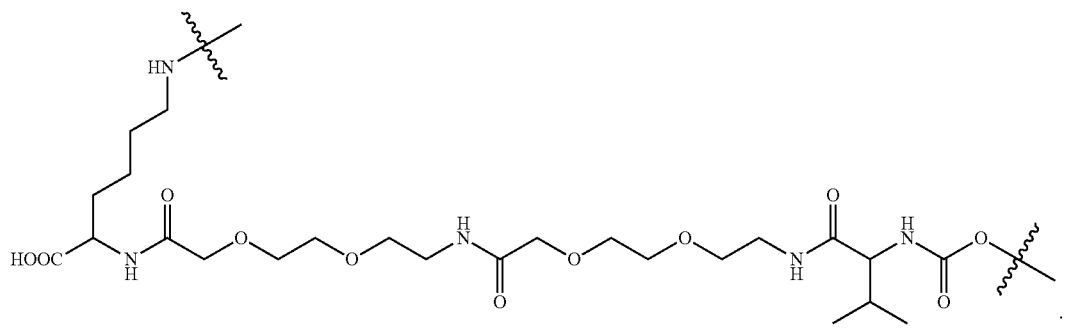 [SMILES: *NCCCCC(NC(=O)COCCOCCNC(=O)COCCOCCNC(=O)C(NC(=O)O*)C(C)C)C(=O)O]

In yet other embodiments, the tethering moiety, -T$^P$-, has the following structure:

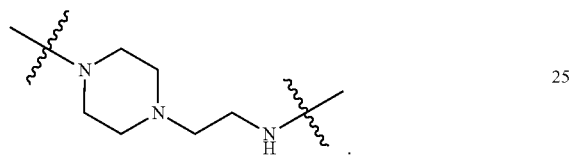

In some embodiments, the tethering moiety, -T$^P$-, has the following structure:

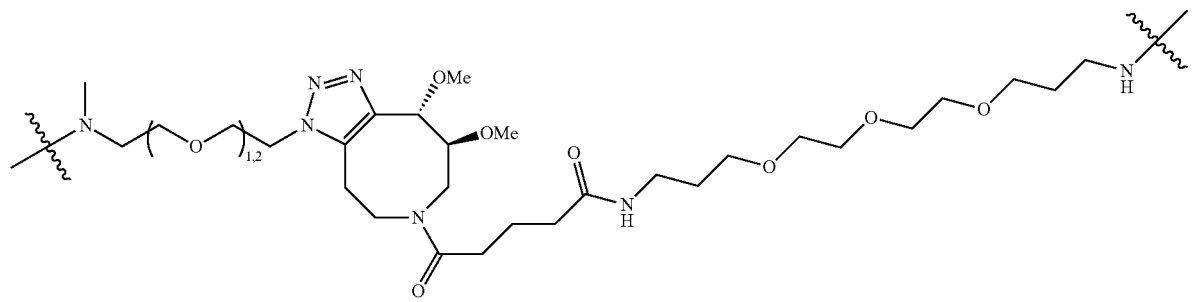

In some embodiments, -T$^P$-R is of the following structure:

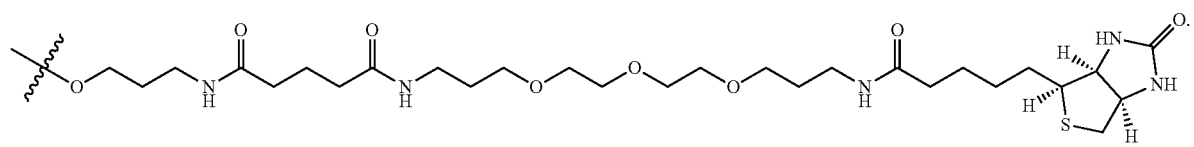 [SMILES: *OCCCNC(=O)CCCC(=O)NCCCOCCOCCOCCCNC(=O)CCCC[C@@H]1SC[C@@H]2NC(=O)N[C@@H]21]

In other embodiments, -T$^P$-R$^P$ is of the following structure:

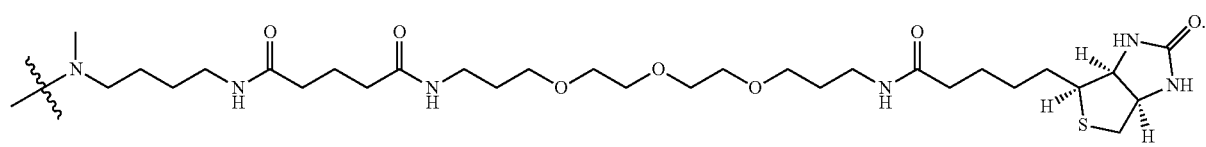 [SMILES: *N(C)CCCCNC(=O)CCCC(=O)NCCCOCCOCCOCCCNC(=O)CCCC[C@@H]1SC[C@@H]2NC(=O)N[C@@H]21]

In certain embodiments, -T$^P$-R$^P$ is of the following structure:

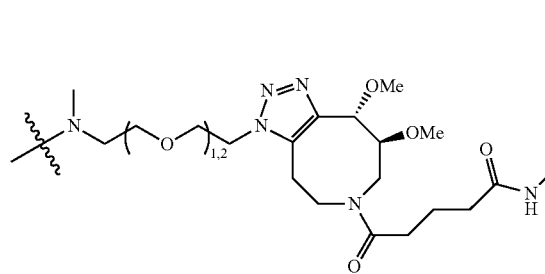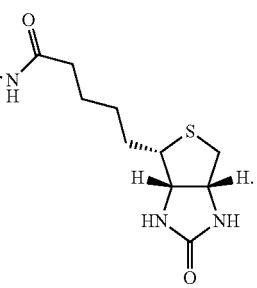

In some embodiments, a probe compound is derived from any compound described herein.

In certain embodiments, the probe compound is one of the following structures:

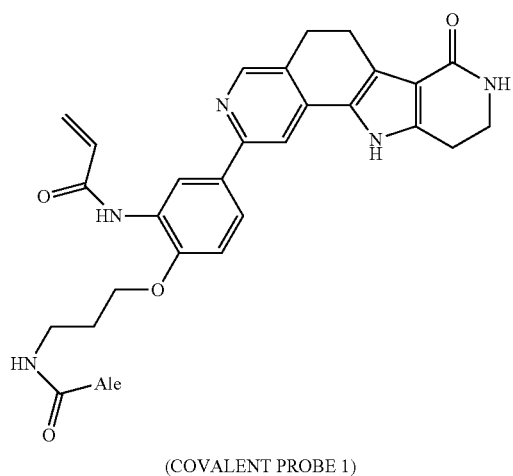

(COVALENT PROBE 1)

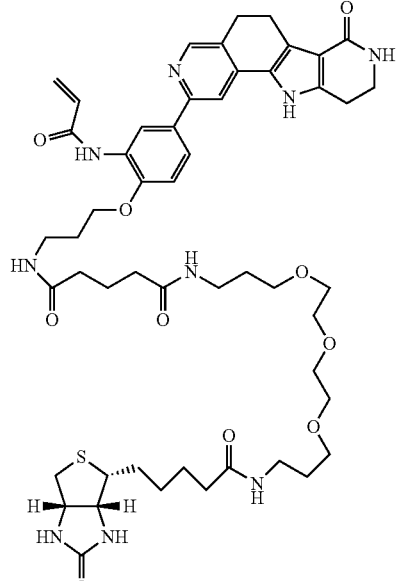

(COVALENT PROBE 2)

It will be appreciated that many -T$^P$-R$^P$ reagents are commercially available. For example, numerous biotinylating reagents are available from, e.g., Thermo Scientific having varying tether lengths. Such reagents include NHS-PEG$_4$-Biotin and NHS-PEG$_{12}$-Biotin.

In some embodiments, analogous probe structures to the ones exemplified above are prepared using click-ready inhibitor moieties and click-ready -T$^P$-R$^P$ moieties, as described herein.

In some embodiments, a provided probe compound covalently modifies a phosphorylated conformation of a protein kinase. In one aspect, the phosphorylated conformation of the protein kinase is either an active or inactive form of the protein kinase. In certain embodiments, the phosphorylated conformation of the protein kinase is an active form of said kinase. In certain embodiments, the probe compound is cell permeable.

In some embodiments, the present invention provides a method for determining occupancy of a protein kinase by a provided irreversible inhibitor (i.e., a compound of any of the formulae presented herein) in a patient, comprising providing one or more tissues, cell types, or a lysate thereof, obtained from a patient administered at least one dose of a compound of said irreversible inhibitor, contacting said tissue, cell type or lysate thereof with a probe compound to covalent modify at least one protein kinase present in said lysate, and measuring the amount of said protein kinase covalently modified by the probe compound to determine occupancy of said protein kinase by said compound as compared to occupancy of said protein kinase by said probe compound. In certain embodiments, the method further comprises the step of adjusting the dose of the compound of formulae presented herein to increase occupancy of the protein kinase. In certain other embodiments, the method further comprises the step of adjusting the dose of the compound of formulae presented herein to decrease occupancy of the protein kinase.

As used herein, the terms "occupancy" or "occupy" refer to the extent to which a protein kinase is modified by a provided covalent inhibitor compound. One of ordinary skill in the art would appreciate that it is desirable to administer the lowest dose possible to achieve the desired efficacious occupancy of the protein kinase.

In some embodiments, the protein kinase to be modified is MK2.

In some embodiments, the probe compound comprises the irreversible inhibitor for which occupancy is being determined.

In some embodiments, the present invention provides a method for assessing the efficacy of a provided irreversible inhibitor in a mammal, comprising administering a provided irreversible inhibitor to the mammal, administering a provided probe compound to tissues or cells isolated from the mammal, or a lysate thereof, measuring the activity of the detectable moiety of the probe compound, and comparing the activity of the detectable moiety to a standard.

In other embodiments, the present invention provides a method for assessing the pharmacodynamics of a provided irreversible inhibitor in a mammal, comprising administering a provided irreversible inhibitor to the mammal, administering a probe compound presented herein to one or more cell types, or a lysate thereof, isolated from the mammal, and measuring the activity of the detectable moiety of the probe compound at different time points following the administration of the inhibitor.

In yet other embodiments, the present invention provides a method for in vitro labeling of a protein kinase comprising contacting said protein kinase with a probe compound described herein. In one embodiment, the contacting step comprises incubating the protein kinase with a probe compound presented herein.

In certain embodiments, the present invention provides a method for in vitro labeling of a protein kinase comprising contacting one or more cells or tissues, or a lysate thereof, expressing the protein kinase with a probe compound described herein.

In certain other embodiments, the present invention provides a method for detecting a labeled protein kinase comprising separating proteins, the proteins comprising a protein kinase labeled by probe compound described herein, by electrophoresis and detecting the probe compound by fluorescence.

In some embodiments, the present invention provides a method for assessing the pharmacodynamics of a provided irreversible inhibitor in vitro, comprising incubating the provided irreversible inhibitor with the target protein kinase, adding the probe compound presented herein to the target protein kinase, and determining the amount of target modified by the probe compound.

In certain embodiments, the probe compound is detected by binding to avidin, streptavidin, neutravidin, or captavidin.

In some embodiments, the probe is detected by Western blot. In other embodiments, the probe is detected by ELISA. In certain embodiments, the probe is detected by flow cytometry.

In other embodiments, the present invention provides a method for probing the kinome with irreversible inhibitors comprising incubating one or more cell types, or a lysate thereof, with a biotinylated probe compound to generate proteins modified with a biotin moiety, digesting the proteins, capturing with avidin or an analog thereof, and performing multi-dimensional LC-MS-MS to identify protein kinases modified by the probe compound and the adduction sites of said kinases.

In certain embodiments, the present invention provides a method for measuring protein synthesis in cells comprising incubating cells with an irreversible inhibitor of the target protein, forming lysates of the cells at specific time points, and incubating said cell lysates with an inventive probe compound to measure the appearance of free protein over an extended period of time.

In other embodiments, the present invention provides a method for determining a dosing schedule in a mammal for maximizing occupancy of a target protein kinase comprising assaying a one or more cell types, or a lysate thereof, isolated from the mammal, (derived from, e.g., splenocytes, peripheral B cells, whole blood, lymph nodes, intestinal tissue, or other tissues) from a mammal administered a provided irreversible inhibitor of any of the formulae presented herein, wherein the assaying step comprises contacting said one or more tissues, cell types, or a lysate thereof, with a provided probe compound and measuring the amount of protein kinase covalently modified by the probe compound.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Enantioenriched compounds of the invention were prepared in enantioenriched form using chiral starting materials, or were separated after reaction with a racemic starting material, using chiral chromatography. For compounds prepared as racemic or diastereomeric mixtures, the single isomers can be prepared in optically pure form by either employing chiral starting materials or performing chiral chromatography.

Compound numbers utilized in the Examples below correspond to compound numbers set forth the Tables provided, supra.

Example 1

Compound I-5

N-(2-((4-(4'-oxo-1',4',5',6'-tetrahydrospiro[piperidine-3,7'-pyrrolo[3,2-c]pyridin]-2'-yl)pyrimidin-2-yl)amino)phenyl)acrylamide (racemic)

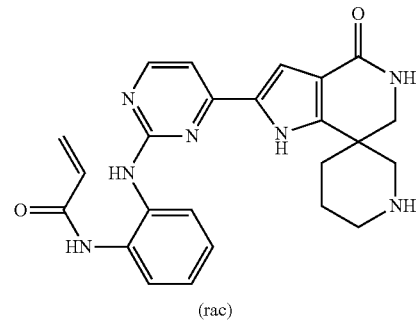 [SMILES: C=CC(=O)Nc1ccccc1Nc1nccc(-c2cc3c([nH]2)C2(CCCNC2)CNC3=O)n1]

(rac)

The title compound was prepared according to the schemes, steps, and intermediates described below.

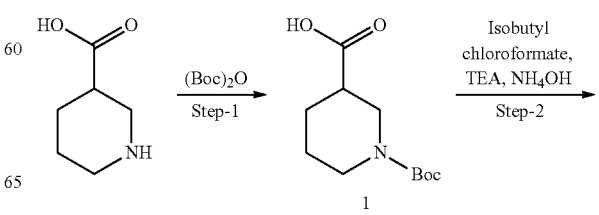

-continued
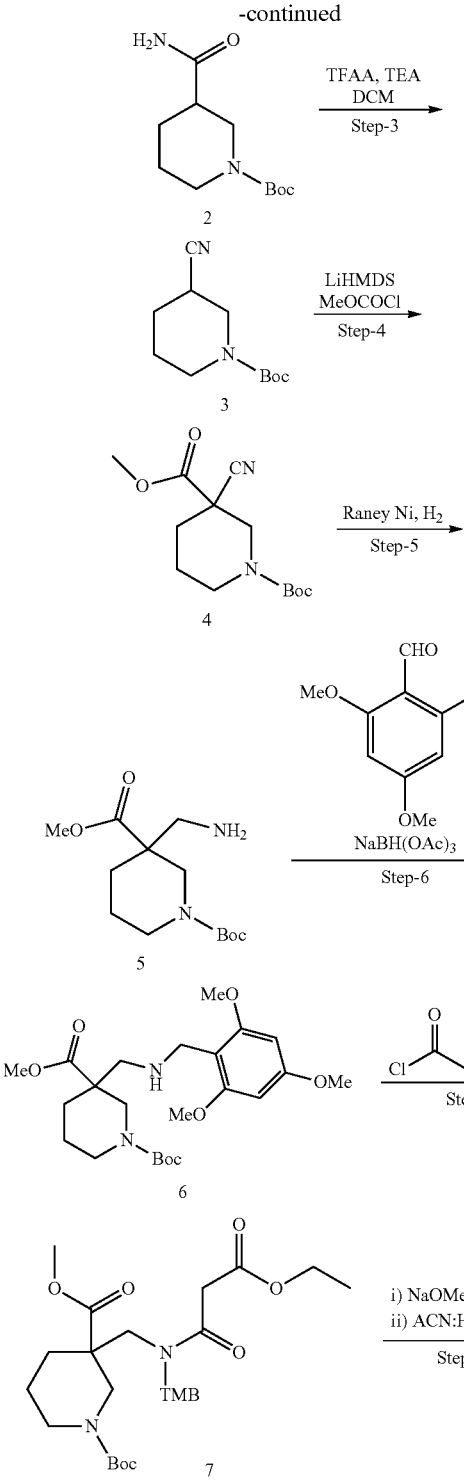
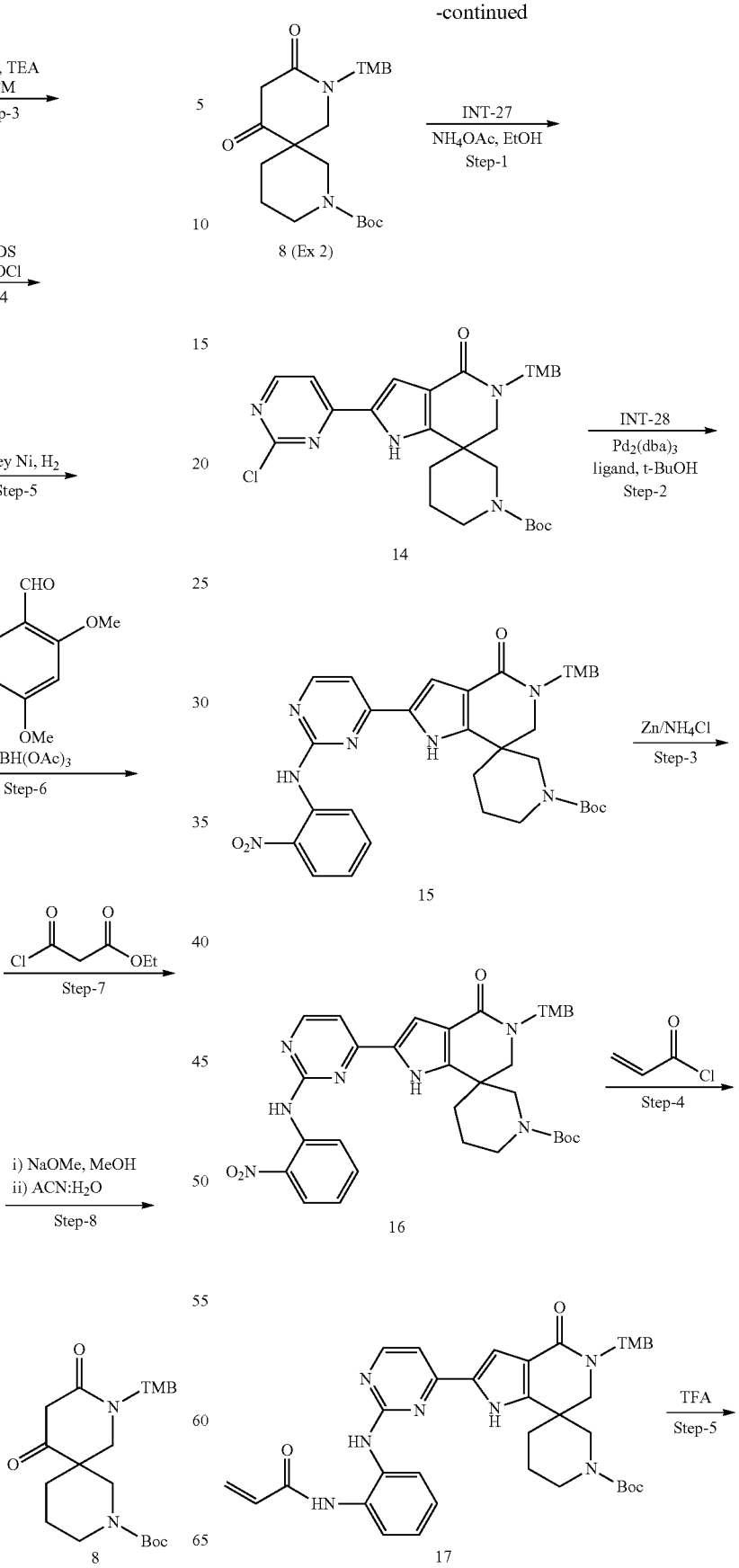

-continued

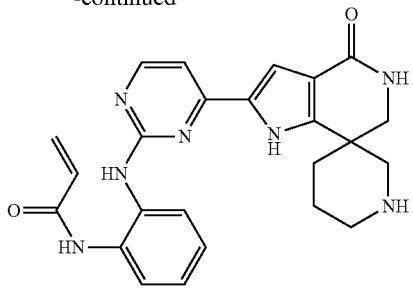

The synthesis of intermediate 8 is provided in detail in Example 2.

Step 1:

tert-butyl 2'-(2-chloropyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (14)

To a solution of tert-butyl 9,11-dioxo-8-(2,4,6-trimethoxybenzyl)-2,8-diazaspiro[5.5]undecane-2-carboxylate 8, prepared as described in Example 2 (1.0 g, 2.0 mmol) in ethanol (10 mL), 2-bromo-l-(2-chloropyrimidin-4-yl) ethanone INT-27 (460 mg, 2.0 mmol) was added at 0° C. To this ammonium acetate (608 mg, 8.0 mmol) and acetic acid (1.0 mL) were added. The resulting mixture was heated at 80° C. for 5 h. The reaction mixture was concentrated under reduced pressure, and the residue was partitioned between water (100 mL) and ethyl acetate (150 mL). The organic phase was dried over anhydrous sodium sulfate and concentrated under reduced pressure. The residue was purified by silica gel column chromatography to afford 14 (380 mg, 29%) as a brown solid. $^1$H NMR (400 MHz, DMSO-$d_6$) δ 1.36 (s, 9H), 1.56 (s, 2H), 3.0 (d, J=12.8 Hz, 1H), 3.3 (brs, 1H), 3.72 (s, 7H), 3.76 (s, 4H), 3.82 (brs, 2H), 4.0 (d, J=13.2 Hz, 1H), 5.0 (brs, 1H), 6.62 (s, 2H), 7.16 (d, J=2.2 Hz, 1H), 7.68-7.69 (dd, J=1.4, 5.3 Hz, 1H), 7.82 (d, J=1.4 Hz, 1H), 8.3 (d, J=4.5 Hz, 1H), 11.5 (s, 1H). MS m/z (M+H): 453.3.

Step 2:

Tert-butyl 2'-(2-(2-nitrophenylamino)pyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (15)

To a solution of tert-butyl 2'-(2-chloropyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate 14 (300 mg, 0.5 mmol) in tert-amyl alcohol (2.0 mL), 2-nitroaniline INT-28 (69 mg, 0.5 mmol) and sodium carbonate (319 mg, 3 mmol) were added and degassed for 15 min with nitrogen. Then Pd$_2$(dba)$_3$ (55 mg, 0.06 mmol) and 2-Dicyclohexylphosphino-2'-(N,N-dimethylamino)biphenyl (79 mg, 0.2 mmol) were added and again degassed for 10 min with nitrogen. The resulting mixture was stirred at 90° C. for 7 h. Reaction mixture was adsorbed on silica gel column and eluted the with 2% methanol in chloroform to yield 15 (180 mg, 51%) as yellow solid. MS m/z (M+H): 700.3

Step 3:

Tert-butyl-2'-(2-(2-aminophenylamino)pyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (16)

To a solution of tert-butyl 2'-(2-(2-nitrophenylamino)pyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate 15 (130 mg, 0.2 mmol) in (3:1) 1,4-dioxane:water (2 mL), ammonium chloride (97 mg, 1.5 mmol) and Zn dust (80 mg, 1.5 mmol) were added at 0° C. The reaction mixture was stirred at RT for 3 hours. Reaction mixture was filtered through celite bed and the filtrate was partitioned between water (10 mL) and ethyl acetate (30 mL). Organic layer was separated, dried over anhydrous sodium sulfate and concentrated. Crude compound was purified by column chromatography to obtain 16 (60 mg, 48%) as yellow solid. MS m/z (M+H): 670.4

Step 4:

Tert-butyl 2'-(2-(2-acrylamidophenylamino)pyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (17)

To a stirred solution of tert-butyl 2'-(2-(2-aminophenylamino)pyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate 16 (65 mg, 0.1 mmol) in dichloromethane (0.5 mL), DIPEA (25 mg, 0.2 mmol) was added and cooled to −78° C., then acryloyl chloride (8 mg, 0.09 mmol) was added. The reaction mixture was stirred for 15 min. The reaction mixture was partitioned between dichloromethane (10 mL) and water (20 mL). The organic layer was dried over anhydrous sodium sulfate and concentrated under reduced pressure to give 17 (60 mg, 85%) as brown solid. MS m/z (M+H): 724.3

Step 5:

A solution of 17 (60 mg) in 1:1 DCM-TFA was stirred at rt for 1 h, concentrated by rotary evaporation, and purified by prep-HPLC to give I-5 as an off-white solid: 6.5 mg, 12%. $^1$H NMR (400 MHz, DMSO-$d_6$) δ 1.67 (m, 1H), 1.82 (d, J=11.6 Hz, 2H), 2.09-2.12 (m, 1H), 2.76-2.83 (m, 1H), 3.27-3.44 (m, 4H), 3.55-3.58 (dd, J=2.5, 12.8 Hz, 1H), 5.73-5.76 (dd, J=1.7, 10.2 Hz, 1H), 6.21-6.26 (dd, J=1.8, 17.0 Hz, 1H), 6.44-6.50 (dd, J=10.0, 17.0 Hz, 1H), 7.09-7.14 (m, 2H), 7.19-7.22 (m, 2H), 7.38 (s, 1H), 7.49 (d, J=7.7 Hz, 1H), 7.79 (d, J=8.0 Hz, 1H), 8.34 (d, J=5.3 Hz, 1H), 8.46-8.49 (m, 1H), 8.52 (s, 1H), 9.09 (d, J=10.9 Hz, 1H), 9.93 (s, 1H), 11.5 (s, 1H). MS m/z (M+H): 442.6

Example 2

Compound I-6

3-acrylamido-N-(4-(4'-oxo-1',4',5',6'-tetrahydrospiro[piperidine-3,7'-pyrrolo[3,2-c]pyridin]-2'-yl)pyridin-2-yl)benzamide (racemic)

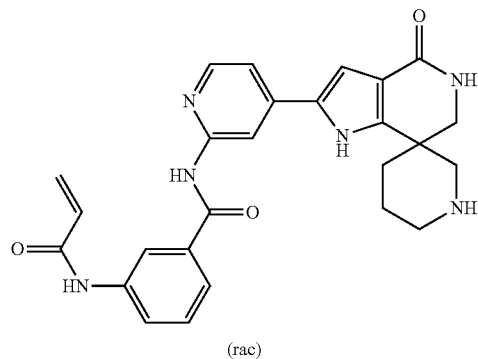 [SMILES: C=CC(=O)Nc1cccc(C(=O)Nc2cc(-c3cc4c([nH]3)C3(CCCNC3)CNC4=O)ccn2)c1]

(rac)

The title compound was prepared according to the schemes, steps, and intermediates
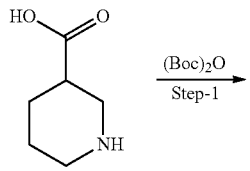
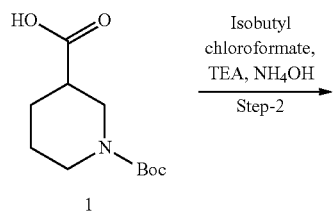
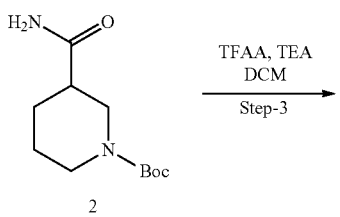
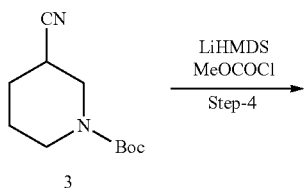
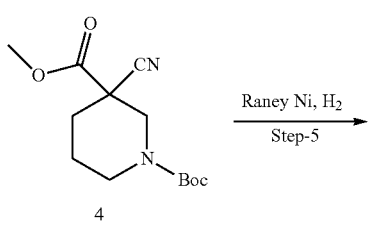
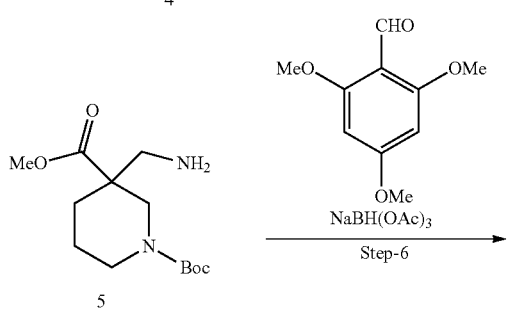
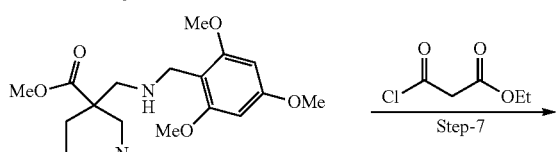
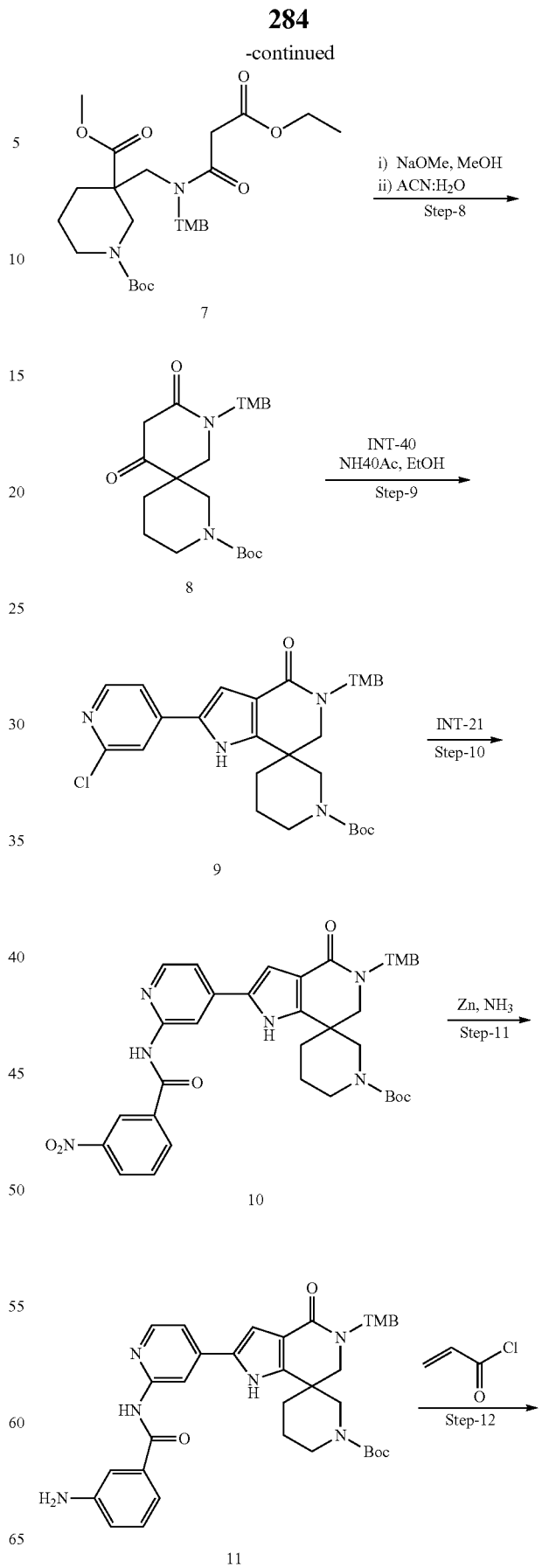

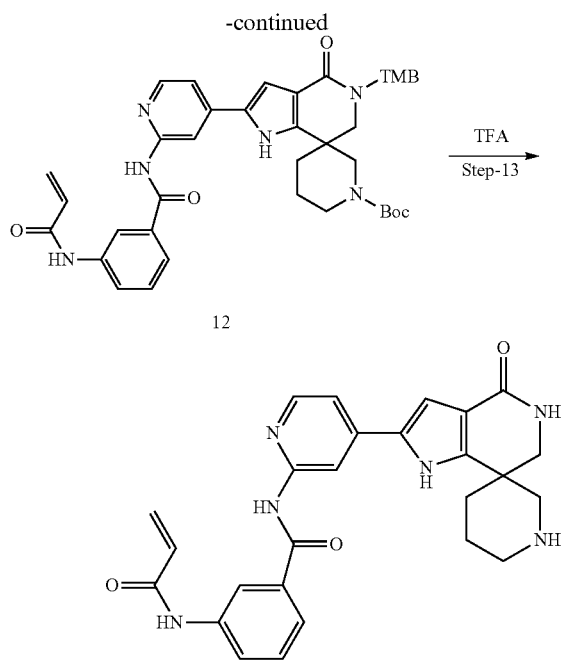

12

Step 1:

1-(tert-butoxycarbonyl) piperidine-3-carboxylic Acid (1)

To a solution of piperidine-3-carboxylic acid (50.0 g, 387.5 mmol) in t-butanol (464.0 mL), IN NaOH solution (464.0 mL) was added at 0° C. and stirred for 10 min followed by the addition of Boc-anhydride (143.6 g, 659.0 mmol). The reaction mixture was stirred for 12 h at room temperature. The reaction mixture was concentrated under reduced pressure and then neutralized with IN HCl. The solid observed was filtered and dried to yield 1 (86.0 g, 97%) as white solid. $^1$H NMR (400 MHz, DMSO-$d_6$) δ 1.38 (s, 9H), 1.47 (m, 1H), 1.59 (dt, J=3.8 Hz, 1H), 1.87 (m, 1H), 2.28 (m, 1H), 2.77-2.84 (dt, J=2.5, 3.0 Hz, 1H), 3.0 (brs, 1H), 3.67 (d, J=11.0 Hz, 1H), 3.87 (brs, 1H), 12.2 (s, 1H).

Step 2:

tert-butyl 3-carbamoylpiperidine-1-carboxylate (2)

To a solution of 1-(tert-butoxycarbonyl) piperidine-3-carboxylic acid 1 (50.0 g, 218.0 mmol) in anhydrous dichloromethane (400 mL), triethylamine (44.1 g, 437 mmol) was added at 0° C. followed by the addition of isobutylchloroformate (596.0 g, 437.0 mmol). The resulting mixture was stirred at room temperature for 1 hour. The reaction mixture was concentrated under reduced pressure. The residue obtained was cooled to 0° C. followed by the addition of NH$_4$OH. The solid observed was filtered, washed with water and dried to yield 2 (40.0 g, 80%) as a white solid. $^1$H NMR (400 MHz, CDCl$_3$) δ 1.47 (s, 9H), 1.63 (m, 1H), 1.85 (s, 2H), 2.36 (m, 1H), 3.07 (m, 1H), 3.29 (brs, 1H), 3.66 (brs, 1H), 3.85 (m, 1H), 5.5 (s, 1H), 6.1 (brs, 1H).

Step 3:

Tert-butyl 3-cyanopiperidine-1-carboxylate (3)

To a solution of tert-butyl-3-carbamoyl piperidine-1-carboxylate 2 (1.0 g, 4 mmol) in anhydrous dichloromethane (20 mL), triethylamine (3.1 g, 31.0 mmol) was added followed by the dropwise addition of trifluoroaceticanhydride (4.1 g, 20.0 mmol). The resulting mixture was warmed to room temperature and stirred for 16 h. The reaction mixture was partitioned between dichloromethane (50 mL) and water (50 mL). The organic phase was washed with saturated bicarbonate solution (100 mL). The organic phase was dried over anhydrous sodium sulfate and concentrated under reduced pressure to yield 3 (800 mg, 87%) as a thick liquid. $^1$H NMR (400 MHz, CDCl$_3$) δ 1.49 (s, 9H), 1.77 (m, 2H), 1.97 (brs, 1H), 2.66 (m, 1H), 3.35-3.84 (brs, 4H), Step 4:

1-tert-butyl 3-methyl 3-cyanopiperidine-1,3-dicarboxylate (4)

To a solution of tert-butyl 3-cyanopiperidine-1-carboxylate 3 (25.0 g, 119.0 mmol) in anhydrous tetrahydrofuran (500 mL) methylchloroformate (16.8 g, 178.5 mmol) was added at −78° C. followed by the addition of 1M LiHMDS (19.8 g, 357 mmol) at −78° C. The resulting mixture was stirred for 1 h at 0° C. and at room temperature for another 1 h. The reaction mixture was cooled to 0° C., quenched with saturated NH$_4$Cl solution. The solution was partitioned between ethyl acetate (400 mL) and water (200 mL). The organic layer was separated, dried over anhydrous sodium sulfate and concentrated under reduced pressure. The residue was purified by silica gel column chromatography to afford 4 (17.0 g, 53%) as a brown liquid. $^1$H NMR (400 MHz, CDCl$_3$) δ 1.48 (s, 9H), 1.73 (m, 1H), 1.85 (m, 1H), 2.04 (m, 1H), 2.25 (m, 2H), 2.77 (brs, 1H), 3.28 (m, 1H), 3.84 (s, 3H), 4.38 (brs, 1H). GCMS: 268.1

Step 5:

1-tert-butyl 3-methyl 3-(amino methyl) piperidine-1, 3-dicarboxylate (5)

To a solution of 1-tert-butyl 3-methyl 3-cyanopiperidine-1, 3-dicarboxylate 4 (6.0 g, 22.0 mmol) in methanol (60 mL), Raney-Nickel (6.0 g) was added. The resulting mixture was stirred under hydrogen at 70 psi for 16 h. The reaction mixture was filtered through celite, and the filtrate was concentrated under reduced pressure. The residue was purified by neutral alumina column to afford 5 (4.2 g, 69%) as a thick brown liquid. $^1$H NMR (400 MHz, DMSO-$d_6$) δ 1.49 (s, 9H), 1.52 (m, 4H), 1.85 (brs, 2H), 2.61 (q, J=13.0 Hz, 2H), 3.29 (brs, 2H), 3.60 (s, 3H), 3.9 (brs, 1H), 4.3 (brs, 1H).

Step 6:

1-tert-butyl 3-methyl 3-((2, 4, 6-trimethoxybenzylamino) methyl) piperidine-1, 3-dicarboxylate (6)

To a solution mixture of 1-tert-butyl 3-methyl 3-(amino methyl) piperidine-1, 3-dicarboxylate 5 (4.4 g, 16.0 mmol) and 2, 4, 6-trimethoxybenzaldehyde (2.8 g, 14.5 mmol) in ethanol (60.0 mL), sodium triacetoxyborohydride (17.1 g, 81 mmol) was added. The resulting mixture was stirred for 16 h. The reaction mixture was concentrated under reduced pressure. The residue was partitioned between ethyl acetate (100 mL) and water (70 mL). The organic phase was dried over anhydrous sodium sulfate and concentrated under reduced pressure to obtain 6 (7.0 g, 95%) as a thick liquid. $^1$H NMR (400 MHz, CDCl$_3$) δ 1.48 (s, 9H), 1.58 (brs, 3H), 1.62 (brs, 1H), 1.9 (brs, 2H), 2.65 (brs, 1H), 2.68 (d, J=12.2 Hz, 1H), 3.33 (brs, 3H), 3.63 (s, 3H), 3.65 (d, J=4.1 Hz, 1H), 3.79 (d, J=6.5 Hz, 9H), 6.1 (s, 2H). MS m/z (M+H): 453.3.

Step 7:

1-tert-butyl 3-methyl 3-((3-ethoxy-3-oxo-N-(2, 4, 6-trimethoxybenzyl) propanamido) methyl) piperidine-1, 3-dicarboxylate (7)

To a solution of 1-tert-butyl 3-methyl 3-((2, 4, 6-trimethoxybenzylamino)methyl)-piperidine-1,3-dicarboxylate 6 (15.0 g, 33.0 mmol) in dichloro methane (350 mL), triethylamine (6.7 g, 66.0 mmol) and ethyl malonyl chloride (5.9 g, 40.0 mmol) were added at 0° C. The reaction mixture was warmed to room temperature and stirred for 3 h. The reaction mixture was partitioned between dichloromethane (400 mL) and water (200 mL). The organic phase was washed with saturated bicarbonate solution (100 mL) and brine solution (100 mL). The organic phase was dried over anhydrous sodium sulfate and concentrated under reduced pressure to yield compound 7 (10.0 g, 54%) as a thick liquid. $^1$H NMR (400 MHz, CDCl$_3$) δ 1.27 (m, 3H), 1.49 (s, 9H), 1.62 (brs, 3H), 2.18 (d, J=12.3 Hz, 1H), 2.85-2.92 (m, 2H), 3.42 (brs, 1H), 3.74 (m, 6H), 3.81 (s, 9H), 4.20 (q, J=7.1 Hz, 2H), 4.42 (t, J=10.3 Hz, 2H), 6.1 (s, 2H).

Step 8:

tert-butyl 9,11-dioxo-8-(2,4,6-trimethoxybenzyl)-2, 8-diazaspiro[5.5]undecane-2-carboxylate (8)

Sodium metal (800 mg) was dissolved in freshly distilled ethanol (48 mL) and the resulting sodium ethoxide solution was added to 1-tert-butyl-3-methyl-3-((3-ethoxy-3-oxo-N-(2,4,6-trimethoxybenzyl)propanamido)methyl)piperidine-1, 3-dicarboxylate 7 (4.2 g, 7 mmol) in toluene (48 mL). The resulting mixture was refluxed at 80° C. for 2 h. The reaction mixture was concentrated under reduced pressure, and the residue was partitioned between water (50 mL) and ethyl acetate (100 mL). The organic layer was washed with brine solution (100 mL), dried over anhydrous sodium sulfate and concentrated under reduced pressure. The brown solid obtained was dissolved in acetonitrile (10 mL) and water (2 mL). The resulting mixture was heated at 90° C. for 36 h. The reaction mixture was concentrated under reduced pressure and the residue obtained was triturated with diethyl ether to afford compound 8 (1.3 g, 38%) as a brown solid. $^1$H NMR (400 MHz, DMSO-d$_6$) δ 1.35 (s, 9H), 2.8 (brs, 2H), 3.26 (brs, 4H), 3.58 (brs, 1H), 3.71 (s, 9H), 3.76 (s, 3H), 4.26 (brs, 1H), 4.71-4.75 (d, J=13.4 Hz, 2H), 6.23 (s, 2H).

Step 9:

tert-butyl-2'-(2-chloropyridin-4-yl)-4'-oxo-5'-(2,4,6-trimethoxybenzyl)-1',4',5',6'-tetrahydro spiro[piperidine-3,7'-pyrrolo[3,2-c]pyridine]-1-carboxylate (9)

To a solution of tert-butyl 9,11-dioxo-8-(2,4,6-trimethoxybenzyl)-2,8-diazaspiro[5.5]undecane-2-carboxylate 8 (1.0 g, 2.0 mmol) in ethanol (30 mL), 2-bromo-1-(2-chloropyridin-4-yl)ethanone INT-40 (1.0 g, 4.0 mmol) was added at 0° C. To this ammonium acetate (499 mg, 6 mmol) and acetic acid (250 mg, 4.0 mmol) were added. The resulting mixture was heated at 80° C. and for 5 h. The reaction mixture was concentrated under reduced pressure and the residue was partitioned between water (100 mL) and ethyl acetate (150 mL). The organic phase was dried over anhydrous sodium sulfate and concentrated under reduced pressure. The residue was purified by silica gel column chromatography to afford 9 (350 mg, 27%) as a brown solid. $^1$H NMR (400 MHz, DMSO-d$_6$) δ 1.36 (s, 9H), 1.56 (s, 2H), 3.0 (d, J=12.8 Hz, 1H), 3.3 (brs, 1H), 3.72 (s, 7H), 3.76 (s, 4H), 3.82 (brs, 2H), 4.0 (d, J=13.2 Hz, 1H), 5.0 (brs, 1H), 6.62 (s, 2H), 7.16 (d, J=2.2 Hz, 1H), 7.68-7.69 (dd, J=1.4, 5.3 Hz, 1H), 7.82 (d, J=1.4 Hz, 1H), 8.3 (d, J=4.5 Hz, 1H), 11.5 (s, 1H). MS m/z (M+H): 453.3.

Step 10:

tert-butyl 2'-(2-(3-nitrobenzamido)pyridin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (10)

To a solution tert-butyl-2'-(2-chloropyridin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate 9 (850 mg, 1.0 mmol) and 3-nitrobenzamide INT-21 (100 mg, 2.0 mmol) in 1, 4-dioxane (20.0 mL), cesium carbonate (927 mg, 3.0 mmol) was added and degassed for 15 min. To this mixture, xantphos (164 mg, 0.3 mmol) and Pd$_2$(dba)$_3$ (65 mg, 0.1 mmol) were added and again degassed for another 15 min. The resulting mixture was heated at 150° C. in a microwave reactor for 20 min. The reaction mixture was cooled to rt and concentrated under reduced pressure. The residue was diluted with ethyl acetate and filtered through celite. The filtrate was concentrated under reduced pressure and the residue was purified by silica gel column chromatography to afford 10 (750 mg, 85%) as a brown solid. MS m/z (M+H): 727.4

Step 11:

tert-butyl 2'-(2-(3-aminobenzamido)pyridin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (11)

To a solution of nitro compound 10 (1.0 eq) in dioxane/H$_2$O, Zn dust (8.0 eq) was added followed by the addition of NH$_4$Cl (8.0 eq) at room temperature. The reaction mixture was then stirred at room temperature for 16 h. After completion of the starting material, the reaction mixture was diluted with water and extracted with ethyl acetate. The organic layer was dried over anhydrous sodium sulfate and concentrated under reduce pressure to obtain the desired amino compound 11: MS m/z (M+H): 697.3.

Step 12:

tert-butyl 2'-(2-(3-acrylamidobenzamido)pyridin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (12)

To a solution of amine 11 (0.032 mmol) in THF (2.0 mL), diisopropylethylamine (0.03 mmol) and acryloyl chloride (0.03 mmol) were added at −78° C. The resulting mixture was warmed to room temperature and stirred for 16 h. After completion of reaction, solvent was removed under reduced pressure. The crude obtained was purified by silica gel column chromatography to yield compound 12: MS m/z (M+H): 751.3

Step 13:

To a solution of compound 12 in dichloromethane, trifluoroacetic acid (excess) was added at 0° C. and stirred at room temperature for 3 h. After completion of the reaction, excess TFA was removed under reduced pressure, and the residue obtained was triturated with diethyl ether. Solid obtained was purified by preparative HPLC to yield compound I-6: Off-white solid, 10.0 mg, $^1$H NMR (400 MHz, CD$_3$OD) δ 1.93-1.96 (m, 1H), 2.0-2.12 (m, 2H), 2.31-2.39

(dt, J=4.0, 13.5, 1H), 3.02-3.10 (dt, J=3.6, 13.0, 1H), 3.32-3.39 (m, 1H), 3.48-3.51 (m, 1H), 3.56-3.65 (m, 2H), 3.75 (d, J=13.2, 1H), 5.83-5.86 (dd, J=2.8, 9.0, 1H), 6.45-6.52 (m, 2H), 7.29 (s, 1H), 7.57 (t, J=8.0, 1H), 7.71 (d, J=5.9, 1H), 7.82-7.84 (m, 2H), 8.24 (s, 1H), 8.35 (d, J=5.8, 1H), 8.46 (s, 1H). MS m/z (M−H): 469.5

Example 3

Compound I-1

3-acrylamido-4-methoxy-N-(4-(4'-oxo-1',4',5',6'-tetrahydrospiro[piperidine-3,7'-pyrrolo[3,2-c]pyridin]-2'-yl)pyridin-2-yl)benzamide (racemic)

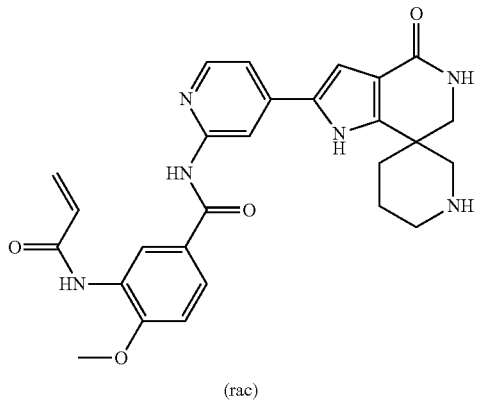 [SMILES: C=CC(=O)Nc1cc(C(=O)Nc2cc(-c3cc4c([nH]3)C3(CCCNC3)CNC4=O)ccn2)ccc1OC]

(rac)

The title compound I-1 was prepared as described in Example 2, by substituting primary amide INT-25 for INT-21 in the Buchwald coupling (step 10): Yellow solid, 35 mg, 30%. $^1$H NMR (400 MHz, DMSO-d$_6$) δ 1.65-1.78 (m, 1H), 1.80-1.90 (m, 2H), 2.70-2.83 (m, 1H), 3.25-3.40 (m, 4H), 3.41-3.46 (m, 1H), 3.66-3.72 (m, 1H), 3.93 (s, 3H), 5.73-5.76 (dd, J=1.9, 10.3 Hz, 1H), 6.23-6.28 (dd, J=1.9, 16.9 Hz, 1H), 6.68-6.75 (dd, J=1.9, 16.8 Hz, 1H), 6.96 (s, 1H), 7.16 (d, J=3.4 Hz, 1H), 7.36 (s, 1H), 7.47-7.48 (dd, J=1.4, 5.4 Hz, 1H), 7.90-7.92 (dd, J=2.2, 8.7 Hz, 1H), 8.33-8.37 (m, 2H), 8.4-8.53 (m, 1H), 8.74 (s, 1H), 9.03 (d, J=9.5 Hz, 1H), 9.52 (s, 1H), 10.69 (s, 1H), 11.75 (s, 1H). MS m/z (M−H): 499.6

Example 4

Compound I-4

2-acrylamido-N-(4-(4'-oxo-1',4',5',6'-tetrahydrospiro[piperidine-3,7'-pyrrolo[3,2-c]pyridin]-2'-yl)pyridin-2-yl)benzamide (racemic)

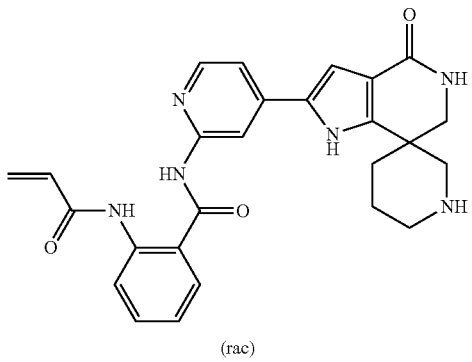 [SMILES: C=CC(=O)Nc1ccccc1C(=O)Nc1cc(-c2cc3c([nH]2)C2(CCCNC2)CNC3=O)ccn1]

(rac)

The title compound I-4 was prepared as described in Example 2, by substituting primary amide INT-22 for INT-21 in the Buchwald coupling (step 10): $^1$H NMR (400 MHz, DMSO-d$_6$) δ 1.69-1.76 (m, 1H), 1.85 (d, J=2.5, 2H), 2.09-2.16 (m, 1H), 2.71-2.80 (m, 1H), 3.28-3.45 (m, 4H), 3.57-3.60 (m, 1H), 5.73-5.76 (dd, J=1.5, 10.2, 1H), 6.19-6.23 (dd, J=1.5, 17.0, 1H), 6.40-6.47 (dd, J=10.2, 17.0, 1H), 6.94 (s, 1H), 7.24 (t, J=7.7, 1H), 7.35 (s, 1H), 7.48-7.49 (dd, J=1.3, 5.3, 1H), 7.54 (t, J=7.2, 1H), 7.81 (d, J=7.4, 1H), 8.11 (d, J=8.1 Hz, 1H), 8.28 (s, 1H), 8.34 (d, J=5.3, 1H), 8.47 (m, 1H), 9.05 (d, J=11.0, 1H), 10.5 (s, 1H), 10.8 (s, 1H), 11.7 (s, 1H). MS m/z (M+H): 471.2

Example 5

Compound I-7

N-(2-(2-methoxyethoxy)-5-(4-(4'-oxo-1',4',5',6'-tetrahydrospiro[piperidine-3,7'-pyrrolo[3,2-c]pyridin]-2'-yl)pyrimidin-2-yl)phenyl)acrylamide (racemic)

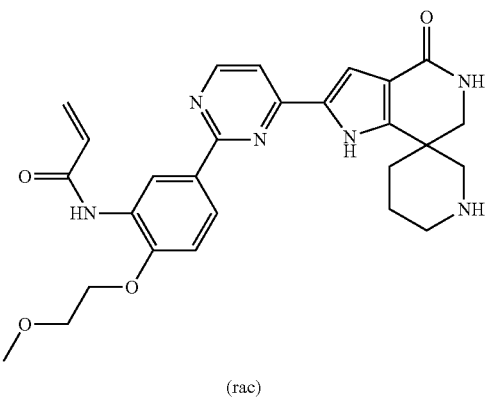 [SMILES: C=CC(=O)Nc1cc(-c2nccc(-c3cc4c([nH]3)C3(CCCNC3)CNC4=O)n2)ccc1OCCOC]

(rac)

The title compound was prepared according to the schemes, steps, and intermediates described below.

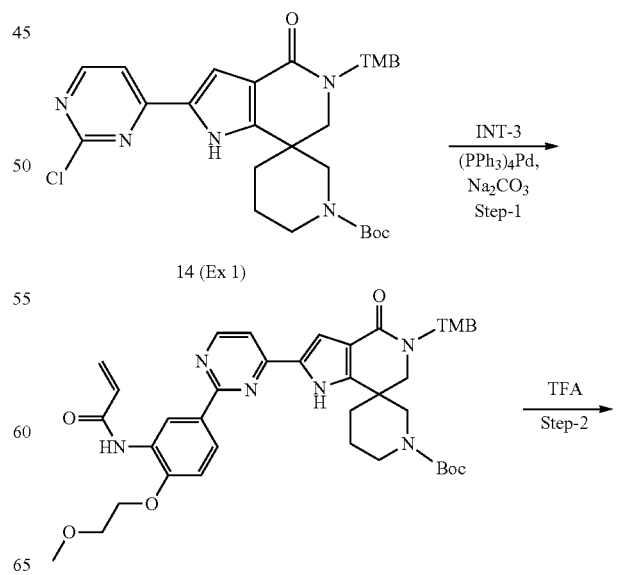

14 (Ex 1)

18

291
-continued

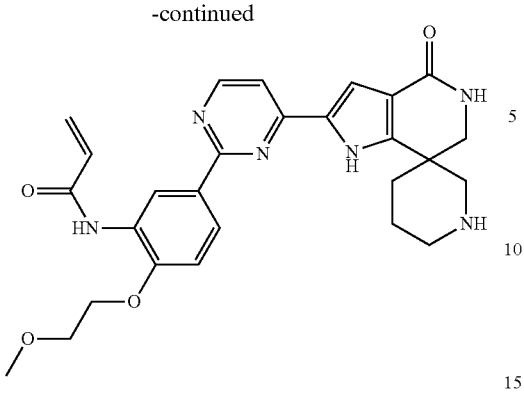

Step 1:

Tert-butyl 2'-(2-(3-acrylamido-4-(2-methoxyethoxy) phenyl) pyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (18)

To a solution of tert-butyl 2'-(2-chloropyrimidin-4-yl)-4'-oxo-5'-(2,4,6-trimethoxybenzyl)-1',4',5',6'-tetrahydrospiro [piperidine-3,7'-pyrrolo[3,2-c]pyridine]-1-carboxylate 14, prepared as described in Example 1 (200 mg, 0.3 mmol), in (3:1) 1,4-dioxane:water (2 mL), N-(2-(2-methoxyethoxy)-5-(4,4,5,5-tetramethyl-1,3,2-dioxaborolan-2-yl)phenyl) acrylamide INT-3 (175 mg, 0.5 mmol) and sodium carbonate (191 mg, 1.8 mmol) were added and degassed for 15 min, then Pd(PPh$_3$)$_4$(35 mg, 0.03 mmol) was added and again degassed for 10 min. The reaction mixture was heated to 90° C. for 6 hours. The reaction mixture was concentrated and partitioned between ethyl acetate (50 mL) and water (30 mL). The organic layer was dried over anhydrous sodium sulfate and concentrated under reduced pressure. Crude compound was purified by Prep-HPLC to obtain 18 (50 mg, 14%) as a white solid. MS m/z (M+H): 783.5

Step 2:

To a stirred solution of tert-butyl 2'-(2-(3-acrylamido-4-(2-methoxyethoxy)phenyl)pyrimidin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate 18 (50 mg, 0.06 mmol) in dichloromethane (2 mL), trifluoroacetic acid (0.5 mL) was added at 0° C. The reaction mixture was stirred at RT for 1 hour. Reaction mixture was concentrated and co-distilled with dichloromethane for 2-3 times. The residue was triturated with diethyl ether to give 1-7 (28.0 mg, 60%) as yellow solid. $^1$H NMR (400 MHz, DMSO-d$_6$); δ 1.75 (m, 1H), 1.86 (d, J=11.5 Hz, 2H), 2.23 (m, 1H), 2.82 (m, 1H), 3.33 (s, 3H), 3.39 (m, 2H), 3.47 (d, J=1.9 Hz, 2H), 3.59-3.62 (dd, J=2.5, 12.8 Hz, 1H), 3.74 (t, J=4.6 Hz, 2H), 4.27 (t, J=4.8 Hz, 2H), 5.74-5.77 (dd, J=1.9, 10.2 Hz, 1H), 6.24-6.29 (dd, J=1.9, 17.0 Hz, 1H), 6.63-6.70 (dd, J=10.3, 16.8 Hz, 1H), 7.24 (d, J=8.7 Hz, 1H), 7.33 (d, J=2.7 Hz, 1H), 7.42 (brs, 1H), 7.70 (d, J=5.3 Hz, 1H), 8.36-8.39 (dd, J=2.1, 8.6 Hz, 1H), 8.47 (brs, 1H), 8.75 (d, J=7.4 Hz, 1H), 9.05 (brs, 2H), 9.31 (s, 1H), 11.7 (s, 1H). MS m/z (M+H): 503.3

Example 6

Compound I-10

N-(2-(4-methylpiperazin-1-yl)-5-(4-(4'-oxo-1',4',5',6'-tetrahydrospiro[piperidine-3,7'-pyrrolo[3,2-c]pyridin]-2'-yl)pyridin-2-yl)phenyl)acrylamide (racemic)

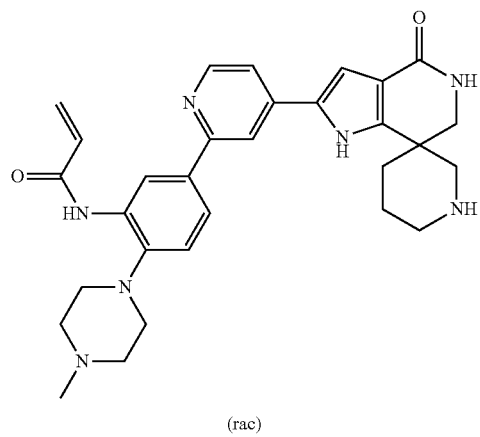 [SMILES: C=CC(=O)Nc1cc(-c2cc(-c3cc4c([nH]3)C3(CCCNC3)CNC4=O)ccn2)ccc1N1CCN(C)CC1]
(rac)

The title compound was prepared according to the schemes, steps, and intermediates described below.

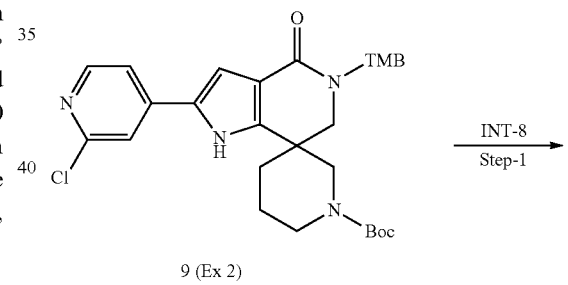
9 (Ex 2)

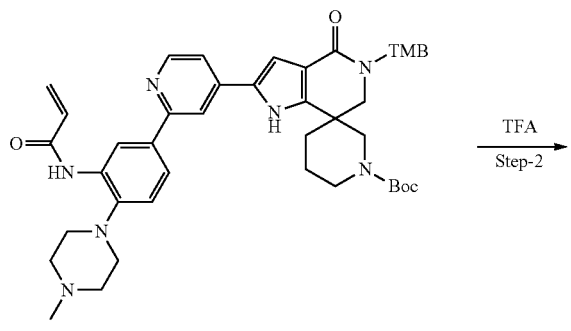
13

-continued

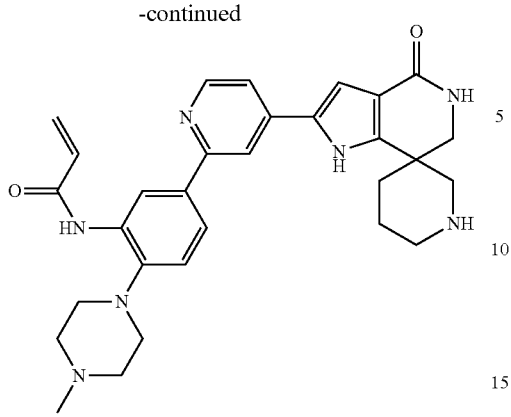

Step 1:

tert-butyl 2'-(2-(3-acrylamido-4-(4-methylpiperazin-1-yl)phenyl)pyridin-4-yl)-5'-(2,4,6-trimethoxybenzyl)-4'-oxo-1',4',5',6'-tetrahydrospiro[piperidine-3,7'-pyrrolo[3,2-c]pyridine]-1-carboxylate (13)

tert-butyl 2'-(2-chloropyridin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate 9 (70 mg, 0.12 mmol) from Example 2 was dissolved in 1,4-dioxane and treated with N-(2-(4-methylpiperazin-1-yl)-5-(4,4,5,5-tetramethyl-1,3,2-dioxaborolan-2-yl)phenyl) acrylamide (INT-8, 174 mg, 0.47 mmol), Na₂CO₃ (37 mg, 0.36 mmol), and Pd(PPh3)₄ (14.0 mg, 0.01 mmol) at 105° C. for 5 h. After completion of the starting material, the reaction mixture was diluted with water and extracted with ethyl acetate. The organic layer was dried over anhydrous sodium sulfate and concentrated under reduced pressure. The residue obtained was purified by preparative HPLC to afford 13 as a yellow solid (30 mg, 32%). MS m/z (M−H): 804.6

Step 2:

30 mg of tert-butyl-2'-(2-(3-acrylamido-4-(4-methylpiperazin-1-yl)phenyl)pyridin-4-yl)-4'-oxo-5'-(2,4,6-tri methoxybenzyl)-1',4',5',6'-tetrahydrospiro[piperidine-3,7'-pyrrolo[3,2-c]pyridine]-1-carboxylate was treated with trifluoroacetic acid/dichloromethane (1:1) at 0° C. and stirred for 3 h at room temperature. After completion of the reaction, excess trifluoroacetic acid was removed under reduced pressure, and the residue obtained was triturated with diethyl ether. The solid obtained was purified by preparative HPLC to afford 1-10 as a yellow gummy solid (8.0 mg, 40%). ¹H NMR (400 MHz, DMSO-d₆) δ 1.97-2.13 (m, 3H), 2.33-2.37 (m, 2H), 3.03 (s, 3H), 3.04-3.08 (m, 1H), 3.15-3.24 (m, 2H), 3.32-3.36 (m, 4H), 3.45-3.53 (m, 2H), 3.55-3.66 (m, 2H), 3.65-3.70 (m, 2H), 5.90-5.93 (dd, J=1.6, 10.2 Hz, 1H), 6.48-6.52 (dd, J=1.6, 17.0 Hz, 1H), 6.64-6.71 (dd, J=10.2, 17.0 Hz, 1H), 7.47-7.50 (m, 2H), 7.86 (dd, J=2.3, 8.5 Hz, 1H), 7.97-7.99 (dd, J=1.8, 6.1 Hz, 1H), 8.39 (d, J=1.5 Hz, 1H), 8.61 (d, J=6.1 Hz, 2H). MS m/z (M−H): 524.6.

Example 7

Compound I-3

3-acrylamido-4-(2-methoxyethoxy)-N-(4-(4'-oxo-1',4',5',6'-tetrahydrospiro[piperidine-3,7'-pyrrolo[3,2-c]pyridin]-2'-yl)pyridin-2-yl)benzamide (racemic)

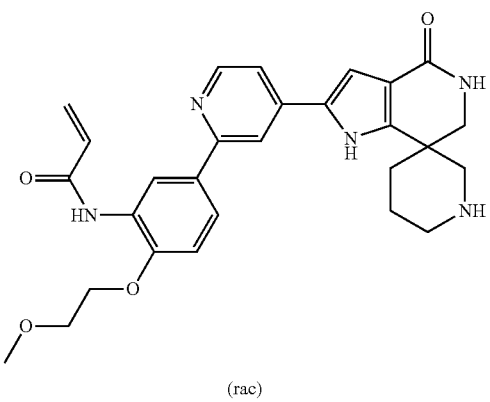 [SMILES: C=CC(=O)Nc1cc(-c2cc(-c3cc4c([nH]3)C3(CCCNC3)CNC4=O)ccn2)ccc1OCCOC]

The title compound I-3 was prepared as described in Example 6, by substituting boronate ester INT-3 for INT-8 in the Suzuki coupling reaction (step 1): Yellow solid, 27 mg, 24%. ¹H NMR (400 MHz, DMSO-d₆) δ 1.70-1.73 (m, 1H), 1.84-1.90 (m, 2H), 2.09-2.17 (m, 1H), 2.77-2.79 (m, 1H), 3.20-3.27 (m, 1H), 3.33 (s, 3H), 3.34-3.45 (m, 2H), 3.58-3.66 (m, 2H), 3.74 (t, J=4.7 Hz, 2H), 4.27 (t, J=4.7 Hz, 2H), 5.75-5.78 (dd, J=2.0, 10.3 Hz, 1H), 6.24-6.29 (dd, J=2.0, 17.0 Hz, 1H), 6.64-6.71 (dd, J=10.3, 17.0 Hz, 1H), 7.25 (d, J=8.8 Hz, 1H), 7.30 (brs, 1H), 7.39 (brs, 1H), 7.71 (brs, 1H), 7.87-7.89 (dd, J=2.2, 8.6 Hz, 1H), 8.20 (s, 1H), 8.45-8.55 (m, 1H), 8.60 (d, J=5.6 Hz, 1H), 8.73 (m, 1H), 9.03-9.05 (m, 1H), 9.36 (s, 1H), 11.7 (s, 1H). MS m/z (M−H): 500.6

Example 8

Compound I-8

3-acrylamido-4-fluoro-N-(4-(4'-oxo-1',4',5',6'-tetrahydrospiro[piperidine-3,7'-pyrrolo[3,2-c]pyridin]-2'-yl)pyridin-2-yl)benzamide (racemic)

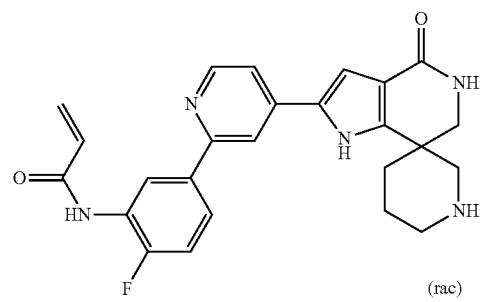 [SMILES: C=CC(=O)Nc1cc(-c2cc(-c3cc4c([nH]3)C3(CCCNC3)CNC4=O)ccn2)ccc1F]

The title compound I-8 was prepared as described in Example 6, by substituting primary amide INT-6 for INT-8 in the Suzuki coupling reaction (step 1): Yellow solid, 28 mg, 26%. ¹H NMR (400 MHz, CD₃OD) δ 1.93-1.97 (m, 1H), 2.04-2.14 (m, 2H), 2.31-2.38 (m, 1H), 3.01-3.10 (m, 1H), 3.31-3.38 (m, 1H), 3.44-3.56 (m, 1H), 3.58-3.66 (m, 2H), 3.76-3.79 (m, 1H), 5.87-5.90 (dd, J=1.8, 10.1 Hz, 1H), 6.46-6.51 (dd, J=1.8, 16.9 Hz, 1H), 6.60-6.67 (dd, J=10.1, 16.9 Hz, 1H), 7.46-7.51 (m, 2H), 7.80-7.84 (m, 1H), 8.02-8.04 (dd, J=1.8, 6.1 Hz, 1H), 8.41 (d, J=1.6 Hz, 1H), 8.62 (d, J=6.1 Hz, 1H), 8.74-8.76 (dd, J=2.4, 7.2 Hz, 1H). MS m/z (M−H): 444.5

1H), 1.82-1.93 (m, 2H), 2.08-2.17 (m, 1H), 2.72-2.83 (m, 1H), 3.21-3.37 (m, 2H), 3.38-3.48 (m, 2H), 3.58-3.64 (m, 1H), 5.82-5.85 (dd, J=2.0, 10.0 Hz, 1H), 6.30-6.35 (dd, J=1.9, 17.0 Hz, 1H), 6.43-6.49 (dd, J=1.8, 17.0 Hz, 1H), 7.31 (d, J=2.2 Hz, 1H), 7.36 (brs, 1H), 7.73-7.75 (dd, J=1.5, 5.2 Hz, 1H), 8.18 (s, 1H), 8.31 (d, J=7.3 Hz, 1H), 8.45-8.55 (m, 1H), 8.64-8.67 (m, 2H), 9.06 (d, J=10.3 Hz, 1H), 10.6 (s, 1H), 11.7 (s, 1H). MS m/z (M−H): 494.7

Example 9

Compound I-9

3-acrylamido-N-(4-(4'-oxo-1',4',5',6'-tetrahydrospiro[piperidine-3,7'-pyrrolo[3,2-c]pyridin]-2'-yl)pyridin-2-yl)-5-(trifluoromethyl)benzamide (racemic)

Example 10

Compound I-23

3-acrylamido-N-(4-(4'-oxo-1',4',5',6'-tetrahydrospiro[piperidine-3,7'-pyrrolo[3,2-c]pyridin]-2'-yl)pyridin-2-yl)-4-(trifluoromethoxy)benzamide (racemic)

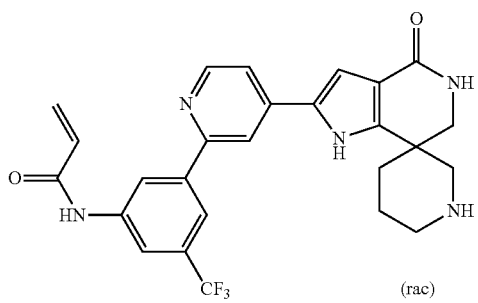 [SMILES: C=CC(=O)Nc1cc(-c2cc(-c3cc4c([nH]3)C3(CCCNC3)CNC4=O)ccn2)cc(C(F)(F)F)c1]

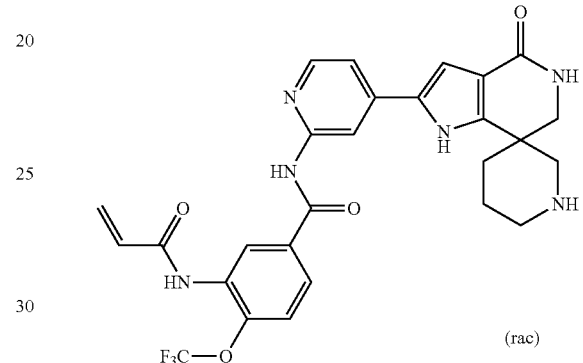

The title compound I-9 was prepared as described in Example 6, by substituting primary amide INT-26 for INT-8 in the Suzuki coupling reaction (step 1): Yellow solid, 21 mg, 19%. ¹H NMR (400 MHz, DMSO-d$_6$) δ 1.65-1.79 (m, The title compound was prepared according to the schemes, steps, and intermediates described below.

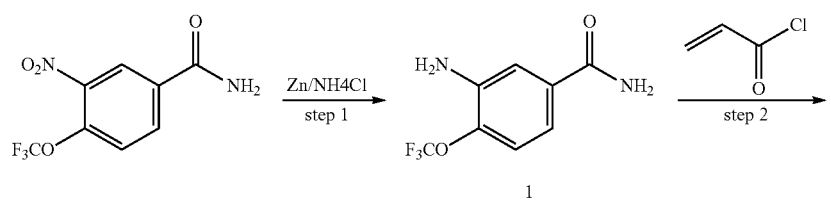

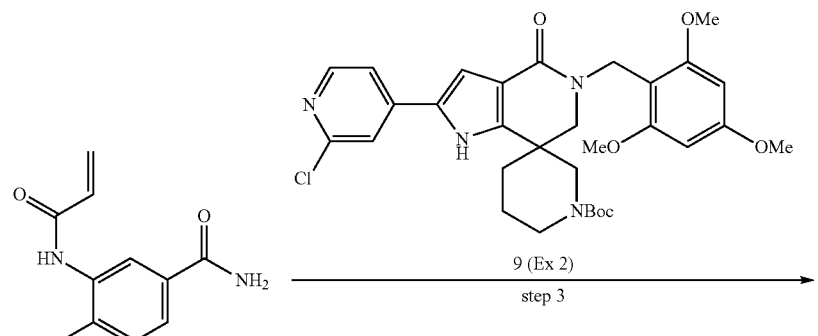

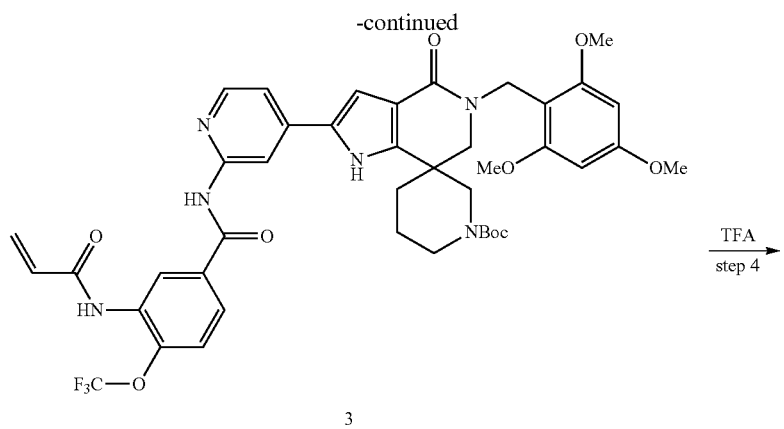

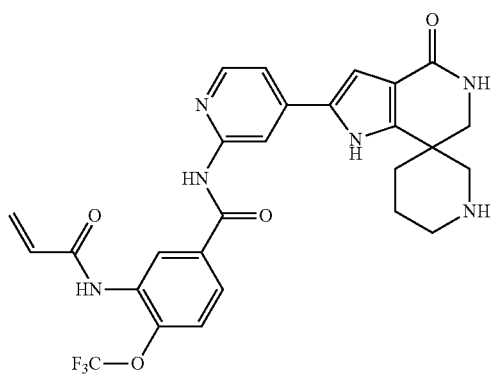 [SMILES: C=CC(=O)Nc1cc(C(=O)Nc2cc(-c3cc4c([nH]3)C3(CCCNC3)CNC4=O)ccn2)ccc1OC(F)(F)F]

Step 1:

3-amino-4-(trifluoromethoxy)benzamide (1)

To a solution of 3-nitro-4-(trifluoromethoxy)benzamide (1.0 g, 3.9 mmol) in dioxane/H$_2$O, Zn dust (1.3 g, 19.5 mmol) was added followed by the addition of NH$_4$Cl (1.06 g, 19.5 mmol) at room temperature. The reaction mixture was then stirred at room temperature for 16 h. After completion of the starting material, the reaction mixture was diluted with water and extracted with ethyl acetate. The organic layer was dried over anhydrous sodium sulfate and concentrated under reduce pressure to afford 1 (680 mg, 78%) as an off white solid. $^1$H NMR (400 MHz, DMSO-d$_6$): δ 5.49 (brs, 2H), 6.99 (dd, J=1.4, 8.4 Hz, 1H), 7.11 (d, J=8.3 Hz, 1H), 7.23 (brs, 1H), 7.28 d, J=1.5 Hz, 1H), 7.80 (brs, 1H).

Step 2:

3-acrylamido-4-(trifluoromethoxy)benzamide

To a solution of 3-amino-4-(trifluoromethoxy)benzamide (670 mg, 3.0 mmol) in DCM/THF (2:1, 5.0 mL), diisopropylethylamine (776 mg, 6.0 mmol) and acryloyl chloride (273 mg, 2.9 mmol) were added at −78° C. The resulting mixture was warmed to room temperature and stirred for 1 h. After completion of reaction, solvent was removed under reduced pressure. The residue obtained was purified by silica gel column chromatography to afford 2 (700 mg, 84%) as an off white solid. δ 5.78 (dd, J=1.9, 10.2 Hz, 1H), 6.26 (dd, J=1.9, 17.0 Hz, 1H), 6.57 (dd, J=10.2, 17.0 Hz, 1H), 7.47 (d, J=1.4 Hz, 1H), 7.49 (d, J=1.4 Hz, 1H), 7.72 (dd, J=2.1, 8.6 Hz, 1H), 8.04 (brs, 1H), 8.38 (d, J=2.0 Hz, 1H), 10.0 (brs, 1H).

Step 3:

tert-butyl 2'-(2-(3-acrylamido-4-(trifluoromethoxy)benzamido)pyridin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate (3)

To a solution of tert-butyl 2'-(2-chloropyridin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate 9 (200 mg, 0.33 mmol) in 1,4-dioxane (2.0 mL) from Example 2, tris(dibenzylideneacetone)dipalladium(0) (15 mg, 0.04 mmol), Xantphos (38.6 mg, 0.06 mmol), 3-acrylamido-4-(trifluoromethoxy)benzamide (156 mg, 0.5 mmol) were added. Then, caesium carbonate (218 mg, 0.6 mmol) was added and the resulting mixture was degassed under nitrogen for 20 min. The reaction mixture was heated at 150° C.

under microwave conditions for 1 h. After completion of the reaction, solid suspension was filtered and the filtrate obtained was concentrated to dryness under vacuum. The residue obtained was washed with diethyl ether and purified by preparative HPLC to afford 3 (48 mg, 16%). MS m/z (M−H): 833.3

Step 4:

To a solution of 3-acrylamido-N-(4-(4'-oxo-5'-(2,4,6-trimethoxybenzyl)-1',4',5',6'-tetrahydrospiro[piperidine-3,7'-pyrrolo[3,2-c]pyridine]-2'-yl)pyridin-2-yl)-4-(trifluoromethoxy)benzamide (48 mg, 0.06 mmol) in dichloromethane, excess trifluoroacetic acid was added at 0° C. The resulting mixture was stirred at room temperature for 1 h. After completion of the reaction, the reaction mixture was concentrated under reduced pressure and co-distilled with dichloromethane. The residue obtained was purified by preparative HPLC to afford the title compound (9.0 mg, 28%) as an off-white solid. $^1$H NMR (400 MHz, DMSO-d$_6$): δ 1.61-1.71 (m, 1H), 1.85 (m, 2H), 2.11-2.15 (m, 1H), 3.30-3.45 (m, 6H), 5.85 (dd, J=1.7, 10.1 Hz, 1H), 6.3 (dd, J=1.8, 16.9 Hz, 1H), 6.62-6.70 (dd, J=10.1, 16.9 Hz, 1H), 6.95 (d, J=2.2 Hz, 1H), 7.36 (brs, 1H), 7.49 (dd, J=1.4, 5.3 Hz, 1H), 7.55 (d, J=7.3 Hz, 1H), 7.92 (dd, J=2.2 Hz, 8.6 Hz, 1H), 8.32-8.46 (m, 3H), 8.67 (d, J=2.1 Hz, 1H), 10.0 (s, 1H), 10.9 (s, 1H), 11.7 (s, 1H). MS m/z (M−H): 553.5.

Example 11

Compound I-24

3-acrylamido-4-fluoro-N-(4-(4'-oxo-1',4',5',6'-tetrahydrospiro[piperidine-3,7'-pyrrolo[3,2-c]pyridin]-2'-yl)pyridin-2-yl)benzamide (racemic)

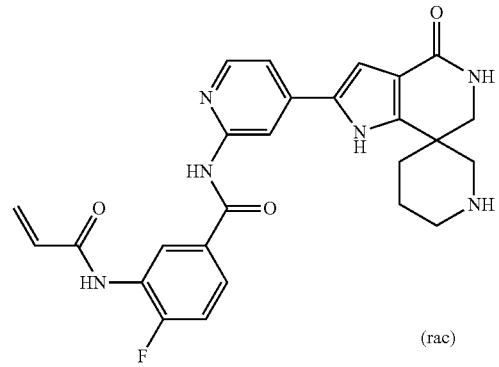 [SMILES: C=CC(=O)Nc1cc(C(=O)Nc2cc(-c3cc4c([nH]3)C3(CCCNC3)CNC4=O)ccn2)ccc1F]

The title compound was prepared according to the schemes, steps, and intermediates

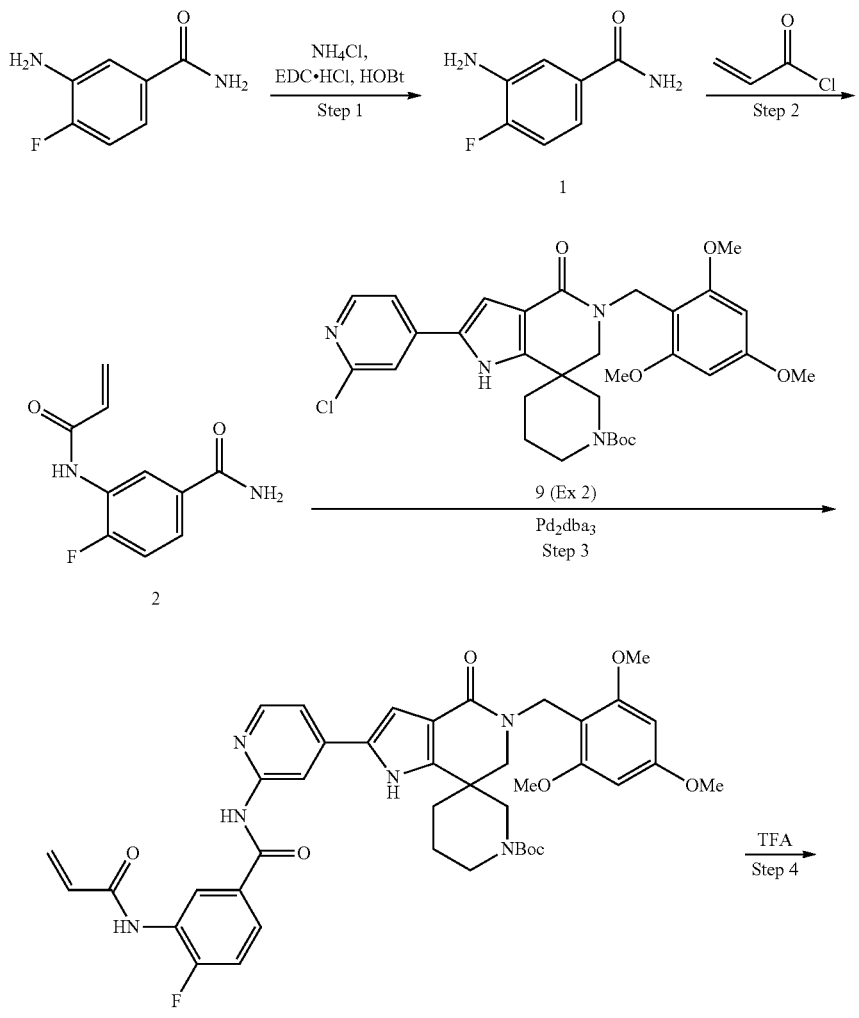

-continued

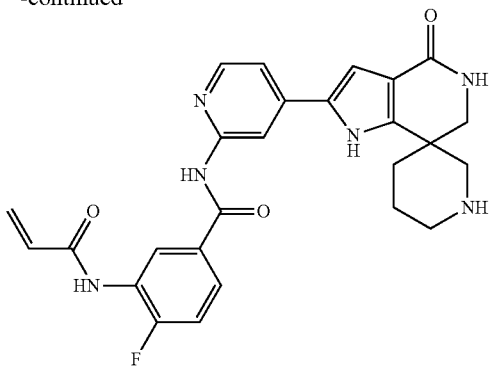

3-amino-4-fluorobenzamide (1)

To a solution of 3-amino-4-fluorobenzoic acid (1.0 g, 6.4 mmol) in dimethylformamide (5.0 mL), 1-Ethyl-3-(3-dimethylaminopropyl)carbodiimide hydrochloride. HCl (1.2 g, 7.7 mmol), ammonium chloride (1.4 g, 26.9 mmol) and hydroxybenzotriazole (1.1 g, 8.3 mmol) were added at 0° C. The resulting mixture was stirred at room temperature for 12 h. After completion of the reaction, ice-cold water was added to the reaction mixture and the aqueous layer was extracted with ethyl acetate. The organic layer was dried over anhydrous sodium sulfate and concentrated under reduce pressure to afford 1 (600 mg, 61%) as an orange-red solid. $^1$H NMR (400 MHz, DMSO-$d_6$): δ 5.24 (brs, 2H), 6.97 (m, 2H), 7.13 (brs, 1H), 7.26 (d, J=7.8 Hz, 1H), 7.74 (brs, 1H).

Step 2:

3-acrylamido-4-fluorobenzamide (2)

To a solution of 3-amino-4-fluorobenzamide (0.5 g, 3.2 mmol) in dichloromethane (3.0 mL) at −78° C., diisopropylethylamine (1.1 mL, 6.4 mmol) and acryloyl chloride (265 mg, 2.9 mmol) were added, and the resulting mixture was stirred at room temperature for 30 min. The reaction mixture was concentrated under reduced pressure. The residue obtained was diluted with water and extracted with ethyl acetate. The organic layer was dried over anhydrous sodium sulfate and concentrated under rotary evaporator to afford 2 (308 mg, 45%) as an orange solid. $^1$H NMR (400 MHz, DMSO-$d_6$): δ 5.77 (dd, J=1.9, 10.1 Hz, 1H), 6.25 (dd, J=1.9, 16.7 Hz, 1H), 6.56 (dd, J=10.1, 17.0 Hz, 1H), 7.31 (m, 2H), 7.65 (m, 1H), 7.95 (brs, 1H), 8.42 (dd, J=2.0, 7.6 Hz, 1H), 10.0 (s, 1H). MS m/z (M+H): 209.2

Step 3:

tert-butyl 2'-(2-(3-acrylamido-4-fluorobenzamido)pyridin-4-yl)-4'-oxo-5'-(2,4,6-trimethoxy benzyl)-1',4',5',6'-tetrahydrospiro[piperidine-3,7'-pyrrolo[3,2-c]pyridine]-1-carboxylate (3)

To a solution of tert-butyl 2'-(2-chloropyridin-4-yl)-4'-oxo-5'-(2,4,6-trimethoxybenzyl)-1',4',5',6'-tetrahydrospiro[piperidine-3,7'-pyrrolo[3,2-c]pyridine]-1-carboxylate 9 from Example 2 (200 mg, 0.3 mmol) in 1,4-dioxane (2.0 mL), tris(dibenzylideneacetone)dipalladium(0) (16 mg, 0.04 mmol), Xantphos (40 mg, 0.06 mmol), and 3-acrylamido-4-fluorobenzamide 2 (104 mg, 0.48 mmol) were added. Then, caesium carbonate (220 mg, 0.6 mmol) was added, and the resulting mixture was degassed under nitrogen for 20 min. The reaction mixture was heated at 150° C. under microwave conditions for 1 h. After completion of the reaction, the solid suspension was filtered and the filtrate obtained was concentrated to dryness under vacuum. The residue obtained was washed with diethyl ether and used as such for the next step without further purification. MS m/z (M+H): 769.3

Step 4:

3-acrylamido-4-fluoro-N-(4-(4'-oxo-1',4',5',6'-tetrahydrospiro[piperidine-3,7'-pyrrolo[3,2-c]pyridine]-2'-yl)pyridin-2-yl)benzamide tert-butyl 2'-(2-(3-acrylamido-4-fluorobenzamido)pyridin-4-yl)-4'-oxo-5'-(2,4,6-trimethoxybenzyl)-1',4',5',6'-tetrahydrospiro [piperidine-3,7'-pyrrolo[3,2-c]pyridine]-1-carboxylate (150 mg, crude) was treated with excess trifluoroacetic acid in dichloromethane (1.0 mL) at 0° C. The reaction mixture was stirred at room temperature for 2 h. After completion of the reaction, the reaction mixture was concentrated under reduced pressure and co-distilled with dichloromethane. The residue obtained was purified by preparative HPLC to afford the title compound (25 mg, 15% after 2 steps, pale yellow solid). $^1$H NMR (400 MHz, CD$_3$OD) δ 1.93-1.99 (m, 1H), 2.04-2.14 (m, 2H), 2.31-2.37 (m, 1H), 3.03-3.09 (m, 1H), 3.38 (s, 1H), 3.48-3.51 (m, 1H), 3.58 (d, J=2.8 Hz, 1H), 3.65 (d, J=13.3 Hz, 1H), 3.75 (d, J=13.3 Hz, 1H), 5.86-5.89 (dd, J=1.8, 10.8 Hz, 1H), 6.44-6.49 (dd, J=1.8, 17.0 Hz, 1H), 6.57-6.64 (dd, J=10.1, 17.0 Hz, 1H), 7.25 (s, 1H), 7.39-7.43 (dd, J=8.4, 10.4 Hz, 1H), 7.65-7.67 (dd, J=1.6, 6.0 Hz, 1H), 7.89-7.93 (m, 1H), 8.27 (d, J=1.3 Hz, 1H), 8.35 (d, J=6.0 Hz, 1H), 8.77-8.79 (dd, J=2.2, 7.3 Hz, 1H). MS m/z (M−H): 487.2.

Example 12

Compound II-7

N-(2-(2-methoxyethoxy)-5-(11'-methyl-7'-oxo-5',6',7',8',10',11'-hexahydrospiro[cyclopropane-1,9'-pyrido[3',4':4,5]pyrrolo[2,3-f]isoquinolin]-2'-yl)phenyl)acrylamide

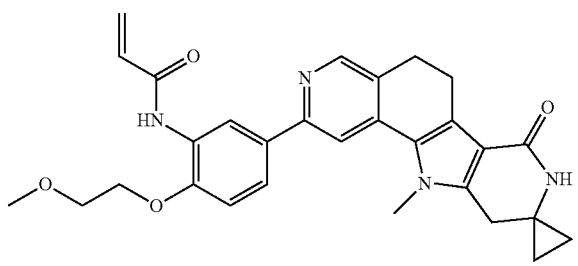 [SMILES: C=CC(=O)Nc1cc(-c2cc3c(cn2)CCc2c4c(n(C)c2-3)CC2(CC2)NC4=O)ccc1OCCOC]

The title compound was prepared according to the schemes, steps, and intermediates described below.

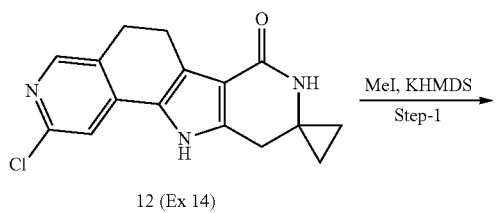

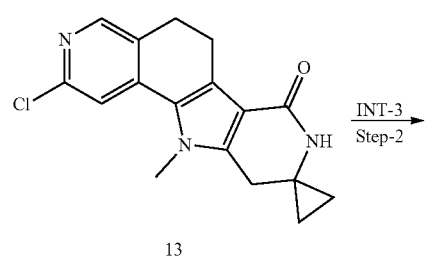

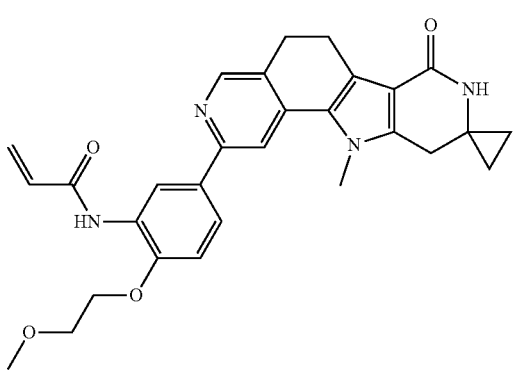

The synthesis of intermediate 12 is provided in detail in Example 14.

Step 1:

2'-chloro-11'-methyl-5',6',10',11'-tetrahydrospiro[cyclopropane-1,9'-pyrido[3',4':4,5]pyrrolo[2,3-f]isoquinolin]-7'(8'H)-one (13)

To a solution of 12 from Example 14 (30 mg, 0.1 mmol) in tetrahydrofuran (2.0 mL), KHMDS (25 mg, 0.1 mmol) was added slowly at 0° C. and stirred for 10 min. To this, a solution of methyl iodide (14 mg, 0.1 mmol) was added slowly over 10 min. The reaction mixture was stirred for 10 min at room temperature. After completion of the reaction, the reaction mixture was quenched with ammonium chloride solution (10 mL) and extracted with ethyl acetate (20 mL). The organic phase was dried over anhydrous sodium sulfate and concentrated under reduced pressure. The residue was purified by preparative TLC to afford 13 (20.0 mg, 64.5%) as pale brown solid. MS m/z (M+H): 314.2

Step 2:

To a stirred solution of Compound 13 (0.16 mmol) in pronane-1-ol (2.0 mL) was added the arylboronic ester (INT-3, 0.33 mmol), triphenylphosphine (0.17 mmol), and 0.5 mL of saturated sodium carbonate solution followed by degassing under nitrogen for 20 min. To the resulting mixture Pd(dppf)Cl$_2$.DCM (0.05 mmol) and Pd(PPh$_3$)$_2$Cl$_2$ (0.05 mmol) were added and degassed for another 5 min. The reaction mixture was irradiated under microwave conditions (150° C., 200W) for 20 min. After completion of the reaction, solid formed was filtered, and the filtrate obtained was concentrated to dryness under vacuum. The crude solid was washed with diethyl ether and purified by preparative HPLC to afford II-7 as a yellow solid (4.5 mg, 16%). 1H NMR (400 MHz, MeOH-d$_4$) δ 0.84 (m, 2H), 0.89 (m, 2H), 2.89 (m, 2H), 2.97 (s, 2H), 3.03 (m, 2H), 3.5 (s, 3H), 3.86 (m, 2H), 3.96 (q, J=5.0 Hz, 3H), 4.31 (m, 2H), 5.81-5.84 (dd, J=1.6, 10.2 Hz, 1H), 6.39-6.43 (dd, J=1.6, 17.0 Hz, 1H), 6.60-6.64 (dd, J=6.7, 11.3 Hz, 1H), 7.20 (d, J=8.6 Hz, 1H), 7.73 (d, J=2.2 Hz, 1H), 7.84 (s, 1H), 8.76 (d, J=1.9 Hz, 1H). MS m/z (M+H): 499.3

Example 13

Compound II-10

N-(2-(3-aminopropoxy)-5-(7-ox-6,7,8,9,11-hexahydro-5H-pyrido[3',4':4,5]pyrrolo[2,3-f]isoquinolin-2-yl)phenyl)acrylamide

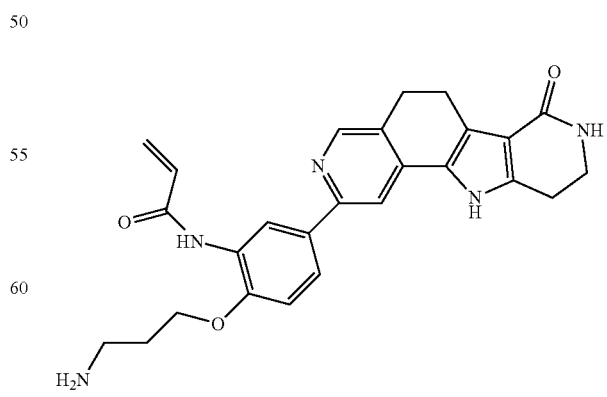

The title compound was prepared according to the schemes, steps, and intermediates described below.

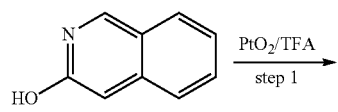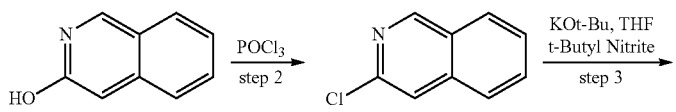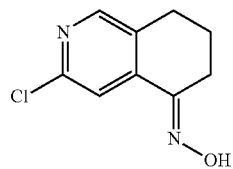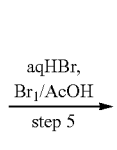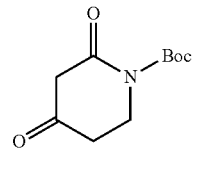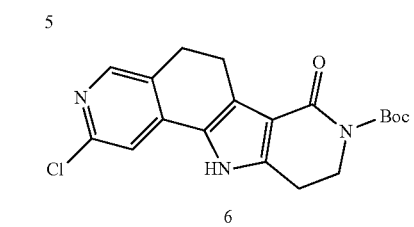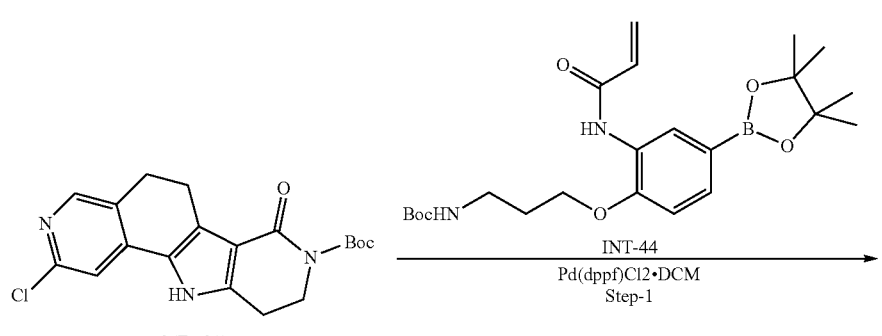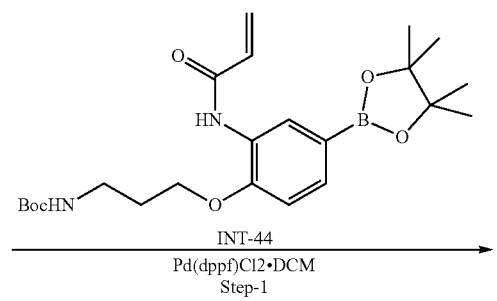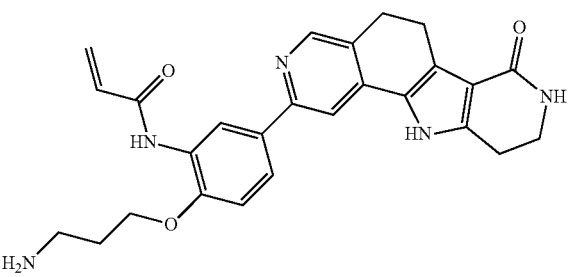

The synthesis of intermediate 6 is provided in detail at Example 21.

Step 1:

tert-butyl (3-(2-acrylamido-4-(7-oxo-6,7,8,9,10,11-hexahydro-5H-pyrido[3',4':4,5]pyrrolo[2,3-f]isoquinolin-2-yl)phenoxy)propyl)carbamate (1)

To a stirred solution of compound 6 from Example 21 (100 mg, 0.27 mmol) in pronane-1-ol (2.0 mL), tert-butyl 3-(2-acrylamido-4-(4,4,5,5-tetramethyl-1,3,2-dioxaborolan-2-yl)phenoxy)propylcarbamate (INT-44, 240 mg, 0.54 mmol), triphenylphosphine (70 mg, 0.23 mmol), and 0.5 mL of saturated sodium carbonate solution were added and degassed under nitrogen for 20 min. To the resulting mixture, Pd(dppf)Cl$_2$.DCM (66 mg, 0.08 mmol) and Pd(PPh$_3$)$_2$Cl$_2$ (56 mg, 0.08 mmol) were added and degassed for another 5 min. The reaction mixture was irradiated under microwave conditions (150° C., 200W) for 20 min. After completion of the reaction, the solid formed was filtered, and the filtrate obtained was concentrated to dryness under reduced pressure. The residue obtained was washed with diethyl ether and purified by preparative HPLC to yield desired compound 1: Yellow solid, 42.0 mg, 30%. $^1$H NMR (400 MHz, DMSO-d$_6$) δ 1.36 (s, 9H), 1.89 (t, J=6.5 Hz, 2H), 2.82-2.89 (m, 6H), 3.12-3.14 (m, 2H), 3.38-3.39 (m, 2H), 4.11 (t, J=6.0 Hz, 2H), 5.75 (d, J=10.9 Hz, 1H), 6.27 (d, J=17.6 Hz, 1H), 6.67-6.74 (dd, J=10.4, 17.3 Hz, 1H), 6.93 (m, 1H), 7.0 (brs, 1H), 7.16 (d, J=8.3 Hz, 1H), 7.77 (d, J=7.1 Hz, 1H), 7.82 (s, 1H), 8.32 (s, 1H), 8.7 (s, 1H), 9.26 (s, 1H), 11.9 (s, 1H). MS m/z (M+H): 558.3

Step 2:

To a stirred solution of compound 1 (42 mg) in DCM was added TFA (1 mL), and the reaction was stirred for 4 h at room temperature. The reaction was concentrated at reduced pressure and purified by prep-HPLC to yield II-10 as a yellow solid (19 mg): MS m/z (M+H): 458.3

Example 14

Compound II-12

2'-(4-acryloyl-3,4-dihydro-2H-benzo[b][1,4]oxazin-6-yl)-5',6',10',11'-tetrahydrospiro[cyclopropane-1,9'-pyrido[3',4':4,5]pyrrolo[2,3-f]isoquinolin]-7'(8'H)-one

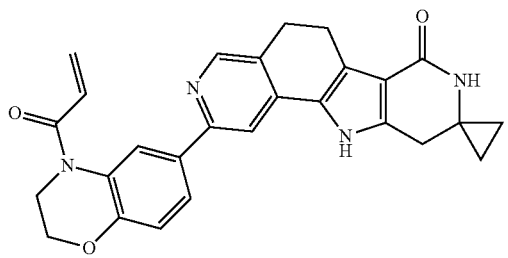 [SMILES: C=CC(=O)N1CCOc2ccc(-c3cc4c(cn3)CCc3c-4[nH]c4c3C(=O)NC3(CC3)C4)cc21]

The title compound was prepared according to the schemes, steps, and intermediates described below.

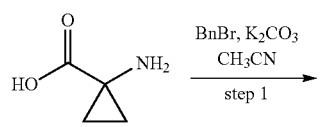

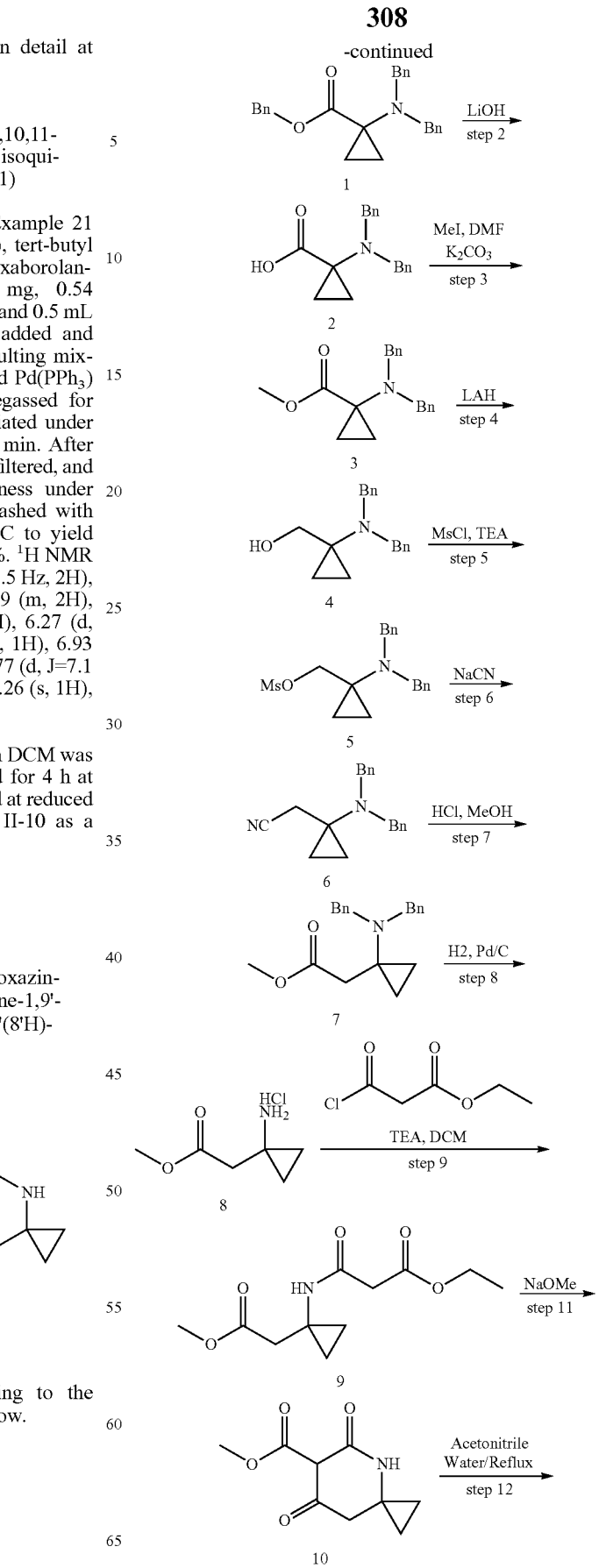

-continued

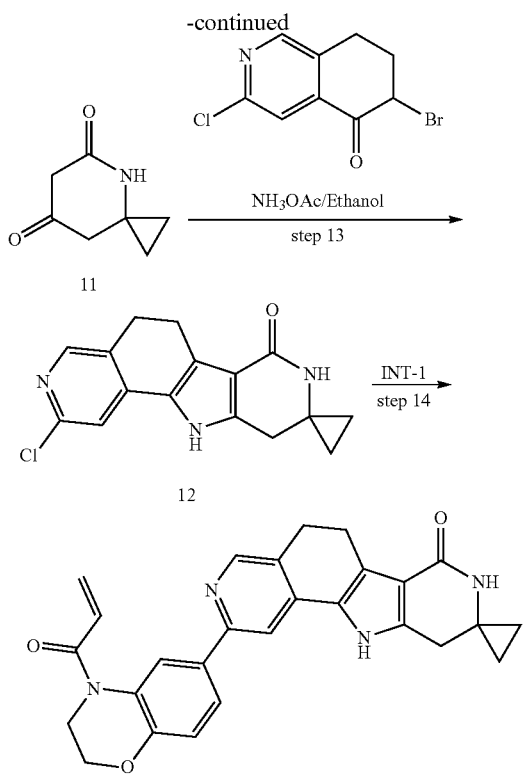

Step 1:

benzyl 1-(dibenzylamino)cyclopropanecarboxylate (1)

To a stirred solution of 1-aminocyclopropanecarboxylic acid (10.0 g, 99.0 mmol) in acetonitrile (300 mL), potassium carbonate (39.4 g, 285 mmol) and benzyl bromide (41.0 mL, 346.0 bmmol) were added. The reaction mixture was heated to reflux for 3 h. After completion of reaction, the reaction mixture was quenched with water, extracted with ethyl acetate, dried over sodium sulfate and concentrated under reduced pressure. The crude product was purified by silica gel (60-120 mesh) column chromatography by using 10% ethyl acetate in hexane to obtain Compound 1 (30 g, 78%) as white solid. $^1$H NMR (400 MHz, DMSO-$d_6$) δ 0.66-0.72 (q, J=2.8 Hz, 2H), 1.03-1.06 (q, J=2.8 Hz, 2H), 3.91 (s, 4H), 5.14 (s, 2H), 7.13-7.26 (m, 10H), 7.34-7.43 (m, 5H).

Step 2:

1-(dibenzylamino) cyclopropanecarboxylic acid (2)

To a stirred solution of benzoic 1-(dibenzylamino) cyclopropanecarboxylic anhydride (25.0 g, 67.4 mmol) in methanol/THF/water (500 mL, 1:1:1), LiOH (100.0 g, 1347.7 mmol) was added and heated to reflux for 20 h. TLC showed completion of the starting material. The reaction mixture was concentrated under reduced pressure, and the residue obtained was diluted with water and acidified with acetic acid (pH~6). The solid obtained was filtered, washed with water, hexane and dried under vacuum to obtain Compound 2 (18.0 g, 95%) as white solid. $^1$H NMR (400 MHz, DMSO-$d_6$) δ 0.59-0.61 (q, J=2.6 Hz, 2H), 0.95-0.97 (q, J=2.6 Hz, 2H), 3.93 (s, 4H), 7.15-7.18 (m, 6H), 7.22-7.26 (m, 4H).

Step 3:

methyl 1-(dibenzylamino) cyclopropanecarboxylate (3)

To a stirred solution of 1-(dibenzylamino) cyclopropanecarboxylic acid (21.0 g, 74.7 mmol) in DMF (63.0 mL), potassium carbonate (31.0 g, 224.0 mmol) and methyl iodide (11.6 mL, 187.0 mmol) were added at 0° C. and stirred at rt for 1 h. After completion of the reaction, the reaction mixture was quenched with water, extracted with ethyl acetate, dried over anhydrous sodium sulfate and concentrated under vacuum to obtain compound 3 (22.0 g, 99%) as colorless liquid. $^1$H NMR (400 MHz, DMSO-$d_6$) δ 0.69-0.72 (q, J=2.8 Hz, 2H), 1.0-1.03 (q, J=2.8 Hz, 2H), 3.62 (s, 3H), 3.90 (s, 4H), 7.16-7.20 (m, 6H), 7.23-7.27 (m, 4H).

Step 4:

(1-(dibenzylamino) cyclopropyl) methanol (4)

To a stirred solution of methyl-1-(dibenzylamino) cyclopropanecarboxylate (20.0 g, 67.7 mmol) in THF (200 mL), LAH (5.6 g, 203.4 mmol) was added slowly at 0° C. and for 1 h. The reaction mixture was stirred at room temperature for 3 h. After completion of the reaction, the reaction mixture was quenched with saturated sodium sulfate solution. The solid solution was filtered and the filtrate was extracted with ethyl acetate. The organic layer was dried over anhydrous sodium sulfate and concentrated under vacuum to obtain Compound 4 (18.0 g, 99%) as colorless liquid.

Step 5

(1-(dibenzylamino)cyclopropyl)methyl methanesulfonate (5)

To a stirred solution of (1-(dibenzylamino)cyclopropyl) methanol (10.0 g, 39.3 mmol) in DCM, triethylamine (20.0 mL, 137.6 mmol), methanesulfonyl chloride (3.7 mL, 47.2 mmol) were added at −78° C. under nitrogen atmosphere. The reaction mixture was allowed to stir at room temperature for 30 min. After completion of the reaction, the reaction mixture was diluted with water and extracted with DCM. The organic layer was washed with saturated sodium bicarbonate solution, brine, dried over anhydrous sodium sulfate and concentrated under reduced pressure to obtain compound 5 (14.0 g, 61%) as pale yellow syrup. 1H NMR (400 MHz, DMSO-$d_6$) δ 0.52 (s, 4H), 2.44 (s, 2H), 3.09 (s, 3H), 3.78 (s, 4H), 7.11-7.44 (m, 10H).

Step 6:

2-(1-(dibenzylamino)cyclopropyl)acetonitrile (6)

To a solution of (1-(dibenzylamino)cyclo propyl)methylmethanesulfonate (14.0 g, 40.6 mmol) in DMF (150.0 mL), 18-crown-6-ether (550 mg) and sodium cyanide (5.3 g, 81.0 mmol) were added at 0° C. and stirred at rt for 16 h. The reaction mixture was quenched with water and extracted with ethyl acetate. The organic layer was dried over anhydrous sodium sulfate and concentrated under reduced pressure. The crude product was purified by silica gel column chromatography by using 10% ethyl acetate in hexane to obtain Compound 6 (3.8 g, 34%) as off white solid. 1H NMR (400 MHz, CDCl$_3$) δ 0.61-0.62 (m, 2H), 0.66-0.67 (m, 2H), 2.62 (s, 2H), 3.81 (s, 4H), 7.22-7.28 (m, 10H).

Step 7:

methyl 2-(1-(dibenzylamino)cyclopropyl)acetate (7)

Solution of 2-(1-(dibenzylamino) cyclopropyl)acetonitrile (3.8 g, 13.8 mmol) in methanol (40.0 mL) was saturated with anhydrous HCl gas. The reaction mixture was kept standing for 16 h. After completion of the reaction, the reaction mixture was concentrated to dryness. The crude obtained was stirred in water for 15 min, extracted with ethyl acetate. The organic layer was dried over anhydrous sodium sulfate and concentrated under vacuum to get compound 7 (4.0 g, 94%) as pale yellow liquid. $^1$H NMR (400 MHz, CDCl$_3$) δ 0.51-0.54 (m, 4H), 2.61 (s, 2H), 3.75 (s, 4H), 7.23-7.34 (m, 10H).

Step 8:

methyl 2-(1-aminocyclopropyl) acetate (8)

2-(1-(dibenzylamino)cyclopropyl) acetate (4.0 g, 12.9 mmol) was treated with methanol-HCl (20.0 mL) and concentrated to dryness under reduced pressure. The gummy liquid obtained was dissolved in methanol (100.0 mL) followed by the addition of Pd/C (1.0 g). The resulting mixture was stirred under hydrogen pressure for 16 h. After completion of the starting material, the reaction mixture was filtered through the celite bed and the filtrate obtained was concentrated to dryness under reduced pressure to obtain Compound 8 (HCl salt, 2.0 g, 93%) as light brown gummy liquid. 1H NMR (400 MHz, CDCl$_3$) δ 0.77 (brs, 2H), 1.45 (brs, 2H), 2.77 (s, 2H), 3.75 (s, 3H), 8.67 (brs, 3H).

Step 9:

ethyl 3-(1-(2-methoxy-2-oxoethyl)cyclopropylamino)-3-oxopropanoate (9)

To a solution of methyl 2-(1-amino cyclopropyl)acetate (2.0 g, 12.1 mmol) in dichloromethane (50.0 mL), triethylamine (5.0 mL, 36.3 mmol) and chloroformyl acetic acid (1.5 mL, 12.1 mmol) were added and stirred at room temperature for 1 h. After completion of the reaction, the reaction mixture was quenched with saturated sodium bicarbonate solution and extracted with ethyl acetate. The organic layer was dried over anhydrous sodium sulphate and concentrated under reduced pressure. The crude residue was purified by silica gel column chromatography by using 30% acetone/hexane to obtain Compound 9 (1.3 g, 44%) as light yellow liquid. $^1$H NMR (400 MHz, CDCl$_3$) δ 0.78 (m, 2H), 0.89 (m, 2H), 1.27 (t, J=7.2 Hz, 3H), 2.03 (s, 3H), 2.61 (s, 2H), 3.22 (s, 2H), 3.69 (s, 3H), 4.15 (q, J=7.2 Hz, 2H), 7.42 (s, 1H).

Step 10:

methyl 5,7-dioxo-4-azaspiro[2.5]octane-6-carboxylate (10)

To a solution of sodium metal (435.0 mg, 18.9 mmol) in methanol (8.0 mL), a solution of ethyl 3-(1-(2-methoxy-2-oxoethyl) cyclopropylamino)-3-oxopropanoate (1.3 g, 7.8 mmol) in dry toluene (26.0 mL) was added dropwise at room temperature. The resulting mixture was heated to 85° C. for 2 h. After completion of the reaction, the reaction mixture was quenched with water and washed with tert-butyl methyl ether (MTBE). The aqueous layer was acidified (pH~4 to 5) with 3N HCl and concentrated to dryness. The yellow colored crude compound 10 (1.5 g, 96%) was used for next step without further purification. 1H NMR (400 MHz, CDCl$_3$) δ 0.63 (m, 2H), 0.73 (m, 2H), 2.45 (s, 2H), 3.7 (s, 3H), 8.25 (brs, 1H).

Step 11:

4-azaspiro[2.5]octane-5,7-dione (11)

A solution of methyl 5,7-dioxo-4-azaspiro[2.5]octane-6-carboxylate (1.5 g) in acetonitrile (45.0 mL) and water (5.0 mL) was heated to reflux for 2 h. The reaction mixture was concentrated to dryness. The residue obtained was dissolved 10% methanol/ethyl acetate and filtered. The filtrate was washed with water, and the organic layer was concentrated under vacuum to obtain compound 11 (50 mg, 5%) as brown solid. $^1$H NMR (400 MHz, DMSO-d$_6$) δ 0.67 (m, 2H), 0.8 (m, 2H), 2.46 (s, 2H), 3.3 (s, 2H), 8.26 (brs, 1H).

Step 12:

2'-chloro-5',6',10',11'-tetrahydrospiro[cyclopropane-1,9'-pyrido[3',4':4,5]pyrrolo[2,3-f]isoquinolin]-7'(8'H)-one (12)

To a solution of 6-bromo-3-chloro-7,8-dihydroisoquinolin-5(6H)-one (2.1 g, 8.3 mmol) in methanol (70.0 mL), 4-azaspiro[2.5]octane-5,7-dione (1.5 g, 10.8 mmol) and sodium acetate (680.0 mg, 8.3 mmol) were added at room temperature and stirred for 10 min. To the reaction mixture ammonium acetate (1.3 g, 16.602 mmol) was added and stirred at RT for 16 h. The reaction mixture was absorbed on silica (100-200mesh) and purified by column chromatography by using 3% methanol/DCM. The obtained light brown color solid was washed with chloroform to obtain compound 12 (420 mg, 15%) as off white solid. $^1$H NMR (400 MHz, DMSO-d$_6$) δ 0.65-0.68 (m, 2H), 0.72-0.75 (m, 2H), 2.81-2.83 (m, 4H), 2.87-2.91 (m, 2H), 7.19 (s, 1H), 7.39 (s, 1H), 8.09 (s, 1H), 11.9 (s, 1H).

Step 13:

50 mg of Intermediate 12 was treated with the aryl acrylamide-containing pinacol boronate INT-1 (2 eq), sat. Sodium carbonate (0.5 mL) in n-propanol, then degassed with N$_2$ for 10 min. then Pd (dppf)Cl$_2$ (30 mo %), Pd$_2$(PPh$_3$)Cl$_2$ (30 mol %) and TPP(1 eq) were added and heated in microwave at 140 C for 20 min. TLC indicated the starting material was consumed. The reaction mixture was concentrated at reduced pressure, dissolved in EtOAc, washed with water, and dried over Na$_2$SO$_4$. The crude product was purified by PREP HPLC to afford II-12 as a Yellow solid, 5.0 mg, 8% (after 2 steps). $^1$H NMR (400 MHz, DMSO-d$_6$) δ 0.68-0.69 (m, 2H), 0.73-.74 (m, 2H), 2.84-2.86 (m, 4H), 2.90-2.91 (m, 2H), 4.0 (t, J=4.5, 2H), 4.34 (t, J=4.5, 2H), 5.84-5.87 (dd, J=1.9 and 10.5 Hz, 1H), 6.29-6.34 (dd, J=1.9 and 16.6, 1H), 6.79-6.86 (dd, J=10.4, 16.6 Hz, 1H), 7.04 (d, J=8.6, 1H), 7.14 (s, 1H), 7.72-7.74 (dd, J=1.9 and 8.5, 1H), 7.84 (brs, 1H), 8.3 (s, 1H), 11.89 (s, 1H).

Example 15

Compound II-5

N-(2-methoxy-5-(7'-oxo-5',6',7',8',10',11'-hexahydrospiro[cyclopropane-1,9'-pyrido[3',4':4,5]pyrrolo[2,3-f]isoquinolin]-2'-yl)pyridin-3-yl)acrylamide

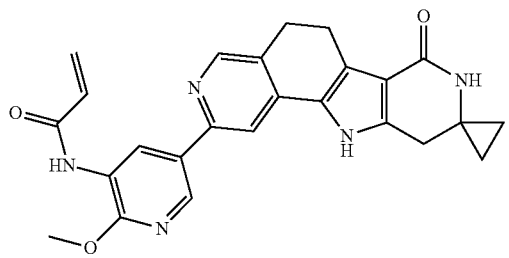 [SMILES: C=CC(=O)Nc1cc(-c2cc3c(cn2)CCc2c-3[nH]c3c2C(=O)NC2(CC2)C3)cnc1OC]

The title compound II-5 was prepared as described in Example 14, by substituting boronic ester INT-5 for INT-1 in step 13: (1.2 mg). $^1$H NMR (400 MHz, CD$_3$OD) δ ppm 9.05 (d, J=2.76 Hz, 1H), 8.40 (dd, J=2.76 Hz, 1H), 8.34 (s, 1H), 7.90 (s, 1H), 6.65 (dd, J=17.0, 10.1 Hz, 1H), 6.45 (dd, J=17.0, 1.8 Hz, 1H), 5.84 (dd, J=10.1, 1.8 Hz, 1H), 4.14 (s, 3H), 3.30 (m, 4H), 3.25 (s, 2H), 0.89 (m, 2H), 0.80 (m, 2H). MS m/z (M+H): 442.4

Example 16

Compound II-6

N-(2-fluoro-5-(7'-oxo-5',6',7',8',10',11'-hexahydrospiro[cyclopropane-1,9'-pyrido[3',4':4,5]pyrrolo[2,3-f]isoquinolin]-2'-yl)phenyl)acrylamide

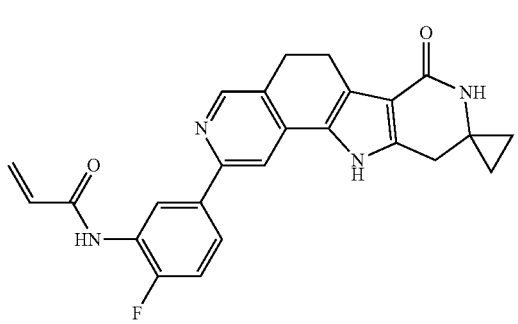 [SMILES: C=CC(=O)Nc1cc(-c2cc3c(cn2)CCc2c-3[nH]c3c2C(=O)NC2(CC2)C3)ccc1F]

The title compound II-6 was prepared as described in Example 14, by substituting boronic ester INT-6 for INT-1 in step 13: (1.2 mg). $^1$H NMR (400 MHz, CD$_3$OD) δ ppm 8.73 (dd, J=7.4, 2.3 Hz, 1H), 8.35 (s, 1H), 7.90 (s, 1H), 7.66 (m, 1H), 7.50 (dd, J=10.5, 8.7 Hz, 1H), 6.60 (dd, J=17.0, 10.1 Hz, 1H), 6.48 (d, J=17.0 Hz, 1H), 5.87 (dd, J=10.1, 1.8 Hz, 1H), 3.30 (m, 4H), 3.25 (s, 2H), 0.89 (m, 2H), 0.81 (m, 2H). MS m/z (M+H): 429.3

Example 17

Compound II

N-(2-(2-methoxyethoxy)-5-(7'-oxo-5',6',7',8'8',1',11'-hexahydrospiro[cyclopropane-1,9'-pyrido[3',4':4,5]pyrrolo[2,3-f]isoquinolin]-2'-yl)pyridin-3-yl)acrylamide

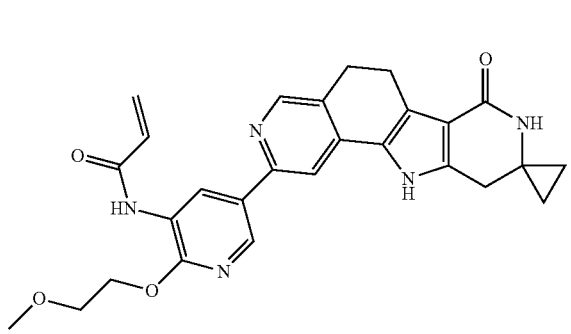 [SMILES: C=CC(=O)Nc1cc(-c2cc3c(cn2)CCc2c-3[nH]c3c2C(=O)NC2(CC2)C3)cnc1OCCOC]

The title compound II-8 was prepared as described in Example 14, by substituting boronic ester INT-4 for INT-1 in step 13: Yellow solid, 8.0 mg, 8%. $^1$H NMR (400 MHz, DMSO-d$_6$) δ 0.68-0.70 (m, 2H), 0.75-0.76 (m, 2H), 2.88 (s, 2H), 2.94 (m, 4H), 3.25 (s, 3H), 3.68 (m, 2H), 4.24 (t, J=5.4, 2H), 5.75-5.78 (dd, J=1.7 and 10.2 Hz, 1H), 6.25 (d, J=1.9 Hz, 1H), 6.81-6.87 (dd, J=10.2 and 17.0 Hz, 1H), 7.77 (s, 1H), 8.07 (s, 1H), 8.36 (s, 1H), 8.94 (s, 1H). MS m/z (M+H): 486.2

Example 18

Compound II-9

2'-(1-acryloyl-2,3-dihydro-1H-pyrido[2,3-b][1,4]oxazin-7-yl)-5',6',10',11'-tetrahydrospiro[cyclopropane-1,9'-pyrido[3',4':4,5]pyrrolo[2,3-f]isoquinolin]-7'(8'H)-one

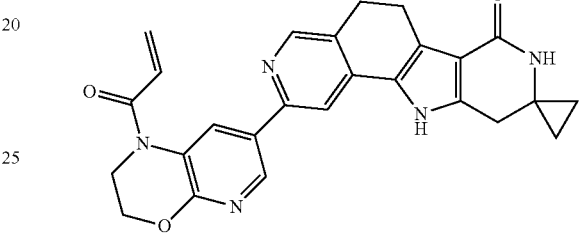

The title compound II-9 was prepared as described in Example 14, by substituting boronic ester INT-2 for INT-1 in step 13: Yellow solid, 5.0 mg, 9%. $^1$H NMR (400 MHz, DMSO-d$_6$) δ 0.71-0.72 (m, 2H), 0.75-0.76 (m, 2H), 2.89 (s, 2H), 3.0 (m, 4H), 4.05 (t, J=4.4 Hz, 2H), 4.50 (t, J=4.6 Hz, 2H), 5.89-5.92 (dd, J=1.9 and 10.4 Hz, 1H), 6.30-6.35 (dd, J=1.9 and 16.7 Hz, 1H), 6.87-6.93 (dd, J=10.5 and 16.7 Hz, 1H), 7.31 (s, 1H), 7.98 (s, 1H), 8.44 (s, 1H), 8.52 (s, 1H), 8.77 (s, 1H), 12.2 (s, 1H). MS m/z (M+H): 454.5

Example 19

Compound II-11

N-(2-(2-methoxyethoxy)-5-(7'-oxo-5',6',7',8'8',1',11'-hexahydrospiro[cyclopropane-1,9'-pyrido[3',4':4,5]pyrrolo[2,3-f]isoquinolin]-2'-yl)phenyl)acrylamide

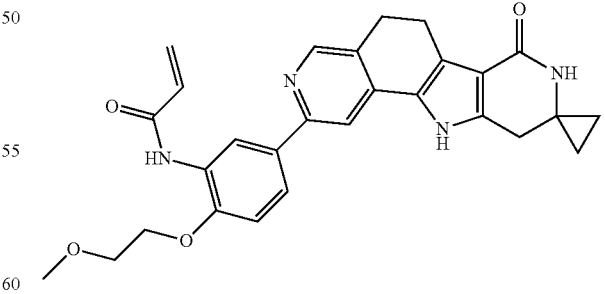

The title compound II-11 was prepared as described in Example 14, by substituting boronic ester INT-3 for INT-1 in step 13: Yellow solid, 4.0 mg, 4%. $^1$H NMR (400 MHz, DMSO-d$_6$) δ 0.71-0.72 (m, 2H), 0.76 (brs, 2H), 2.49 (s, 2H), 2.99 (m, 4H), 3.3 (m, 3H), 3.45 (t, J=4.7 Hz, 2H), 3.75 (t, J=4.5 Hz, 2H), 5.78 (d, J=11.7 Hz, 1H), 3.26-3.30 (dd, J=1.6 and 17.0 Hz, 1H), 6.67-6.74 (dd, J=10.4 and 17.0 Hz, 1H), 7.33-7.39 (m, 2H), 7.70 (d, J=7.3 Hz, 1H), 7.98 (s, 1H), 8.39 (s, 1H), 8.62 (s, 1H), 9.46 (s, 1H), 12.3 (s, 1H). MS m/z (M+H): 485.3

Example 20

Compound II-27

N-(2-(4-methylpiperazin-1-yl)-5-(7'-oxo-5',6',7',8', 10',11'-hexahydrospiro[cyclopropane-1,9'-pyrido[3', 4':4,5]pyrrolo[2,3-f]isoquinolin]-2'-yl)phenyl)acrylamide

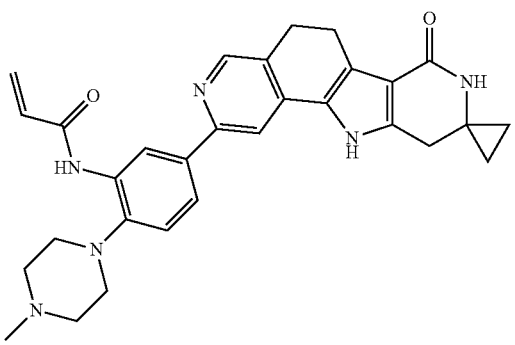 [SMILES: C=CC(=O)Nc1cc(-c2cc3c(cn2)CCc2c-3[nH]c3c2C(=O)NC2(CC2)C3)ccc1N1CCN(C)CC1]

The title compound II-27 was prepared as described in Example 14, by substituting boronic ester INT-8 for INT-1 in step 13: $^1$H NMR (400 MHz, DMSO-d$_6$) δ ppm 9.90 (br s, 1H), 9.35 (s, 1H), 8.58 (s, 1H), 8.42 (s, 1H), 7.99 (s, 1H), 7.72 (d, J=8.7 Hz, 1H), 7.40 (d, J=8.7 Hz, 1H), 7.35 (s, 1H), 6.70 (dd, J=17.0, 10.0 Hz, 1H), 6.31 (d, J=17.0 Hz, 1H), 5.83 (d, J=10.0 Hz, 1H), 2.80-3.30 (m, 17H), 0.75 (m, 4H). MS m/z (M+H): 509.1

Example 21

Compound II-20

2-(4-acryloyl-3,4-dihydro-2H-benzo[b][1,4]oxazin-6-yl)-8,9,10,11-tetrahydro-5H-pyrido[3',4':4,5]pyrrolo[2,3-f]isoquinolin-7(6H)-one

III-1

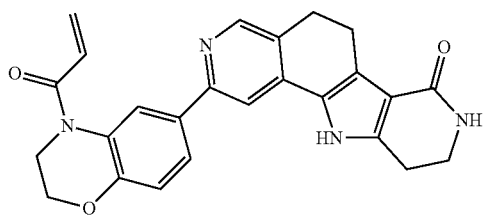

The title compound was prepared according to the schemes, steps, and intermediates described below.

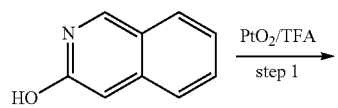

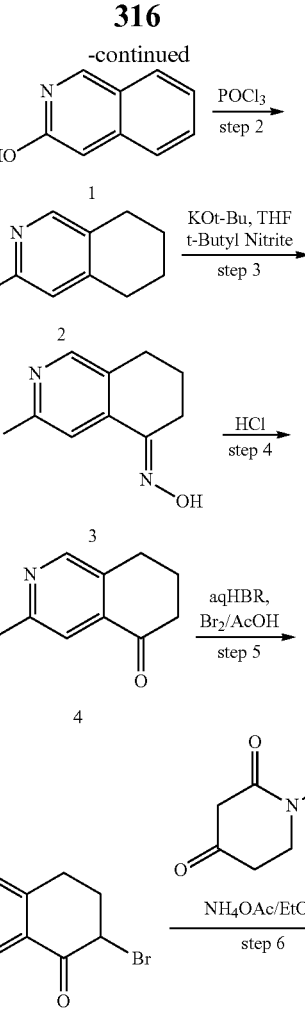

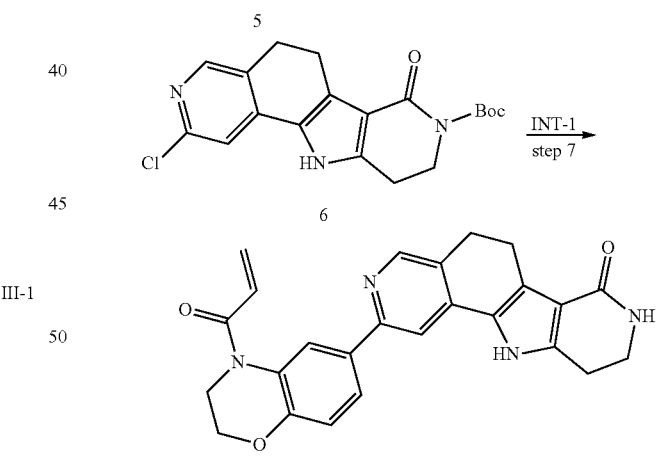

Step 1:

5, 6, 7, 8-tetrahydroisoquinolin-3-ol (1)

To a solution of 3-hydroxy-isoquinoline (10.0 g, 69 mmol) in trifluoroacetic acid (200 mL), PtO$_2$ (2.0 g) was added and heated to 65° C. under hydrogen atmosphere for 16 h. The reaction mixture was filtered through celite, and the filtrate was concentrated to minimum (30.0 mL) under reduced pressure. The solution was diluted with water and quenched with sodium bicarbonate solution. The aqueous layer was then extracted with 10% methanol/dichloromethane, and the organic layer was dried over anhydrous sodium sulfate and concentrated under vacuum. The crude solid was washed with diethyl ether to obtain compound 1 (4.5 g, 44%) as off white solid. $^1$H NMR (400 MHz, DMSO-$d_6$) δ 1.61 (m, 4H), 2.43 (m, 2H), 2.54 (m, 2H), 6.02 (s, 1H), 7.06 (s, 1H), 11.15 (s, 1H).

Step 2:

3-chloro-5, 6, 7, 8-tetrahydroisoquinoline (2)

5, 6, 7, 8-tetrahydroisoquinolin-3-ol (2.0 g, 13 mmol) taken in a sealed tube was treated with POCl$_3$ (10.0 mL), and the resulting suspension was heated at 170° C. for 16 h. The reaction mixture was poured in ice water, neutralized with saturated sodium bicarbonate solution and extracted with ethyl acetate. The organic layer was dried over anhydrous sodium sulfate and concentrated under reduced pressure. The crude was purified by silica gel column chromatography using 5% ethyl acetate/hexane to obtain compound 2 (850 mg, 38%) as a light yellow liquid. $^1$H NMR (400 MHz, DMSO-$d_6$) δ 1.70 (m, 4H), 2.68 (m, 4H), 7.19 (s, 1H), 8.08 (s, 1H).

Step 3:

(E)-3-chloro-7,8-dihydroisoquinolin-5(6H)-one oxime (3)

To a suspension of potassium tert-butoxide (1.6 g, 14.4 mmol) in THF (15.0 mL), a solution of 3-chloro-5,6,7,8-tetrahydro isoquinoline (1.2 g, 7.2 mmol) in THF was added dropwise over 10 min. The resulting mixture was stirred at room temperature for 4 h. The reaction mixture was cooled to 0° C., and tert-butyl nitrite (2.6 mL, 21.5 mmol) was added and stirred at room temperature for 1 h. The reaction mixture was poured into saturated sodium chloride solution and extracted with ethyl acetate. The organic layer was dried over sodium sulfate and concentrated under vacuum. The crude obtained was washed with n-pentane to obtain compound 3 (1.2 g, 42%) as brown solid. $^1$H NMR (400 MHz, DMSO-$d_6$) δ 1.75 (m, 2H), 2.64 (t, J=6.6 Hz, 2H), 2.70 (t, J=6.0 Hz, 2H), 7.66 (s, 1H), 8.28 (s, 1H), 11.8 (s, 1H).

Step 4:

3-chloro-7,8-dihydroisoquinolin-5(6H)-one (4)

To a solution of (E)-3-chloro-7,8-dihydro isoquinolin-5 (6H)-one oxime (1.2 g, 6.1 mmol) in acetone (15.0 mL), conc. HCl (15.0 mL) was added and heated to reflux for 1 h. The reaction mixture was poured into saturated sodium carbonate solution and extracted with ethyl acetate. The organic layer was dried over anhydrous sodium sulfate and concentrated under rotary evaporator. The crude obtained was purified by silica gel column chromatography by using 5% ethyl acetate/hexane to obtain compound 4 (950 mg, 86%) as yellow solid. 1H NMR (400 MHz, DMSO-$d_6$) δ 2.06 (m, 2H), 2.67 (t, J=6.8 Hz, 2H), 2.92 (t, J=6.0 Hz, 2H), 7.65 (s, 1H), 8.55 (s, 1H).

Step 5:

6-bromo-3-chloro-7,8-dihydroisoquinolin-5(6H)-one (5)

To a solution of 3-chloro-7,8-dihydroisoquinolin-5(6H)-one (950 mg, 5.2 mmol) in acetic acid (10.0 mL), bromine (0.2 mL, 5.2 mmol) and aqueous HBr (0.4 mL, 5.2 mmol, 47% in water) were added and stirred at room temperature for 3 h. The reaction mixture was poured in saturated sodium carbonate solution and extracted with ethyl acetate. The organic layer was dried over sodium sulfate and concentrated under rotary evaporator. The crude obtained was washed with n-pentane and dried under vacuum to obtain compound 5 (1.2 g, 92%) as brown solid. $^1$H NMR (400 MHz, CDCl$_3$) δ 2.52 (m, 2H), 2.91-2.97 (t, J=4.0 Hz, 1H), 3.26 (m, 1H), 4.73 (t, J=3.8 Hz, 1H), 7.87 (s, 1H), 8.48 (s, 1H).

Step 6:

tert-butyl 2-chloro-7-oxo-7,9,10,11-tetrahydro-5H-pyrido[3',4'4,5]pyrrolo[2,3-f]isoquinoline-8(6H)-carboxylate (6)

To a solution of 6-bromo-3-chloro-7,8-dihydroisoquinolin-5(6H)-one (1.3 g, 5.0 mmol) in methanol (30.0 mL), tert-butyl 2,4-dioxopiperidine-1-carboxylate (1.5 g, 7.0 mmol) and ammonium acetate (1.2 g, 15.0 mmol) were added and heated to reflux for 2 h. The reaction mixture was stirred at room temperature for 16 h followed by heating to reflux for another 2 h. After completion of the reaction, the reaction mixture was concentrated under vacuum, and the residue obtained was dissolved in chloroform. The resulting solid solution was filtered, and the filtrate was concentrated under vacuum. Crude obtained was purified by silica gel column chromatography using 3% methanol/CH$_2$Cl$_2$ to obtain 6 (450 mg, 24%) as off white solid. $^1$H NMR (400 MHz, DMSO-$d_6$) δ 1.45 (s, 9H), 2.83-2.89 (m, 2H), 2.91-2.94 (m, 4H), 3.94 (t, J=6.2 Hz, 2H), 7.41 (s, 1H), 8.12 (s, 1H), 12.14 (s, 1H).

Step 7:

A mixture of 6 (15 mg, 0.05 mmol), INT-1 (15 mg, 0.05 mmol), Pd(dppf)Cl$_2$ (2 mg, 0.0027 mmol) and Cs$_2$CO$_3$ (32.5 mg, 0.1 mmol) was stirred in a microwave reactor at 100° C. for 1 hour. After cooling to rt, EtOAc and water were added, and two layers were separated. The organic layer was concentrated and triturated with Et$_2$O to give the crude Boc-protected product. This compound was dissolved in CH$_2$Cl$_2$ (4 mL) and to the solution was added trifluoroacetic acid (0.3 mL). The reaction mixture was stirred at room temperature for 30 minutes. Solvent was removed by rotary evaporation, and the crude product was purified by reverse phase HPLC (Varian Dynamax, 250×21.4 mm) to give the title compound II-20 as a TFA salt: yellow solid, 10.0 mg, 9%. $^1$H NMR (400 MHz, DMSO-$d_6$) δ 2.89 (m, 4H), 3.34 (d, J=5.0 Hz, 2H), 3.9 (t, J=4.4 Hz, 2H), 4.3 (t, J=4.95 Hz, 2H), 5.83-5.86 (dd, J=2.0, 10.3 Hz, 1H), 6.28-6.33 (dd, J=1.9, 16.8 Hz, 1H), 6.78-6.85 (dd, J=10.5, 16.8 Hz, 1H), 7.0 (s, 1H), 7.05 (d, J=8.5 Hz, 1H), 7.71-7.74 (dd, J=2.0, 8.5 Hz, 1H), 7.86 (s, 1H), 8.1 (brs, 1H), 11.9 (s, 1H). MS m/z (M+H): 435.2

Example 22

Compound II-1

N-(2-(4-methylpiperazin-1-yl)-5-(7-oxo-6,7,8,9,10,11-hexahydro-5H-pyrido[3',4':4,5]pyrrolo[2,3-f]isoquinolin-2-yl)phenyl)acrylamide

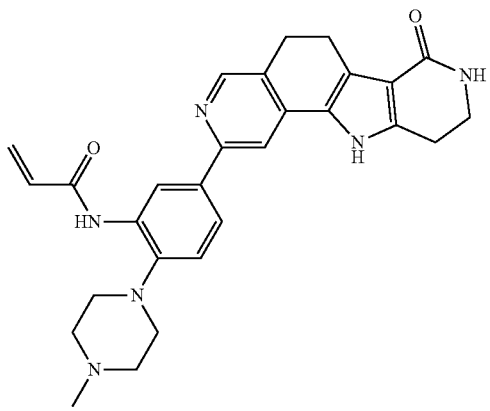 [SMILES: C=CC(=O)Nc1cc(-c2cc3c(cn2)CCc2c-3[nH]c3c2C(=O)NCC3)ccc1N1CCN(C)CC1]

The title compound II-1 was prepared as described in Example 21, by substituting boronic ester INT-8 for INT-1 in step 7 to give the desired product as a TFA salt: $^1$H NMR (400 MHz, DMSO-d6) δ ppm 9.90 (br s, 1H), 9.37 (s, 1H), 8.55 (s, 1H), 8.41 (s, 1H), 7.98 (s, 1H), 7.70 (d, J=8.7 Hz, 1H), 7.40 (d, J=8.7 Hz, 1H), 7.25 (s, 1H), 6.71 (dd, J=18.5, 12.0 Hz, 1H), 6.31 (d, J=18.8 Hz, 1H), 5.83 (d, J=11.9 Hz, 1H), 2.80-3.30 (m, 19H). MS m/z (M+H): 483.3

Example 23

Compound II-2

N-(2-methoxy-5-(7-oxo-6,7,8,9,10,11-hexahydro-5H-pyrido[3',4':4,5]pyrrolo[2,3-f]isoquinolin-2-yl)phenyl)acrylamide

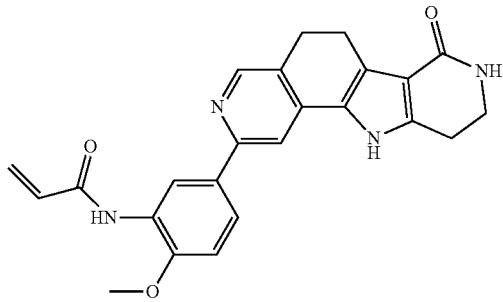 [SMILES: C=CC(=O)Nc1cc(-c2cc3c(cn2)CCc2c-3[nH]c3c2C(=O)NCC3)ccc1OC]

The title compound II-2 was prepared as described in Example 21, by substituting boronic ester INT-7 for INT-1 in step 7 to give the desired product as a TFA salt: $^1$H NMR (400 MHz, DMSO-d6) δ ppm 12.42 (br s, 1H), 9.69 (s, 1H), 8.66 (s, 1H), 8.39 (s, 1H), 7.98 (s, 1H), 7.68 (m, 1H), 7.35 (m, 1H), 7.27 (s, 1H), 6.71 (dd, J=17.0, 12.0 Hz, 1H), 6.28 (d, J=17.0, 1H), 5.77 (d, J=12 Hz, 1H), 3.95 (s, 3H), 2.87-2.95 (m, 8H). MS m/z (M+H): 415.3

Example 24

Compound II-3

N-(2-fluoro-5-(7-oxo-6,7,8,9,10,11-hexahydro-5H-pyrido[3',4':4,5]pyrrolo[2,3-f]isoquinolin-2-yl)phenyl)acrylamide

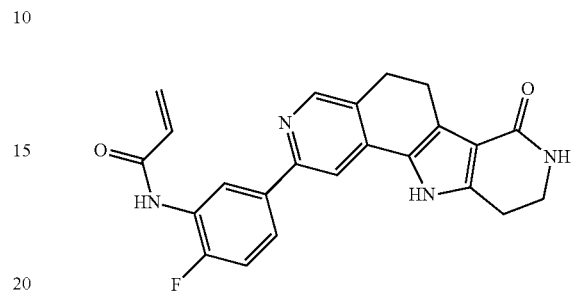

The title compound II-3 was prepared as described in Example 21, by substituting boronic ester INT-6 for INT-1 in step 7 to give the desired product as a TFA salt (7.4 mg, 32% for two steps): 1H NMR (400 MHz, DMSO-d$_6$) δ ppm 12.26 (br s, 1H), 10.19 (s, 1H), 8.65 (d, J=7.3 Hz, 1H), 8.43 (s, 1H), 7.95 (s, 1H), 7.73 (s, 1H), 7.54 (m, 1H), 7.20 (s, 1H), 6.66 (dd, J=17.0, 10.1 Hz, 1H), 6.30 (dd, J=17.0, 1.8 Hz, 1H), 5.83 (d, J=12 Hz, 1H), 2.87-2.95 (m, 8H). MS m/z (M+H): 403.2

Example 25

Compound II-4

N-(2-methoxy-5-(7-oxo-6,7,8,9,10,11-hexahydro-5H-pyrido[3',4':4,5]pyrrolo[2,3-f]isoquinolin-2-yl)pyridin-3-yl)acrylamide

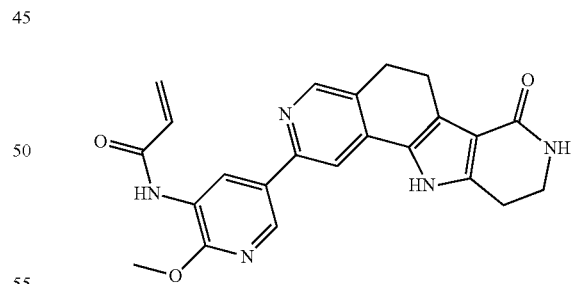

The title compound II-4 was prepared as described in Example 21, by substituting boronic ester INT-5 for INT-1 in step 7 to give the desired product as a TFA salt (7.7 mg, 11% for two steps): 1H NMR (400 MHz, DMSO-d$_6$) δ ppm 12.30 (br s, 1H), 9.88 (s, 1H), 9.01 (s, 1H), 8.47 (d, J=2.3 Hz, 1H), 8.43 (s, 1H), 7.95 (s, 1H), 7.25 (s, 1H), 6.79 (dd, J=17.0, 10.6 Hz, 1H), 6.30 (d, J=18.5 Hz, 1H), 5.80 (d, J=12 Hz, 1H), 4.05 (s, 3H), 2.87-2.95 (m, 8H). MS m/z (M+H): 416.2

Example 26

Compound II-14

N-(2-(2-methoxyethoxy)-5-(7-oxo-6,7,8,9,10,11-hexahydro-5H-pyrido[3',4':4,5]pyrrolo[2,3-f]isoquinolin-2-yl)pyridin-3-yl)acrylamide

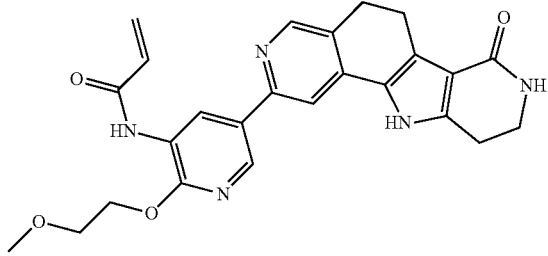 [SMILES: C=CC(=O)Nc1cc(-c2cc3c(cn2)CCc2c-3[nH]c3c2C(=O)NCC3)cnc1OCCOC]

The title compound II-14 was prepared as described in Example 21, by substituting boronic ester INT-4 for INT-1 in step 7 to give the desired product as a TFA salt: Yellow solid, 20.0 mg, 32%. $^1$H NMR (400 MHz, DMSO-d$_6$) δ 2.89 (m, 6H), 3.25 (s, 3H), 3.4 (t, J=4.5 Hz, 2H), 3.67 (t, J=5.2 Hz, 2H), 4.25 (t, J=5.1 Hz, 2H), 5.73-5.76 (dd, J=2.0, 10.3 Hz, 1H), 6.24-6.29 (dd, J=1.7, 16.9 Hz, 1H), 6.82-6.89 (dd, J=10.2, 19.0 Hz, 1H), 7.0 (s, 1H), 7.67 (s, 1H), 8.0 (s, 1H), 8.3 (s, 1H), 12.0 (s, 1H). MS m/z (M+H)+: 460.2

Example 27

Compound II-16

N-(2-(2-methoxyethoxy)-5-(7-oxo-6,7,8,9,10,11-hexahydro-5H-pyrido[3',4':4,5]pyrrolo[2,3-f]isoquinolin-2-yl)phenyl)acrylamide

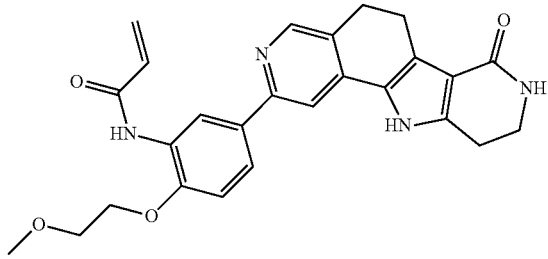 [SMILES: C=CC(=O)Nc1cc(-c2cc3c(cn2)CCc2c-3[nH]c3c2C(=O)NCC3)ccc1OCCOC]

The title compound II-16 was prepared as described in Example 21, by substituting boronic ester INT-3 for INT-1 in step 7 to give the desired product as a TFA salt: Yellow solid, 15.0 mg, 24%. $^1$H NMR (400 MHz, DMSO-d$_6$) δ 2.8 (m, 4H), 2.9 (d, J=7.1 Hz, 2H), 3.3 (s, 3H), 3.39 (t, J=4.4 Hz, 2H), 3.72-3.74 (q, J=4.5 Hz, 2H), 4.2 (t, J=4.8 Hz, 2H), 5.74-5.77 (dd, J=2.0, 10.2 Hz, 1H), 6.23-6.28 (dd, J=1.9, 17 Hz, 1H), 6.65 (dd, J=10.2, 16.9 Hz, 1H), 6.99 (s, 1H), 7.2 (d, J=8.7 Hz, 1H), 7.78 (dd, J=2.2, 8.6 Hz, 1H), 7.8 (s, 1H), 8.3 (s, 1H), 8.6 (s, 1H), 9.29 (s, 1H), 11.9 (s, 1H). MS m/z (M+H): 459.2

Example 28

Compound II-18

2-(1-acryloyl-2,3-dihydro-1H-pyrido[2,3-b][1,4]oxazin-7-yl)-8,9,10,11-tetrahydro-5H-pyrido[3',4':4,5]pyrrolo[2,3-f]isoquinolin-7(6H)-one

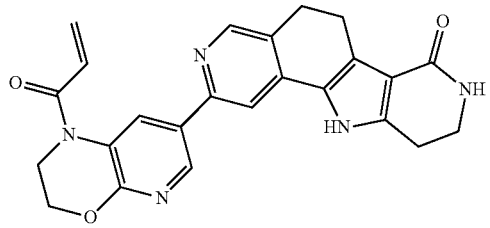 [SMILES: C=CC(=O)N1CCOc2ncc(-c3cc4c(cn3)CCc3c-4[nH]c4c3C(=O)NCC4)cc21]

The title compound II-18 was prepared as described in Example 21, by substituting boronic ester INT-2 for INT-1 in step 7 to give the desired product as a TFA salt: Yellow solid, 25.0 mg, 60%. $^1$H NMR (400 MHz, CD$_3$OD) δ 2.95-2.99 (m, 4H), 3.59 (t, J=6.9 Hz, 2H), 4.12 (t, J=4.5 Hz, 2H), 4.56 (t, J=4.8 Hz, 2H), 5.94-5.97 (dd, J=1.79, 10.5 Hz, 1H), 6.44-6.49 (dd, J=1.75, 16.7 Hz, 1H), 6.88-6.95 (dd, J=10.5, 16.7 Hz, 1H), 7.73 (s, 1H), 8.37 (s, 1H), 8.53 (d, J=1.9 Hz, 1H), 8.7 (brs, 1H). MS m/z (M+H): 428.2

Example 29

Compound II-25

2-(2-(4-acryloyl-3,4-dihydro-2H-benzo[b][1,4]oxazin-6-yl)pyrimidin-4-yl)-6,7-dihydro-1H-pyrrolo[3,2-c]pyridin-4(5H)-one

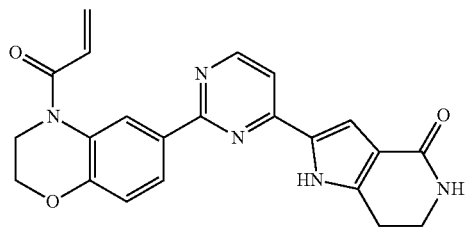 [SMILES: C=CC(=O)N1CCOc2ccc(-c3nccc(-c4cc5c([nH]4)CCNC5=O)n3)cc21]

The title compound was prepared according to the schemes, steps, and intermediates described below.

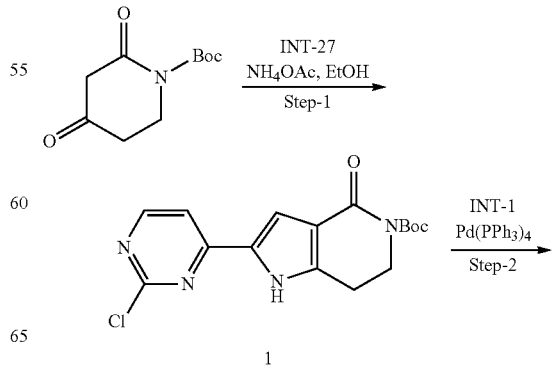

-continued

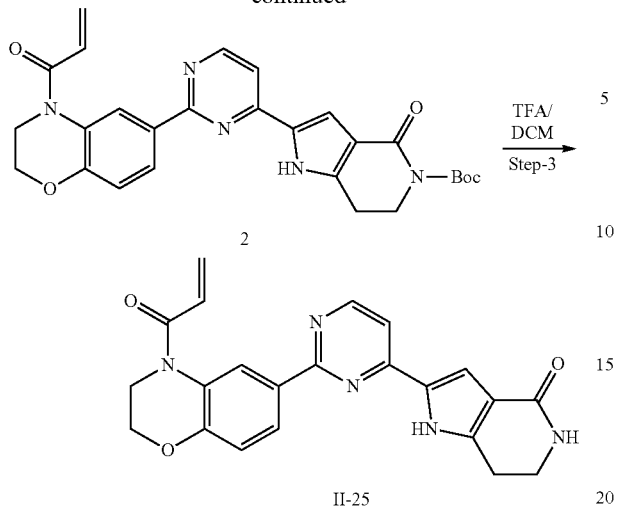

Step 1:
To a solution of 2-bromo-1-(2-chloropyrimidin-4-yl)ethanone INT-27 (190 mg, 0.8 mmol) in ethanol (5.0 mL), tert-butyl 2,4-dioxopiperidine-1-carboxylate (190 mg, 0.9 mmol), ammonium acetate (250 mg, 3.2 mmol) was added. The resulting mixture was stirred at room temperature for 16 h. After completion of the reaction, the reaction mixture was quenched with water. The solid suspension was filtered, and the solid collected was washed with diethyl ether followed by drying under vacuum to afford compound 1 (60 mg, 21%) as an off white solid. $^1$H NMR (400 MHz, DMSO-$d_6$) δ 1.45 (s, 9H), 2.94 (t, J=6.2 Hz, 2H), 3.94 (t, J=6.2 Hz, 2H), 7.45-7.47 (dd, J=1.9, 5.7 Hz, 1H), 7.86-7.90 (dd, J=5.4, 8.9 Hz, 1H), 8.51-8.60 (dd, J=5.4, 30.8 Hz, 1H), 12.39 (d, J=16.4 Hz, 1H). MS m/z (M+H): 349.1

Step 2:
To a solution of compound 1 (0.1 mmol) in 1,2-dimethoxyethane (10.0 mL), ethanol (1.2 mL), boronate ester (INT-1, 0.3 mmol) and saturated sodium carbonate (2.2 mL) were added. The resulting solution was degassed for 10 min under nitrogen followed by the addition of Pd(PPh$_3$)$_4$ (0.02 mmol). The reaction mixture was degassed for 10 min and then heated at 90° C. for 6 h. TLC showed the completion of the starting material. The reaction mixture was quenched with water, extracted with ethyl acetate, dried over anhydrous sodium sulfate and concentrated. The crude compound was purified by preparative HPLC to obtain compound 2: Pale yellow solid, 50 mg, 88%. MS m/z (M−H): 500.2

Step 3:
To a solution of compound 2 in dichloromethane, trifluoro acetic acid (excess) was added at 0° C. and stirred at room temperature for 1 h. After completion of the reaction, excess TFA was removed under reduced pressure and the residue obtained was triturated with diethyl ether. Solid obtained was purified by prep-HPLC to yield II-25 as a yellow solid (7 mg, 18%): 1H NMR (400 MHz, DMSO-$d_6$) δ 2.90 (t, J=6.79 Hz, 2H), 3.4 (m, 2H), 3.99-4.01 (m, 2H), 4.37 (t, J=4.5 Hz, 2H), 5.83-5.96 (dd, J=1.8, 10.7 Hz, 1H), 6.29-6.34 (dd, J=1.7, 16.8 Hz, 1H), 6.79-6.86 (dd, J=10.6, 17.0 Hz, 1H), 7.04-7.06 (d, J=8.6 Hz, 1H), 7.11 (s, 1H), 7.27-7.28 (d, J=2.2 Hz, 1H), 7.60-7.62 (d, J=5.4 Hz, 1H), 8.40-8.41 (d, J=1.9 Hz, 1H), 8.64-8.66 (d, J=4.8 Hz, 1H). MS m/z (M+H): 402.2.

Example 30

Compound II-21

N-(2-(2-methoxyethoxy)-5-(4-(4-oxo-4,5,6,7-tetrahydro-1H-pyrrolo[3,2-c]pyridin-2-yl)pyrimidin-2-yl)pyridin-3-yl)acrylamide

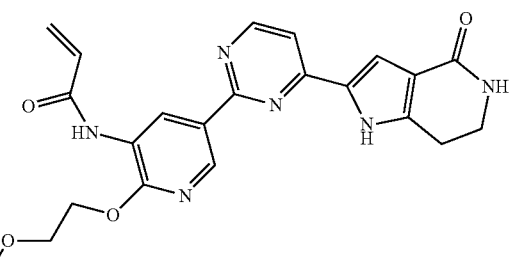

The title compound II-21 was prepared as described in Example 29, by substituting boronic ester INT-4 for INT-1 in step 2: Yellow solid, 3.5 mg, 43%. $^1$H NMR (400 MHz, DMSO-$d_6$) δ 2.93 (t, J=7.0 Hz, 2H), 3.25 (s, 3H), 3.42 (m, 2H), 3.71 (t, J=5.2 Hz, 2H), 4.30 (t, J=5.2 Hz, 2H), 5.72-5.75 (m, 1H), 6.25-6.29 (dd, J=1.9, 16.8 Hz, 1H), 6.80-6.87 (dd, J=10.2, 16.9 Hz, 1H), 7.13 (br s, 1H), 7.32 (d, J=2.3 Hz, 1H), 7.60 (d, J=5.4 Hz, 1H), 8.67 (d, J=7.5 Hz, 1H), 8.69 (s, 1H), 9.30 (s, 1H), 9.63 (s, 1H), 12.0 (s, 1H). MS m/z (M+H): 435.2

Example 31

Compound II-22

N-(2-(2-methoxyethoxy)-5-(4-(4-oxo-4,5,6,7-tetrahydro-1H-pyrrolo[3,2-c]pyridin-2-yl)pyrimidin-2-yl)phenyl)acrylamide

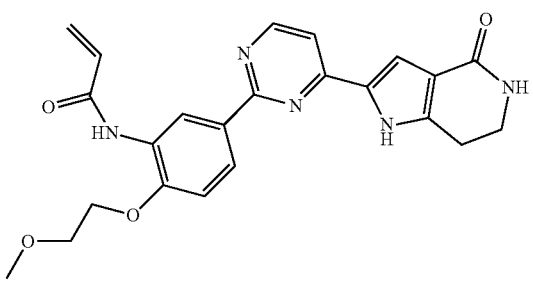 [SMILES: C=CC(=O)Nc1cc(-c2nccc(-c3cc4c([nH]3)CCNC4=O)n2)ccc1OCCOC]

The title compound II-22 was prepared as described in Example 29, by substituting boronic ester INT-3 for INT-1 in step 2: Yellow solid, 5 mg, 61%. $^1$H NMR (400 MHz, DMSO-$d_6$) δ 2.90 (t, J=6.7 Hz, 2H), 3.33 (s, 3H), 3.42 (t, J=6.6 Hz, 2H), 3.74 (t, J=4.5 Hz, 2H), 4.27 (t, J=4.6 Hz, 2H), 5.75 (d, J=11.5 Hz, 1H), 6.24-6.28 (dd, J=1.6, 17.1 Hz, 1H), 6.62-6.66 (m, 1H), 7.11 (br s, 1H), 7.21 (d, J=8.8 Hz, 1H), 7.27 (d, J=2.1 Hz, 1H), 7.61 (d, J=5.4 Hz, 1H), 8.41-8.43 (dd, J=2.0, 8.7 Hz, 1H), 8.67 (d, J=5.4 Hz, 1H), 9.01 (s, 1H), 9.31 (s, 1H), 12.06 (s, 1H). MS m/z (M+H): 434.2.

Example 32

Compound II-23

2-(2-(1-acryloyl-2,3-dihydro-1H-pyrido[2,3-b][1,4]oxazin-7-yl)pyrimidin-4-yl)-6,7-dihydro-1H-pyrrolo[3,2-c]pyridin-4(5H)-one

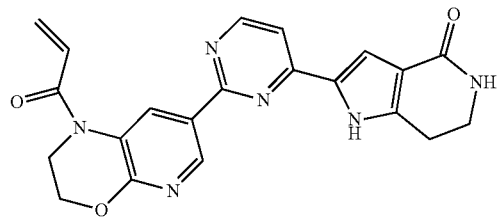 [SMILES: C=CC(=O)N1CCOc2ncc(-c3nccc(-c4cc5c([nH]4)CCNC5=O)n3)cc21]

The title compound II-23 was prepared as described in Example 29, by substituting boronic ester INT-2 for INT-1 in step 2: Off-white solid, 3 mg, 3% over 2 steps. $^1$H NMR (400 MHz, DMSO-$d_6$) δ 2.90 (t, J=6.8 Hz, 2H), 3.40-3.44 (m, 2H), 4.03 (t, J=4.5 Hz, 2H), 4.49 (t, J=4.4 Hz, 2H), 5.86-5.89 (dd, J=1.7, 10.2 Hz, 1H), 6.30-6.34 (dd, J=1.8, 16.6 Hz, 1H), 6.81-6.88 (dd, J=10.2, 16.6 Hz, 1H), 7.12 (s, 1H), 7.30 (d, J=2.0 Hz, 1H), 7.67 (d, J=5.4 Hz, 1H), 8.68 (d, J=5.4 Hz, 1H), 8.97 (brs, 1H), 9.26 (d, J=2.0 Hz, 1H), 12.0 (s, 1H). MS m/z (M+H): 403.2.

Example 33

Compound II-24

2-(4-acryloyl-3,4-dihydro-2H-benzo[b][1,4]oxazin-6-yl)-8,9,10,11-tetrahydro-5H-pyrido[3',4':4,5]pyrrolo[3,2-h]i quinazolin-7(6H)-one

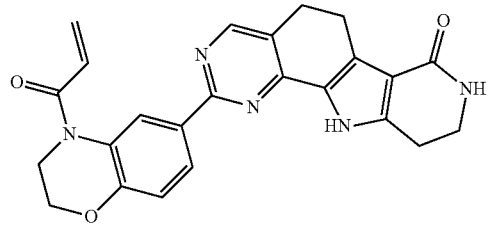 [SMILES: C=CC(=O)N1CCOc2ccc(-c3ncc4c(n3)-c3[nH]c5c(c3CC4)C(=O)NCC5)cc21]

The title compound was prepared according to the schemes, steps, and intermediates

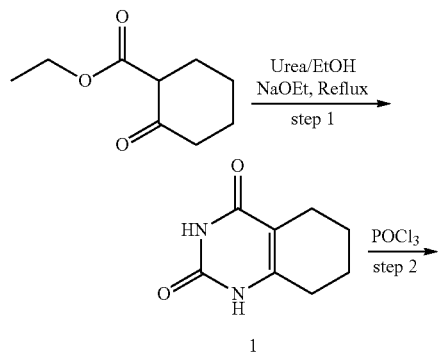

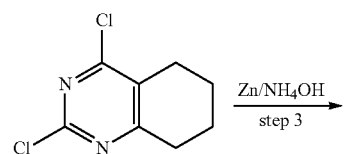

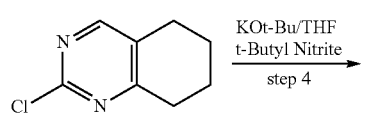

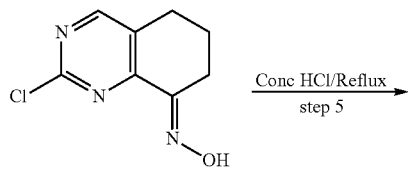

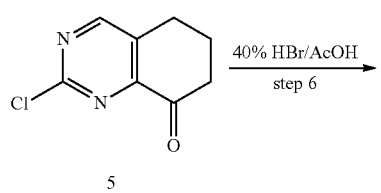

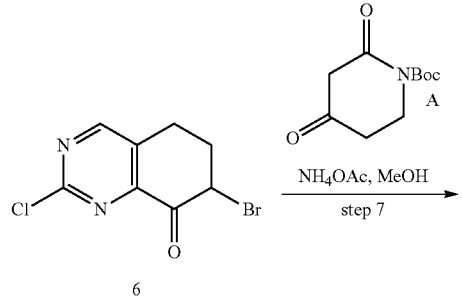

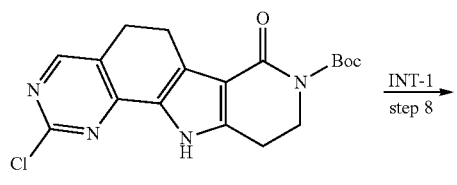

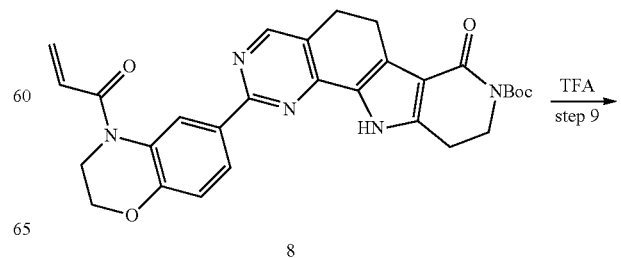

-continued

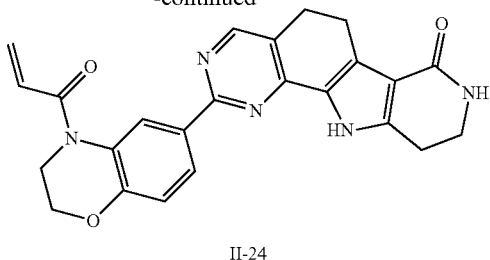

II-24

Step 1:

5,6,7,8-tetrahydroquinazoline-2,4(1H,3H)-Dione (1)

To a solution of ethyl 2-oxocyclohexanecarboxylate (10.0 g, 58.8 mmol) in ethanol (200 mL), sodium methoxide (29.4 mL, 118 mmol) and urea (4.6 g, 76 mmol) were added at room temperature. The reaction mixture was then heated at 80° C. for 15 hours. The reaction mixture was cooled to room temperature and filtered. The resulting solid was washed with cold a solution of diethyl ether to obtain 1 (6.0 g, 61%) as off white solid. $^1$H NMR (400 MHz, DMSO-$d_6$) δ 2.12 (t, J=6.0 Hz, 4H), 2.16 (t, J=5.6 Hz, 4H), 5.44 (s, 1H). MS m/z (M−H): 165.2

Step 2:

2,4-dichloro-5,6,7,8-tetrahydroquinazoline (2)

5,6,7,8-tetrahydroquinazoline-2,4(1H,3H)-dione (8.0 g) was treated with phosphorousoxychloride (40 mL) and heated to 1200 C for 1 h. The reaction mixture was cooled to room temperature and then excess of phosphorousoxychloride was distilled off under reduced pressure. The residue obtained was partitioned between ethyl acetate (400 mL) and water (200 mL). The organic phase was then washed with saturated NaHCO$_3$ (200 mL) followed by brine solution (200 mL). The organic phase was dried over anhydrous sodium sulfate and concentrated under reduce pressure. The residue was purified by column chromatography to obtain 2 (4.0 g, 57%) as a yellow solid. $^1$H NMR (400 MHz, CDCl$_3$) δ 1.8 (br s, 4H), 2.73 (br s, 2H), 2.88 (br s, 2H). MS m/z (M+H): 203.1

Step 3:

2-chloro-5,6,7,8-tetrahydroquinazoline (3)

To a solution of 2,4-dichloro-5,6,7,8-tetrahydroquinazoline (4.0 g) in DCM (50 mL), NH$_4$OH (50 mL) and Zinc (4.0 g) were added and the resulting mixture was heated to reflux overnight. After filtration through celite, the organic layer was washed with water, dried and concentrated under vacuum to obtain 3 (2.5 g, 75%). MS m/z (M+H): 169.1

Step 4:

(E)-2-chloro-6,7-dihydroquinazolin-8(5H)-one oxime (4)

To a solution of 2-chloro-5,6,7,8-tetrahydroquinazoline (500 mg, 0.029 mmol) in dry THF (10 mL), a solution of KOtBu (660 mg, 0.059 mmol) in THF was added followed by the addition of t-butyl nitrite (1.5 g, 0.148 mmol) at −78° C. The resulting mixture was stirred at room temperature for 2 h. Reaction mixture was diluted with water (10 mL) and extracted with ethyl acetate (2×10 mL). The organic layer was dried and concentrated under reduced pressure. The crude obtained was purified by silica gel column chromatography to afford 4 (210 mg, 36%) as a pale yellow solid. MS m/z (M+H): 198.0

Step 5:

2-chloro-6,7-dihydroquinazolin-8(5H)-one (5)

To a solution of (E)-2-chloro-6,7-dihydroquinazolin-8 (5H)-one oxime (100 mg) in acetone:water (5:1, 10 mL), conc. HCl (2 mL) was added and stirred at 80° C. for 3 h. The reaction mixture was diluted with ice water (20 ml) and basified to pH -9 using sat. NaHCO$_3$. The aqueous layer was extracted with ethyl acetate (10.0 mL). The organic layer was dried and concentrated under reduced pressure to obtain crude compound. The crude obtained was purified by silica gel column chromatography to afford 5 (70.0 mg, 76%) as a white solid. $^1$H NMR (400 MHz, DMSO-$d_6$) δ 2.12 (m, 2H), 2.73 (t, J=6.8 Hz, 2H), 2.95 (t, J=6.0 Hz, 2H), 8.99 (s, 1H).

Step 6:

7-bromo-2-chloro-6,7-dihydroquinazolin-8(5H)-one (6)

To a solution of 2-chloro-6,7-dihydroquinazolin-8(5H)-one (260 mg, 1.428 mmol) in conc. HCl (6.0 mL), a solution of bromine in conc. HCl was added dropwise and stirred at 35° C. for 10 min. The reaction mixture was poured into water, extracted with ethyl acetate, and dried over anhydrous sodium sulfate. The organic layer was concentrated under reduced pressure to obtain crude 6 (230.0 mg, 62%) as a yellow solid. As the compound was unstable, crude was used as such for the next step.

Step 7:

tert-butyl 2-chloro-7-oxo-7,9,10,11-tetrahydro-5H-pyrido[3',4'4,5]pyrrolo[3,2-h]quinazoline-8(6H)-carboxylate Compound (7)

To a solution of 7-bromo-2-chloro-6,7-dihydroquinazolin-8(5H)-one (230 mg, 0.894 mmol) in methanol (5.0 mL), tert-butyl 2,4-dioxopiperidine-1-carboxylate (285 mg, 1.342 mmol), sodium acetate (73 mg, 0.894 mmol) and ammonium acetate (137 mg, 1.7 mmol) were added and stirred for 16 h at room temperature. The reaction mixture was concentrated, and the residue obtained was dissolved in ethyl acetate. The organic layer was washed with water, brine, dried over anhydrous sodium sulfate, and concentrated under reduced pressure. The obtained crude was purified by silica gel column chromatography to obtain 7 (180 mg, 75%) as a pale yellow solid. 1H NMR (400 MHz, DMSO-$d_6$) δ 1.45 (s, 9H), 2.85 (t, J=6.0 Hz, 4H), 2.95 (t, J=19.6 Hz, 2H), 3.92 (t, J=6.2 Hz, 2H), 8.3 (s, 1H), 9.0 (s, 1H), 12.5 (s, 1H).

Step 8:

tert-butyl 2-(4-acryloyl-3,4-dihydro-2H-benzo[b][1,4]oxazin-6-yl)-7-oxo-7,9, 10,11-tetrahydro-5H-pyrrolo[3',4':4,5]pyrrolo[3,2-h]quinazoline-8(6H)-carboxylate (8)

To a solution of 7 (1.0 equiv) in n-pronanol (2.0 mL/50 mg of 7), 1-(6-(4,4,5,5-tetramethyl-1,3,2-dioxaborolan-2-yl)-2H-benzo[b][1,4]oxazin-4(3H)-yl)prop-2-en-1-one INT-1 (2.0 equiv), triphenylphosphine (1.0 equiv) and 0.5 mL of saturated sodium carbonate solution were added. The resulting solution was degassed with nitrogen for 20 min followed by the addition of Pd(dppf)$_2$.DCM (0.3 equiv) and Pd(PPh$_3$)$_2$Cl$_2$ (0.3 equiv). The reaction mixture was degassed with nitrogen for another 5 min. The reaction mixture was then irradiated under microwave (130° C., 200W) for 20 min. The reaction mixture was filtered, and the filtrate obtained was concentrated to dryness under reduced pressure. The crude solid obtained (8) was washed with diethyl ether and used in the next step without further purification.

Step 9:

To a solution of Boc-compound 8 in DCM (0.5 mL), TFA (0.5 mL) was added at 0° C. and stirred at RT for 2 h. The reaction mixture was then concentrated under vacuum. The crude solid obtained was washed with diethyl ether and purified by preparative HPLC to obtain the desired compound II-24 as a pale yellow solid, 5.0 mg, 15%. $^1$H NMR (400 MHz, DMSO-d$_6$) δ 2.85 (q, J=6.7 Hz, 4H), 2.95 (d, J=6.9 Hz, 2H), 3.3 (d, J=6.5 Hz, 2H), 3.9 (t, J=3.2 Hz, 2H), 4.3 (t, J=4.1 Hz, 2H), 5.82-5.85 (dd, J=11.6 Hz, 1H), 6.28-6.33 (dd, J=16.8 Hz, 1H), 6.76-6.83 (dd, J=9.9, 16.5 Hz, 1H), 7.0 (d, J=8.6 Hz, 1H), 8.22-8.23 (dd, J=7.1, 8.5 Hz, 1H), 8.4 (s, 2H), 12.0 (s, 1H). MS m/z (M+H): 428.2

Example 34

Compound II-17

2-(1-acryloyl-2,3-dihydro-1H-pyrido[2,3-b][1,4]oxazin-7-yl)-8,9,10,11-tetrahydro-SH-pyrido[3',4':4,5]pyrrolo[3,2-h]quinazolin-7(6H)-one

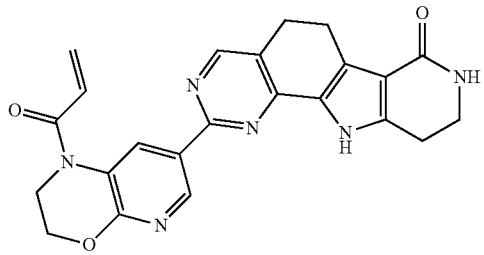 [SMILES: C=CC(=O)N1CCOc2ncc(-c3ncc4c(n3)-c3[nH]c5c(c3CC4)C(=O)NCC5)cc21]

The title compound II-17 was prepared as described in Example 33, by substituting boronic ester INT-2 for INT-1 in step 8: Off-white solid, 11 mg, 30%. $^1$H NMR (400 MHz, DMSO-d$_6$) δ 1.22 (s, 1H), 2.84-2.87 (q, J=6.8 Hz, 2H), 2.91-2.95 (dd, J=14.0, 21.1 Hz, 2H), 3.4 (m, 4H), 4.0 (q, J=4.3 Hz, 2H), 4.4 (t, J=4.7 Hz, 2H), 5.86-5.89 (dd, J=1.9, 10.4 Hz, 1H), 6.29-6.34 (dd, J=1.9, 16.7 Hz, 1H), 6.80-6.87 (dd, J=10.1, 16.8 Hz, 1H), 7.1 (s, 1H), 8.4 (s, 1H), 9.05 (s, 1H), 12.0 (s, 1H). MS m/z (M+H): 429.2

Example 35

Compound II-13

N-(2-(2-methoxyethoxy)-5-(7-oxo-6,7,8,9,10,11-hexahydro-5H-pyrido[3',4':4,5]pyrrolo[3,2-h]quinazolin-2-yl)pyridin-3-yl)acrylamide

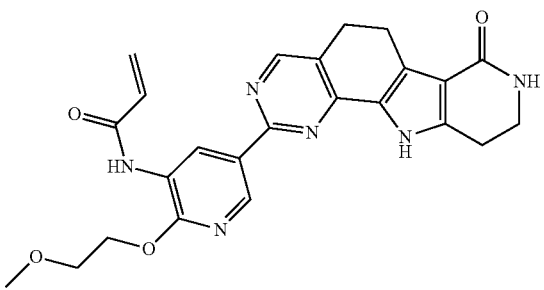 [SMILES: C=CC(=O)Nc1cc(-c2ncc3c(n2)-c2[nH]c4c(c2CC3)C(=O)NCC4)cnc1OCCOC]

The title compound II-13 was prepared as described in Example 33, by substituting boronic ester INT-4 for INT-1 in step 8: Yellow solid, 8.0 mg, 19%. $^1$H NMR (400 MHz, DMSO-d$_6$) δ 1.6 (s, 4H), 2.93-2.95 (d, J=7.3 Hz, 2H), 3.25 (s, 3H), 3.67-3.70 (t, J=5.0 Hz, 3H), 4.25 (t, J=5.4 Hz, 3H), 5.73-5.76 (dd, J=1.9, 10.1 Hz, 1H), 6.23-6.28 (dd, J=1.9, 16.9 Hz, 1H), 6.77-6.84 (dd, J=10.2, 17.0 Hz, 1H), 8.4 (d, J=3.8 Hz, 1H), 8.48 (d, J=2.3 Hz, 1H), 9.25 (s, 1H), 12.03 (s, 1H). MS m/z (M+H): 461.2

Example 36

Compound II-15

N-(2-(2-methoxyethoxy)-5-(7-oxo-6,7,8,9,10,11-hexahydro-5H-pyrido[3',4':4,5]pyrrolo[3,2-h]quinazolin-2-yl)phenyl)acrylamide

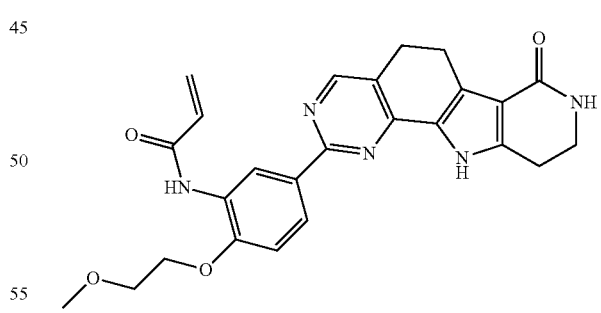

The title compound II-15 was prepared as described in Example 33, by substituting boronic ester INT-3 for INT-1 in step 8: Yellow solid, 4.0 mg, 11%. $^1$H NMR (400 MHz, DMSO-d$_6$) δ 2.85 (m, 4H), 2.95 (t, J=7.0 Hz, 2H), 3.4 (t, J=1.5 Hz, 2H), 3.7-3.75 (t, J=4.4 Hz, 2H), 4.25 (t, J=4.8 Hz, 2H), 5.72-5.76 (dd, J=1.7, 10.3 Hz, 1H), 6.23-6.27 (dd, J=1.7, 17 Hz, 1H), 6.60-6.67 (dd, J=10.2, 16.6 Hz, 1H), 7.1 (s, 1H), 7.2 (d, 1H), 8.25-8.28 (dd, J=2.0, 8.6 Hz, 1H), 8.45 (s, 1H), 8.9 (s, 1H), 9.29 (s, 1H), 12 (s, 1H). MS m/z (M−H): 458.2

Example 37

Compound II-26

N-(2-(4-methylpiperazin-1-yl)-5-(7-oxo-6,7,8,9,10,11-hexahydro-5H-pyrido[3',4':4,5]pyrrolo[2,3-f]isoquinolin-2-yl)pyridin-3-yl)acrylamide

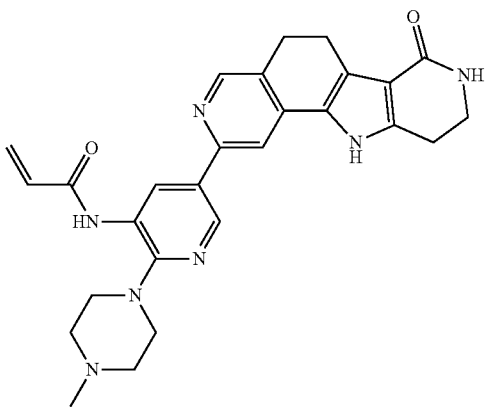

The title compound II-30 was prepared as described in Example 21, by substituting boronic ester INT-9 for INT-1 in step 7 to give the desired product as a TFA salt: $^1$H NMR (400 MHz, DMSO-d$_6$) δ ppm 12.15 (br s, 1H), 9.71 (br s, 1H), 9.63 (s, 1H), 8.68 (s, 1H), 8.40 (s, 1H), 7.94 (s, 1H), 7.16 (s, 1H), 6.64 (dd, J=17.0, 10.1 Hz, 1H), 6.31 (d, J=16.9 Hz, 1H), 5.83 (d, J=11.4 Hz, 1H), 2.80-3.80 (m, 19H). MS m/z (M+H): 484.2

Example 38

Compound II-e-3

N-(2-fluoro-5-(7-oxo-7,8,9,1-tetrahydrocyclopenta[4,5]pyrrolo[2,3-f]isoquinolin-2-yl)phenyl)acrylamide

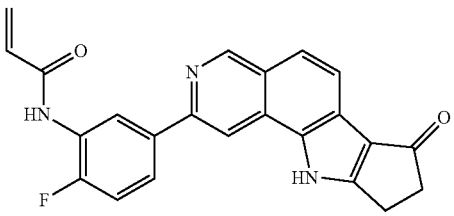

The title compound was prepared according to the schemes, steps, and intermediates described below.

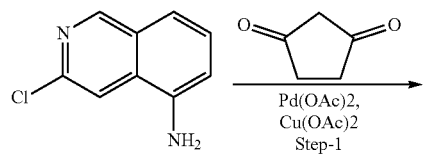

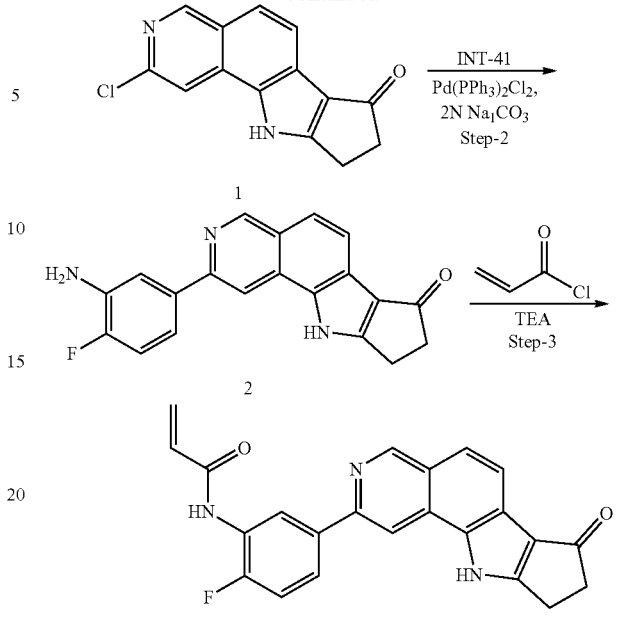

Step 1:

2-chloro-8,9-dihydrocyclopenta[4,5]pyrrolo[2,3-f]isoquinolin-7(1OH)-one (1)

A mixture of 3-chloro-5-amino isoquinoline (100 mg, 0.55 mmol) and 1, 3-cyclopentane dione (80 mg, 0.78 mmol) was dissolved in MeOH (5 mL) and concentrated on rotavapor and dried under vacuum. The reaction mixture was heated to 120° C. for 25 minutes then dry DMF (5 mL) was added and purged with argon for 10 min. Pd(OAc)$_2$ (37 mg, 0.16 mmol) and Cu(OAc)$_2$ (334 mg, 1.67 mmol) were then added and stirring continued for another 1 h. After completion of the reaction (by TLC), the reaction mixture was brought to room temperature and quenched with water (5 mL) and IN HCl (5 mL) and extracted with EtOAc (2×50 mL). The combined organic layers were dried over anhydrous sodium sulfate and concentrated under reduced pressure. The residue was purified by silica gel column chromatography to obtain 1 (50 mg, 35%) as brown solid. 1H NMR (400 MHz, DMSO-d$_6$) δ 2.92 (m, 2H), 3.22 (m, 2H), 7.87 (d, J=8.4 Hz, 1H), 7.97 (d, J=8.4 Hz, 1H), 8.38 (s, 1H), 9.21 (s, 1H), 13.12 (bs, 1H). MS m/z (M+H): 257.2

Step 2:

2-(3-amino-4-fluorophenyl)-8, 9-dihydrocyclopenta[4, 5]pyrrolo[2, 3-f]isoquinolin-7 (10H)-one (2)

To a stirred solution of 2-chloro-8, 9-dihydrocyclopenta[4, 5]pyrrolo[2, 3-f]isoquinolin-7 (10H)-one 1 (300 mg, 1.17 mmol) in isopropanol (5 mL) under inert atmosphere were added 2-fluoro-5-(4,4,5,5-tetramethyl-1,3,2-dioxaborolan-2-yl)aniline INT-41 (416 mg, 1.75 mmol) and 2N sodium carbonate solution (3 mL) at RT and purged under argon for 20 minutes. Then Pd(PPh$_3$)$_2$Cl$_2$ (82 mg, 0.117 mmol) was added to the reaction mass and purged with argon for 20 minutes, heated to 160° C. under Microwave and stirred for 45 minutes. Starting materials were not consumed by TLC and again 2-fluoro-5-(4,4,5,5-tetramethyl-1,3,2-dioxaborolan-2-yl)aniline (138 mg, 0.58 mmol) and Pd(PPh$_3$)$_2$Cl$_2$ (82 mg, 0.117 mmol) were added to the reaction mass and stirred at 160° C. for 2 h. The reaction mixture was cooled to room temperature and filtered through celite pad, and the volatiles were evaporated under reduced pressure. The residue was purified by silica gel column chromatography to obtain 2 (60 mg, 16%) as green solid. 1H NMR (400 MHz, DMSO-d$_6$): δ 2.93 (m, 2H), 3.24 (m, 2H), 5.30 (s, 2H), 7.18 (m, 1H), 7.32 (m, 1H), 7.72-7.75 (dd, J=2.0, 9.2 Hz, 1H), 7.82 (d, J=8.4 Hz, 1H), 7.91 (d, J=8.4 Hz, 1H), 8.73 (s, 1H), 9.35 (s, 1H), 13.15 (s, 1H). MS m/z (M+H): 332.2

Step 3:

To a stirred solution of 2-(3-amino-4-fluorophenyl)-8,9-dihydrocyclopenta[4,5]pyrrolo[2,3-f]isoquinolin-7(10H)-one (2) (60 mg, 0.18 mmol) in dry DCM (5 mL) under inert atmosphere were added triethyl amine (0.02 mL, 0.18 mmol) and acryloyl chloride (0.01 mL, 0.18 mmol) at 0° C. The reaction mixture was warmed to room temperature and stirred for 2 h; starting material was not consumed by TLC and again triethyl amine (0.02 mL) was added to the reaction mass and stirred for 1 h. The reaction mixture was diluted with water (15 mL) and extracted with DCM (2×15 mL). The combined organic layers were washed with water (15 mL), dried over anhydrous sodium sulfate and concentrated under reduced pressure. The residue was purified by silica gel column chromatography to obtain compound II-e-3 (20 mg, 29%) as an off-white solid. $^1$H NMR (400 MHz, DMSO-d$_6$): δ 2.93 (m, 2H), 3.26 (m, 2H), 5.82 (d, J=10.4 Hz, 1H), 6.33 (d, J=17.2 Hz, 1H), 6.64-6.71 (dd, J=10.4, 17.2 Hz, 1H), 7.48 (m, 1H), 7.85 (d, J=8.4 Hz, 1H), 7.94 (d, J=8.4 Hz, 1H), 8.03 (s, 1H), 8.85 (m, 2H), 9.40 (s, 1H), 10.08 (s, 1H), 13.23 (s, 1H). MS m/z (M+H): 386.2.

Example 39

Compound II-e-1

N-(3-(7-oxo-7,8,9,10-tetrahydrocyclopenta[4,5]pyrrolo[2,3-f]isoquinolin-2-yl)phenyl)acrylamide

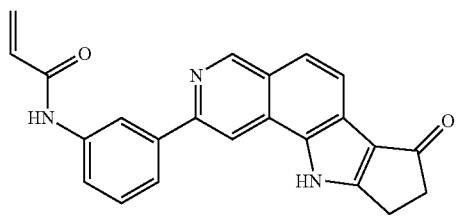 [SMILES: C=CC(=O)Nc1cccc(-c2cc3c(ccc4c5c([nH]c43)CCC5=O)cn2)c1]

The title compound was prepared in a manner similar to Example 38, substituting (3-aminophenyl)boronic acid for INT-41 according to the schemes, steps, and intermediates described below.

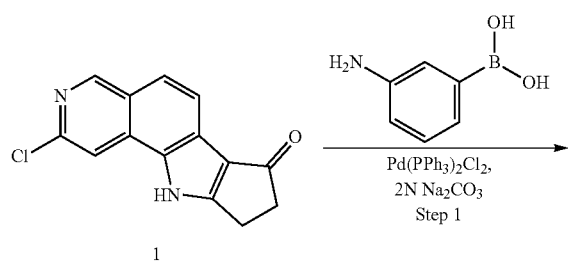

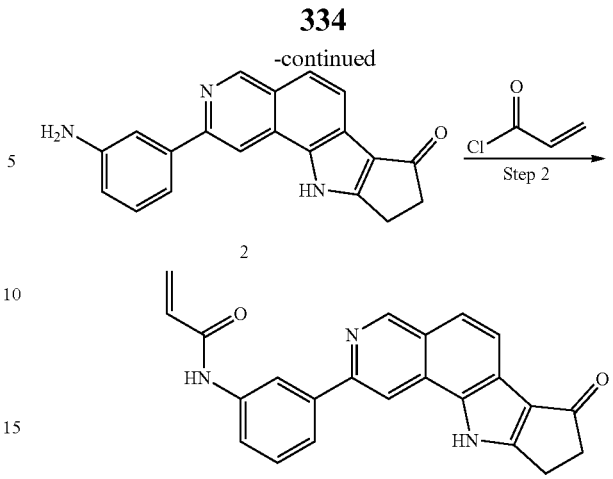

Step 1:

To a solution of 2-chloro-8,9-dihydrocyclopenta[4,5]pyrrolo[2,3-f]isoquinolin-7(10H)-one (1) (100 mg, 0.39 mmol), from Example 38, in 2-propanol (5 mL) were added (3-aminophenyl)boronic acid (80 mg, 0.58 mmol), 2N Na$_2$CO$_3$ (2.5 mL) and Pd(PPh$_3$)$_2$Cl$_2$ (27 mg, 0.039 mmol). The resulting reaction mixture was degassed with argon for 20 min and then heated to 150° C. for 1.5 h. The reaction mixture was brought to room temperature, quenched with 10% MeOH/DCM (10 mL) and filtered through a celite pad. The filtrate was dried over anhydrous sodium sulfate and concentrated under reduced pressure. The residue was purified by silica gel column chromatography to obtain 2 (60 mg, 50%) as brown solid. 1H NMR (400 MHz, CD$_3$OD) δ 3.04 (m, 2H), 3.24 (m, 2H), 6.82-6.84 (dd, J=1.6, 8.0 Hz, 1H), 7.27 (t, J=8.0 Hz, 1H), 7.39 (m, 1H), 7.43 (t, J=2.0 Hz, 1H), 7.82 (m, 2H), 8.03 (d, J=8.8 Hz, 1H), 8.10 (d, J=8.4 Hz, 1H), 8.43 (s, 1H), 9.23 (s, 2H). MS m/z (M+H): 314

Step 2:

A solution of 2-(3-aminophenyl)-8,9-dihydrocyclopenta[4,5]pyrrolo[2,3-f]isoquinolin-7(10OH)-one (2) (60 mg, 0.19 mmol) in DCM (5 mL) was cooled to 0° C. and acryl chloride (0.01 mL, 0.21 mmol) was added dropwise. The reaction was brought to room temperature and stirred for 16 h. Starting material was still present by TLC; again acryl chloride (0.01 mL, 0.21 mmol) was added and continued stirring for another 16 h. After completion of the reaction by TLC, saturated NaHCO$_3$ (5 mL) was added and extracted with DCM (3×5 mL). The combined organic layers were dried over anhydrous sodium sulfate and concentrated under reduced pressure. The residue was purified by silica gel column chromatography followed by preparative TLC to obtain the title compound (10 mg, 14%) as an off white solid. $^1$H NMR (400 MHz, DMSO-d$_6$): δ 2.94 (m, 2H), 4.13 (m, 2H), 5.79 (m, 1H), 6.29-6.33 (dd, J=1.6, 16.8 Hz, 1H), 6.47-6.54 (dd, J=10.0, 16.8 Hz, 1H), 7.53 (t, J=8.4 Hz, 1H), 7.69 (t, J=1.6 Hz, 1H), 7.78 (d, J=8.4 Hz, 1H), 7.89 (m, 2H), 7.95 (d, J=8.4 Hz, 1H), 8.62 (s, 1H), 8.86 (s, 1H), 10.34 (s, 1H), 13.24 (s, 1H). MS m/z (M+H): 368.1.

Example 40

Compound III-12

(R)—N-(3-acrylamidophenyl)-3-methyl-5-oxo-2,3,4,5-tetrahydro-1H-benzo[4,5]thieno[3,2-e][1,4]diazepine-9-carboxamide

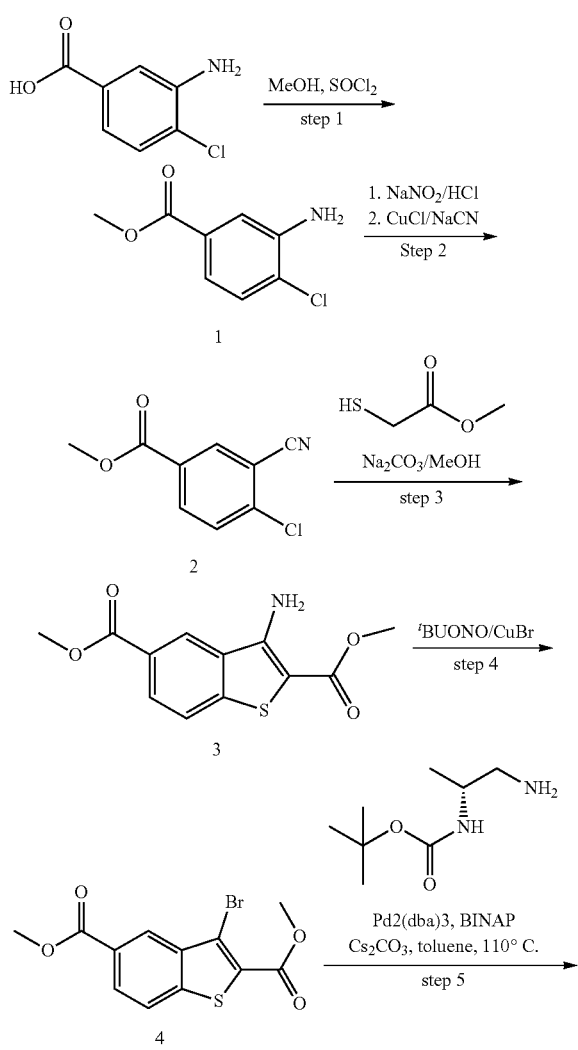

The title compound was prepared according to the schemes, steps, and intermediates

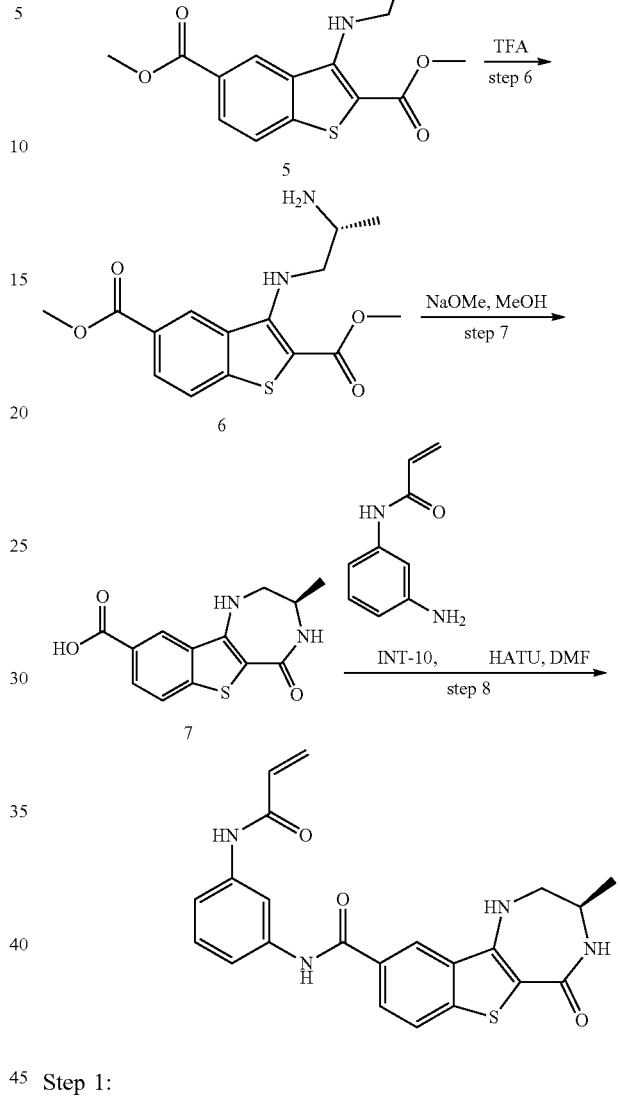

Step 1:

Methyl 3-amino-4-chlorobenzoate (1)

To a solution of 3-amino-4-chlorobenzoic acid (15.0 g, 88.0 mmol) in methanol (90.0 mL), thionyl chloride (13.0 mL) was added drop-wise at 0° C. The resulting mixture was refluxed for 12 h. After completion of the reaction, the reaction mixture was concentrated under reduced pressure. The residue obtained was diluted with water (150 mL), and extracted with ethyl acetate. The organic layer was washed with sodium bicarbonate solution (50 mL), brine solution (50 mL) and finally dried over sodium sulfate. The organic layer was removed under rotary evaporator to yield 1 (15.0 g, 92.5%) as an off-white solid. $^1$H NMR (400 MHz, CDCl$_3$) δ 3.88 (s, 3H), 4.26 (brs, 2H), 7.29 (d, J=8.2 Hz, 1H), 7.34-7.37 (dd, J=1.9, 8.2 Hz, 1H), 7.45 (d, J=1.9 Hz, 1H).

Step 2:

Methyl 4-chloro-3-cyanobenzoate (2)

To a solution of methyl 3-amino-4-chlorobenzoate (15.0 g, 81.0 mmol) in H$_2$O/conc. HCl (150 mL/17 mL), nitrous acid solution (5.6 g, 81 mmol) was added drop-wise at 0° C. and stirred for 30 min. The reaction mixture was neutralized with sodium hydroxide solution. The resulting diazonium salt solution was added to a solution of cuprous chloride (8.0 g, 81.0 mmol) and sodium cyanide (10.7 g, 218.0 mmol) at 0° C. and stirred at room temperature for 4 h. The reaction mixture was quenched with water (150 mL) and extracted with ethyl acetate (200 mL). The organic layer was separated, dried over anhydrous sodium sulfate and concentrated under reduced pressure. The crude obtained was triturated with diethyl ether and n-pentane to yield 2 (8.0 g, 51%) as a white solid. $^1$H NMR (400 MHz, CDCl$_3$) δ 3.88 (s, 3H), 4.26 (brs, 2H), 7.29 (d, J=8.2 Hz, 1H), 7.34-7.37 (dd, J=1.9, 8.2 Hz, 1H), 7.45 (d, J=1.9 Hz, 1H)

Step 3:

Dimethyl 3-aminobenzo[b]thiophene-2, 5-dicarboxylate (3)

To a solution of methyl 4-chloro-3-cyanobenzoate (8.0 g, 41.0 mmol) in methanol, sodium carbonate (4.3 g, 41.0 mmol) and methyl thioglyoxalate (3.6 mL, 41.0 mmol) were added and refluxed for 3 h. The reaction mixture was concentrated, and the residue obtained was diluted with ice-cold water. A brown solid obtained which was filtered and dried to yield 3 (9.0 g, 83%). $^1$H NMR (400 MHz, CDCl$_3$) δ 3.90 (s, 3H), 3.96 (s, 3H), 5.99 (brs, 2H), 7.77 (d, J=8.5 Hz, 1H), 8.08-8.11 (dd, J=1.5, 8.5 Hz, 1H), 8.38 (d, J=1.0 Hz, 1H).

Step 4:

Dimethyl-3-bromobenzo[b]thiophene-2, 5-dicarboxylate (4)

To a solution of copper bromide (9.0 g, 40.0 mmol) in acetonitrile, tert-butylnitrite (5.2 mL, 44 mmol) was added at 0° C. and stirred for 10 min. Then, dimethyl-3-aminobenzo[b]thiophene-2, 5-dicarboxylate (9.0 g, 34 mmol) was added in small portions at 0° C. and stirred at room temperature for 5 h. After completion of the reaction, ice-cold water was added to the reaction mixture. The yellow solid solution obtained was filtered and dried to yield 4 (7.0 g, 64%) as yellow solid. $^1$H NMR (400 MHz, CDCl$_3$) δ 3.92 (s, 6H), 8.12 (d, J=8.3 Hz, 1H), 8.28 (d, J=8.5 Hz, 1H), 8.46 (s, 1H).

Step 5:

(R)-Dimethyl-3-(2-(tert-butoxycarbonylamino) propylamino) benzo[b]thiophene-2, 5-dicarboxylate (5)

To a solution of dimethyl-3-bromobenzo[b]thiophene-2, 5-dicarboxylate (2.0 g, 6.0 mmol) and (R)-tert-butyl 1-aminopropan-2-ylcarbamate (1.3 g, 7.0 mmol) in toluene (30 mL), cesium carbonate (3.9 g, 12 mmol) was added, and the resulting solution was degassed for 10 min. To this mixture, BINAP (381.0 mg, 0.6 mmol) and trisdibenzylidenedipalladium (56 mg, 0.6 mmol) were added and further degassed for another 5 min. The resulting mixture was refluxed at 80° C. for 48 h. After completion of the reaction, the reaction mixture was diluted with water (200 mL) and extracted with ethyl acetate (200 mL). The organic layer was washed with brine, dried over anhydrous sodium sulfate and concentrated under reduced pressure. The residue obtained was purified by silica gel column chromatography to yield 5 (1.5 g, 59%) as a pale yellow solid. $^1$H NMR (400 MHz, CDCl$_3$) δ 1.29 (d, J=6.7 Hz, 3H), 1.40 (s, 9H), 3.75 (m, 1H), 3.88 (s, 3H), 3.90 (s, 3H), 3.96 (m, 1H), 4.6 (brs, 1H), 7.51 (m, 1H), 7.75 (d, J=8.5 Hz, 1H), 8.04-8.07 (dd, J=1.5, 8.5 Hz, 1H), 8.74 (d, J=0.8 Hz, 1H).

Step 6:

(R)-2-ethyl 5-methyl 3-(2-aminopropylamino) benzo[b]thiophene-2, 5-dicarboxylate (6)

To a solution of (R)-Dimethyl-3-(2-(tert-butoxycarbonylamino)propylamino) benzo[b]thiophene-2,5-dicarboxylate (1.5 g, 3.5 mmol) in dichloromethane (15.0 mL), trifluoroacetic acid (3.0 mL) was added at 0° C. and stirred at room temperature for 2 h. The reaction mixture was co-distilled with dichloromethane 4-5 times under reduced pressure and triturated with diethyl ether to yield 6 (1.3 g, 95%) as an off-white solid. 1H NMR (400 MHz, CDCl$_3$+ DMSO-d$_6$) δ 1.45 (d, J=6.6 Hz, 3H), 3.5 (brs, 2H), 3.80 (s, 3H), 3.87 (m, 6H), 7.68 (d, J=8.5 Hz, 1H), 7.97-7.99 (dd, J=1.3, 8.5 Hz, 1H), 8.57 (s, 1H), 8.60 (s, 1H). d$_6$ Step 7:

(R)-3-methyl-5-oxo-2,3,4,5-tetrahydro-1H-benzo[4,5]thieno[3,2-e][1,4]diazepine 9-carboxylic acid (7)

To a solution of R-2-ethyl-5-methyl-3-(2-aminopropylamino)benzo[b]thiophene-2, 5-dicarboxylate (300 mg, 1.0 mmol) in methanol (10.0 mL), sodium methoxide (176.0 mg, 3.0 mmol) was added and refluxed for 12 h. To the resulting mixture, lithium hydroxide (78.0 mg, 2.0 mmol) and water (2.0 mL) were added and further refluxed for another 4 h. After completion of the reaction, the reaction mixture was concentrated under reduced pressure. The residue obtained was acidified with 2N HCl (5 mL). The solid solution was filtered to yield 7 (120 mg, 47%) as a white solid. $^1$H NMR (400 MHz, DMSO-d$_6$) δ 1.13 (d, J=6.7 Hz, 3H), 3.34 (t, J=3.6 Hz, 2H), 3.56 (m, 1H), 7.84 (m, 3H), 7.91-7.94 (dd, J=1.4, 8.4 Hz, 1H), 8.64 (d, J=0.8 Hz, 1H), 12.9 (s, 1H).

Step 8:

To a stirred solution of carboxylic acid 7 (120 mg), amine INT-10 (1.1 equiv), and DIPEA (3 equiv) in DMF (1 mL) was added HATU (1.1 equiv). After 15 min, the reaction was diluted with water (0.5 mL) and purified directly by PREP-HPLC to give the TFA salt of III-12 as an off-white solid, 48.0 mg, 39%: $^1$H NMR (400 MHz, DMSO-d$_6$) δ 1.14 (d, J=6.2 Hz, 3H), 3.38 (m, 2H), 3.58 (m, 1H), 5.72-5.75 (dd, J=2.1, 10.1 Hz, 1H), 6.23-6.25 (dd, J=2.0, 17.0 Hz, 1H), 6.43-6.50 (dd, J=10.1, 16.9 Hz, 1H), 7.28 (t, J=8.0 Hz, 1H), 7.43-7.45 (dd, J=1.7, 9.1 Hz, 2H), 7.74 (t, J=4.0 Hz, 1H), 7.83 (d, J=4.4 Hz, 1H), 7.90-7.96 (m, 2H), 8.19 (t, J=1.8 Hz, 1H), 8.66 (d, J=0.9 Hz, 1H), 10.1 (s, 1H), 10.3 (s, 1H). MS m/z (M+H): 421.1

Example 41

Compound III-2

(R)—N-(4-fluoro-3-((4-methyl-2-oxopent-3-en-1-yl)oxy)phenyl)-3-methyl-5-oxo-2,3,4,5-tetrahydro-1H-benzo[4,5]thieno[3,2-e][1,4]diazepine-9-carboxamide

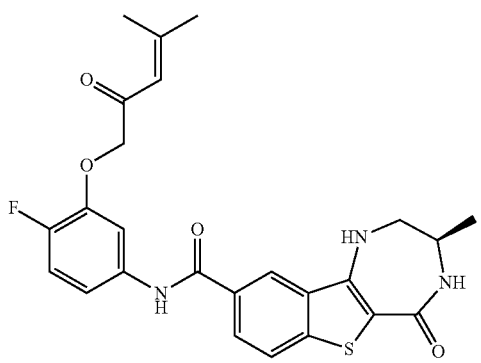 [SMILES: CC(C)=CC(=O)COc1cc(NC(=O)c2ccc3sc4c(c3c2)NC[C@@H](C)NC4=O)ccc1F]

The title compound III-2 was prepared as described in Example 40, by substituting amine INT-19 for INT-10 in step 8: Off-white solid, 11.0 mg, 9%, $^1$H NMR (400 MHz, CDCl$_3$) δ 1.14 (d, J=6.7 Hz, 3H), 1.9 (s, 3H), 2.12 (s, 3H), 3.36 (m, 2H), 3.58 (m, 1H), 4.8 (s, 2H), 6.27 (m, 1H), 7.18-7.23 (dd, J=8.8, 11.2 Hz, 1H), 7.36-7.38 (dd, J=2.4, 3.7 Hz, 1H), 7.44-7.47 (dd, J=2.3, 7.9 Hz, 1H), 7.76 (t, J=4.1 Hz, 1H), 7.84 (d, J=4.5 Hz, 1H), 7.88 (d, J=8.1 Hz, 2H), 8.4 (s, 1H), 10.2 (s, 1H). MS m/z (M+H): 482.2

Example 42

Compound III-3

(R)—N-(3-acrylamido-4-(pyrrolidin-1-yl)phenyl)-3-methyl-5-oxo-2,3,4,5-tetrahydro-1H-benzo[4,5]thieno[3,2-e][1,4]diazepine-9-carboxamide

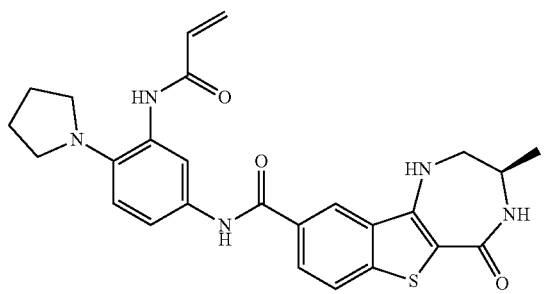 [SMILES: C=CC(=O)Nc1cc(NC(=O)c2ccc3sc4c(c3c2)NC[C@@H](C)NC4=O)ccc1N1CCCC1]

The title compound III-3 was prepared as described in Example 40, by substituting amine INT-18 for INT-10 in step 8: Pale yellow solid, 12.4 mg, 13%. $^1$H NMR (400 MHz, DMSO-d$_6$): δ 1.14 (d, J=6.7 Hz, 3H), 1.86 (brs, 4H), 3.11 (brs, 4H), 3.37 (brs, 2H), 3.58 (brs, 1H), 5.7 (d, J=9.9 Hz, 1H), 6.19-6.24 (dd, J=1.8, 17.1 Hz, 1H), 6.52-6.59 (dd, J=10.1, 16.7 Hz, 1H), 6.90 (d, J=8.8 Hz, 1H), 7.55-7.58 (dd, J=2.28, 8.8 Hz, 1H), 7.73 (brs, 1H), 7.86 (t, J=14.2 Hz, 3H), 7.95 (d, J=8.3 Hz, 1H), 8.53 (s, 1H), 9.4 (s, 1H), 10.1 (s, 1H). MS m/z (M+H): 490.6

Example 43

Compound III-4

(R)—N-(3-acrylamido-4-(4-methylpiperazin-1-yl)phenyl)-3-methyl-5-oxo-2,3,4,5-tetrahydro-1H-benzo[4,5]thieno[3,2-e][1,4]diazepine-9-carboxamide

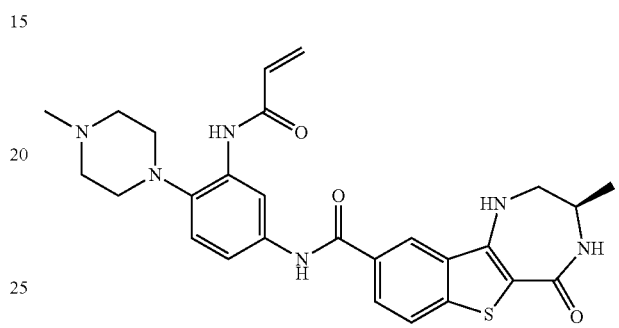

The title compound III-4 was prepared as described in Example 40, by substituting amine INT-17 for INT-10 in step 8: Brown solid, 16.0 mg, 17%. $^1$H NMR (400 MHz, DMSO-d$_6$) δ 1.15 (d, J=6.7 Hz, 3H), 2.24 (s, 3H), 2.49 (m, 2H), 2.8 (t, J=4.7 Hz, 4H), 3.37 (brs, 4H), 3.58 (m, 1H), 5.74-5.77 (dd, J=1.69, 10.3 Hz, 1H), 6.57-6.64 (dd, J=10.2, 17.0 Hz, 1H), 7.16 (d, J=8.7 Hz, 1H), 7.60-7.63 (dd, J=2.4, 8.7 Hz, 1H), 7.83 (m, 2H), 7.88 (d, J=8.4 Hz, 1H), 7.95-7.98 (dd, J=1.4, 8.4 Hz, 1H), 8.37 (s, 1H), 8.59 (s, 1H), 9.0 (s, 1H), 10.3 (s, 1H). MS m/z (M+H): 519.6

Example 44

Compound III-5

(R)—N-(3-acrylamido-4-(piperazin-1-yl)phenyl)-3-methyl-5-oxo-2,3,4,5-tetrahydro-1H-benzo[4,5]thieno[3,2-e][1,4]diazepine-9-carboxamide

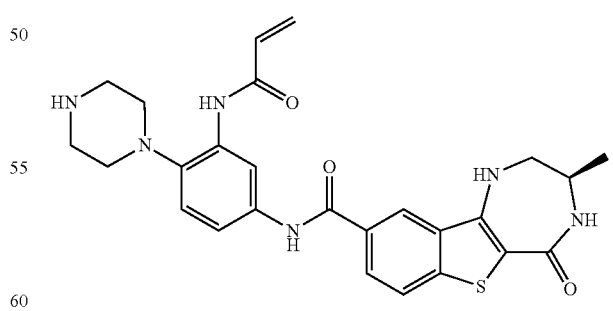

The title compound III-5 was prepared as described in Example 40, by substituting Boc-piperazine-containing amine INT-16 for INT-10 in step 8. The resulting amide product was dissolved in DCM (2 mL) and treated with TFA (1 mL). After 4 h, the reaction was complete and the solvent was removed on the rotary evaporator. The desired product III-5 was obtained as the TFA salt after purification by PREP-HPLC: Yellow solid, 40.0 mg, 60% H NMR (400 MHz, DMSO-d$_6$): δ 1.15 (d, J=6.7 Hz, 3H), 2.98 (t, J=5.0 Hz, 4H), 3.31 (brs, 4H), 3.37 (brs, 2H), 3.58 (t, J=3.1 Hz, 1H), 5.77-5.80 (dd, J=1.8, 10.2 Hz, 1H), 6.25-6.30 (dd, J=1.8, 17.0 Hz, 1H), 6.68-6.76 (dd, J=10.2, 17.0 Hz, 1H), 7.19 (d, J=8.7 Hz, 1H), 7.64-7.67 (dd, J=2.4, 8.7 Hz, 1H), 7.73 (s, 1H), 7.84 (d, J=4.4 Hz, 1H), 7.89 (d, J=8.4 Hz, 1H), 7.95-7.98 (dd, J=1.4, 8.4 Hz, 1H), 8.48 (d, J=2.0 Hz, 1H), 8.5 (d, J=0.97 Hz, 1H), 8.7 (s, 2H), 10.3 (s, 1H). MS m/z (M+H): 505.5

Example 45

Compound III-6

(R)—N-(3-acrylamido-4-fluorophenyl)-3-methyl-5-oxo-2,3,4,5-tetrahydro-1H-benzo[4,5]thieno[3,2-e][1,4]diazepine-9-carboxamide

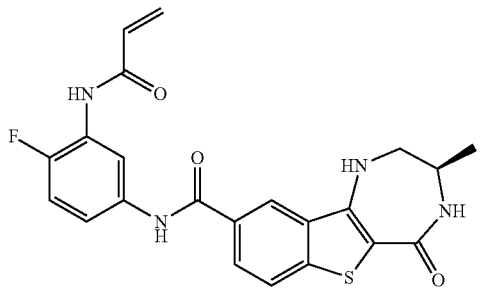 [SMILES: C=CC(=O)Nc1cc(NC(=O)c2ccc3sc4c(c3c2)NC[C@@H](C)NC4=O)ccc1F]

The title compound III-6 was prepared as described in Example 40, by substituting amine INT-15 for INT-10 in step 8: White solid, 10.0 mg, 13% $^1$H NMR (400 MHz, DMSO-d$_6$): δ 1.15 (d, J=6.2 Hz, 3H), 3.37 (brs, 3H), 3.6 (brs, 1H), 5.76-5.79 (dd, J=1.9, 10.2 Hz, 1H), 6.25-6.30 (dd, J=1.9, 17.0 Hz, 1H), 6.58-6.65 (dd, J=10.2, 17.0 Hz, 1H), 7.24 (m, 1H), 7.61 (m, 1H), 7.7 (brs, 1H), 7.84 (t, J=4.4 Hz, 1H), 7.9 (d, J=8.4 Hz, 1H), 7.94-7.97 (dd, J=1.4, 8.4 Hz, 1H), 8.41 (d, J=4.7 Hz, 1H), 8.5 (s, 1H), 9.94 (s, 1H), 10.37 (s, 1H). MS m/z (M+H): 439.3

Example 46

Compound III-7

(R)—N-(3-acrylamido-4-(2-methoxyethoxy)phenyl)-3-methyl-5-oxo-2,3,4,5-tetrahydro-1H-benzo[4,5]thieno[3,2-e][1,4]diazepine-9-carboxamide

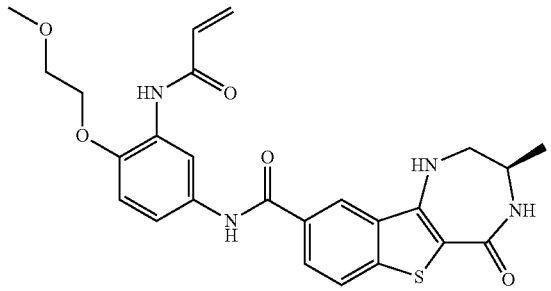

The title compound III-7 was prepared as described in Example 40, by substituting amine INT-14 for INT-10 in step 8: Yellow solid, 21.6 mg, %. $^1$H NMR (400 MHz, DMSO-d$_6$); δ 1.15 (d, J=6.7 Hz, 3H), 3.29 (s, 3H), 3.37 (m, 2H), 3.60 (m, 1H), 3.69 (t, J=4.5 Hz, 2H), 4.15 (t, J=4.8 Hz, 2H), 5.73-5.76 (dd, J=1.89, 10.2 Hz, 1H), 6.21-6.26 (dd, J=1.9, 17.0 Hz, 1H), 6.59-6.66 (dd, J=10.2, 17.0 Hz, 1H), 7.08 (d, J=8.9 Hz, 1H), 7.56-7.59 (dd, J=2.5, 8.8 Hz, 1H), 7.73 (m, 1H), 7.82 (d, J=4.4 Hz, 1H), 7.88 (d, J=8.4 Hz, 1H), 7.94-7.97 (dd, J=1.3, 8.4 Hz, 1H) 8.4 (s, 1H), 8.54 (s, 1H), 9.18 (s, 1H), 10.2 (s, 1H). MS m/z (M+H): 495.2

Example 47

Compound III-9

(R,E)-N-(4-(4-(dimethylamino)but-2-enoyl)-3,4-dihydro-2H-benzo[b][1,4]oxazin-6-yl)-3-methyl-5-oxo-2,3,4,5-tetrahydro-1H-benzo[4,5]thieno[3,2-e][1,4]diazepine-9-carboxamide

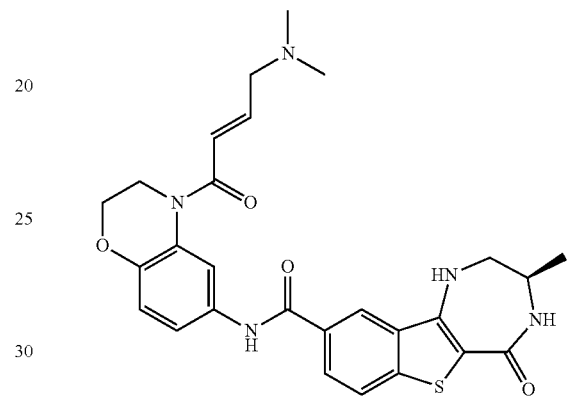

The title compound III-9 was prepared as described in Example 40, by substituting amine INT-12 for INT-10 in step 8: Brown solid, 5.0 mg, 9%. $^1$H NMR (400 MHz, DMSO-d$_6$); δ 1.14 (d, J=6.7 Hz, 3H), 1.89 (s, 2H), 2.20 (s, 6H), 3.16 (m, 2H), 3.58 (m, 1H), 3.92 (t, J=4.1 Hz, 2H), 4.26 (t, J=4.5 Hz, 2H), 6.75 (d, J=5.7 Hz, 1H), 6.77-6.80 (m, 1H), 6.90 (d, J=8.8 Hz, 1H), 7.38-7.41 (dd, J=2.1, 9.0 Hz, 1H), 7.73 (m, 1H), 7.83 (d, J=4.2 Hz, 1H), 7.88-7.93 (m, 2H), 7.97 (brs, 1H), 8.52 (s, 1H), 10.2 (s, 1H). MS m/z (M+H): 520.2

Example 48

Compound III-10

(R)—N-(2-acrylamidophenyl)-3-methyl-5-oxo-2,3,4,5-tetrahydro-1H-benzo[4,5]thieno[3,2-e][1,4]diazepine-9-carboxamide

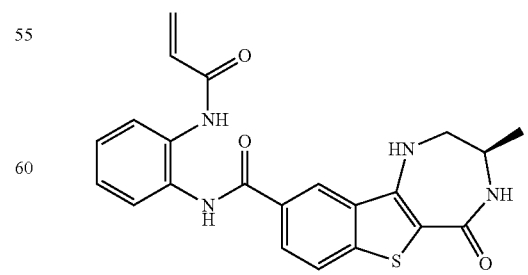

The title compound III-10 was prepared as described in Example 40, by substituting amine INT-13 for INT-10 in step 8: Off-white solid, 44.0 mg, 21%. 1H NMR (400 MHz, DMSO-$d_6$) δ 1.14 (d, J=6.7 Hz, 3H), 3.36 (brs, 2H), 3.56-3.59 (m, 1H), 5.54-5.57 (dd, J=1.9, 10.2 Hz, 1H), 6.24-6.28 (dd, J=1.9, 17.0 Hz, 1H), 6.45-6.52 (dd, J=10.2, 17.0 Hz, 1H), 7.22-7.26 (m, 2H), 7.62-7.67 (m, 2H), 7.77 (t, J=4.0 Hz, 1H), 7.84 (d, J=6.4 Hz, 1H), 7.90-7.96 (m, 2H), 8.6 (s, 1H), 9.81 (s, 1H), 9.92 (s, 1H). MS m/z (M+H): 421.3

Example 49

Compound III-11

(R)—N-(4-acryloyl-3,4-dihydro-2H-benzo[b][1,4]oxazin-6-yl)-3-methyl-5-oxo-2,3,4,5-tetrahydro-1H-benzo[4,5]thieno[3,2-e][1,4]diazepine-9-carboxamide

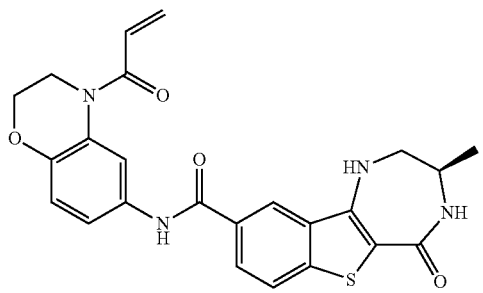 [SMILES: C=CC(=O)N1CCOc2ccc(NC(=O)c3ccc4sc5c(c4c3)NC[C@@H](C)NC5=O)cc21]

The title compound III-11 was prepared as described in Example 40, by substituting amine INT-11 for INT-10 in step 8: Off-white solid, 140.0 mg, 56%. $^1$H NMR (400 MHz, DMSO-$d_6$) δ 1.14 (d, J=6.7 Hz, 3H), 3.36 (m, 2H), 3.57 (m, 1H), 3.93 (t, J=4.3 Hz, 2H), 4.27 (t, J=4.8 Hz, 2H), 5.82-5.85 (dd, J=1.9, 10.3 Hz, 1H), 6.28-6.32 (dd, J=1.9, 16.7 Hz, 1H), 6.82-6.89 (dd, J=10.3, 16.7 Hz, 1H), 6.91 (d, J=8.8 Hz, 1H), 7.45-7.48 (dd, J=2.3, 8.8 Hz, 1H), 7.74 (m, 1H), 7.83 (d, J=4.7 Hz, 1H), 7.88-7.96 (m, 3H), 8.54 (s, 1H), 10.24 (s, 1H). MS m/z (M+H): 463.2

Example 50

Compound III-35

(R)—N-(3-acrylamido-4-(2-(dimethylamino)ethoxy)phenyl)-3-methyl-5-oxo-2,3,4,5-tetrahydro-1H-benzo[4,5]thieno[3,2-e][1,4]diazepine-9-carboxamide

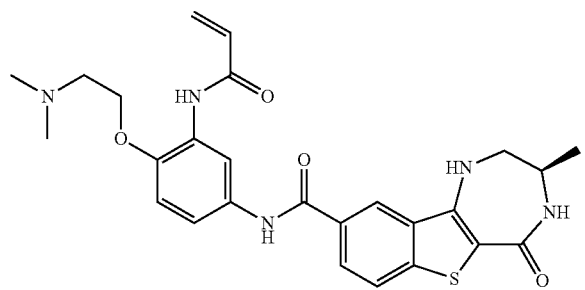

The title compound was prepared according to the schemes, steps, and intermediates

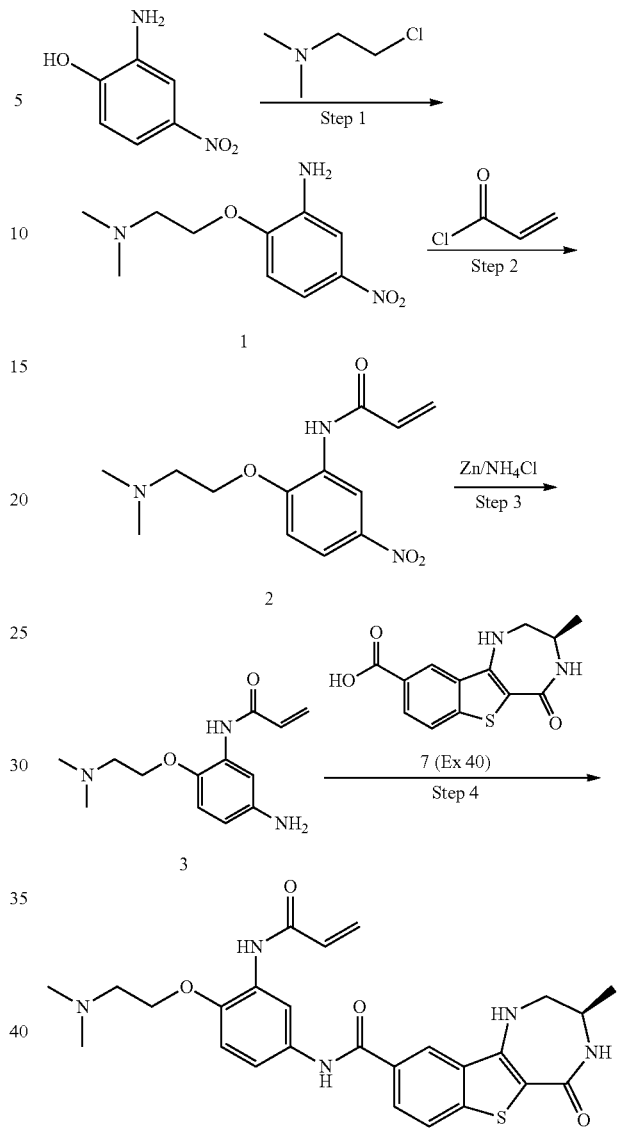

Step 1:

2-(2-(dimethylamino)ethoxy)-5-nitroaniline (1)

To a solution of 2-amino-4-nitrophenol (1.0 g, 6.4 mmol) in tetrahydrofuran (30 mL), 2-(dimethylamino)ethylchloride.HCl (1.1 g, 7.79 mmol), cesium carbonate (5.2 g, 16.2 mmol) and potassium iodide (25 mg, 0.13 mmol) were added and the reaction mixture was stirred at 80° C. for 3 h. After completion of the reaction, the reaction mixture was quenched with water and extracted with 10% methanol/dichloromethane. The organic layer was dried over anhydrous sodium sulfate and concentrated under reduced pressure. The obtained residue was purified by silica gel column chromatography to afford 1 (600 mg, 41%) as a brown gummy solid. MS m/z (M+H): 226.29

Step 2:

N-(2-(2-(dimethylamino)ethoxy)-5-nitrophenyl)acrylamide (2)

To a solution of 2-(2-(dimethylamino)ethoxy)-5-nitroaniline (560 mg, 2.5 mmol) in dichloromethane/tetrahydrofuran (1:1, 5 mL), diisopropylethylamine (642 mg, 5.0 mmol) and acryloyl chloride (0.225 g, 2.5 mmol) were added at −78° C., and the reaction mixture was stirred at room temperature for 3 h. After completion of the reaction, the reaction mixture was concentrated under reduced pressure. The residue obtained was diluted with water and extracted with 20% methanol/chloroform. The organic layer was washed with brine, dried over anhydrous sodium sulfate and concentrated under reduced pressure to afford 2 (600 mg, 86%) as an orange liquid. MS m/z (M+H): 280.35
Step 3:

N-(5-amino-2-(2-(dimethylamino)ethoxy)phenyl) acrylamide (3)

To a solution of N-(2-(2-(dimethylamino)ethoxy)-5-nitrophenyl)acrylamide (600 mg, 2.1 mmol) in 1,4-dioxane/water (1:1, 5.0 mL), Zinc (1.1 g, 16.9 mmol) and ammonium chloride (0.9 g, 16.9 mmol) were added at room temperature. The resulting mixture was stirred at room temperature for 4 h. After completion of the reaction, the reaction mixture was filtered through celite and washed with 30% methanol/chloroform. The organic layer was washed with brine, dried over anhydrous sodium sulfate and concentrated under reduced pressure to afford 3 (230 mg, 44%) as a brown liquid. MS m/z (M+H): 250.2
Step 4:

To a solution of compound 7 from Example 40 (25 mg, 0.09 mmol) in N,N-dimethylformamide (2.0 mL), diisopropylethylamine (35 mg, 0.27 mmol) and 1-[bis(dimethylamino)methylene]-1H-1,2,3-triazolo[4,5-b]pyridinium 3-oxid hexafluorophosphate (HATU) (69 mg, 0.18 mmol) were added. The reaction mixture was stirred at 0° C. for 15 min followed by the addition of N-(5-amino-2-(2-(dimethylamino)ethoxy)phenyl)acrylamide (34 mg, 0.13 mmol). The resulting mixture was stirred at room temperature for 2 h. The residue was purified by preparative thin layer chromatography to afford the title compound (28 mg, 41%) as a brown solid. $^1$H NMR (400 MHz, DMSO-d$_6$): δ 1.15 (d, J=6.7 Hz, 3H), 2.90-2.91 (d, J=4.7 Hz, 6H), 3.34-3.56 (m, 5H), 4.34 (t, J=4.6 Hz, 2H), 5.79 (d, J=1.8, 10.2 Hz, 1H), 6.31 (dd, J=1.69 Hz, 16.9 Hz, 1H), 6.55-6.64 (dd, J=10.1, 16.9 Hz, 1H), 7.12 (d, J=8.9 Hz, 1H), 7.62 (dd, J=2.5, 8.9, 1H), 7.75 (brs, 1H), 7.85-7.95 (m, 3H), 8.41 (brs, 1H), 8.55 (brs, 1H), 9.27 (s, 1H), 10.27 (s, 1H). MS m/z (M+H): 508.2.

Example 51

Compound III-8

(R)—N-(2-(2-methoxyethoxy)-5-(10-methyl-8-oxo-9,10,11,12-tetrahydro-8H-[1,4]diazepino[5',6':4,5]thieno[3,2-f]quinolin-3-yl)phenyl)acrylamide

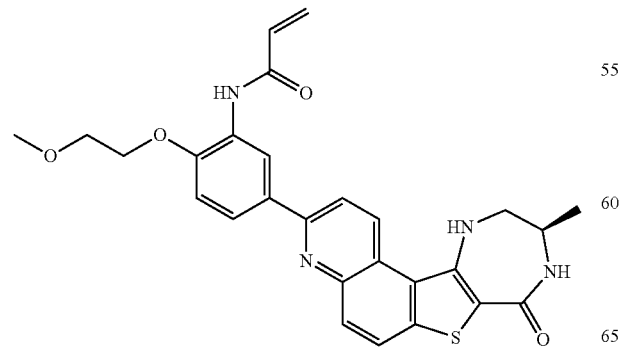

The title compound was prepared according to the schemes, steps, and intermediates

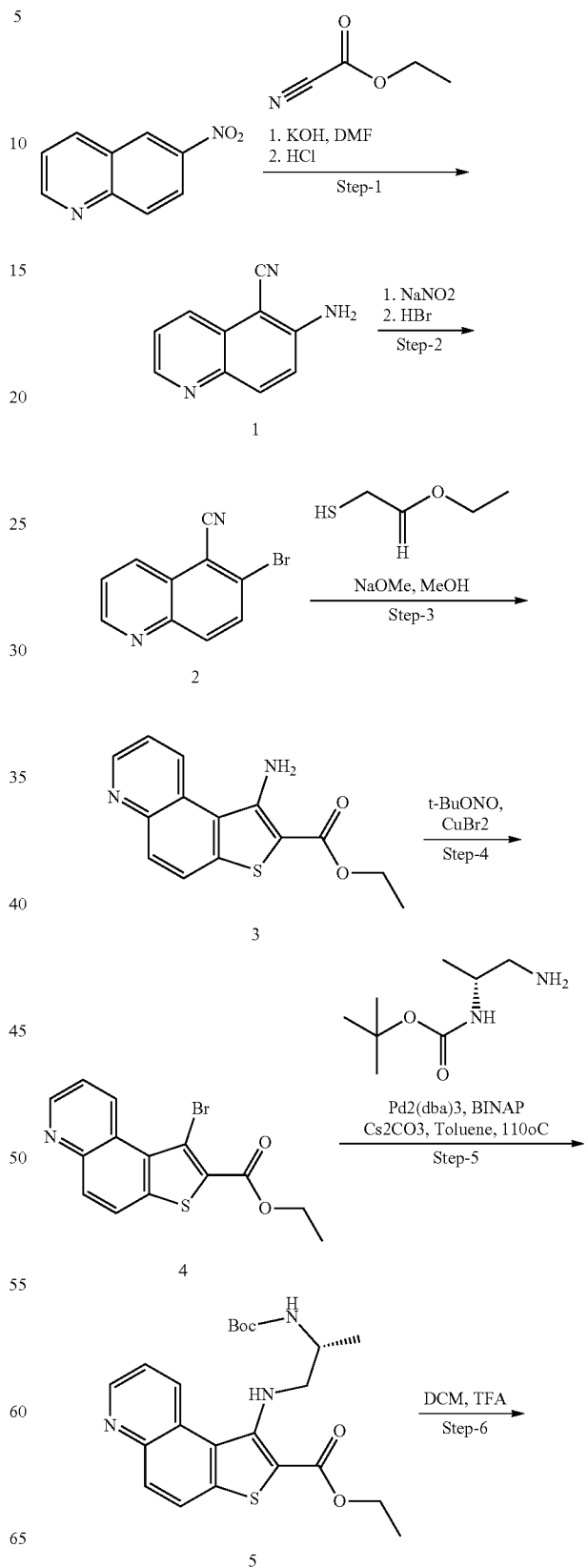

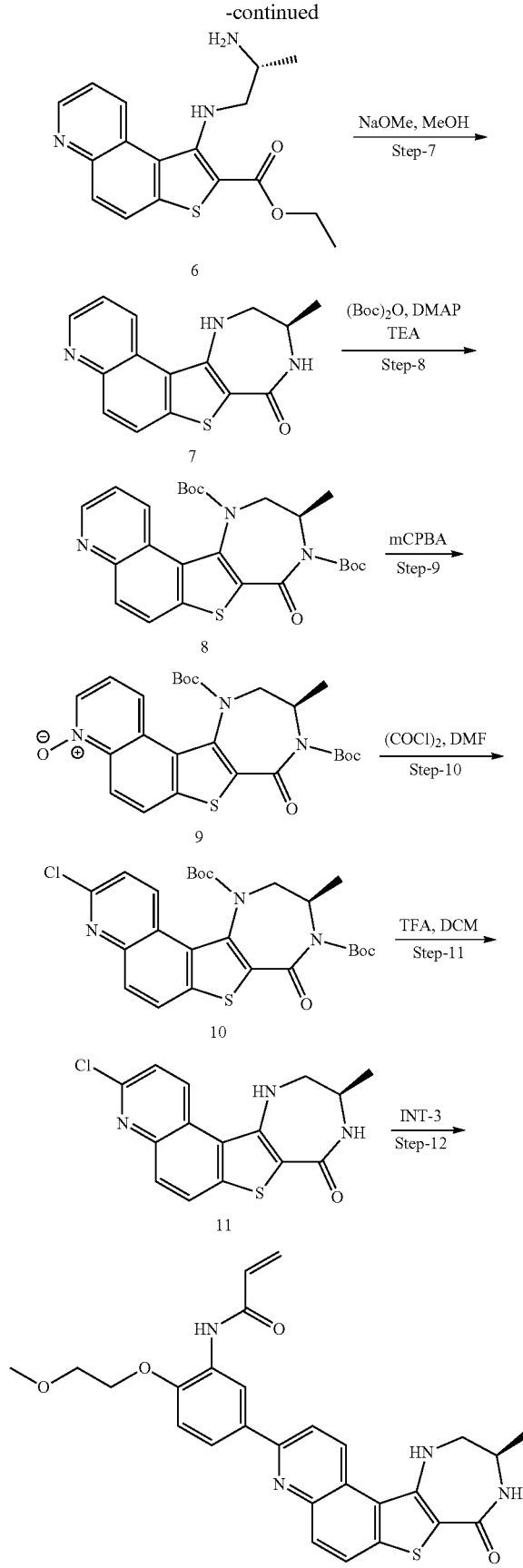

Step 1:

6-aminoquinoline-5-carbonitrile (1)

To a solution of 6-nitroquinoline (20.0 g, 115.0 mmol) in dimethylformamide (200.0 mL), potassium hydroxide (19.3 g, 345.0 mmol) and ethyl cyanoacetate (39.0 g, 345.0 mmol) were added at room temperature. The reaction mixture was stirred for 48 hours. Dimethylformamide was removed under reduced pressure, and the residue was treated with 10% HCl (50 mL) and refluxed at 100° C. for 3 hours. The reaction mixture was neutralized with 1N NaOH solution and extracted with ethyl acetate (300 mL). The organic phase was dried over anhydrous sodium sulfate and concentrated under reduced pressure. The residue was purified by silica gel column chromatography to obtain 1 (8.0 g, 41%) as light brown solid. $^1$H NMR (400 MHz, DMSO-$d_6$) δ 6.89 (s, 2H), 7.25 (d, J=9.3 Hz, 1H), 7.50 (q, J=4.2 Hz, 1H), 7.89 (d, J=9.3 Hz, 1H), 8.01-8.04 (dd, J=0.6, 8.4 Hz, 1H), 8.58-8.60 (dd, J=1.5, 4.2 Hz, 1H). MS m/z (M+H): 170.22

Step 2:

6-bromoquinoline-5-carbonitrile (2)

To a solution of 6-aminoquinoline-5-carbonitrile (8.0 g, 47.0 mmol) in 1, 4-dioxane (8.0 mL), 48% HBr (95.0 mL) was added followed by the dropwise addition of solution of sodium nitrite in water (6.5 g, 94.6 mmol) at 0° C. The reaction mixture was stirred for 1.5 h at 0° C. The reaction mixture was poured into a solution mixture of cupper bromide (20.0 g, 142.0 mmol) in aqueous HBr at 0° C. and stirred for 3 h at 50° C. The reaction mixture was partitioned between ethyl acetate (200 mL) and water (100 mL). The organic phase was dried over anhydrous sodium sulfate and concentrated under reduced pressure. The residue was purified by silica gel column chromatography to obtain 2 (6.0 g, 55%) as a light brown solid. $^1$H NMR (400 MHz, DMSO-$d_6$) δ 7.83 (q, J=4.2 Hz, 1H), 8.16 (d, J=9.0 Hz, 1H), 8.28 (d, J=9.0 Hz, 1H), 8.47-8.49 (dd, J=0.6, 8.5 Hz, 1H), 9.0-9.1 (dd, J=1.4, 4.1 Hz, 1H). MS m/z (M+H): 233.2

Step 3:

Ethyl 1-aminothieno [3, 2-f] quinoline-2-carboxylate (3)

To a solution of 6-bromoquinoline-5-carbonitrile (6.0 g, 25.8 mmol) in methanol (100.0 mL), sodium methoxide (2.8 g, 51.7 mmol) and ethyl thioglycolate (4.6 g, 38.7 mmol) were added at room temperature and stirred for 5 h. The resulting mixture was heated to reflux for 5 h. The reaction mixture was partitioned between ethyl acetate (200 mL) and water (100 mL). The organic phase was dried over anhydrous sodium sulfate and concentrated under reduce pressure to obtain 3 (4.5 g, 63.7%) as a yellow solid. 1H NMR (400 MHz, DMSO-$d_6$) δ 1.32 (t, J=7.0 Hz, 3H), 4.33 (q, J=7.0 Hz, 2H), 7.1 (s, 2H), 768 (q, J=4.2 Hz, 1H), 8.0 (d, J=9.0 Hz, 1H), 8.16 (d, J=8.9 Hz, 1H), 8.92-8.94 (dd, J=1.3, 4.6 Hz, 1H), 9.1 (d, J=8.3 Hz, 1H).

Step 4:

Ethyl 1-bromothieno [3, 2-f] quinoline-2-carboxylate (4)

To a solid suspension of copper bromide (4.4 g, 19.9 mmol) in acetonitrile (100 mL), t-butyl nitrite (2.6 g, 25.0 mmol) was added at 0° C. followed by the solution of ethyl-1-aminothieno[3,2-f]quinoline-2-carboxylate (4.5 g, 16.6 mmol) in acetonitrile (10.0 mL) at 0° C. The resulting mixture was stirred at room temperature for 3 h. The reaction mixture turned to green colour from dark blue. Solvent was removed under reduced pressure, and the residue was diluted with water (50 mL). The solid formed was filtered and dried to afford 4 (5.0 g, 90%) as a light brown solid. $^1$H NMR (400 MHz, DMSO-d$_6$) δ 1.36 (t, J=7.0 Hz, 3H), 4.40 (q, J=7.0 Hz, 2H), 7.75-7.78 (dd, J=3.8, 8.4 Hz, 1H), 8.14 (d, J=8.0 Hz, 1H), 8.4 (d, J=8.8 Hz, 1H), 9.0 (s, 1H), 10.1 (d, J=8.6 Hz, 1H).

Step 5:

(R)-ethyl 1-(2-(tert-butoxycarbonylamino)propylamino)thieno[3,2-f]quinoline-2-carboxylate (5)

To a solution of ethyl-1-bromothieno [3, 2-f] quinoline-2-carboxylate (2.0 g, 6.0 mmol) and (R)-tert-butyl 1-aminopropan-2-ylcarbamate (1.2 g, 7.2 mmol) in toluene (60.0 mL), cesium carbonate (3.9 g, 12.0 mmol) was added and degassed for 10 min. BINAP (374.0 mg, 0.6 mmol) and Pd$_2$(dba)$_3$ (550 mg, 0.6 mmol) were added and again degassed for another 5 min. The resulting mixture was heated at 110° C. for 16 h. The reaction mixture was filtered through celite and the filtrate was partitioned between water (100 mL) and ethyl acetate (150 mL). The organic phase was dried over anhydrous sodium sulfate and concentrated under reduce pressure. The residue was purified by silica gel column chromatography to afford 5 (1.0 g, 39%) as a yellow solid. 1H NMR (400 MHz, DMSO-d$_6$) δ 1.0 (t, J=6.5 Hz, 3H), 1.33 (t, J=4.8 Hz, 3H), 1.38 (s, 9H), 3.1 (t, J=6.4 Hz, 2H), 3.63 (brs, 1H), 4.34 (q, J=7.0 Hz, 2H), 6.53 (t, J=6.3 Hz, 1H), 6.76 (d, J=8.1 Hz, 1H), 7.70 (q, J=4.2 Hz, 1H), 8.05 (d, J=9.0 Hz, 1H), 8.21 (d, J=8.9 Hz, 1H), 8.92-8.94 (dd, J=1.5, 4.2 Hz, 1H), 9.03 (d, J=8.3 Hz, 1H).

Step 6:

(R)-ethyl 1-(2-aminopropylamino)thieno[3,2-f]quinoline-2-carboxylate (6)

To a solution of (R)-ethyl-1-(2-(tert-butoxycarbonylamino)propylamino)thieno[3,2-f]quinoline-2-carboxylate (700 mg, 1.6 mmol) in dichloromethane (10.0 mL), trifluoroacetic acid (3.0 mL) was added at 0° C. and stirred at room temperature for 2 h. The reaction mixture was concentrated and co-distilled with dichloromethane thrice under reduced pressure. The residue was washed with diethyl ether to yield 6 (600 mg, 92%) as a yellow solid. 1H NMR (400 MHz, DMSO-d$_6$) δ 1.34 (d, J=7.0 Hz, 3H), 1.36 (t, J=7.0 Hz, 3H), 3.15 (t, J=5.1 Hz, 1H), 3.36 (m, 2H), 4.36 (q, J=7.0 Hz, 2H), 6.41 (brs, 1H), 7.78 (q, J=4.3 Hz, 1H), 7.87 (s, 2H), 8.0 (d, J=9.0 Hz, 1H), 8.29 (d, J=9.0 Hz, 1H), 8.99-9.0 (dd, J=1.4, 4.3 Hz, 1H), 9.11 (d, J=7.9 Hz, 1H).

Step 7:

(R)-10-methyl-9,10,11,12-tetrahydro-8H-[1,4]diazepino[5',6':4,5]thieno[3,2-f]quinolin-8-one (7)

To a solution of (R)-ethyl 1-(2-aminopropylamino)thieno[3,2-f]quinoline-2-carboxylate (400 mg, 1.2 mmol) in methanol (10.0 mL), sodium methoxide (230 mg, 4.3 mmol) was added and heated at 75° C. for 16 h. The reaction mixture was concentrated, and the residue obtained was purified by silica gel column chromatography to yield 7 (180 mg, 52%) as a pale orange solid. MS m/z (M+H): 284.3

Step 8:

(R)-di-tert-butyl 10-methyl-8-oxo-10,11-dihydro-8H-[1,4]diazepino[5',6':4,5]thieno[3,2-f]quinoline-9,12-dicarboxylate (8)

To a solution of 7 (750.0 mg, 2.6 mmol) in dichloromethane (10.0 mL), triethylamine (669.0 mg, 6.6 mmol) and dimethylaminopyridine (76.0 mg, 0.6 mmol) were added and stirred for 5 min followed by the addition of Boc-anhydride (2.3 g, 10.6 mmol) at room temperature. The resulting mixture was stirred for 4 h at room temperature. The reaction mixture was partitioned between water (50 mL) and dichloromethane (100 mL). The organic layer was dried over anhydrous sodium sulfate and concentrated under reduced pressure to afford 8 (700 mg, 56%) as a brown solid. MS m/z (M+H): 484.2

Step 9:

(R)-9,12-bis(tert-butoxycarbonyl)-10-methyl-8-oxo-9,10,11,12-tetrahydro-8H-[1,4]diazepino[5',6':4,5]thieno[3,2-f]quinoline 4-oxide (9)

To a solution of 8 (50.0 mg, 0.1 mmol) in dichloromethane (5.0 mL), mCPBA (17.0 mg, 0.1 mmol) was added at 0° C. The reaction mixture was stirred for 1.5 h at room temperature. The reaction mixture was diluted with water (10 mL) and extracted with ethyl acetate (30 mL). The organic phase was separated, dried over anhydrous sodium sulfate and concentrated under reduced pressure to afford 9 (50 mg, 98%) as a white solid. MS m/z (M+H): 500.2

Step 10:

(R)-di-tert-butyl 3-chloro-10-methyl-8-oxo-10,11-dihydro-8H-[1,4]diazepino [5',6':4,5]thieno[3,2-f]quinoline-9,12-dicarboxylate (10)

To a solution of 9 (50.0 mg, 0.1 mmol) in dry dimethylformamide (2.5 mL), oxalylchloride (16.5 mg, 0.1 mmol) was added dropwise at 0° C. The reaction mixture was stirred at room temperature for 2 h. The reaction mixture was quenched with methanol and excess methanol was concentrated under reduced pressure. The residue obtained was diluted with ice-cold water. The solid observed was filtered and dried to afford 10 (50 mg, 98%) as a white solid. MS m/z (M+H): 517.1

Step 11:

(R)-3-chloro-10-methyl-9,10,11,12-tetrahydro-8H-[1,4]diazepino [5',6':4,5]thieno[3,2-f]quinolin-8-one (11)

To a solution of 10 (50 mg, 0.1 mmol) in dichloromethane (2.0 mL), trifluoroacetic acid (2.0 mL) was added at 0° C. and stirred at room temperature for 2 h. The reaction mixture was concentrated and co-distilled with dichloromethane thrice under reduced pressure. The residue obtained was triturated with diethyl ether to yield 11 (25.0 mg, 83%) as a white solid. $^1$H NMR (400 MHz, DMSO-d$_6$) δ 1.17 (d, J=6.7 Hz, 3H), 3.44 (s, 2H), 3.58 (d, J=3.3 Hz, 1H), 7.08 (s, 1H), 7.71 (d, J=8.9 Hz, 1H), 7.88 (d, J=8.9 Hz, 1H), 8.11 (d, J=3.9 Hz, 1H), 8.19 (d, J=8.9 Hz, 1H), 9.20 (d, J=8.9 Hz, 1H). MS m/z (M+H): 318.2

Step 12:

To a solution of Compound 11 (0.6 mmol) and arylboronic ester INT-3 (0.3 mmol) in 1, 4-dioxane/water, sodium carbonate (0.5 mmol) was added followed by degassing for 10 min. Tetrakis(triphenylphosphine)palladium(0) (36.0 mg, 0.3 mmol) was added and the resulting mixture was again degassed for 10 min. The reaction mixture was heated to 110° C. for 7 hours. The reaction mixture was cooled to room temperature and was partitioned between ethyl acetate (100 mL) and water (50 mL). The organic layer was dried over anhydrous sodium sulfate and concentrated under reduced pressure. The residue was purified by prep-HPLC to yield compound III-8: Yellow solid, 25.0 mg, $^1$H NMR (400 MHz, DMSO-d$_6$); δ 1.19 (d, J=6.7 Hz, 3H), 3.35 (s, 3H), 3.46 (m, 2H), 3.60 (m, 1H), 3.75 (t, J=4.5 Hz, 2H), 4.27 (t, J=4.8 Hz, 2H), 5.76-5.79 (dd, J=1.8, 10.3 Hz, 1H), 6.26-6.30 (dd, J=1.9, 17.0 Hz, 1H), 6.65-6.72 (dd, J=10.2, 17.0 Hz, 1H), 7.12 (t, J=5.3 Hz, 1H), 7.26 (d, J=8.7 Hz, 1H), 7.97 (d, J=8.9 Hz, 1H), 8.01-8.05 (m, 2H), 8.09-8.12 (dd, J=3.6, 8.9 Hz, 2H), 8.9 (s, 1H), 9.19 (d, J=8.9 Hz, 1H), 9.35 (s, 1H). MS m/z (M+H): 503.4

Example 52

Compound III-1

(R)—N-(2-methyl-5-(10-methyl-8-oxo-9,10,11,12-tetrahydro-8H-[1,4]diazepino[5',6':4,5]thieno[3,2-f]quinolin-3-yl)pyridin-3-yl)acrylamide

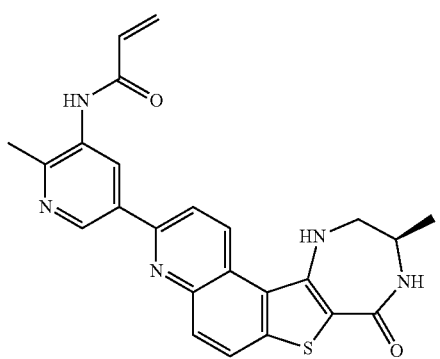

The title compound III-1 was prepared as described in Example 51, by substituting boronic ester INT-20 for INT-3 in step 12: Yellow solid, 9.0 mg, 9%. $^1$H NMR (400 MHz, DMSO-d$_6$) δ 1.19 (d, J=6.7 Hz, 3H), 2.49 (s, 3H), 3.47 (m, 2H), 3.61 (m, 1H), 5.81-5.84 (dd, J=2.2, 10.2 Hz, 1H), 6.29-6.34 (dd, J=2.1, 17.0 Hz, 1H), 6.57-6.64 (dd, J=10.2, 17.0 Hz, 1H), 7.15 (t, J=4.9 Hz, 1H), 8.20 (d, J=8.9 Hz, 1H), 8.06 (d, J=4.2 Hz, 1H), 8.14 (d, J=8.9 Hz, 1H), 8.27 (d, J=8.9 Hz, 1H), 8.78 (d, J=1.4 Hz, 1H), 9.17 (d, J=1.8 Hz, 1H), 9.25 (d, J=8.9 Hz, 1H), 9.85 (s, 1H). MS m/z (M+H): 444.5

Example 53

Compound III-13

(R)—N-(2-fluoro-5-(10-methyl-8-oxo-9,10,11,12-tetrahydro-8H-[1,4]diazepino[5',6':4,5]thieno[3,2-f]quinolin-3-yl)phenyl)acrylamide

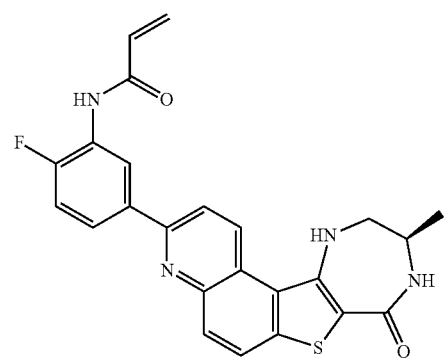 [SMILES: C=CC(=O)Nc1cc(-c2ccc3c(ccc4sc5c(c43)NC[C@@H](C)NC5=O)n2)ccc1F]

The title compound III-13 was prepared as described in Example 51, by substituting boronic ester INT-6 for INT-3 in step 12: Yellow solid, 40.0 mg, 21%. $^1$H NMR (400 MHz, DMSO-d$_6$) δ 1.25 (d, J=6.7 Hz, 3H), 3.47 (t, J=4.1 Hz, 2H), 3.61 (s, 1H), 5.80-5.83 (dd, J=1.9, 10.2 Hz, 1H), 6.30-6.34 (dd, J=1.9, 17.0 Hz, 1H), 6.61-6.68 (dd, J=10.2, 17.0 Hz, 1H), 7.14 (t, J=5.1 Hz, 1H), 7.43-7.48 (q, J=8.6 Hz, 1H), 8.01 (d, J=8.0 Hz, 1H), 8.05-8.09 (m, 2H), 8.12-8.18 (q, J=8.9 Hz, 2H), 8.88-8.91 (dd, J=1.9, 7.7 Hz, 1H), 9.23 (d, J=8.9 Hz, 1H), 10.1 (s, 1H). MS m/z (M+H): 447.1

Example 54

Compound III-37

(R)—N-(2-methyl-5-(10-methyl-8-oxo-9,10,11,12-tetrahydro-8H-[1,4]diazepino[5',6':4,5]thieno[3,2-f]quinolin-3-yl)phenyl)acrylamide

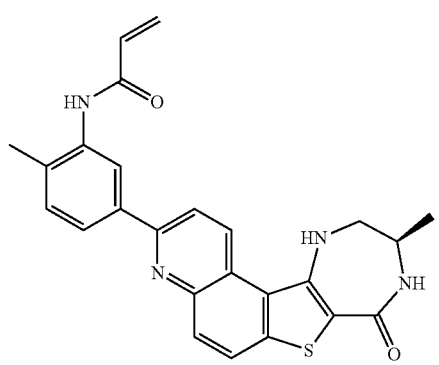

The title compound was prepared according to the schemes, steps, and intermediates

353

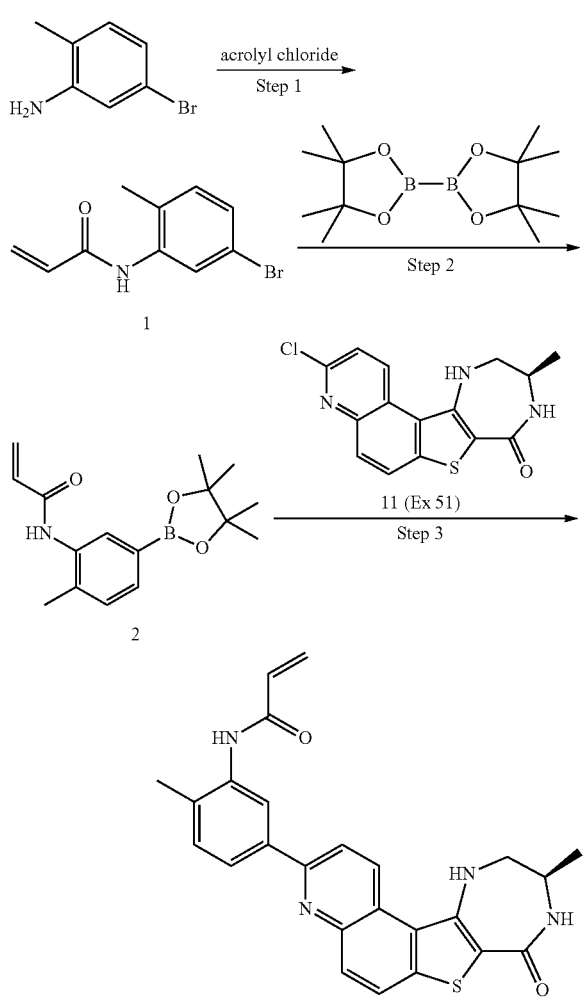

Step 1:

N-(5-bromo-2-methylphenyl)acrylamide (1)

To a solution of 5-bromo-2-methylaniline (2.0 g, 10.8 mmol) in dichloromethane (10 mL), diisopropylethylamine (4.18 g, 32.3 mmol) and acryloyl chloride (1.16 g, 12.8 mmol) were added at −78° C. The resulting mixture was stirred at room temperature for 30 min. After completion of reaction, the reaction mixture was quenched with water and the aqueous solution was extracted with dichloromethane (2×40.0 mL). The organic layer was washed with water followed by brine solution. The organic layer was dried over anhydrous sodium sulfate and concentrated over reduced pressure. The residue was triturated with n-pentane to afford 1 (2.2 g, 85%) as an off white solid. 1H NMR (400 MHz, CDCl$_3$) δ 2.23 (s, 3H), 5.79-5.82 (dd, J=1.1, 10.2 Hz, 1H), 6.23-6.30 (dd, J=10.2, 16.8 Hz, 1H), 6.42 (dd, J=1.1, 16.8 Hz, 1H), 6.99 (brs, 1H), 7.04 (d, J=8.1 Hz, 1H), 7.20 (m, 1H), 8.20 (brs, 1H). MS m/z (M−H): 238.0

Step 2:

N-(2-methyl-5-(4,4,5,5-tetramethyl-1,3,2-dioxaborolan-2-yl)phenyl)acrylamide (2)

To a solution of N-(5-bromo-2-methylphenyl)acrylamide (600 mg, 2.5 mmol) in 1,4-dioxane (6.0 mL), bis (pinaco-

354 latediborane) (764 mg, 3.0 mmol), PdCl$_2$(dppf).DCM complex (102 mg, 0.13 mmol), and potassium acetate (738 mg, 7.5 mmol) were added. The resulting mixture was degassed for 20 min and heated at 100° C. for 16 h. After completion of the reaction, the reaction mixture was filtered, and the filtrate was concentrated under reduced pressure. The obtained residue was purified by silica gel column chromatography using chloroform/methanol to afford 2 (600 mg, 83%) as a brown gummy liquid. MS m/z (M+H): 288.2

Step 3:

To a solution of intermediate 11 of Example 51 (100 mg, 0.3 mmol) in 1,4-dioxane/water (1:1), N-(2-methyl-5-(4,4,5,5-tetramethyl-1,3,2-dioxaborolan-2-yl)phenyl) acrylamide (271 mg, 0.9 mmol) and sodium bicarbonate (100 mg, 0.94 mmol) were added followed by the addition of tetrakis (triphenylphosphine)palladium(0) (72 mg, 0.06 mmol). The resulting mixture was degassed under nitrogen atmosphere for 15 min and heated at 100° C. for 12 h in a sealed tube. After completion of reaction, the reaction mixture was filtered through celite and washed with ethyl acetate. The organic layer was dried over anhydrous sodium sulfate and concentrated under reduced pressure to afford the title compound (21 mg, 16%) as a pale yellow solid. $^1$H NMR (400 MHz, DMSO-d$_6$) δ 1.19 (d, J=6.7 Hz, 3H), 2.29 (s, 3H), 3.46 (brs, 2H), 3.61 (brs, 1H), 5.77-5.80 (dd, J=1.9, 10.1 Hz, 1H), 6.26-6.31 (dd, J=1.9, 17.0 Hz, 1H), 6.54 (m, 1H), 7.13 (t, J=5.2 Hz, 1H), 7.42 (d, J=8.1 Hz, 1H), 8.98-8.06 (m, 3H), 8.11 (d, J=8.9 Hz, 1H), 8.17 (d, J=8.9 Hz, 1H), 8.40 (s, 1H), 9.21 (d, J=8.9 Hz, 1H), 9.69 (s, 1H). MS m/z (M+H): 443.62.

Example 55

Compound III-40

(R)—N-(2-(2-(dimethylamino)ethoxy)-5-(10-methyl-8-oxo-9,10,11,12-tetrahydro-8H-[1,4]diazepino[5',6':4,5]thieno[3,2-f]quinolin-3-yl)phenyl) acrylamide

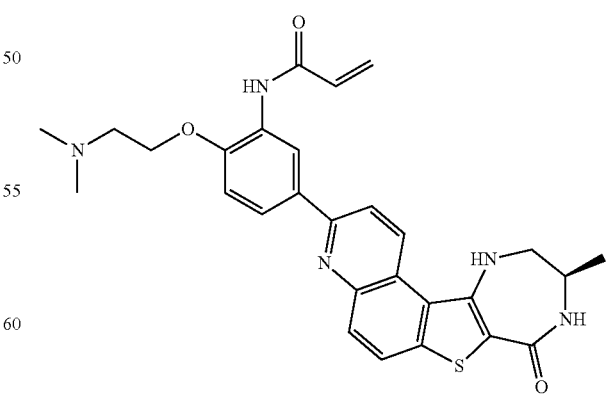

The title compound was prepared according to the schemes, steps, and intermediates described below, utilizing intermediate 11 from Example 51.

355

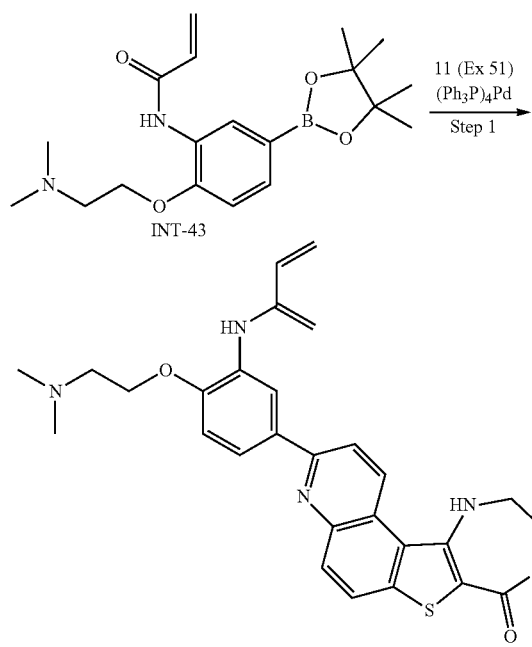

Step 1:

To a solution of compound 11 from Example 51 (75 mg, 0.23 mmol) in 1,4-dioxane/water (1:1), N-(2-(2-(dimethylamino)ethoxy)-5-(4,4,5,5-tetramethyl-1,3,2-dioxaborolan-2-yl)phenyl)acrylamide INT-43 (136 mg, 0.3 mmol) and sodium bicarbonate (75 mg, 0.8 mmol) were added followed by the addition of tetrakis(triphenylphosphine)palladium(0) (27 mg, 0.02 mmol). The resulting mixture was degassed under nitrogen atmosphere for 5 min and heated at 100° C. for 12 h in a sealed tube. After completion of reaction, the reaction mixture was filtered through celite and washed with ethyl acetate. The organic layer was dried over anhydrous sodium sulfate and concentrated under reduced pressure to afford the title compound (20 mg, 16%) as a pale yellow solid. $^1$H NMR (400 MHz, DMSO-$d_6$): δ 1.15-1.20 (d, J=6.1 Hz, 3H), 2.25 (s, 6H), 2.65 (t, J=5.7 Hz, 2H), 3.45 (brs, 2H), 3.61 (m, 1H), 4.22 (t, J=5.6 Hz, 2H), 5.8 (d, J=11.5 Hz, 1H), 6.29 (dd, J=1.7, 16.8 Hz, 1H), 6.52-6.62 (dd, J=10.4, 16.8 Hz, 1H), 7.12 (t, J=4.7 Hz, 1H), 7.3 (d, J=8.6 Hz, 1H), 7.95-8.09 (m, 3H), 8.12 (m, 2H), 8.95 (brs, 1H), 9.18 (d, J=8.9 Hz, 1H), 9.66 (brs, 1H). MS m/z (M−H): 514.39.

Example 56

Compounds III-51

(3R)—N-(1-acryloylpiperidin-3-yl)-3-methyl-5-oxo-2,3,4,5-tetrahydro-1H-benzo[4,5]thieno[3,2-e][1,4]diazepine-9-carboxamide

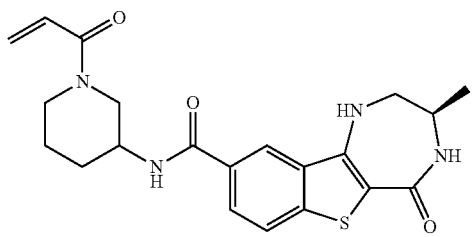 [SMILES: C=CC(=O)N1CCCC(NC(=O)c2ccc3sc4c(c3c2)NC[C@@H](C)NC4=O)C1]

356

The title compound was prepared according to the schemes, steps, and intermediates

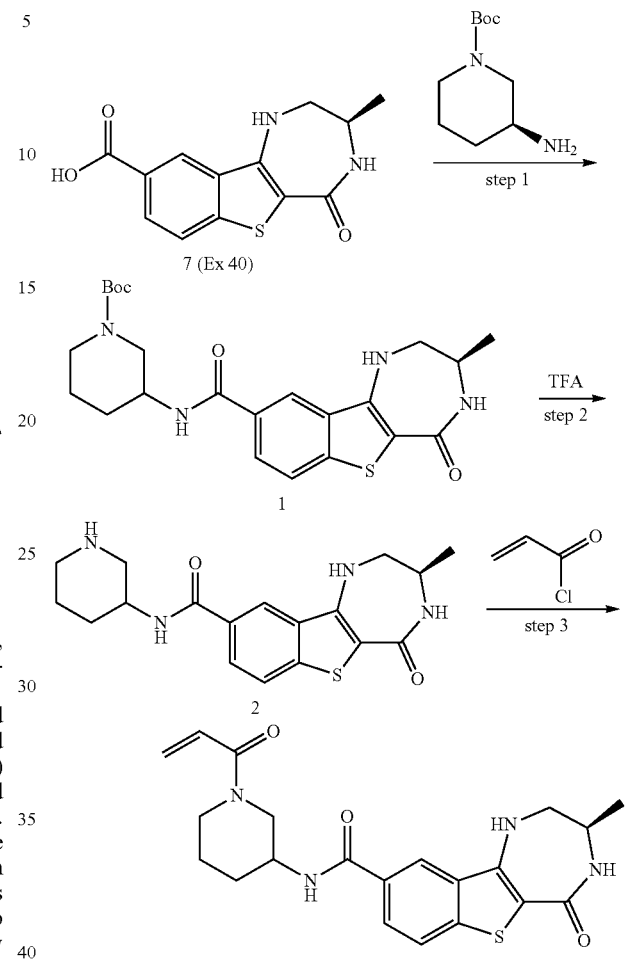

Step 1:

Compound 1:

To a solution of acid compound 7 (Ex 40; 200 mg, 0.7 mmol) in dimethylformamide (3.0 mL), 1-[Bis(dimethylamino)methylene]-1H-1,2,3-triazolo[4,5-b]pyridinium3-oxidehexafluorophosphate (HATU) (550 mg, 1.4 mmol) and diisopropylethylamine (280 mg, 2.1 mmol) were added at 0° C. followed by the addition of (S)-1-Boc-3-aminopiperidine (173 mg, 0.8 mmol). The resulting mixture was stirred at room temperature for 1 h. After completion of the reaction, the reaction mixture was diluted with water and extracted with ethyl acetate. The organic layer was dried over anhydrous sodium sulfate and concentrated under reduced pressure. The residue obtained was triturated with n-pentane to afford 1 (250 mg, 63%) as a brown gummy solid. MS m/z (M+H): 459.4

Step 2:

Compound 2:

To a solution of 1 (250 mg, 0.55 mmol) in dichloromethane (3.0 mL), excess trifluoroacetic acid (3.0 mL) was added at 0° C. and the resulting mixture was stirred at room temperature for 12 h. After completion of the reaction mixture, the reaction mixture was concentrated under reduced pressure and the residue was triturated with diethyl ether to afford 2 (190 mg, quantitative) as a pale brown solid. MS m/z (M+H): 359.5

Step 3:

To a solution of 2 (50 mg, 0.1 mmol) in dichloromethane/dimethylamide (1:1), diisopropylethylamine (52 mg, 0.4 mmol), acryloyl chloride (12.6 mg, 0.4 mmol) were added at −78° C. and the reaction mixture was stirred at room temperature for 1 h. The reaction mixture was diluted with water and extracted with ethyl acetate. The organic layer was dried over anhydrous sodium sulfate and concentrated under reduced pressure. The crude residue was purified by preparative HPLC to afford the title compound (22 mg, 53%) as a mixture of diastereomers. White solid: $^1$H NMR (400 MHz, DMSO-$d_6$) δ 1.13 (d, J=6.8 Hz, 3H), 1.38-1.52 (m, 1H), 1.55-1.70 (m, 1H), 1.75-1.82 (m, 1H), 1.96 (d, J=1.7 Hz, 1H), 2.90-3.06 (m, 1H), 3.15-3.23 (m, 1H), 3.35 (s, 2H), 3.57 (brs, 1H), 3.81 (brs, 1H), 3.97-4.03 (m, 2H), 5.65 (m, 1H), 6.08 (m, 1H), 6.65-6.85 (m, 1H), 7.70 (s, 1H), 7.82-7.84 (m, 3H), 8.34 (d, J=4.9 Hz, 1H), 8.46 (s, 1H). MS m/z (M+H): 413.4.

Example 57

Compound III-52

(3R)-3-methyl-5-oxo-N-(1-(vinylsulfonyl)piperidin-3-yl)-2,3,4,5-tetrahydro-1H-benzo[4,5]thieno[3,2-e][1,4]diazepine-9-carboxamide( )

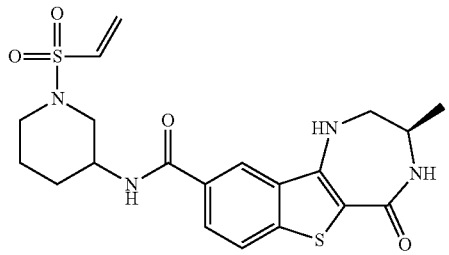 [SMILES: C=CS(=O)(=O)N1CCCC(NC(=O)c2ccc3sc4c(c3c2)NC[C@@H](C)NC4=O)C1]

The title compound was prepared using compound 2 from Example 56, as described below.

To a solution of 2 (150 mg, 0.4 mmol), in dichloromethane/tetrahydrofuran (1:1), diisopropylethylamine (162 mg, 1.2 mmol) was added at 0° C. followed by the addition of solution of 2-chloro ethanesulfonyl chloride (102 mg, 0.6 mmol) in dichloromethane. The resulting mixture was stirred at room temperature for 20 min. The reaction mixture was diluted with water and extracted with 5% methanol/chloroform. The organic layer was dried over anhydrous sodium sulfate and concentrated under reduced pressure. The residue was purified by preparative HPLC to afford the title compound (16 mg, 9%) as a mixture of diastereomers. Off white solid: $^1$H NMR (400 MHz, DMSO-$d_6$) δ 1.13 (d, J=6.8 Hz, 3H), 1.46-1.60 (m, 2H), 1.83-1.91 (m, 3H), 2.59-2.64 (m, 1H), 3.35 (d, J=3.8 Hz, 2H), 3.44 (d, J=12.1 Hz, 1H), 3.52-3.65 (m, 2H), 3.97 (brs, 1H), 6.09-6.16 (m, 2H), 6.78-6.85 (dd, J=10.1, 17.5 Hz, 1H), 7.70 (brs, 1H), 7.81-7.84 (m, 3H), 8.33 (d, J=7.5 Hz, 1H), 8.45 (s, 1H). MS m/z (M+H): 449.6.

Example 58

Compound III-45

(R)—N-(5-(10-methyl-8-oxo-9,10,11,12-tetrahydro-8H-[1,4]diazepino[5',6':4,5]thieno[3,2-f]quinolin-3-yl)-2-(trifluoromethoxy)phenyl)acrylamide

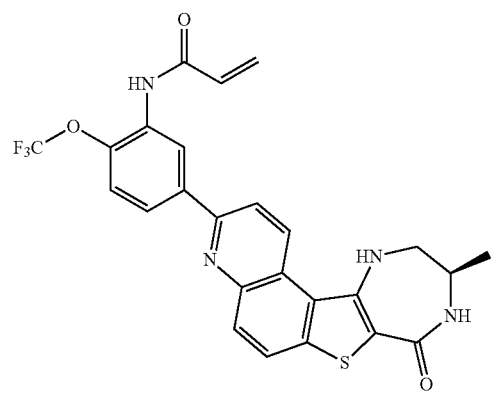 [SMILES: C=CC(=O)Nc1cc(-c2ccc3c(ccc4sc5c(c43)NC[C@@H](C)NC5=O)n2)ccc1OC(F)(F)F]

The title compound was prepared according to the schemes, steps, and intermediates described below.

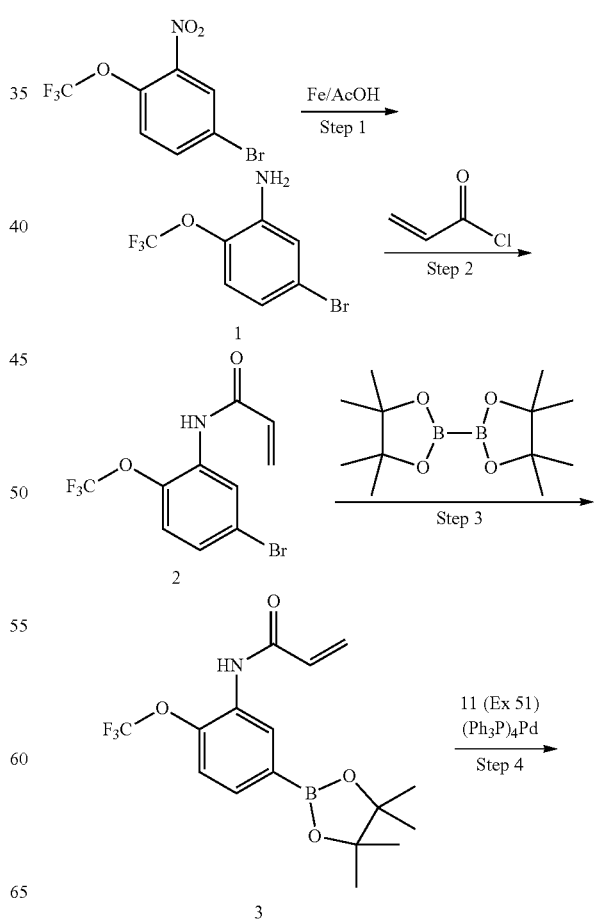

359

-continued

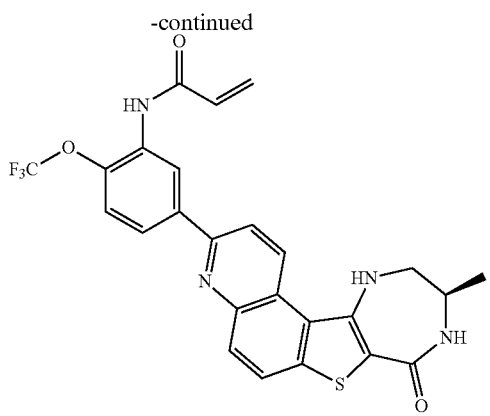

Step 1:

5-bromo-2-(trifluoromethoxy)aniline (1)

To a solution of 4-bromo-2-nitro-1-(trifluoromethoxy) benzene (2.0 g, 7.0 mmol) in acetic acid (10.0 mL) was added Fe -powder (1.0 g, 17.9 mmol) at 0-10° C. The reaction mixture was allowed to stir at room temperature for 2 h. After completion of the reaction, acetic acid was distilled and the residue was diluted with water, basified with saturated sodium bicarbonate solution and extracted with ethyl acetate (2×50 mL). The organic layer was dried over anhydrous sodium sulfate and concentrated under reduced pressure to afford 1 (1.2 g, 70%) as a brown gummy solid. $^1$H NMR (400 MHz, DMSO-$d_6$): δ 5.68 (s, 2H), 6.65-6.66 (dd, J=2.4 Hz, 6.2 Hz, 1H), 6.95-6.96 (d, J=2.5 Hz, 1H), 7.01-7.01 (dd, J=1.4 Hz, 8.6 Hz, 1H). MS m/z (M+H): 256.3.

Step 2:

N-(5-bromo-2-(trifluoromethoxy)phenyl)acrylamide (2)

To a solution of 5-bromo-2-(trifluoromethoxy)aniline (1.2 g, 4.7 mmol) in dichloromethane (5.0 mL), diisopropylethylamine (727 mg, 5.64 mmol) and acryloyl chloride (382 mg, 4.22 mmol) were added at −78° C. The reaction mixture was allowed to stir at 0° C. for 2 h. After completion of the reaction, the reaction mixture was diluted with water and extracted with ethyl acetate. The organic layer was dried over anhydrous sodium sulfate and concentrated under reduced pressure to afford 2 (1.4 g, 93%) as an off white solid. $^1$H NMR (400 MHz, DMSO-$d_6$): δ 5.79-5.80 (dd, J=1.82 Hz, 10.2 Hz, 1H), 6.26-6.27 (dd, J=1.8, 17.0 Hz, 1H), 6.61-6.63 (dd, J=17.0 Hz, 1H), 7.38-7.40 (m, 2H), 8.28-8.29 (d, J=2.3 Hz, 1H), 10.07 (brs, 1H). MS m/z (M+H): 310.45

Step 3:

N-(5-(4,4,5,5-tetramethyl-1,3,2-dioxaborolan-2-yl)-2-(trifluoromethoxy) phenyl)acrylamide (3)

To a solution of N-(5-bromo-2-(trifluoromethoxy)phenyl) acrylamide (600 mg, 2.0 mmol) and bispinacolatediborane (591 mg, 253.9 mmol) in 1,4-dioxane (5.0 mL), bis(diphenylphosphino)ferrocene-palladium(II)dichloride dichloromethane complex (80 mg, 0.1 mmol) and potassium acetate (571 mg, 5.81 mmol) were added and degassed for 15 min. The reaction mixture was heated to reflux for 5 h. After completion of the reaction, the reaction mixture was concentrated to obtain solid residue which was diluted with water (25 mL) and extracted with ethyl acetate (2×50 mL). The organic layer was dried over anhydrous sodium sulfate and concentrated under reduced pressure to afford 3 (1.1 g, crude) as a brown gummy liquid. The crude material was used as such for next step without further purification. MS m/z (M+H): 358.3

Step 4:

To a solution of N-(5-(4,4,5,5-tetramethyl-1,3,2-dioxaborolan-2-yl)-2-(trifluoromethoxy)phenyl)acrylamide (225 mg, 0.63 mmol) in (3:1) 1,4-dioxane/water, compound 11 from Example 51 (100 mg, 0.3 mmol) and sodium carbonate (100 mg, 1.0 mmol) were added and degassed for 10 min. To this reaction mixture (Ph$_3$P)$_4$ Pd (18.0 mg. 0.015 mmol) was added and degassed for 10 min. The reaction mixture was refluxed for 5 h at 110° C. After completion of the reaction, the reaction mixture was concentrated and the residue obtained was diluted with water, extracted with ethyl acetate (2×40 mL). The organic layer was dried over anhydrous sodium sulfate and concentrated under reduced pressure. The residue was purified by preparative thin layer chromatography to afford the title compound (30 mg, 10%) as a yellow solid. $^1$H NMR (400 MHz, DMSO-$d_6$): δ 1.21 (d, J=6.9 Hz, 3H), 3.45 (brs, 2H), 3.61 (brs, 1H), 5.82 (dd, J=1.8 Hz, 10.1 Hz, 1H), 6.30 (dd, J=1.82 Hz, 17.0 Hz, 1H), 6.63 (dd, J=10.2 Hz, 17.0 Hz, 1H), 7.12-7.19 (m, 1H), 7.6 (d, J=1.4 Hz, 1H), 8.05 (d, J=8.9 Hz, 1H), 8.09 (d, J=4.2 Hz, 1H), 8.12-8.25 (m, 3H), 8.85 (s, 1H), 9.25 (d, J=8.9 Hz, 1H), 10.1 (brs, 1H). MS m/z (M+H): 513.1.

Example 59

Compound III-46

(R)—N-(5-(10-methyl-8-oxo-9,10,11,12-tetrahydro-8H-[1,4]diazepino[5',6':4,5]thieno[3,2-f]quinolin-3-yl)-2-(trifluoromethoxy)phenyl)acrylamide

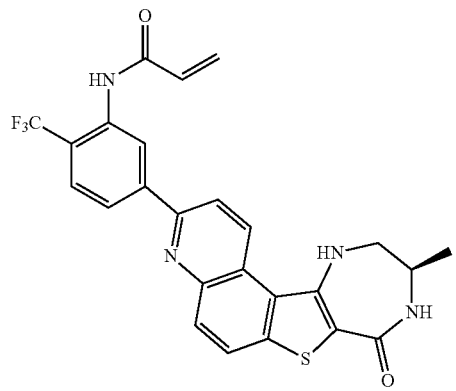 [SMILES: C=CC(=O)Nc1cc(-c2ccc3c(ccc4sc5c(c43)NC[C@@H](C)NC5=O)n2)ccc1C(F)(F)F]

The title compound was prepared according to the schemes, steps, and intermediates described below, utilizing intermediate 11 from Example 51.

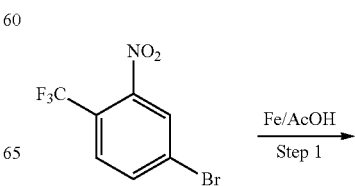

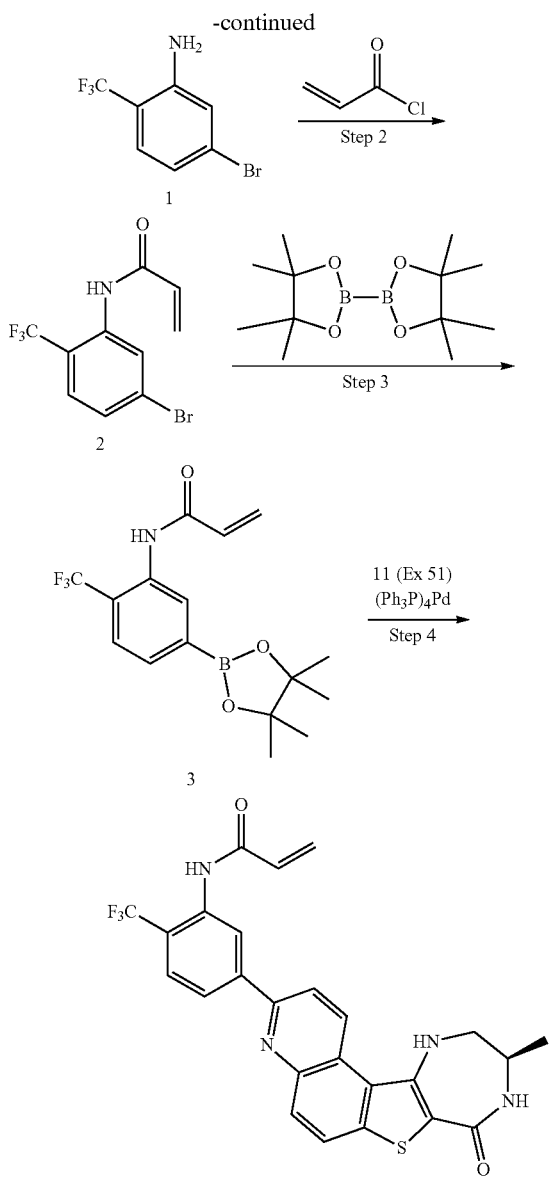

Step 1:

5-bromo-2-(trifluoromethyl)aniline (1)

To a solution of 4-bromo-2-nitro-1-(trifluoromethyl)benzene (2.0 g, 7.4 mmol) in acetic acid (10.0 mL), Iron powder (1.2 g, 21.8 mmol) was added at 0° C. The resulting reaction mixture was stirred at room temperature for 2 h. After completion of reaction, the reaction mixture was concentrated under reduced pressure. The residue obtained was diluted with water, basified with saturated sodium bicarbonate solution and extracted with ethyl acetate (2×50 mL). The organic layer was dried over anhydrous sodium sulfate and concentrated under reduced pressure to afford 1 (1.4 g, 79%) as a brown gummy solid. $^1$H NMR (400 MHz, DMSO-$d_6$): δ 5.86 (brs, 2H), 6.73-6.73 (dd, J=1.2, 8.4 Hz, 1H), 7.02 (s, 1H), 7.23-7.25 (d, J=8.4 Hz, 1H). MS m/z (M+H): 240.1

Step 2:

N-(5-bromo-2-(trifluoromethyl)phenyl)acrylamide (2)

To a solution of 5-bromo-2-(trifluoromethyl) aniline (1.4 g, 5.8 mmol) in dichloromethane (5.0 mL), diisopropylethylamine (1.2 mL, 6.5 mmol) and acryloyl chloride (0.6 g, 6.6 mmol) were added at −78° C. The resulting mixture was at 0° C. for 2 h. After completion of reaction, the reaction mixture was concentrated under reduced pressure. The residue obtained was diluted with sodium bicarbonate solution and extracted with ethyl acetate. The organic layer was dried over anhydrous sodium sulfate and concentrated under reduced pressure to afford 2 (600 mg, 35%) as an off white solid. $^1$H NMR (400 MHz, DMSO-$d_6$): δ 5.783-5.788 (dd, J=1.8, 10.2 Hz, 1H), 6.23-6.23 (dd, J=1.8, 17.0 Hz, 1H), 6.52-6.54 (dd, J=6.8, 17.0 Hz, 1H), 7.69 (m, 2H), 7.82 (s, 1H), 9.88 (brs, 1H). MS m/z (M+H): 294.0

Step 3:

N-(5-(4,4,5,5-tetramethyl-1,3,2-dioxaborolan-2-yl)-2-(trifluoromethyl)phenyl)acrylamide (3)

To a solution of N-(5-bromo-2-(trifluoromethyl)phenyl) acrylamide (600 mg, 2.0 mmol) in 1,4-dioxane (5.0 mL) bispinacolatediborane (520 mg, 2.0 mmol), bis(diphenylphosphino)ferrocene-palladium(II)dichloride dichloromethane complex (84 mg, 0.10 mmol), and potassium acetate (602 mg, 6.1 mmol) were added and the resulting mixture was degassed under nitrogen atmosphere for 15 min. The reaction mixture was refluxed at 110° C. for 5 h. After completion of reaction, the reaction mixture was concentrated under reduced pressure and the residue was diluted with water and extracted with ethyl acetate (2×50 mL). The organic layer was dried over anhydrous sodium sulfate and concentrated under reduced pressure to afford 3 (260 mg, 37%) as an off white solid. MS m/z (M+H): 342.4

Step 4:

To a solution of intermediate 11 (prepared as in Example 51) (94 mg, 0.16 mmol) in 1, 4 dioxane/water (3:1) was treated with N-(5-(4,4,5,5-tetramethyl-1,3,2-dioxaborolan-2-yl)-2-(trifluoromethyl)phenyl)acrylamide (94 mg, 0.27 mmol), sodium carbonate (75 mg, 0.7 mmol) and tetrakis (triphenylphosphine) palladium (13.6 mg, 0.01 mmol) at 100° C. for 12 h. After completion of the reaction, the reaction mixture was diluted with ethyl acetate and washed with water. The organic layer was dried over anhydrous sodium sulfate and concentrated under reduced pressure. The obtained residue was purified by silica gel column chromatography using methanol in chloroform to afford the title compound (29 mg, 21%) as a yellow solid. 1H NMR (400 MHz, DMSO-$d_6$): δ 1.18 (d, J=6.7 Hz, 3H), 3.49 (brm, 2H), 3.60 (brm, 1H), 5.81 (dd, J=1.8 Hz, 10.2 Hz, 1H), 6.26 (dd, J=1.8 Hz, 17.0 Hz, 1H), 6.51-6.61 (dd, J=10.2 Hz, 17.0 Hz 1H), 7.16 (t, J=5.1 Hz, 1H), 7.92 (d, J=8.4 Hz, 1H), 8.04 (d, J=9.0 Hz, 1H), 8.08 (d, J=4.4 Hz, 1H), 8.19 (d, J=8.9 Hz, 1H), 8.31 (d, J=8.9 Hz, 1H), 8.41 (d, J=13.7 Hz, 1H), 8.45 (brs, 1H), 9.27 (d, J=8.9 Hz, 1H), 9.96 (brs, 1H). MS m/z (M+H): 497.1

Example 60

Compound III-d-1

(R)—N-(2-(2-methoxyethoxy)-5-(4-(3-methyl-5-oxo-2,3,4,5-tetrahydro-1H-thieno[3,2-e][1,4]diazepin-7-yl)pyridin-2-yl)phenyl)acrylamide

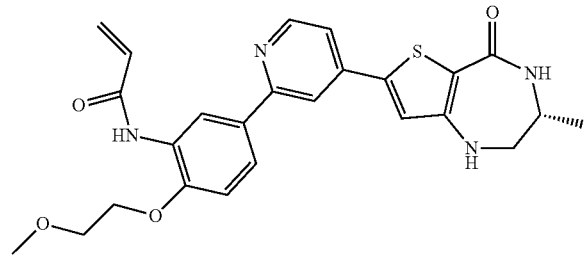

The title compound was prepared according to the schemes, steps, and intermediates

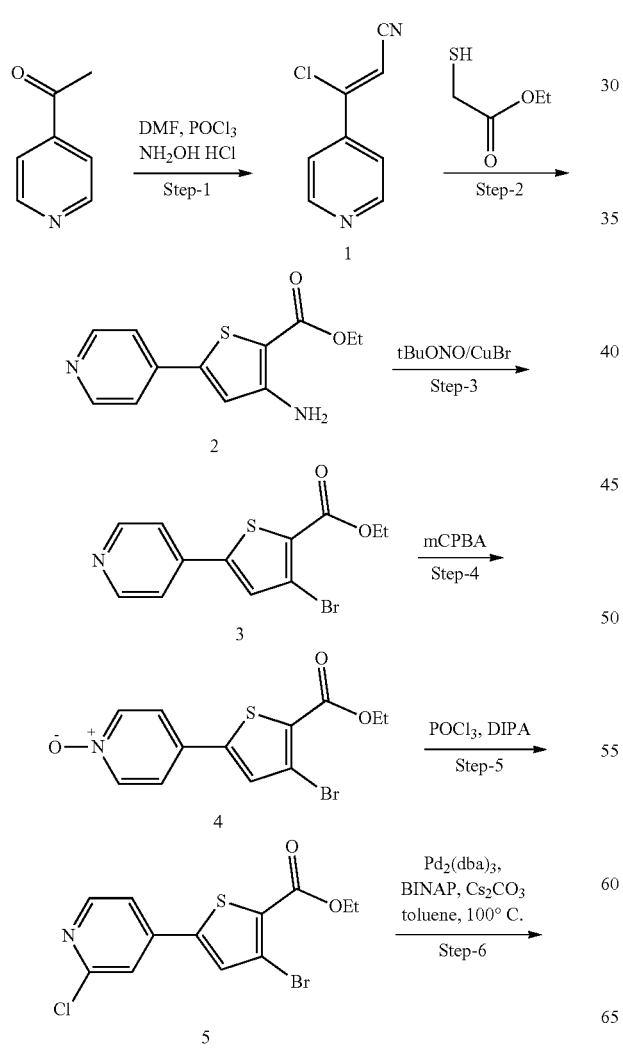

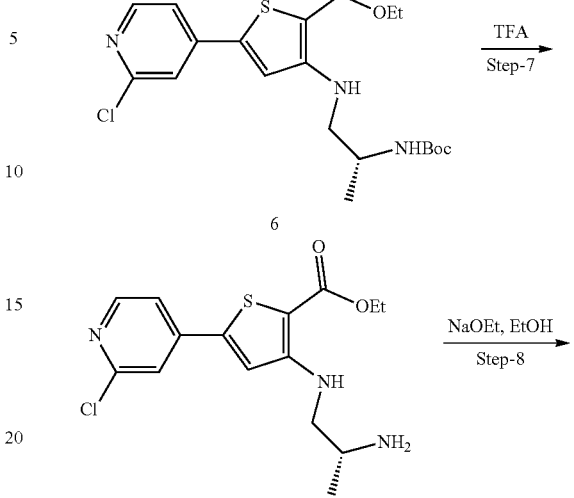

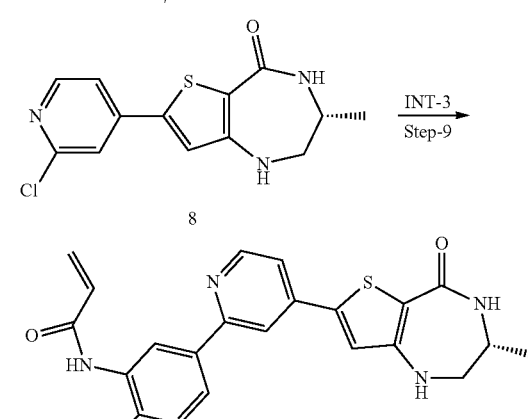

Step 1:

(Z)-3-chloro-3-(pyridin-4-yl) acrylonitrile (1)

To a solution mixture of phosphorous oxychloride (63.3 g, 413 mmol) in dimethylformamide (64 mL) at 0° C., 4-acetylpyridine (25.0 g, 207 mmol) in dimethylformamide was added stirred for 1.5 h at room temperature. To this, hydroxylamine hydrochloride (57.4 g, 826 mmol) was added slowly maintaining the reaction temperature below 60° C. (highly exothermic). The resulting mixture was heated at 90° C. for 4 h. The reaction mixture was cooled to room temperature, diluted with water, basified with bicarbonate solution and extracted with ethyl acetate (500 mL). The organic phase was separated, dried over anhydrous sodium sulfate and concentrated under reduced pressure to yield 1 (8 g, 24%) as grey solid. $^1$H NMR (400 MHz, DMSO-$d_6$) δ 7.2 (s, 1H), 7.74-7.76 (dd, J=1.6, 4.5 Hz, 2H), 8.74-8.76 (dd, J=1.7, 4.5 Hz, 2H).

Step 2:

Ethyl 3-amino-5-(pyridin-4-yl) thiophene-2-carboxylate (2)

To a stirred solution of (Z)-3-chloro-3-(pyridin-4-yl)acrylonitrile (8.0 g, 49 mmol) in ethanol (80 mL), ethyl-2- mercaptoacetate (7.0 g, 58.5 mmol) and sodium methoxide (4.6 g, 69 mmol) were added at 0° C. The reaction mixture was heated at 90° C. for 12 h. The reaction mixture was partitioned between ethyl acetate (400 mL) and water (200 mL). The organic phase was dried over anhydrous sodium sulfate and concentrated under reduced pressure. The residue was re-crystallized from n-hexane to obtain 2 (3.7 g, 31%) as a pale yellow solid. $^1$H NMR (400 MHz, DMSO-$d_6$) δ 1.26 (t, J=7.1 Hz, 3H), 4.42 (q, J=7.1 Hz, 2H), 6.60 (s, 2H), 7.19 (s, 1H), 7.58 (dd, J=2.3, 4.0 Hz, 2H), 8.60-8.61 (dd, J=1.6, 4.5 Hz, 2H). MS m/z (M+H): 249.1

Step 3:

Ethyl 3-bromo-5-(pyridin-4-yl) thiophene-2-carboxylate (3)

To a stirred solution of ethyl 3-amino-5-(pyridin-4-yl) thiophene-2-carboxylate (2.0 g, 8 mmol) in $H_2SO_4$ (15 mL), $NaNO_2$ solution (667 mg in 10 mL of water) was added below 5° C. followed by the addition of copper bromide (2.7 g, 12 mmol) in hydrogen bromide (15 mL) at 70° C. for 30 min. The resulting mixture was heated at 80° C. for 1 h. The reaction mixture was diluted with water, and the solid obtained was filtered and dried to obtain 3 (1 g, 40%) as a brown solid. $^1$H NMR (400 MHz, DMSO-$d_6$) δ 1.31 (t, J=7.0 Hz, 3H), 4.31 (q, J=7.1 Hz, 2H), 7.76-7.78 (dd, J=1.6, 4.5 Hz, 2H), 8.02 (s, 1H), 8.64-8.66 (dd, J=1.5, 4.6 Hz, 2H). MS m/z (M+H): 312.5

Step 4:

4-(4-bromo-5-(ethoxycarbonyl) thiophen-2-yl) pyridine 1-oxide (4)

To a stirred solution of ethyl 3-bromo-5-(pyridin-4-yl) thiophene-2-carboxylate (600 mg, 2 mmol) in dichloromethane (12 mL), mCPBA (588 mg, 5 mmol) was added at 0° C. The resulting mixture was stirred at room temperature for 2 h. The reaction mixture was diluted with bicarbonate solution (30 mL) and extracted with ethyl acetate (50 mL). The organic layer was dried over anhydrous sodium sulfate and concentrated under reduced pressure to afford 4 (600 mg, 95%) as off-white solid. 1H NMR (400 MHz, DMSO-$d_6$) δ 1.31 (t, J=3.5 Hz, 3H), 4.31 (q, J=7.1 Hz, 2H), 7.81-7.83 (dd, J=2.0, 5.3 Hz, 2H), 7.92 (s, 1H), 8.24-8.26 (dd, J=2.0, 5.3 Hz, 2H). MS m/z (M+H): 328.4

Step 5:

Ethyl 3-bromo-5-(2-chloropyridin-4-yl) thiophene-2-carboxylate (5)

To a stirred solution of 4-(4-bromo-5-(ethoxycarbonyl) thiophen-2-yl)pyridine 1-oxide (600 mg, 2 mmol) in dichloromethane (10 mL), $POCl_3$ (2 mL, 4 mmol) and diisopropylamine (1 mL, 2 mmol) were added at 0° C. for 10 min. The reaction mixture was allowed to stir at room temperature for 2 h. The reaction mixture was diluted with bicarbonate solution (50 ml) and extracted with ethyl acetate (50 mL). The organic layer was dried over sodium sulfate and concentrated under reduced pressure to obtain crude compound. The crude obtained was purified by silica gel column chromatography to afford 5 (400 mg, 63%) as a white solid. $^1$H NMR (400 MHz, DMSO-$d_6$) δ 1.31 (t, J=7.0 Hz, 3H), 4.33 (q, J=7.0 Hz, 2H), 7.78-7.80 (dd, J=1.6, 5.2 Hz, 1H), 7.98 (d, J=1.1 Hz, 1H), 8.1 (s, 1H), 8.47 (d, J=5.2 Hz, 1H). MS m/z (M+H): 346.9

Step 6:

(R)-Ethyl 3-(2-(tert-butoxycarbonylamino) propylamino)-5-(2-chloropyridin-4-yl) thiophene-2-carboxylate (6)

To a stirred solution of Ethyl 3-bromo-5-(2-chloropyridin-4-yl) thiophene-2-carboxylate (400 mg, 1 mmol) in toluene (20.0 mL), (R)-tert-butyl 1-aminopropan-2-ylcarbamate (403 mg, 2 mmol), $Pd_2(dba)_3$ (106 mg, 0.1 mmol), cesium carbonate (755 mg, 2 mmol) and BINAP (72 mg, 0.1 mmol) were added and degassed for 15 min. The resulting mixture was heated at 120° C. for 12 h. The reaction mixture was concentrated and separated between ethyl acetate (100 mL) and water (50 mL). The organic layer was dried over anhydrous sodium sulfate and concentrated under reduced pressure. The crude compound was purified by silica gel column chromatography to obtain 6 (200 mg, 39%) as a yellow solid. $^1$H NMR (400 MHz, DMSO-$d_6$) δ 1.06 (d, J=6.6 Hz, 3H), 1.25 (t, J=7.0 Hz, 3H), 1.31 (s, 9H), 3.22 (m, 1H), 3.38 (m, 1H), 3.65 (m, 1H), 4.22 (q, J=7.0 Hz, 2H), 6.85 (d, J=8.1 Hz, 1H), 6.97 (d, J=6.2 Hz, 1H), 7.66-7.68 (dd, J=1.5, 5.2 Hz, 1H), 7.75 (s, 1H), 7.92 (d, J=1.2 Hz, 1H), 8.43 (d, J=5.2 Hz, 1H). MS m/z (M+H): 440.2

Step 7:

(R)-Ethyl 3-(2-aminopropylamino)-5-(2-chloropyridin-4-yl)thiophene-2-carboxylate (7)

(R)-Ethyl 3-(2-(tert-butoxycarbonylamino) propylamino)-5-(2-chloropyridin-4-yl) thiophene-2-carboxylate (200 mg, 0.4 mmol) was treated with (1:1) trifluoroacetic acid and dichloromethane (10 mL) at 0° C. and stirred for 1 h. The reaction mixture was concentrated and co-distilled with dichloromethane thrice. The TFA salt was basified with bicarbonate solution and extracted with ethyl acetate (50 mL). The organic layer was dried over anhydrous sodium sulfate and concentrated under reduced pressure to obtain compound 7 (120 mg, 78%) as a yellow solid. MS m/z (M+H): 340.2

Step 8:

(R)-7-(2-chloropyridin-4-yl)-3-methyl-3,4-dihydro-1H-thieno[3,2-e][1,4]diazepin-5(2H)-one (8)

To a stirred solution of (R)-ethyl 3-(2-aminopropylamino)-5-(2-chloropyridin-4-yl)thiophene-2-carboxylate (160 mg, 0.5 mmol) in ethanol (5.0 mL), sodium ethoxide (48 mg, 0.7 mmol) was added. The reaction mixture was heated at 90° C. for 10 h. The reaction mixture was diluted with water (50 mL), solid observed was filtered and dried to obtain compound 8 (30 mg, 22%) as yellow solid. 1H NMR (400 MHz, DMSO-$d_6$) δ 1.10 (d, J=6.7 Hz, 3H), 3.21 (d, J=4.0 Hz, 2H), 3.49 (d, J=4.0 Hz, 1H), 7.18 (s, 2H), 7.56-7.58 (dd, J=1.4, 5.2 Hz, 1H), 7.68 (s, 1H), 7.71 (d, J=4.2 Hz, 1H), 8.40 (d, J=5.2 Hz, 1H). MS m/z (M+H): 294.3

Step 9:

To a stirred solution of (R)-7-(2-chloropyridin-4-yl)-3-methyl-3,4-dihydro-1H-thieno[3,2-e][1,4]diazepin-5(2H)-one 8 (30 mg, 0.1 mmol) in 1,4-dioxane/water (2.0 mL: 1 mL), N-(2-(2-methoxyethoxy)-5-(4,4,5,5-tetramethyl-1,3,2-dioxaborolan-2-yl)phenyl)acrylamide (INT-3) (71 mg, 0.2 mmol), sodium carbonate (32.5 mg, 0.3 mmol) were added and degassed for 20 min. To this, $Pd(PPh_3)$ (12 mg, 0.01 mmol) was added and heated at 100° C. for 3 h. The reaction mixture was diluted with water (10 mL) and extracted with ethyl acetate (20 mL). The organic layer was dried over anhydrous sodium sulfate and concentrated under reduced pressure. The obtained crude was purified by prep-HPLC to obtain III-d-1 (17 mg, 94%) as a pale yellow solid. 1H NMR (400 MHz, DMSO-d$_6$) δ; 1.12 (d, J=6.7 Hz, 3H), 3.23 (m, 2H), 3.31 (s, 3H), 3.50 (m, 1H), 3.74 (q, J=4.6 Hz, 2H), 4.25 (q, J=3.4 Hz, 2H), 5.74-5.77 (dd, J=2.0, 10.2 Hz, 1H), 6.25-6.29 (dd, J=1.9, 17.0 Hz, 1H), 6.64-6.68 (dd, J=10.3, 17.0 Hz, 1H), 7.20 (m, 3H), 7.45-7.47 (dd, J=1.6, 5.1 Hz, 1H), 7.67 (d, J=4.4 Hz, 1H), 7.87-7.90 (dd, J=2.2, 8.6 Hz, 2H), 8.63 (d, J=5.2 Hz, 1H), 8.8 (s, 1H), 9.2 (s, 1H). MS m/z (M+H): 479.5

Example 61

Compound IV-1

N-(2-ethoxy-5-((6-methyl-5-(piperidin-3-ylamino)pyrazolo [1,5-a]pyrimidin-7-yl)amino)phenyl)acrylamide

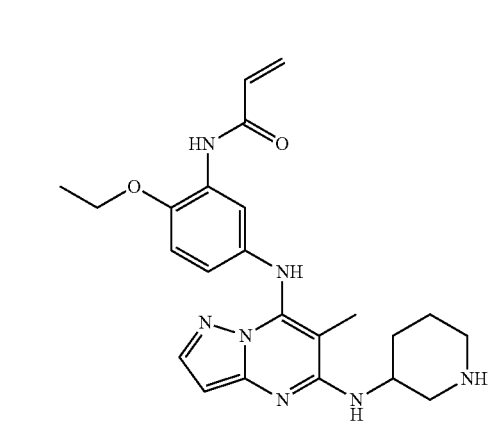 [SMILES: C=CC(=O)Nc1cc(Nc2c(C)c(NC3CCCNC3)nc3ccnn23)ccc1OCC]

The title compound was prepared according to the schemes, steps, and intermediates

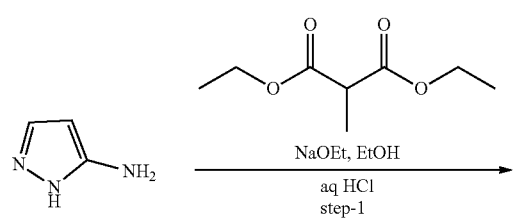

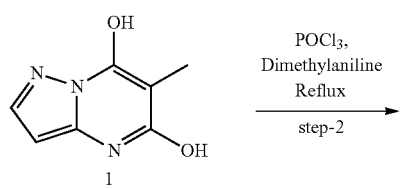

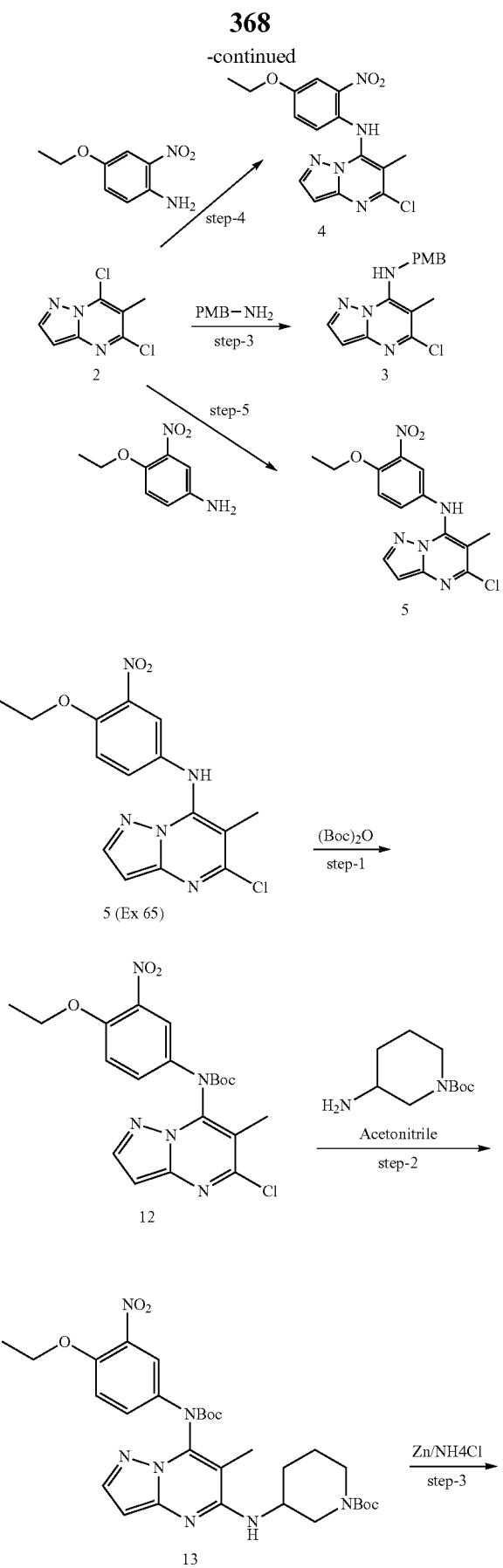

-continued

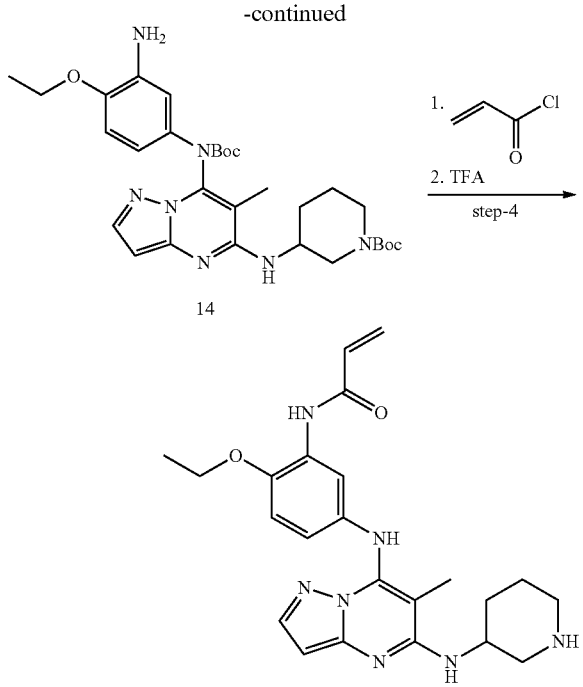

The synthesis of intermediate 5 is provided in detail in Example 65.

Step 1:

Tert-butyl 5-chloro-6-methylpyrazolo [1,5-a]pyrimidin-7-yl(4-ethoxy-3-nitrophenyl)carbamate (12)

To a stirred solution of 5-chloro-N-(4-ethoxy-3-nitrophenyl)-6-methylpyrazolo[1,5-a]pyrimidin-7-amine 5, prepared as described in Example 65 (250 mg, 0.7 mmol), in 1,4-dioxane (10.0 mL), (Boc)$_2$O (314 mg, 1.4 mmol) and DMAP (catalytic amount) were added. The reaction mixture was heated at 60° C. for 12 h. The reaction mixture was partitioned between ethyl acetate (100 mL) and water (50 mL). The organic layer was washed with bicarbonate solution (50 mL), dried over anhydrous sodium sulfate and concentrated under reduced pressure. Crude compound was purified by silica gel column chromatography to obtain 12 (200 mg, 44%) as a gummy liquid. $^1$H NMR (400 MHz, DMSO-d$_6$) δ 1.32 (t, J=6.9 Hz, 3H), 1.37 (s, 9H), 2.25 (s, 3H), 4.19 (q, J=6.9 Hz, 2H), 6.81 (d, J=2.2 Hz, 1H), 7.28 (d, J=9.1 Hz, 1H), 7.50-7.53 (dd, J=2.7, 9.0 Hz, 1H), 7.87 (d, J=2.7 Hz, 1H), 8.26 (s, 1H). MS m/z (M+H): 448.1

Step 2:

Tert-butyl 3-(7-(tert-butoxycarbonyl(4-ethoxy-3-nitrophenyl)amino)-6-methylpyrazolo[1,5-a]pyrimidin-5-ylamino)piperidine-1-carboxylate (13)

To a stirred solution of tert-butyl 5-chloro-6-methylpyrazolo[1,5-a]pyrimidin-7-yl(4-ethoxy-3-nitrophenyl)carbamate 12 (200 mg, 0.4 mmol) in acetonitrile (3 mL), tert-butyl 3-aminopiperidine-1-carboxylate (268 mg, 1.3 mmol) was added. The reaction mixture was heated at 90° C. for 12 h. The reaction mixture was partitioned between ethyl acetate (100 mL) and water (50 mL). The organic layer was dried over anhydrous sodium sulfate and concentrated under reduced pressure to yield 13 (180 mg, 70%) as white solid. MS m/z (M+H): 612.3

Step 3:

Tert-butyl 3-(7-((3-amino-4-ethoxyphenyl)(tert-butoxycarbonyl)amino)-6-methylpyrazolo[1,5-a]pyrimidin-5-ylamino)piperidine-1-carboxylate (14)

To a stirred solution of tert-butyl 3-(7-(tert-butoxycarbonyl(4-ethoxy-3-nitrophenyl)amino)-6-methylpyrazolo[1,5-a]pyrimidin-5-ylamino)piperidine-1-carboxylate 13 (280 mg, 0.45 mmol) in 1,4-dioxane/water (5 mL: 5 mL), zinc powder (297 mg, 4.5 mmol) and ammonium chloride (238.5 mg, 4.5 mmol) were added. The reaction mixture was stirred at room temperature for 3 h. The reaction mixture was partitioned between ethyl acetate (100 mL) and water (50 mL). The organic layer was washed with brine solution (50 mL), dried over anhydrous sodium sulfate and concentrated under reduced pressure. Crude compound was purified by preparative thin layer chromatography to obtain 14 (86 mg, 32%) as off-white solid. MS m/z (M+H): 582.3

Step 4:

To a stirred solution of tert-butyl 3-(7-((3-amino-4-ethoxyphenyl)(tert-butoxycarbonyl)amino)-6-methylpyrazolo [1,5-a]pyrimidin-5-ylamino)piperidine-1-carboxylate 14 (86 mg, 0.15 mmol) in dichloromethane (10 mL), DIPEA (29 mg, 0.2 mmol) and acryloyl chloride (13.5 mg, 0.15 mmol) were added at −78° C. The reaction mixture was stirred for 10 min. The reaction mixture was quenched with bicarbonate solution (20 mL). The resulting mixture was partitioned between dichloromethane (100 mL) and water (50 mL). The organic layer was dried over anhydrous sodium sulfate and concentrated under reduced pressure to yield the Boc-protected acrylamide intermediate (90 mg, 96%) as off-white solid. MS m/z (M+H): 636.5. This material was treated with (1:1) trifluoroacetic acid/dichloromethane (3.0 mL) at 0° C. The reaction mixture was stirred at room temperature for 1 h. The reaction mixture was concentrated and co-distilled with dichloromethane thrice. The residue was purified by prep-HPLC to yield TFA salt of IV-1 (28 mg, 26%) as off-white solid. $^1$H NMR (400 MHz, DMSO-d$_6$) δ 1.35 (t, J=6.9 Hz, 3H), 1.68 (m, 1H), 1.73 (s, 3H), 1.87-1.97 (m, 2H), 2.83 (q, J=9.6 Hz, 2H), 3.20 (d, J=12.0 Hz, 1H), 3.41 (d, J=10.6 Hz, 1H), 4.06 (q, J=6.9 Hz, 2H), 4.40 (q, J=3.3 Hz, 1H), 5.69-5.72 (dd, J=1.9, 10.2 Hz, 1H), 6.0 (d, J=2.1 Hz, 1H), 6.15-6.19 (dd, J=1.9, 17.0 Hz, 1H), 6.31 (d, J=8.0 Hz, 1H), 6.42-6.70 (dd, J=10.3, 16.9 Hz, 1H), 6.47-6.77 (dd, J=2.7, 8.7 Hz, 1H), 6.97 (d, J=8.8 Hz, 1H), 7.79 (d, J=2.0 Hz, 1H), 8.58 (s, 1H), 8.65 (brs, 2H), 9.2 (s, 1H). MS m/z (M+H): 436.2

Example 62

Compound IV-2

N-(5-ethoxy-2-((6-methyl-5-(piperidin-3-ylamino)pyrazolo [1,5-a]pyrimidin-7-yl)amino)phenyl)acrylamide

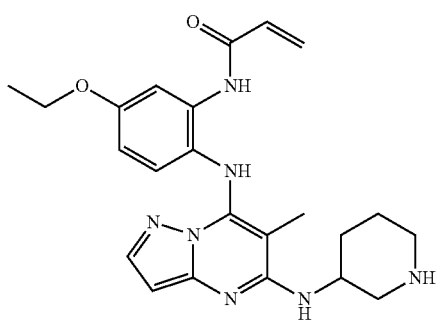 [SMILES: C=CC(=O)Nc1cc(OCC)ccc1Nc1c(C)c(NC2CCCNC2)nc2ccnn12]

The title compound was prepared according to the schemes, steps, and intermediates

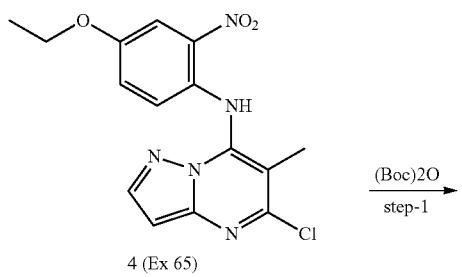

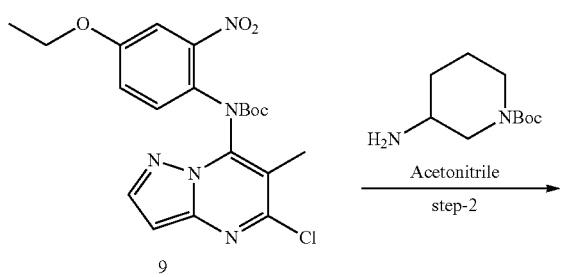

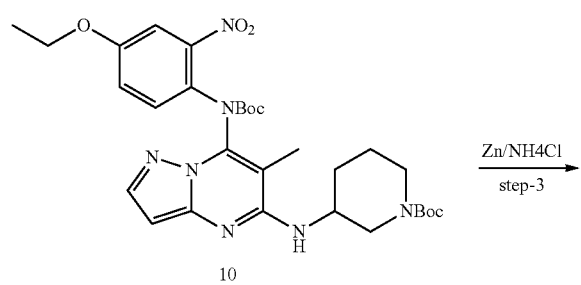

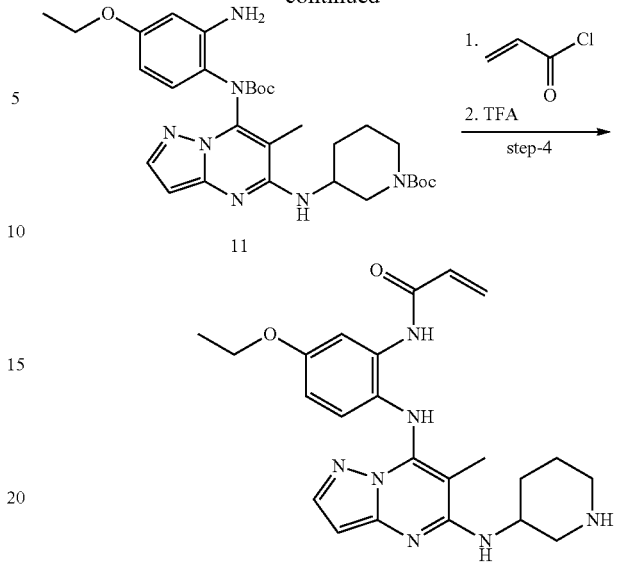

The synthesis of intermediate 4 is provided in detail in Example 65.

Step 1:

Tert-butyl 5-chloro-6-methylpyrazolo [1, 5-a]pyrimidin-7-yl (4-ethoxy-2-nitrophenyl) carbamate (9)

To a stirred solution of 5-chloro-N-(4-ethoxy-2-nitrophenyl)-6-methylpyrazolo [1, 5-a]pyrimidin-7-amine 4, prepared as described in Example 65 (250 mg, 0.7 mmol), in 1,4-dioxane (10.0 mL), (Boc)₂O (314 mg, 1.4 mmol) and DMAP (catalytic) were added. The reaction mixture was heated at 60° C. for 12 h. The reaction mixture was partitioned between ethyl acetate (100 mL) and water (50 mL). The organic layer was washed with bicarbonate solution (50 mL). The organic layer was dried over anhydrous sodium sulfate and concentrated under reduced pressure. Crude compound obtained was purified by silica gel column chromatography to obtain 9 (300 mg, 93%) as a gummy liquid. MS m/z (M+H): 448.12

Step 2:

tert-butyl 3-(7-(tert-butoxycarbonyl(4-ethoxy-2-nitrophenyl)amino)-6-methylpyrazolo[1,5-a]pyrimidin-5-ylamino)piperidine-1-carboxylate (10)

To a stirred solution of tert-butyl 5-chloro-6-methylpyrazolo [1, 5-a]pyrimidin-7-yl (4-ethoxy-2-nitrophenyl) carbamate 9 (300 mg, 0.67 mmol) in acetonitrile (3 mL), tert-butyl 3-aminopiperidine-1-carboxylate (402 mg, 2 mmol) was added. The reaction mixture was heated at 90° C. for 12 h. Reaction mixture was partitioned between ethyl acetate (100 mL) and water (50 mL). The organic layer was dried over anhydrous sodium sulfate and concentrated under reduced pressure to give 10 (200 mg, 49%) as white solid. MS m/z (M+H): 612.45

Step 3:

Tert-butyl 3-(7-((2-amino-4-ethoxyphenyl)(tert-butoxycarbonyl)amino)-6-methylpyrazolo[1,5-a]pyrimidin-5-ylamino)piperidine-1-carboxylate (11)

To a stirred solution of Tert-butyl 3-(7-(tert-butoxycarbonyl(4-ethoxy-2-nitrophenyl)amino)-6-methylpyrazolo[1,5- a]pyrimidin-5-ylamino)piperidine-1-carboxylate 10 (200 mg, 0.3 mmol) in 1,4-dioxane/water (5.0 mL: 5.0 mL), zinc powder (212 mg, 3.2 mmol) and ammonium chloride (170 mg, 3.2 mmol) were added. The reaction mixture was stirred at room temperature for 3 h. The reaction mixture was partitioned between ethyl acetate (100 mL) and water (50 mL). The organic layer was washed with brine solution (50 mL), dried over anhydrous sodium sulfate and concentrated under reduced pressure to afford 11 (90 mg, 47%) as off-white solid. MS m/z (M+H): 582.32

Step 4:

To a stirred solution of tert-butyl 3-(7-((2-amino-4-ethoxyphenyl)(tert-butoxycarbonyl)amino)-6-methylpyrazolo [1,5-a]pyrimidin-5-ylamino)piperidine-1-carboxylate 11 (90 mg, 0.15 mmol) in dichloromethane (10 mL), DIPEA (30 mg, 0.2 mmol) and acryloyl chloride (13.5 mg, 0.15 mmol) were added at −78° C. The reaction mixture was stirred for 10 min. Reaction mixture was quenched with bicarbonate solution (20 mL) and the resulting solution was partitioned between ethyl acetate (100 mL) and water (50 mL). The organic layer was dried over anhydrous sodium sulfate and concentrated under reduced pressure. The residue was purified by preparative thin layer chromatography to yield the Boc-protected acrylamide compound (17 mg, 17%) as off-white solid: MS m/z (M+H): 636.4. This material (17 mg, 0.03 mmol) was treated with (1:1) trifluoroacetic acid/dichloromethane (3.0 mL) at 0° C. The reaction mixture was stirred at room temperature for 1 hour. The reaction mixture was concentrated and co-distilled with dichloromethane thrice. The residue was purified by prep-HPLC to yield TFA salt of IV-2 (15 mg, 99%) as off-white solid. $^1$H NMR (400 MHz, DMSO-d$_6$) δ 1.32 (t, J=6.9 Hz, 3H), 1.48 (s, 3H), 1.59-1.72 (m, 2H), 1.90 (m, 2H), 2.77 (m, 2H), 3.20 (d, J=12.3 Hz, 1H), 3.99 (q, J=6.9 Hz, 2H), 4.37 (m, 1H), 5.75-5.78 (dd, J=1.8, 10.1 Hz, 1H), 5.98 (d, J=2.1 Hz, 1H), 6.16 (d, J=7.6 Hz, 1H), 6.25-6.30 (dd, J=2.2, 17.0 Hz, 1H), 6.45-6.52 (dd, J=10.2, 17.0 Hz, 1H), 6.71-6.74 (dd, J=2.8, 8.8 Hz, 1H), 6.85 (d, J=8.7 Hz, 1H), 7.21 (d, J=2.7 Hz, 1H), 7.80 (d, J=2.1 Hz, 1H), 8.18 (s, 1H), 8.55 (brs, 2H), 10.03 (s, 1H). MS m/z (M+H): 436.2

Example 63

Compound IV-4

N-(2-ethoxy-5-((5-(piperidin-3-ylamino)pyrazolo[1,5-a]pyrimidin-7-yl)amino)phenyl)acrylamide

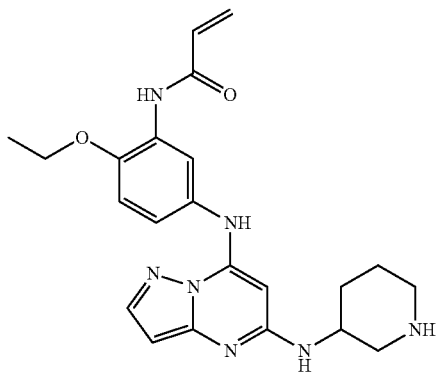 [SMILES: C=CC(=O)Nc1cc(Nc2cc(NC3CCCNC3)nc3ccnn23)ccc1OCC]

The title compound IV-4 was prepared as described for Example 61, with substitution of diethyl malonate as the starting material: Off-white solid (28 mg, 26%). $^1$H NMR (400 MHz, DMSO-d$_6$) δ 1.37 (t, J=6.9 Hz, 3H), 1.45 (m, 1H), 1.65 (m, 1H), 1.83 (m, 2H), 2.63 (m, 1H), 2.83 (m, 1H), 3.12 (brm, 1H), 3.36 (m, 1H), 4.09 (brs, 1H), 4.12 (q, J=7.0 Hz, 2H), 5.35 (s, 1H), 5.72 (dd, J=1.8, 10.2 Hz, 1H), 5.97 (s, 1H), 6.20-6.24 (dd, J=1.8, 16.9 Hz, 1H), 6.69 (dd, J=10.2, 16.9 Hz, 1H), 7.04-7.13 (m, 2H), 7.86 (d, J=1.7 Hz, 1H), 8.13 (s, 1H), 8.53 (brs, 2H), 9.32 (s, 1H). MS m/z (M+H): 422.3

Example 64

Compound IV-3

N-(5-ethoxy-2-((5-(piperidin-3-ylamino)pyrazolo [1,5-a]pyrimidin-7-yl)amino)phenyl)acrylamide

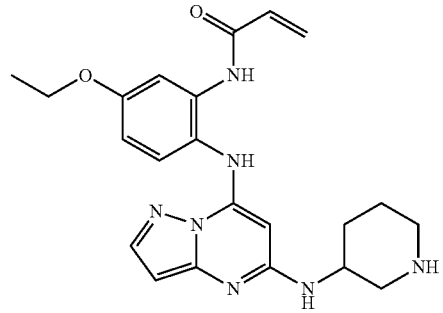 [SMILES: C=CC(=O)Nc1cc(OCC)ccc1Nc1cc(NC2CCCNC2)nc2ccnn12]

The title compound IV-3 was prepared as described for Example 62, with substitution of diethyl malonate as the starting material: Off-white solid, (15 mg, 99%). $^1$H NMR (400 MHz, DMSO-d$_6$) δ 1.33 (t, J=6.9 Hz, 3H), 1.60-1.65 (m, 2H), 1.83-1.86 (m, 2H), 2.82-2.87 (m, 2H), 3.11-3.18 (m, 2H), 4.01 (q, J=6.9 Hz, 2H), 4.07 (m, 1H), 5.72 (dd, J=1.9, 10.2 Hz, 1H), 5.93 (d, J=2.0 Hz, 1H), 6.22 (dd, J=1.8, 17.0 Hz, 1H), 6.42 (dd, J=9.9, 17.0 Hz, 1H), 6.84 (dd, J=2.8, 8.8 Hz, 1H), 7.31 (d, J=8.8 Hz, 1H), 7.39 (d, J=2.8 Hz, 1H), 7.83 (d, J=2.0 Hz, 1H), 8.48 (brm, 3H), 9.84 (s, 1H). MS m/z (M+H): 422.3

Example 65

Compound IV-b-1

N-(6-methyl-5-(piperidin-3-ylamino)pyrazolo [1,5-a]pyrimidin-7-yl)acrylamide

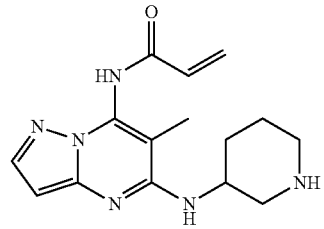 [SMILES: C=CC(=O)Nc1c(C)c(NC2CCCNC2)nc2ccnn12]

The title compound was prepared according to the schemes, steps, and intermediates described below.

Synthesis of 6-methylpyrazolopyrimidine Intermediates

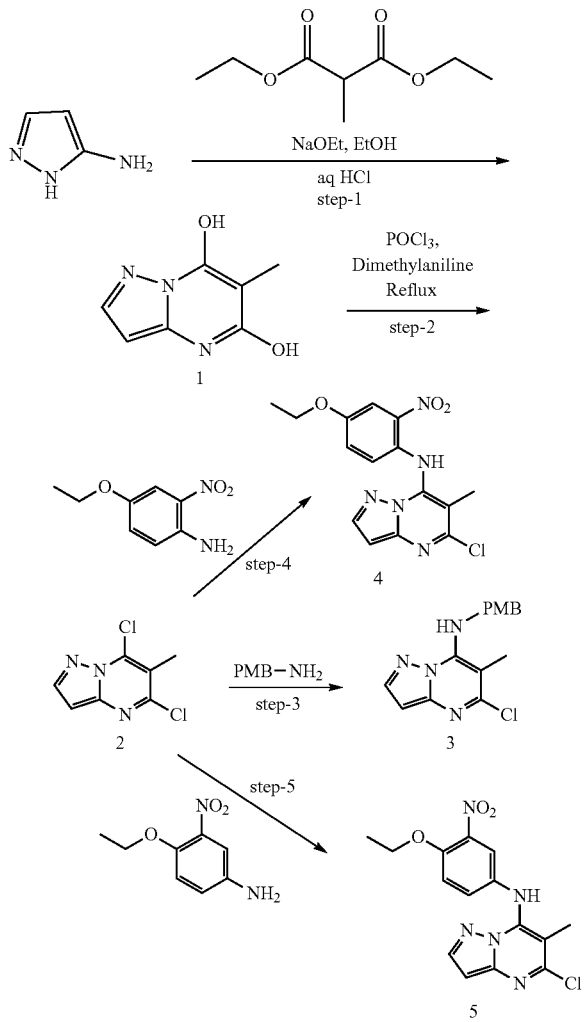

Step 1:

6-methylpyrazolo [1, 5-a]pyrimidine-5, 7-diol (1)

To a solution of sodium metal (8.6 g, 151.0 mmol) in ethanol (125 mL), 1H-pyrazol-5-amine (12.5 g, 151.0 mmol) and diethyl methyl malonate (2.6 g, 151.0 mmol) were added at room temperature. The reaction mixture was heated at 90° C. and stirred for 10 h. The solid formed was filtered. The solid was dissolved in water (1000 mL) and acidified with cold 2N HCl solution to pH~2. The solid obtained was filtered and dried to obtain 1 (11.0 g, 44%) as off-white solid. MS m/z (M−H): 164.1

Step 2:

5, 7-dichloro-6-methylpyrazolo [1, 5-a]pyrimidine (2)

6-methylpyrazolo [1, 5-a]pyrimidine-5, 7-diol (12.3 g, 74.5 mmol) was treated with excess POCl$_3$ (120 mL) and N,N-dimethylaniline (11.7 g, 97 mmol) at 0° C. The reaction mixture was heated at 80° C. for 12 h. The reaction mixture was concentrated to remove excess POCl$_3$ and neutralized with bicarbonate solution. The aqueous phase was extracted with ethyl acetate (500 mL). The organic phase was dried over anhydrous sodium sulfate and concentrated under reduced pressure. The residue was purified by silica gel column chromatography to obtain 2 (7.0 g, 47%) as a grey solid. 1H NMR (400 MHz, CDCl$_3$) δ 2.54 (s, 3H), 6.69 (d, J=2.2 Hz, 1H), 8.15 (d, J=2.2 Hz, 1H).

Step 3:

5-chloro-N-(4-methoxybenzyl)-6-methylpyrazolo [1,5-a]pyrimidin-7-amine (3)

To a solution of 5, 7-dichloro-6-methylpyrazolo [1, 5-a] pyrimidine (1.0 g, 5.0 mmol) in 2-propanol (50 mL), p-methoxybenzylamine (817 mg, 6.0 mmol) and triethylamine (989 mg, 10.0 mmol) were added at room temperature, and the resulting mixture was heated to 80° C. for 10 h. The reaction mixture was concentrated under reduced pressure. The residue was partitioned between ethyl acetate (100 mL) and water (50 mL). The organic phase was dried over anhydrous sodium sulfate and concentrated under reduce pressure. The residue was triturated with n-pentane to afford 3 (1.3 g, 87%) as an off-white solid. $^1$H NMR (400 MHz, DMSO-d$_6$) δ 2.28 (s, 3H), 3.68 (s, 3H), 5.03 (d, J=6.88 Hz, 2H), 6.35 (d, J=2.2 Hz, 1H), 6.86 (d, J=2.8 Hz, 2H), 7.20 (d, J=8.6 Hz, 2H), 7.92 (t, J=6.8 Hz, 1H), 8.08 (d, J=2.2 Hz, 1H). MS m/z (M+H): 303.1

Step 4:

5-chloro-N-(4-ethoxy-2-nitrophenyl)-6-methylpyrazolo [1,5-a]pyrimidin-7-amine (4)

To a solution of sodium hydride (750 mg, 0.5 mmol) in dimethylformamide (5.0 mL), 5,7-dichloro-6-methylpyrazolo[1,5-a]pyrimidine (2; 450 mg, 2.2 mmol) in tetrahydrofuran (8.0 mL) and 4-ethoxy-2-nitroaniline (455 mg, 2.5 mmol) was added at 0° C. The reaction mixture was heated to 70° C. for 4 h. The reaction mixture was partitioned between ethyl acetate (150 mL) and water (100 mL). The reaction mixture was dried over anhydrous sodium sulfate and concentrated under reduced pressure to obtain 4 (250 mg, 32%) as a yellow solid. $^1$H NMR (400 MHz, CDCl$_3$) δ 1.36 (t, J=6.9 Hz, 3H), 2.03 (s, 3H), 4.08 (q, J=6.9 Hz, 2H), 6.60 (d, J=2.3 Hz, 1H), 6.87 (d, J=9.0 Hz, 1H), 7.16-7.19 (dd, J=2.9, 9.0 Hz, 1H), 7.68 (d, J=2.9 Hz, 1H), 8.07 (d, J=2.2 Hz, 1H), 9.54 (s, 1H). MS m/z (M+H): 348.1

Step 5:

5-chloro-N-(4-ethoxy-3-nitrophenyl)-6-methylpyrazolo[1,5-a]pyrimidin-7-amine (IV-b-1)

To a solution of sodium hydride (750 mg, 0.5 mmol) in dimethylformamide (5.0 mL), 5,7-dichloro-6-methylpyrazolo[1,5-a]pyrimidine (2; 450 mg, 2.2 mmol) in tetrahydrofuran (8.0 mL) and 4-ethoxy-3-nitroaniline (455 mg, 2.5 mmol) was added at 0° C. The reaction mixture was heated to 70° C. for 4 h. The reaction mixture was partitioned between ethyl acetate (150 mL) and water (100 mL). The reaction mixture was dried over anhydrous sodium sulfate and concentrated under reduced pressure to obtain 5 (300 mg, 39%) as a yellow solid. $^1$H NMR (400 MHz, DMSO-d$_6$) δ 1.32 (t, J=6.9 Hz, 3H), 1.9 (s, 3H), 4.17 (q, J=6.9 Hz, 2H), 6.53 (d, J=2.2 Hz, 1H), 7.31 (d, J=9.0 Hz, 1H), 7.36-7.39 (dd, J=2.7, 9.0 Hz, 1H), 7.61 (d, J=2.6 Hz, 1H), 8.14 (d, J=2.2 Hz, 1H), 9.8 (s, 1H). MS m/z (M+H): 348.1

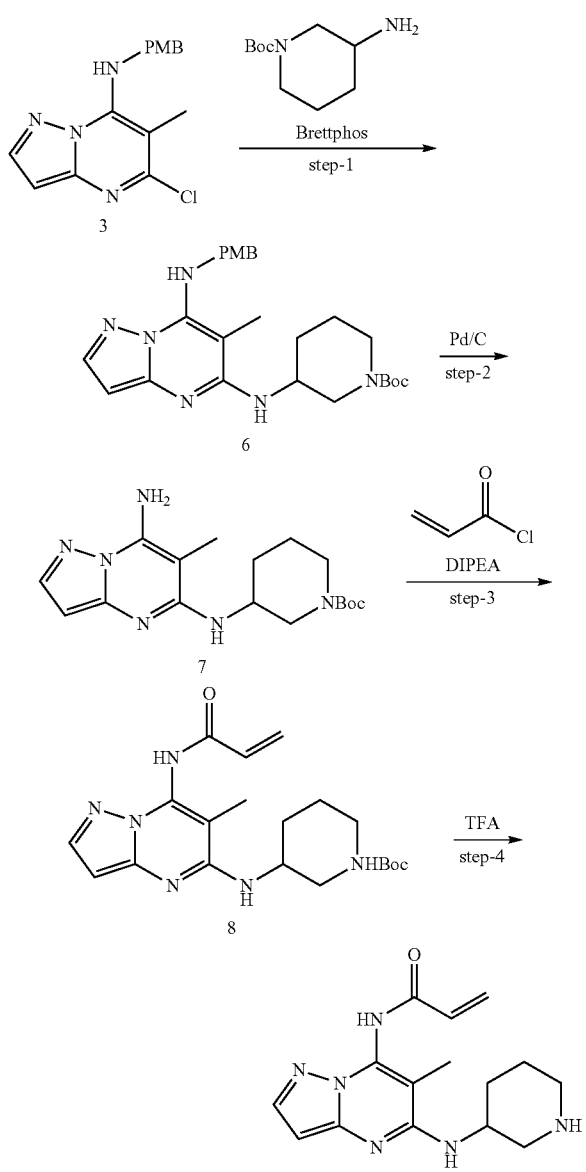

Step 1:

Tert-butyl 3-(7-(4-methoxybenzylamino)-6-methylpyrazolo [1,5-a]pyrimidin-5-ylamino)piperidine-1-carboxylate (6)

5-chloro-N-(4-methoxybenzyl)-6-methylpyrazolo[1,5-a]pyrimidin-7-amine (3; 600 mg, 2 mmol) was treated with 1-Boc-3-aminopiperidine (1.2 g, 6 mmol) followed by the addition of Brettphos (16 mg, 0.02 mmol) and Brettphos ligand (11 mg, 0.02 mmol) at room temperature under nitrogen. To this, LiHMDS (1M in tetrahydrofuran) (5 mL) was added, and the reaction mixture was heated to 100° C. for 12 h. Reaction mixture was quenched with IN HCl solution (5 mL) and partitioned between ethyl acetate (100 mL) and water (50 mL). The organic layer was dried over anhydrous sodium sulfate and concentrated under reduce pressure to yield 6 (320 mg, 34.5%) as yellow gummy solid. MS m/z (M+H): 467.3

Step 2:

Tert-butyl 3-(7-amino-6-methylpyrazolo [1,5-a]pyrimidin-5-ylamino)piperidine-1-carboxylate (7)

To a stirred solution of tert-butyl 3-(7-(4-methoxybenzylamino)-6-methylpyrazolo[1,5-a]pyrimidin-5-ylamino)piperidine-1-carboxylate (100 mg, 0.2 mmol) in methanol (10 mL), 10% palladium/carbon (20 mg) was added at room temperature under 50 psi hydrogen pressure. The reaction mixture was stirred at room temperature for 4 h. The reaction mixture was filtered through celite, and the filtrate was concentrated under reduce pressure. The residue was purified by preparative thin layer chromatography to yield 7 (60 mg, 81%) as white solid. MS m/z (M+H): 347.2

Step 3:

tert-butyl 3-((7-acrylamido-6-methylpyrazolo [1,5-a]pyrimidin-5-yl)amino)piperidine-1-carboxylate (8)

To a stirred solution of tert-butyl 3-(7-amino-6-methylpyrazolo[1,5-a]pyrimidin-5-ylamino)piperidine-1-carboxylate (60 mg, 0.2 mmol) in dichloromethane (5 mL), acryloyl chloride (8 mg, 0.1 mmol) was added at -20 OC. The reaction mixture was stirred at room temperature for 1 h. The reaction mixture was quenched with bicarbonate solution (20 mL). The resulting solution was partitioned between dichloromethane (50 mL) and water (30 mL). The organic layer was dried over anhydrous sodium sulfate and concentrated under reduced pressure. The residue was purified by preparative thin layer chromatography to yield 8 (20 mg, 28%) as white solid. MS m/z (M+H): 402.2

Step 4:

Compound 8 (20 mg, 0.05 mmol) was treated with (1:1) trifluoroacetic acid:dichloromethane (3.0 mL) at 0° C. The reaction mixture was stirred at room temperature for 1 h. The reaction mixture was concentrated and co-distilled with dichloromethane thrice. The residue was purified by preparative HPLC to yield TFA salt of compound IV-b-1 (14 mg, 74%) as off-white solid. $^1$H NMR (400 MHz, DMSO-d$_6$) δ 1.70 (m, 2H), 1.91 (s, 3H), 1.98 (m, 1H), 2.84 (m, 2H), 3.21 (d, J=12.9 Hz, 1H), 3.39 (d, J=10.1 Hz, 1H), 3.41 (m, 1H), 5.85-5.88 (dd, J=1.6, 10.2 Hz, 1H), 6.06 (d, J=2.1 Hz, 1H), 6.29-6.34 (dd, J=2.3, 17.1 Hz, 1H), 6.57-6.64 (m, 2H), 7.80 (d, J=2.1 Hz, 1H), 8.6 (brs, 2H), 10.7 (s, 1H). MS m/z (M+H): 301.1

Example 66

Compound V-7

N-(3-acrylamidophenyl)-1-oxo-1,2,3,4-tetrahydropyrazino[1,2-a]indole-7-carboxamide

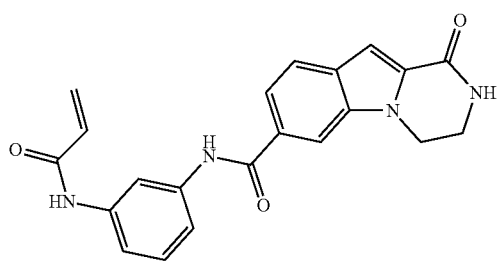 [SMILES: C=CC(=O)Nc1cccc(NC(=O)c2ccc3cc4n(c3c2)CCNC4=O)c1]

The title compound was prepared according to the schemes, steps, and intermediates described below.

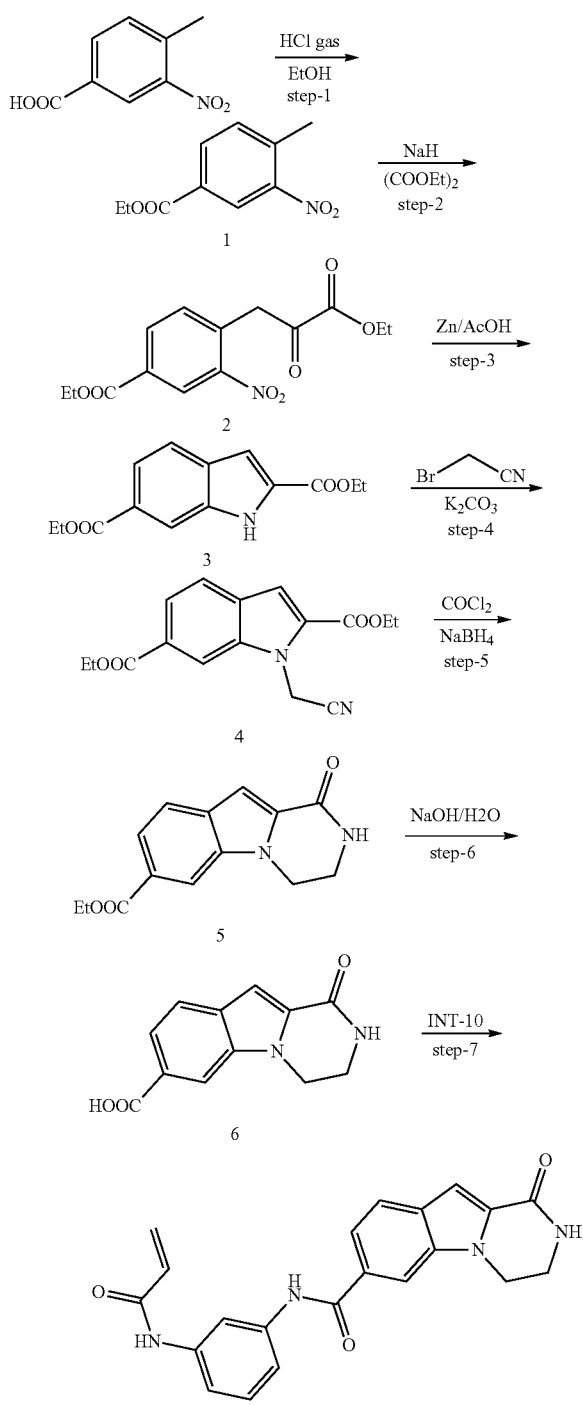

Step 1:

Ethyl 4-methyl-3-nitrobenzoate (1)

A stirring solution of 4-methyl-3-nitrobenzoic acid (10 g, 55.2 mmol) in EtOH (120 mL) at −5° C. was bubbled dry HCl gas for 10 minutes and then refluxed at 80° C. for 16 h. The reaction mixture was distilled off to obtain crude compound. Crude was dissolved in EtOAc (200 mL) and washed with cold saturated NaHCO₃ (2×200 mL), water (200 mL). The organic layer was dried over anhydrous sodium sulfate and concentrated under reduced pressure to obtain 1 (10.5 g, 91%) as colorless liquid. ¹H NMR (500 MHz, DMSO-d₆) δ 1.33 (t, J=7.0 Hz, 3H), 2.58 (s, 3H), 4.34 (q, J=7.0 Hz, 2H), 7.66 (d, J=7.5 Hz, 1H), 8.43 (d, J=7.5 Hz, 1H), 8.42 (s, 1H).

Step 2:

Ethyl 4-(3-ethoxy-2,3-dioxopropyl)-3-nitrobenzoate (2)

To a stirring solution of activated 60% NaH (4.65 g, 193.75 mmol) in dry THF (200 mL) was added ethyl 4-methyl-3-nitrobenzoate (1) (9.0 g, 43.02 mmol) and diethyl oxalate (12.6 g, 86.1 mmol) under nitrogen atmosphere for 5 minutes. The resulting reaction mixture was stirred at 60-70° C. for 12 h. After completion of the reaction (by TLC), the reaction mixture was cooled to room temperature, quenched with cold diluted HCl (pH=5) and partitioned between water (50 mL) and EtOAc (2×250 mL). The combined organic layers were dried over anhydrous sodium sulfate and concentrated under reduced pressure. The residue was purified by silica gel column chromatography to obtain 2 (8.5 g, 64%) as a yellow solid. ¹H NMR (400 MHz, CDCl₃) δ 1.42 (m, 6H), 4.42 (m, 4H), 6.86 (s, 1H), 6.93 (s, 1H), 8.21-8.24 (dd, J=1.6, 8.4 Hz, 1H), 8.35 (d, J=8.4 Hz, 1H), 8.52 (d, J=2.0 Hz, 1H). MS m/z (M−H): 308.2

Step 3:

Diethyl 1H-indole-2,6-dicarboxylate (3)

Ethyl 4-(3-ethoxy-2,3-dioxopropyl)-3-nitrobenzoate (2) (8.5 g, 27.5 mmol) was suspended in acetic acid (75 mL) and heated to 75° C. After the solid material was dissolved, water (56 mL) followed by activated zinc dust (17.9 g, 27.5 mmol) was added in small portions and the temperature was kept at 80° C. and stirred for 2 h. The reaction mixture was cooled to room temperature, diluted with EtOAc (50 mL) and filtered through a celite pad. Filtrate was washed with water (2×100 mL), saturated NaHCO₃ (2×100 mL) and brine solution (100 mL). The organic layer was dried over anhydrous sodium sulfate and concentrated under reduced pressure. The residue was purified by silica gel column chromatography to obtain 3 (6.0 g, 83%) as a yellow solid. ¹H NMR (500 MHz, DMSO-d₆) δ 1.33 (m, 6H), 4.34 (m, 4H), 7.21 (s, 1H), 7.65 (d, J=8.5 Hz, 1H), 7.75 (d, J=8.5 Hz, 1H), 8.12 (s, 1H), 12.25 (s, 1H). MS m/z (M−H): 259.9

Step 4:

Diethyl 1-(cyanomethyl)-1H-indole-2,6-dicarboxylate (4)

A stirring solution of diethyl 1H-indole-2,6-dicarboxylate (3) (6.0 g, 22.9 mmol) in dry DMF (60 mL) was added K₂CO₃ (9.52 g, 68.9 mmol) at room temperature and stirred under nitrogen atmosphere for 30 min. Then bromoacetonitrile (5.5 g, 45.9 mmol) was added to the reaction mixture and heated to 80° C. for 4 h. The reaction mixture was cooled to room temperature and treated with EtOAc (50 mL), brine solution (50 mL) and cold water (50 mL). The organic layer was separated, dried over anhydrous sodium sulfate and concentrated under reduced pressure. The residue was purified by silica gel column chromatography to obtain 4 (6.0 g, 87%) as off white solid. ¹H NMR (400 MHz, CDCl₃) δ 1.45 (m, 6H), 4.44 (m, 4H), 5.65 (s, 2H), 7.41 (s, 1H), 7.75 (d, J=8.4 Hz, 1H), 7.92-7.94 (dd, J=1.2, 8.4 Hz, 1H), 8.18 (s, 1H). MS m/z (M+H): 301.4

Step 5:

Ethyl 1-oxo-1,2,3,4-tetrahydropyrazino[1,2-a]indole-7-carboxylate (5)

To a suspension of diethyl 1-(cyanomethyl)-1H-indole-2,6-dicarboxylate (4) (200 mg, 0.66 mmol) in THF:MeOH (3 mL:4 mL) was added CoCl$_2$ (317 mg, 1.33 mmol). The resultant bright blue suspension was cooled to 0° C., and NaBH$_4$ (247 mg, 6.67 mmol) was added carefully in small portions. After the addition, the black colored reaction mixture was kept at room temperature for 1 h and then heated to 60-70° C. for 3 h. The reaction mixture was cooled to room temperature, diluted with EtOAc (100 mL) and filtered through celite pad. The filtrate was washed with 3N HCl (20 mL), water (20 mL), saturated NaHCO$_3$ (20 mL) and brine solution (30 mL). The organic layer was dried over anhydrous sodium sulfate and concentrated under reduced pressure. The residue was purified by silica gel column chromatography to obtain 5 (120 mg, 71%) as pale yellow solid. $^1$H NMR (400 MHz, DMSO-d$_6$) δ 1.35 (t, J=7.2 Hz, 3H), 3.67 (q, J=7.2 Hz, 2H), 4.37 (m, 4H), 7.11 (s, 1H), 7.68-7.71 (dd, J=1.2, 8.4 Hz, 1H), 7.77 (d, J=8.4 Hz, 1H), 8.19 (s, 1H), 8.27 (s, 1H). MS m/z (M+H): 259.1

Step 6:

1-oxo-1,2,3,4-tetrahydropyrazino[1,2-a]indole-7-carboxylic acid (6)

To a stirred solution of ethyl 1-oxo-1,2,3,4-tetrahydropyrazino[1,2-a]indole-7-carboxylate (5) (270 mg, 1.04 mmol) in THF:MeOH (5 mL:5 mL) was added IN NaOH solution (3 mL) dropwise and the resulting reaction was heated to 70° C. for 2 h. The reaction mixture was cooled to 0° C., water (10 mL) was added, and the mixture was acidified (pH=2) with 3N HCl (10 mL). The resulting white precipitate was filtered, washed with water and methanol and dried under vacuum to obtain 6 (170 mg, 71%) as off white solid. $^1$H NMR (400 MHz, DMSO-d$_6$) δ 3.66 (t, J=6.8 Hz, 2H), 4.37 (t, J=6.8 Hz, 2H), 7.09 (s, 1H), 7.67-7.69 (dd, J=1.2, 8.4 Hz, 1H), 7.74 (d, J=8.4 Hz, 1H), 8.17 (s, 1H), 8.24 (s, 1H), 12.77 (s, 1H). MS m/z (M−H): 229.2

Step 7:

To a solution of 1-oxo-1,2,3,4-tetrahydropyrazino[1,2-a]indole-7-carboxylic acid 6 (100 mg, 0.4 mmol) and N-(3-aminophenyl) acrylamide INT-10 (176 mg, 1 mmol) in dimethylformamide (2.0 mL), DIPEA (140 mg, 1 mmol) and HATU (344 mg, 0.9 mmol) were added at 0° C. The reaction mixture was warmed to room temperature and stirred for 30 min. The reaction mixture was quenched with water, and the solid suspension formed was filtered and dried. The residue was purified by preparative HPLC to afford V-7 (98.0 mg, 61%) as a white solid. $^1$H NMR (400 MHz, DMSO-d$_6$); δ 3.68 (t, J=6.8 Hz, 2H), 4.37 (t, J=6.2 Hz, 2H), 5.73-5.76 (dd, J=2.0, 10.1 Hz, 1H), 6.23-6.27 (dd, J=2.1, 17.1 Hz, 1H), 6.43-6.50 (dd, J=10.1, 16.9 Hz, 1H), 7.10 (d, J=0.5 Hz, 1H), 7.28 (t, J=8.0 Hz, 1H), 7.44 (m, 2H), 7.69-7.72 (dd, J=1.4, 8.4 Hz, 1H), 7.76-7.79 (d, J=8.4 Hz, 1H), 8.21 (s, 2H), 8.25 (s, 1H), 10.17 (s, 1H), 10.25 (s, 1H).

Example 67

Compound V-1

N-(3-acrylamido-4-(4-ethylpiperazin-1-yl)phenyl)-1-oxo-1,2,3,4-tetrahydropyrazino[1,2-a]indole-7-carboxamide

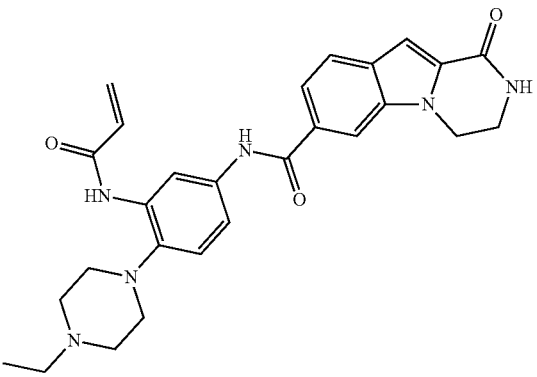 [SMILES: C=CC(=O)Nc1cc(NC(=O)c2ccc3cc4n(c3c2)CCNC4=O)ccc1N1CCN(CC)CC1]

The title compound V-1 was prepared as described in Example 66, by substituting amine INT-36 for INT-10 in step 7: White powder, 3.6 mg, 18% (2 steps). $^1$H NMR (400 MHz, DMSO-d$_6$) δ 1.25 (t, 3H), 2.98 (m, 2H), 3.15 (m, 2H), 3.20-3.40 (m, 6H), 3.55 (m, 2H), 3.70 (m, 1H), 4.38 (m, 1H), 5.80 (d, 1H), 6.30 (d, 1H), 6.72 (dd, 1H), 7.10 (s, 1H), 7.21 (d, 1H), 7.70 (m, 1H), 7.75 (d, 1H), 8.20 (s, 1H), 8.28 (s, 1H), 8.50 (s, 1H), 9.12 (s, 1H), 9.31 (s, br, 1H), 10.28 (s, 1H). MS m/z (M+H): 487.3

Example 68

Compound V-2

N-((3R,4R)-4-methyl-1-(1-oxo-1,2,3,4-tetrahydropyrazino[1,2-a]indole-7-carbonyl)piperidin-3-yl)acrylamide

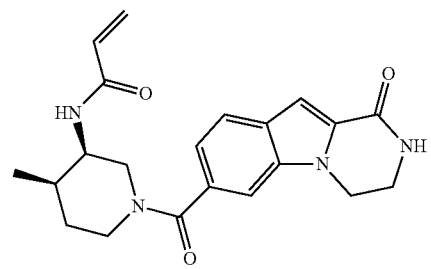 [SMILES: C=CC(=O)N[C@H]1CN(C(=O)c2ccc3cc4n(c3c2)CCNC4=O)CC[C@H]1C]

The title compound V-2 was prepared as described in Example 66, by substituting amine INT-35 (R,R-isomer) for INT-10 in step 7: White powder, 15 mg, 15%. $^1$H NMR (400 MHz, DMSO-d$_6$) δ 0.80 (d, 3H), 1.50 (m, 1H), 1.65 (m, 1H), 1.92 (m, 1H), 2.80 (m, 1H), 3.11 (m, 1H), 3.30-3.55 (m, 3H), 3.80 (m, 1H), 4.10-4.30 (m, 2H), 4.45 (m, 1H), 5.60 (d, 1H), 6.00 (m, 1H), 6.50 (m, 1H), 7.01 (m, 2H), 7.40-7.68 (m, 2H), 7.90 (s, 1H), 8.20 (s, 1H). MS m/z (M+H): 381.1

Example 69

Compound V-3

(R)—N-(1-acryloylpiperidin-3-yl)-1-oxo-1,2,3,4-tetrahydropyrazino[1,2-a]indole-7-carboxamide

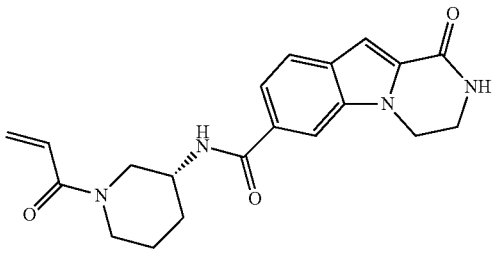 [SMILES: C=CC(=O)N1CCC[C@@H](NC(=O)c2ccc3cc4n(c3c2)CCNC4=O)C1]

The title compound V-3 was prepared as described in Example 66, by substituting amine INT-34 (R-isomer) for INT-10 in step 7: Off white powder, 38 mg, 26% (2 steps). $^1$H NMR (400 MHz, DMSO-$d_6$) δ 1.46 (m, 1H), 1.55-1.75 (m, 1H), 1.81 (m, 1H), 1.92 (m, 1H), 2.90-3.08 (m, 1H), 3.15 (m, 1H), 3.62 (m, 1H), 3.80 (m, 1H), 3.90-4.10 (m, 2H), 4.29 (m, 2H), 5.70 (t, 1H), 6.10 (dd, 1H), 6.70-6.90 (m, 1H), 7.05 (s, 1H), 7.58 (d, 1H), 7.65 (d, 1H), 8.02 (s, 1H), 8.23 (s, 1H), 8.30 (d, 1H). MS m/z (M+H): 367.1

Example 70

Compound V-8

N-(2-acrylamidophenyl)-1-oxo-1,2,3,4-tetrahydropyrazino[1,2-a]indole-7-carboxamide

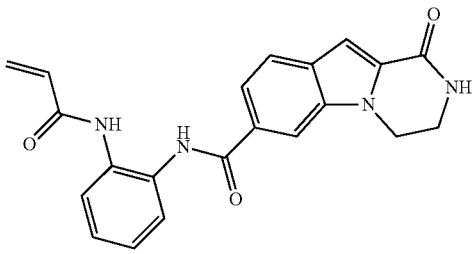 [SMILES: C=CC(=O)Nc1ccccc1NC(=O)c1ccc2cc3n(c2c1)CCNC3=O]

The title compound V-8 was prepared as described in Example 66, by substituting amine INT-13 for INT-10 in step 7: (82 mg, 51%) as a brown solid. $^1$H NMR (400 MHz, DMSO-$d_6$); δ 3.68 (t, J=7.3 Hz, 2H), 4.34 (t, J=6.1 Hz, 2H), 5.76-5.79 (dd, J=1.9, 10.1 Hz, 1H), 6.28-6.32 (dd, J=1.8, 17.0 Hz, 1H), 6.47-6.54 (dd, J=10.1, 17.0 Hz, 1H), 7.10 (d, J=0.5 Hz, 1H), 7.26 (m, 2H), 7.61 (d, J=6.7 Hz, 1H), 7.68 (m, 2H), 7.78 (d, J=8.3 Hz, 1H), 8.17 (s, 1H), 8.25 (s, 1H), 9.91 (s, 2H).

Example 71

Compound V-9

N-(1-acryloylindolin-6-yl)-1-oxo-1,2,3,4-tetrahydropyrazino[1,2-a]indole-7-carboxamide

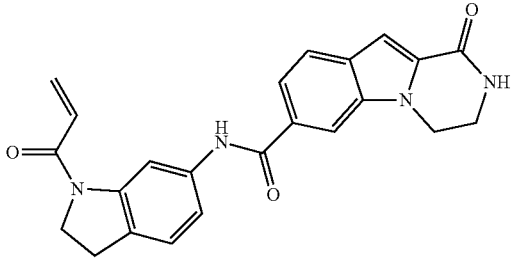 [SMILES: C=CC(=O)N1CCc2ccc(NC(=O)c3ccc4cc5n(c4c3)CCNC5=O)cc21]

The title compound V-9 was prepared as described in Example 66, by substituting amine INT-32 for INT-10 in step 7: Off white solid, 70 mg, 41%. 1H NMR (400 MHz, DMSO-$d_6$) δ 3.14 (t, J=7.6 Hz, 2H), 3.69 (s, 2H), 4.24 (t, J=7.2 Hz, 2H), 4.38 (t, J=6.0 Hz, 2H), 5.83 (d, J=11.6 Hz, 1H), 6.29-6.33 (dd, J=1.6, 16.4 Hz, 1H), 6.74-6.80 (dd, J=10.8, 16.0 Hz, 1H), 7.10 (s, 1H), 7.22 (d, J=8.0 Hz, 1H), 7.57 (d, J=8.0 Hz, 1H), 7.75 (m, 2H), 8.24 (s, 2H), 8.57 (s, 1H), 10.21 (s, 1H). MS m/z (M+H): 401.2

Example 72

Compound V-10

Racemic N-((1S,2R)-2-acrylamidocyclohexyl)-1-oxo-1,2,3,4-tetrahydropyrazino[1,2-a]indole-7-carboxamide

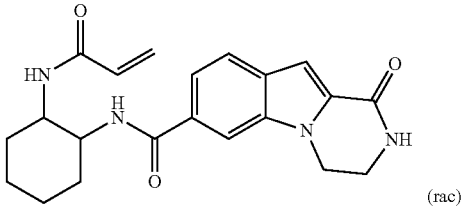 [SMILES: C=CC(=O)NC1CCCCC1NC(=O)c1ccc2cc3n(c2c1)CCNC3=O]

The title compound V-10 was prepared as described in Example 66, by substituting amine INT-33 (rac) for INT-10 in step 7: Off white solid, 57 mg, 35%. $^1$H NMR (500 MHz, DMSO-$d_6$) δ 1.66 (m, 8H), 3.65 (s, 2H), 4.10 (bs, 1H), 4.18 (bs, 1H), 4.30 (d, J=5.5 Hz, 1H), 4.31 (d, J=5.5 Hz, 1H), 5.56-5.58 (dd, J=2.0, 10.0 Hz, 1H), 6.06-6.09 (dd, J=2.0, 17.0 Hz, 1H), 6.34-6.39 (dd, J=10.0, 17.0 Hz, 1H), 7.05 (s, 1H), 7.52 (d, J=9.0 Hz, 1H), 7.69 (d, J=8.5 Hz, 1H), 7.80 (d, J=8.0 Hz, 1H), 7.91 (d, J=7.0 Hz, 1H), 7.96 (s, 1H), 8.21 (s, 1H). MS m/z (M+H): 381.2

Example 73

Compound V-11

(R)—N-(1-acryloylpiperidin-3-yl)-1-oxo-1,2,3,4-tetrahydropyrazino[1,2-a]indole-7-carboxamide

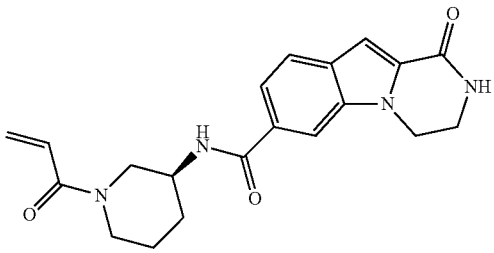 [SMILES: C=CC(=O)N1CCC[C@H](NC(=O)c2ccc3cc4n(c3c2)CCNC4=O)C1]

The title compound V-11 was prepared as described in Example 66, by substituting amine INT-38 (S-isomer) for INT-10 in step 7: 40 mg, off white solid. $^1$H NMR (400 MHz, DMSO-d$_6$): δ 1.46 (m, 1H), 1.67 (m, 1H), 1.81 (m, 1H), 1.97 (m, 1H), 3.00 (m, 1H), 3.18 (m, 1H), 3.67 (s, 2H), 3.83 (s, 1H), 4.02 (m, 2H), 4.33 (m, 2H), 5.66 (t, J=8.0 Hz, 1H), 6.06-6.12 (dd, J=7.2, 16.8 Hz, 1H), 6.76 (m, 1H), 7.07 (s, 1H), 7.60 (d, J=8.4 Hz, 1H), 7.72 (d, J=8.0 Hz, 1H), 8.07 (s, 1H), 8.22 (s, 1H), 8.29 (t, J=7.2 Hz, 1H). MS m/z (M+H): 367

Example 74

Compound V-19

N-(2-acryloylisoindolin-4-yl)-1-oxo-1,2,3,4-tetrahydropyrazino[1,2-a]indole-7-carboxamide

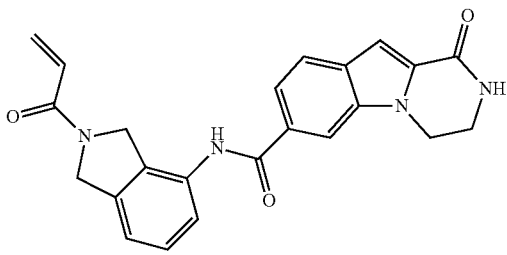 [SMILES: C=CC(=O)N1Cc2cccc(NC(=O)c3ccc4cc5n(c4c3)CCNC5=O)c2C1]

The title compound V-19 was prepared as described in Example 66, by substituting amine INT-37 for INT-10 in step 7: Off white solid, 42 mg, 24%. $^1$H NMR (500 MHz, DMSO-d$_6$): δ 3.68 (m, 2H), 4.37 (m, 2H), 4.74 (s, 1H), 4.78 (s, 1H), 4.96 (s, 1H), 5.02 (s, 1H), 5.73 (m, 1H), 6.19-6.23 (dd, J=7.0, 16.5 Hz, 1H), 6.67 (m, 1H), 7.11 (s, 1H), 7.21 (m, 1H), 7.37 (m, 2H), 7.76 (m, 2H), 8.22 (s, 1H), 8.25 (s, 1H), 10.14 (s, 1H). MS m/z (M+H): 401.4

Example 75

Compound V-6

N-(4-acryloyl-3,4-dihydro-2H-benzo[b][1,4]oxazin-6-yl)-1-oxo-1,2,3,4-tetrahydropyrazino[1,2-a]indole-7-carboxamide

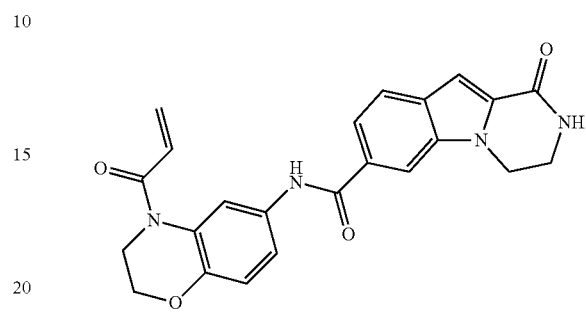

The title compound was prepared according to the schemes, steps, and intermediates described below.

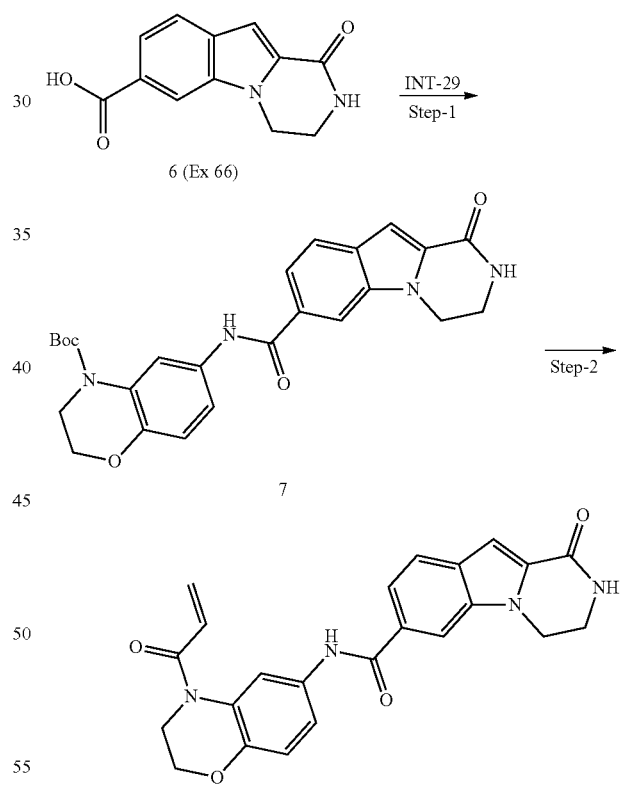

Step 1:

tert-butyl 6-(1-oxo-1,2,3,4-tetrahydropyrazino[1,2-a]indole-7-carboxamido)-2H-benzo[b][1,4]oxazine-4(3H)-carboxylate (7)

To a solution of 1-oxo-1,2,3,4-tetrahydropyrazino[1,2-a]indole-7-carboxylic acid 6 from Example 66 (300 mg, 1.3 mmol) in dimethylformamide (5 mL), DIPEA (504 mg, 4 mmol) and HATU (991 mg, 3 mmol) were added at 0° C.

followed by the addition of tert-butyl 6-amino-2H-benzo[b][1,4]oxazine-4(3H)-carboxylate INT-29 (487 mg, 1.9 mmol). The reaction mixture was stirred at room temperature for 5 h. The reaction mixture was quenched with water (50 mL), and the solid obtained was filtered and dried. The residue was purified by silica gel column chromatography to afford 7 (150 mg, 25%) as a white solid.

Step 2:

To a solution of 7 (150 mg, 0.3 mmol) in dichloromethane (5.0 mL) at 0° C., trifluoroacetic acid (3.0 mL) was added. The reaction mixture was stirred at room temperature for 2 h. The reaction mixture was concentrated under reduced pressure and co-distilled with dichloromethane thrice. The residue was triturated with n-pentane and diethyl ether to afford a pale yellow solid (100 mg, 85%) which was used without further purification. To a solution of crude TFA salt (50 mg, 0.14 mmol) in N-methyl pyrrolidinone (2.0 mL), DIPEA (53.0 mg, 0.4 mmol) and acryloyl chloride (19.0 mg, 0.2 mmol) were added at 0° C. The reaction mixture was stirred at room temperature for 2 h. The reaction mixture was partitioned between ethyl acetate (50 mL) and water (50 mL). The organic layer was dried over anhydrous sodium sulfate and concentrated under reduced pressure. The residue was purified by preparative HPLC to yield V-6 (23 mg, 40%) as white solid. $^1$H NMR (400 MHz, DMSO-$d_6$); δ 3.69 (t, J=7.0 Hz, 2H), 3.92 (t, J=4.3 Hz, 2H), 4.27 (t, J=4.9, Hz, 2H), 4.36 (t, J=6.3 Hz, 2H), 5.83-5.86 (dd, J=2.0, 10.3 Hz, 1H), 6.28-6.33 (dd, J=2.0, 16.7 Hz, 1H), 6.83-6.90 (dd, J=10.3, 16.7 Hz, 1H), 6.92 (s, 1H), 7.09 (s, 1H), 7.46-7.49 (dd, J=2.4, 8.8 Hz, 1H), 7.68 (d, J=1.3 Hz, 1H), 7.70 (d, J=1.2 Hz, 1H) 7.95 (brs, 1H), 8.18 (s, 1H), 8.25 (s, 1H), 10.1 (s, 1H).

Example 76

Compound V-4

(E)-N-(4-(4-(dimethylamino)but-2-enoyl)-3,4-di-hydro-2H-benzo[b][1,4]oxazin-6-yl)-1-oxo-1,2,3,4-tetrahydropyrazino[1,2-a]indole-7-carboxamide

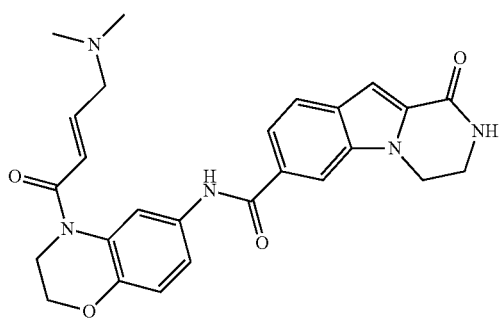 [SMILES: CN(C)C/C=C/C(=O)N1CCOc2ccc(NC(=O)c3ccc4cc5n(c4c3)CCNC5=O)cc21]

The title compound V-4 was prepared as described in Example 75 by substituting (E)-4-(dimethylamino)but-2-enoyl chloride INT-30 for acryloyl chloride in step 2. To a stirred solution of 7 (50 mg, 0.14 mmol) in N-methyl pyrrolidinone (2.0 mL), DIPEA (53.0 mg, 0.4 mmol) and (E)-4-(dimethylamino)but-2-enoyl chloride INT-30 (31.0 mg, 0.2 mmol) were added at 0° C. The reaction mixture was stirred at room temperature for 1 h. The reaction mixture was partitioned between ethyl acetate (50 mL) and water (50 mL). The organic layer was dried over anhydrous sodium sulfate and concentrated under reduced pressure. The residue was purified by preparative HPLC to afford V-4 (5.0 mg, 8%) as a white solid. $^1$H NMR (400 MHz, DMSO-$d_6$) δ 2.13 (s, 6H), 3.07 (d, J=4.8 Hz, 2H), 3.67 (m, 2H), 3.92 (t, J=4.6 Hz, 2H), 4.26 (t, J=4.6 Hz, 2H), 4.35 (t, J=5.8 Hz, 2H), 6.65 (d, J=15.2 Hz, 1H), 6.74-6.81 (dt, J=5.8, 11.6 Hz, 1H), 6.90 (d, J=8.8 Hz, 1H), 7.09 (s, 1H), 7.40-7.43 (dd, J=2.3, 8.8 Hz, 1H), 7.67-7.69 (dd, J=1.4, 8.5 Hz, 1H), 7.76 (d, J=8.4 Hz, 1H), 7.98 (brs, 1H), 8.17 (s, 1H), 8.24 (s, 1H), 10.16 (d, J=3.8 Hz, 1H).

Example 77

Compound V-5

(E)-N-(2-(4-(dimethylamino)but-2-enamido)phenyl)-1-oxo-1,2,3,4-tetrahydropyrazino[1,2-a]indole-7-carboxamide

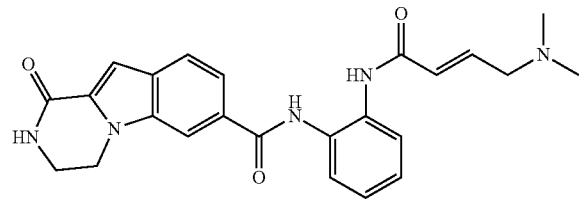 [SMILES: CN(C)C/C=C/C(=O)Nc1ccccc1NC(=O)c1ccc2cc3n(c2c1)CCNC3=O]

The title compound was prepared according to the schemes, steps, and intermediates described below.

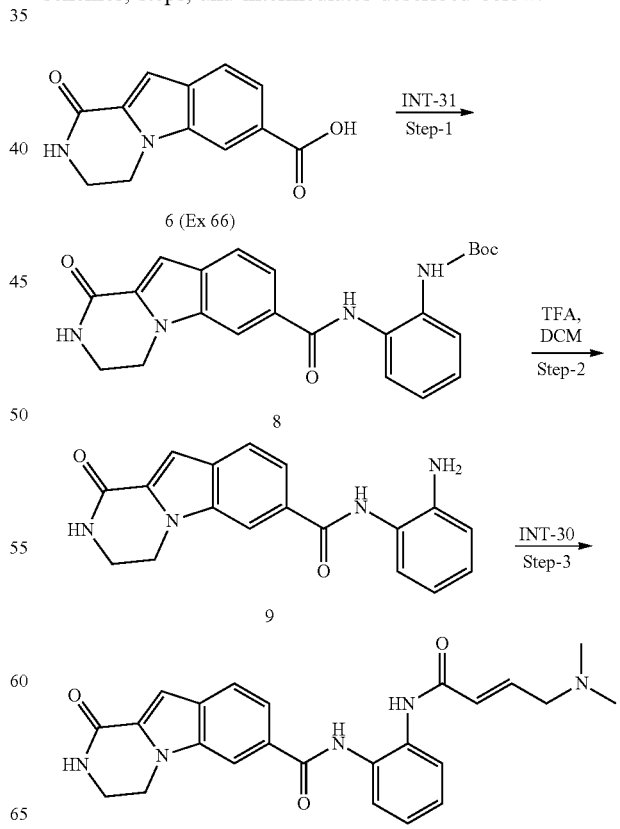

Step 1:

Tert-butyl 2-(1-oxo-1,2,3,4-tetrahydropyrazino[1,2-a]indole-7-carboxamido) phenylcarbamate (8)

To a solution of 1-oxo-1,2,3,4-tetrahydropyrazino[1,2-a]indole-7-carboxylic acid 6 from Example 66 (300 mg, 1.3 mmol) in dimethylformamide (5 mL), DIPEA (504 mg, 4 mmol) and HATU (991 mg, 3 mmol) were added at 0° C. followed by the addition of tert-butyl 2-aminophenylcarbamate INT-31 (407 mg, 2.0 mmol). The reaction mixture was stirred at room temperature for 4 h. The reaction mixture was quenched with water (50 mL), and the solid observed was filtered and dried. The crude residue was purified by silica gel column chromatography to afford 8 (150 mg, 27%) as a pale yellow solid. MS m/z (M+H): 421.2

Step 2:

N-(2-aminophenyl)-1-oxo-1,2,3,4-tetrahydropyrazino[1,2-a]indole-7-carboxamide (9)

To a stirred solution of tert-butyl 2-(1-oxo-1,2,3,4-tetrahydropyrazino[1,2-a]indole-7-carboxamido) phenylcarbamate 8 (150 mg, 0.35 mmol) in dichloromethane (5.0 mL), trifluoroacetic acid (3.0 mL) was added at 0° C. The reaction mixture was stirred at room temperature for 2 h. The reaction mixture was concentrated under reduced pressure and co-distilled with dichloromethane thrice. The residue was triturated with n-pentane and diethyl ether to afford 9 (100 mg, 88%) as a yellow solid. Crude compound was used as such without further purification for the next step. MS m/z (M+H): 321.2

Step 3:

To a solution of N-(2-aminophenyl)-1-oxo-1,2,3,4-tetrahydropyrazino[1,2-a]indole-7-carboxamide 9 (50.0 mg, 0.15 mmol) in N-methyl pyrrolidinone (2.0 mL), DIPEA (60.0 mg, 0.5 mmol) and (E)-4-(dimethylamino)but-2-enoyl chloride INT-30 (33.0 mg, 0.2 mmol) were added at 0° C. The reaction mixture was stirred at room temperature for 2 h. The reaction mixture was partitioned between ethyl acetate (50 mL) and water (50 mL). The organic layer was dried over anhydrous sodium sulfate and concentrated under reduced pressure. The residue obtained was purified by preparative HPLC to afford V-5 (11 mg, 16%) as a brown solid. 1H NMR (400 MHz, DMSO-d$_6$) δ 2.13 (s, 6H), 3.02 (d, J=4.9 Hz, 2H), 3.67 (m, 2H), 4.34 (t, J=6.0 Hz, 2H), 6.33 (d, J=15.5 Hz, 1H), 6.76-6.83 (dt, J=6.0, 11.8 Hz, 1H), 7.10 (s, 1H), 7.19-7.26 (m, 2H), 7.57-7.60 (m, 1H), 7.66-7.70 (m, 2H), 7.78 (d, 8.4, 1H), 8.17 (s, 1H), 8.25 (s, 1H), 9.89 (s, 1H), 9.95 (s, 1H); MS m/z (M+H): 432.3

Example 78

Compound V-23

N-(4-acryloyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide

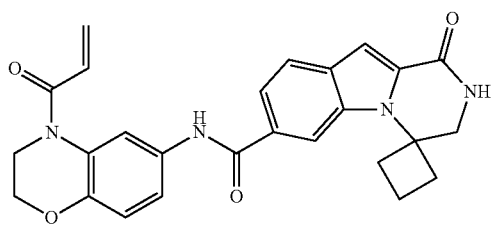 [SMILES: C=CC(=O)N1CCOc2ccc(NC(=O)c3ccc4cc5n(c4c3)C3(CCC3)CNC5=O)cc21]

The title compound was prepared according to the schemes, steps, and intermediates

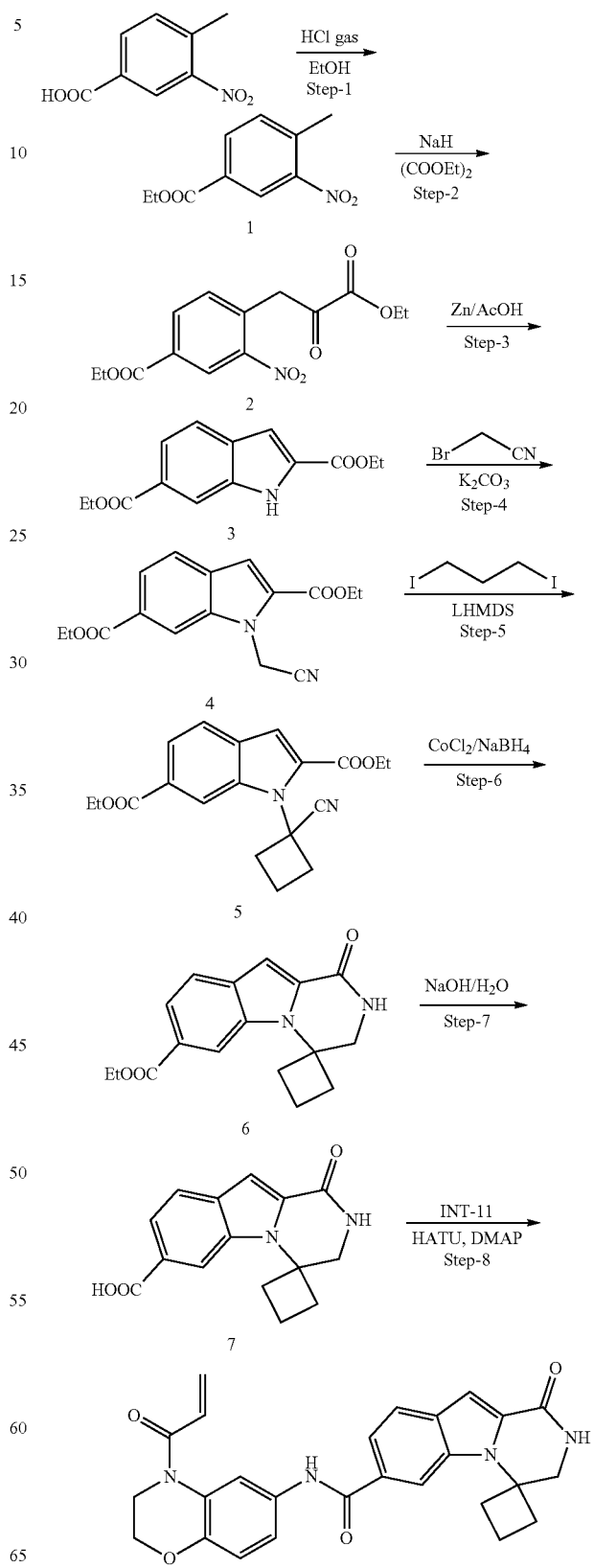

Step 1:

Ethyl 4-methyl-3-nitrobenzoate (1)

A stirring solution of 4-methyl-3-nitrobenzoic acid (10 g, 55.2 mmol) in EtOH (120 mL) at −5° C. was bubbled with dry HCl gas for 10 minutes and then refluxed at 80° C. for 16 h. The reaction mixture was distilled off to obtain crude compound. Crude was dissolved in EtOAc (200 mL) and washed with cold saturated NaHCO$_3$ (2×200 mL), water (200 mL). The organic layer was dried over anhydrous sodium sulfate and concentrated under reduced pressure to obtain 1 (10.5 g, 91%) as colorless liquid. $^1$H NMR (500 MHz, DMSO-d$_6$): δ 1.33 (t, J=7.0 Hz, 3H), 2.58 (s, 3H), 4.34 (q, J=7.0 Hz, 2H), 7.66 (d, J=7.5 Hz, 1H), 8.43 (d, J=7.5 Hz, 1H), 8.42 (s, 1H).

Step 2:

Ethyl 4-(3-ethoxy-2,3-dioxopropyl)-3-nitrobenzoate (2)

To a stirring solution of activated 60% NaH (4.65 g, 193.75 mmol) in dry THF (200 mL) was added ethyl 4-methyl-3-nitrobenzoate (1) (9.0 g, 43.02 mmol) and diethyl oxalate (12.6 g, 86.1 mmol) under nitrogen atmosphere for 5 minutes. The resulting reaction mixture was stirred at 60-70° C. for 12 h. The reaction mixture was cooled to room temperature, quenched with cold diluted HCl (pH=5) and partitioned between water (50 mL) and EtOAc (2×250 mL). The combined organic layers were dried over anhydrous sodium sulfate and concentrated under reduced pressure. The residue was purified by silica gel column chromatography to obtain 2 (8.5 g, 64%) as a yellow solid. $^1$H NMR (400 MHz, CDCl$_3$): δ 1.42 (m, 6H), 4.42 (m, 4H), 6.86 (s, 1H), 6.93 (s, 1H), 8.21-8.24 (dd, J=1.6, 8.4 Hz, 1H), 8.35 (d, J=8.4 Hz, 1H), 8.52 (d, J=2.0 Hz, 1H). MS m/z (M−H): 308.2

Step 3:

Diethyl 1H-indole-2,6-dicarboxylate (3)

Ethyl 4-(3-ethoxy-2,3-dioxopropyl)-3-nitrobenzoate (2) (8.5 g, 27.5 mmol) was suspended in acetic acid (75 mL) and heated to 75° C. After the solid material was dissolved, water (56 mL) followed by activated zinc dust (17.9 g, 27.5 mmol) was added in small portions while the temperature was kept at 80° C. with stirring for 2 h. The reaction mixture was cooled to room temperature, diluted with EtOAc (50 mL) and filtered through a celite pad. Filtrate was washed with water (2×100 mL), saturated NaHCO$_3$ (2×100 mL) and brine solution (100 mL). The organic layer was dried over anhydrous sodium sulfate and concentrated under reduced pressure. The residue was purified by silica gel column chromatography to obtain 3 (6.0 g, 83%) as a yellow solid. $^1$H NMR (500 MHz, DMSO-d$_6$): δ 1.33 (m, 6H), 4.34 (m, 4H), 7.21 (s, 1H), 7.65 (d, J=8.5 Hz, 1H), 7.75 (d, J=8.5 Hz, 1H), 8.12 (s, 1H), 12.25 (s, 1H). MS m/z (M−H): 259.9

Step 4:

Diethyl 1-(cyanomethyl)-1H-indole-2,6-dicarboxylate (4)

A stirring solution of diethyl 1H-indole-2,6-dicarboxylate (3) (6.0 g, 22.9 mmol) in dry DMF (60 mL) was added K$_2$CO$_3$ (9.52 g, 68.9 mmol) at room temperature and stirred under nitrogen atmosphere for 30 min. Then bromoacetonitrile (5.5 g, 45.9 mmol) was added to the reaction mixture and heated to 80° C. for 4 h. The reaction mixture was cooled to room temperature and treated with EtOAc (50 mL), brine solution (50 mL) and cold water (50 mL). The organic layer was separated, dried over anhydrous sodium sulfate and concentrated under reduced pressure. The residue was purified by silica gel column chromatography to obtain 4 (6.0 g, 87%) as off white solid. $^1$H NMR (400 MHz, CDCl$_3$): δ 1.45 (m, 6H), 4.44 (m, 4H), 5.65 (s, 2H), 7.41 (s, 1H), 7.75 (d, J=8.4 Hz, 1H), 7.92-7.94 (dd, J=1.2, 8.4 Hz, 1H), 8.18 (s, 1H). MS m/z (M+H): 301.4

Step 5:

Diethyl 1-(1-cyanocyclobutyl)-1H-indole-2,6-dicarboxylate (5)

To a mixture of diethyl 1-(cyanomethyl)-1H-indole-2,6-dicarboxylate (4) (1.0 g, 3.33 mmol) and 1,3-diiodopropane (1.48 g, 4.99 mmol) in dry THF (25 mL) was added LiHMDS (1 M in THF) (7.33 mL, 7.33 mmol) dropwise for 20 minutes at 0° C. and then further continued for 15 minutes. Progress of the reaction was monitored by TLC and LCMS. The reaction mass was quenched with diluted HCl solution (pH=5.0) and extracted with EtOAc (2×30 mL). Combined organic layers were dried over anhydrous sodium sulfate and concentrated under reduced pressure. The residue was purified by silica gel column chromatography to obtain 5 (400 mg, 35%) as yellow solid. $^1$H NMR (400 MHz, CDCl$_3$): δ 1.41 (m, 6H), 2.00 (m, 1H), 2.42 (m, 1H), 2.81 (m, 2H), 3.33 (m, 2H), 4.41 (m, 4H), 7.29 (s, 1H), 7.69 (d, J=8.0 Hz, 1H), 7.86-7.89 (dd, J=1.2, 8.4 Hz, 1H), 8.10 (s, 1H). MS m/z (M+H): 341.3

Step 6:

Ethyl 1'-oxo-2',3'-dihydro-1'H-spiro[cyclobutane-1,4'-pyrazino[1,2-a]indole]-7'-carboxylate (6)

To a suspension of diethyl 1-(1-cyanocyclobutyl)-1H-indole-2,6-dicarboxylate (5) (325 mg, 0.95 mmol) in THF:MeOH (12 mL:6 mL) was added CoCl$_2$ (455 mg, 1.9 mmol). Resultant bright blue suspension was cooled to 0° C. and NaBH$_4$ (354 mg, 9.5 mmol) was added carefully in small portions. After the addition, black colored reaction mixture was kept at room temperature for 1 h and then heated to 70° C. for 3 h. The reaction mixture was cooled to room temperature diluted with EtOAc (100 mL) and filtered through celite pad and washed with EtOAc (2×15 mL). The filtrate was dried over anhydrous sodium sulfate and concentrated under reduced pressure. The residue was purified by silica gel column chromatography to obtain 6 (160 mg, 56%) as pale yellow solid. $^1$H NMR (500 MHz, DMSO-d$_6$): δ 1.35 (t, J=7.2 Hz, 3H), 2.08 (t, J=9.0 Hz, 2H), 2.34 (t, J=10.0 Hz, 2H), 2.92 (m, 2H), 3.72 (s, 2H), 4.35 (q, J=7.5 Hz, 2H), 7.17 (s, 1H), 7.72 (d, J=9.0 Hz, 1H), 7.80 (d, J=8.0 Hz, 1H), 8.34 (s, 1H), 8.55 (s, 1H). MS m/z (M+H): 299.3

Step 7:

1'-oxo-2',3'-dihydro-1'H-spiro[cyclobutane-1,4'-pyrazino[1,2-a]indole]-7'-carboxylic acid (7)

To a stirred solution of ethyl 1'-oxo-2',3'-dihydro-1'H-spiro[cyclobutane-1,4'-pyrazino[1,2-a]indole]-7'-carboxylate (6) (160 mg, 0.53 mmol) in THF:MeOH (7 mL:7 mL) was added 1N NaOH solution (1.6 mL) dropwise, and the resulting reaction mixture was heated to 70° C. for 2 h. The reaction mixture was cooled to 0° C., water (25 mL) was added, and the mixture was acidified with diluted HCl (10 mL) (pH=4) and extracted with EtOAc (2×20 mL). Combined organic layers were dried over anhydrous sodium sulfate and concentrated under reduced pressure. The residue was washed with pentane (2×5 mL) and dried under vacuum to obtain 7 (120 mg, 83%) as yellow solid. ¹H NMR (400 MHz, DMSO-d₆): δ 2.13 (m, 2H), 2.33 (m, 2H), 2.90-2.98 (dd, J=10.0, 21.6 Hz, 2H), 3.73 (s, 2H), 7.17 (s, 1H), 7.70-7.73 (dd, J=1.2, 8.4 Hz, 1H), 7.78 (d, J=8.4 Hz, 1H), 8.33 (s, 1H), 8.55 (s, 1H). MS m/z (M−H): 271.3

Step 8:

To a mixture of 1'-oxo-2',3'-dihydro-1'H-spiro[cyclobutane-1,4'-pyrazino[1,2-a]indole]-7'-carboxylic acid (7) (45 mg, 0.16 mmol), HATU (130 mg, 0.33 mmol) and DMAP (51 mg, 0.41 mmol) in dry DMF (5.0 mL) was added the amine compound INT-11 (41 mg, 0.2 mmol) and then stirred at room temperature under nitrogen atmosphere for 12 h. The reaction mixture was diluted with water (50 mL) and extracted with 20% MeOH-DCM (2×20 mL). The combined organic layer was further washed with brine solution (20 mL), dried over anhydrous sodium sulfate and concentrated under reduced pressure. The residue was purified by silica gel column chromatography to obtain V-23 (25 mg, 33%) as off white solid. 1H NMR (400 MHz, DMSO-d₆): δ 2.18 (m, 1H), 2.20 (m, 1H), 2.32 (m, 2H), 3.07 (m, 2H), 3.71 (s, 2H), 3.96 (m, 2H), 4.28 (m, 2H), 5.86 (d, J=8.0 Hz, 1H), 6.33 (d, J=16.8 Hz, 1H), 6.91 (dd, J=8.8 Hz, 17.6 Hz, 2H), 7.17 (s, 1H), 7.49 (d, J=7.6 Hz, 1H), 7.49 (d, J=8.4 Hz, 1H), 7.81 (d, J=8.4 Hz, 1H), 7.94 (bs, 1H), 8.28 (s, 1H), 8.44 (s, 1H), 10.26 (s, 1H).MS m/z (M+H): 457

Example 79

Compound V-15

N-(3-acrylamido-4-(4-methylpiperazin-1-yl)phenyl)-1'-oxo-2',3'-dihydro-1'H-spiro[cyclobutane-1,4'-pyrazino[1,2-a]indole]-7'-carboxamide

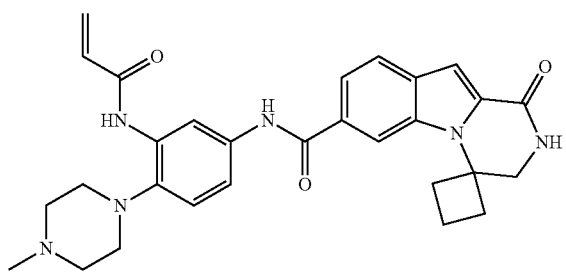 [SMILES: C=CC(=O)Nc1cc(NC(=O)c2ccc3cc4n(c3c2)C2(CCC2)CNC4=O)ccc1N1CCN(C)CC1]

The title compound was prepared in a manner similar to Example 78, substituting INT-17 for INT-11 according to the schemes, steps, and intermediates described below.

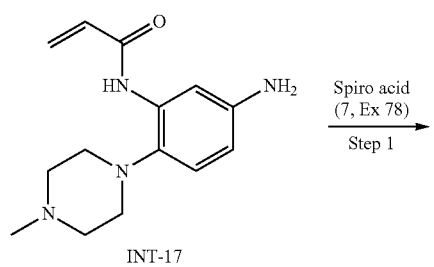

INT-17

Step 1:

To a stirred solution of 1'-oxo-2',3'-dihydro-1'H-spiro[cyclobutane-1,4'-pyrazino[1,2-a]indole]-7'-carboxylic acid (7, Example 78) (70 mg, 0.25 mmol) in dry DMF (5 mL) were added HATU (252.7 mg, 0.64 mmol), DIPEA (0.22 mL, 1.29 mmol) and N-(5-amino-2-(4-methylpiperazin-1-yl)phenyl)acrylamide (INT-17) (74.2 mg, 0.28 mmol) at room temperature under nitrogen atmosphere. The resultant reaction mixture was heated to 70° C. and stirred for 8 h. The reaction mixture was cooled to room temperature, diluted with water (20 mL) and extracted with 20% MeOH-DCM (3×20 mL). Combined organic layers were dried over anhydrous sodium sulfate and concentrated under reduced pressure. The residue was purified by silica gel column chromatography and then further purified by preparative TLC to obtain the title compound (10 mg, 8%) as pale yellow solid. 1H NMR (400 MHz, DMSO-d₆): δ 2.04 (m, 1H), 2.19 (m, 1H), 2.32 (m, 4H), 2.50 (s, 3H), 2.66 (m, 2H), 2.84 (m, 4H), 3.01-3.09 (m, 2H), 3.73 (s, 2H), 5.76 (m, 1H), 6.23-6.28 (m, 1H), 6.60-6.67 (m, 1H), 7.18 (m, 2H), 7.61 (m, 1H), 7.78 (m, 2H), 8.31 (s, 1H), 8.44 (m, 2H), 9.08 (s, 1H), 10.33 (s, 1H). MS m/z (M+H): 513.6.

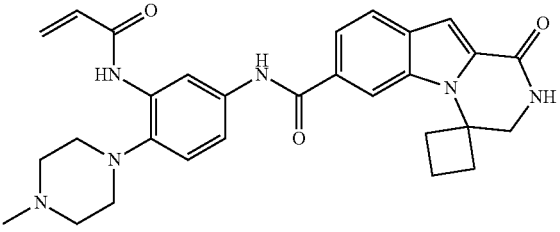

Example 80

Compound V-c-1

N-(2-methoxy-5-(4-(1-oxo-1,2,3,4-tetrahydropyrrolo[1,2-a]pyrazin-7-yl)pyridin-2-yl)phenyl)acrylamide

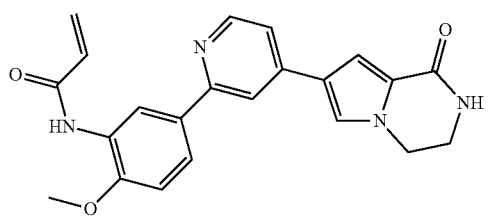 [SMILES: C=CC(=O)Nc1cc(-c2cc(-c3cc4n(c3)CCNC4=O)ccn2)ccc1OC]

The title compound was prepared according to the schemes, steps, and intermediates described below.

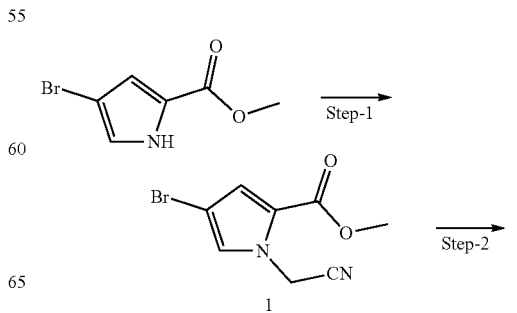

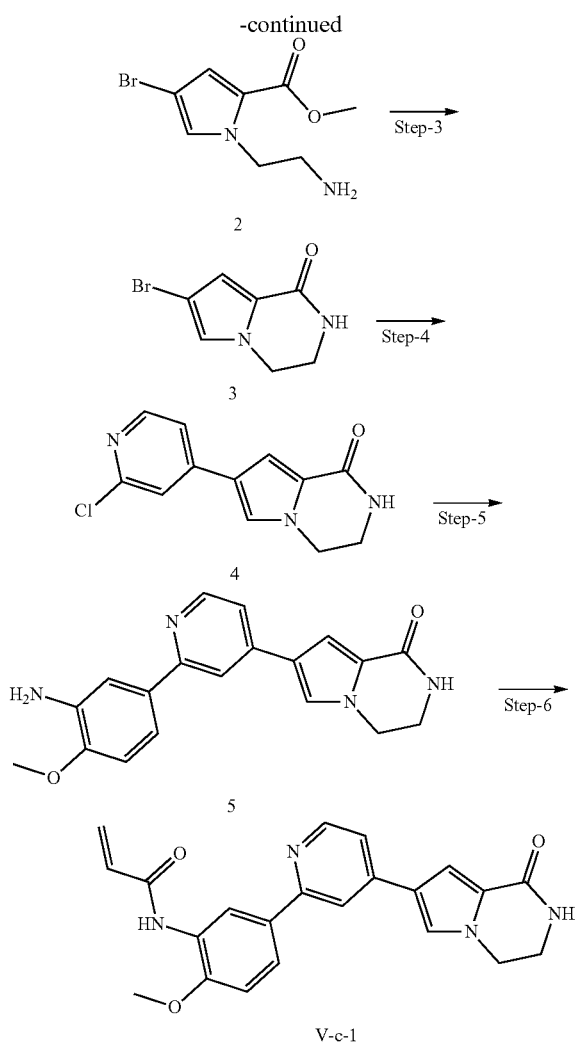

Step 1:

Methyl 4-bromo-1-(cyanomethyl)-1H-pyrrole-2-carboxylate (1)

To a mixture of methyl 4-bromo-1H-pyrrole-2-carboxylate (202 mg, 1 mmol) and bromo acetonitrile (144 mg, 1.2 mmol) in 8 mL DMF was added K$_2$CO$_3$ (276 mg, 2 mmol). The resulting mixture was stirred at 80° C. for 3 h. Water was added, and the reaction was extracted with ethyl acetate, washed with brine and dried over magnesium sulfate, and concentrated under reduced pressure. The residue was used without further purification. LCMS indicated clean product MS m/z (M+H): 243.1

Step 2:

Methyl 1-(2-aminoethyl)-4-bromo-1H-pyrrole-2-carboxylate (2)

To a solution of Methyl 4-bromo-1-(cyanomethyl)-1H-pyrrole-2-carboxylate (242 mg, 1 mmol) in tetrahydrofuran (10 mL) was added BH$_3$-THF compex (1.0 M in THF, 5 mL) dropwise at room temperature. The resulting mixture was stirred at 60° C. overnight. The reaction was quenched with saturated sodium bicarbonate solution at 0° C., extracted with ethyl acetate, washed with brine and dried over magnesium sulfate, and concentrated under reduced pressure. The residue was used without further purification. LCMS indicated clean product MS m/z (M+H): 247.2

Step 3:

7-bromo-3,4-dihydropyrrolo[1,2-a]pyrazin-1(2H)-one (3)

To a solution of crude Methyl 1-(2-aminoethyl)-4-bromo-1H-pyrrole-2-carboxylate (246 mg, 1 mmol) in 10 mL ethanol was added ammonium hydroxide (28%, 1 mL). The final mixture was stirred at room temperature overnight. Water was added, and the reaction was extracted with ethyl acetate, washed with brine and dried over magnesium sulfate, concentrated under reduced pressure. The residue was purified by column purification (20% methanol in dichloromethane) to provide the product as an offwhite powder (90 mg, 42%). MS m/z (M+H): 215.1

Step 4:

7-(2-chloropyridin-4-yl)-3,4-dihydropyrrolo[1,2-a]pyrazin-1(2H)-one (4)

A mixture of 7-bromo-3,4-dihydropyrrolo[1,2-a]pyrazin-1(2H)-one (21 mg, 0.1 mmol), 2-chloro-4-pyrridoboronic acid (25 mg, 0.15 mmol), PdCl$_2$(dppf) (8 mg, 0.01 mmol) and cesium carbonate (65 mg, 0.2 mmol) in a 40 mL vial was vacuumed and refilled with nitrogen, followed by addition of dioxane/water (5/1 mL). The final mixture was stirred at 100° C. for 4 h. The reaction was cooled to room temperature. Water was added, and the reaction was extracted with ethyl acetate, washed with brine and dried over magnesium sulfate, and concentrated under reduced pressure. The residue was purified by column purification (10% methanol in dichloromethane) to provide the product a light yellow powder (10 mg, 40%). MS m/z (M+H): 248.1

Step 5:

7-(2-(3-amino-4-methoxyphenyl)pyridin-4-yl)-3,4-dihydropyrrolo[1,2-a]pyrazin-1(2H)-one (5)

A mixture of 7-(2-chloropyridin-4-yl)-3,4-dihydropyrrolo[1,2-a]pyrazin-1(2H)-one (20 mg, 0.08 mmol), 3-amino-4-methoxyphenylboronic acid (25 mg, 0.096 mmol), PdCl2 (dppf) (6 mg, 0.008 mmol) and cesium carbonate (52 mg, 0.16 mmol) in a 40 mL vial was vacuumed and refilled with nitrogen, followed by addition of dioxane/water (5/1 mL). The final mixture was stirred at 100° C. for 2 h. The reaction was cooled to room temperature. Water was added, and the reaction was extracted with ethyl acetate, washed with brine and dried over magnesium sulfate, and concentrated under reduced pressure. The residue was purified by column purification (10% methanol in dichloromethane) to provide the product an offwhite powder (10 mg, 38%). MS m/z (M+H): 335.1

Step 6:

To a solution of 7-(2-(3-amino-4-methoxyphenyl)pyridin-4-yl)-3,4-dihydropyrrolo[1,2-a]pyrazin-1(2H)-one 5 (10 mg, 0.03 mmol) in 4 mL of dichloromethane was added 1 mL dichloromethane solution of acroyl chloride (3 mg, 0.03 mmol) at −78° C. The reaction was slowly warmed to room temperature for 3 h. Water was added, and the reaction was extracted with ethyl acetate, washed with brine and dried over magnesium sulfate, and concentrated under reduced pressure. The residue was purified by HPLC (5-95% acetonitrile in water with trifluoroacetic acid as modifier) to provide compound V-c-1 as an offwhite powder (5 mg, 45%). $^1$H NMR (400 MHz, DMSO-d$_6$) δ 3.55 (m, 2H), 3.92 (s, 3H), 4.20 (m, 2H), 5.75 (d, 1H), 6.25 (d, 1H), 6.72 (dd, 1H), 7.26 (d, 1H), 7.52 (s, br, 1H), 7.80-7.95 (m, 3H), 8.08 (s, br, 1H), 8.25 (s, br, 1H), 8.55 (d, 1H), 8.72 (s, 1H), 9.61 (s, 1H). MS m/z (M+H): 389.1

Example 81

Compound V-c-2

N-(2-methoxy-5-(4-(1-oxo-1,2,3,4-tetrahydropyrrolo[1,2-a]pyrazin-7-yl)pyrimidin-2-yl)phenyl)acrylamide

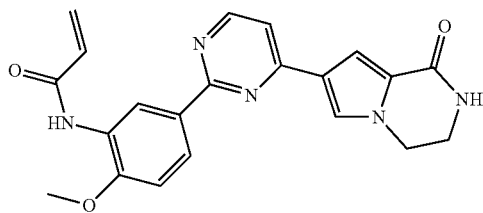 [SMILES: C=CC(=O)Nc1cc(-c2nccc(-c3cc4n(c3)CCNC4=O)n2)ccc1OC]

The title compound was prepared according to the schemes, steps, and intermediates described below.

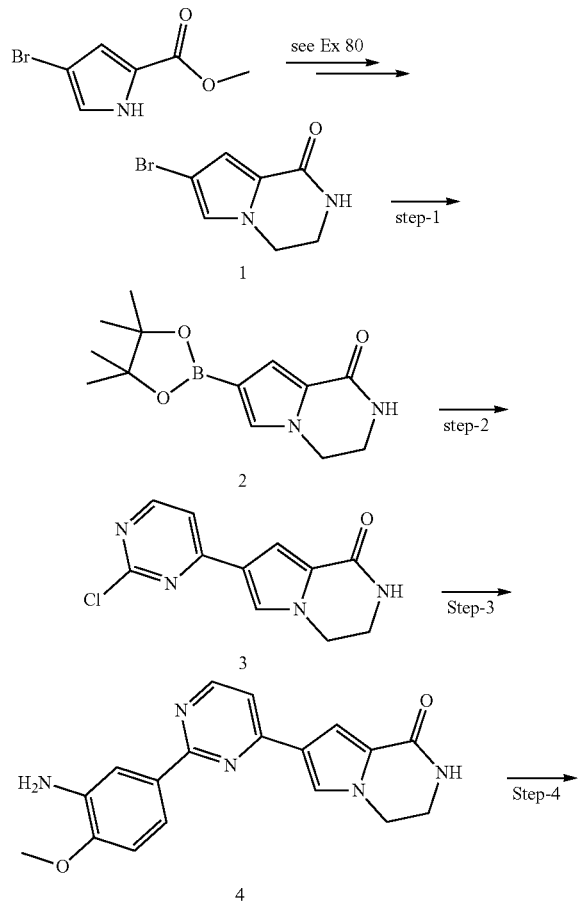

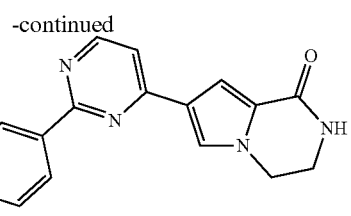

Step 1:

7-(4,4,5,5-tetramethyl-1,3,2-dioxaborolan-2-yl)-3,4-dihydropyrrolo[1,2-a]pyrazin-1(2H)-one (2)

A mixture of 7-bromo-3,4-dihydropyrrolo[1,2-a]pyrazin-1 (2H)-one (230 mg, 1.07 mmol), 4,4,4',4',5,5,5',5'-octamethyl-2,2'-bi(1,3,2-dioxaborolane) (1.36 g, 5.35 mmol), PdCl$_2$(dppf) (80 mg, 0.11 mmol), and potassium acetate (315 mg, 3.21 mmol) in 6 mL 1,4-dioxane was degassed, and the final mixture was stirred at 80° C. overnight. Solvent was removed by rotavap, and the residue was used in next step without further purification. LCMS indicated desired product 2. MS m/z (M+H): 263.1

Step 2:

7-(2-chloropyrimidin-4-yl)-3,4-dihydropyrrolo[1,2-a]pyrazin-1(2H)-one (3)

A mixture of 2-chloro-4-bromopyrimidine (175 mg, 0.9 mmol), 7-(4,4,5,5-tetramethyl-1,3,2-dioxaborolan-2-yl)-3,4-dihydropyrrolo[1,2-a]pyrazin-1 (2H)-one (crude from step 1, 1.0 mmol), PdCl$_2$(dppf) (66 mg, 0.09 mmol) and cesium carbonate (586 mg, 1.8 mmol) in a 40 mL vial was vacuumed and refilled with nitrogen, followed by addition of dioxane/water (8/2 mL). The final mixture was stirred at 100° C. for 3 h. The reaction was cooled to room temperature. Water was added, and the reaction was extracted with ethyl acetate, washed with brine, dried over magnesium sulfate, and concentrated under reduced pressure. The residue was purified by column purification (10% methanol in dichloromethane) to provide the product a light yellow powder (42 mg, 22% over 2 steps). MS m/z (M+H): 249.1

Step 3:

7-(2-(3-amino-4-methoxyphenyl)pyrimidin-4-yl)-3,4-dihydropyrrolo[1,2-a]pyrazin-1(2H)-one (4)

A mixture of 7-(2-chloropyrimidin-4-yl)-3,4-dihydropyrrolo[1,2-a]pyrazin-1(2H)-one (20 mg, 0.08 mmol), 3-amino-4-methoxyphenylboronic acid (25 mg, 0.096 mmol), PdCl2 (dppf) (8 mg, 0.01 mmol) and cesium carbonate (58 mg, 0.176 mmol) in a 40 mL vial was vacuumed and refilled with nitrogen, followed by addition of dioxane/water (5/1 mL). The final mixture was stirred at 100° C. for 2 h. The reaction was cooled to room temperature. Water was added, and the reaction was extracted with ethyl acetate, washed with brine, dried over magnesium sulfate, and concentrated under reduced pressure. The residue was purified by column purification (10% methanol in dichloromethane) to provide the product as an off white powder (5 mg, 18%). MS m/z (M+H): 336.1

Step 4:

N-(2-methoxy-5-(4-(1-oxo-1,2,3,4-tetrahydropyrrolo[1,2-a]pyrazin-7-yl)pyrimidin-2-yl)phenyl)acrylamide To a solution of 7-(2-(3-amino-4-methoxyphenyl)pyridin-4-yl)-3,4-dihydropyrrolo[1,2-a]pyrazin-1 (2H)-one (5 mg, 0.015 mmol) in 4 mL of dichloromethane was added 1 mL dichloromethane solution of acroyl chloride (3 mg, 0.03 mmol) at −78° C. The reaction was slowly warmed to room temperature for 3 h. Water was added, and the reaction was extracted with ethyl acetate, washed with brine, dried over magnesium sulfate, and concentrated under reduced pressure. The residue was purified by HPLC (5~95% acetonitrile in water with trifluoroacetic acid as modifier) to provide the title compound as an off-white powder (3 mg, 52%). MS m/z (M+H): 390.2.

Example 82

Compound V-c-3

7-(2-(4-acryloyl-3,4-dihydro-2H-benzo[b][1,4]oxazin-6-yl)pyrimidin-4-yl)-3,4-dihydropyrrolo[1,2-a]pyrazin-1(2H)-one

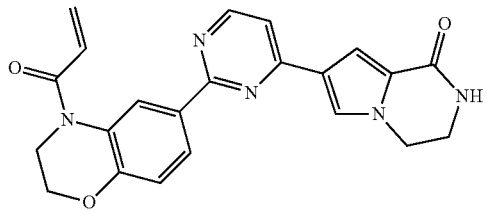 [SMILES: C=CC(=O)N1CCOc2ccc(-c3nccc(-c4cc5n(c4)CCNC5=O)n3)cc21]

The title compound was prepared in a manner similar to Example 81, by substituting 6-(4,4,5,5-tetramethyl-1,3,2-dioxaborolan-2-yl)-3,4-dihydro-2H-benzo[b][1,4]oxazine (INT-1) in step 3: Yellow solid, 12.0 mg, 60%. $^1$H NMR (400 MHz, DMSO-$d_6$) δ 3.52 (m, 2H), 4.00 (m, 2H), 4.19 (m, 2H), 4.36 (m, 2H), 5.88 (d, 1H), 6.32 (d, 1H), 6.84 (dd, 1H), 7.04 (d, 1H), 7.38 (s, 1H), 7.60 (d, 1H), 7.85 (s, 1H), 7.91 (s, 1H), 8.18 (d, 1H), 8.50 (br, 1H), 8.68 (d, 1H). MS m/z (M+H): 402.2.

Example 83

Compound VI-9

(R)—N-(5-(4-((3,4-dioxo-2-((1-phenylethyl)amino)cyclobut-1-en-1-yl)amino)pyridin-2-yl)-2-methoxyphenyl)acrylamide

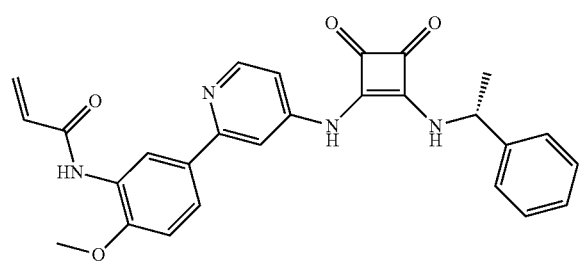 [SMILES: C=CC(=O)Nc1cc(-c2cc(Nc3c(N[C@H](C)c4ccccc4)c(=O)c3=O)ccn2)ccc1OC]

The title compound was prepared according to the schemes, steps, and intermediates

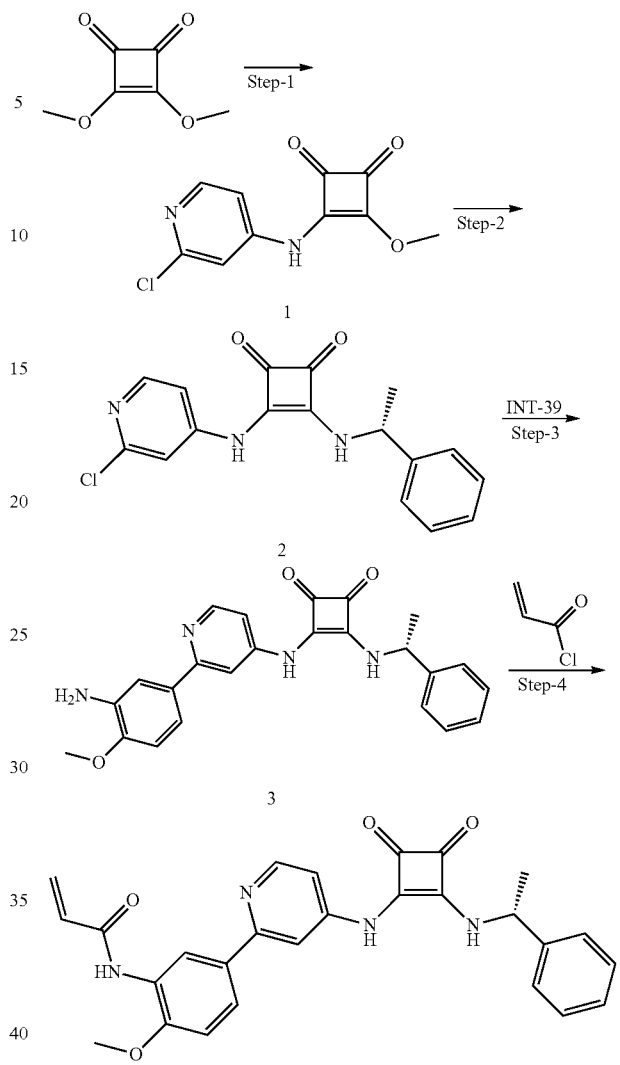

Step 1:

3-(2-chloropyridin-4-ylamino)-4-methoxycyclobut-3-ene-1,2-dione (1)

A solution of 3,4-dimethoxycyclobut-3-ene-1,2-dione (3 g, 17.6 mmol) and 2-chloro-4-aminopyridine (2.2 g, 17.6 mmol) in 50 mL absolute ethanol was refluxed at 100° C. overnight. Solvent was removed under reduced pressure. The residue was purified by column chromatography (0-40% ethyl acetate in heptane) to provide 1 as an offwhite powder (300 mg, 7%). MS m/z (M+H): 253.1

Step 2:

(R)-3-(2-chloropyridin-4-ylamino)-4-(1-phenylethylamino)cyclobut-3-ene-1,2-dione (2)

A mixture of 3-(2-chloropyridin-4-ylamino)-4-methoxycyclobut-3-ene-1,2-dione (1) (25 mg, 0.1 mmol) and (R)-methyl benzylamine (12 mg, 0.1 mmol) in 4 mL of absolute ethanol was stirred at 80° C. for 1.5 h. The white precipitate was filtered and washed with ethyl ether to provide 2 as an offwhite powder (23 mg, 72%). MS m/z (M+H): 328.1

Step 3:

(R)-3-(2-(3-amino-4-methoxyphenyl)pyridin-4-ylamino)-4-(1-phenylethylamino)cyclobut-3-ene-1,2-dione (3)

To a solution of (R)-3-(2-chloropyridin-4-ylamino)-4-(1-phenylethylamino)cyclobut-3-ene-1,2-dione (2, 32 mg, 0.1 mmol) in wet isopropanol (1 mL) under inert atmosphere were added 2-methoxy-5-(4,4,5,5-tetramethyl-1,3,2-dioxaborolan-2-yl)aniline (INT-39, 30 mg, 0.12 mmol) and cesium carbonate (65 mg, 0.2 mmol), and purged with argon for 20 minutes. Then $PdCl_2$(dppf) (7.5 mg, 0.01 mmol) was added, and the reaction purged again for 20 minutes before heating in the microwave at 160° C. for 45 minutes. The reaction was cooled to RT, filtered through a pad of Celite, and concentrated. The residue was purified by silica gel chromatography to afford the desired product (3) as an offwhite powder (10 mg, 24%). MS m/z (M+H): 415.1

Step 4:

To a stirred solution of (R)-3-(2-(3-amino-4-methoxyphenyl)pyridin-4-ylamino)-4-(1-phenylethylamino)cyclobut-3-ene-1,2-dione (3, 10 mg, 0.024 mmol) in dry DCM (1 mL) under inert atmosphere at 0° C. were added triethyl amine (0.003 mL, 0.024 mmol) and acryloyl chloride (0.002 mL, 0.024 mmol). The reaction mixture was warmed to room temperature and stirred for 2 h. The reaction mixture was diluted with water (15 mL) and extracted with DCM (2×15 mL). The combined organic layers were washed with water (15 mL), dried over anhydrous sodium sulfate and concentrated under reduced pressure. The residue was purified by silica gel column chromatography to obtain compound VI-9 as a light yellow powder (5.2 mg, 47%). $^1$H NMR (400 MHz, DMSO-$d_6$) δ 1.58 (d, 3H), 3.90 (s, 3H), 5.30 (m, 1H), 5.75 (d, 1H), 6.25 (d, 1H), 6.75 (dd, 1H), 7.25 (m, 1H), 7.38 (m, 3H), 7.51 (m, 1H), 7.70 (d, 1H), 7.95 (s, br, 1H), 8.50 (d, 1H), 8.70 (s, 1H), 9.65 (s, 1H), 10.55 (s, br, 1H). MS m/z (M+H): 469.1

Example 84

Compound VI-10

(R)-3-((2-(4-acryloyl-3,4-dihydro-2H-benzo[b][1,4]oxazin-6-yl)pyridin-4-yl)amino)-4-((1-phenylethyl)amino)cyclobut-3-ene-1,2-dione

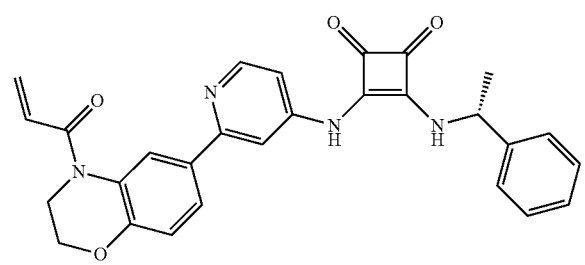 [SMILES: C=CC(=O)N1CCOc2ccc(-c3cc(Nc4c(N[C@H](C)c5ccccc5)c(=O)c4=O)ccn3)cc21]

The title compound VI-10 was prepared as described in Example 83, by substituting boronic ester INT-1 for INT-39 in step 3: Yellow powder, 8 mg, 31%. $^1$H NMR (400 MHz, DMSO-$d_6$) δ 1.60 (d, 3H), 4.00 (m, 2H), 4.38 (m, 2H), 5.31 (m, 1H), 5.85 (d, 1H), 6.31 (d, 1H), 6.85 (dd, 1H), 7.30 (m, 2H), 7.38 (m, 3H), 7.51 (m, 1H), 7.68 (d, 1H), 8.05 (s, br, 1H), 8.48 (d, 1H), 8.55 (d, 1H), 10.65 (s, br, 1H). MS m/z (M+H): 481.1

Example 85

Compound Covalent probe 2

N1-(3-(2-acrylamido-4-(7-oxo-6,7,8,9,10,11-hexahydro-5H-pyrido[3',4':4,5]pyrrolo[2,3-f]isoquinolin-2-yl)phenoxy)propyl)-N5-(15-oxo-19-((3aR,4R,6aS)-2-oxohexahydro-1H-thieno[3,4-d]imidazol-4-yl)-4,7,10-trioxa-14-azanonadecyl)glutaramide

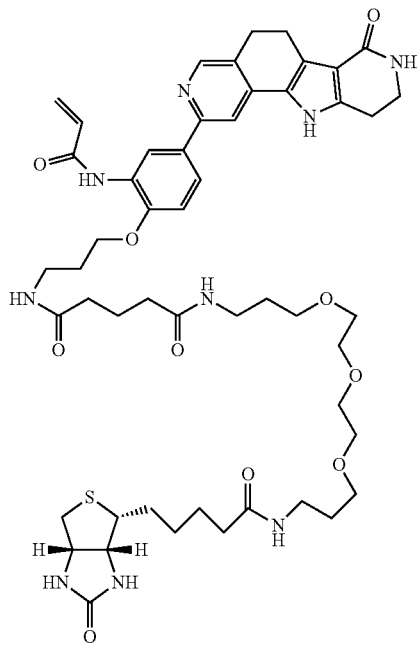 [SMILES: C=CC(=O)Nc1cc(-c2cc3c(cn2)CCc2c-3[nH]c3c2C(=O)NCC3)ccc1OCCCNC(=O)CCCC(=O)NCCCOCCOCCOCCCNC(=O)CCCC[C@H]1SC[C@H]2NC(=O)N[C@H]21]

The title compound was prepared according to the schemes, steps, and intermediates described below.

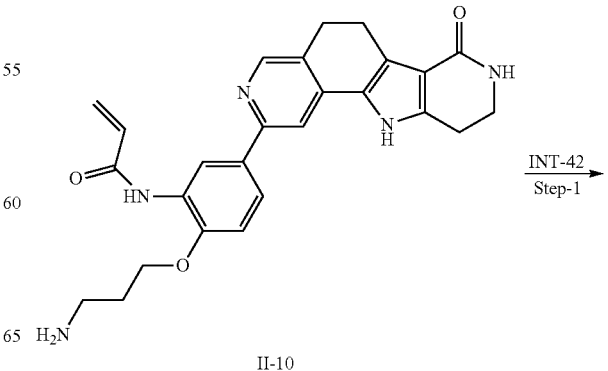

403
-continued

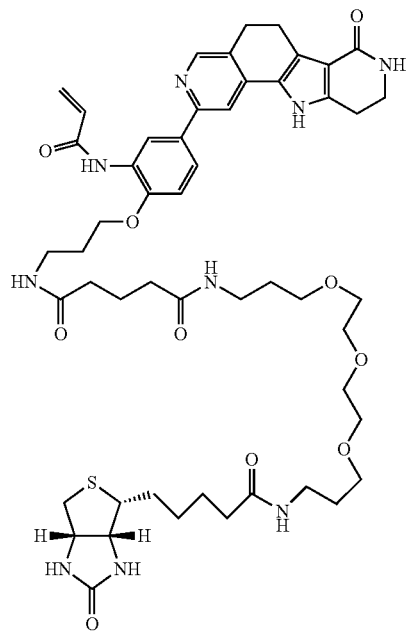

To a solution of carboxylic acid INT-42 (1.0 equiv) in DMF was added HATU (1.5 equiv) and DIEA (5.0 equiv), and the reaction was stirred at room temperature for 15 min. The amine compound II-10 (19 mg, 1.2 equiv) was added and the reaction stirred at room temperature for an additional 15 min. At this point, LCMS analysis indicated INT-42 had been consumed and Covalent probe 2 had formed. The reaction mixture was diluted with water and purified directly by prep-HPLC: 5 mg yellow solid. MS m/z (M+H): 998.3.

Example 86

Compound Covalent Probe 1

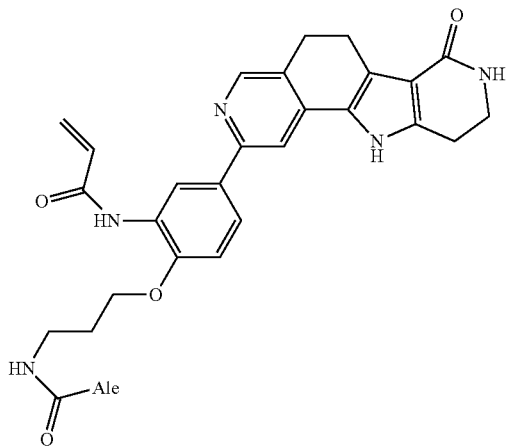

The title compound was prepared in a manner according to Example 85, substituting Ale-C(O)OH for INT-42.

404

Example 87

TABLE 14

Intermediates (INT) utilized for the synthesis of compounds described herein:

| INTERMEDIATE | STRUCTURE |
| --- | --- |
| INT-1 | 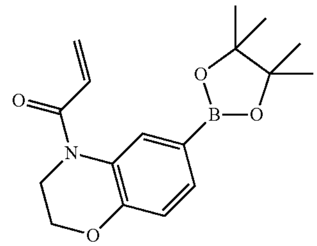 [SMILES: C=CC(=O)N1CCOc2ccc(B3OC(C)(C)C(C)(C)O3)cc21] |
| INT-2 | 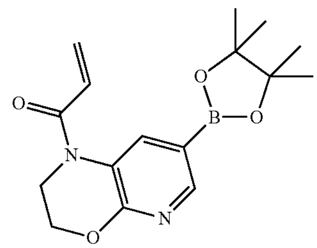 [SMILES: C=CC(=O)N1CCOc2ncc(B3OC(C)(C)C(C)(C)O3)cc21] |
| INT-3 | 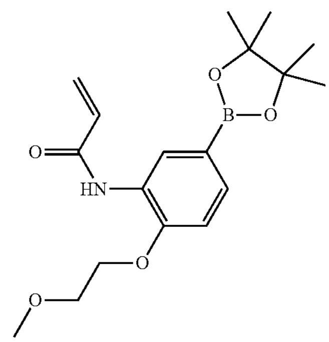 |
| INT-4 | 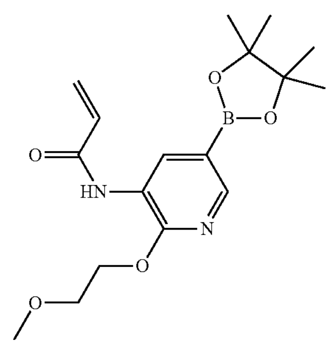 |
| INT-5 | 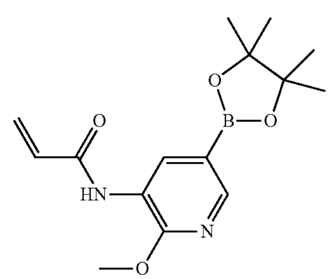 [SMILES: C=CC(=O)Nc1cc(B2OC(C)(C)C(C)(C)O2)cnc1OC] |

TABLE 14-continued

Intermediates (INT) utilized for the synthesis of compounds described herein:

| INTERMEDIATE | STRUCTURE |
|---|---|
| INT-6 | *(structure: acrylamide-NH on phenyl with F and pinacol boronate)* |
| INT-7 | *(structure: acrylamide-NH on phenyl with OMe and pinacol boronate)* |
| INT-8 | *(structure: acrylamide-NH on phenyl with 4-methylpiperazinyl and pinacol boronate)* |
| INT-9 | *(structure: acrylamide-NH on pyridine with 4-methylpiperazinyl and pinacol boronate)* |
| INT-10 | *(structure: 3-acrylamido aniline)* |
| INT-11 | *(structure: 4-acryloyl-3,4-dihydro-2H-benzo[b][1,4]oxazine with 6-NH2)* |
| INT-12 | *(structure: 4-(4-(dimethylamino)but-2-enoyl)-3,4-dihydro-2H-benzo[b][1,4]oxazine with 6-NH2)* |
| INT-13 | *(structure: 2-acrylamido aniline)* |
| INT-14 | *(structure: N-(5-amino-2-(2-methoxyethoxy)phenyl)acrylamide)* |

TABLE 14-continued

Intermediates (INT) utilized for the synthesis of compounds described herein:

| INTERMEDIATE | STRUCTURE |
|---|---|
| INT-15 | N-(2-fluoro-5-aminophenyl)acrylamide |
| INT-16 | N-(2-(4-Boc-piperazin-1-yl)-5-aminophenyl)acrylamide |
| INT-17 | N-(2-(4-methylpiperazin-1-yl)-5-aminophenyl)acrylamide |
| INT-18 | N-(2-(pyrrolidin-1-yl)-5-aminophenyl)acrylamide |
| INT-19 | 1-(2-fluoro-5-aminophenoxy)-4-methylpent-3-en-2-one |
| INT-20 | N-(2-methyl-5-(4,4,5,5-tetramethyl-1,3,2-dioxaborolan-2-yl)pyridin-3-yl)acrylamide |
| INT-21 | 3-nitrobenzamide |
| INT-22 | 2-nitrobenzamide (with additional nitro) |
| INT-23 | 3-acrylamido-4-(2-methoxyethoxy)benzamide |
| INT-24 | 3-acrylamido-4-fluorobenzamide |
| INT-25 | 3-acrylamido-4-methoxybenzamide |

TABLE 14-continued

Intermediates (INT) utilized for the synthesis of compounds described herein:

| INTERMEDIATE | STRUCTURE |
|---|---|
| INT-26 | (acrylamide-phenyl-Bpin with CF₃) |
| INT-27 | 2-bromo-1-(2-chloropyrimidin-4-yl)ethan-1-one |
| INT-28 | 2-nitroaniline |
| INT-29 | 4-Boc-6-amino-3,4-dihydro-2H-benzo[b][1,4]oxazine |
| INT-30 | (E)-4-(dimethylamino)but-2-enoyl chloride |
| INT-31 | N-Boc-1,2-phenylenediamine |
| INT-32 | 1-acryloyl-6-amino-2,3-dihydro-1H-indole |
| INT-33 | N-((1R,2S)-2-aminocyclohexyl)acrylamide |
| INT-34 | 1-acryloyl-3-aminopiperidine |
| INT-35 | N-(4-methylpiperidin-3-yl)acrylamide |
| INT-36 | N-(2-(4-ethylpiperazin-1-yl)-5-aminophenyl)acrylamide |
| INT-37 | 1-acryloyl-4-amino-2,3-dihydro-1H-isoindole |
| INT-38 | 1-acryloyl-3-aminopiperidine |
| INT-39 | 3-amino-4-methoxyphenylboronic acid pinacol ester |
| INT-40 | 2-bromo-1-(2-chloropyridin-4-yl)ethan-1-one |

TABLE 14-continued

Intermediates (INT) utilized for the synthesis of compounds described herein:

| INTERMEDIATE | STRUCTURE |
|---|---|
| INT-41 | (3-amino-4-fluorophenyl pinacol boronate) |
| INT-42 | (HOOC-CH₂CH₂-C(O)NH-propyl-PEG-biotin conjugate) |
| INT-43 | (acrylamide phenyl pinacol boronate with dimethylaminoethoxy substituent) |
| INT-44 | (acrylamide phenyl pinacol boronate with BocNH-propyloxy substituent) |
| INT-45 | (N-(2-(trifluoromethoxy)-5-pinacolboronate-phenyl)acrylamide) |
| INT-46 | (N-(2-(trifluoromethyl)-5-pinacolboronate-phenyl)acrylamide) |

The intermediate compounds (INT) were either commercially available or were prepared according to the schemes and steps described below.

INT-1

(1-(6-(4,4,5,5-tetramethyl-1,3,2-dioxaborolan-2-yl)-2H-benzo[b][1,4]oxazin-4(3H)-yl)prop-2-en-1-one)

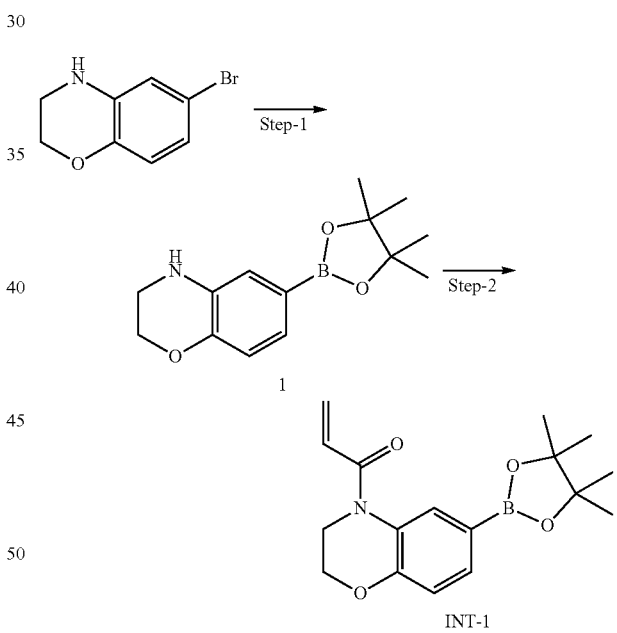

Step 1:
A stirred mixture of 6-bromo-3,4-dihydro-2H-1,4-benzoxazine (1.0 mmol), KOAc (5 mmol), bis(pinacolato)diboron (1.2 mmol), and Pd(dppf)₂Cl₂ (0.2 mmol) in dioxane (1 mL) was heated at 80° C. for 12 h, cooled to room temperature, filtered through Celite, dissolved in EtOAc (100 mL), washed with water (3×25 mL), dried over sodium sulfate, and concentrated to give the crude product 1, which was purified by flash chromatography: Yellow oil (200 mg, 75%). MS m/z (M+H): 262.2

Step 2:
To a stirred solution of 1 (200 mg, 0.7 mmol) in DCM (5 mL) was added DIPEA (2.1 mmol), and the solution was cooled to −78° C. Acryloyl chloride (0.7 mmol) was added and the cold bath removed allowing the reaction to warm to room temperature over 30 min. The reaction was diluted with DCM (25 mL), washed with water (25 mL), dried over sodium sulfate, and concentrated to give the crude product which was purified by flash chromatography to give INT-1 as a white solid (100 mg, 45%): MS m/z (M+H): 316.3

INT-2, INT-3, INT-4, INT-5, INT-6, INT-7, INT-20, INT-26, INT-39, and INT-41 were prepared using analogous methods to INT-1 and substituting the appropriate aryl bromide starting material.

INT-8

N-(2-(4-methylpiperazin-1-yl)-5-(4,4,5,5-tetramethyl-1,3,2-dioxaborolan-2-yl)phenyl)acrylamide

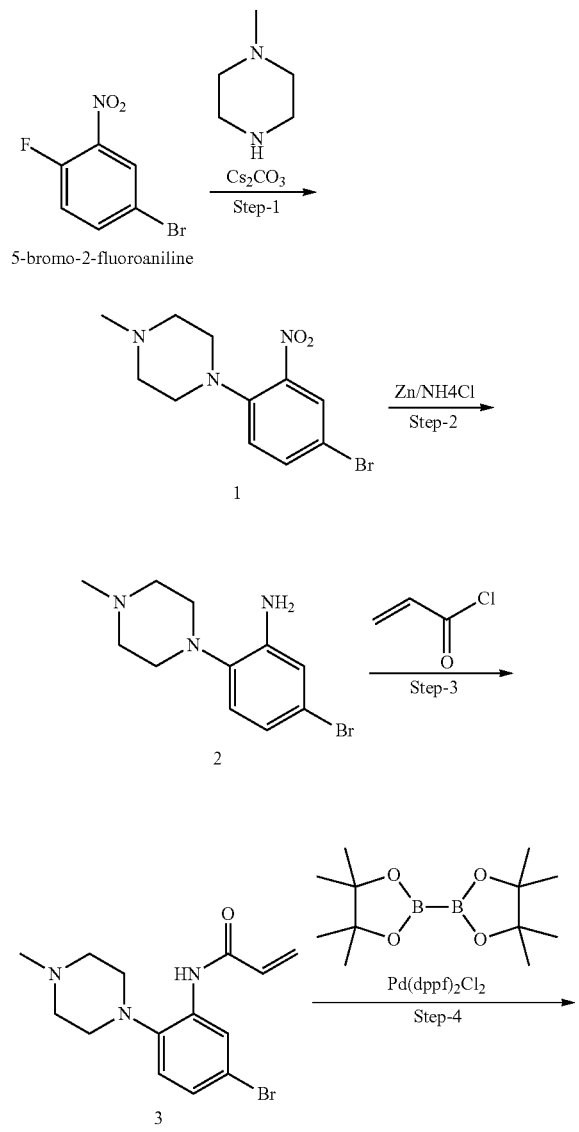

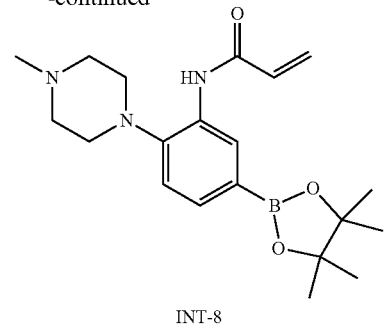

INT-8

Step 1:
To a solution of 2-fluoro-5-bromo-nitrobenzene (4.0 g, 20.0 mmol) in dimethylacetamide, caesium carbonate (11.8 g, 40 mmol) was added followed by the addition of N-methylpiperazine (2.7 g, 30 mmol). The reaction mixture was heated at 80° C. overnight. After completion of the reaction, the reaction mixture was diluted with water and extracted with ethyl acetate. The organic layer was washed with brine, dried over anhydrous sodium sulfate and concentrated under reduced pressure. The residue was purified by silica gel column chromatography to afford 1 as yellow gummy material (3.8 g, 70%). $^1$H NMR (400 MHz, DMSO-$d_6$) δ 2.19 (s, 3H), 2.38 (t, J=4.8 Hz, 4H), 2.96 (t, J=4.8 Hz, 2H), 7.25 (d, J=8.9 Hz, 1H), 7.70-7.73 (dd, J=2.5, 8.9 Hz, 1H), 7.99 (d, J=2.5 Hz, 1H)

Step 2:
To a solution of 1-(4-bromo-2-nitrophenyl)-4-methylpiperazine 1 (2.5 g, 8.4 mmol) in 1,4-dioxane/$H_2O$, Zn (2.0 g, 67.2 mmol) was added followed by the addition of $NH_4Cl$ (3.6 g, 67.2 mmol) at room temperature. The resulting mixture was stirred at room temperature for 4 h. After completion of the reaction, the solution was filtered, and the filtrate obtained was extracted with ethyl acetate. The organic layer was brine washed, dried over anhydrous sodium sulfate and concentrated under reduced pressure to afford 2 as an off-white solid (2.0 g, 91%). $^1$H NMR (400 MHz, DMSO-$d_6$) δ 2.20 (s, 3H), 2.45-2.49 (m, 4H), 2.74 (m, 4H), 4.95 (brs, 2H), 6.61-6.64 (dd, J=2.4, 8.3 Hz, 1H), 6.64-6.81 (m, 2H). MS m/z (M+H): 270.5

Step 3:
To a solution of 5-bromo-2-(4-methylpiperazin-1-yl)aniline (1.0 g, 3.7 mmol) in dichloromethane, acryloyl chloride (0.4 g, 4.4 mmol) was added followed by the addition of diisopropylethylamine (0.8 g, 7.4 mmol) at −20° C. The resulting mixture was stirred at 0° C. for 30 min. After completion of the reaction, the reaction mixture was quenched with water, and the aqueous solution was extracted with ethyl acetate. The organic layer was washed with brine, dried over anhydrous sodium sulfate and concentrated under reduced pressure to afford 3 (0.9 g, 75%) as a pale yellow solid. $^1$H NMR (400 MHz, DMSO-$d_6$) δ 2.24 (s, 3H), 2.53 (m, 4H), 2.79 (t, J=4.7 Hz, 4H), 5.76-5.79 (dd, J=1.7, 10.2 Hz, 1H), 6.22-6.27 (dd, J=1.8, 17.0 Hz, 1H), 6.59-6.66 (dd, J=10.2, 17.0 Hz, 1H), 7.11 (d, J=8.5 Hz, 1H), 7.24-7.27 (dd, J=2.3, 8.5 Hz, 1H), 8.16 (d, J=1.9 Hz, 1H), 9.1 (s, 1H). MS m/z (M+H): 324.6

Step 4:
N-(5-bromo-2-(4-methylpiperazin-1-yl)phenyl)acrylamide (500 mg, 1.5 mmol) in 1,4-dioxane was treated with bis-pinacolatodiborane (471 mg, 1.8 mmol), potassium acetate (455 mg, 4.5 mmol), Pd(dppf)$Cl_2$.$CH_2Cl_2$ (63 mg, 0.07 mmol) at 100° C. for 5 h. After completion of the reaction, the reaction mixture was diluted with water and extracted with ethyl acetate. The organic layer was dried over anhydrous sodium sulfate and concentrated under reduced pressure to afford INT-8 (400 mg, 67%) as a brown gummy solid. MS m/z (M+H): 372.6

INT-9 was prepared using analogous methods to INT-8 and substituting 5-Bromo-2-fluoro-3-nitropyridine for the starting material.

INT-15

N-(5-amino-2-fluorophenyl)acrylamide

INT-10, INT-11, INT-13, INT-14, INT-29, INT-32, INT-37 and were prepared using analogous methods to INT-15 and substituting the appropriate nitro-containing aryl amine compound for the starting material. For INT-12, 6-nitro-3,4-dihydro-2H-1,4-benzoxazine was used as the starting material and in step 1, 4-dimethylaminocrotonic acid and HATU were used in place of acryloyl chloride.

INT-17

N-(5-amino-2-(4-methylpiperazin-1-yl)phenyl)acrylamide

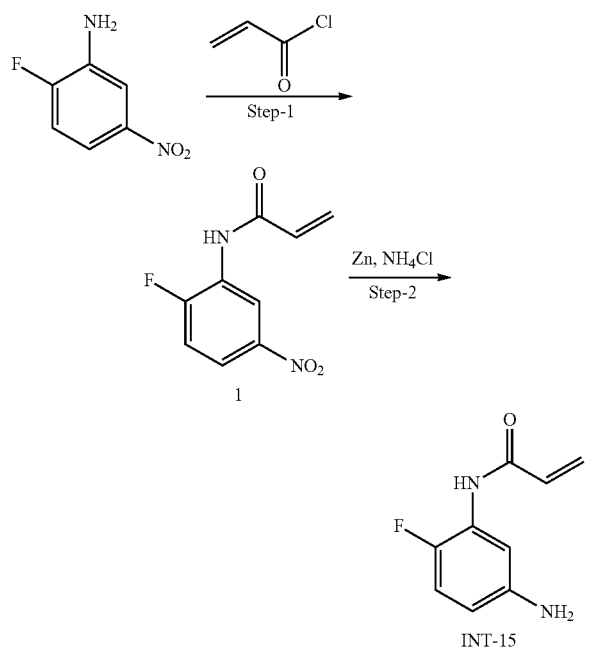

Step 1:

To a solution of 2-fluoro-5-nitroaniline (1.0 g, 6.4 mmol) and diisopropyl ethylamine (2.06 g, 16.0 mmol) in DCM (5 mL) at −50° C., acryloyl chloride (0.58 g, 6.4 mmol) was added slowly and the resulting mixture was stirred at the same temperature for 30 min. The reaction mixture was diluted with water (50.0 mL) and extracted with DCM (50.0 mL). The organic layer was dried over anhydrous sodium sulfate and concentrated under reduce pressure. The residue was purified by silica gel column chromatography to obtain 1 (1.0 g, 74.4%) as a yellow solid. $^1$H NMR (400 MHz, CDCl$_3$): δ 5.88-5.91 (dd, J=0.7, 10.2 Hz, 1H), 6.27-6.34 (dd, J=10.2, 16.8 Hz, 1H), 6.50-6.54 (dd, J=0.7, 16.8 Hz, 1H), 7.25 (t, J=11.3 Hz, 1H), 7.54 (s, 1H), 8.0 (dd, J=2.9, 4.4 Hz, 1H), 9.39-9.42 (dd, J=2.7, 6.7 Hz, 1H). MS m/z (M+H): 211.1

Step 2:

To a solution of N-(2-fluoro-5-nitrophenyl)acrylamide 1 (0.5 g, 2.38 mmol) in 1,4-dioxane:water (1:1, 5.0 mL), Zinc dust (1.23 g, 19.0 mmol) and NH$_4$Cl (1.0 g, 19.0 mmol) were added, and the resulting mixture was stirred at room temperature for 4 h. The reaction mixture was diluted with water (30.0 mL) and extracted with DCM (30.0 mL). The organic layer was dried over anhydrous sodium sulfate and concentrated under reduced pressure to obtain INT-15 (0.36 g, 84%) as off-white solid. MS m/z (M+H): 181.1

Step 1:

To a solution of 2-fluoro-5-nitroaniline (2.0 g, 12 mmol) in DMF (16.0 mL), Cs$_2$CO$_3$ (8.3 g, 25 mmol) and N-methyl piperazine (1.53 g, 15 mmol) were added, and the resulting mixture was heated to 80° C. for 16 h. The reaction mixture was cooled to room temperature, diluted with water (50.0 mL) and extracted with ethyl acetate (50.0 mL). The organic layer was dried over anhydrous sodium sulfate and concentrated under reduce pressure. The residue was purified by silica gel column chromatography to obtain 1 (2.3 g, 82%) as a yellow solid. $^1$H NMR (400 MHz, DMSO-d$_6$): δ 2.22 (s, 3H), 2.49 (m, 4H), 2.9 (brs, 4H), 5.2 (s, 2H), 6.98 (d, J=8.6 Hz, 1H), 7.41-7.44 (dd, J=2.7, 8.6 Hz, 1H), 7.52 (d, J=2.7 Hz, 1H). MS m/z (M+H): 237.1

Step 2:

To a solution of 2-(4-methylpiperazin-1-yl)-5-nitroaniline (1.0 g, 4.2 mmol) and diisopropyl ethylamine (1.35 g, 10.9 mmol) in DCM (8.0 mL) at −50° C., acryloyl chloride (0.38 g, 4.2 mmol) was added slowly, and the resulting mixture was stirred at the same temperature for 30 min. The reaction mixture was diluted with water (50.0 mL) and extracted with DCM (50.0 mL). The organic layer was dried over anhydrous sodium sulfate and concentrated under reduce pressure. The residue was purified by silica gel column chromatography to obtain 2 (1.0 g, 83%) as yellow solid. MS m/z (M+H): 291.4

Step 3:

To a solution of N-(2-(4-methylpiperazin-1-yl)-5-nitrophenyl)acrylamide (1.0 g, 3.4 mmol) in 1,4-dioxan:water (1:1, 20 mL), Zinc dust (1.8 g, 27.5 mmol) and NH$_4$Cl (1.45 g, 27.5 mmol) were added, and the resulting mixture was stirred at room temperature for 4 h. The reaction mixture was diluted with water (50.0 mL) and extracted with ethyl acetate (50.0 mL). The organic layer was dried over anhydrous sodium sulfate and concentrated under reduce pressure to obtain INT-17 (0.8 g, 90.4%) as off-white solid. $^1$H NMR (400 MHz, DMSO-d$_6$) δ; 2.21 (s, 3H), 2.49 (m, 4H), 2.66 (t, J=4.6 Hz, 4H), 4.9 (s, 2H), 5.71-5.74 (dd, J=1.6, 10.2 Hz, 1H), 6.15-6.21 (dd, J=1.7, 17.0 Hz, 1H), 6.25-6.28 (dd, J=2.5, 8.4 Hz, 1H), 6.46-6.53 (dd, J=10.2, 16.9 Hz, 1H), 6.90 (d, J=8.4 Hz, 1H), 8.9 (s, 1H). MS m/z (M+H): 261.1

INT-16, INT-18, INT-36, and INT-37 were prepared using analogous methods to INT-17 and substituting the appropriate nitro-containing aryl amine compound.

INT-19

1-(5-amino-2-fluorophenoxy)-4-methylpent-3-en-2-one

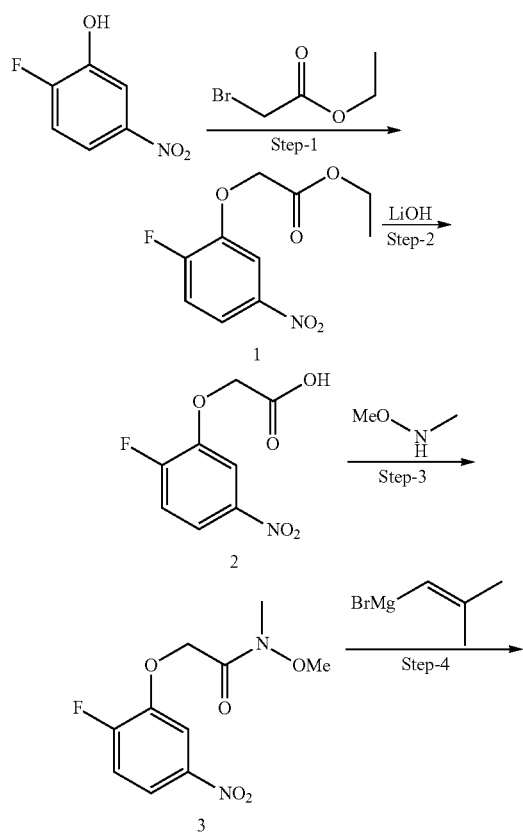

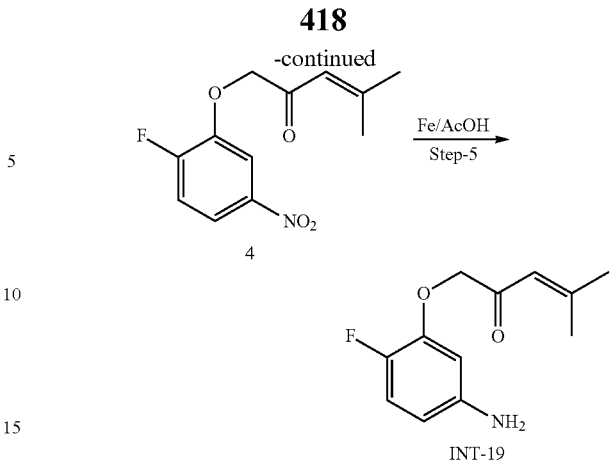

Step 1:

To a solution of 2-fluoro-5-nitrophenol (2.0 g, 12.7 mmol) in acetone (30.0 mL), K$_2$CO$_3$ (2.12 g, 15.3 mmol) and ethyl 2-bromoacetate (2.54 g, 15.2 mmol) were added, and the resulting mixture was heated to reflux for 16 h. The reaction mixture was cooled to room temperature and concentrated under reduced pressure. The residue was diluted with water (50.0 mL) and extracted with ethyl acetate (50.0 mL). The organic layer was dried over anhydrous sodium sulfate and concentrated under reduce pressure. The residue was purified by silica gel column chromatography to obtain 1 (2.2 g, 71.4%) as yellow liquid. $^1$H NMR (400 MHz, CDCl$_3$) δ 1.31 (t, J=7.1 Hz, 3H), 4.30 (q, J=7.1 Hz, 2H), 4.78 (s, 2H), 7.22-7.26 (dd, J=9.6, 15.8 Hz, 1H), 7.79-7.81 (dd, J=2.5, 7.1 Hz, 1H), 7.92 (m, 1H). MS m/z (M+H): 244

Step 2:

To a solution of ethyl 2-(2-fluoro-5-nitrophenoxy)acetate (2.0 g, 8.2 mmol) in THF:water (1:1, 20.0 mL), LiOH (1.68 g, 70 mmol) was added, and the resulting mixture was stirred at room temperature for 2 h. The reaction mixture was neutralized with 1M aq. citric acid solution (50.0 mL) and extracted with ethyl acetate (50.0 mL). The organic layer was dried over anhydrous sodium sulfate and concentrated under reduce pressure. The residue was purified by silica gel column chromatography to obtain 2 (1.4 g, 79.5%) as white solid. $^1$H NMR (400 MHz, DMSO-d$_6$) δ 4.98 (s, 2H), 7.53 (q, J=9.1 Hz, 1H), 7.93 (m, 2H), 13.2 (s, 1H). MS m/z (M+H): 216

Step 3:

To a solution of 2-(2-fluoro-5-nitrophenoxy)acetic acid (700 mg, 3.2 mmol) in dimethylformamide (10 mL), DIPEA (1.25 g, 9.7 mmol) was added and cooled to 0° C. Then EDC. HCl (1.2 g, 6.5 mmol), HOBt (879 mg, 6.5 mmol) and N,O-dimethylhydroxylamine (473 mg, 4.9 mmol) were added, and the resulting mixture was stirred at room temperature for 30 min. The reaction mixture was diluted with water (50.0 mL) and extracted with ethyl acetate (50.0 mL). The organic layer was dried over anhydrous sodium sulfate and concentrated under reduced pressure. The residue was purified by silica gel column chromatography to obtain 3 (400 mg, 83%) as gummy liquid. $^1$H NMR (400 MHz, CDCl$_3$) δ 3.25 (s, 3H), 3.80 (s, 3H), 5.0 (s, 2H), 7.26 (q, 1H), 7.80-7.82 (dd, J=2.6, 7.2 Hz, 1H), 7.88 (m, 1H). MS m/z (M+H): 259

Step 4:

To a solution of 2-(2-fluoro-5-nitrophenoxy)-N-methoxy-N-methylacetamide (0.32 g, 1.2 mmol) in dry tetrahydrofuran (5 mL), (2-methylprop-1-enyl)magnesium bromide (591 mg, 3.7 mmol) was added at −78° C., and the resulting mixture was stirred at room temperature for 4 h. The reaction mixture was diluted with water (30 mL) and extracted with ethyl acetate (50 mL). The organic layer was dried over anhydrous sodium sulfate and concentrated under reduced pressure. The residue was purified by column chromatography to obtain 4 (140 mg, 42.5%) as yellow colored semi-solid. 1H NMR (400 MHz, CDCl$_3$) δ 1.98 (s, 9H), 2.23 (s, 3H), 4.7 (s, 4H), 6.27 (s, 1H), 7.23 (t, J=9.5 Hz, 1H), 7.70-7.73 (dd, J=2.5, 7.1 Hz, 1H), 7.90 (m, 1H). MS m/z (M+H): 254

Step 5:

To solution of 1-(2-fluoro-5-nitrophenoxy)-4-methylpent-3-en-2-one (140 mg, 0.55 mmol) in acetic acid:water (2 mL: 0.2 mL), iron powder (93 mg, 1.7 mmol) was added at room temperature, and the resulting mixture was heated to 60° C. for 4 h. The reaction mixture was diluted with water (30 mL) and extracted with ethyl acetate (50 mL). The organic layer was dried over anhydrous sodium sulfate and concentrated under reduced pressure to obtain INT-19 (80 mg, 65%) as gummy solid. MS m/z (M+H): 224.2

INT-25

3-acrylamido-4-methoxybenzamide

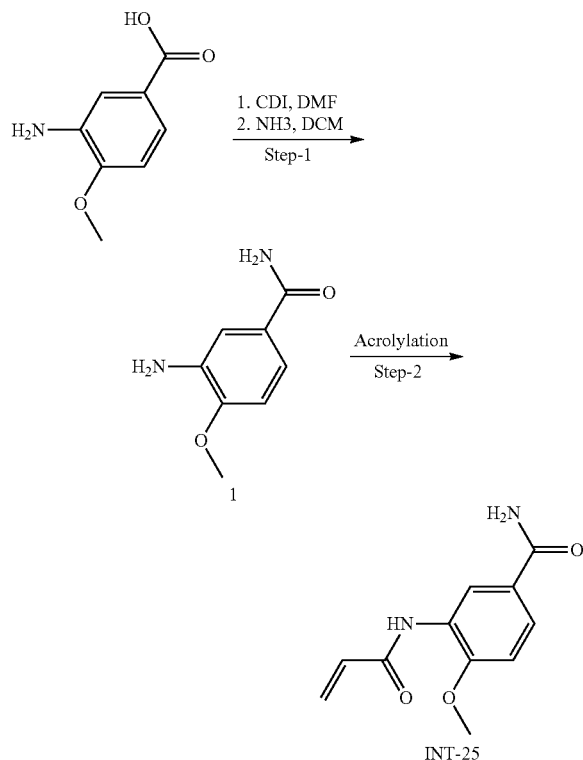

Step 1:

To a solution of 3-amino-4-methoxy-benzoic acid (1.0 g) in DMF (20 mL), CDI (1.0 eq) was added, and the reaction mixture was heated at 70° C. for 2 h. The reaction mixture was then cooled to RT and a solution of aq. ammonia (25%, 25 mL) was added dropwise and stirred for 5 h. The reaction was diluted with sat. NaCl (aq.) and extracted with 1:1 heptane/EtOAc (10×50 mL). The organic fractions were dried over sodium sulfate and concentrated to give 600 mg 1 as a white solid. MS m/z (M+H): 167.1

Step 2:

Compound 1 (1.3 g) in DCM/THF (30 mL/20 mL) was treated with acryloyl chloride (1.0 eq) and DIPEA (2.0 eq) at −78° C. and stirred at room temperature for 30 min. The reaction was concentrated, and the crude product dissolved in EtOAc, washed with water, dried over sodium sulfate, and concentrated before purification by flash chromatography: INT-25 (800 mg, 46%). MS m/z (M+H): 221.2

INT-23, INT-24, and INT-26 were prepared using analogous methods to INT-25 and substituting the appropriate amino benzoic acid compound.

INT-27

2-bromo-1-(2-chloropyrimidin-4-yl)ethanone

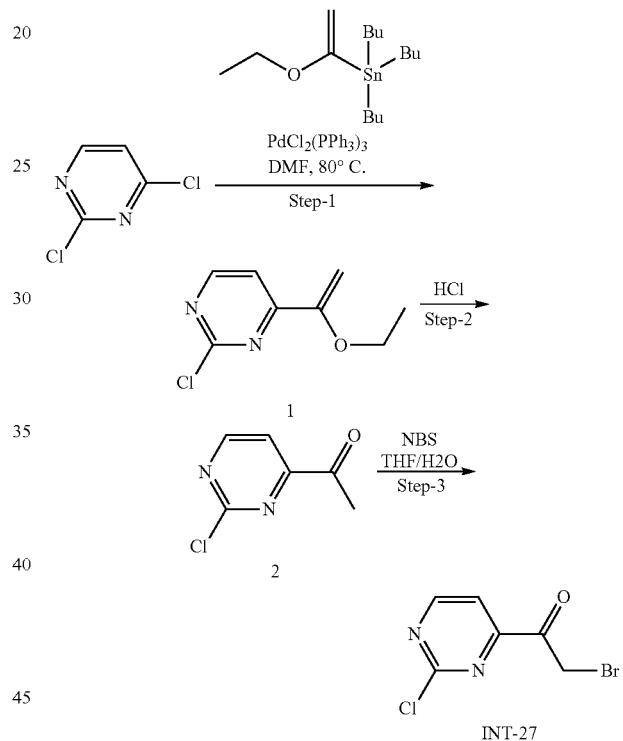

Step 1:

To a solution of 2,4-dichloropyrimidine (3.0 g, 20.0 mmol) in dry DMF (30.0 mL), ethoxyvinyltin-n-butyltin (14.0 g, 40.0 mmol) was added and degassed for 10 min. To the resulting solution, PdCl$_2$(PPh$_3$)$_2$(0.7 g, 1.0 mmol) was added and again degassed for 5 min. The reaction mixture was heated at 80° C. for 8 h. TLC showed completion of the starting material. The reaction mixture was quenched with water, extracted with ethyl acetate, dried over anhydrous sodium sulfate. The organic layer was concentrated under vacuum to afford the crude desired product 1 which was used for the next step without further purification. MS m/z (M+H): 185.0

Step 2:

To a solution of 2-chloro-4-(1-ethoxyvinyl)pyrimidine 1 (6.0 g, crude) in acetone (30.0 mL), 1N HCl (3.0 mL) was added and refluxed for 30 min. After completion of the reaction, the reaction mixture was concentrated under reduced pressure, and the residue obtained was diluted with water, extracted with ethyl acetate and dried over anhydrous sodium sulfate. The organic layer was removed under vacuum, and the residue obtained was purified by silica gel column chromatography using 2% ethyl acetate/hexane to afford compound 2 (1.0 g, 32%) as a light yellow liquid. $^1$H NMR (400 MHz, CDCl$_3$) δ 2.72 (s, 3H), 7.83 (d, J=4.9 Hz, 1H), 8.85 (d, J=4.9 Hz, 1H).

Step 3:

To a solution of 1-(2-chloropyrimidin-4-yl)ethanone 2 (1.0 g, 6.4 mmol) in acetic acid (15.0 mL), bromine (0.3 mL, 6.4 mmol) and HBr (47%, 0.7 mL, 6.4 mmol) were added. The resulting mixture was stirred at room temperature for 6 h. After completion of the reaction, solvent was distilled off, and the residue obtained was washed with diethyl ether to afford INT-27 (0.7 g, 46%) as a light brown solid. $^1$H NMR (400 MHz, CDCl$_3$+DMSO-d$_6$) δ 4.68 (s, 2H), 8.86 (d, J=4.9 Hz, 1H), 8.80 (d, J=4.8 Hz, 1H).

INT-33

N-((1S,2R)-2-aminocyclohexyl)acrylamide

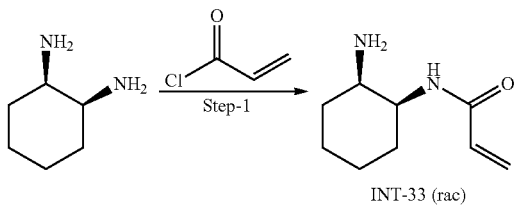

Step 1:

A solution of (1R,2S)-cyclohexane-1,2-diamine (50 mg, 0.43 mmol) in DCM (5 mL) was cooled to 0° C. and acryloyl chloride (0.03 mL, 0.44 mmol) was added dropwise for 10 min. The reaction mixture was quenched with saturated NaHCO$_3$ (5 mL) and extracted with DCM (2×10 mL). The organic layer was dried over anhydrous sodium sulfate and concentrated under reduced pressure to obtain crude amine INT-33 (135 mg, crude) as off white solid. This was used without any further purification. MS m/z (M+H): 169.1

INT-43

N-(2-(2-(dimethylamino)ethoxy)-5-(4,4,5,5-tetramethyl-1,3,2-dioxaborolan-2-yl)phenyl)acrylamide

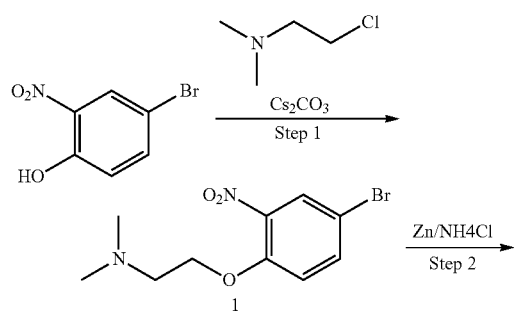

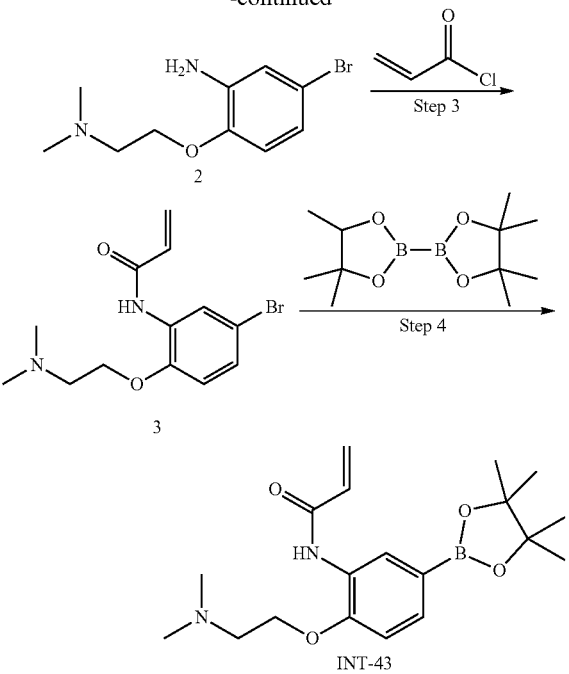

Step 1:

2-(4-bromo-2-nitrophenoxy)-N,N-dimethylethanamine (1)

To a solution of 4-bromo-2-nitrophenol (1.0 g, 4.6 mmol) in tetrahydrofuran (20 mL), 2-chloro-N,N-dimethyl ethanamine. HCl (799 mg, 7.4 mmol), cesium carbonate (3.7 g, 11.3 mmol), and potassium iodide (150 mg, 0.9 mmol) were added, and the resulting mixture was refluxed for 16 h. After completion of reaction, the reaction mixture was concentrated under reduced pressure. The residue obtained was diluted with water and extracted with ethyl acetate. The organic layer was dried over anhydrous sodium sulfate and concentrated under reduced pressure to afford 1 (1.2 g, 91%) as an yellow liquid. $^1$H NMR (400 MHz, CDCl$_3$): δ 2.4 (s, 6H), 2.72-2.73 (t, J=5.7 Hz, 2H), 4.17-4.20 (t, J=5.7 Hz, 2H), 6.97-6.99 (d, J=8.9 Hz, 1H), 7.60-7.61 (dd, J=2.5, 8.9 Hz, 1H), 7.95-7.95 (d, J=2.4 Hz, 1H). MS m/z (M+H): 289.4

Step 2:

5-bromo-2-(2-(dimethylamino)ethoxy)aniline (2)

To a solution of -(4-bromo-2-nitrophenoxy)-N,N-dimethylethanamine (2.0 g, 6.9 mmol) in 1,4-dioxane/water (1:1), Zinc (3.6 g, 55.0 mmol) and ammonium chloride (3.0 g, 55.0 mmol) were added at room temperature. The resulting mixture was stirred at room temperature for 4 h. After completion of the reaction, the reaction mixture was filtered through celite and washed with ethyl acetate. The organic layer was washed with brine, dried over anhydrous sodium sulfate and concentrated under reduced pressure to afford 2 (1.62 g, 90%). $^1$H NMR (400 MHz, DMSO-d$_6$): δ 2.20 (s, 6H), 2.59-2.60 (t, J=5.7 Hz, 2H), 3.96-3.97 (t, J=5.7 Hz, 2H), 4.99 (brs, 2H), 6.57-6.59 (dd, J=2.4, 8.4 Hz, 1H), 6.71-6.73 (d, J=8.5 Hz, 1H), 6.75 (d, J=2.4 Hz, 1H). MS m/z (M+H): 259.3

Step 3:

N-(5-bromo-2-(2-(dimethylamino)ethoxy)phenyl) acrylamide (3)

To a solution of 5-bromo-2-(2-(dimethylamino)ethoxy) aniline (500 mg, 1.9 mmol) in dichloromethane (20 mL), diisopropyl ethylamine (0.74 g, 5.7 mmol) and acryloyl chloride (200 mg, 2.2 mmol) were added at −78° C. and the resulting mixture was stirred at room temperature for 3 h. After completion of reaction, the reaction mixture was quenched with water and partitioned between dichloromethane and water. The organic phase was washed with brine solution, dried over anhydrous sodium sulfate and concentrated under reduced pressure. The residue obtained was purified by silica gel column chromatography to afford 3 (300 mg, 50%) as a brown viscous liquid. $^1$H NMR (400 MHz, DMSO-$d_6$): δ 2.23 (s, 6H), 2.60-2.62 (t, 2H), 4.11-4.13 (t, 2H), 5.74-5.75 (dd, J=7.4 Hz, 9.3 Hz, 1H), 6.22-6.23 (dd, J=1.8, 16.9 Hz, 1H), 6.51-6.53 (dd, J=10.1 Hz, 16.9 Hz, 1H), 7.08-7.10 (d, J=8.7 Hz, 1H), 7.21-7.22 (dd, J=2.49 Hz, 8.6 Hz, 1H), 8.30 (s, 1H), 9.73 (s, 1H). MS m/z (M+H): 313.5

Step 4:

N-(2-(2-(dimethylamino)ethoxy)-5-(4,4,5,5-tetramethyl-1,3,2-dioxaborolan-2-yl)phenyl) acrylamide (INT-43)

To a solution of N-(5-bromo-2-(2-(dimethylamino) ethoxy)phenyl) acrylamide (800 mg, 2.5 mmol) in 1,4-dioxane (20 mL), bispinacolatediborane (700 mg, 2.7 mmol), 1,1'-bis(diphenylphosphino)ferrocene-palladium(II) dichloride dichloromethane complex (104 mg, 0.12 mmol), and potassium acetate (753 mg, 7.6 mmol) were added and the resulting mixture was degassed under nitrogen atmosphere for 15 min. The reaction mixture was heated at 110° C. for 12 h. After completion of reaction, the reaction mixture was concentrated under reduced pressure. The residue was diluted with water and extracted with ethyl acetate (2×50 mL). The organic layer was dried over anhydrous sodium sulfate and concentrated under reduced pressure to afford INT-43 (500 mg, 54%) as a gummy solid. MS m/z (M+H): 361.3

INT-44 tert-butyl (3-(2-acrylamido-4-(4,4,5,5-tetramethyl-1,3,2-dioxaborolan-2-yl)phenoxy)propyl)carbamate

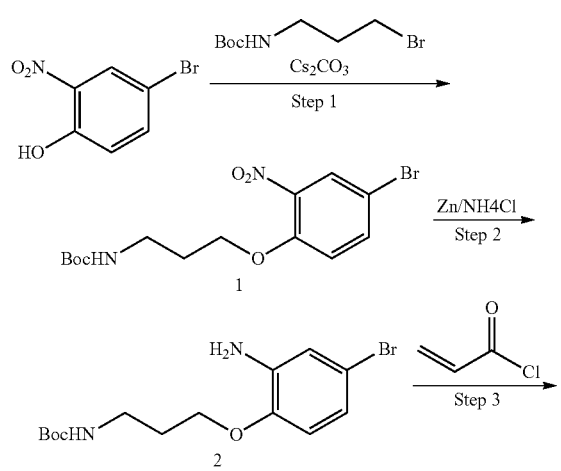

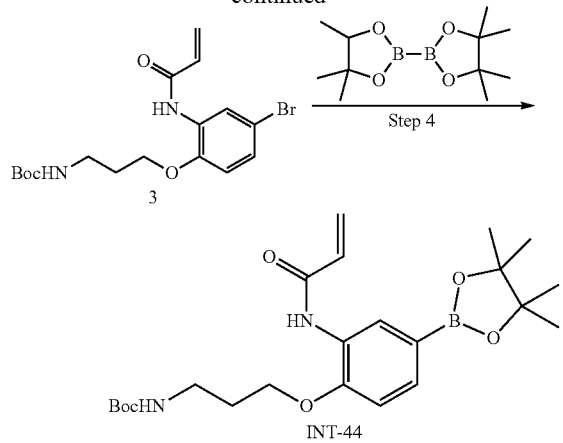

Step 1:

tert-butyl (3-(4-bromo-2-nitrophenoxy)propyl)carbamate (1)

A solution of 4-bromo-2-nitrophenol, tert-butyl (3-bromopropyl)carbamate, cesium carbonate, and potassium iodide in tetrahydrofuran was heated at reflux overnight. After completion of reaction, the reaction mixture was concentrated under reduced pressure. The residue obtained was diluted with water and extracted with ethyl acetate. The organic layer was dried over anhydrous sodium sulfate and concentrated under reduced pressure to afford 1 which was used without further purification.

Step 2:

tert-butyl (3-(2-amino-4-bromophenoxy)propyl) carbamate (2)

To a solution of compound 1 in 5:1 1,4-dioxane/water, were added Zinc and ammonium chloride at room temperature. The resulting mixture was stirred at room temperature for 4 h. After completion of the reaction, the mixture was filtered through celite and diluted with ethyl acetate. The organic layer was washed with brine, dried over anhydrous sodium sulfate and concentrated under reduced pressure to afford 2.

Step 3:

tert-butyl (3-(2-acrylamido-4-bromophenoxy)propyl)carbamate (3)

To a solution of 2 in dichloromethane was added DIPEA and acryloyl chloride at −78° C. The resulting mixture was stirred at room temperature for 3 h. After completion of reaction, the reaction mixture was quenched with water and partitioned between dichloromethane and water. The organic phase was washed with brine solution, dried over anhydrous sodium sulfate and concentrated under reduced pressure. The residue obtained was purified by silica gel column chromatography to afford 3.

Step 4:

tert-butyl (3-(2-acrylamido-4-(4,4,5,5-tetramethyl-1,3,2-dioxaborolan-2-yl)phenoxy)propyl)carbamate (4)

To a solution of compound 3 in 1,4-dioxane, bispinacolatediborane, 1,1'-bis(diphenylphosphino)ferrocene-palladium(II)dichloride dichloromethane complex, and potassium acetate were added and the resulting mixture was degassed under nitrogen atmosphere for 15 min. The reaction mixture was heated at 110° C. for 12 h. After completion of reaction, the reaction mixture was concentrated under reduced pressure. The residue was diluted with water and extracted with ethyl acetate. The organic layer was dried over anhydrous sodium sulfate and concentrated under reduced pressure to afford INT-44.

INT-45

N-(5-(4,4,5,5-tetramethyl-1,3,2-dioxaborolan-2-yl)-2-(trifluoromethoxy)phenyl)acrylamide

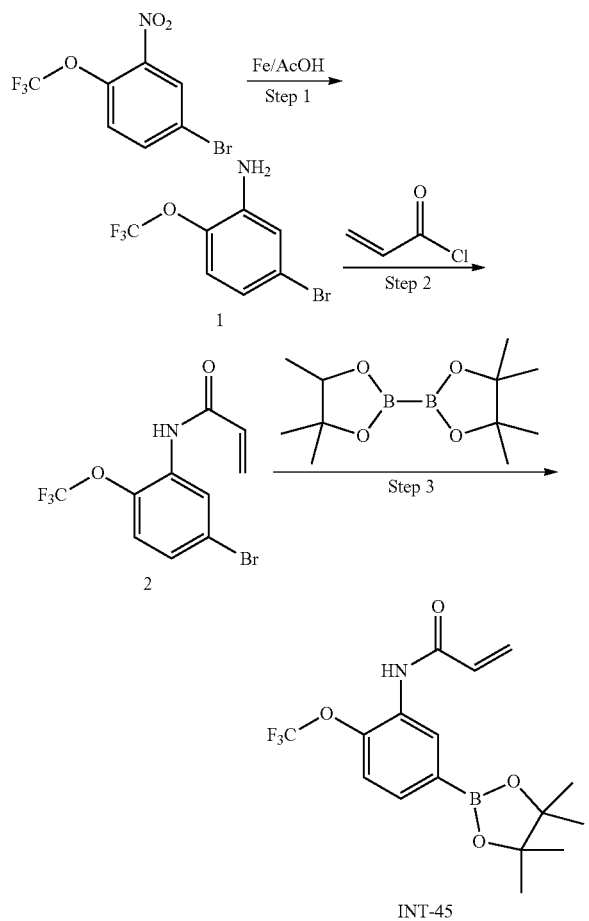

Step 1:

5-bromo-2-(trifluoromethoxy)aniline (1)

To a solution of 4-bromo-2-nitro-1-(trifluoromethoxy) benzene (2.0 g, 7.0 mmol) in acetic acid (10.0 mL) was added Fe-powder (1.0 g, 17.9 mmol) at 0-10° C. The reaction mixture was allowed to stir at room temperature for 2 h. After completion of reaction, acetic acid was distilled and the residue was diluted with water, basified with saturated sodium bicarbonate solution and extracted with ethyl acetate (2×50 mL). The organic layer was dried over anhydrous sodium sulfate and concentrated under reduced pressure to afford 1 (1.2 g, 70%) as a brown gummy solid. $^1$H NMR (400 MHz, DMSO-$d_6$): δ 5.68 (s, 2H), 6.65-6.66 (dd, J=2.4 Hz, 6.2 Hz, 1H), 6.95-6.96 (d, J=2.5 Hz, 1H), 7.01-7.01 (dd, J=1.4 Hz, 8.6 Hz, 1H). MS m/z (M+H): 256.3.

Step 2:

N-(5-bromo-2-(trifluoromethoxy)phenyl)acrylamide (2)

To a solution of 5-bromo-2-(trifluoromethoxy)aniline (1.2 g, 4.7 mmol) in dichloromethane (5.0 mL), diisopropylethylamine (727 mg, 5.64 mmol), acryloyl chloride (382 mg, 4.22 mmol) were added at −78° C. The reaction mixture was allowed to stir at 0° C. for 2 h. After completion of the reaction, the reaction mixture was diluted with water and extracted with ethyl acetate. The organic layer was dried over anhydrous sodium sulfate and concentrated under reduced pressure to afford 2 (1.4 g, 93%) as an off white solid. $^1$H NMR (400 MHz, DMSO-$d_6$): δ 5.79-5.80 (dd, J=1.82 Hz, 10.2 Hz, 1H), 6.26-6.27 (dd, J=1.8, 17.0 Hz, 1H), 6.61-6.63 (dd, J=17.0 Hz, 1H), 7.38-7.40 (m, 2H), 8.28-8.29 (d, J=2.3 Hz, 1H), 10.07 (brs, 1H). MS m/z (M+H): 310.45

Step 3:

N-(5-(4,4,5,5-tetramethyl-1,3,2-dioxaborolan-2-yl)-2-(trifluoromethoxy) phenyl)acrylamide (3)

To a solution of N-(5-bromo-2-(trifluoromethoxy)phenyl) acrylamide (600 mg, 2.0 mmol) and bispinacolatediborane (591 mg, 253.9 mmol) in 1,4-dioxane (5.0 mL), bis(diphenylphosphino)ferrocene-palladium(II)dichloride dichloromethane complex (80 mg, 0.1 mmol), potassium acetate (571 mg, 5.81 mmol) were added and degassed for 15 min. The reaction mixture was heated to reflux for 5 h. After completion of the reaction, the reaction mixture was concentrated to obtain solid residue which was diluted with water (25 mL) and extracted with ethyl acetate (2×50 mL). The organic layer was dried over anhydrous sodium sulfate and concentrated under reduced pressure to afford INT-45 (1.1 g, crude) as a brown gummy liquid. The crude material was used as such for next step without further purification. MS m/z (M+H): 358.3

INT-46

N-(5-(4,4,5,5-tetramethyl-1,3,2-dioxaborolan-2-yl)-2-(trifluoromethyl)phenyl)acrylamide

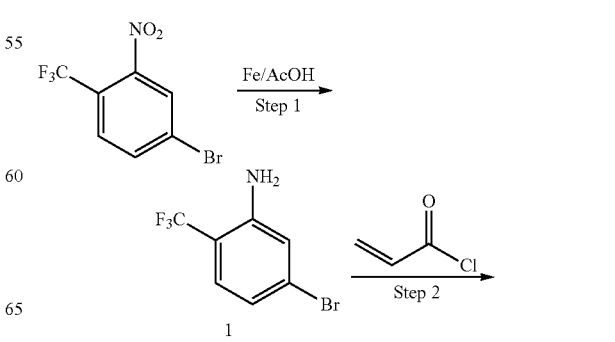

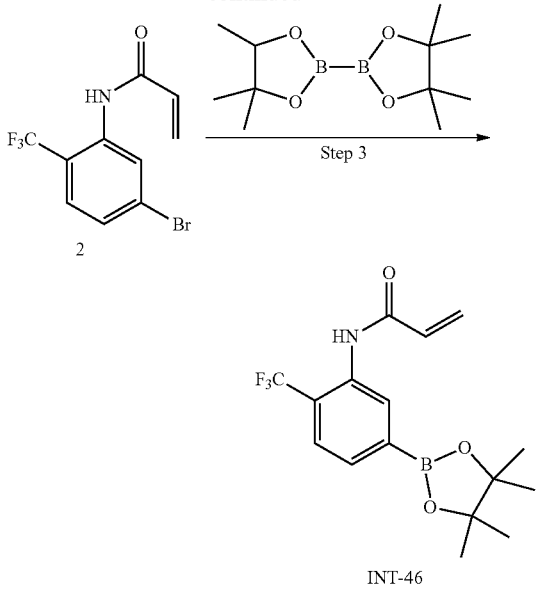

Step 1:

5-bromo-2-(trifluoromethyl)aniline (1)

To a solution of 4-bromo-2-nitro-1-(trifluoromethyl)benzene (2.0 g, 7.4 mmol) in acetic acid (10.0 mL), Iron powder (1.2 g, 21.8 mmol) was added at 0° C. The resulting reaction mixture was stirred at room temperature for 2 h. After completion of reaction, the reaction mixture was concentrated under reduced pressure. The residue obtained was diluted with water, basified with saturated sodium bicarbonate solution and extracted with ethyl acetate (2×50 mL). The organic layer was dried over anhydrous sodium sulfate and concentrated under reduced pressure to afford 1 (1.4 g, 79%) as a brown gummy solid. $^1$H NMR (400 MHz, DMSO-$d_6$): δ 5.86 (brs, 2H), 6.73-6.73 (dd, J=1.2, 8.4 Hz, 1H), 7.02 (s, 1H), 7.23-7.25 (d, J=8.4 Hz, 1H). MS m/z (M+H): 240.1

Step 2:

N-(5-bromo-2-(trifluoromethyl)phenyl)acrylamide (2)

To a solution of 5-bromo-2-(trifluoromethyl) aniline (1.4 g, 5.8 mmol) in dichloromethane (5.0 mL), diisopropylethylamine (1.2 mL, 6.5 mmol) and acryloyl chloride (0.6 g, 6.6 mmol) were added at −78° C. The resulting mixture was at 0° C. for 2 h. After completion of reaction, the reaction mixture was concentrated under reduced pressure. The residue obtained was diluted with sodium bicarbonate solution and extracted with ethyl acetate. The organic layer was dried over anhydrous sodium sulfate and concentrated under reduced pressure to afford 2 (600 mg, 35%) as an off white solid. $^1$H NMR (400 MHz, DMSO-$d_6$): δ 5.783-5.788 (dd, J=1.8, 10.2 Hz, 1H), 6.23-6.23 (dd, J=1.8, 17.0 Hz, 1H), 6.52-6.54 (dd, J=6.8, 17.0 Hz, 1H), 7.69 (m, 2H), 7.82 (s, 1H), 9.88 (brs, 1H). MS m/z (M+H): 294.0

Step 3:

N-(5-(4,4,5,5-tetramethyl-1,3,2-dioxaborolan-2-yl)-2-(trifluoromethyl)phenyl)acrylamide (3)

To a solution of N-(5-bromo-2-(trifluoromethyl)phenyl) acrylamide (600 mg, 2.0 mmol) in 1,4-dioxane (5.0 mL) bispinacolatediborane (520 mg, 2.0 mmol), bis(diphenylphosphino)ferrocene-palladium(II)dichloride dichloromethane complex (84 mg, 0.10 mmol), potassium acetate (602 mg, 6.1 mmol) were added and the resulting mixture was degassed under nitrogen atmosphere for 15 min. The reaction mixture was refluxed at 110° C. for 5 h. After completion of reaction, the reaction mixture was concentrated under reduced pressure and the residue was diluted with water, extracted with ethyl acetate (2×50 mL). The organic layer was dried over anhydrous sodium sulfate and concentrated under reduced pressure to afford INT-46 (260 mg, 37%) as an off white solid. MS m/z (M+H): 342.4

Example 88

Using the techniques described herein, the following compounds can be prepared. For compounds prepared as racemic or diastereomeric mixtures, the single isomers can be prepared in optically pure form by either employing chiral starting materials or performing chiral chromatography.

Compound I-11

N-(6'-methyl-4-(4'-oxo-1',4',5',6'-tetrahydrospiro[piperidine-3,7'-pyrrolo[3,2-c]pyridin]-2'-yl)-[2,3'-bipyridin]-5'-yl)acrylamide (racemic)

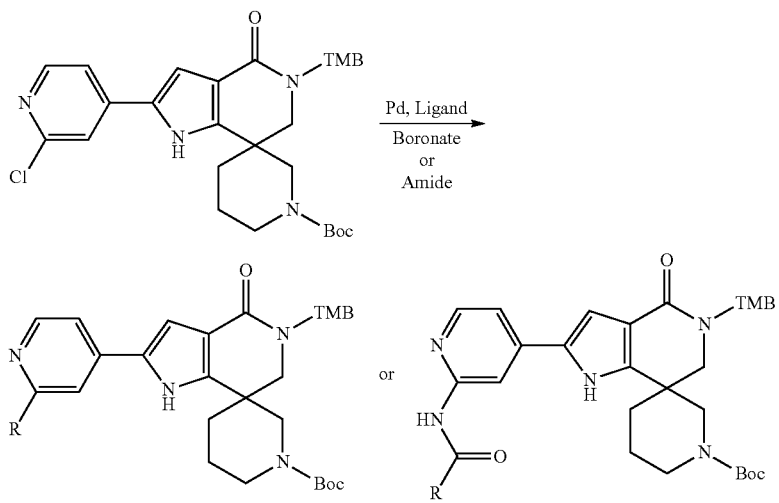

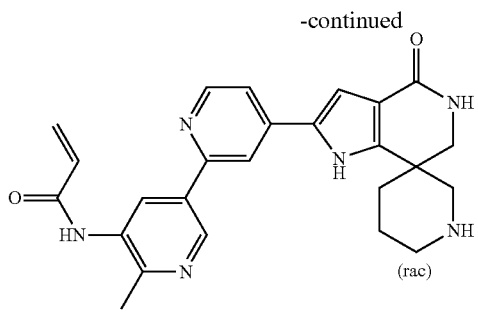

(rac)

Compound I-11 is prepared similarly to Compound I-10 (N-(2-(4-methylpiperazin-1-yl)-5-(4-(4'-oxo-1',4',5',6'-tetrahydrospiro[piperidine-3,7'-pyrrolo[3,2-c]pyridin]-2'-yl)pyridin-2-yl)phenyl)acrylamide), by substituting INT-20 for INT-8 in Example 6. The enantiomers are obtained upon chiral separation. Alternatively, the enantiomers are also used as mixtures of different ratios.

Compound I-2

N-(6'-fluoro-4-(4'-oxo-1',4',5',6'-tetrahydrospiro[piperidine-3,7'-pyrrolo[3,2-c]pyridin]-2'-yl)-[2,3'-bipyridin]-5'-yl)acrylamide (racemic)

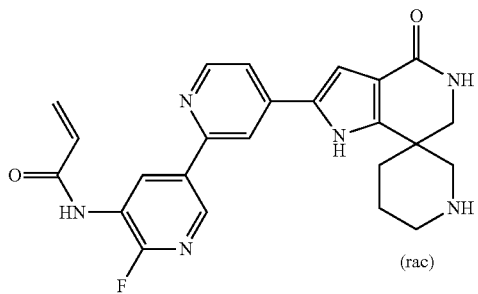 [SMILES: C=CC(=O)Nc1cc(-c2cc(-c3cc4c([nH]3)C3(CCCNC3)CNC4=O)ccn2)cnc1F]

(rac)

Compound I-2 is prepared similarly to Compound I-10 (N-(2-(4-methylpiperazin-1-yl)-5-(4-(4'-oxo-1',4',5',6'-tetrahydrospiro[piperidine-3,7'-pyrrolo[3,2-c]pyridin]-2'-yl)pyridin-2-yl)phenyl)acrylamide), by substituting INT-6 for INT-8 in Example 6. The enantiomers are obtained upon chiral separation. Alternatively, the enantiomers are also used as mixtures of different ratios.

Compound I-12

N-(2-methoxy-5-(4-(4'-oxo-1',4',5',6'-tetrahydrospiro[piperidine-3,7'-pyrrolo[3,2-c]pyridin]-2'-yl)pyridin-2-yl)phenyl)acrylamide (racemic)

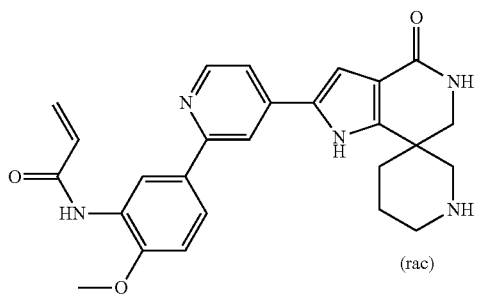 [SMILES: C=CC(=O)Nc1cc(-c2cc(-c3cc4c([nH]3)C3(CCCNC3)CNC4=O)ccn2)ccc1OC]

(rac)

Compound I-12 is prepared similarly to Compound I-10 (N-(2-(4-methylpiperazin-1-yl)-5-(4-(4'-oxo-1',4',5',6'-tetrahydrospiro[piperidine-3,7'-pyrrolo[3,2-c]pyridin]-2'-yl)pyridin-2-yl)phenyl)acrylamide), by substituting N-(2-methoxy-5-(4,4,5,5-tetramethyl-1,3,2-dioxaborolan-2-yl)phenyl)acrylamide INT-7 for INT-8 in Example 6. The enantiomers are obtained upon chiral separation. Alternatively, the enantiomers are also used as mixtures of different ratios.

Compound I-13

N-(2-(2-(dimethylamino)ethoxy)-5-(4-(4'-oxo-1',4',5',6'-tetrahydrospiro[piperidine-3,7'-pyrrolo[3,2-c]pyridin]-2'-yl)pyridin-2-yl)phenyl)acrylamide (racemic)

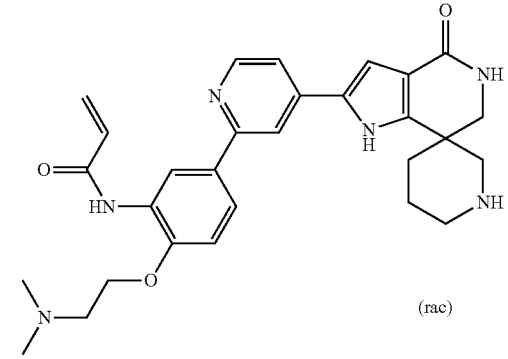 [SMILES: C=CC(=O)Nc1cc(-c2cc(-c3cc4c([nH]3)C3(CCCNC3)CNC4=O)ccn2)ccc1OCCN(C)C]

(rac)

Compound I-13 is prepared similarly to Compound I-10 (N-(2-(4-methylpiperazin-1-yl)-5-(4-(4'-oxo-1',4',5',6'-tetrahydrospiro[piperidine-3,7'-pyrrolo[3,2-c]pyridin]-2'-yl)pyridin-2-yl)phenyl)acrylamide), by substituting N-(2-(2-(dimethylamino)ethoxy)-5-(4,4,5,5-tetramethyl-1,3,2-dioxaborolan-2-yl)phenyl)acrylamide INT-43 for INT-8 in Example 6. The enantiomers are obtained upon chiral separation. Alternatively, the enantiomers are also used as mixtures of different ratios.

Compound I-14

N-(5-(4-(4'-oxo-1',4',5',6'-tetrahydrospiro[piperidine-3,7'-pyrrolo[3,2-c]pyridin]-2'-yl)pyridin-2-yl)-2-(trifluoromethoxy)phenyl)acrylamide (racemic)

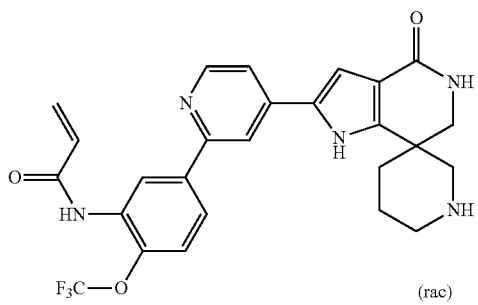 [SMILES: C=CC(=O)Nc1cc(-c2cc(-c3cc4c([nH]3)C3(CCCNC3)CNC4=O)ccn2)ccc1OC(F)(F)F]

Compound I-14 is prepared similarly to Compound I-10 (N-(2-(4-methylpiperazin-1-yl)-5-(4-(4'-oxo-1',4',5',6'-tetrahydrospiro[piperidine-3,7'-pyrrolo[3,2-c]pyridin]-2'-yl)pyridin-2-yl)phenyl)acrylamide), by substituting N-(5-(4,4,5,5-tetramethyl-1,3,2-dioxaborolan-2-yl)-2-(trifluoromethoxy)phenyl)acrylamide INT-45 for INT-8 in Example 6. The enantiomers are obtained upon chiral separation. Alternatively, the enantiomers are also used as mixtures of different ratios.

Compound I-15

N-(5-(4-(4'-oxo-1',4',5',6'-tetrahydrospiro[piperidine-3,7'-pyrrolo[3,2-c]pyridin]-2'-yl)pyridin-2-yl)-2-(trifluoromethyl)phenyl)acrylamide (racemic)

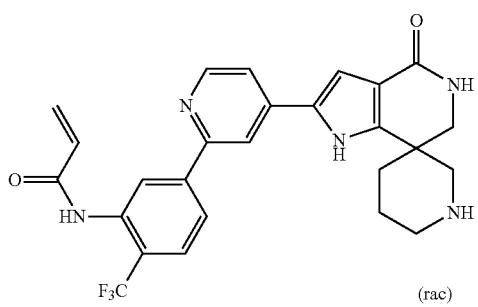 [SMILES: C=CC(=O)Nc1cc(-c2cc(-c3cc4c([nH]3)C3(CCCNC3)CNC4=O)ccn2)ccc1C(F)(F)F]

Compound I-15 is prepared similarly to Compound I-10 (N-(2-(4-methylpiperazin-1-yl)-5-(4-(4'-oxo-1',4',5',6'-tetrahydrospiro[piperidine-37'-pyrrolo[3,2-c]pyridin]-2'-yl)pyridin-2-yl)phenyl)acrylamide), by substituting N-(5-(4,4,5,5-tetramethyl-1,3,2-dioxaborolan-2-yl)-2-(trifluoromethyl)phenyl)acrylamide INT-46 for INT-8 in Example 6. The enantiomers are obtained upon chiral separation. Alternatively, the enantiomers are also used as mixtures of different ratios.

Compound I-16

3-acrylamido-4-(2-(dimethylamino)ethoxy)-N-(4-(4'-oxo-1',4',5',6'-tetrahydrospiro[piperidine-3,7'-pyrrolo[3,2-c]pyridin]-2'-yl)pyridin-2-yl)benzamide (racemic)

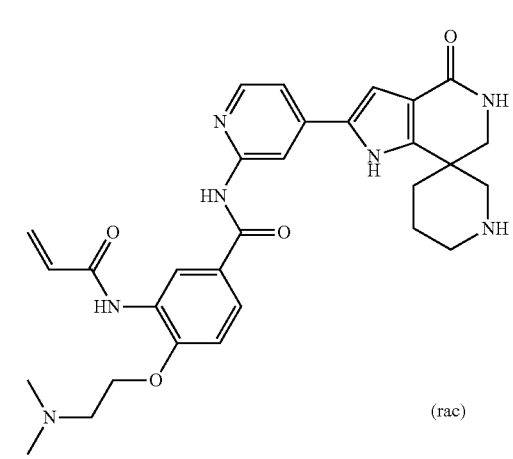 [SMILES: C=CC(=O)Nc1cc(C(=O)Nc2cc(-c3cc4c([nH]3)C3(CCCNC3)CNC4=O)ccn2)ccc1OCCN(C)C]

Compound I-16 is prepared similarly to Compound I-6 in Example 2, by substituting 3-acrylamido-4-(2-(dimethylamino)ethoxy)benzamide for INT-21. The enantiomers are obtained upon chiral separation. Alternatively, the enantiomers are also used as mixtures of different ratios.

Compound I-17

2-acrylamido-3-(2-(dimethylamino)ethoxy)-N-(4-(4'-oxo-1',4',5',6'-tetrahydrospiro[piperidine-3,7'-pyrrolo[3,2-c]pyridin]-2'-yl)pyridin-2-yl)benzamide (racemic)

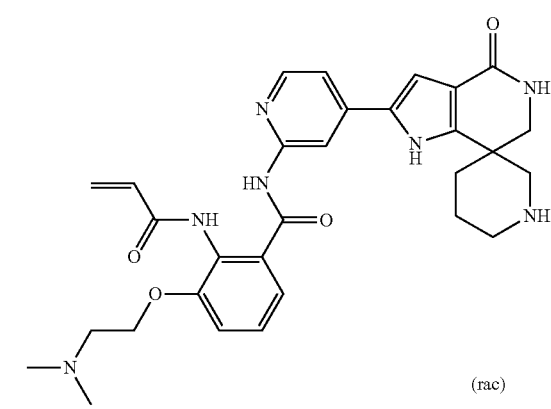 [SMILES: C=CC(=O)Nc1c(OCCN(C)C)cccc1C(=O)Nc1cc(-c2cc3c([nH]2)C2(CCCNC2)CNC3=O)ccn1]

Compound I-17 is prepared similarly to Compound I-6 (3-acrylamido-N-(4-(4'-oxo-1',4',5',6'-tetrahydrospiro[piperidine-3,7'-pyrrolo[3,2-c]pyridin]-2'-yl)pyridin-2-yl)benzamide), by substituting 3-(2-(dimethylamino)ethoxy)-2-nitrobenzamide for INT-21. The enantiomers are obtained upon chiral separation. Alternatively, the enantiomers are also used as mixtures of different ratios.

433

Compound I-18

3-acrylamido-N-(4-(4'-oxo-1',4',5',6'-tetrahydrospiro[piperidine-3,7'-pyrrolo[3,2-c]pyridin]-2'-yl)pyridin-2-yl)-5-(trifluoromethyl)benzamide (racemic)

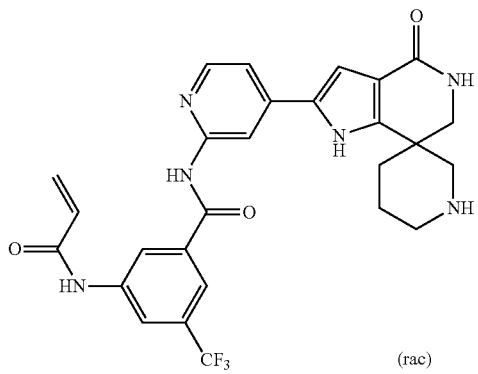 [SMILES: C=CC(=O)Nc1cc(C(=O)Nc2cc(-c3cc4c([nH]3)C3(CCCNC3)CNC4=O)ccn2)cc(C(F)(F)F)c1]

(rac)

Compound I-18 is prepared similarly to Compound I-6 (3-acrylamido-N-(4-(4'-oxo-1',4',5',6'-tetrahydrospiro[piperidine-3,7'-pyrrolo[3,2-c]pyridin]-2'-yl)pyridin-2-yl)benzamide), by substituting 3-nitro-5-(trifluoromethyl)benzamide for INT-21. The enantiomers are obtained upon chiral separation. Alternatively, the enantiomers are also used as mixtures of different ratios.

Compound I-19

5-acrylamido-6-methyl-N-(4-(4'-oxo-1',4',5',6'-tetrahydrospiro[piperidine-3,7'-pyrrolo[3,2-c]pyridin]-2'-yl)pyridin-2-yl)nicotinamide (racemic)

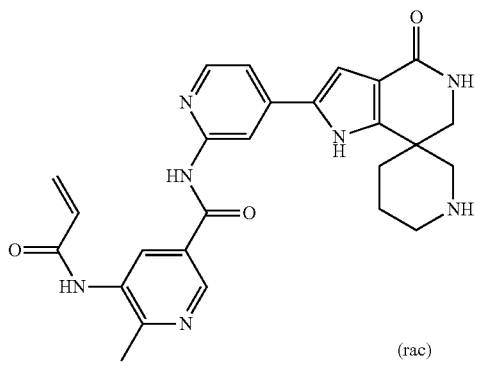 [SMILES: C=CC(=O)Nc1cc(C(=O)Nc2cc(-c3cc4c([nH]3)C3(CCCNC3)CNC4=O)ccn2)cnc1C]

(rac)

Compound I-19 is prepared similarly to Compound I-6 (3-acrylamido-N-(4-(4'-oxo-1',4',5',6'-tetrahydrospiro[piperidine-3,7'-pyrrolo[3,2-c]pyridin]-2'-yl)pyridin-2-yl)benzamide), by substituting 6-methyl-5-nitronicotinamide for INT-21. The enantiomers are obtained upon chiral separation. Alternatively, the enantiomers are also used as mixtures of different ratios.

434

Compound I-20

3-acrylamido-4-(4-methylpiperazin-1-yl)-N-(4-(4'-oxo-1',4',5',6'-tetrahydrospiro[piperidine-3,7'-pyrrolo[3,2-c]pyridin]-2'-yl)pyridin-2-yl)benzamide (racemic)

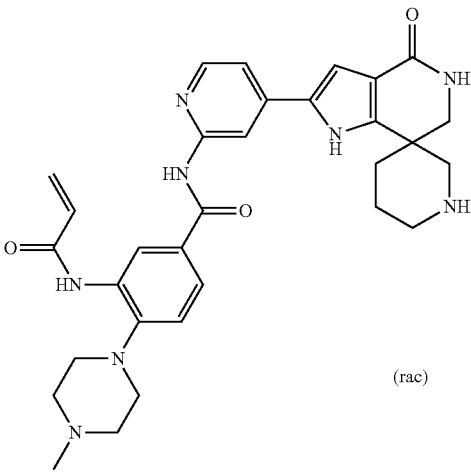 [SMILES: C=CC(=O)Nc1cc(C(=O)Nc2cc(-c3cc4c([nH]3)C3(CCCNC3)CNC4=O)ccn2)ccc1N1CCN(C)CC1]

(rac)

Compound I-20 is prepared similarly to Compound I-6 (3-acrylamido-N-(4-(4'-oxo-1',4',5',6'-tetrahydrospiro[piperidine-3,7'-pyrrolo[3,2-c]pyridin]-2'-yl)pyridin-2-yl)benzamide), by substituting 6-(4-methylpiperazin-1-yl)-5-nitronicotinamide for INT-21. The enantiomers are obtained upon chiral separation. Alternatively, the enantiomers are also used as mixtures of different ratios.

Compound I-21

2-acrylamido-4-(2-(dimethylamino)ethoxy)-N-(4-(4'-oxo-1',4',5',6'-tetrahydrospiro[piperidine-3,7'-pyrrolo[3,2-c]pyridin]-2'-yl)pyridin-2-yl)benzamide (racemic)

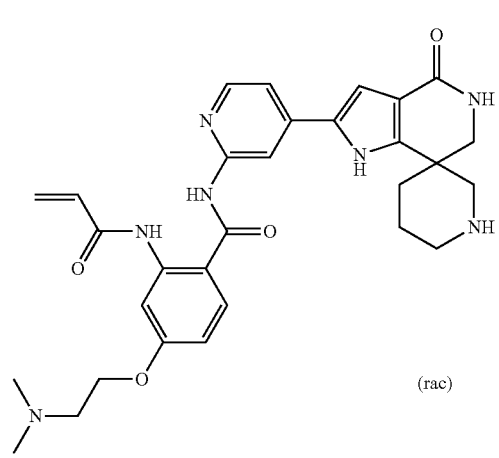 [SMILES: C=CC(=O)Nc1cc(OCCN(C)C)ccc1C(=O)Nc1cc(-c2cc3c([nH]2)C2(CCCNC2)CNC3=O)ccn1]

(rac)

Compound I-21 is prepared similarly to Compound I-6 (3-acrylamido-N-(4-(4'-oxo-1',4',5',6'-tetrahydrospiro[piperidine-3,7'-pyrrolo[3,2-c]pyridin]-2'-yl)pyridin-2-yl)benzamide), by substituting 4-(2-(dimethylamino)ethoxy)-2-nitrobenzamide for INT-21. The enantiomers are obtained upon chiral separation. Alternatively, the enantiomers are also used as mixtures of different ratios.

Compound I-22

3-acrylamido-N-(4-(4'-oxo-1',4',5',6'-tetrahydrospiro [piperidine-3,7'-pyrrolo[3,2-c]pyridin]-2'-yl)pyridin-yl)-4-(trifluoromethyl)benzamide (racemic)

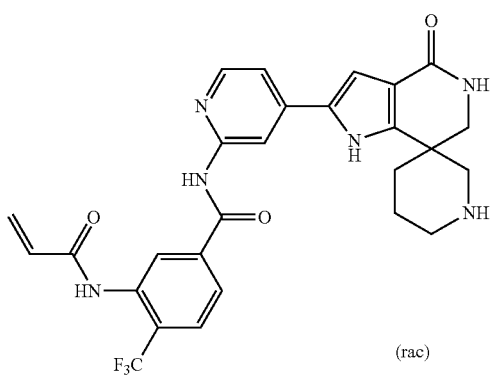 [SMILES: C=CC(=O)Nc1cc(C(=O)Nc2cc(-c3cc4c([nH]3)C3(CCCNC3)CNC4=O)ccn2)ccc1C(F)(F)F]

Compound I-22 is prepared similarly to Compound I-6 (3-acrylamido-N-(4-(4'-oxo-1',4',5',6'-tetrahydrospiro[piperidine-3,7'-pyrrolo[3,2-c]pyridin]-2'-yl)pyridin-2-yl)benzamide), by substituting 5-nitro-6-(trifluoromethyl)nicotinamide for INT-21. The enantiomers are obtained upon chiral separation. Alternatively, the enantiomers are also used as mixtures of different ratios.

Compound II-28

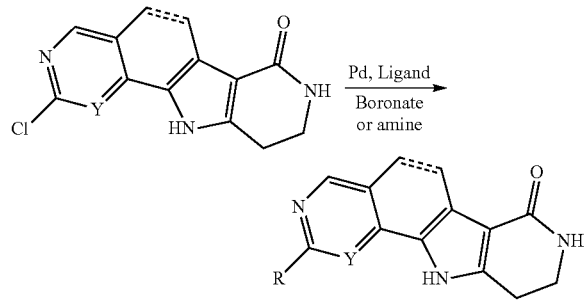

N-((1R,2S)-2-((4-(4-oxo-4,5,6,7-tetrahydro-1H-pyrrolo[3,2-c]pyridin-2-yl)pyrimidin-2-yl)amino)cyclopentyl)acrylamide (racemic)

Step 1: N-((1R,2S)-2-aminocyclopentyl)acrylamide (rac) is prepared similarly to INT-33 in Example 87, by substituting (1R,2S)-cyclopentane-1,2-diamine (rac) for (1R,2S)-cyclohexane-1,2-diamine.

Step 2: tert-butyl 2-(2-chloropyrimidin-4-yl)-4-oxo-6,7-dihydro-1H-pyrrolo[3,2-c]pyridine-5(4H)-carboxylate (Intermediate 1, Example 29) is treated with N-((1R,2S)-2-aminocyclopentyl)acrylamide (rac) from step 1, followed by the addition of Brettphos Palladacycle and Brettphos ligand at room temperature under nitrogen. To this, LiHMDS (1M in tetrahydrofuran) is added, and the reaction mixture is heated to 100° C. The reaction mixture is quenched with 1N HCl solution and partitioned between ethyl acetate (100 mL) and water (50 mL). The organic layer is dried over anhydrous sodium sulfate, concentrated, and purified to yield the title compound. The enantiomers are obtained upon chiral separation. Alternatively, the enantiomers are also used as mixtures of different ratios.

Compound II-29

N-((3S,4R)-4-((4-(4-oxo-4,5,6,7-tetrahydro-1H-pyrrolo[3,2-c]pyridin-2-yl)pyrimidin-2-yl)amino) tetrahydrofuran-3-yl)acrylamide (racemic)

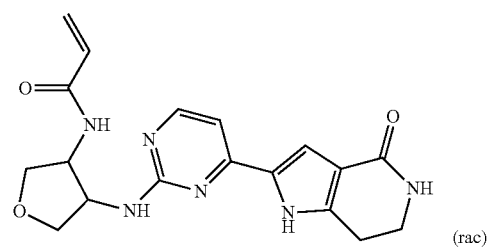 [SMILES: C=CC(=O)NC1COCC1Nc1nccc(-c2cc3c([nH]2)CCNC3=O)n1]

Step 1: N-((3S,4R)-4-aminotetrahydrofuran-3-yl)acrylamide (rac) is prepared similarly to INT-33 in Example 87, by substituting (3R,4S)-tetrahydrofuran-3,4-diamine (rac) for (1R,2S)-cyclohexane-1,2-diamine.

Step 2: The title compound is prepared similarly to Compound II-28, by substituting N-((3S,4R)-4-aminotetrahydrofuran-3-yl)acrylamide (rac) prepared here in step 1 for N-((1R,2S)-2-aminocyclopentyl)acrylamide (rac) in the reaction with Intermediate 1 from Example 29. The enantiomers are obtained upon chiral separation. Alternatively, the enantiomers are also used as mixtures of different ratios.

Compound II-30

N-((3R,4S)-1-methyl-4-((4-(4-oxo-4,5,6,7-tetrahydro-1H-pyrrolo[3,2-c]pyridin-2-yl)pyrimidin-2-yl) amino)pyrrolidin-3-yl)acrylamide (racemic)

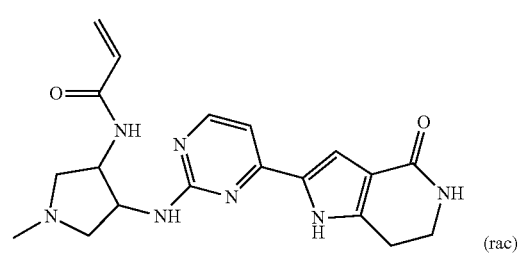 [SMILES: C=CC(=O)NC1CN(C)CC1Nc1nccc(-c2cc3c([nH]2)CCNC3=O)n1]

Step 1: N-((3R,4S)-4-amino-1-methylpyrrolidin-3-yl)acrylamide (rac) is prepared similarly to INT-33 in Example 87, by substituting (3R,4S)-1-methylpyrrolidine-3,4-diamine (rac) for (1R,2S)-cyclohexane-1,2-diamine.

Step 2: The title compound is prepared similarly to Compound II-28, by substituting N-((3R,4S)-4-amino-1-methylpyrrolidin-3-yl)acrylamide (rac) prepared here in step 1 for N-((1R,2S)-2-aminocyclopentyl)acrylamide (rac)) in the reaction with Intermediate 1 from Example 29. The enantiomers are obtained upon chiral separation. Alternatively, the enantiomers are also used as mixtures of different ratios.

Compound II-31

N-(2-(2-(dimethylamino)ethoxy)-5-(4-(4-oxo-4,5,6,7-tetrahydro-1H-pyrrolo[3,2-c]pyridin-2-yl)pyrimidin-2-yl)phenyl)acrylamide

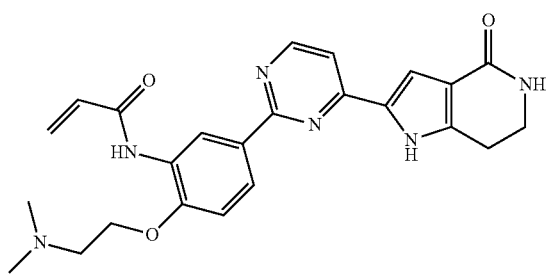 [SMILES: C=CC(=O)Nc1cc(-c2nccc(-c3cc4c([nH]3)CCNC4=O)n2)ccc1OCCN(C)C]

The title compound is prepared similarly to Compound II-25 in Example 29, by substituting INT-43 for INT-1 in step 2.

Compound II-32

N-(2-methyl-5-(4-(4-oxo-4,5,6,7-tetrahydro-1H-pyrrolo[3,2-c]pyridin-2-yl)pyrimidin-2-yl)pyridin-3-yl)acrylamide

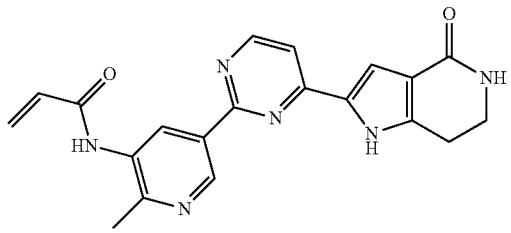 [SMILES: C=CC(=O)Nc1cc(-c2nccc(-c3cc4c([nH]3)CCNC4=O)n2)cnc1C]

Compound II-32 is prepared similarly to Compound II-25 in Example 29, by substituting INT-20 for INT-1 in step 2.

Compound II-33

N-((1R,2S)-2-((7-oxo-6,7,8,9,10,11-hexahydro-5H-pyrido[3',4':4,5]pyrrolo[2,3-f]isoquinolin-2-yl)amino)cyclopentyl)acrylamide (racemic)

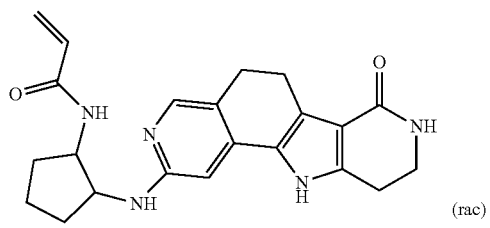 [SMILES: C=CC(=O)NC1CCCC1Nc1cc2c(cn1)CCc1c-2[nH]c2c1C(=O)NCC2]

Compound II-33 is prepared similarly to Compound II-28, by substituting Intermediate 6 from Example 21 for Intermediate 1 from Example 29 in the reaction with N-((1R,2S)-2-aminocyclopentyl)acrylamide (rac). The enantiomers are obtained upon chiral separation. Alternatively, the enantiomers are also used as mixtures of different ratios.

Compound II-34

N-((3S,4R)-4-((7-oxo-6,7,8,9,10,11-hexahydro-5H-pyrido[3',4':4,5]pyrrolo[2,3-f]isoquinolin-2-yl)amino)tetrahydrofuran-3-yl)acrylamide (racemic)

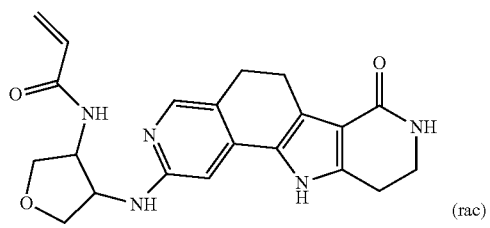

Compound II-34 is prepared similarly to Compound II-29, by substituting Intermediate 6 from Example 21 for Intermediate 1 from Example 29 in the reaction with N-((3S,4R)-4-aminotetrahydrofuran-3-yl)acrylamide (rac). The enantiomers are obtained upon chiral separation. Alternatively, the enantiomers are also used as mixtures of different ratios.

Compound II-35

N-((3R,4S)-1-methyl-4-((7-oxo-6,7,8,9,10,11-hexahydro-5H-pyrido[3',4':4,5]pyrrolo[2,3-f]isoquinolin-2-yl)amino)pyrrolidin-3-yl)acrylamide (racemic)

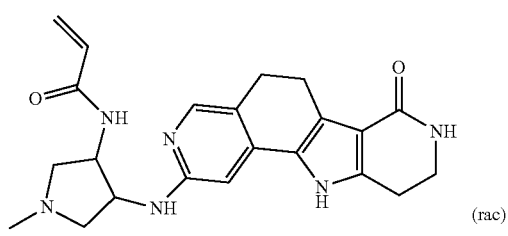 [SMILES: C=CC(=O)NC1CN(C)CC1Nc1cc2c(cn1)CCc1c-2[nH]c2c1C(=O)NCC2]

Compound II-35 is prepared similarly to Compound II-30, by substituting 6 from Example 21 for Intermediate 1 from Example 29 in the reaction with N-((3R,4S)-4-amino-1-methylpyrrolidin-3-yl)acrylamide (rac). The enantiomers are obtained upon chiral separation. Alternatively, the enantiomers are also used as mixtures of different ratios.

Compound II-36

N-(2-(2-(dimethylamino)ethoxy)-5-(7-oxo-6,7,8,9,10,11-hexahydro-5H-pyrido[3',4':4,5]pyrrolo[3,2-h]quinazolin-2-yl)phenyl)acrylamide

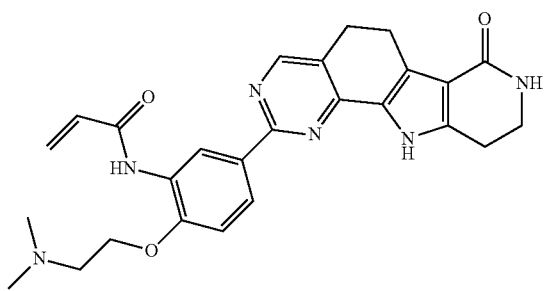 [SMILES: C=CC(=O)Nc1cc(-c2ncc3c(n2)-c2[nH]c4c(c2CC3)C(=O)NCC4)ccc1OCCN(C)C]

Compound II-36 is prepared similarly to Compound II-31, by substituting Intermediate 7 from Example 33 for Intermediate 1 from Example 29 in the reaction with INT-43.

Compound II-37

N-(2-methyl-5-(7-oxo-6,7,8,9,10,11-hexahydro-5H-pyrido[3',4':4,5]pyrrolo[3,2-h]quinazolin-2-yl)pyridin-3-yl)acrylamide

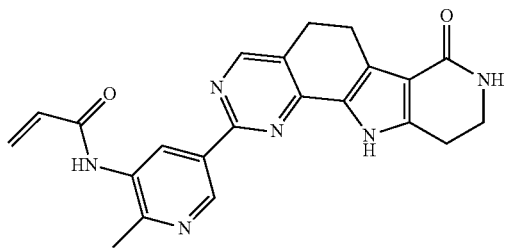 [SMILES: C=CC(=O)Nc1cc(-c2ncc3c(n2)-c2[nH]c4c(c2CC3)C(=O)NCC4)cnc1C]

Compound II-37 is prepared similarly to Compound II-32, by substituting Intermediate 7 from Example 33 for Intermediate 1 from Example 29 in the reaction with INT-20.

Compound II-38

N-((1R,2S)-2-((7-oxo-6,7,8,9,10,11-hexahydro-5H-pyrido[3',4':4,5]pyrrolo[3,2-h]quinazolin-2-yl)amino)cyclopentyl)acrylamide (racemic)

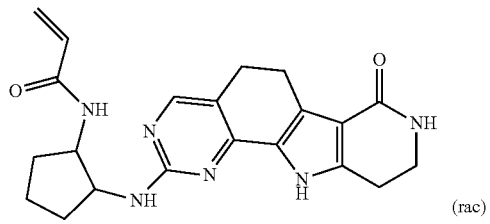 [SMILES: C=CC(=O)NC1CCCC1Nc1ncc2c(n1)-c1[nH]c3c(c1CC2)C(=O)NCC3]

Compound II-38 is prepared similarly to Compound II-28, by substituting Intermediate 7 from Example 33 for Intermediate 1 from Example 29 in the reaction with N-((1R,2S)-2-aminocyclopentyl)acrylamide (rac). The enantiomers are obtained upon chiral separation. Alternatively, the enantiomers are also used as mixtures of different ratios.

Compound II-39

N-((3S,4R)-4-((7-oxo-6,7,8,9,10,11-hexahydro-5H-pyrido[3',4':4,5]pyrrolo[3,2-h]quinazolin-2-yl)amino)tetrahydrofuran-3-yl)acrylamide (racemic)

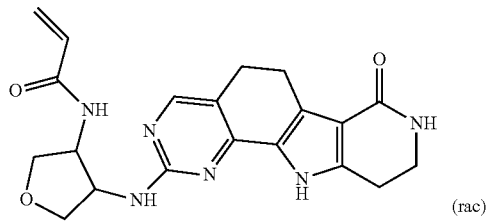 [SMILES: C=CC(=O)NC1COCC1Nc1ncc2c(n1)-c1[nH]c3c(c1CC2)C(=O)NCC3]

Compound II-39 is prepared similarly to Compound II-29, by substituting Intermediate 7 from Example 33 for Intermediate 1 from Example 29 in the reaction with N-((3S,4R)-4-aminotetrahydrofuran-3-yl)acrylamide (rac). The enantiomers are obtained upon chiral separation. Alternatively, the enantiomers are also used as mixtures of different ratios.

Compound II-40

N-((3R,4S)-1-methyl-4-((7-oxo-6,7,8,9,10,11-hexahydro-5H-pyrido[3',4':4,5]pyrrolo[3,2-h]quinazolin-2-yl)amino)pyrrolidin-3-yl)acrylamide (racemic)

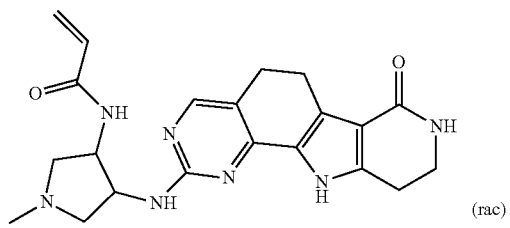 [SMILES: C=CC(=O)NC1CN(C)CC1Nc1ncc2c(n1)-c1[nH]c3c(c1CC2)C(=O)NCC3]

Compound II-40 is prepared similarly to Compound II-30, by substituting Intermediate 7 from Example 33 for Intermediate 1 from Example 29 in the reaction with N-((3R,4S)-4-amino-1-methylpyrrolidin-3-yl)acrylamide (rac). The enantiomers are obtained upon chiral separation. Alternatively, the enantiomers are also used as mixtures of different ratios.

Compound II-41

N-(2-(2-(dimethylamino)ethoxy)-5-(7-oxo-6,7,8,9,10,11-hexahydro-5H-pyrido[3',4':4,5]pyrrolo[2,3-f]isoquinolin-2-yl)phenyl)acrylamide

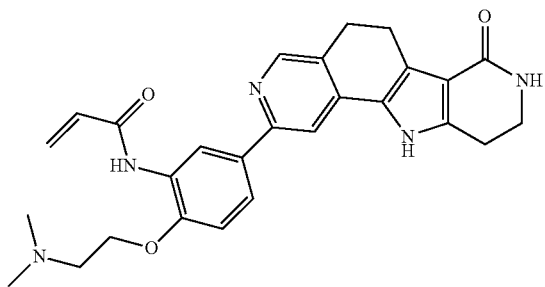 [SMILES: C=CC(=O)Nc1cc(-c2cc3c(cn2)CCc2c-3[nH]c3c2C(=O)NCC3)ccc1OCCN(C)C]

Compound II-41 is prepared similarly to Compound II-31, by substituting Intermediate 6 from Example 21 for Intermediate 1 from Example 29 in the reaction with INT-43.

Compound II-42

N-(2-methyl-5-(7-oxo-6,7,8,9,10,11-hexahydro-5H-pyrido[3',4':4,5]pyrrolo[2,3-f]isoquinolin-2-yl)pyridin-3-yl)acrylamide

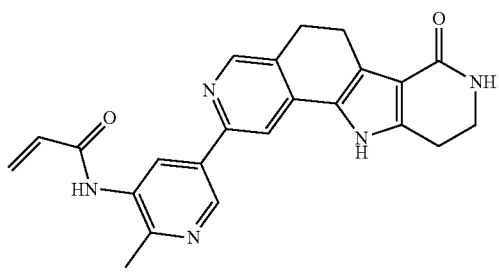 [SMILES: C=CC(=O)Nc1cc(-c2cc3c(cn2)CCc2c-3[nH]c3c2C(=O)NCC3)cnc1C]

Compound II-42 is prepared similarly to Compound II-32, by Intermediate 6 from Example 21 for Intermediate 1 from Example 29 in the reaction with INT-20-.

Compound II-43

N-((1R,2S)-2-((7'-oxo-5',6',7',8',10',11'-hexahydrospiro[cyclopropane-1,9'-pyrido[3',4':4,5]pyrrolo[2,3-f]isoquinolin]-2'-yl)amino)cyclopentyl)acrylamide (racemic)

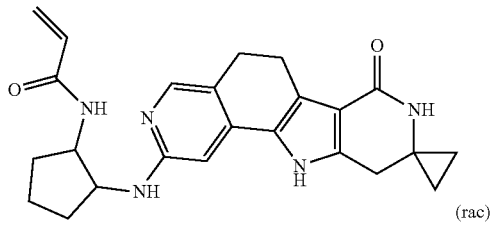

Compound II-43 is prepared similarly to Compound II-28, by substituting Intermediate 12 from Example 14 for Intermediate 1 from Example 29 in the reaction with N-((1R,2S)-2-aminocyclopentyl)acrylamide (rac)-. The enantiomers are obtained upon chiral separation. Alternatively, the enantiomers are also used as mixtures of different ratios.

Compound II-44

N-((3S,4R)-4-((7'-oxo-5',6',7',8',10',11'-hexahydrospiro[cyclopropane-1,9'-pyrido[3',4':4,5]pyrrolo[2,3-f]isoquinolin]-2'-yl)amino)tetrahydrofuran-3-yl)acrylamide (racemic)

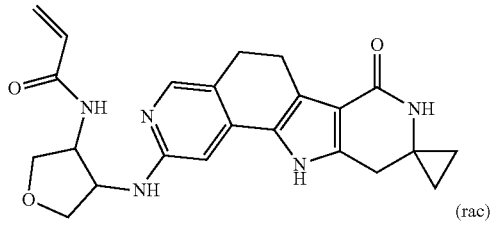 [SMILES: C=CC(=O)NC1COCC1Nc1cc2c(cn1)CCc1c-2[nH]c2c1C(=O)NC1(CC1)C2]

Compound II-44 is prepared similarly to Compound II-29, by substituting Intermediate 12 from Example 14 for Intermediate 1 from Example 29 in the reaction with N-((3S,4R)-4-aminotetrahydrofuran-3-yl)acrylamide (rac)-. The enantiomers are obtained upon chiral separation. Alternatively, the enantiomers are also used as mixtures of different ratios.

Compound II-45

N-((3R,4S)-1-methyl-4-((7'-oxo-5',6',7',8',10',11'-hexahydrospiro[cyclopropane-1,9'-pyrido[3',4':4,5]pyrrolo[2,3-f]isoquinolin]-2'-yl)amino)pyrrolidin-3-yl)acrylamide (racemic)

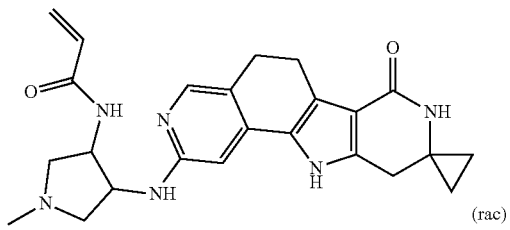 [SMILES: C=CC(=O)NC1CN(C)CC1Nc1cc2c(cn1)CCc1c-2[nH]c2c1C(=O)NC1(CC1)C2]

(rac)

Compound II-45 is prepared similarly to Compound II-30, by substituting Intermediate 12 from Example 14 for Intermediate 1 from Example 29 in the reaction with N-((3R,4S)-4-amino-1-methylpyrrolidin-3-yl)acrylamide (rac). The enantiomers are obtained upon chiral separation. Alternatively, the enantiomers are also used as mixtures of different ratios.

Compound II-46

N-(2-(2-(dimethylamino)ethoxy)-5-(7'-oxo-5',6',7',8',10',11'-hexahydrospiro[cyclopropane-1,9'-pyrido[3',4':4,5]pyrrolo[2,3-f]isoquinolin]-2'-yl)phenyl)acrylamide

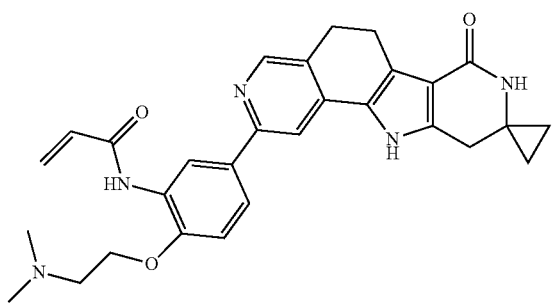 [SMILES: C=CC(=O)Nc1cc(-c2cc3c(cn2)CCc2c-3[nH]c3c2C(=O)NC2(CC2)C3)ccc1OCCN(C)C]

Compound II-46 is prepared similarly to Compound II-12 in Example 14, by substituting INT-43 for INT-1 in step-14.

Compound II-47

N-(2-methyl-5-(7'-oxo-5',6',7',8',10',11'-hexahydrospiro[cyclopropane-1,9'-pyrido[3',4':4,5]pyrrolo[2,3-f]isoquinolin]-2'-yl)pyridin-3-yl)acrylamide

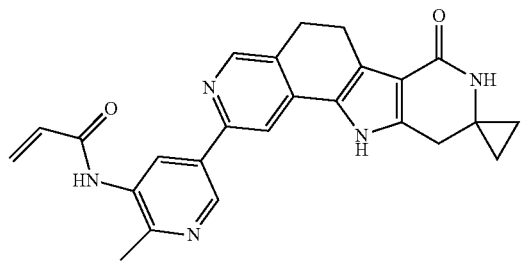 [SMILES: C=CC(=O)Nc1cc(-c2cc3c(cn2)CCc2c-3[nH]c3c2C(=O)NC2(CC2)C3)cnc1C]

Compound II-47 is prepared similarly to Compound II-12 in Example 14, by substituting INT-20 for INT-1 in step-14.

Compound II-e-2

N-(2-methoxy-5-(7-oxo-7,8,9,1-tetrahydrocyclopenta[4,5]pyrrolo[2,3-f]isoquinolin-2-yl)phenyl)acrylamide

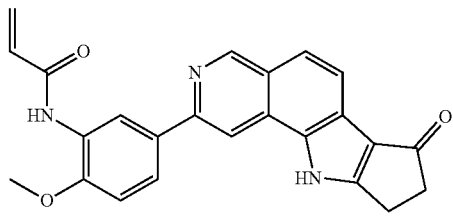

Compound II-e-2 is prepared similarly to Compound II-e-3 in Example 38, by substituting INT-39 for INT-41.

Compound II-e-4

N-(2-(4-methylpiperazin-1-yl)-5-(7-oxo-7,8,9,10-tetrahydrocyclopenta[4,5]pyrrolo[2,3-f]isoquinolin-2-yl)phenyl)acrylamide

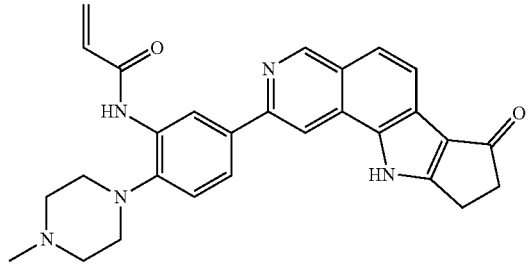 [SMILES: C=CC(=O)Nc1cc(-c2cc3c(ccc4c5c([nH]c43)CCC5=O)cn2)ccc1N1CCN(C)CC1]

Compound II-e-4 was prepared similarly to Compound II-e-3 in Example 38, by substituting INT-41 in step 2 of Example 38 with pinacol boronate 3, depicted below, to give the desired product as a pale yellow solid (3.5 mg, 12.5% yield). $^1$H NMR (400 MHz, DMSO-d$_6$): δ: 2.71 (brs, 4H), 2.92 (s, 3H), 3.12 (s, 4H), 3.24 (s, 4H), 5.84 (dd, J=10.5, 16.5 Hz, 1H), 6.32 (d, J=17 Hz, 1H), 6.76 (dd, J=10.5, 16.4 Hz, 1H), 7.35 (d, J=8.4 Hz, 1H), 7.82 (d, J=8.5 Hz, 1H), 7.91 (d, J=8.5 Hz, 1H), 8.03 (dd, J=6.6, 8.3 Hz, 1H), 8.84 (d, J=6.6 Hz, 2H), 9.25 (s, 1H), 9.37 (s, 1H), 13.37 (s, 1H). MS m/z (M+H): 466.3.

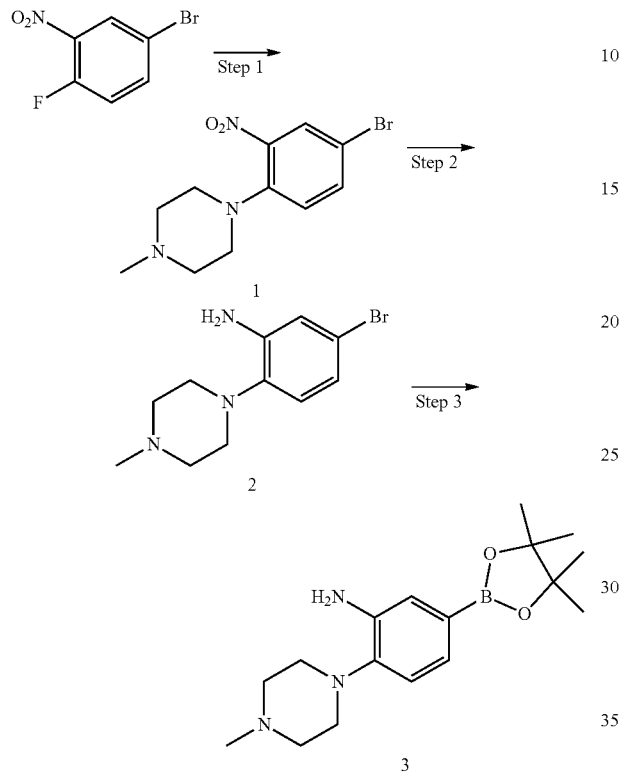

Step 1:

1-(4-bromo-2-nitrophenyl)-4-methylpiperazine (1)

To a stirred solution of 4-bromo-1-fluoro-2-nitrobenzene (3 g, 13.6 mmol), 1-methyl piperidine (2.7 g, 27.2 mmol) in DMF (10 mL), cesium carbonate (8.86 g, 27.2 mmol) was added at room temperature. The reaction mixture was heated for 16 h at 80° C. After completion of reaction, the reaction mixture was quenched with ice cold water and extracted with ethyl acetate. The combined organic phase was washed with water and brine, dried over anhyd. Na$_2$SO$_4$, and concentrated under reduced pressure. The crude compound was purified by column chromatography (neutral alumina, 30% ethyl acetate in pet. ether as eluent) to afford 1 (2.3 g, 56% yield) as an off white solid. MS m/z (M+H): 300.4

Step 2:

5-bromo-2-(4-methylpiperazin-1-yl)aniline (2)

To a stirred solution of 1-(4-bromo-2-nitrophenyl)-4-methylpiperazine (800 mg, 2.67 mmol) in 1,4-dioxane:water (16 mL, 3:1 ratio), zinc (1.39 g, 21.4 mmol) and NH$_4$Cl (1.18 g, 22.2 mmol) were added at 0° C. and stirred for 3 h at room temperature. After completion of reaction, the reaction mixture was filtered through celite and washed with dioxane. Filtrate was concentrated under reduced pressure to afford 2 (600 mg, 83% yield) as an off white solid. MS m/z (M+H): 270.4

Step 3:

2-(4-methylpiperazin-1-yl)-5-(4,4,5,5-tetramethyl-1,3,2-dioxaborolan-2-yl)aniline (3)

To a stirred solution of 5-bromo-2-(4-methylpiperazin-1-yl)aniline (600 mg, 2.97 mmol), bis (pinacolato)diborane (677 mg, 2.67 mmol) in 1,4-dioxane (30 mL) was added KOAc (4.37 mg, 4.45 mmol) and degassed for 30 min with argon. To the reaction mixture Pd(dppf)$_2$Cl$_2$.DCM (364 mg, 0.44 mmol) was added, again degassed for 10 min and stirred for 2 h at 90° C. After completion of the reaction, solvent was removed under reduced pressure. The crude compound was purified by column chromatography (100-200 silica gel, 2-5% methanol in DCM as eluent) to afford 3 (420 mg, 59% yield) as a brown solid. MS m/z (M+H): 318.39.

Compound II-e-5

N-(1-(7-oxo-7,8,9,10-tetrahydrocyclopenta[4,5]pyrrolo[2,3-f]isoquinolin-2-yl)piperidin-3-yl)acrylamide (racemic)

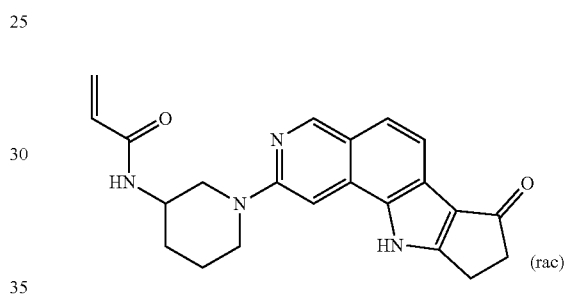

Compound II-e-5 is prepared by reacting N-(piperidin-3-yl)acrylamide (racemic) with Intermediate 1 from Example 38 under Buchwald conditions with Ruphos (LiHMDS, 100° C., dioxane). The reaction mixture is quenched with IN HCl solution and partitioned between ethyl acetate and water. The organic layer is dried over anhydrous sodium sulfate, concentrated, and purified to yield the title compound. The enantiomers are obtained upon chiral separation. Alternatively, the enantiomers are also used as mixtures of different ratios.

Compound II-e-6

N-(2-(7-oxo-7,8,9,10-tetrahydrocyclopenta[4,5]pyrrolo[2,3-f]isoquinolin-2-yl)pyridin-4-yl)acrylamide

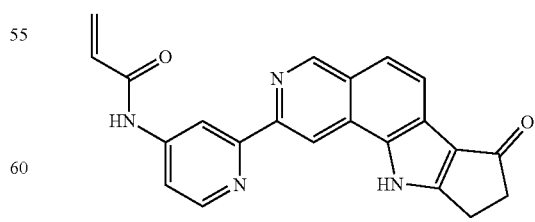

Compound II-e-6 is prepared similarly to Compound II-e-3 in Example 38, by substituting 2-(4,4,5,5-tetramethyl-1,3,2-dioxaborolan-2-yl)pyridin-4-amine for INT-41 in step 2.

Compound II-e-7

N N-(4-(7-oxo-7,8,9,10-tetrahydrocyclopenta[4,5]pyrrolo[2,3-f]isoquinolin-2-yl)pyridin-2-yl)acrylamide

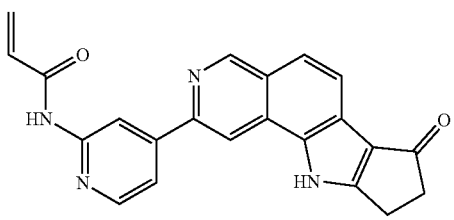 [SMILES: C=CC(=O)Nc1cc(-c2cc3c(ccc4c5c([nH]c43)CCC5=O)cn2)ccn1]

Compound II-e-7 is prepared similarly to Compound II-e-3 in Example 38, by substituting 4-(4,4,5,5-tetramethyl-1,3,2-dioxaborolan-2-yl)pyridin-2-amine for INT-41 in step 2.

Compound II-e-8

2-(4-acryloyl-3,4-dihydro-2H-benzo[b][1,4]oxazin-6-yl)-8,9-dihydrocyclopenta[4,5]pyrrolo[2,3-f]isoquinolin-7(10H)-one

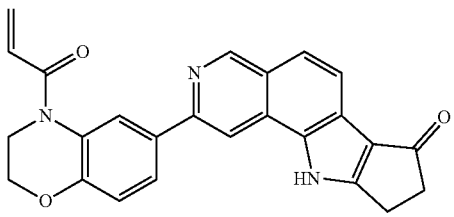 [SMILES: C=CC(=O)N1CCOc2ccc(-c3cc4c(ccc5c6c([nH]c54)CCC6=O)cn3)cc21]

Compound II-e-8 was prepared similarly to Compound II-e-3 in Example 38, by substituting INT-41 in step 2 of Example 38 with boronate 3, depicted below, to afford the desired product (12 mg, 35% yield) as a yellow solid. $^1$H NMR (400 MHz, DMSO-d$_6$): δ: 2.84 (t, J=2 Hz, 2H), 3.13 (t, J=2 Hz, 2H), 4.01 (t, J=4.3 Hz, 2H), 4.36 (t, J=4 Hz, 2H), 5.87 (dd, J=2, 10 Hz, 1H), 6.35 (dd, J=2, 17 Hz, 1H), 6.88 (dd, J=10, 17 Hz, 1H), 7.07 (d, J=8.5 Hz, 1H), 7.65 (d, J=8.5 Hz, 1H), 7.85 (d, J=8.5 Hz, 1H), 7.92 (dd, J=2, 8.5 Hz, 1H), 8.33 (s, 1H), 8.72 (s, 1H), 9.26 (s, 1H). MS m/z (M+H): 410.5.

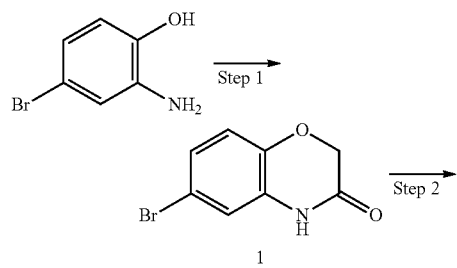

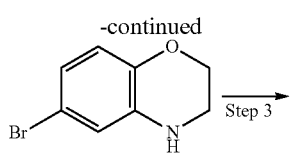

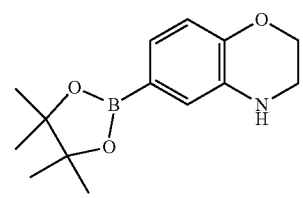

Step 1:

6-bromo-2H-benzo[b][1,4]oxazin-3(4H)-one (1)

To a stirred solution of 2-amino-4-bromophenol (5 g, 26.59 mmol) in ACN (10 mL), was added K$_2$CO$_3$ (8.5 g, 37.2 mmol) followed by 2-bromoacetyl bromide (10.6 g, 53.19 mmol) at room temperature and stirred at reflux temperature for 4 h. After completion of reaction, solvent was removed under reduced pressure. Water was added to the crude and extracted with ethyl acetate. The combined organic layer was washed with water and brine, dried over anhydrous sodium sulfate and concentrated under reduced pressure to afford 1 (7 g, crude yield) as a brown solid. MS m/z (M+H): 228.0

Step 2:

6-bromo-3,4-dihydro-2H-benzo[b][1,4]oxazine (2)

To a stirred solution of 6-bromo-2H-benzo[b][1,4]oxazin-3(4H)-one (7 g, 30.8 mmol) in THF (20 mL) was added 1M borane in THF (15.41 mL) at 0° C. and stirred for 3 h at reflux temperature. After completion of the reaction, methanol (2 mL) was added to the reaction mixture at 0° C. and stirred for 2 h at reflux. After completion of the reaction, conc. HCl (2 mL) was added to reaction mixture at 0° C. and again stirred for 2 h at reflux. The reaction mixture was then neutralized with 2N NaOH solution at 0° C. and extracted with ethyl acetate. The combined organic layer was washed with water and brine, dried over anhydrous sodium sulfate, and concentrated under reduced pressure. The crude compound was purified by column chromatography (100-200 mesh silica gel, 15% ethyl acetate in pet. ether as eluent) to afford 2 (3.2 g, 49% yield) as a brown solid. MS m/z (M+H): 214.4

Step 3:

6-(4,4,5,5-tetramethyl-1,3,2-dioxaborolan-2-yl)-3,4-dihydro-2H benzo[b][1,4]oxazine (3)

To a stirred solution of 6-bromo-3,4-dihydro-2H-benzo[b][1,4]oxazine (2.5 g, 11.6 mmol), bis (pinacolato) diborane (3.56 g, 14.0 mmol) in 1,4-dioxane (20 mL) was added KOAc (3.4 g, 55.0 mmol) and degassed for 20 min with argon. Then Pd(dppf)$_2$Cl$_2$.DCM (476 mg, 0.58 mmol) was added, again degassed for 5 min, and stirred for 2 h at 95-100° C. After completion of the reaction, the solvent was removed under reduced pressure. Water and ethyl acetate were then added to the reaction mixture, which mixture was then filtered through celite. The filtrate was extracted with ethyl acetate. The combined organic phase was washed with water and brine, dried over anhydrous Na$_2$SO$_4$, and concentrated under reduced pressure to afford 3 (2.4 gm, 78% yield) as yellow solid. MS m/z (M+H): 262.2

Compound II-e-9

N-(2-(2-methoxyethoxy)-5-(7-oxo-7,8,9,10-tetrahydrocyclopenta[4,5]pyrrolo[2,3-f]isoquinolin-2-yl)phenyl)acrylamide

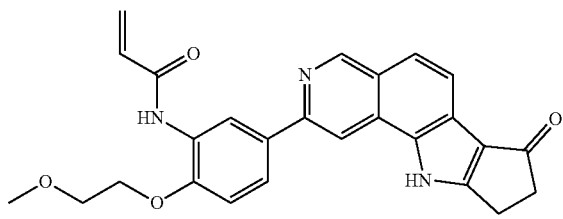 [SMILES: C=CC(=O)Nc1cc(-c2cc3c(ccc4c5c([nH]c43)CCC5=O)cn2)ccc1OCCOC]

Compound II-e-9 is prepared similarly to Compound II-e-3 in Example 38, by substituting INT-3 for INT-41 in step 2.

Compound II-e-10

N-(2-methoxy-5-(7-oxo-5,6,7,8,9, 10-hexahydrocyclopenta [4,5]pyrrolo[2,3-f]isoquinolin-2-yl)phenyl)acrylamide

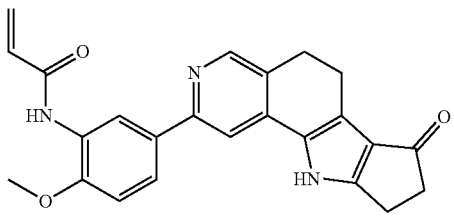 [SMILES: C=CC(=O)Nc1cc(-c2cc3c(cn2)CCc2c-3[nH]c3c2C(=O)CC3)ccc1OC]

Compound II-e-10 is prepared similarly to Compound II-e-11 (N-(2-fluoro-5-(7-oxo-5,6,7,8,9,10-hexahydrocyclopenta[4,5]pyrrolo[2,3-f]isoquinolin-2-yl)phenyl)acrylamide), by substituting INT-39 for INT-41.

Compound II-e-11

N-(2-fluoro-5-(7-oxo-5,6,7,8,9,10-hexahydrocyclopenta [4,5]pyrrolo[2,3-f]isoquinolin-2-yl)phenyl)acrylamide

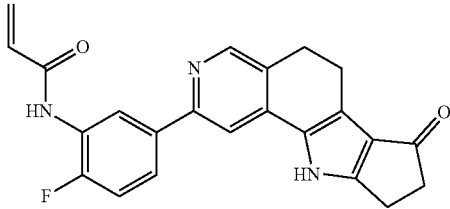 [SMILES: C=CC(=O)Nc1cc(-c2cc3c(cn2)CCc2c-3[nH]c3c2C(=O)CC3)ccc1F]

Compound II-e-11 is prepared similarly to Compound II-e-3 in Example 38, by substituting 3-chloro-7,8-dihydroisoquinolin-5-amine for the staring material.

Compound II-e-12

2-(4-acryloyl-3,4-dihydro-2H-benzo[b][1,4]oxazin-6-yl)-5,6,8,9-tetrahydrocyclopenta[4,5]pyrrolo[2,3-f]isoquinolin-7(10H)-one

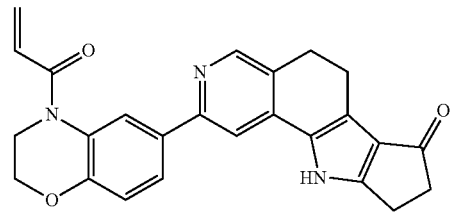 [SMILES: C=CC(=O)N1CCOc2ccc(-c3cc4c(cn3)CCc3c-4[nH]c4c3C(=O)CC4)cc21]

Compound II-e-12 is prepared similarly to Compound II-e-11 (N-(2-fluoro-5-(7-oxo-7,8,9,10-tetrahydrocyclopenta[4,5]pyrrolo[2,3-f]isoquinolin-2-yl)phenyl)acrylamide), by substituting INT-1 for INT-41.

Compound II-e-13

N-(2-methyl-5-(7-oxo-7,8,9, 1-tetrahydrocyclopenta [4,5]pyrrolo[2,3-f]isoquinolin-2-yl)pyridin-3-yl)acrylamide

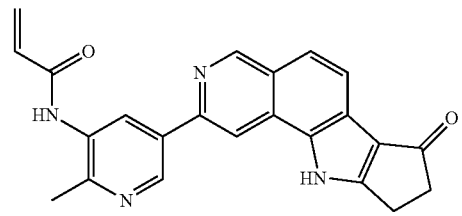 [SMILES: C=CC(=O)Nc1cc(-c2cc3c(ccc4c5c([nH]c43)CCC5=O)cn2)cnc1C]

Compound II-e-13 is prepared similarly to Compound II-e-3 in Example 38, by substituting INT-20 for INT-41.

Compound II-e-14

N-(3-(7-oxo-5,6,7,8,9,10-hexahydrocyclopenta [4,5]pyrrolo[2,3-f]isoquinolin-2-yl)phenyl)acrylamide

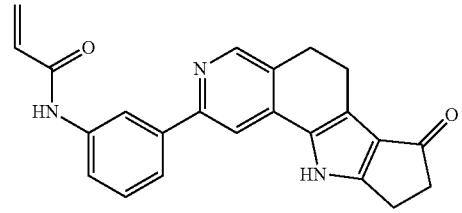 [SMILES: C=CC(=O)Nc1cccc(-c2cc3c(cn2)CCc2c-3[nH]c3c2C(=O)CC3)c1]

Compound II-e-14 is prepared similarly to Compound II-e-11 (N-(2-fluoro-5-(7-oxo-5,6,7,8,9,10-hexahydrocyclopenta[4,5]pyrrolo[2,3-f]isoquinolin-2-yl)phenyl)acrylamide), by substituting 3-(4,4,5,5-tetramethyl-1,3,2-dioxaborolan-2-yl)aniline for INT-41.

Compound III-14

(R,E)-4-(dimethylamino)-N-(3-((3-methyl-5-oxo-2,3,4,5-tetrahydro-1H-benzo[4,5]thieno[3,2-e][1,4]diazepin-9-yl)oxy)phenyl)but-2-enamide

The title compound III-14 is prepared similarly to Example 40, by substituting (E)-4-(dimethylamino)-N-(3-hydroxyphenyl)but-2-enamide for INT-10.

Compound III-15

(R,E)-N-(2-(4-(dimethylamino)but-2-enamido)phenyl)-3-methyl-5-oxo-2,3,4,5-tetrahydro-1H-benzo[4,5]thieno[3,2-e][1,4]diazepine-9-carboxamide

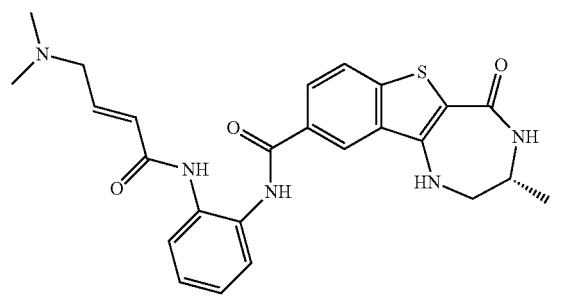

The title compound III-15 is prepared similarly to Example 40, by substituting (E)-N-(2-aminophenyl)-4-(dimethylamino)but-2-enamide for INT-10.

Compound III-16

(R,E)-N-(3-(4-(dimethylamino)but-2-enamido)phenyl)-3-methyl-5-oxo-2,3,4,5-tetrahydro-1H-benzo[4,5]thieno[3,2-e][1,4]diazepine-9-carboxamide

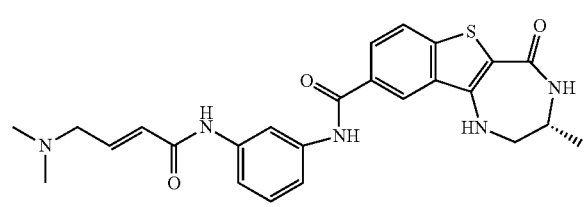

The title compound III-16 is prepared similarly to Example 40, by substituting (E)-N-(3-aminophenyl)-4-(dimethylamino)but-2-enamide for INT-10.

Compound III-17

(R)—N-(2-((10-methyl-8-oxo-9,10,11,12-tetrahydro-8H-[1,4]diazepino[5',6':4,5]thieno[3,2-f]quinolin-3-yl)amino)phenyl)acrylamide

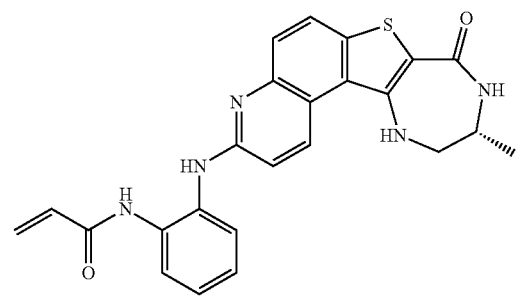 [SMILES: C=CC(=O)Nc1ccccc1Nc1ccc2c(ccc3sc4c(c32)NC[C@@H](C)NC4=O)n1]

The title compound III-17 is prepared similarly to Example 51, by substituting N-(2-(4,4,5,5-tetramethyl-1,3,2-dioxaborolan-2-yl)phenyl)acrylamide for INT-3.

Compound III-18

(R,E)-4-(dimethylamino)-N-(2-((10-methyl-8-oxo-9,10,11,12-tetrahydro-8H-[1,4]diazepino[5',6':4,5]thieno[3,2-f]quinolin-3-yl)amino)phenyl)but-2-enamide

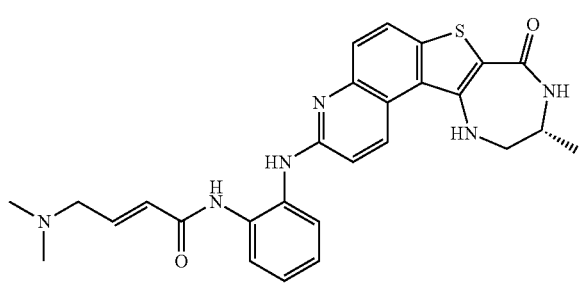

The title compound III-18 is prepared similarly to Example 51, by substituting (E)-4-(dimethylamino)-N-(2-(4,4,5,5-tetramethyl-1,3,2-dioxaborolan-2-yl)phenyl)but-2-enamide for INT-3.

Compounds III-19 and III-20

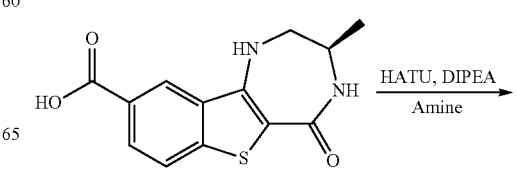

453
-continued

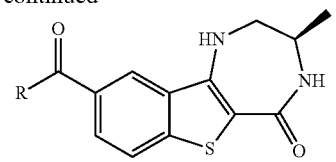

(R)—N-((1S,2R)-2-acrylamidocyclopentyl)-3-methyl-5-oxo-2,3,4,5-tetrahydro-1H-benzo[4,5]thieno[3,2-e][1,4]diazepine-9-carboxamide (III-19) and (R)—N-((1R,2S)-2-acrylamidocyclopentyl)-3-methyl-5-oxo-2,3,4,5-tetrahydro-1H-benzo[4,5]thieno[3,2-e][1,4]diazepine-9-carboxamide (III-20)

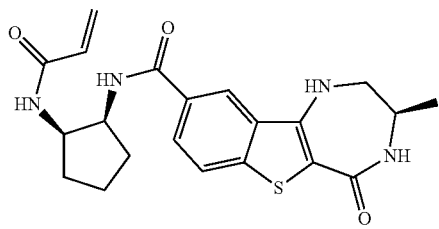

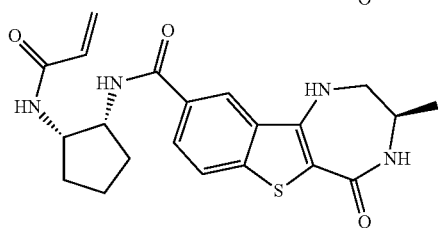

To a stirred solution of (R)-3-methyl-5-oxo-2,3,4,5-tetrahydro-1H-benzo[4,5]thieno[3,2-e][1,4]diazepine-9-carboxylic acid, N-((1R,2S)-2-aminocyclopentyl)acrylamide (rac), and DIPEA (3 equiv) in DMF is added HATU (1.1 equiv). The reaction is stirred and monitored, and later diluted with water. The crude products are purified to produce compounds III-19 and III-20. Compounds III-19 and III-20 are also used as mixtures of different ratios.

Compounds III-21 and III-22

(R)—N-((1S,2S)-2-acrylamidocyclopentyl)-3-methyl-5-oxo-2,3,4,5-tetrahydro-1H-benzo[4,5]thieno[3,2-e][1,4]diazepine-9-carboxamide (III-26) and (R)—N-((1R,2R)-2-acrylamidocyclopentyl)-3-methyl-5-oxo-2,3,4,5-tetrahydro-1H-benzo[4,5]thieno[3,2-e][1,4]diazepine-9-carboxamide (III-22)

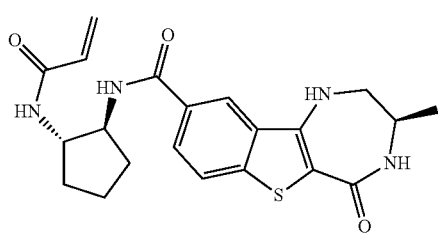

454
-continued

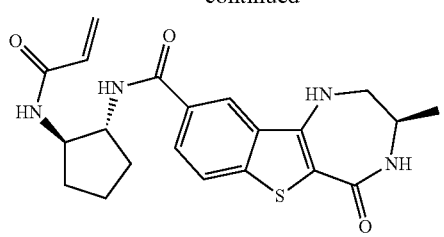

Compounds III-21 and III-22 are prepared similarly to Compounds III-19 and III-20, by substituting N-((1R,2R)-2-aminocyclopentyl)acrylamide (rac) for N-((1R,2S)-2-aminocyclopentyl)acrylamide. N-((1R,2R)-2-aminocyclopentyl)acrylamide (rac) is prepared similarly to N-((1R,2S)-2-aminocyclopentyl)acrylamide (rac), by substituting (1R,2R)-cyclopentane-1,2-diamine (rac) for (1R,2S)-cyclopentane-1,2-diamine (rac). The crude products are purified to produce compounds III-21 and III-22. Compounds III-21 and III-22 are also used as mixtures of different ratios.

Compounds III-23 and III-24

(R)—N-((3R,4S)-4-acrylamidotetrahydrofuran-3-yl)-3-methyl-5-oxo-2,3,4,5-tetrahydro-1H-benzo[4,5]thieno[3,2-e][1,4]diazepine-9-carboxamide (III-23) and (R)—N-((3S,4R)-4-acrylamidotetrahydrofuran-3-yl)-3-methyl-5-oxo-2,3,4,5-tetrahydro-1H-benzo[4,5]thieno[3,2-e][1,4]diazepine-9-carboxamide (III-24)

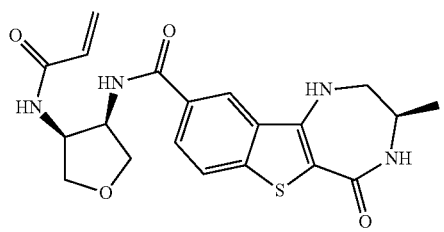

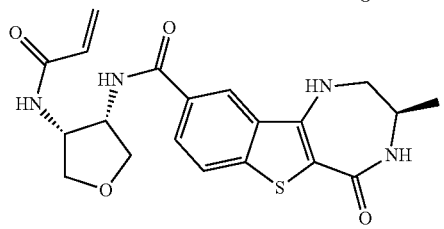

Compounds III-23 and III-24 are prepared similarly to Compounds III-19 and III-20, by substituting N-((3S,4R)-4-aminotetrahydrofuran-3-yl)acrylamide (rac) for N-((1R,2S)-2-aminocyclopentyl)acrylamide. The crude products are purified to produce compounds III-23 and III-24. Compounds III-23 and III-24 are also used as mixtures of different ratios.

Compounds III-25 and III-26

(R)—N-((3R,4S)-4-acrylamido-1,1-dioxidotetrahydrothiophen-3-yl)-3-methyl-5-oxo-2,3,4,5-tetrahydro-1H-benzo[4,5]thieno[3,2-e][1,4]diazepine-9-carboxamide (III-25) and (R)—N-((3S,4R)-4-acrylamido-1,1-dioxidotetrahydrothiophen-3-yl)-3-methyl-5-oxo-2,3,4,5-tetrahydro-1H-benzo[4,5]thieno[3,2-e][1,4]diazepine-9-carboxamide (III-26)

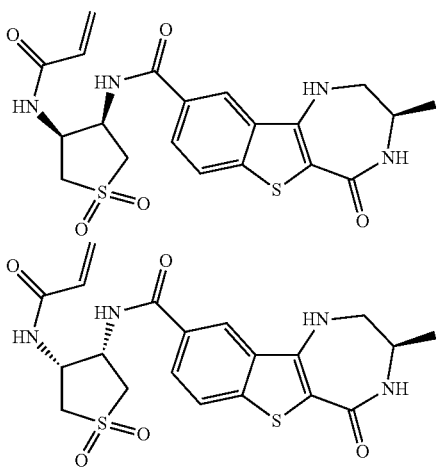

Compounds III-25 and III-26 are prepared similarly to Compounds III-19 and III-20, by substituting N-((3S,4R)-4-amino-1,1-dioxidotetrahydrothiophen-3-yl)acrylamide (rac) for N-((1R,2S)-2-aminocyclopentyl)acrylamide. N-((3S,4R)-4-amino-1,1-dioxidotetrahydrothiophen-3-yl)acrylamide (rac) is prepared similarly to N-((1R,2S)-2-aminocyclopentyl)acrylamide (rac), by substituting (3R,4S)-3,4-diaminotetrahydrothiophene 1,1-dioxide (rac) for (1R,2S)-cyclopentane-1,2-diamine (rac). The crude products are purified to produce compounds III-25 and III-26. Compounds III-25 and III-26 are also used as mixtures of different ratios.

Compounds III-27 and III-28

(R)—N-((3S,4R)-4-acrylamido-1-methylpyrrolidin-3-yl)-3-methyl-5-oxo-2,3,4,5-tetrahydro-1H-benzo[4,5]thieno[3,2-e][1,4]diazepine-9-carboxamide (III-27) and (R)—N-((3R,4S)-4-acrylamido-1-methylpyrrolidin-3-yl)-3-methyl-5-oxo-2,3,4,5-tetrahydro-1H-benzo[4,5]thieno[3,2-e][1,4]diazepine-9-carboxamide (III-28)

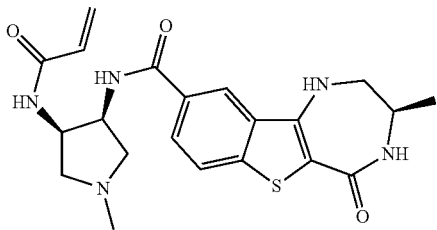

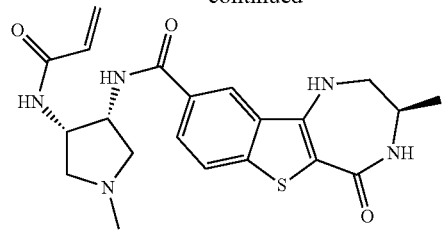

Compounds III-27 and III-28 are prepared similarly to Compounds III-19 and III-20, by substituting N-((3R,4S)-4-amino-1-methylpyrrolidin-3-yl)acrylamide (rac) for N-((1R,2S)-2-aminocyclopentyl)acrylamide. The crude products are purified to produce compounds III-27 and III-28. Compounds III-27 and III-28 are also used as mixtures of different ratios.

Compound III-29

(R)—N-(5-acrylamidopyridin-3-yl)-3-methyl-5-oxo-2,3,4,5-tetrahydro-1H-benzo[4,5]thieno[3,2-e][1,4]diazepine-9-carboxamide

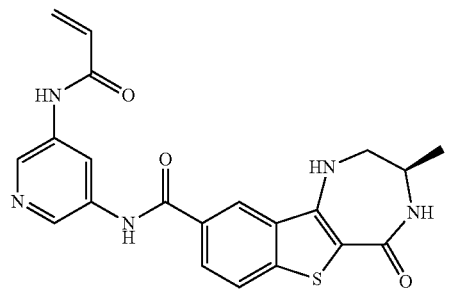 [SMILES: C=CC(=O)Nc1cncc(NC(=O)c2ccc3sc4c(c3c2)NC[C@@H](C)NC4=O)c1]

Compound III-29 is prepared similarly to Compound III-12 in Example 40, by substituting N-(5-aminopyridin-3-yl)acrylamide for INT-10 in step 8.

Compound III-30

(R)—N-(1-acryloyl-1,2,3,4-tetrahydroquinolin-7-yl)-3-methyl-5-oxo-2,3,4,5-tetrahydro-1H-benzo[4,5]thieno[3,2-e][1,4]diazepine-9-carboxamide

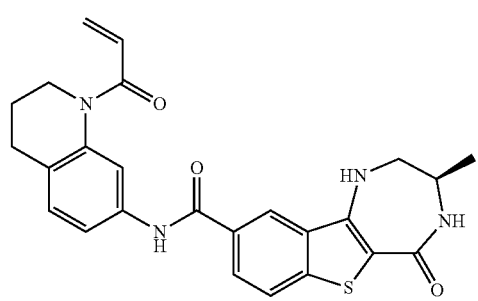 [SMILES: C=CC(=O)N1CCCc2ccc(NC(=O)c3ccc4sc5c(c4c3)NC[C@@H](C)NC5=O)cc21]

Compound III-30 is prepared similarly to Compound III-12 in Example 40, by substituting 1-(7-amino-3,4-dihydroquinolin-1(2H)-yl)prop-2-en-1-one for INT-10 in step 8.

Compound III-31

(R)—N—((R)-4-acryloyl-2-methyl-3,4-dihydro-2H-benzo[b][1,4]oxazin-6-yl)-3-methyl-5-oxo-2,3,4,5-tetrahydro-1H-benzo[4,5]thieno[3,2-e][1,4]diazepine-9-carboxamide (III-31) and (R)—N—((S)-4-acryloyl-2-methyl-3,4-dihydro-2H-benzo[b][1,4]oxazin-6-yl)-3-methyl-5-oxo-2,3,4,5-tetrahydro-1H-benzo[4,5]thieno[3,2-e][1,4]diazepine-9-carboxamide (III-53)

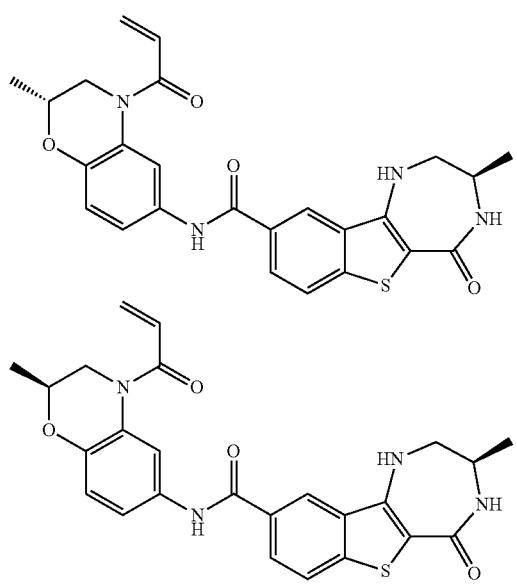

Compounds III-31 and III-53 were prepared similarly to Compound III-12 in Example 40, by substituting INT-10 in step 8 of Example 40 with amine 4, depicted below. The products were obtained as a mixture (45 mg, 41%) as an off-white solid. ¹H NMR (400 MHz, DMSO-d₆): δ 1.13-1.15 (d, J=7.0 Hz, 3H), 1.28-1.29 (d, J=6.2 Hz, 3H), 3.34-3.39 (m, 3H), 3.58 (m, 1H), 4.25-4.28 (d, J=13.1 Hz, 1H), 4.35 (m, 1H), 5.82-5.85 (dd, J=2.0, 10.3 Hz, 1H), 6.29-6.33 (dd, J=2.0, 17.0 Hz, 1H), 6.84 (dd, J=6.5, 10.3 Hz, 1H), 6.88 (d, J=8.8 Hz, 1H), 7.45-7.47 (dd, J=2.1, 9.0 Hz, 1H), 7.74-7.76 (t, J=4.0 Hz, 1H), 7.83-7.84 (d, J=4.5 Hz, 1H), 7.94-7.96 (m, 3H), 8.54 (s, 1H), 10.24 (s, 1H). MS m/z (M+H): 477.

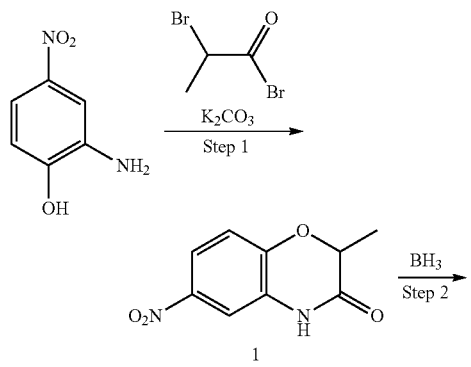

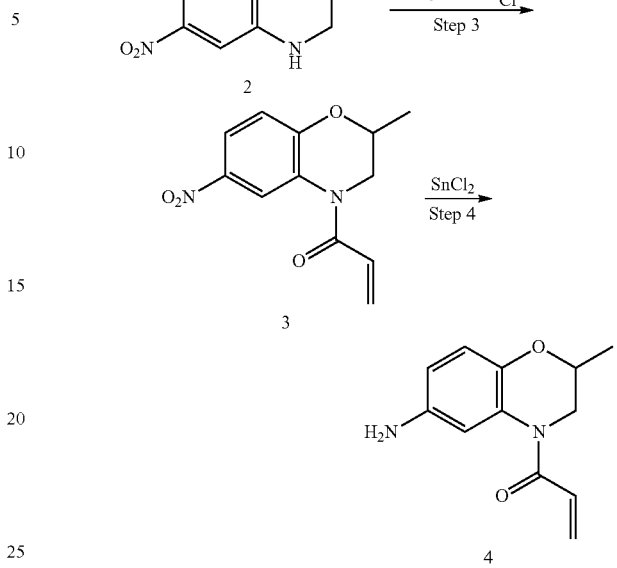

Step 1:

2-methyl-6-nitro-2H-benzo[b][1,4]oxazin-3(4H)-one (1)

To a solution of 2-amino-4-nitrophenol (2 g, 12.9 mmol) in acetonitrile (20 mL), potassium carbonate (3.58 g, 25.9 mmol) was added, followed by the addition of 2-bromo-2-methylpropanoyl bromide (3.92 g, 18.1 mmol), at 0° C. The resulting mixture was refluxed overnight. After completion of the reaction, ice-cold water was added to the reaction mixture. The residue obtained was filtered and purified by prep HPLC to afford 1 (2.4 g, 90%) as a brown solid. ¹H NMR (400 MHz, DMSO-d₆): δ 1.45-1.46 (d, J=7.0 Hz, 3H), 4.87-4.89 (q, J=7.0 Hz, 1H), 7.13-7.15 (d, J=9.0 Hz, 1H), 7.72-7.73 (d, J=3.0 Hz, 1H), 7.81-7.84 (dd, J=3.0, 9.0 Hz, 1H), 10.97 (s, 1H). MS m/z (M+H): 207.1

Step 2:

2-methyl-6-nitro-3,4-dihydro-2H-benzo[b][1,4]oxazine (2)

To a solution of 2-methyl-6-nitro-2H-benzo[b][1,4]oxazin-3(4H)-one (2 g, 9.6 mmol) in tetrahydrofuran (25 mL), borane tetrahydrofuran complex (22.0 mL, 1.0M) was added at 0° C. The resulting mixture was refluxed for 2.5 h. Methanol (10 mL) was added to the reaction mixture and refluxed for another 90 min. The reaction mixture was further refluxed for 2 h after addition of conc. HCl (4 mL). After completion of the reaction, the reaction mixture was concentrated under reduced pressure. The resulting residue was diluted with sodium hydroxide solution and extracted with ethyl acetate. The organic layer was dried over anhydrous sodium sulfate and concentrated under reduced pressure to afford 2 (1.79 g, 96%) as a brown solid. ¹H NMR (400 MHz, DMSO-d₆): δ 1.28-1.30 (d, J=6.2 Hz, 3H), 2.93-2.98 (m, 1H), 3.36-3.41 (td, J=3.0, 6.0 Hz, 1H), 4.19-4.25 (m, 1H), 6.46 (s, 1H), 6.79-6.81 (d, J=9.0 Hz, 1H), 7.36-7.39 (dd, J=3.0, 9.0 Hz, 1H), 7.44 (d, J=3.0 Hz, 1H). MS m/z (M+H): 195.2

Step 3:

1-(2-methyl-6-nitro-2H-benzo[b][1,4]oxazin-4(3H)-yl)prop-2-en-1-one (3)

To a solution of 2-methyl-6-nitro-3,4-dihydro-2H-benzo[b][1,4]oxazine (1.0 g, 5.1 mmol) in dichloromethane (5 mL), diisopropyl ethylamine (1.3 g, 10.2 mmol) and acryloyl chloride (468 mg, 5.2 mmol) were added at 0° C. and the reaction mixture was stirred at room temperature for 2 h. After completion of the reaction, the reaction mixture was concentrated under reduced pressure. The obtained residue was diluted with water and extracted with dichloromethane. The organic layer was washed with brine, dried over anhydrous sodium sulfate, and concentrated under reduced pressure. The crude obtained was purified by silica gel column chromatography to afford 3 (700 mg, 55%) as a pale yellow solid. $^1$H NMR (400 MHz, DMSO-$d_6$): δ 1.32-1.33 (d, J=6.3 Hz, 3H), 3.45-3.51 (dd, J=8.0, 13.5 Hz, 1H), 4.26-4.30 (dd, J=3.0, 13.5 Hz, 1H), 4.50-4.55 (m, 1H), 5.88-5.91 (dd, J=2.0, 10.4 Hz, 1H), 6.29-6.34 (dd, J=2.0, 17.0 Hz, 1H), 6.85-6.91 (dd, J=10.4, 17.0 Hz, 1H), 7.09-7.11 (d, J=9.0 Hz, 1H), 7.93-7.96 (dd, J=3.0, 9.0 Hz, 1H), 8.64 (s, 1H). MS m/z (M+H): 249.3

Step 4:

1-(6-amino-2-methyl-2H-benzo[b][1,4]oxazin-4(3H)-yl)prop-2-en-1-one (4)

To a solution of 1-(2-methyl-6-nitro-2H-benzo[b][1,4]oxazin-4(3H)-yl)prop-2-en-1-one (700 mg, 2.81 mmol) in ethanol (5 mL), tin (II) chloride (2.8 gm, 14.7 mmol) was added at 0° C. The resulting mixture was stirred at room temperature for 10 min followed by reflux for 4 h. After completion of the reaction, ice-cold water was added to the reaction mixture. The residue obtained was diluted with a 20% sodium hydroxide solution and the aqueous layer was extracted with ethyl acetate. The organic layer was dried over anhydrous sodium sulfate and concentrated under reduced pressure to afford 4 (560 mg, 91%) as a brown oily liquid. 1H NMR (400 MHz, DMSO-$d_6$): δ 1.21-1.22 (d, J=6.2 Hz, 3H), 3.20-3.25 (dd, J=8.2, 13.2 Hz, 1H), 4.14-4.21 (m, 2H), 4.69 (s, 2H), 5.77-5.80 (dd, J=2.1, 10.1 Hz, 1H), 6.23-6.27 (dd, J=2.1, 17.0 Hz, 1H), 6.32-6.34 (dd, J=2.5, 9.0 Hz, 1H), 6.57-6.59 (d, J=9.0 Hz, 1H), 6.75-6.82 (dd, J=10.3, 17.0 Hz, 1H). MS m/z (M+H): 219.2

Compound III-32

(R)—N-(4-acryloyl-2,2-dimethyl-3,4-dihydro-2H-benzo[b][1,4]oxazin-6-yl)-3-methyl-5-oxo-2,3,4,5-tetrahydro-1H-benzo[4,5]thieno[3,2-e][1,4]diazepine-9-carboxamide

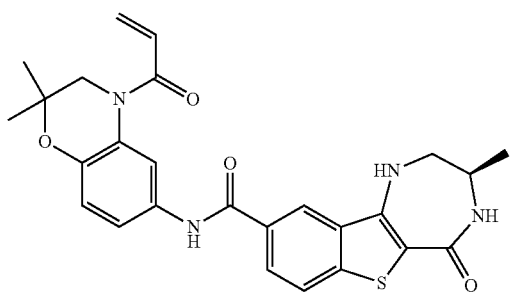

Compound III-32 was prepared similarly to Compound III-12 in Example 40, by substituting INT-10 in step 8 of Example 40 with amine 4, depicted below, to afford the desired product (25 mg, 18%) as a brown solid. $^1$H NMR (400 MHz, DMSO-$d_6$): δ 1.13-1.15 (d, J=6.7 Hz, 3H), 1.26 (s, 6H), 3.35-3.36 (m, 2H), 3.58 (m, 1H), 3.76 (s, 2H), 5.85-5.88 (dd, J=2.0, 10.2 Hz, 1H), 6.31-6.36 (dd, J=2.0, 17.0 Hz, 1H), 6.85-6.87 (d, J=8.8 Hz, 1H), 6.00-6.94 (dd, J=6.3, 10.3 Hz, 1H), 7.45-7.47 (dd, J=2.4, 9.0 Hz, 1H), 7.75 (t, J=4.0 Hz, 1H), 7.83 (d, J=4.5 Hz, 1H), 7.90-7.96 (m, 3H), 8.54 (s, 1H), 10.23 (s, 1H). MS m/z (M+H): 491.1.

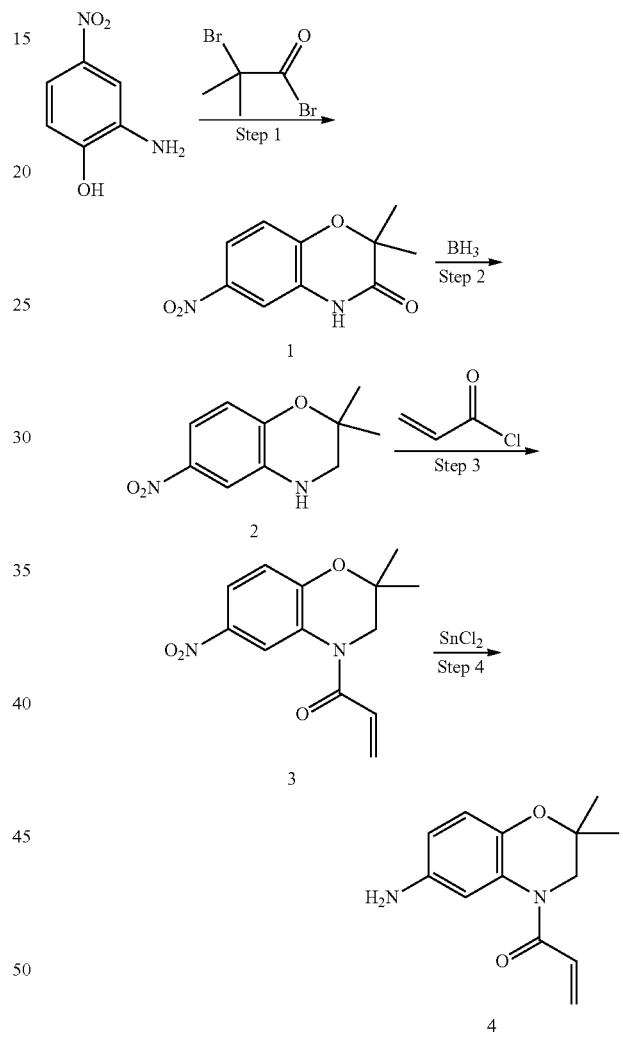

Step 1:

2,2-dimethyl-6-nitro-2H-benzo[b][1,4]oxazin-3(4H)-one (1)

To a solution of 2-amino-4-phenol (2.0 g, 12.9 mmol) in acetonitrile (20 mL), potassium carbonate (3.5 g, 25.3 mmol) was added, followed by the addition of 2-bromo-2-methylpropanoyl bromide (4.18 g, 18.18 mmol) at 0° C. The resulting mixture was refluxed overnight. After completion of reaction, ice-cold water was added and the resulting solid obtained was filtered and purified by silica gel column chromatography to afford 1 (2.2 gm, 76%) as a brown solid.

¹H NMR (400 MHz, DMSO-d₆): δ 1.45 (s, 6H), 7.12-7.15 (d, J=9.0 Hz, 1H), 7.73-7.74 (d, J=3.0 Hz, 1H), 7.82-7.85 (dd, J=3.0, 9.0 Hz, 1H), 11.00 (s, 1H). MS m/z (M−H): 221.2

Step 2:

2,2-dimethyl-6-nitro-3,4-dihydro-2H-benzo[b][1,4]oxazine (2)

To a solution of 2,2-dimethyl-6-nitro-2H-benzo[b][1,4]oxazin-3(4H)-one (1.0 g, 4.5 mmol) in tetrahydrofuran (20 mL), borane tetrahydrofuran (10.4 mL, 1.0M) was added at 0° C. The resulting mixture was refluxed for 2.5 h. Methanol (5 mL) was added to the reaction mixture and refluxed for another 90 min. The reaction mixture was further refluxed for 2 h after addition of conc. HCl (2 mL). After completion of the reaction, the reaction mixture was concentrated under reduced pressure. The resulting residue was diluted with sodium hydroxide solution and extracted with ethyl acetate. The organic layer was dried over anhydrous sodium sulfate and concentrated under reduced pressure to afford 2 (800 mg, 85%) as a brown solid. ¹H NMR (400 MHz, DMSO-d₆): δ 1.26 (s, 6H), 3.06 (d, J=2.3 Hz, 2H), 6.55 (s, 1H), 6.76-6.78 (d, J=9.0 Hz, 1H), 7.38-7.40 (dd, J=3.0, 9.0 Hz, 1H), 7.46-7.47 (d, J=3.0 Hz, 1H). MS m/z (M+H): 209.3

Step 3:

1-(2,2-dimethyl-6-nitro-2H-benzo[b][1,4]oxazin-4(3H)-yl)prop-2-en-1-one (3)

To a solution of 2,2-dimethyl-6-nitro-3,4-dihydro-2H-benzo[b][1,4]oxazine (800 mg, 3.8 mmol) in dichloromethane (5 mL), diisopropylethylamine (992 mg, 7.7 mmol) and acryloyl chloride (350 mg, 3.9 mmol) were added at 0° C. The resulting reaction mixture was stirred at room temperature for 2 h. After completion of the reaction, the reaction mixture was concentrated under reduced pressure. The resulting residue was diluted with water and extracted with dichloromethane. The organic layer was washed with brine, dried over anhydrous sodium sulfate, and concentrated under reduced pressure. The residue was purified by silica gel column chromatography to afford 3 (750 mg, 75%) as a yellow solid. ¹H NMR (400 MHz, DMSO-d₆): δ 1.25 (d, J=2.0 Hz, 1H), 1.30 (s, 6H), 3.84 (s, 2H), 5.90-5.93 (dd, J=2.0, 10.3 Hz, 1H), 6.33-6.38 (dd, J=2.0, 17.0 Hz, 1H), 6.90-6.97 (dd, J=10.4, 17.0 Hz, 1H), 7.06-7.09 (d, J=9.0 Hz, 1H), 7.94-7.97 (dd, J=3.0, 9.0 Hz, 1H). MS m/z (M+H): 263.4

Step 4:

1-(6-amino-2,2-dimethyl-2H-benzo[b][1,4]oxazin-4(3H)-yl)prop-2-en-1-one (4)

To a solution of 1-(2,2-dimethyl-6-nitro-2H-benzo[b][1,4]oxazin-4(3H)-yl)prop-2-en-1-one (730 mg, 2.8 mmol) in ethanol (5 mL), tin (II) chloride (2.8 g, 14.7 mmol) was added at 0° C. The resulting mixture was stirred at room temperature for 10 min followed by reflux for 4 h. After completion of the reaction, ice-cold water was added to the reaction mixture. The residue obtained was diluted with a 20% sodium hydroxide solution and the aqueous layer was extracted with ethyl acetate. The organic layer was dried over anhydrous sodium sulfate and concentrated under reduced pressure to afford 4 (310 mg, 48%) as a pale yellow solid. ¹H NMR (400 MHz, DMSO-d₆): δ 1.16 (s, 6H), 3.65 (s, 2H), 4.67 (s, 2H), 5.79-5.83 (dd, J=2.1, 10.3 Hz, 1H), 6.25-6.30 (dd, J=2.0, 17.0 Hz, 1H), 6.32-6.35 (dd, J=2.5, 9.0 Hz, 1H), 6.53-6.55 (d, J=9.0 Hz, 2H), 6.78-6.85 (dd, J=10.3, 17.0 Hz, 1H). MS m/z (M+H): 233.3.

Compound III-33

(R)—N-(5-acrylamido-2-(piperidin-1-yl)thiazol-4-yl)-3-methyl-5-oxo-2,3,4,5-tetrahydro-1H-benzo[4,5]thieno[3,2-e][1,4]diazepine-9-carboxamide

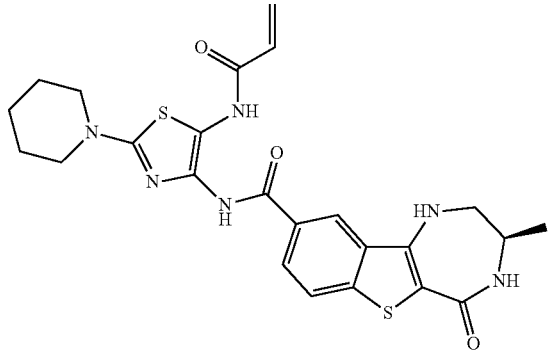 [SMILES: C=CC(=O)Nc1sc(N2CCCCC2)nc1NC(=O)c1ccc2sc3c(c2c1)NC[C@@H](C)NC3=O]

Compound III-33 is prepared similarly to Compound III-12 in Example 40, by substituting N-(4-amino-2-(piperidin-1-yl)thiazol-5-yl)acrylamide for N-(5-aminopyridin-3-yl)acrylamide for INT-10 in step 8.

Compound III-34

(R)—N-(5-acrylamido-6-methylpyridin-3-yl)-3-methyl-5-oxo-2,3,4,5-tetrahydro-1H-benzo[4,5]thieno[3,2-e][1,4]diazepine-9-carboxamide

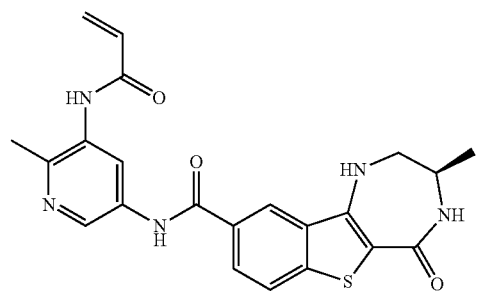

Compound III-34 is prepared similarly to Compound III-12 in Example 40, by substituting N-(5-amino-2-methylpyridin-3-yl)acrylamide for N-(5-aminopyridin-3-yl)acrylamide for INT-10 in step 8.

Compound III-36

(R)—N-(2-methoxy-5-(10-methyl-8-oxo-9,10,11,12-tetrahydro-8H-[1,4]diazepino[5',6':4,5]thieno[3,2-f]quinolin-3-yl)phenyl)acrylamide

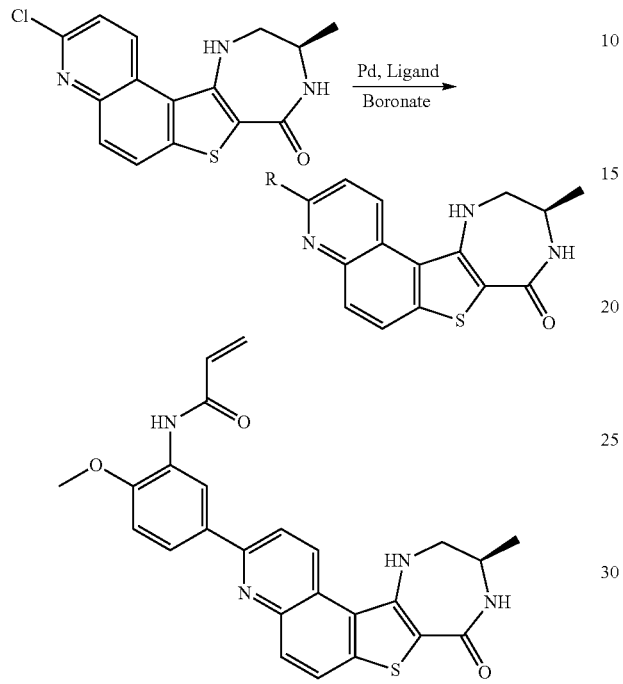

Compound III-36 is prepared similarly to Compound III-8 ((R)—N-(2-(2-methoxyethoxy)-5-(10-methyl-8-oxo-9,10,11,12-tetrahydro-8H-[1,4]diazepino[5',6':4,5]thieno[3,2-f]quinolin-3-yl)phenyl)acrylamide) in Example 51, by substituting N-(2-methoxy-5-(4,4,5,5-tetramethyl-1,3,2-dioxaborolan-2-yl)phenyl)acrylamide for INT-3 in step 12.

Compound III-38

(R)—N-(5-(10-methyl-8-oxo-9,10,11,12-tetrahydro-8H-[1,4]diazepino[5',6':4,5]thieno[3,2-f]quinolin-3-yl)-2-(4-methylpiperazin-1-yl)phenyl)acrylamide

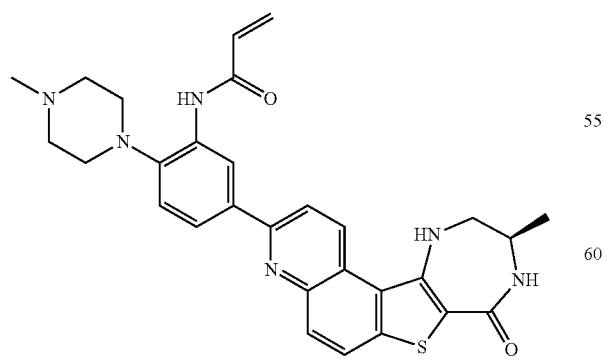

Compound III-38 is prepared similarly to Compound III-8 ((R)—N-(2-(2-methoxyethoxy)-5-(10-methyl-8-oxo-9,10, 11,12-tetrahydro-8H-[1,4]diazepino[5',6':4,5]thieno[3,2-f]quinolin-3-yl)phenyl)acrylamide) in Example 51, by substituting INT-9 for INT-3 in step 12.

Compound III-39

(R)—N-(3-(10-methyl-8-oxo-9,10,11,12-tetrahydro-8H-[1,4]diazepino[5',6':4,5]thieno[3,2-f]quinolin-3-yl)phenyl)acrylamide

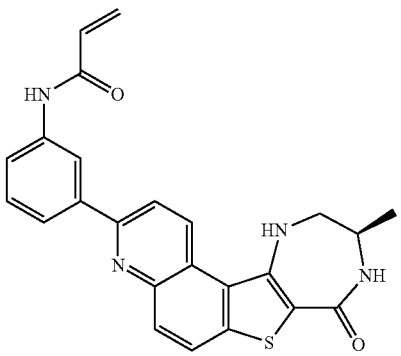 [SMILES: C=CC(=O)Nc1cccc(-c2ccc3c(ccc4sc5c(c43)NC[C@@H](C)NC5=O)n2)c1]

Compound III-39 is prepared similarly to Compound III-8 ((R)—N-(2-(2-methoxyethoxy)-5-(10-methyl-8-oxo-9,10, 11,12-tetrahydro-8H-[1,4]diazepino[5',6':4,5]thieno[3,2-f]quinolin-3-yl)phenyl)acrylamide), by substituting N-(3-(4, 4,5,5-tetramethyl-1,3,2-dioxaborolan-2-yl)phenyl)acrylamide for INT-3.

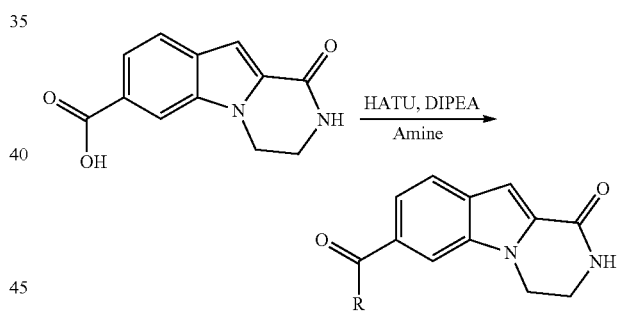

Compound V-35

N-((3R,4S)-4-acrylamidotetrahydrofuran-3-yl)-1-oxo-1,2,3,4-tetrahydropyrazino[1,2-a]indole-7-carboxamide (racemic)

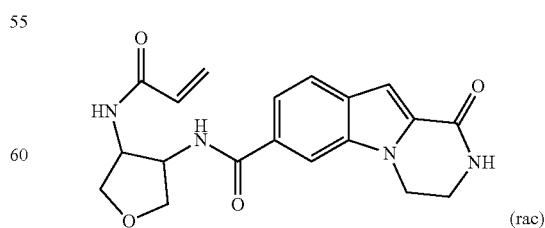

Compound V-35 is prepared similarly to Compound V-7 (N-(3-acrylamidophenyl)-1-oxo-1,2,3,4-tetrahydropyrazino[1,2-a]indole-7-carboxamide) in Example 66, by substituting N-((3S,4R)-4-aminotetrahydrofuran-3-yl)acrylamide (racemic) for N-(3-aminophenyl)acrylamide. The enantiomers are obtained upon chiral separation. Alternatively, the enantiomers are also used as mixtures of different ratios.

Compound V-12

N-(5-methyl-2-(1'-oxo-2',3'-dihydro-1'H-spiro[cyclobutane-1,4'-pyrazino [1,2-a]indol]-7'-yl)benzo[d]oxazol-4-yl)acrylamide

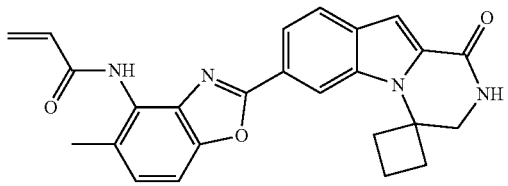

Compound V-12 was prepared similarly to Compound V-39 by substituting 2-amino-3-nitrophenol in step 1 of the Compound V-39 synthesis with 2-amino-4-methyl-3-nitrophenol to give the desired product (100 mg, 53%) as an off white solid. $^1$H NMR (400 MHz, DMSO-$d_6$): δ 2.10 (m, 1H), 2.22 (m, 1H), 2.26 (s, 3H), 2.39 (m, 2H), 3.01 (m, 2H), 3.75 (d, J=2.4 Hz, 2H), 5.79 (m, 1H), 6.29 (m, 1H), 6.62 (m, 1H), 7.22 (s, 1H), 7.31 (d, J=8.4 Hz, 1H), 7.64 (d, J=8.4 Hz, 1H), 7.91 (d, J=8.4 Hz, 1H), 7.98 (m, 1H), 8.34 (s, 1H), 8.71 (s, 1H), 10.17 (s, 1H). MS m/z (M+H): 427.5

Compound V-13

(R)—N-(1-(1'-oxo-2',3'-dihydro-1'H-spiro[cyclobutane-1,4'-pyrazino [1,2-a]indol]-7'-ylcarbonyl)piperidin-3-yl)acrylamide

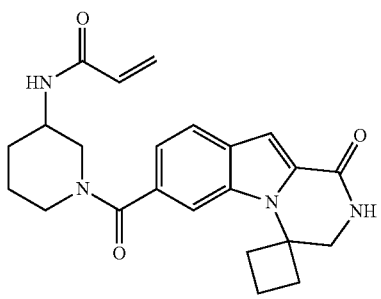 [SMILES: C=CC(=O)NC1CCCN(C(=O)c2ccc3cc4n(c3c2)C2(CCC2)CNC4=O)C1]

The title compound V-13 is prepared as described in Example 78, by substituting (R)—N-(piperidin-3-yl)acrylamide for INT-11 in step 8.

Compound V-14

N-(2-acrylamidophenyl)-1'-oxo-2',3'-dihydro-1'H-spiro[cyclobutane-1,4'-pyrazino [1,2-a]indole]-7'-carboxamide

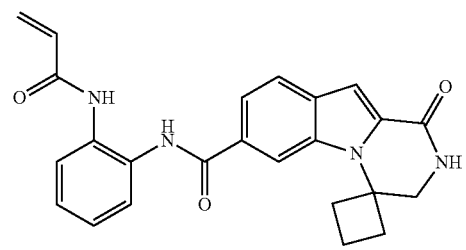 [SMILES: C=CC(=O)Nc1ccccc1NC(=O)c1ccc2cc3n(c2c1)C1(CCC1)CNC3=O]

Compound V-14 was prepared as described in Example 78, by substituting INT-11 in step 8 of Example 78 with benzene-1,2-diamine, depicted below, and subsequently forming the acrylamide according to the schemes, steps, and intermediates described below.

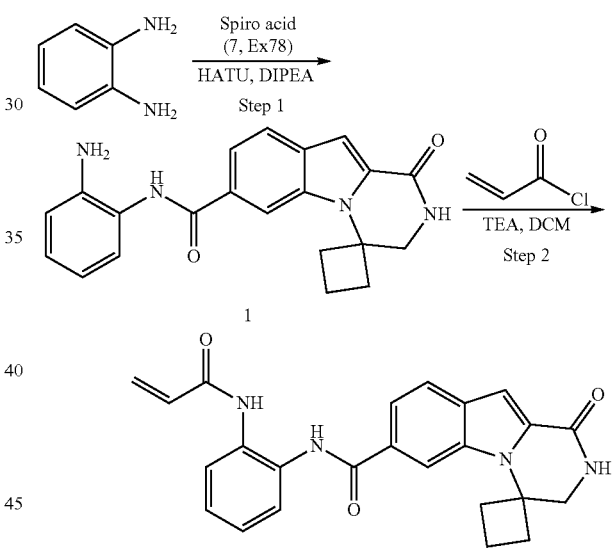

Step 1:

N-(2-Aminophenyl)-1'-oxo-2',3'-dihydro-1'H-spiro[cyclobutane-1,4'-pyrazino[1,2-a]indole]-7'-carboxamide (1)

To a solution of 1'-oxo-2',3'-dihydro-1'H-spiro[cyclobutane-1,4'-pyrazino[1,2-a]indole]-7'-carboxylic acid (120 mg, 0.44 mmol) in DMF (3.0 mL) were added HATU (252 mg, 0.66 mmol) and DIPEA (0.25 mL, 1.37 mmol) at room temperature under nitrogen atmosphere. The resulting reaction mixture was stirred for 10 minutes and then benzene-1,2-diamine (49 mg, 0.45 mmol) was added. Stirring was continued at room temperature for 12 h. The reaction mixture was then diluted with EtOAc (10 mL) and washed with water (2×20 mL). The organic layer was dried over anhydrous sodium sulfate and concentrated under reduced pressure. The residue was purified by silica gel column chromatography to obtain 1 (100 mg, 63%) as an off white solid. 1H NMR (400 MHz, DMSO-d₆): δ 2.05 (m, 1H), 2.20 (m, 1H), 2.32 (m, 2H), 3.04 (m, 2H), 3.73 (d, J=2.4 Hz, 2H), 4.92 (s, 2H), 6.21 (m, 1H), 6.81 (m, 1H), 6.99 (m, 1H), 7.19 (m, 1H), 7.78 (m, 2H), 8.30 (s, 1H), 8.50 (s, 1H), 9.80 (s, 1H). MS m/z (M+H): 361.4

Step 2:

To a stirring solution of N-(2-aminophenyl)-1'-oxo-2',3'-dihydro-1'H-spiro[cyclobutane-1,4'-pyrazino[1,2-a]indole]-7'-carboxamide (1) (100 mg, 0.27 mmol) in DCM (10 mL) was added acryloyl chloride (0.03 mL, 0.4 mmol) dropwise at 0° C. under nitrogen atmosphere for 3 minutes. Then Et₃N (3 drops) was added and stirring was continued for 3 h. The reaction mixture was then diluted with DCM (10 mL) and washed with saturated NaHCO₃ solution (2×10 mL). The organic layer was dried over anhydrous sodium sulfate and concentrated under reduced pressure. The residue was purified by silica gel column chromatography to obtain the desired product (30 mg, 27%) as an off white solid. ¹H NMR (400 MHz, DMSO-d₆): δ 2.03 (m, 1H), 2.28 (m, 3H), 3.07 (m, 2H), 3.73 (d, J=2.4 Hz, 2H), 5.77 (m, 1H), 6.29 (m, 1H), 6.51 (m, 1H), 7.17 (s, 1H), 7.26 (m, 2H), 7.58 (m, 1H), 7.76 (m, 3H), 8.31 (s, 1H), 8.51 (s, 1H), 10.05 (s, 2H). MS m/z (M+H): 415.3

Compound V-17

7-(6-vinyl-9H-purin-8-yl)-3,4-dihydropyrazino [1,2-a]indol-1(2H)-one

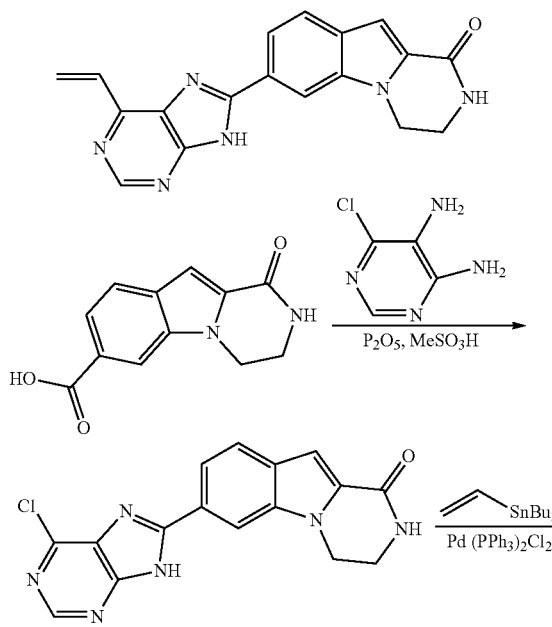

1-oxo-1,2,3,4-tetrahydropyrazino[1,2-a]indole-7-carboxylic acid is reacted with 6-chloropyrimidine-4,5-diamine, P₂O₅ and MeSO₃H to afford 7-(6-chloro-9H-purin-8-yl)-3,4-dihydropyrazino[1,2-a]indol-1 (2H)-one, which undergoes Pd(PPh₃)₂Cl₂-catalyzed coupling with tributyl(vinyl)stannane to yield the title compound.

Compound V-16

(E)-N-(3-(4-(dimethylamino)but-2-enamido)phenyl)-1-oxo-1,2,3,4-tetrahydropyrazino[1,2-a]indole-7-carboxamide

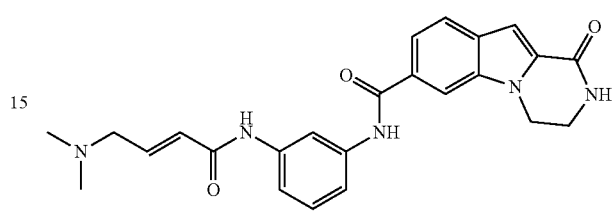

The title compound V-16 is prepared as described for Compound V-7 in Example 66, by substituting (E)-N-(3-aminophenyl)-4-(dimethylamino)but-2-enamide for INT-10 in step 7.

Compound V-18

N-(4-acryloyl-3,4-dihydro-2H-benzo[b][1,4]oxazin-6-yl)-2-(2-hydroxyethyl)-1-oxo-1,2,3,4-tetrahydropyrazino[1,2-a]indole-7-carboxamide

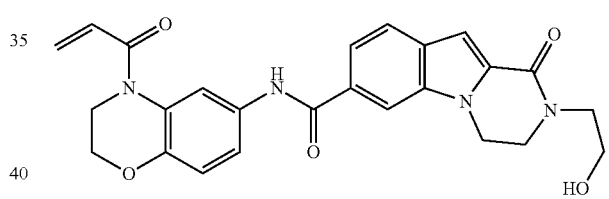

The title compound V-18 is prepared as described for Compound V-7 in Example 66, by substituting 2-(2-hydroxyethyl)-1-oxo-1,2,3,4-tetrahydropyrazino[1,2-a]indole-7-carboxylic acid for Intermediate 6 and INT-11 for INT-10.

Compound V-20

N-((1 S,2S)-2-acrylamidocyclopentyl)-1-oxo-1,2,3,4-tetrahydropyrazin[1,2-a]indole-7-carboxamide (racemic)

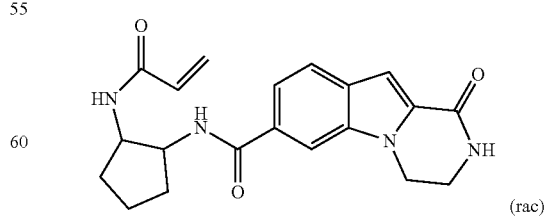

(rac)

The title compound V-20 is prepared as described for Compound V-7 in Example 66, by substituting N-((1S,2S)-2-aminocyclopentyl)acrylamide (racemic) for INT-10. The

Compound V-21

N-(2-(1-oxo-1,2,3,4-tetrahydropyrazino[1,2-a]indol-7-yl)-1H-benzo[d]imidazol-4-yl)acrylamide

The title compound V-21 is prepared as described for Compound V-17, by substituting N-(2,3-diaminophenyl)acrylamide for 6-chloropyrimidine-4,5-diamine.

Compound V-22

N-(3-acrylamido-4-(4-methylpiperazin-1-yl)phenyl)-1-oxo-1,2,3,4-tetrahydropyrazino[1,2-a]indole-7-carboxamide

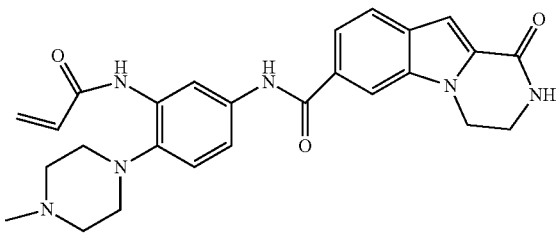 [SMILES: C=CC(=O)Nc1cc(NC(=O)c2ccc3cc4n(c3c2)CCNC4=O)ccc1N1CCN(C)CC1]

The title compound V-22 is prepared as described for Compound V-7 in Example 66, by substituting INT-17 for INT-10.

Compound V-24

N-(4-acrylamidopyridin-3-yl)-1-oxo-1,2,3,4-tetrahydropyrazino[1,2-a]indole-7-carboxamide

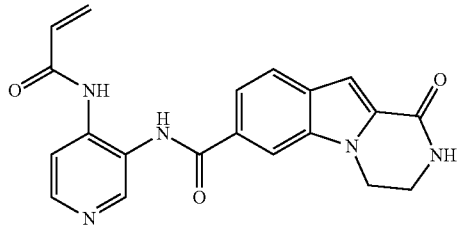 [SMILES: C=CC(=O)Nc1ccncc1NC(=O)c1ccc2cc3n(c2c1)CCNC3=O]

Compound V-24 is prepared similarly to Compound V-7 (N-(3-acrylamidophenyl)-1-oxo-1,2,3,4-tetrahydropyrazino[1,2-a]indole-7-carboxamide), by substituting N-(3-aminopyridin-4-yl)acrylamide for N-(3-aminophenyl)acrylamide.

Compound V-25

(R)—N-(1-(1-oxo-1,2,3,4-tetrahydropyrazino[1,2-a]indole-7-carbonyl)piperidin-3-yl)acrylamide

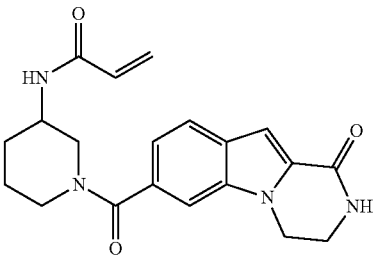 [SMILES: C=CC(=O)NC1CCCN(C(=O)c2ccc3cc4n(c3c2)CCNC4=O)C1]

The title compound V-25 is prepared as described for Compound V-7, by substituting (R)—N-(piperidin-3-yl)acrylamide for INT-10.

Compound V-26

N-(5-methyl-2-(1-oxo-1,2,3,4-tetrahydropyrazino[1,2-a]indol-7-yl)benzo[d]oxazol-4-yl)acrylamide

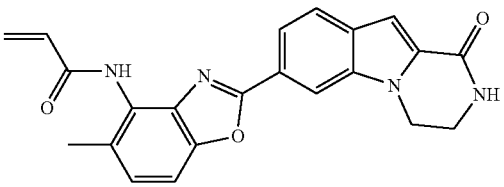 [SMILES: C=CC(=O)Nc1c(C)ccc2oc(-c3ccc4cc5n(c4c3)CCNC5=O)nc12]

The title compound was prepared according to the schemes, steps, and intermediates described below.

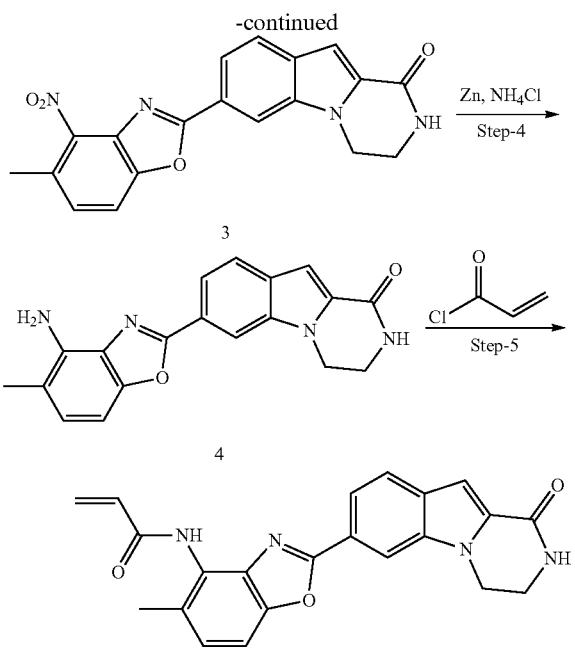

Step 1:

4-methyl-2,3-dinitrophenol (1)

To a solution of 4-methyl-3-nitrophenol (10 g, 65.36 mmol) in acetic acid (60 mL) was slowly added nitric acid (3.3 mL, 78.4 mmol) at 0° C. Then the reaction mixture was stirred at room temperature for 1 h. The reaction mixture was diluted with water (10 mL) and extracted with EtOAc (3×200 mL). The combined organic layers were dried over anhydrous sodium sulfate and concentrated under reduced pressure. The residue was purified by silica gel column chromatography to obtain 1 (5 g, 39%) as light yellow solid. $^1$H NMR (400 MHz, CDCl$_3$): 2.30 (s, 3H), 7.25 (d, J=8.4 Hz, 1H), 7.51 (d, J=8.4 Hz, 1H), 10.40 (s, 1H). MS m/z (M−H): 197

Step 2:

2-amino-4-methyl-3-nitrophenol (2)

To a stirred solution of 4-methyl-2,3-dinitrophenol (1) (5 g, 25.25 mmol) in EtOH (60 mL) were added zinc powder (8.25 g, 126.26 mmol) and ammonium chloride (6.8 g, 126.26 mmol). The resulting reaction mixture was then heated to 90° C. for 6 h. The reaction mixture was cooled to room temperature, filtered through celite pad and volatiles were evaporated under reduced pressure. The residue was purified by silica gel column chromatography to obtain 2 (2.5 mg, 59%) as thick dark brown solid. 1H NMR (400 MHz, DMSO-d$_6$): 2.21 (s, 1H), 5.70 (s, 2H), 6.38 (d, J=8.2 Hz, 1H), 6.78 (d, J=8.2 Hz, 1H). MS m/z (M−H): 167

Step 3:

7-(5-methyl-4-nitrobenzo[d]oxazol-2-yl)-3,4-dihydropyrazino[1,2-a]indol-1(2H) one (3)

To a stirred suspension of P$_2$O$_5$(926 mg, 6.52 mmol) in MeSO$_3$H (10 mL) were added 1-oxo-1,2,3,4-tetrahydropyrazino[1,2-a]indole-7-carboxylic acid (Int-7) (500 mg, 2.17 mmol) and 2-amino-4-methyl-3-nitrophenol (2, 438 mg, 2.61 mmol) at 0° C. The resulting mixture was heated to 120° C. for 4 h. The reaction mixture was cooled to room temperature and diluted with water (50 mL), solid was filtered and washed with water (10 mL). The resulting solid was dissolved in 50% MeOH/DCM (100 mL), dried over anhydrous sodium sulfate and concentrated under reduced pressure. The residue was purified by silica gel column chromatography to obtain 3 (350 mg, 44%) as yellow solid. $^1$H NMR (500 MHz, DMSO-d$_6$): δ 2.27 (s, 3H), 3.68 (t, J=6.0 Hz, 2H), 4.45 (t, J=6.0 Hz, 2H), 7.15 (s, 1H), 7.48 (d, J=8.5 Hz, 1H), 7.89 (d, J=8.5 Hz, 1H), 7.94 (d, J=8.5 Hz, 1H), 8.01 (d, J=8.0 Hz, 1H), 8.29 (s, 1H), 8.43 (s, 1H). MS m/z (M+H): 363

Step 4:

7-(4-amino-5-methylbenzo[d]oxazol-2-yl)-3,4-dihydropyrazino [1,2-a]indol-1(2H)-one (4)

To a stirred solution of 7-(5-methyl-4-nitrobenzo[d]oxazol-2-yl)-3,4-dihydropyrazino[1,2-a]indol-1(2H)-one (3, 350 mg, 0.96 mmol) in EtOH (20 mL) were added zinc powder (316 mg, 4.83 mmol) and ammonium chloride (261 mg, 4.83 mmol). The resulting mixture was then heated to 90° C. for 3 h. The reaction mixture was cooled to room temperature, filtered through celite pad using 50% MeOH/DCM and filtrate were evaporated under reduced pressure. The residue was washed with 20% EtOAc/hexane and dried to obtain 4 (250 mg, 78%) as yellow solid. 1H NMR (400 MHz, DMSO-d$_6$): δ 2.18 (s, 3H), 3.72 (t, J=5.8 Hz, 2H), 4.42 (t, J=5.8 Hz, 2H), 5.36 (br s, 2H), 6.83 (d, J=8.4 Hz, 1H), 6.99 (m, 1H), 7.85 (d, J=8.4 Hz, 1H), 7.92 (m, 1H), 8.26 (s, 1H), 8.32 (s, 1H). MS m/z (M+H): 333

Step 5:

To a stirred solution of 7-(4-amino-5-methylbenzo[d]oxazol-2-yl)-3,4-dihydropyrazino[1,2-a]indol-1(2H)-one (4, 120 mg, 0.36 mmol) in NMP (3 mL) was added acryloyl chloride (0.03 mL, 0.43 mmol) in NMP (2 mL) at 0° C. The resulting mixture was stirred for 30 minutes. The reaction mixture was quenched with saturated NaHCO$_3$ (5 mL) and filtered to obtain the resulting solid. The resulting solid was washed with water (10 mL) then dissolved in 15% MeOH/DCM, dried over anhydrous sodium sulfate and concentrated under reduced pressure. The obtained residue was suspended in THF (5 mL) and treated with DBU (0.2 mL) at room temperature for 16 h. The mixture was concentrated and the residue was purified by silica gel column chromatography to obtain the title compound V-26 (60 mg, 43%) as off white solid. $^1$H NMR (400 MHz, DMSO-d$_6$): δ 2.26 (s, 3H), 3.68 (t, J=6.4 Hz, 2H), 4.44 (t, J=6.4 Hz, 2H), 5.80 (m, 1H), 6.29 (m, 1H), 6.62 (m, 1H), 7.14 (s, 1H), 7.31 (d, J=8.4 Hz, 1H), 7.61 (d, J=8.4 Hz, 1H), 7.87 (d, J=8.4 Hz, 1H), 7.94 (m, 1H), 8.26 (s, 1H), 8.38 (s, 1H), 10.14 (s, 1H). MS m/z (M+H): 387.2

Compound V-27

N-(3-acrylamido-4-fluorophenyl)-1-oxo-1,2,3,4-tetrahydropyrazino[1,2-a]indole-7-carboxamide

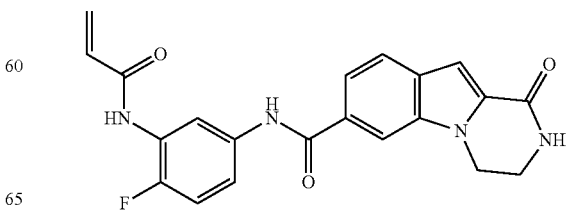

The title compound V-27 is prepared as described for Compound V-7, by substituting N-(5-amino-2-fluorophenyl)acrylamide for INT-10.

Compound V-28

N-(3-acrylamidophenyl)-1-oxo-2,3,4,5-tetrahydro-1H-[1,4]diazepino[1,2-a]indole-8-carboxamide

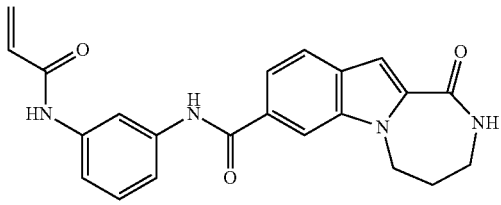 [SMILES: C=CC(=O)Nc1cccc(NC(=O)c2ccc3cc4n(c3c2)CCCNC4=O)c1]

The title compound V-28 is prepared as described for Compound V-17, by substituting N-(3-aminophenyl)acrylamide for 6-chloropyrimidine-4,5-diamine, and starting with 1-oxo-2,3,4,5-tetrahydro-1H-[1,4]diazepino[1,2-a]indole-8-carboxylic acid.

Compound V-29

N-(3-acrylamido-4-(4-methylpiperazin-1-yl)phenyl)-1-oxo-2,3,4,5-tetrahydro-1H-[1,4]diazepino[1,2-a]indole-8-carboxamide

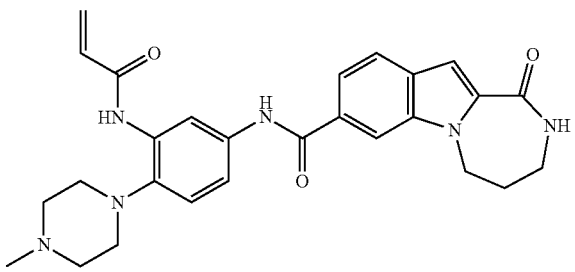 [SMILES: C=CC(=O)Nc1cc(NC(=O)c2ccc3cc4n(c3c2)CCCNC4=O)ccc1N1CCN(C)CC1]

The title compound V-29 is prepared as described for Compound V-17, by substituting N-(5-amino-2-(4-methylpiperazin-1-yl)phenyl)acrylamide for 6-chloropyrimidine-4,5-diamine, and starting with 1-oxo-2,3,4,5-tetrahydro-1H-[1,4]diazepino[1,2-a]indole-8-carboxylic acid.

Compound V-30

N-(2-acrylamidophenyl)-1-oxo-2,3,4,5-tetrahydro-1H-[1,4]diazepino[1,2-a]indole-8-carboxamide

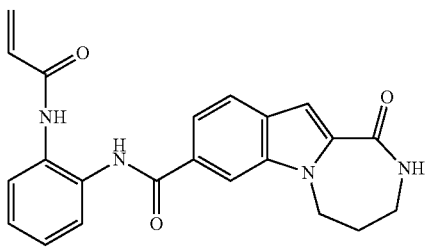 [SMILES: C=CC(=O)Nc1ccccc1NC(=O)c1ccc2cc3n(c2c1)CCCNC3=O]

The title compound V-30 is prepared as described for Compound V-17, by substituting N-(2-aminophenyl)acrylamide for 6-chloropyrimidine-4,5-diamine, and starting with 1-oxo-2,3,4,5-tetrahydro-1H-[1,4]diazepino[1,2-a]indole-8-carboxylic acid.

Compound V-31

N-(2-(1-oxo-1,2,3,4-tetrahydropyrazino[1,2-a]indol-7-yl)benzo[d]oxazol-4-yl)acrylamide

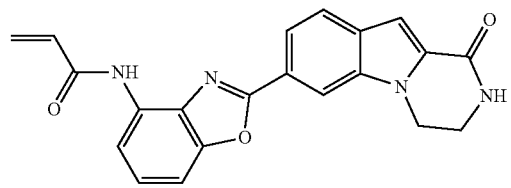

The title compound was prepared according to the schemes, steps, and intermediates described below.

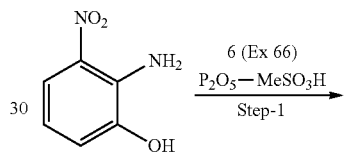

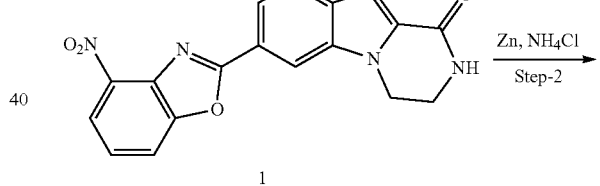

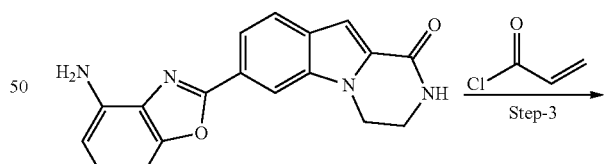

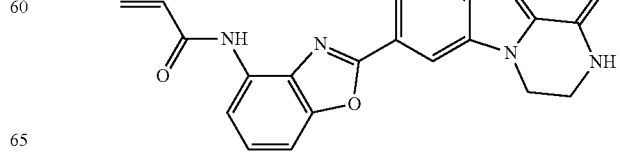

Step 1:

7-(4-nitrobenzo[d]oxazol-2-yl)-3,4-dihydropyrazino[1,2-a]indol-1(2H)-one (1)

To a suspension of $P_2O_5$ (741 mg, 5.22 mmol) in $MeSO_3H$ (8 mL) were added 1-oxo-1,2,3,4-tetrahydropyrazino[1,2-a]indole-7-carboxylic acid (6) (400 mg, 1.74 mmol) and 2-amino-3-nitrophenol (322 mg, 2.1 mmol) at 0° C. The resulting mixture was then heated to 120° C. for 4 h. The reaction mixture was cooled to room temperature and diluted with water (10 mL). The resulting solid was filtered, washed with water (10 mL), and then dissolved in 50% MeOH/DCM (100 mL), dried over anhydrous sodium sulfate and concentrated under reduced pressure. The residue was purified by silica gel column chromatography to obtain 1 (350 mg, 58%) as yellow solid. $^1H$ NMR (500 MHz, DMSO-$d_6$): δ 3.70 (t, J=6.0 Hz, 2H), 4.49 (t, J=6.0 Hz, 2H), 7.18 (s, 1H), 7.64 (m, 1H), 7.94 (d, J=8.5 Hz, 1H), 8.03 (d, J=8.5 Hz, 1H), 8.23 (d, J=8.5 Hz, 1H), 8.27 (d, J=7.5 Hz, 1H), 8.32 (s, 1H), 8.50 (s, 1H). MS m/z (M+H): 349.1

Step 2:

7-(4-aminobenzo[d]oxazol-2-yl)-3,4-dihydropyrazino[1,2-a]indol-1(2H)-one (2)

To a stirred solution of 7-(4-nitrobenzo[d]oxazol-2-yl)-3,4-dihydropyrazino[1,2-a]indol-1(2H)-one (1) (350 mg, 1.0 mmol) in EtOH (15 mL) were added zinc powder (329 mg, 5.0 mmol) and ammonium chloride (271 mg, 5.0 mmol). The resulting mixture was then heated to 90° C. for 3 h. The reaction mixture was cooled to room temperature, filtered through celite pad eluting with 50% MeOH/DCM. The resulting filtrate was evaporated under reduced pressure, the residue was washed with 20% EtOAc/Hexane and dried to obtain 2 (265 mg, 83%) as yellow solid. 1H NMR (500 MHz, DMSO-$d_6$): δ 3.69 (t, J=6.0 Hz, 2H), 4.23 (t, J=6.0 Hz, 2H), 5.66 (s, 2H), 6.56 (d, J=8.0 Hz, 1H), 6.87 (d, J=8.0 Hz, 1H), 7.09 (m, 1H), 7.13 (s, 1H), 7.86 (d, J=8.5 Hz, 1H), 7.93 (d, J=8.0 Hz, 1H), 8.24 (s, 1H), 8.31 (s, 1H). MS m/z (M+H): 319.1

Step 3:

To a solution of 7-(4-aminobenzo[d]oxazol-2-yl)-3,4-dihydropyrazino[1,2-a]indol-1(2H)-one (2, 150 mg, 0.47 mmol) in THF (10 mL) was added TEA (0.03 mL, 0.23 mmol) and acryloyl chloride (0.04 mL, 0.56 mmol) in THF (5 mL) at −78° C. The resulting mixture was then stirred for 30 minutes. The reaction mixture was quenched with saturated $NaHCO_3$ (5 mL) and the resulting solid was filtered and washed with water (10 mL). The resulting solid was dissolved in 5% MeOH/DCM, dried over anhydrous sodium sulfate and concentrated under reduced pressure. The obtained residue was suspended in THF (5 mL) and treated with DBU (0.1 mL) at room temperature for 16 h. The resulting mixture was concentrated and the residue was purified by silica gel column chromatography to obtain the title compound V-31 (70 mg, 40%) as yellow solid $^1H$ NMR (400 MHz, DMSO-$d_6$): δ 3.70 (m, 2H), 4.43 (m, 2H), 5.79-5.82 (dd, J=2.0, 10.0 Hz, 1H), 6.31-6.35 (dd, J=2.0, 17.2 Hz, 1H), 6.84-6.91 (dd, J=10.0, 17.2 Hz, 1H), 7.16 (s, 1H), 7.39 (m, 1H), 7.53 (d, J=8.0 Hz, 1H), 7.90 (d, J=8.4 Hz, 1H), 8.03 (m, 1H), 8.15 (d, J=8.0 Hz, 1H), 8.28 (s, 1H), 8.44 (s, 1H), 10.41 (s, 1H). MS m/z (M+H): 373.2

Compound V-32

N-(5-acrylamido-2-(piperidin-1-yl)thiazol-4-yl)-1-oxo-1,2,3,4-tetrahydropyrazino[,2-a]indole-7-carboxamide

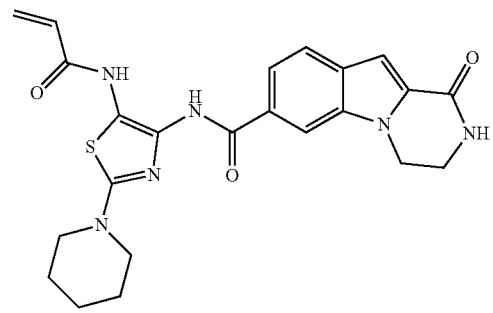 [SMILES: C=CC(=O)Nc1sc(N2CCCCC2)nc1NC(=O)c1ccc2cc3n(c2c1)CCNC3=O]

Compound V-32 is prepared similarly to Compound V-7 (N-(3-acrylamidophenyl)-1-oxo-1,2,3,4-tetrahydropyrazino[1,2-a]indole-7-carboxamide), by substituting N-(4-amino-2-(piperidin-1-yl)thiazol-5-yl)acrylamide for INT-10.

Compound V-33

N-(4-acrylamido-2-(piperidin-1-yl)thiazol-5-yl)-1-oxo-1,2,3,4-tetrahydropyrazino[1,2-a]indole-7-carboxamide

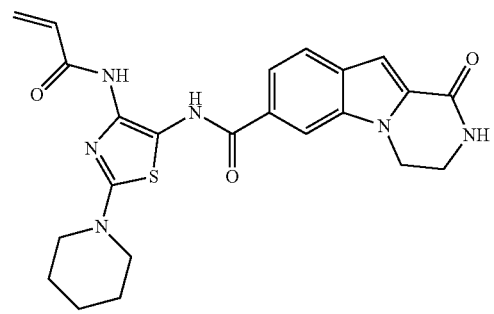 [SMILES: C=CC(=O)Nc1nc(N2CCCCC2)sc1NC(=O)c1ccc2cc3n(c2c1)CCNC3=O]

Compound V-33 is prepared similarly to Compound V-7 (N-(3-acrylamidophenyl)-1-oxo-1,2,3,4-tetrahydropyrazino[1,2-a]indole-7-carboxamide), by substituting N-(5-amino-2-(piperidin-1-yl)thiazol-4-yl)acrylamide for INT-10.

Compound V-34

N-((1 S,2R)-2-acrylamidocyclopentyl)-1-oxo-1,2,3,4-tetrahydropyrazino[1,2-a]indole-7-carboxamide (racemic)

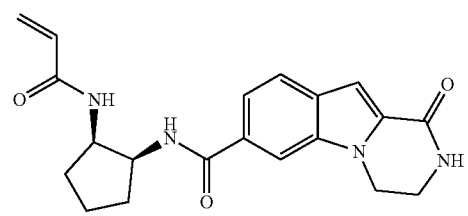

477

-continued

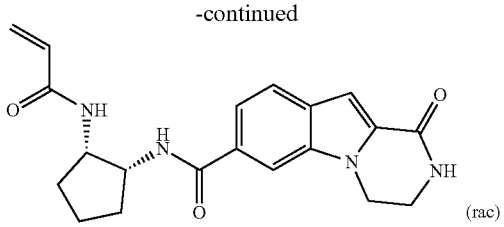
(rac)

Compound V-34 is prepared similarly to Compound V-7 (N-(3-acrylamidophenyl)-1-oxo-1,2,3,4-tetrahydropyrazino[1,2-a]indole-7-carboxamide), by substituting N-((1R,2S)-2-aminocyclopentyl)acrylamide (racemic) for INT-10. The enantiomers are obtained upon chiral separation. Alternatively, the enantiomers are also used as mixtures of different ratios.

Compound V-36

N-(4-acrylamidothiazol-2-yl)-1-oxo-1,2,3,4-tetrahydropyrazino[1,2-a]indole-7-carboxamide

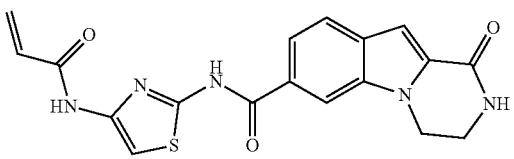 [SMILES: C=CC(=O)Nc1csc(NC(=O)c2ccc3cc4n(c3c2)CCNC4=O)n1]

Compound V-36 is prepared similarly to Compound V-7 (N-(3-acrylamidophenyl)-1-oxo-1,2,3,4-tetrahydropyrazino[1,2-a]indole-7-carboxamide), by substituting N-(2-aminothiazol-4-yl)acrylamide for INT-10.

Compound V-37

N-(4-(acrylamidomethyl)thiazol-2-yl)-1-oxo-1,2,3,4-tetrahydropyrazino[1,2-a]indole-7-carboxamide

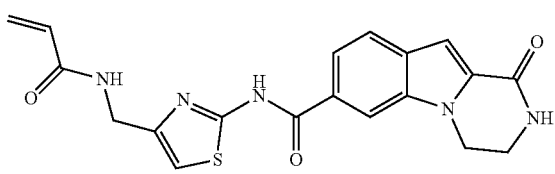 [SMILES: C=CC(=O)NCc1csc(NC(=O)c2ccc3cc4n(c3c2)CCNC4=O)n1]

Compound V-37 is prepared similarly to Compound V-7 (N-(3-acrylamidophenyl)-1-oxo-1,2,3,4-tetrahydropyrazino[1,2-a]indole-7-carboxamide), by substituting N-((2-aminothiazol-4-yl)methyl)acrylamide for INT-10.

478

Compound V-38

N-(4-((N-methylacrylamido)methyl)thiazol-2-yl)-1-oxo-1,2,3,4-tetrahydropyrazino[1,2-a]indole-7-carboxamide

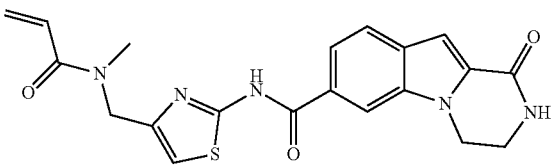 [SMILES: C=CC(=O)N(C)Cc1csc(NC(=O)c2ccc3cc4n(c3c2)CCNC4=O)n1]

Compound V-38 is prepared similarly to Compound V-7 (N-(3-acrylamidophenyl)-1-oxo-1,2,3,4-tetrahydropyrazino[1,2-a]indole-7-carboxamide), by substituting N-((2-aminothiazol-4-yl)methyl)-N-methylacrylamide for INT-10.

Compound V-39

N-(2-(1'-oxo-2',3'-dihydro-1'H-spiro[cyclobutane-1,4'-pyrazino[1,2-a]indol]-7'-yl)benzo[d]oxazol-4-yl)acrylamide

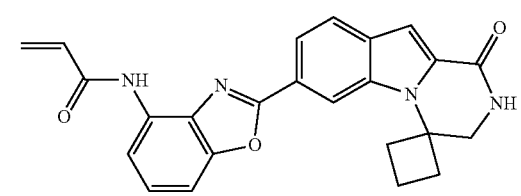 [SMILES: C=CC(=O)Nc1cccc2oc(-c3ccc4cc5n(c4c3)C3(CCC3)CNC5=O)nc12]

The title compound was prepared according to the schemes, steps, and intermediates described below.

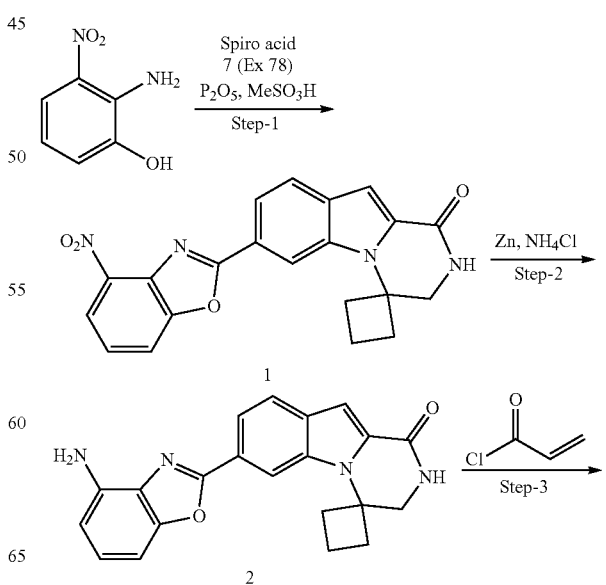

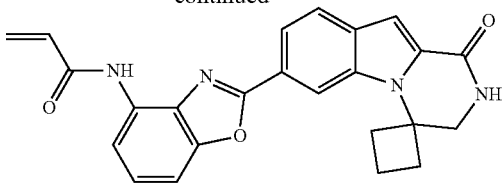

Step 1:

7'-(4-nitrobenzo[d]oxazol-2-yl)-2',3'-dihydro-1'H-spiro[cyclobutane-1,4'-pyrazino[1,2-a]indol]-1'-one (1)

To a stirred solution of $P_2O_5$ (131.4 mg, 0.92 mmol) in $MeSO_3H$ (1.4 mL) were added 1'-oxo-2',3'-dihydro-1'H-spiro[cyclobutane-1,4'-pyrazino[1,2-a]indole]-7'-carboxylic acid (7, from Ex78) (100 mg, 0.37 mmol) and 2-amino-3-nitrophenol (57 mg, 0.37 mmol) at 0° C. Then the resultant reaction mixture was heated to 110° C. for 4 h, cooled to room temperature, diluted with water (10 mL) and extracted with 5% MeOH/EtOAc (2×20 mL). The combined organic layers were dried over anhydrous sodium sulfate and concentrated under reduced pressure. The residue was purified by silica gel column chromatography to obtain 1 (90 mg, 63%) as orange solid. 1H NMR (400 MHz, DMSO-$d_6$): δ 2.17 (m, 2H), 2.28 (m, 1H), 2.41 (m, 1H), 3.04 (m, 2H), 3.78 (d, J=2.8 Hz, 1H), 7.26 (s, 1H), 7.67 (m, 1H), 7.97 (d, J=8.4 Hz, 1H), 8.07 (m, 1H), 8.23 (d, J=8.4 Hz, 1H), 8.30 (m, 2H), 8.39 (s, 1H), 8.83 (s, 1H) MS m/z (M+H): 389

Step 2:

7'-(4-aminobenzo[d]oxazol-2-yl)-2',3'-dihydro-1'H-spiro[cyclobutane-1,4'-pyrazino[1,2-a]indol]-1'-one (2)

To a stirred solution of 7'-(4-nitrobenzo[d]oxazol-2-yl)-2',3'-dihydro-1'H-spiro[cyclobutane-1,4'-pyrazino[1,2-a]indol]-1'-one (1, 90 mg, 0.23 mmol) in EtOH (10 mL) were added zinc powder (76 mg, 1.16 mmol) and ammonium chloride (63 mg, 1.16 mmol). The resulting mixture was then heated at 90° C. for 2 h. The reaction mixture was cooled to room temperature, filtered through a Celite® pad eluting with 10% MeOH/DCM. The eluent was concentrated under reduced pressure and the resulting residue washed with 20% EtOAc/hexane and dried to obtain 2 (65 mg, 79%) as a yellow solid. The resulting crude compound was used directly in Step 3 without any further purification. MS m/z (M+H): 359

Step 3:

To a solution of 7'-(4-aminobenzo[d]oxazol-2-yl)-2',3'-dihydro-1'H-spiro[cyclobutane-1,4'-pyrazino[1,2-a]indol]-1'-one (2) (110 mg, 0.3 mmol) in dry THF (15 mL) was added acryloyl chloride (0.02 mL, 0.33 mmol) in dry THF (2 mL) at −78° C. The resulting mixture was stirred for 30 minutes. The reaction mixture was quenched with saturated $NaHCO_3$ (5 mL) and extracted with 5% MeOH/DCM. The organic layer was dried over anhydrous sodium sulfate and concentrated under reduced pressure. The obtained residue was suspended in THF (3 mL) and treated with DBU (0.1 mL) for 16 h. The resulting mixture was concentrated and the residue was purified by silica gel column chromatography to obtain the title compound V-39 (40 mg, 32%) as yellow solid. 1H NMR (400 MHz, DMSO-$d_6$): δ 2.13 (m, 1H), 2.31 (m, 1H), 2.39 (m, 2H), 3.07 (m, 2H), 3.77 (d, J=2.4 Hz, 2H). 5.79-5.82 (dd, J=2.0, 10.4 Hz, 1H). 6.31-6.66 (dd, J=2.0, 16.8 Hz, 1H), 6.84-6.91 (dd, J=10.4, 16.8 Hz, 1H), 7.23 (s, 1H), 7.39 (m, 1H), 7.56 (d, J=7.6 Hz, 1H), 7.94 (d, J=8.4 Hz, 1H), 8.05 (m, 1H), 8.17 (d, J=8.2 Hz, 1H), 8.37 (s, 1H), 8.77 (s, 1H), 10.44 (s, 1H) MS m/z (M+H): 413

Compound V-40

N-(5-acrylamido-2-(piperidin-1-yl)thiazol-4-yl)-1'-oxo-2',3'-dihydro-1'H-spiro[cyclobutane-1,4'-pyrazino[1,2-a]indole]-7'-carboxamide

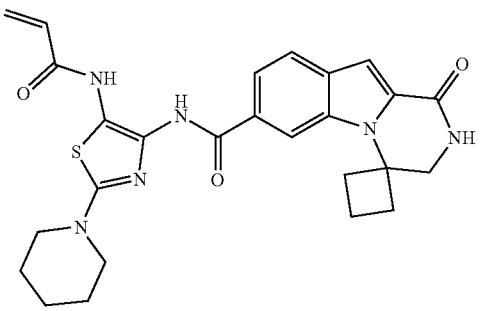 [SMILES: C=CC(=O)Nc1sc(N2CCCCC2)nc1NC(=O)c1ccc2cc3n(c2c1)C1(CCC1)CNC3=O]

Compound V-42 is prepared similarly to Compound V-23 (N-(4-acryloyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide) in Example 78, by substituting N-(4-amino-2-(piperidin-1-yl)thiazol-5-yl)acrylamide for INT-11.

Compound V-41

N-(4-acrylamido-2-(piperidin-1-yl)thiazol-5-yl)-1'-oxo-2',3'-dihydro-1'H-spiro[cyclobutane-1,4'-pyrazino[1,2-a]indole]-7'-carboxamide

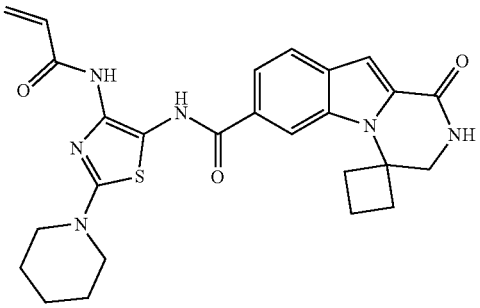 [SMILES: C=CC(=O)Nc1nc(N2CCCCC2)sc1NC(=O)c1ccc2cc3n(c2c1)C1(CCC1)CNC3=O]

Compound V-41 is prepared similarly to Compound V-23 (N-(4-acryloyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide) in Example 78, by substituting N-(5-amino-2-(piperidin-1-yl)thiazol-4-yl)acrylamide for INT-11.

Compound V-42

N-(4-acrylamidothiazol-2-yl)-1'-oxo-2',3'-dihydro-1'H-spiro[cyclobutane-1,4'-pyrazino[1,2-a]indole]-7'-carboxamide

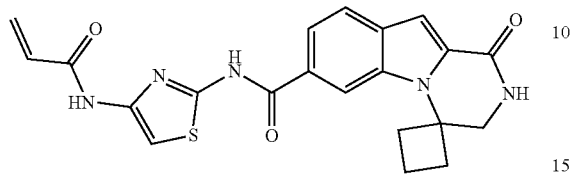

Compound V-42 is prepared similarly to Compound V-23 (N-(4-acryloyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide) in Example 78, by substituting N-(2-aminothiazol-4-yl)acrylamide for INT-11.

Compound V-43

N-(4-(acrylamidomethyl)thiazol-2-yl)-1'-oxo-2',3'-dihydro-1'H-spiro[cyclobutane-1,4'-pyrazino[1,2-a]indole]-7'-carboxamide

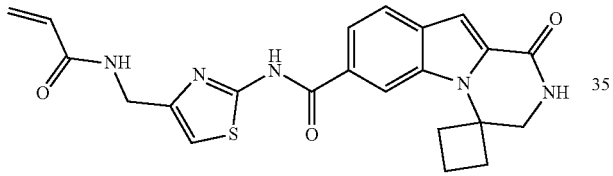

Compound V-43 was prepared similarly to Compound V-23 in Example 78, by substituting INT-11 in step 8 of Example 78 with N-((2-aminothiazol-4-yl)methyl)acrylamide 7, depicted below, to afford the desired product (15 mg, 18%) as an off white solid. $^1$H NMR (500 MHz, DMSO-d$_6$): δ 2.07 (m, 2H), 2.31 (m, 4H), 3.07 (m, 2H), 4.41 (d, J=6 Hz, 2H), 5.61-5.63 (dd, J=2, 10 Hz, 1H), 6.11-6.15 (dd, J=2.0, 17 Hz, 1H), 6.27-6.33 (dd, J=10.0, 17 Hz, 1H), 6.99 (s, 1H), 7.16 (s, 1H), 7.81 (s, 2H), 8.33 (s, 1H), 8.53 (d, J=8.4 Hz, 1H), 8.62 (d, J=8.6 Hz, 1H), 12.86 (s, 1H). MS m/z (M+H): 436.4

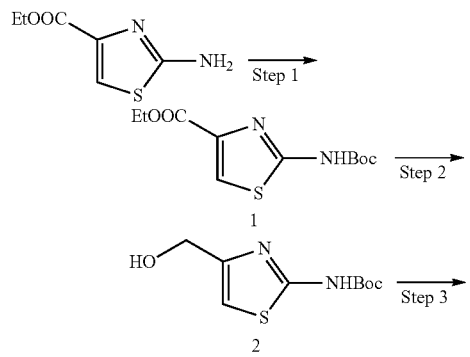

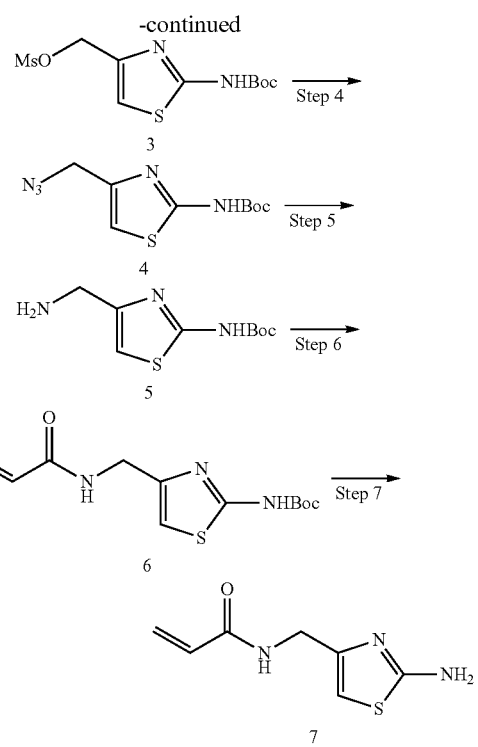

Step 1:

Ethyl-2-((tert-butoxycarbonyl)amino)thiazole-4-carboxylate3-nitropyridin-2-amine (1)

To a stirred solution of ethyl 2-aminothiazole-4-carboxylate (1 g, 5.8 mmol) in DCM (30 ml) was added DMAP (121 mg, 0.98 mmol) and (Boc)$_2$O (2.78 g, 12.76 mmol) dropwise at 0° C. and stirred at room temperature for 16 h. The reaction mixture was diluted with DCM and washed with 10% citric acid solution. The organic layer was separated, dried over anhydrous sodium sulfate, and concentrated under reduced pressure. The residue was purified by silica gel column chromatography to obtain 1 (2.5 g) as an off white solid. MS m/z (M+H): 272.3

Step 2:

tert-Butyl (4-(hydroxymethyl)thiazol-2-yl)carbamate (2)

To a suspension of LiAlH$_4$ (489 mg, 12.87 mmol) in THF (15 ml) was added ethyl 2-((tert-butoxycarbonyl)amino)thiazole-4-carboxylate3-nitropyridin-2-amine (1) (1 g, 3.67 mmol) in THF (2 mL) at 0° C. and stirred at room temperature for 16 h. The reaction mixture was quenched with saturated aqueous sodium sulfate at 0° C., filtered through a celite pad, and washed with ethyl acetate (100 ml). The obtained organic filtrate was dried over anhydrous sodium sulfate and concentrated under reduced pressure. The residue was purified by silica gel column chromatography to obtain 2 (0.5 g, 59%) as color less syrup. $^1$H NMR (500 MHz, DMSO-d$_6$): δ 1.48 (s, 9H), 4.39 (d, J=5.5 Hz, 2H), 5.14 (t, J=11.5 Hz, 1H), 6.82 (s, 1H), 11.3 (s, 1H)). MS m/z (M+H): 229.0

Step 3:

tert-Butyl (4-(methylsulfonyl)methyl)thiazol-2-yl) carbamate (3)

To a solution of tert-butyl (4-(hydroxymethyl)thiazol-2-yl)carbamate (2) (0.5 g, 2.17 mmol) in DCM (13 ml) were added triethylamine (0.6 ml, 4.34 mmol) and methane sulfonyl chloride (0.2 ml, 2.6 mmol) in DCM (2 ml) at 0° C. and stirred at room temperature for 1 h. The reaction mixture was diluted with DCM and water. The organic layer was separated, dried over anhydrous sodium sulfate, and concentrated under reduced pressure. The residue was purified by silica gel column chromatography to obtain 3 (0.3 g) as syrup. MS m/z (M+Na): 328.2

Step 4:

tert-Butyl (4-(azidomethyl)thiazol-2-yl)carbamate (4)

To a solution of tert-butyl (4-(methylsulfonyl)methyl)thiazol-2-yl)carbamate (3) (0.3 g, 0.97 mmol) in DMF (10 ml) was added sodium azide (127 mg, 1.94 mmol) at 0° C. and stirred at room temperature for 16 h. The reaction mixture was diluted with ethyl acetate and water. The organic layer was separated, dried over anhydrous sodium sulfate, and concentrated under reduced pressure to obtain 4 (170 mg) as a syrup. The crude was used for the next step without any further purification. 1H NMR (400 MHz, DMSO-d$_6$, crude): δ 1.48 (s, 9H), 4.33 (s, 2H), 7.12 (s, 1H), 11.5 (s, 1H). MS m/z (M−H): 254.2

Step 5:

tert-Butyl(4-(aminomethyl)thiazol-2-yl)carbamate (5)

To a solution of tert-butyl (4-(azidomethyl)thiazol-2-yl) carbamate (4) (0.17 g, 0.66 mmol) in ethanol (15 ml) was added Pd/C (50 mg, 30%) and stirred at room temperature for 4 h under H$_2$ atmosphere. The reaction mixture was filtered through a celite pad using EtOAc (30 mL). The combined organic layers were evaporated to obtain 5 (70 mg) as a syrup. The crude was used for next step without any further purification. MS m/z (M+H): 230.2

Step 6:

tert-Butyl (4-acylamidomethyl)thiazol-2-yl)carbamate (6)

To a solution of tert-butyl(4-(aminomethyl)thiazol-2-yl) carbamate (5) (70 mg, 0.305 mmol) in THF (8 ml) was added acryloyl chloride (41 mg, 0.46 mmol) in THF (2 ml) at 0° C. and stirred at room temperature for 1 h. The reaction mixture was quenched with saturated sodium bicarbonate and extracted with ethyl acetate. The organic layer was separated, dried over anhydrous sodium sulfate, and concentrated under reduced pressure. The residue was purified by silica gel column chromatography to obtain 6 (80 mg) as a syrup. $^1$H NMR (500 MHz, DMSO-d$_6$): 1.48 (s, 9H), 4.31 (d, J=6 Hz, 2H), 5.61-5.63 (dd, J=2, 10 Hz, 1H), 6.11-6.15 (dd, J=2.0, 17 Hz, 1H), 6.27-6.33 (dd, J=10.0, 17 Hz, 1H), 6.82 (s, 1H), 8.51 (d, J=8.4 Hz, 1H), 11.42 (s, 1H). MS m/z (M+H): 284.3

Step 7:

N-((2-aminothiazol-4-yl)methyl)acrylamide (7)

To a solution of tert-butyl (4-acylamidomethyl)thiazol-2-yl)carbamate (6) (80 mg, 0.28 mmol) in DCM (2 ml) was added trifluoroacetic acid (1 ml, 14 mmol) at 0° C. and stirred at room temperature for 16 h. The volatiles were removed under reduced pressure to obtain 8 (80 mg, TFA salt) as an off white semi solid. The crude was used for the next step without any further purification. MS m/z (M+H): 184.1

Compound V-44

N-(4-((N-methylacrylamido)methyl)thiazol-2-yl)-1'-oxo-2',3'-dihydro-1'H-spiro[cyclobutane-1,4'-pyrazino[1,2-a]indole]-7'-carboxamide

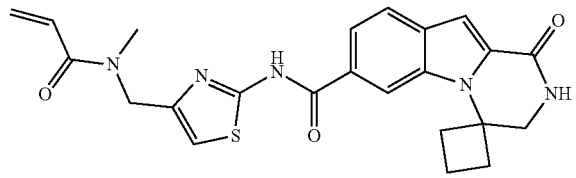 [SMILES: C=CC(=O)N(C)Cc1csc(NC(=O)c2ccc3cc4n(c3c2)C2(CCC2)CNC4=O)n1]

Compound V-44 is prepared similarly to Compound V-23 (N-(4-acryloyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide), by N-((2-aminothiazol-4-yl)methyl)-N-methylacrylamide for INT-11.

Compound VI-1

(R)—N-(2-(4-((3,4-dioxo-2-((1-phenylethyl)amino) cyclobut-1-en-1-yl)amino)pyridin-2-yl)phenyl)acrylamide

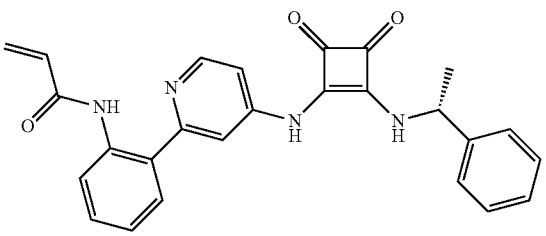 [SMILES: C=CC(=O)Nc1ccccc1-c1cc(Nc2c(N[C@H](C)c3ccccc3)c(=O)c2=O)ccn1]

The title compound VI-1 was prepared as described in Example 83, by substituting N-(2-(4,4,5,5-tetramethyl-1,3,2-dioxaborolan-2-yl)phenyl)acrylamide for INT-39 in step 3. Yellow powder, 5.5 mg, 60%. $^1$H NMR (400 MHz, DMSO-d$_6$) δ 1.60 (d, 3H), 5.32 (m, 1H), 5.75 (d, 1H), 6.18 (d, 1H), 6.35 (dd, 1H), 7.35 (m, 2H), 7.38-7.42 (m, 5H), 7.52 (br, 1H), 7.70 (br, 1H), 7.98 (s, br, 1H), 8.48-8.56 (m, 2H), 10.58 (br, 1H). MS m/z (M+H): 439.3

Compound VI-2

N-((1R,2S)-2-((4-((3,4-dioxo-2-(((R)-1-phenylethyl)amino)cyclobut-1-en-1-yl)amino)pyridin-2-yl)amino)cyclohexyl)acrylamide

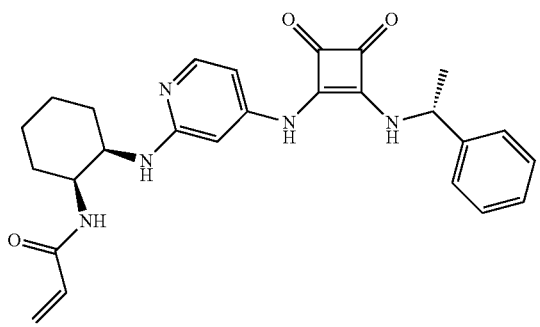 [SMILES: C=CC(=O)N[C@H]1CCCC[C@H]1Nc1cc(Nc2c(N[C@H](C)c3ccccc3)c(=O)c2=O)ccn1]

The title compound VI-2 is prepared as described in Example 83, by substituting INT-33 (rac) for INT-39, RuPhos for PdCl$_2$(dppf), LiHMDS for Cs$_2$CO$_3$, and dry dioxane for isopropanol in step 3. The diastereomers are obtained upon chiral separation. Alternatively, the diastereomers are also used as mixtures of different ratios.

Compound VI-3

(R)—N-(3-((4-((3,4-dioxo-2-((1-phenylethyl)amino)cyclobut-1-en-1-yl)amino)pyridin-2-yl)amino)phenyl)acrylamide

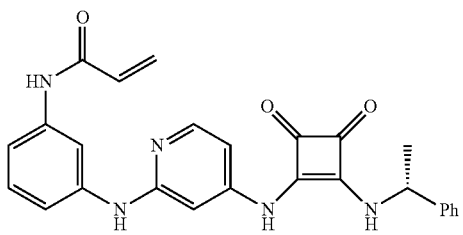 [SMILES: C=CC(=O)Nc1cccc(Nc2cc(Nc3c(N[C@H](C)c4ccccc4)c(=O)c3=O)ccn2)c1]

The title compound VI-3 is prepared as described in Example 83, by substituting N-(3-aminophenyl)acrylamide for INT-39 in step 3.

Compound VI-4

(R)—N-(2-((4-((3,4-dioxo-2-((1-phenylethyl)amino)cyclobut-1-en-1-yl)amino)pyridin-2-yl)amino)phenyl)acrylamide

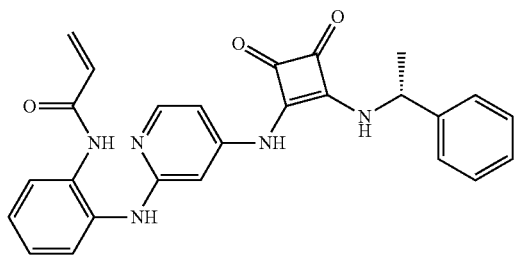 [SMILES: C=CC(=O)Nc1ccccc1Nc1cc(Nc2c(N[C@H](C)c3ccccc3)c(=O)c2=O)ccn1]

The title compound VI-4 is prepared as described in Example 83, by substituting N-(2-aminophenyl)acrylamide for INT-39 in step 3.

Compound VI-5

(R)—N-(3-(4-((3,4-dioxo-2-((1-phenylethyl)amino)cyclobut-1-en-1-yl)amino)pyridin-2-yl)phenyl)acrylamide

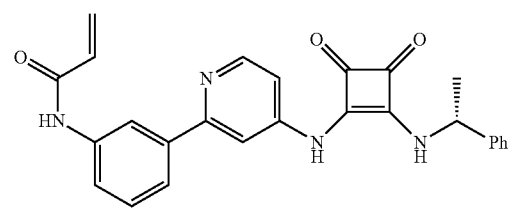 [SMILES: C=CC(=O)Nc1cccc(-c2cc(Nc3c(N[C@H](C)c4ccccc4)c(=O)c3=O)ccn2)c1]

The title compound VI-5 is prepared as described in Example 83, by substituting N-(3-(4,4,5,5-tetramethyl-1,3,2-dioxaborolan-2-yl)phenyl)acrylamide for INT-39 in step 3.

Compound VI-6

N-(1-(4-((3,4-dioxo-2-(((R)-1-phenylethyl)amino)cyclobut-1-en-1-yl)amino)pyridin-2-yl)piperidin-3-yl)acrylamide

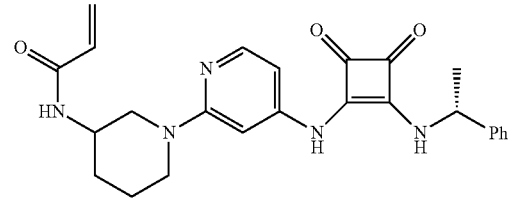 [SMILES: C=CC(=O)NC1CCCN(c2cc(Nc3c(N[C@H](C)c4ccccc4)c(=O)c3=O)ccn2)C1]

The title compound VI-6 is prepared as described for VI-2, by substituting N-(piperidin-3-yl)acrylamide (rac) for N-((1R,2S)-2-aminocyclohexyl)acrylamide. The diastereomers are obtained upon chiral separation. Alternatively, the diastereomers are also used as mixtures of different ratios.

Compound VI-7

N(R)-3-((2-((4-acryloyl-3,4-dihydro-2H-benzo[b][1,4]oxazin-6-yl)amino)pyridin-4-yl)amino)-4-((1-phenylethyl)amino)cyclobut-3-ene-1,2-dione

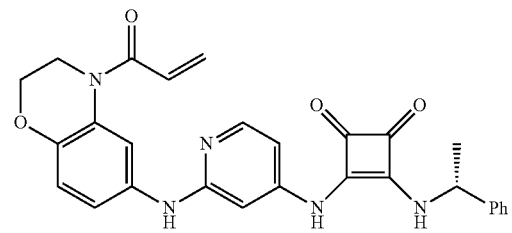 [SMILES: C=CC(=O)N1CCOc2ccc(Nc3cc(Nc4c(N[C@H](C)c5ccccc5)c(=O)c4=O)ccn3)cc21]

The title compound VI-7 is prepared as described for VI-2, by substituting 1-(6-amino-2H-benzo[b][1,4]oxazin-4 (3H)-yl)prop-2-en-1-one for INT-39 in step 3.

Compound VI-8

3-((2-((1-acryloylpiperidin-3-yl)amino)pyridin-4-yl) amino)-4-(((R)-1-phenylethyl)amino)cyclobut-3-ene-1,2-dione

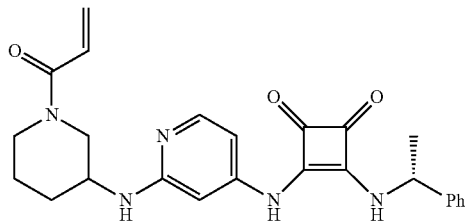 [SMILES: C=CC(=O)N1CCCC(Nc2cc(Nc3c(N[C@H](C)c4ccccc4)c(=O)c3=O)ccn2)C1]

The title compound VI-8 is prepared as described in Example 83, by substituting 1-(3-aminopiperidin-1-yl)prop-2-en-1-one (rac) for N-((1R,2S)-2-aminocyclohexyl)acrylamide. The diastereomers are obtained upon chiral separation. Alternatively, the diastereomers are also used as mixtures of different ratios.

Compound VI-b-1

(R)—N-(4-((3,4-dioxo-2-((1-phenylethyl)amino) cyclobut-1-en-1-yl)amino)pyridin-2-yl)acrylamide

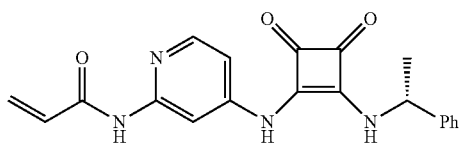 [SMILES: C=CC(=O)Nc1cc(Nc2c(N[C@H](C)c3ccccc3)c(=O)c2=O)ccn1]

The title compound VI-b-1 is prepared as described in Example 83, by substituting acrylamide in step 2.

BIOLOGICAL EXAMPLES

Described below are in vitro assays used to measure the biological activity of provided compounds as selective inhibitors of MK2.

Example 89

Mitogen-Activated Protein Kinase-Activated Protein Kinase 2 Omnia® Assay for Compound Potency Assessment The protocol below describes a continuous-read kinase assay optimized to measure potency of compounds against p38a activated, mitogen-activated protein kinase-activated protein kinase 2 (MAPKAP-K2 or MK-2) enzyme. The mechanics of the assay platform are best described by the vendor (Invitrogen, Carlsbad, Calif.) on their website at the following URL: invitrogen.com/search/global/searchAction.action?resultPage=1 &resultsPerPage=15 &query=omnia&personaFilterTerm=Support+%26+Troubleshoot Briefly, a 1.25× stock of MK-2 enzyme from Invitrogen (PV3317), a 5× stock of ATP (AS001A), and ST3-Sox peptide substrate (KNZ1031C) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT. Compound potency assays were initiated by adding a 0.5 µL volume of 100% DMSO and serially diluted compounds prepared in 100% DMSO to a Corning (#3574) 384-well, white, non-binding surface microtiter plate (Corning, N.Y.) followed immediately by 10 µL of the ST3-Sox peptide and ATP substrate solution. Kinase reactions were started with the addition of 40 µL of MK-2 enzyme and monitored every 71 seconds for 30-240 minutes at $\lambda_{ex}360/\lambda_{em}485$ in a Synergy$^2$, Synergy$^4$ or Synergy H$^4$ plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to +30 minutes) from each reaction was estimated from the slope of a plot of relative fluorescence units vs time (minutes) and normalized to the no enzyme and no inhibitor control groups for % Inhibition. The resulting % Inhibition values were then plotted against inhibitor concentration to estimate $IC_{50}$ from log[Inhibitor] vs Response, Variable Slope model in Graph-Pad Prism from GraphPad Software (San Diego, Calif.). Potency results for the compounds tested are shown in Table A in the column entitled "MK2 $IC_{50}$."

[Reagent] used:
[MK-2]=0.4 nM, [ATP]=1.0 mM and [ST3-Sox]=10 µM (ATP $^{app}K_M$=8-10 µM)

Example 90

MK2 Cellular Assay

Compounds were assayed in Thp-1 human acute monocytic leukemia cells to measure inhibition of MK2 activity. Thp-1 were grown in suspension in T225 flasks. Two days prior to assay, Thp-1 cells were spun down, counted and plated at $1\times10^6$ cells per well of a 12 well plate in complete media containing 10 ng/ml PMA (phorbol myristate acetate) to differentiate the cells. On day of assay, cells were washed with complete media, and compound was added to differentiated Thp-1 cells for 1 hour. Cells were washed again, and complete media containing 50 ng/ml LPS (lipopolysaccharide) was added. After 15 minutes, cells were washed once with PBS and lysed on ice with BioRad Bioplex lysis buffer. 20 µg total protein from lysates were loaded on gel and blots were probed for phosphorylation of the MK2 substrate Hsp27. Dose response inhibition of MK2 signaling in differentiated Thp-1 cells was used to determine the $EC_{50}$ for compounds reported in Table A in the column entitled "MK2 $EC_{50}$."

Example 91

MK2 Target Occupancy Assay

This experiment measured occupancy of the MK2 target by compounds according to the invention. Thp-1 cells (human acute monocytic leukemia) were grown in suspension in T225 flasks. Two days prior to assay, Thp-1 cells were spun down, counted and plated at $1\times10^6$ cells per well of a 12 well plate in compete media containing 10 ng/ml PMA (phorbol myristate acetate) to differentiate the cells. On day of assay, cells were washed with complete media, and a -test compound was added to cells at a concentration of 1 μM in complete media and incubated for 1 hour at 37° C. Cells were washed 1× with PBS and lysed on ice with BioRad Bioplex lysis buffer. The lysates were incubated with 1 μM biotinylated MK2 Covalent probe 2 at room temperature for 1 hour. 50 μg of total protein from lysates was loaded on gel and blots were probed for total MK2 with SC-100393 antibody and for probe with streptavidin-800. The amount of covalent probe signal divided by the amount of MK2 signal for samples with no test compound treatment represents the maximum probe signal (MPS). In samples treated with test compound prior to covalent probe, the ratio of probe signal to MK2 signal (the test probe signal, TPS) will be reduced by the degree of target occupancy by the test compound which blocks covalent probe binding. The difference between the MPS and the TPS, divided by the MPS gives the target occupancy by the test compound. This ratio is then expressed as a percent occupancy. Compound III-8 (92%) and compound II-11 (95%) showed near complete target occupancy in this assay.

Example 92

MK2 Modification Assessment by Mass Spectrometry

Modification of target MK2 by a test compound indicates that the compound covalently binds to MK2. Modification of MK2 is measured by whole protein MS analysis. Intact MK2 (Invitrogen PV3317, Lot 36559K) was incubated for 60 min. at a 10-fold excess of compound to protein. 5 μL aliquots of the samples were diluted with 15 μL of 0.2% TFA prior to micro C4 ZipTipping directly onto the MALDI target using sinapinic acid as the desorption matrix (10 mg/ml in 0.1% TFA:Acetonitrile 50:50). Analysis was performed on a AB Sciex 4800 MALDI TOF/TOF retro fitted with an HM2 detector (CovalX). Percent modification of target MK2 (i.e., the percent of total MK2 modified by the test compound) for each compound was calculated by subtracting the centroid mass of the compound treated MK2 from the centroid mass of the control MK2 and dividing that value with the mass of the compound. An exemplary depiction of the data for one test compound (compound II-20) is shown in FIG. 1, with other compounds having similar data that was analyzed to provide the percent modification shown in Table A in the column entitled "MK2 Mass Mod."

Example 93

In-Solution Trypsin Digest Protocol

This experiment shows that a compound according to the invention binds to the cys140 of MK2. After the reaction of test compound with MK2 as previously described in Example 92, water was added to the reaction mixture at a 1:1 ratio and lightly mixed. The MK2 protein was then precipitated by addition of 100 μL of ice cold acetone to each sample and incubated on wet ice for 10 minutes with gentle mixing periodically. The precipitated protein was then pelleted and washed 3-times by centrifuging at 12,000 g for 5 minutes, decanting the supernatant, and adding an addition 100 μL of ice-cold acetone. This process was repeated 3 additional times to ensure that excess compound was adequately removed. After the final wash, the pellet was dried by vacuum centrifugation at the highest drying rate for 8 minutes. Once dry, the pellet was reconstituted in 21 μL of DTT solution (0.1M ammonium bicarbonate, 1 mM dithiothreitol, and 0.15% Rapi-gest), sonicated for 5 minutes, and vortexed. Once the pellet dissolved, it was incubated at 70° C. for 10 minutes to reduce disulfide bonds. Then 7 μL of a 1.9 mg/mL iodoacetamide solution was added to each sample and incubated at room temperature for 30 minutes. Trypsin was then added at a ratio of 1:10 protease to protein and incubated at 37° C. overnight. Digest was quenched by the addition of 4 μL of 2% formic acid. For sample analysis, the peptides were purified using C18 ziptips, spotted on the MALDI target plate with alpha cyano 4-hydroxycinnamic acid as the desorption matrix (10 mg/mL in 0.1% TFA: acetonitrile 20:80), and analyzed in reflectron mode on an AB Sciex 4800 TOF/TOF. The peptide fingerprints from the digests of control and treated proteins were overlayed and visually compared to identify differences. Those observed differences were then selected for MS/MS analysis and manually validated to confirm peptide modification and the target amino acid. An exemplary depiction of the digest data for one test compound (compound II-20) is shown in FIGS. 2 and 3.

Figure 2:
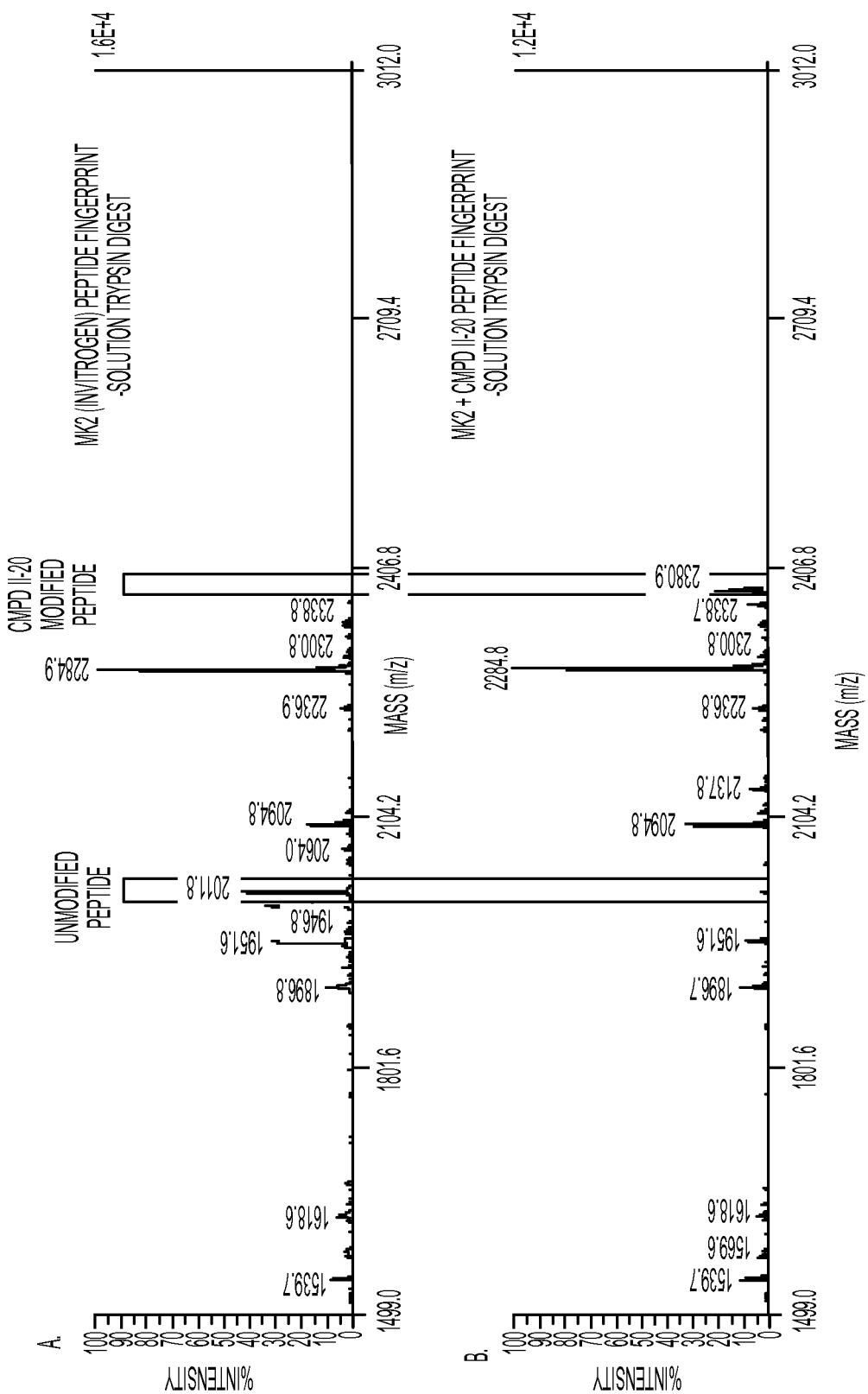
FIG. 2. Panel A shows the peptide fingerprint from a trypsin digest of untreated MK2 protein, and panel B shows the fingerprint of compound II-20 treated MK2
Figure 3:
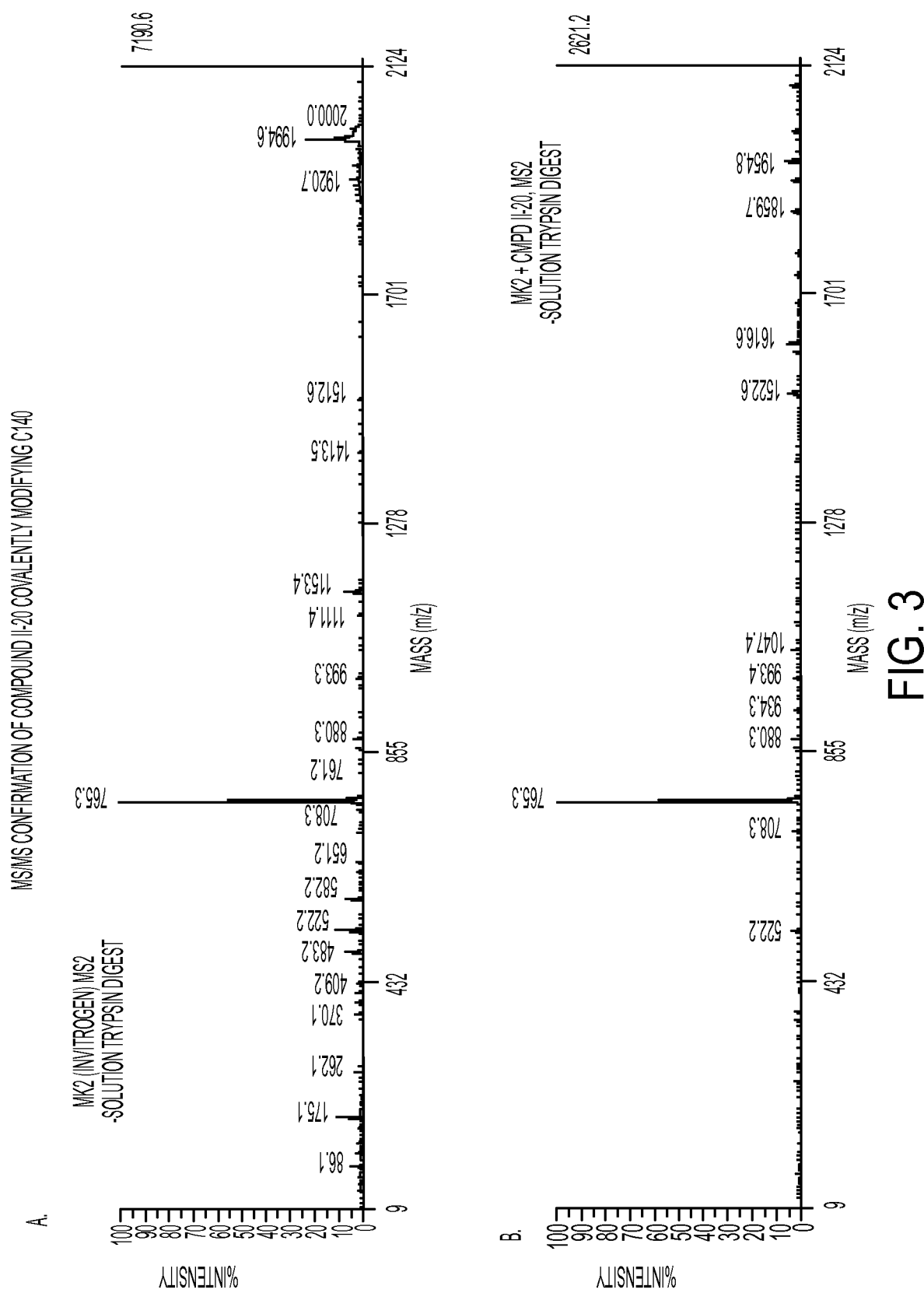
FIG. 3. Panel A shows the MS/MS of an unmodified peptide containing CYS140 (alkylated with acetamide). Panel B shows the MS/MS of the peptide modified by compound II-20.

FIG. 2, Panel A shows the peptide fingerprint from a trypsin digest of the untreated MK2 protein, and panel B shows the fingerprint of the compound II-20 treated MK2. The boxes highlight the masses of the unmodified and compound II-20 modified peptide containing CYS140. A peak corresponding to the mass of the CYS140 containing peptide modified by compound II-20 is only observed in panel B. No unmodified peptide is observed in the treated sample digest FIG. 3, Panel A shows the MS/MS of an unmodified peptide containing CYS140 (alkylated with acetamide). Panel B shows the MS/MS of the peptide modified by compound II-20. A m/z of 2,380 Da is indicative of CYS140 (the unmodified peptide has mass of 1954 Da) being covalently modified by Cmpd II-20 (mass=426.48). No unmodified peptide was observed in the treated sample digest. The peaks corresponding to the compound II-20 modified and control peptides were selected for MS2 analysis, which confirmed CYS140 is covalently modified by compound II-20. These figures collectively show that compound II-20 covalently binds to MK2 and that this modification occurs at CYS140.

Example 94

Tables A shows data for selected compounds in various assays. Compounds having an activity designated as "A" provided an $EC_{50}/IC_{50} \leq 100$ nM; compounds having an activity designated as "B" provided an $EC_{50}/IC_{50}$ of 101-500 nM; compounds having an activity designated as "C" provided an $EC_{50}/IC_{50}$ of 501-999 nM; compounds having an activity designated as "D" provided an $EC_{50}/IC_{50}$ of $\geq 1000$ nM. Compounds having an activity designated as "E" provided a mass modification of $\geq 70\%$; compounds having an activity designated as "F" provided a mass modification of 31-69%; compounds having an activity designated as "G" provided a mass modification $\leq 30\%$.

TABLE A

| Compound | MK2 $IC_{50}$ | MK2$EC_{50}$ | MK2 Mass Mod |
|---|---|---|---|
| I-1 | B | D | F |
| I-8 | A | D | E |
| I-3 | A | D | E |
| I-4 | A | D | E |
| I-5 | D | | F |

TABLE A-continued

| Compound | MK2 IC$_{50}$ | MK2EC$_{50}$ | MK2 Mass Mod |
|---|---|---|---|
| I-6 | B | | G |
| I-7 | A | C | E |
| I-9 | A | D | E |
| I-10 | A | | E |
| I-23 | A | C | E |
| I-24 | B | | F |
| II-1 | A | A | E |
| II-2 | A | A | E |
| II-3 | A | A | F |
| II-4 | A | A | E |
| II-5 | A | A | E |
| II-6 | A | A | E |
| II-7 | B | | E |
| II-8 | A | A | E |
| II-9 | A | D | E |
| II-10 | A | C | E |
| II-11 | A | A | E |
| II-12 | A | C | E |
| II-13 | A | B | E |
| II-14 | A | A | E |
| II-15 | A | A | E |
| II-16 | A | A | E |
| II-17 | A | | E |
| II-18 | A | | E |
| II-19 | A | | |
| II-20 | A | | E |
| II-21 | A | | E |
| II-22 | A | | E |
| II-23 | A | | E |
| II-24 | A | | E |
| II-25 | A | | E |
| II-26 | A | B | E |
| II-27 | A | A | E |
| II-e-1 | B | C | E |
| III-1 | A | A | E |
| III-2 | D | | G |
| III-3 | A | A | E |
| III-4 | A | A | E |
| III-5 | A | D | E |
| III-6 | A | A | E |
| III-7 | A | D | E |
| III-8 | B | A | E |
| III-9 | D | | F |
| III-10 | B | D | E |
| III-11 | A | A | E |
| III-12 | A | C | F |
| III-13 | A | A | F |
| III-d-1 | D | | E |
| III-35 | A | B | E |
| III-37 | A | A | E |
| III-40 | A | A | E |
| III-41 | D | | G |
| III-43 | D | | G |
| III-45 | A | A | E |
| III-46 | A | A | E |
| IV-1 | C | | G |
| IV-2 | B | D | E |
| IV-b-1 | B | | F |
| V-1 | C | | E |
| V-2 | D | | G |
| V-3 | D | | G |
| V-4 | D | | G |
| V-5 | D | | G |
| V-6 | A | D | E |
| V-7 | D | | F |
| V-8 | D | | E |
| V-9 | B | | E |
| V-10 | D | | G |
| V-c-1 | A | | F |
| V-c-2 | A | D | E |
| V-c-3 | A | D | E |
| V-15 | A | B | E |
| VI-9 | D | | G |
| Probe 1 | A | | |
| Probe 2 | A | | |
| II-e-4 | A | A | E |
| II-e-15 | A | B | E |
| II-e-8 | A | D | E |
| II-e-17 | A | C | E |
| II-e-19 | A | A | E |
| II-e-20 | A | B | E |
| II-e-21 | C | D | E |
| II-e-22 | B | B | E |
| II-e-23 | A | C | E |
| III-31 | A | A | E |
| III-32 | A | A | E |
| III-40 | A | A | F |
| III-41 | A | B | E |
| III-42 | A | D | E |
| III-43 | A | A | E |
| III-44 | A | B | E |
| III-45 | A | A | G |
| III-46 | A | D | G |
| III-47 | A | A | E |
| III-48 | A | | G |
| III-49 | A | | G |
| III-50 | A | | G |
| III-51 | A | A | E |
| III-53 | A | D | E |
| III-54 | A | B | E |
| III-55 | A | | G |
| III-56 | A | A | E |
| III-57 | C | | G |
| III-58 | A | B | E |
| V-12 | D | | E |
| V-14 | D | | E |
| V-43 | D | | G |
| V-45 | A | B | E |
| V-46 | D | | G |
| V-47 | D | | G |
| V-48 | D | | G |
| V-49 | D | | G |
| V-50 | A | B | E |
| V-51 | A | B | E |
| V-52 | D | | G |
| V-53 | D | | E |
| V-54 | B | B | E |
| V-55 | D | | G |
| V-56 | D | D | F |
| V-57 | A | B | E |
| V-58 | A | A | E |
| V-59 | A | | G |
| V-60 | A | | G |
| V-61 | A | A | E |
| V-62 | B | B | E |
| V-63 | A | A | E |
| V-64 | D | | G |
| VI-26 | D | D | G |
| V-39 | B | B | E |
| V-31 | C | | E |
| V-12 | D | | G |

Example 95

MK2 Thp-1 Washout Assay

This example shows the extended activity of compounds according to the invention. Test compounds were assayed in Thp-1 human acute monocytic leukemia cells. Thp-1 were grown in suspension in T225 flasks. Two days prior to assay, Thp-1 cells were spun down, counted and plated at 1×10$^6$ cells per well of a 12 well plate in complete media containing 10 ng/ml PMA (phorbol myristate acetate) to differentiate the cells. On the day of the assay, the differentiated Thp-1 cells were washed with complete media, and test compounds (final concerntration=10×EC$_{50}$) were added to the cells and incubated at 37° C. for 1 hour. Cells were thoroughly washed to remove the unbound test compound and placed back in the 37° C. tissue culture incubator for the washout period (0 h, 2 h, 6 h, or 16 h). After the washout, complete media containing 50 ng/ml LPS (lipopolysaccharide) was added for 15 minute stimulation, the cells were washed once with PBS, and protein lysates were prepared on ice with BioRad Bioplex lysis buffer. 20 μg total protein from each lysate was loaded on the gel and analyzed by SDS-PAGE. Western blots were probed for phosphorylation of the MK2 substrate Hsp27. Prolonged inhibition of MK2 signaling was observed for compound II-11 which maintains >95% inhibition of p-hsp27 (phosphorylated hsp27) up to 6 hours after a 100 nM exposure (1 hour) and subsequent washout.

Example 96

IV Mouse PD Experiment

This example shows the effect of compounds according to the invention on release of TNFα. CD-1 male mice, approximately 5 weeks old were acquired from Charles River Laboratories. Animals were housed in ventilated cages with a 12/12 light cycle and provided rodent chow and water ad libitum. Mice were acclimated at least 1 week prior to study initiation (approximately 6 weeks old). Five (5) mice per group were predosed with one of the following compounds: II-14, III-32, III-8, III-4, II-27 and III-40 (intravenously by lateral tail vein), 1 hour prior to LPS administration. LPS (E.Coli 055:B5 from Sigma, Cat #L2880) was diluted in 0.9% sterile saline (Webster Veterinary Supply, Cat #07-883-6734) to a final concentration of 30 μg/mL. Animals were administered 15 μg in 0.5 mL/mouse (approximately 0.5 mg/kg LPS) intraperitoneally. One hour post LPS administration, the mice were sacrificed via $CO_2$ and whole blood was collected by cardiac puncture. Blood was placed in EDTA K2 tubes (Braintree Scientific, Cat #MT-1395), inverted 3 times and placed on wet ice until centrifugation at 4° C. Plasma was collected and stored on dry ice until stored at −80° C. until processing. TNFα levels were quantified using the "Mouse TNF-alpha Ultra-Sensitive Kit" from mesoscale.com (catalog number K152BHC-2) in conjunction with an MSD plate reader. The six tested compounds, II-14, 111-32, 111-8, 111-4, 11-27, and III-40, showed greater than 90% reduction in TNFα release compared to untreated control samples with less than 10 mg/kg IV dosing.

Example 97

PO Mouse PD Experiment

This example shows the effect of compounds according to the invention on release of TNFα. CD-1 male mice, approximately 5 weeks old were acquired from Charles River Laboratories. Animals were housed in ventilated cages with a 12/12 light cycle and provided rodent chow and water ad libitum. Mice were acclimated at least 1 week prior to study initiation (approximately 6 weeks old). Five (5) mice per group were predosed at 30 mg/kg PO with one of the following compounds: III-8, III-35, II-27, III-47, III-56, V-39, II-27, III-37, II-e-1, II-e-3, III-40, and V-58 (by oral gavage as a suspension in 0.5% methyl cellulose/0.25% Tween 80 in deionized water), 1 hour prior to LPS administration. LPS (E.Coli 055:B5 from Sigma, Cat #L2880) was diluted in 0.9% sterile saline (Webster Veterinary Supply, Cat #07-883-6734) to a final concentration of 30 μg/mL. Animals were administered 15 μg in 0.5 mL/mouse (approximately 0.5 mg/kg LPS) intraperitoneally. One hour post LPS administration, the mice were sacrificed via $CO_2$ and whole blood was collected by cardiac puncture. Blood was placed in EDTA K2 tubes (Braintree Scientific, Cat #MT-1395), inverted 3 times and placed on wet ice until centrifugation at 4° C. Plasma was collected and stored on dry ice until stored at −80° C. until processing. TNFα levels were quantified using the "Mouse TNF-alpha Ultra-Sensitive Kit" from mesoscale.com (catalog number K152BHC-2) in conjunction with an MSD plate reader.

Table C shows data for selected compounds in the above-described assay. Compounds having an activity designated as "X" provided a percent inhibition of ≤20%; compounds having an activity designated as "Y" provided a percent inhibition of 21%-80%; compounds having an activity designated as "Z" provided a percent inhibition of ≥81%.

TABLE C

Inhibition of TNFα Release After LPS Challenge in Mice (30 mg/kg PO).

| Cmpd | % Inhibition of TNFa |
|---|---|
| III-8* | Y |
| III-35 | X |
| II-27 | X |
| III-47 | X |
| III-56 | X |
| V-39 | Z |
| III-37 | X |
| II-e-1 | X |
| II-e-3 | X |
| III-40 | X |
| V-58 | X |

*100 mg/kg PO.

Example 98

Additional Compounds

Compound II-e-15

N-(5-(10-methyl-7-oxo-7,8,9,10-tetrahydrocyclopenta[4,5]pyrrolo[2,3-f]isoquinolin-2-yl)-2-(4-methylpiperazin-1-yl)phenyl)acrylamide

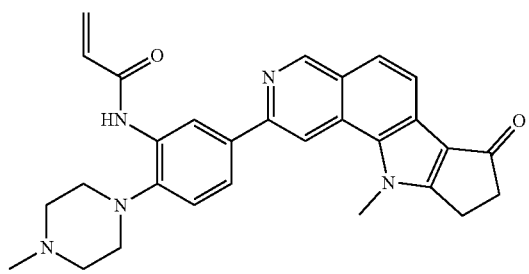 [SMILES: C=CC(=O)Nc1cc(-c2cc3c(ccc4c5c(n(C)c43)CCC5=O)cn2)ccc1N1CCN(C)CC1]

Compound II-e-15 was prepared similarly to compound II-e-4, which compound was prepared similarly to compound II-e-3 in Example 38. Compound II-e-15 was accessed by substituting intermediate 1 of step one of Example 38 (i.e., 2-chloro-8,9-dihydrocyclopenta[4,5]pyrrolo[2,3-f]isoquinolin-7(10OH)-one) with the N-methylated derivative thereof, depicted in the scheme below as compound 1, the synthesis of which is also described below. The remainder of the synthesis of compound II-e-15 was completed as indicated above to afford the desired product as a pale yellow powder (20 mg, 87%). $^1$H NMR (400 MHz, DMSO-d$_6$): δ 2.85 (s, 3H), 2.92 (m, 2H), 3.05 (m, 2H), 3.25 (m, 2H), 3.30-3.50 (m, 6H), 3.65 (m, 2H), 4.30 (s, 3H), 5.80 (d, 1H), 6.35 (d, 1H), 6.72 (dd, 1H), 7.35 (d, 1H), 7.90-8.05 (m, 2H), 8.70 (s, 1H), 8.95 (s, 1H), 9.20 (s, 1H), 9.45 (s, 1H), 9.72 (s, br, 1H). MS m/z (M+H): 480.2

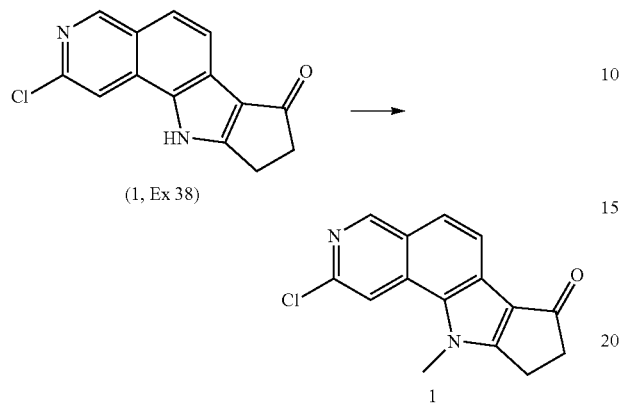

Step 1:

To a suspension of 2-chloro-8,9-dihydrocyclopenta[4,5]pyrrolo[2,3-f]isoquinolin-7(10H)-one (52 mg, 0.2 mmol) in 4 mL THF was added sodium hydride (60%, 16 mg, 0.4 mmol) at 0° C. and stirred at 0° C. for 15 min, then a 1 mL THF solution of iodomethane (42 mg, 0.3 mmol) was added dropwise at 0° C., then warmed to rt for 4 h. The reaction was quenched with a sodium carbonate solution, extracted with ethyl acetate (3×), and washed with brine. Column purification eluting with 20-100% ethyl acetate in heptane provided 31 mg of an off white powder (60%). MS m/z (M+H): 271.2

Compound II-e-17

2-(4-acryloyl-2-methyl-3,4-dihydro-2H-benzo[b][1,4]oxazin-6-yl)-8,9-dihydrocyclopenta[4,5]pyrrolo[2,3-f]isoquinolin-7(10H)-one

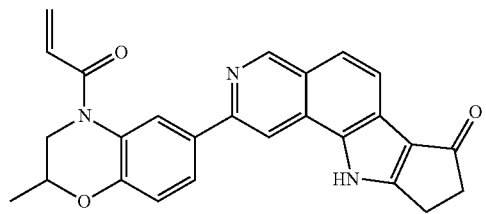 [SMILES: C=CC(=O)N1CC(C)Oc2ccc(-c3cc4c(ccc5c6c([nH]c54)CCC6=O)cn3)cc21]

Compound II-e-17 was prepared similarly to Compound II-e-3 in Example 38, by substituting INT-41 in step 2 of Example 38 with compound 3, depicted below, to give the desired product (15 mg, 65% yield) as white solid. $^1$H NMR (400 MHz, DMSO-d$_6$): δ: 1.33 (d, J=6.3 Hz, 3H), 2.89-2.91 (m, 2H), 3.21 (d, J=3 Hz, 2H), 3.47 (dd, J=8, 13 Hz, 1H), 4.31 (d, J=12 Hz, 1H), 4.45-4.48 (m, 1H), 5.89 (dd, J=2, 10.5 Hz, 1H), 6.36 (dd, J=2, 17 Hz, 1H), 6.90 (dd, J=10.5, 17 Hz, 1H), 7.10 (d, J=8.5 Hz, 1H), 7.77 (d, J=8.5 Hz, 1H), 7.88 (d, J=8.5 Hz, 1H), 7.93 (dd, J=2, 9 Hz, 1H), 8.35 (s, 1H), 8.75 (s, 1H), 9.33 (s, 1H), 13.2 (s, 1H). MS m/z (M+H): 424.7

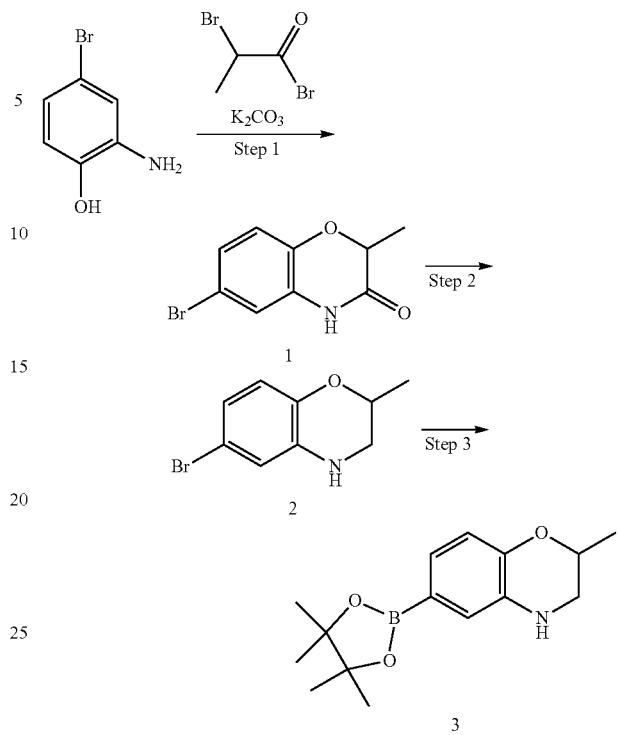

Step 1:

6-bromo-2-methyl-2H-benzo[b][1,4]oxazin-3(4H)-one (1)

To a stirred solution of 2-amino-4-bromophenol (2.5 g, 13.2 mmol) in ACN (20 mL), was added K$_2$CO$_3$ (4.2 g, 18.6 mmol) followed by 2-bromopropanoyl bromide (5.7 g, 26.5 mmol) at room temperature. The reaction was then stirred at reflux for 4 h. After completion of the reaction, the solvent was removed under reduced pressure. Water was added to the crude and extracted with ethyl acetate. The combined organic layer was washed with water and brine, dried over anhydrous sodium sulfate, and concentrated under reduced pressure. The crude compound was purified by column chromatography (100-200 mesh silica gel, 20% ethyl acetate in pet. ether as eluent) to afford 1 (1.2 g, 37% yield) as a brown solid. MS m/z (M+H): 242.0.

Step 2:

6-bromo-2-methyl-3,4-dihydro-2H-benzo[b][1,4]oxazine (2)

To a stirred solution of 6-bromo-2-methyl-2H-benzo[b][1,4]oxazin-3(4H)-one (1.2 g, 5.0 mmol) in THF (15 mL) was added 1M borane in THF (25 mL) at 0° C. and stirred for 3 h at reflux temperature. After completion of the reaction, methanol (2 mL) was added to the reaction mixture at 0° C. and then stirred for 2 h at reflux. After completion of reaction, conc. HCl (2 mL) was added to the reaction mixture at 0° C. and again stirred for 2 h at reflux temperature. After completion of the reaction, the reaction mixture was neutralized with 2N NaOH solution at 0° C. and extracted with ethyl acetate. The combined organic layer was washed with water and brine, dried over anhydrous Na₂SO₄, and concentrated under reduced pressure. The crude compound was purified by column chromatography (100-200 mesh silica gel, 15% ethyl acetate in pet. ether as eluent) to afford 2 (800 mg, 71% yield) as a brown solid. MS m/z (M+H): 228.37.

Step 3:

2-methyl-6-(4,4,5,5-tetramethyl-1,3,2-dioxaborolan-2-yl)-3,4-dihydro-2H-benzo[b][1,4]oxazine (3)

To a stirred solution of 6-bromo-2-methyl-3,4-dihydro-2H-benzo[b][1,4]oxazine (800 mg, 3.524 mmol), bis(pinacolato)diborane (1.07 g, 4.22 mmol) in 1,4-dioxane (10 mL) was added KOAc (1.036 g, 10.57 mmol) and degassed for 20 min with argon. To the reaction mixture Pd(dppf)₂Cl₂.DCM (143 mg, 0.176 mmol) was added and again degassed for 5 min and stirred for 2 h at 95-100° C. After completion of the reaction, the solvent was removed under reduced pressure and water and ethyl acetate were then added to the crude. The reaction mixture was filtered through celite and the filtrate was extracted with ethyl acetate. The combined organic phase was washed with water and brine, dried over anhydrous Na₂SO₄, and concentrated under reduced pressure to afford 3 (500 mg, 52% yield) as a yellow solid. MS m/z (M+H): 276.2.

Compound II-e-19

N-(2-methyl-5-(7-oxo-7,8,9,1-tetrahydrocyclopenta[4,5]pyrrolo[2,3-f]isoquinolin-2-yl)phenyl)acrylamide

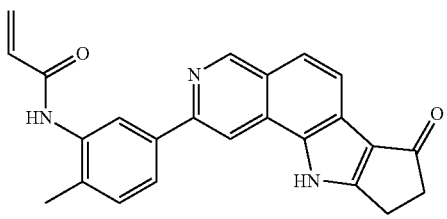 [SMILES: C=CC(=O)Nc1cc(-c2cc3c(ccc4c5c([nH]c43)CCC5=O)cn2)ccc1C]

Compound II-e-19 was prepared similarly to Compound II-e-3 in Example 38, by substituting INT-41 in step 2 of Example 38 with 2-methyl-5-(4,4,5,5-tetramethyl-1,3,2-dioxaborolan-2-yl)aniline, to give the desired product (8 mg, 20% yield) as an off white solid. ¹H NMR (400 MHz, DMSO-d₆): δ: 2.29 (s, 3H), 2.92 (dd, J=2.4, 4.6 Hz, 2H), 3.23 (d, J=3 Hz, 2H), 5.79 (dd, J=1.8, 10.3 Hz, 1H), 6.30 (dd, J=1.8, 17 Hz, 1H), 6.59 (dd, J=10.1, 16.8 Hz, 1H), 7.42 (d, J=8.1 Hz, 1H), 7.82 (d, J=8.5 Hz, 1H), 7.91 (d, J=8.5 Hz, 1H), 8.00 (d, J=6.5 Hz, 1H), 8.34 (s, 1H), 8.83 (s, 1H), 9.37 (s, 1H), 9.66 (s, 1H), 13.09 (s, 1H). MS m/z (M+H): 382.2

Compound II-e-20

N-(2-chloro-5-(7-oxo-7,8,9,10-tetrahydrocyclopenta[4,5]pyrrolo[2,3-f]isoquinolin-2-yl)phenyl)acrylamide

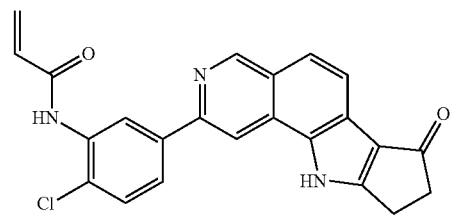 [SMILES: C=CC(=O)Nc1cc(-c2cc3c(ccc4c5c([nH]c43)CCC5=O)cn2)ccc1Cl]

Compound II-e-20 was prepared similarly to Compound II-e-3 in Example 38, by substituting INT-41 in step 2 of Example 38 with 2-chloro-5-(4,4,5,5-tetramethyl-1,3,2-dioxaborolan-2-yl)aniline to give the desired product (7 mg, 26% yield) as an off white solid. ¹H NMR (400 MHz, DMSO-d₆): δ: 2.93 (d, J=2.2 Hz, 2H), 3.25 (brs, 2H), 5.84 (d, J=10.2 Hz, 1H), 6.35 (dd, J=15.5, 17 Hz, 1H), 6.67 (dd, J=10, 17 Hz, 1H), 7.72 (d, J=8.5 Hz, 1H), 7.86 (d, J=8.5 Hz, 1H), 7.95 (d, J=8.6 Hz, 1H), 8.09 (dd, J=2, 7.3 Hz, 1H), 8.62 (s, 1H), 8.89 (s, 1H), 9.41 (s, 1H), 9.91 (s, 1H), 13.22 (s, 1H). MS m/z (M+H): 402.2

Compound II-e-21

N-(2-methoxy-5-(10-methyl-7-oxo-7,8,9,10-tetrahydrocyclopenta[4,5]pyrrolo[2,3-f]isoquinolin-2-yl)pyridin-3-yl)acrylamide

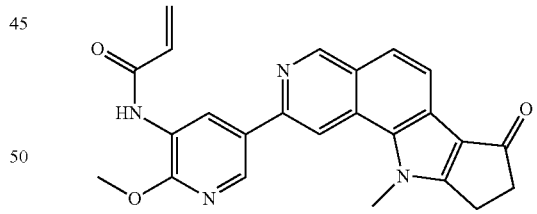

Compound II-e-21 was prepared similarly to Compound II-e-15 by substituting 2-(4-methylpiperazin-1-yl)-5-(4,4,5,5-tetramethyl-1,3,2-dioxaborolan-2-yl)aniline used in the Suzuki reaction during the synthesis of Compound II-e-15 with N-(2-methoxy-5-(4,4,5,5-tetramethyl-1,3,2-dioxaborolan-2-yl)pyridin-3-yl)acrylamide to give the desired product as a white powder (4 mg, 15%). ¹H NMR (400 MHz, DMSO-d₆): δ 2.92 (m, 2H), 3.20 (m, 2H), 4.05 (s, 3H), 4.35 (s, 3H), 5.75 (d, 1H), 6.30 (d, 1H), 6.75 (dd, 1H), 7.90 (d, 1H), 7.95 (d, 1H), 8.75 (s, 1H), 8.80 (s, 1H), 9.30 (s, 1H), 9.45 (s, 1H), 9.75 (s, 1H). MS m/z (M+H): 413.1

Compound II-e-22

N-(3-methyl-5-(7-oxo-7,8,9,1-tetrahydrocyclopenta[4,5]pyrrolo[2,3-f]isoquinolin-2-yl)phenyl)acrylamide

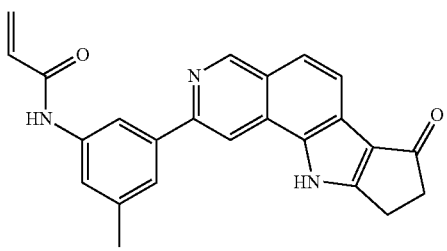 [SMILES: C=CC(=O)Nc1cc(C)cc(-c2cc3c(ccc4c5c([nH]c43)CCC5=O)cn2)c1]

Compound II-e-22 was prepared similarly to Compound II-e-3 in Example 38, by substituting INT-41 in step 2 of Example 38 with 3-methyl-5-(4,4,5,5-tetramethyl-1,3,2-dioxaborolan-2-yl)aniline to give the desired product (11 mg, 24% yield) as a pale yellow solid. $^1$H NMR (400 MHz, DMSO-$d_6$): δ: 2.43 (s, 3H), 2.92 (s, 2H), 3.24 (s, 2H), 5.77 (d, J=10.2 Hz, 1H), 6.29 (d, J=16.7 Hz, 1H), 6.49 (dd, J=10, 16.8 Hz, 1H), 7.63 (s, 1H), 7.74 (s, 1H), 7.83 (d, J=8.5 Hz, 1H), 7.93 (d, J=8.5 Hz, 1H), 8.43 (s, 1H), 8.86 (s, 1H), 9.38 (s, 1H), 10.28 (s, 1H), 13.3 (s, 1H). MS m/z (M+H): 382.2

Compound II-e-23

N-(2-(4-acetylpiperazin-1-yl)-5-(7-oxo-7,8,9,10-tetrahydrocyclopenta[4,5]pyrrolo[2,3-f]isoquinolin-2-yl)phenyl)acrylamide

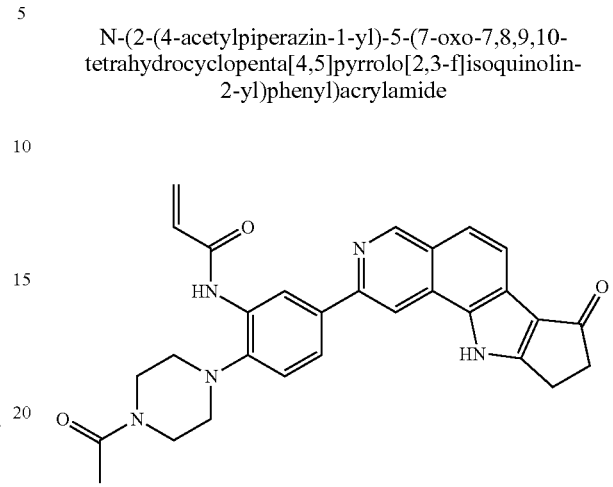

Compound II-e-23 was prepared according to the schemes, steps, and intermediates below utilizing intermediate 1 from Example 38 for step 4.

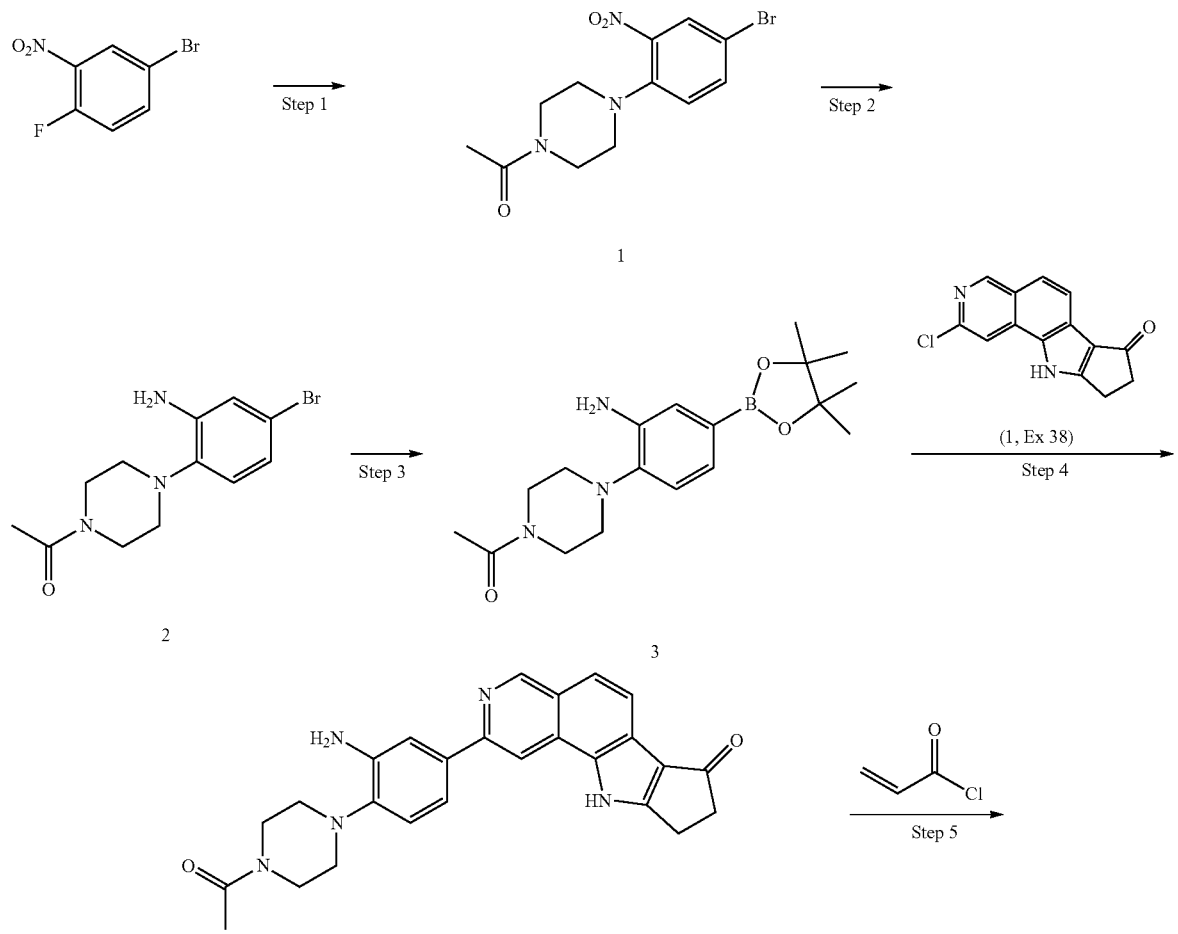

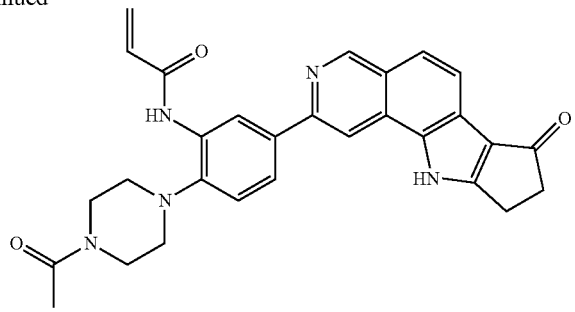

Step 1:

1-(4-(4-bromo-2-nitrophenyl)piperazin-1-yl)ethanone (1)

To a stirred solution of 4-bromo-1-fluoro-2-nitrobenzene (3 g, 13.6 mmol) and 1-(piperazin-1-yl)ethanone (2.1 g, 16.35 mmol) in DMF (10 mL) was added cesium carbonate (8.86 g, 27.2 mmol). The reaction was heated for 16 h at 80° C. After completion of the reaction, the reaction mixture was quenched with ice cold water and extracted with ethyl acetate. The combined organic phase was washed with water and brine, dried over anhyd. $Na_2SO_4$, and concentrated under reduced pressure to afford 1 (3.8 g, 84% yield) as a brown solid. MS m/z (M+H): 328.4

Step 2:

1-(4-(2-amino-4-bromophenyl)piperazin-1-yl)ethanone (2)

To a stirred solution of 1-(4-(4-bromo-2-nitrophenyl)piperazin-1-yl)ethanone (3.8 g, 11.58 mmol) in 1,4-dioxane:water (57 mL, 3:1 ratio), zinc (6 g, 92.68 mmol) and $NH_4Cl$ (4.9 g, 92.68 mmol) were added at 0° C. and stirred for 3 h at room temperature. After completion of the reaction, the reaction mixture was filtered through celite and washed with dioxane. Filtrate was concentrated under reduced pressure to afford 2 (3 g, 87% yield) as pale yellow solid. MS m/z (M+H): 298.5

Step 3:

1-(4-(2-amino-4-(4,4,5,5-tetramethyl-1,3,2-dioxaborolan-2-yl)phenyl)piperazin-1-yl)ethanone (3)

To a stirred solution of 1-(4-(2-amino-4-bromophenyl)piperazin-1-yl)ethanone (500 mg, 1.67 mmol) and bis(pinacolato)diborane (550 mg, 2.18 mmol) in 1,4-dioxane (10 mL) was added KOAc (328 mg, 0.335 mmol) and degassed for 20 min with argon. To the reaction mixture PddppfCl$_2$.DCM (205 mg, 0.25 mmol) was added, and the reaction was again degassed for 10 min and stirred for 2 h at 90° C. After completion of the reaction, the solvent was removed under reduced pressure. The crude compound was purified by column chromatography (100-200 silica gel, 2-5% methanol in DCM as eluent) to afford 3 (450 mg, 77.5% yield) as a pale pink solid. MS m/z (M+H): 346.6

Step 4:

Compound 4:

To a stirred solution of 2-chloro-8,9-dihydrocyclopenta[4,5]pyrrolo[2,3-f]isoquinolin-7(10OH)-one (intermediate 1, Example 38; 100 mg, 0.39 mmol), 1-(4-(2-amino-4-(4,4,5,5-tetramethyl-1,3,2-dioxaborolan-2-yl)phenyl)piperazin-1-yl)ethanone (537 mg, 1.56 mmol) in isopropanol:water (4 mL, 3:1 ratio) was added cesium carbonate (507 mg, 1.56 mmol) and the reaction was again degassed for 10 min with argon. To this reaction mixture PddppfCl$_2$.DCM (127 mg, 0.15 mmol) was added, and the reaction was again degassed for 10 min. The reaction mixture was irradiated using microwave irradiation for 1 h at temperature 150° C. After completion of the reaction, the solvent was removed under reduced pressure. The crude compound was purified by column chromatography (100-200 silica gel, 2% aq. ammonia solution in 10-12% methanol in DCM as eluent) to afford 4 (40 mg, 23% yield) as black sticky solid. MS m/z (M+H): 440.3

Step 5:

To a stirred solution of compound 4 (40 mg, 0.091 mmol) in THF (4 mL) was added DIPEA (47 mg, 0.364 mmol) followed by acryloyl chloride (6.2 mg, 0.063 mmol) at −78° C. The reaction was stirred for 5 min at this temperature. After completion of the reaction, the reaction mixture was quenched with ice cold water and extracted with DCM. The combined organic phase was washed with water and brine, dried over anhyd. $Na_2SO_4$, and concentrated under reduced pressure. The crude compound was purified by column chromatography (100-200 silica gel, 2-3% methanol in CHCl$_3$ as eluent) to afford the desired product (7 mg, 15.5% yield) as a pale yellow solid. $^1$H NMR (400 MHz, DMSO-d$_6$): δ: 2.05 (s, 3H), 2.86 (s, 4H), 2.91 (s, 2H), 3.25 (s, 2H), 3.67 (s, 4H), 5.8 (d, J=10.2 Hz, 1H), 6.32 (d, J=17 Hz, 1H), 6.74 (dd, J=10, 17 Hz, 1H), 7.32 (d, J=8.4 Hz, 1H), 7.83 (d, J=8.5 Hz, 1H), 7.92 (d, J=8.4 Hz, 1H), 8.01 (d, J=8 Hz, 1H), 8.79 (s, 1H), 8.81 (s, 1H), 9.32 (s, 1H), 9.38 (s, 1H), 13.27 (s, 1H). MS m/z (M+H): 494.3

Compound III-54

(R)—N-(2-chloro-5-(10-methyl-8-oxo-9,10,11,12-tetrahydro-8H-[1,4]diazepino[5',6':4,5]thieno[3,2-f]quinolin-3-yl)phenyl)acrylamide

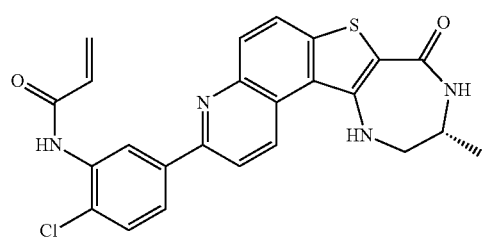 [SMILES: C=CC(=O)Nc1cc(-c2ccc3c(ccc4sc5c(c43)NC[C@@H](C)NC5=O)n2)ccc1Cl]

Compound III-54 was prepared in a similar manner to that described in Example 51, substituting INT-3 in step 12 of Example 51 with boronate 2, depicted below, to give the desired product (15.0 mg, 10%) as a pale yellow solid. 1H NMR (400 MHz, DMSO-d$_6$): δ 1.18-1.20 (d, J=6.7 Hz, 3H), 3.47-3.59 (m, 2H), 3.60-3.62 (m, 1H), 5.81-5.84 (dd, J=1.7, 10.0 Hz, 1H), 6.30-6.34 (dd, J=1.7, 17 Hz, 1H), 6.62-6.69 (dd, J=10.0, 17.0 Hz, 1H), 7.14-7.16 (t, J=5.0 Hz, 1H), 7.68-7.71 (d, J=8.4 Hz, 1H), 8.02 (d, J=9.0 Hz, 1H), 8.06-8.07 (d, J=4.0 Hz, 1H), 8.13-8.15 (m, 2H), 8.20-8.23 (d, J=9.0 Hz, 1H), 8.68 (brs, 1H), 9.23-9.26 (d, J=9.0 Hz, 1H), 9.92 (s, 1H). MS m/z (M+H): 463.1.

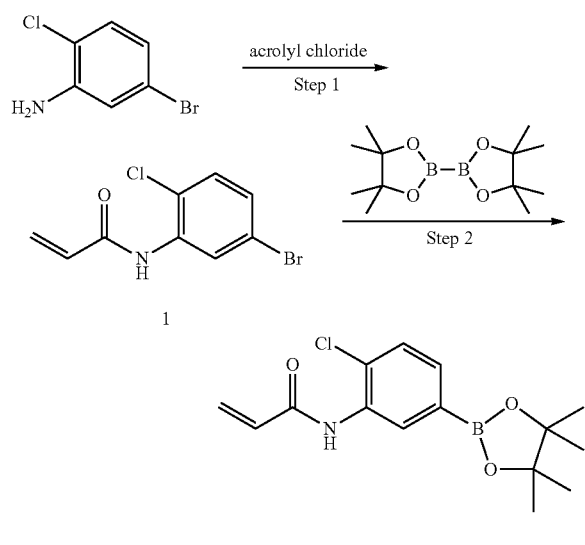

Step 1:

N-(5-bromo-2-chlorophenyl) acrylamide (1)

To a solution of 5-bromo-2-chloroaniline (1.0 g, 4.8 mmol) in dichloromethane (15 mL), diisopropylethylamine (1.2 g, 9.6 mmol), acryloyl chloride (394 mg, 4.3 mmol) were added at −78° C. The resulting mixture was stirred for 30 min at 0° C. After completion of the reaction, the reaction mixture was quenched with water and the aqueous solution was extracted with dichloromethane. The organic layer was washed with water followed by brine solution. The organic layer was then dried over anhydrous sodium sulfate and concentrated in vacuo. The resulting residue was triturated with n-pentane to afford 1 (1.0 g, 79%) as a white solid. $^1$H NMR (400 MHz, CDCl$_3$): δ 5.84-5.86 (dd, J=1.0, 10.0 Hz, 1H), 6.25-6.32 (dd, J=10.0, 17.0 Hz, 1H), 6.44-6.48 (dd, J=1.0, 17.0 Hz, 1H), 7.17-7.20 (dd, J=2.2, 8.5 Hz, 1H), 7.23-7.25 (d, J=8.5 Hz, 1H), 7.70 (s, 1H), 8.73-8.74 (d, J=1.5 Hz, 1H). MS m/z (M+H): 260.4

Step 2:

N-(2-chloro-5-(4,4,5,5-tetramethyl-1,3,2-dioxaborolan-2-yl)phenyl)acrylamide (2)

A solution of N-(5-bromo-2-chlorophenyl)acrylamide (500 mg, 1.9 mmol) in 1,4-dioxane (10 mL) was treated with bis(pinacolatodiboran) (588 mg, 2.3 mmol), potassium acetate (380 mg, 3.9 mmol) and 1,1'-bis(diphenylphosphino)ferrocene-palladium(II)dichloride dichloromethane complex (80 mg, 0.1 mmol) at 110° C. for 6 h. After completion of the reaction, the reaction mixture was filtered through celite and the filtrate was diluted with ethyl acetate and washed with water. The organic layer was dried over anhydrous sodium sulfate and concentrated under reduced pressure to afford 2 (500 mg, 84%) as a brown solid. MS m/z (M+H): 308.7

Compound III-55

(R)-3-(4-acryloyl-2,2-dimethyl-3,4-dihydro-2H-benzo[b][1,4]oxazin-6-yl)-10-methyl-9,10,11,12-tetrahydro-8H-[1,4]diazepino[5',6':4,5]thieno[3,2-f]quinolin-8-one

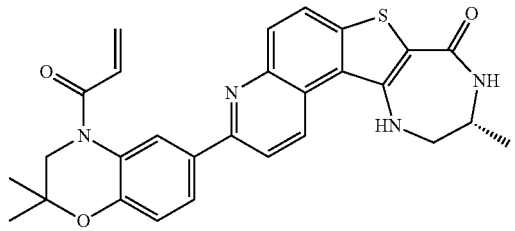

Compound III-55 was prepared in a similar manner to III-8 as described in Example 51 by substituting INT-3 in step 12 of Example 51 with 1-(2,2-dimethyl-6-(4,4,5,5-tetramethyl-1,3,2-dioxaborolan-2-yl)-2H-benzo[b][1,4]oxazin-4(3H)-yl)prop-2-en-1-one to afford the desired product (19 mg, 30%) as a yellow solid. $^1$H NMR (400 MHz, DMSO-d$_6$) δ 9.16 (d, J=9.2 Hz, 1H), 8.07 (m, 4H), 8.02 (m, 1H), 7.92 (d, J=8.7 Hz, 1H), 7.11 (m, 1H), 7.02 (d, J=8.7 Hz, 1H), 6.90 (m, 1H), 6.35 (d, J=17.0 Hz, 1H), 5.87 (d, J=10.5 Hz, 1H), 3.80 (s, 2H), 3.56 (m, 1H), 3.42 (m, 2H), 1.29 (s, 3H), 1.15 (d, J=6.8 Hz, 3H), 1.03 (s, 3H). MS m/z (M+H): 499.1

Compound III-56

(R)—N-(3-acrylamido-4-(1-methylpiperidin-4-yl)phenyl)-3-methyl-5-oxo-2,3,4,5-tetrahydro-1H-benzo[4,5]thieno[3,2-e][1,4]diazepine-9-carboxamide

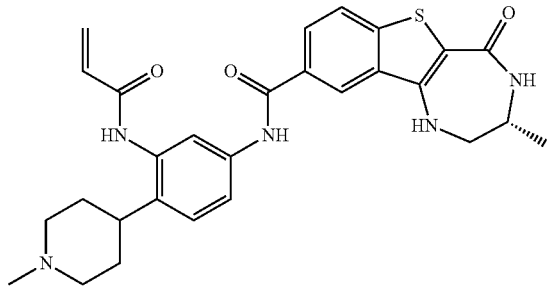

Compound III-56 was prepared according to the schemes, steps, and intermediates below utilizing intermediate 7 from Example 40 for step 2.

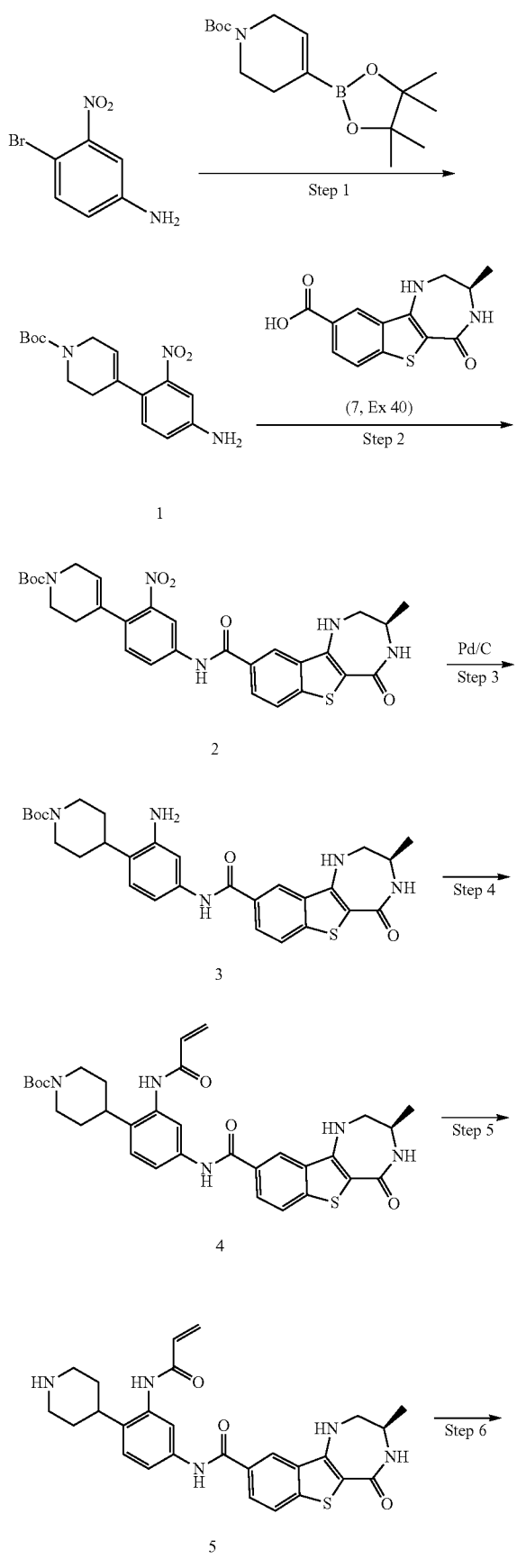

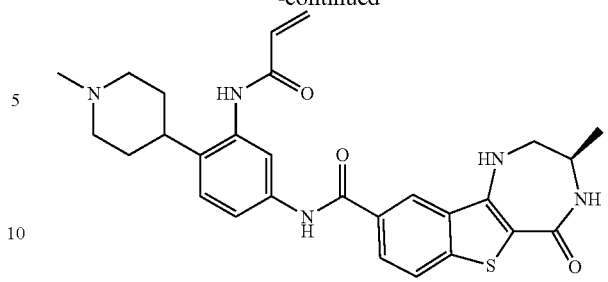

Step 1:

tert-butyl 4-(4-amino-2-nitrophenyl)-5,6-dihydropyridine-1(2H)-carboxylate (1)

To a solution of 4-bromo-3-nitroaniline (1 g, 4.6 mmol) in 1,4-dioxane/water (3:1, 12 mL), tert-butyl 4-(4,4,5,5-tetramethyl-1,3,2-dioxaborolan-2-yl)-5,6-dihydropyridine-1(2H)-carboxylate (1.4 g, 4.6 mmol), tetrakis(triphenylphosphine)palladium(0) (270 mg, 0.23 mmol) and sodium carbonate (1.45 g, 11.5 mmol) were added. The resulting mixture was degassed for 15 min and heated at 80° C. for 10 h. After completion of the reaction, the reaction mixture was filtered through celite and the filtrate was concentrated under reduced pressure. The resulting residue was purified by silica gel column chromatography to afford 1 (1.1 g, 75%) as a brown oily liquid. MS m/z (M+H): 320.1

Step 2:

Compound 2:

To a solution of tert-butyl 4-(4-amino-2-nitrophenyl)-5,6-dihydropyridine-1(2H)-carboxylate (intermediate 7, Example 40; 200 mg, 0.6 mmol) in dimethylformamide (5 mL), HATU (O-(7-azabenzotriazol-1-yl)-N,N,N',N'-tetramethyluronium hexafluorophosphate) (475 mg, 1.2 mmol), acid-A (173 mg, 0.626 mmol) and N,N-diisopropylethylamine (242 mg, 1.9 mmol) were added at 0° C. The resulting reaction mixture was stirred at room temperature for 2 h followed by heating at 50° C. for 2 h. After completion of the reaction, the reaction mixture was diluted with water and extracted with ethyl acetate. The organic layer was washed with brine, dried over anhydrous sodium sulfate, and concentrated under reduced pressure to afford 2 (150 mg, 55%) as an off-white solid. MS m/z (M−H): 576.5

Step 3:

Compound 3:

To a solution of 2 (150 mg, 0.25 mmol) in methanol (5 mL), 10% Pd/C (30 mg) was added and the resulting mixture was maintained under hydrogen at 50 psi for 12 h. After completion of the reaction, the reaction mixture was filtered through celite. The organic layer was concentrated under reduced pressure and the resulting residue was purified by silica gel column chromatography to afford 3 (60 mg, 42%) as an off-white solid. MS m/z (M+H): 550.4

Step 4:

Compound 4:

To a solution of 3 (60 mg, 0.10 mmol) in dichloromethane/tetrahydrofuran (1:1, 3 mL), diisopropylethylamine (42 mg, 0.32 mmol) and acryloyl chloride (8 mg, 0.08 mmol) were added at 0° C. and the resulting reaction mixture was stirred at room temperature for 30 min. After completion of the reaction, the reaction mixture was diluted with water and extracted with ethyl acetate. The organic layer was concentrated under reduced pressure to afford 4 (50 mg, 83%) as an off white solid. MS m/z (M+H): 604.30

Step 5:

Compound 5:

To a solution of 4 (50 mg, 0.08 mmol) in dichloromethane (2 mL), excess trifluoro acetic acid (0.5 mL) was added at 0° C. and the resulting reaction mixture was stirred for 3 h at room temperature. After completion of the reaction, the reaction mixture was co-distilled with dichloromethane and the residue obtained was used as such for the next step.

Step 6:

To a solution of 5 (40 mg, 0.08 mmol) in methanol, formaldehyde (36 mg, 1.2 mmol), sodium cyanoborohydride (5 mg, 0.08 mmol) and acetic acid (0.1 mL) were added at 0° C. The resulting mixture was stirred for 2 h at room temperature. After completion of the reaction, the reaction mixture was concentrated under rotary evaporator and the residue obtained was purified by preparative HPLC to afford the desired product (7 mg, 17% over 2 steps) as a white solid. $^1$H NMR (400 MHz, DMSO-d$_6$): δ 1.14-1.15 (d, J=7.0 Hz, 3H), 1.58-1.62 (m, 4H), 1.89-1.92 (m, 2H), 2.16 (s, 3H), 2.65 (m, 1H), 2.82-2.85 (d, J=10.6 Hz, 2H), 3.30-3.37 (m, 2H), 3.57-3.58 (m, 1H), 5.72-5.75 (dd, J=1.9, 10.0 Hz, 1H), 6.20-6.25 (dd, J=2.0, 17.0 Hz, 1H), 6.48-6.55 (dd, J=10.2, 17.0 Hz, 1H), 7.26-7.28 (d, J=8.5 Hz, 1H), 7.64-7.67 (dd, J=2.0, 8.4 Hz, 1H), 7.73-7.75 (m, 2H), 7.84-7.85 (d, J=4.7 Hz, 1H), 7.88-7.90 (d, J=8.4 Hz, 1H), 7.93-7.96 (dd, J=1.5, 8.4 Hz, 1H), 8.54 (s, 1H), 9.60 (s, 1H), 10.28 (s, 1H). MS m/z (M+H): 518.6

Compound III-57

(R)—N-(3-acrylamido-4-(trifluoromethyl)phenyl)-3-methyl-5-oxo-2,3,4,5-tetrahydro-1H-benzo[4,5]thieno[3,2-e][1,4]diazepine-9-carboxamide

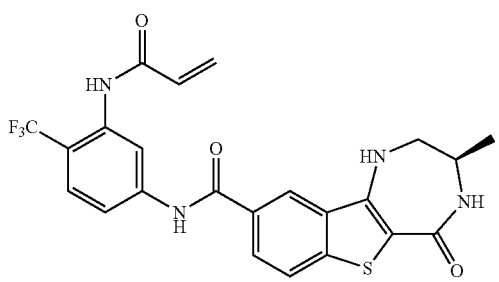 [SMILES: C=CC(=O)Nc1cc(NC(=O)c2ccc3sc4c(c3c2)NC[C@@H](C)NC4=O)ccc1C(F)(F)F]

Compound III-57 was prepared in a similar manner to that described in Example 40 according by substituting INT-10 in step 8 of Example 40 with compound 3, depicted below, to give the desired product (21 mg, 11%) as an off-white solid. $^1$H NMR (400 MHz, DMSO-d$_6$): δ 1.14-1.16 (d, J=7.0 Hz, 3H), 3.37 (s, 2H), 3.58-3.59 (brs, 1H), 5.76-5.79 (dd, J=2.0, 10.1 Hz, 1H), 6.23-6.28 (dd, J=2.0, 17.0 Hz, 1H), 6.49-6.56 (dd, J=10.1, 17.0 Hz, 1H), 7.75-7.76 (d, J=4.1 Hz, 2H), 7.92-7.98 (m, 5H), 8.57 (s, 1H), 9.78 (s, 1H), 10.67 (s, 1H). MS m/z (M+H): 489.1

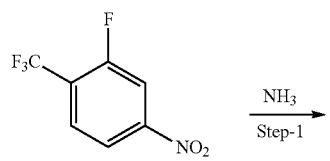

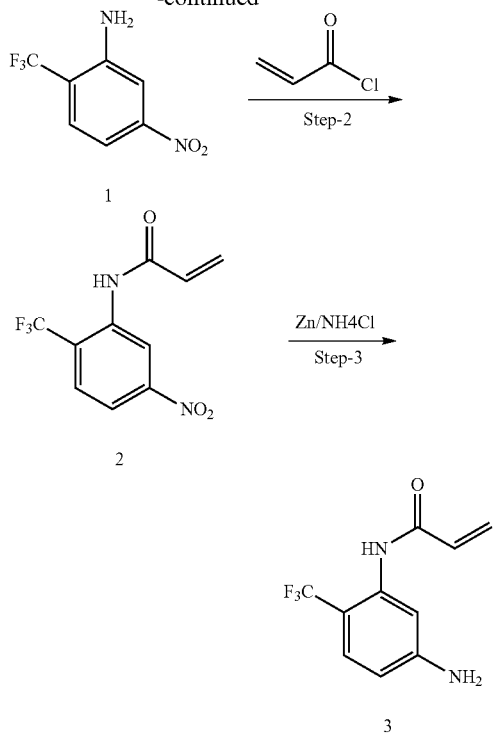

Step 1:

5-nitro-2-(trifluoromethyl)aniline (1)

Solution of 2-fluoro-4-nitro-1-(trifluoromethyl)benzene (1.4 g, 6.7 mmol) in methanol (10 mL) was purged with ammonia at -78° C. for 10 min followed by heating at 100° C. for 16 h. After completion of the reaction, the reaction mixture was concentrated under reduced pressure. The residue obtained was diluted with water and extracted with ethyl acetate. The organic layer was washed once with brine and concentrated under reduced pressure. The resulting residue was purified by silica gel column chromatography to afford 1 (900 mg, 65%) as a yellow solid. $^1$H NMR (400 MHz, DMSO-d$_6$): δ 6.31 (s, 2H), 7.31-7.34 (dd, J=1.4, 9.0 Hz, 1H), 7.58-7.60 (d, J=9.0 Hz, 1H), 7.67 (d, J=2.2 Hz, 1H). MS m/z (M−H): 205.1

Step 2:

N-(5-nitro-2-(trifluoromethyl)phenyl)acrylamide (2)

To a solution of 5-nitro-2-(trifluoromethyl)aniline (900 mg, 4.30 mmol) in dichloromethane (20 mL), diisopropylethylamine (1.7 g, 13.0 mmol) and acryloyl chloride (2.0 g, 22.0 mmol) were added at 0° C. The resulting reaction mixture was stirred at room temperature for 12 h. After completion of the reaction, the reaction mixture was concentrated under reduced pressure. The residue showed mixture of mono and diacylated compounds. The residue was treated with potassium carbonate (200 mg, 1.4 mmol) in methanol (5 mL) for 2 h at room temperature. After completion of the reaction, the reaction mixture was concentrated under reduced pressure. The residue obtained was diluted with water and extracted with ethyl acetate. The organic layer was washed with brine, dried over anhydrous sodium sulfate, and concentrated under reduced pressure. The residue obtained was purified by silica gel column chromatography to afford 2 (350 mg, 31%) as an off-white solid. 1H NMR (400 MHz, DMSO-$d_6$): δ 5.83-5.86 (dd, J=2.0, 10.2 Hz, 1H), 6.28-6.33 (dd, J=2.0, 17.0 Hz, 1H), 6.56-6.63 (dd, J=10.2, 17.0 Hz, 1H), 8.05-8.07 (d, J=9.0 Hz, 1H), 8.22-8.24 (dd, J=1.5, 9.0 Hz, 1H), 8.44-8.45 (d, J=2.0 Hz, 1H), 10.07 (s, 1H). MS m/z (M−H): 259.1

Step 3:

N-(5-amino-2-(trifluoromethyl)phenyl)acrylamide (3)

To a solution of N-(5-nitro-2-(trifluoromethyl) phenyl) acrylamide (200 mg, 0.76 mmol) in 1,4-dioxane/water (1:1, 10 mL) at 0° C., zinc (600 mg, 9.2 mmol) and ammonium chloride (500 mg, 9.36 mmol) were added and the resulting mixture was stirred at room temperature for 16 h. After completion of the reaction, the reaction mixture was filtered through celite and concentrated under reduced pressure. The residue obtained was diluted with water and extracted with ethyl acetate. The organic layer was washed once with brine and concentrated under reduced pressure. The residue obtained was triturated with n-pentane to afford 3 (150 mg, 85%) as an off-white solid. 1H NMR (400 MHz, DMSO-$d_6$): δ 5.69-5.72 (dd, J=2.0, 10.1 Hz, 1H), 5.85 (s, 2H), 6.16-6.21 (dd, J=2.0, 17.0 Hz, 1H), 6.48-6.51 (dd, J=2.0, 8.4 Hz, 2H), 6.60 (s, 1H), 7.28-7.30 (d, J=8.5 Hz, 1H), 9.39 (s, 1H). MS m/z (M+H): 231.1

Compound III-58

(R)—N-(5-(10-methyl-8-oxo-9,10,11,12-tetrahydro-8H-[1,4]diazepino[5',6':4,5]thieno[3,2-f]quinolin-3-yl)-2-(1-methylpiperidin-4-yl)phenyl)acrylamide

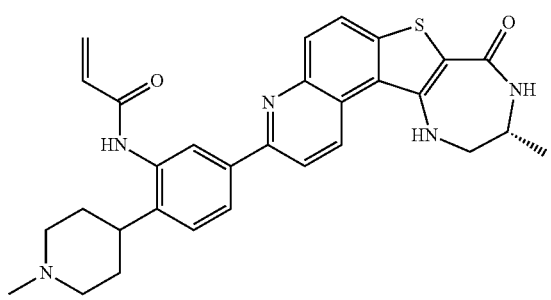

Compound III-58 was prepared according to the schemes, steps, and intermediates below utilizing intermediate 11 from step 11 of Example 51 for step 7 of this example.

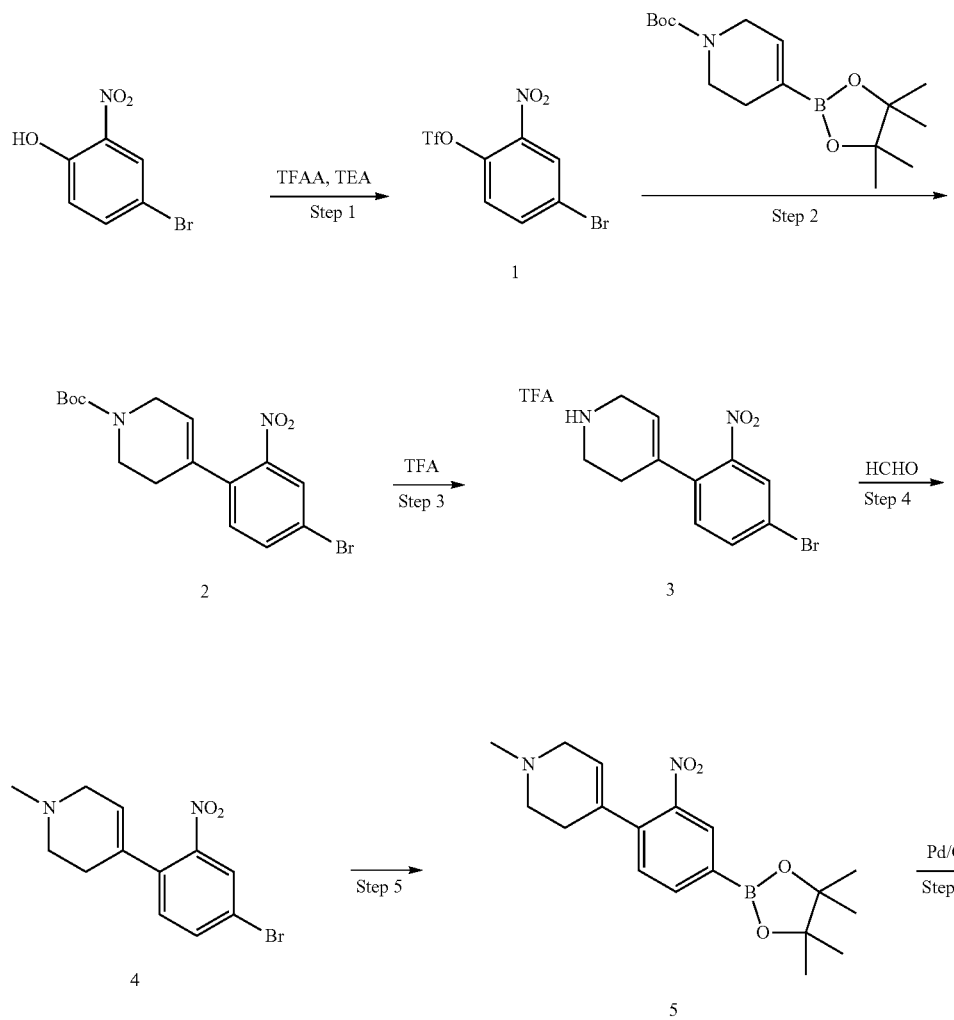

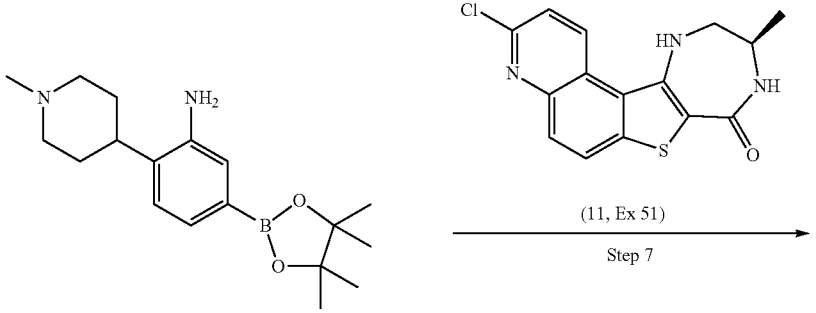

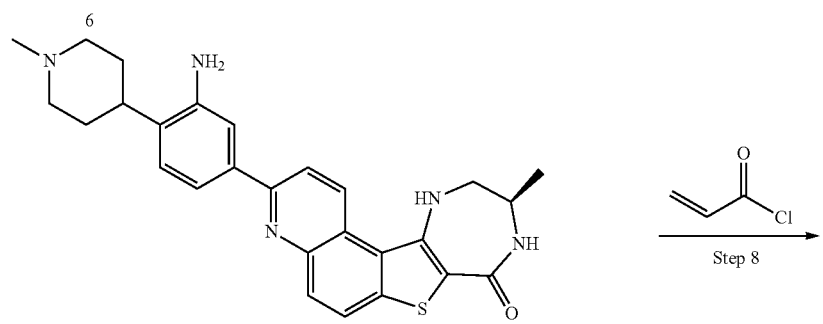

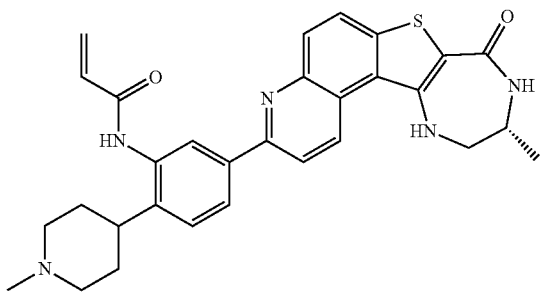

Step 1:

4-bromo-2-nitrophenyltrifluoromethanesulfonate (1)

To a solution of 4-bromo-2-nitrophenol (5.0 g, 22.9 mmol) in dichloromethane (100 mL), triethylamine (2.8 g, 27.5 mmol), 4-dimethyl aminopyridine (280 mg, 2.3 mmol) and trifluoromethanesulfonic anhydride (7.8 g, 27.5 mmol) were added dropwise at 0° C. The resulting mixture was stirred at room temperature for 1 h. After completion of the reaction, the reaction mixture was partitioned between dichloromethane and water. The organic phase was washed with saturated sodium bicarbonate solution followed by brine solution. The organic layer was dried over anhydrous sodium sulfate and concentrated under reduced pressure. The residue obtained was purified by silica gel column chromatography to afford 1 (7.2 g, 90%) as a yellow oily liquid. $^1$H NMR (400 MHz, CDCl$_3$): δ 7.35 (d, J=8.8 Hz, 1H), 7.85-7.87 (dd, J=2.4, 8.8 Hz, 1H), 8.29 (d, J=2.4 Hz, 1H).

Step 2:

tert-butyl 4-(4-bromo-2-nitrophenyl)-5,6-dihydropyridine-1(2H)-carboxylate (2)

To a solution of 4-bromo-2-nitrophenyltrifluoromethanesulfonate (2.0 g, 5.7 mmol) in dimethyl formamide/water (3:1, 20 mL), tert-butyl 4-(4,4,5,5-tetramethyl-1,3,2-dioxaborolan-2-yl)-5,6-dihydropyridine-1(2H)-carboxylate (1.8 g, 5.7 mmol), sodium carbonate (3.0 g, 28.0 mmol) were added. The resulting mixture was degassed under nitrogen for 10 min, followed by the addition of [1,1'-bis(diphenylphosphino)ferrocene]dichloropalladium(II) complex with dichloromethane (140 mg, 0.17 mmol). The resulting mixture was heated at 100° C. for 4 h. After completion of the reaction, the reaction mixture was diluted with ethyl acetate and washed with water. The organic layer was dried over anhydrous sodium sulfate and concentrated under reduced pressure. The residue obtained was purified by silica gel column chromatography to afford 2 (1.1 g, 50%) as a pale yellow solid. $^1$H NMR (400 MHz, CDCl$_3$): δ 1.49 (s, 9H), 2.30 (brs, 2H), 3.62 (t, J=5.4 Hz, 2H), 4.02 (brs, 2H), 5.60 (brs, 1H), 7.17 (d, J=8.2 Hz, 1H), 7.66-7.69 (dd, J=2.0, 8.2 Hz, 1H), 8.04 (d, J=2.0 Hz, 1H). MS m/z (M+H): 382.0

Step 3:

4-(4-bromo-2-nitrophenyl)-1,2,3,6-tetrahydropyridine (3)

Tert-butyl 4-(4-bromo-2-nitrophenyl)-5,6-dihydropyridine-1(2H)-carboxylate (0.7 g, 1.8 mmol) was treated with excess TFA in dichloromethane (1:1) at 0° C. The resulting reaction mixture was stirred at room temperature for 4 h.

After completion of the reaction, the reaction mixture was concentrated under reduced pressure and the residue obtained was co-distilled with dichloromethane thrice. The crude was used as such for the next step. MS m/z (M+H): 283.5

Step 4:

4-(4-bromo-2-nitrophenyl)-1-methyl-1,2,3,6-tetrahydropyridine (4)

To a solution of 4-(4-bromo-2-nitrophenyl)-1,2,3,6-tetrahydropyridine (0.6 g, 2.1 mmol) in methanol (5.0 mL) at 0° C., formaldehyde (1.3 g, 42.5 mmol), sodium cyanoborohydride (131 mg, 2.1 mmol) and acetic acid (0.2 mL) were added. The resulting reaction mixture was stirred at room temperature for 12 h. After completion of the reaction, the reaction mixture was concentrated under reduced pressure. The residue obtained was washed with saturated sodium bicarbonate solution and extracted with ethyl acetate. The organic layer was dried over anhydrous sodium sulfate and concentrated under reduced pressure to afford 4 (400 mg, 74% over 2 steps) as an off-white solid. $^1$H NMR (400 MHz, DMSO-$d_6$): δ 2.47 (s, 3H), 2.77 (t, J=6.0 Hz, 2H), 3.15 (q, J=3.0 Hz, 2H), 4.35 (s, 2H), 5.60-5.62 (m, 1H), 7.22 (d, J=8.2 Hz, 1H), 7.66-7.68 (dd, J=2.0, 8.2 Hz, 1H), 8.02 (dd, J=2.0 Hz, 1H). MS m/z (M+H): 297.6

Step 5:

1-methyl-4-(2-nitro-4-(4,4,5,5-tetramethyl-1,3,2-dioxaborolan-2-yl)phenyl)-1,2,3,6-tetrahydropyridine (5)

Solution of 4-(4-bromo-2-nitrophenyl)-1-methyl-1,2,3,6-tetrahydropyridine (400 mg, 1.35 mmol) in 1,4-dioxane (10 mL) was treated with bis-pinacolatodiborane (370 mg, 1.5 mmol), potassium acetate (367 mg, 3.75 mmol), 1,1'-bis(diphenylphosphino)ferrocene-palladium(II)dichloride dichloromethane complex (51 mg, 0.06 mmol) at 100° C. for 12 h. After completion of the reaction, the reaction mixture was filtered and the filtrate was concentrated under reduced pressure to afford 5 (620 mg, crude) as an oily residue. MS m/z (M+H): 345.6

Step 6:

2-(1-methylpiperidin-4-yl)-5-(4,4,5,5-tetramethyl-1,3,2-dioxaborolan-2-yl)aniline (6)

To a solution of 1-methyl-4-(2-nitro-4-(4,4,5,5-tetramethyl-1,3,2-dioxaborolan-2-yl)phenyl)-1,2,3,6-tetrahydropyridine (0.6 g, 2.0 mmol) in methanol (30.0 mL), 10% Pd/C (100 mg) was added and the resulting reaction mixture was stirred under hydrogen pressure at 50 psi for 12 h. After completion of reaction, the reaction mixture was filtered through celite and the filtrate was concentrated under reduced pressure to afford 6 (400 mg, 72%) as an oily liquid. MS m/z (M+H): 317.3

Step 7:

Compound 7:

(R)-3-chloro-10-methyl-9,10,11,12-tetrahydro-8H-[1,4]diazepino[5',6':4,5]thieno[3,2-f]quinolin-8-one (150 mg, 0.47 mmol) in 1,4-dioxane/water (3:1, 4 mL) was treated with 2-(1-methylpiperidin-4-yl)-5-(4,4,5,5-tetramethyl-1,3,2-dioxaborolan-2-yl)aniline (600 mg, 1.89 mmol), sodium carbonate (150 mg, 1.41 mmol) and tetrakis (triphenylphosphine) palladium (27 mg, 0.023 mmol). The resulting mixture was heated at 100° C. for 12 h. After completion of the reaction, the reaction mixture was diluted with ethyl acetate and washed with water. The organic layer was dried over anhydrous sodium sulfate and concentrated under reduced pressure. The residue was purified by silica gel column chromatography using chloroform/methanol to afford 7 (75 mg, 33%) as a yellow solid. MS m/z (M+H): 472.6

Step 8:

To a solution of compound 7 (50 mg, 0.1 mmol) in tetrahydrofuran/dimethylacetamide (1:1, 2.0 mL), diisopropylethylamine (41 mg, 0.3 mmol) was added followed by the addition of acryloyl chloride (11 mg, 0.1 mmol) at 0° C. The reaction mixture was stirred for 30 min at room temperature. After completion of the reaction, the reaction mixture was concentrated under reduced pressure. The residue obtained was purified by preparative HPLC to afford the desired product (11 mg, 20%) as a pale yellow solid. $^1$H NMR (400 MHz, DMSO-$d_6$): δ 1.18 (d, J=7.0 Hz, 3H), 1.68-1.69 (m, 4H), 1.92 (m, 2H), 2.18 (s, 3H), 2.74 (m, 1H), 2.87 (d, 2H), 3.46 (m, 2H), 3.58-3.60 (m, 1H), 5.78 (dd, J=1.6, 9.9 Hz, 1H), 6.24-6.29 (dd, J=2.0, 17.0 Hz, 1H), 6.53-6.59 (dd, J=10.2, 17.0 Hz, 1H), 7.13 (t, J=5.0 Hz, 1H), 7.49 (d, J=8.2 Hz, 1H), 7.99 (d, J=9.0 Hz, 1H), 8.05 (d, J=4.2 Hz, 1H), 8.10-8.21 (m, 4H), 9.21 (d, J=9.0 Hz, 1H), 9.77 (s, 1H). MS m/z (M−H): 524.4

Compound III-59

(R)—N-(3-(1O-methyl-8-oxo-9,10,11,12-tetrahydro-8H-[1,4]diazepino[5',6':4,5]thieno[3,2-f]quinolin-3-yl)benzyl)acrylamide

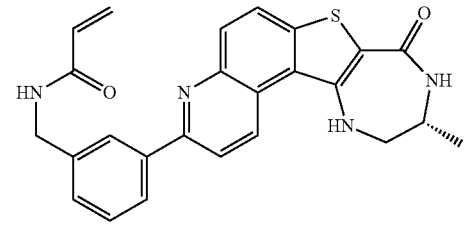 [SMILES: C=CC(=O)NCc1cccc(-c2ccc3c(ccc4sc5c(c43)NC[C@@H](C)NC5=O)n2)c1]

Compound III-59 was prepared according to the schemes, steps, and intermediates below utilizing intermediate 11 from Example 51 as the starting material.

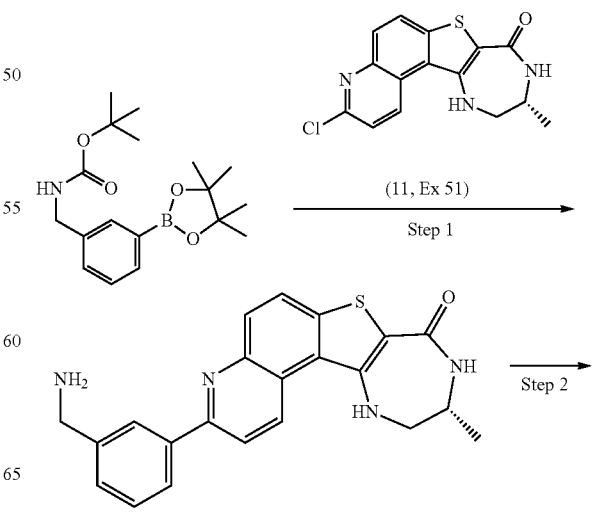

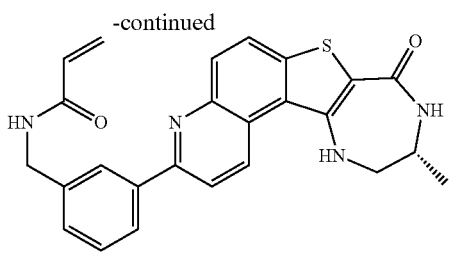

Step 1:

A mixture of (R)-3-chloro-10-methyl-9,10,11,12-tetrahydro-8H-[1,4]diazepino[5',6':4,5]thieno[3,2-f]quinolin-8-one (11, Example 51; 40 mg, 0.126 mmol), (3-(((tert-butoxycarbonyl)amino)methyl)phenyl)boronic acid (38 mg, 0.15 mmol), Pd(dppf)Cl$_2$ (9.2 mg, 0.0126 mmol) and Cs$_2$CO$_3$ (123 mg, 0.378 mmol) in dioxane (3 mL) and water (0.3 mL) was heated at 100° C. for 2 hours. Solvent was removed and CH$_2$Cl$_2$ and water were added and two layers were separated. The organic layer was concentrated and the residue was purified with flash chromatography on silica gel (0-30% MeOH in CH$_2$Cl$_2$) to give the coupling product (50 mg, 81%). The product above was dissolved in CH$_2$Cl$_2$ (3 mL) and to it was added TFA (0.3 mL) and the mixture was stirred at room temperature for 10 minutes. Solvent was removed.

Step 2:

Next, 24 mg of the above product (half of what was obtained from the above step) was dissolved in CH$_2$Cl$_2$ (3 mL) and to it was added acryloyl chloride (6.3 mg, 0.07 mmol) and Et$_3$N (19 mg, 0.189 mmol). The mixture was stirred at room temperature for 15 minutes. Solvent was removed and the crude was purified on the reverse-phase prep-HPLC to give the title compound as the TFA salt (10 mg). $^1$H NMR (400 MHz, DMSO-d$_6$) δ 9.25 (d, J=9.2 Hz, 1H), 8.74 (t, J=6.0 Hz, 1H), 8.10-8.25 (m, 5H), 8.01 (d, J=8.9 Hz, 1H), 7.52 (t, J=7.8 Hz, 1H), 7.40 (d, J=7.3 Hz, 1H), 7.16 (br s, 1H), 6.20 (dd, J=17.0, 10.0 Hz, 1H), 6.15 (dd, J=13.8, 2.0 Hz, 1H), 5.65 (dd, J=10.0, 2.0 Hz, 1H), 4.49 (d, J=6.0 Hz, 2H), 3.40-3.70 (m, 3H), 1.19 (d, J=6.8 Hz, 3H); MS m/z (M+H): 443.1

Compound III-61

(R)—N-(2-(3-methyl-5-oxo-2,3,4,5-tetrahydro-1H-benzo[4,5]thieno[3,2-e][1,4]diazepin-9-yl)benzo[d]oxazol-4-yl)acrylamide

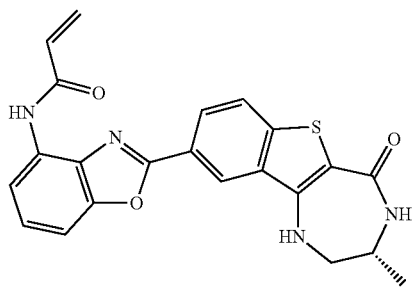 [SMILES: C=CC(=O)Nc1cccc2oc(-c3ccc4sc5c(c4c3)NC[C@@H](C)NC5=O)nc12]

Compound III-61 was prepared according to the schemes, steps, and intermediates below utilizing intermediate 7 from step 7 of Example 40 as the starting material.

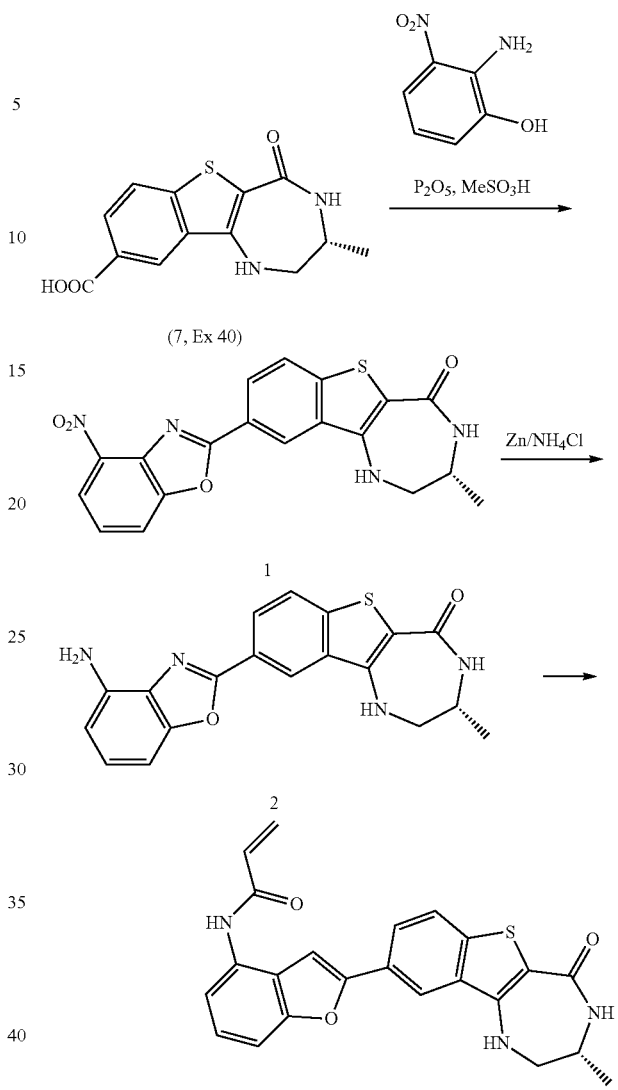

Step 1:

Compound 1:

A solution of phosphoruspentoxide (415 mg, 2.9 mmol) in methanesulfonic acid (2.5 mL) was treated with (R)-3-methyl-5-oxo-2,3,4,5-tetrahydro-1H-benzo[4,5]thieno[3,2-e][1,4]diazepine-9-carboxylic acid (intermediate 7, Example 40; 268 mg, 0.9 mmol) at 0° C., followed by the addition of 2-amino-3-nitrophenol (150 mg, 0.9 mmol). The reaction mixture was stirred at 120° C. for 6 h. After completion of the reaction, the reaction mixture was diluted with saturated sodium bicarbonate solution and extracted with ethyl acetate. The organic layer was dried over anhydrous sodium sulfate and concentrated under reduced pressure to afford 1 (110 mg, 29%) as a brown solid. MS m/z (M+H): 395.5

Step 2:

Compound 2:

To a solution of 1 (110 mg, 0.2 mmol) in dioxane/H$_2$O (3:1, 4 mL), zinc dust (181 mg, 2.7 mmol) was added followed by the addition of ammonium chloride (150 mg, 2.7 mmol) at room temperature. The reaction mixture was stirred at room temperature for 4 h. After completion of the reaction, the reaction mixture was diluted with water and extracted with ethyl acetate. The organic layer was dried over anhydrous sodium sulfate and concentrated under reduced pressure. The residue obtained was triturated with pentane to afford 2 (70 mg, 69%) as a brown solid. MS m/z (M+H): 365.1

Step 3:

To a solution of 2 (50 mg, 0.1 mmol) in dichloromethane (3.0 mL), diisopropylethylamine (53 mg, 0.4 mmol) and acryloyl chloride (8.7 mg, 0.09 mmol) were added at 0° C. The resulting mixture was warmed to room temperature and stirred for 1 h. After completion of the reaction, the reaction mixture was concentrated under reduced pressure. The resulting residue was diluted with water and extracted with dichloromethane. The organic layer was dried over anhydrous sodium sulfate and concentrated under reduced pressure. The residue obtained was purified by preparative HPLC to afford the desired product (12 mg, 18%) as a yellow solid. $^1$H NMR (400 MHz, DMSO-$d_6$): δ 1.16 (d, J=6.7 Hz, 3H), 3.39 (brs, 2H), 3.60 (brs, 1H), 5.80 (dd, J=2.0, 11.7 Hz, 1H), 6.32 (dd, J=1.7, 17.1 Hz, 1H), 6.83 (dd, J=10.1, 17.1 Hz, 1H), 7.40 (t, J=8.1 Hz, 1H), 7.52 (d, J=8.1 Hz, 1H), 7.88 (d, J=4.5 Hz, 1H), 7.96 (brs, 1H), 8.02 (d, J=8.4 Hz, 1H), 8.11 (d, J=8.3 Hz, 1H), 8.27 (d, J=8.5 Hz, 1H), 8.86 (s, 1H), 10.41 (s, 1H). MS m/z (M+H): 419.5

Compound III-62

(R)—N-(2-(3-methyl-5-oxo-2,3,4,5-tetrahydro-1H-benzo[4,5]thieno[3,2-e][1,4]diazepin-9-yl)benzo[d]oxazol-5-yl)acrylamide

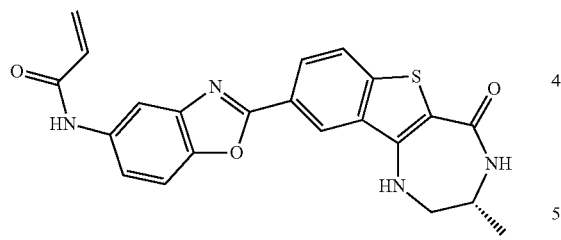

Compound III-62 was prepared as described for compound III-61 by substituting 2-amino-4-nitrophenol for 2-amino-3-nitrophenol in step 1 to afford the desired product (18 mg, 16%) as a yellow solid. $^1$H NMR (400 MHz, DMSO-$d_6$): δ 1.16 (d, J=6.7 Hz, 3H), 3.39 (brs, 2H), 3.60 (brs, 1H), 5.78 (dd, J=1.8, 10.0 Hz, 1H), 6.29 (dd, J=1.7, 16.8 Hz, 1H), 6.46 (dd, J=10.1, 17.0 Hz, 1H), 7.58 (dd, J=1.8, 8.8 Hz, 1H), 7.74 (d, J=8.8 Hz, 1H), 7.87 (d, J=4.5 Hz, 1H), 7.97 (m, 2H), 8.19 (dd, J=1.3, 8.4 Hz, 1H), 8.25 (d, J=1.5 Hz, 1H), 8.88 (s, 1H), 10.33 (s, 1H). MS m/z (M+H): 419.5.

Compound III-63

(R)-3-(2-acryloylisoindolin-4-yl)-10-methyl-9,10,11,12-tetrahydro-8H-[1,4]diazepino[5',6':4,5]thieno[3,2-f]quinolin-8-one

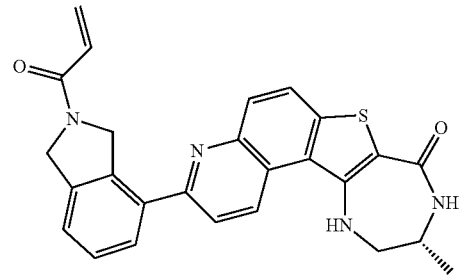 [SMILES: C=CC(=O)N1Cc2cccc(-c3ccc4c(ccc5sc6c(c54)NC[C@@H](C)NC6=O)n3)c2C1]

Compound III-63 was prepared in a similar manner to that described in Example 51 by substituting INT-3 in step 12 of Example 51 with boronate 2, depicted below, to give the desired product (32 mg, 28%) as a yellow solid. 1H NMR (400 MHz, DMSO-$d_6$): δ 1.19 (d, J=6.7 Hz, 3H), 3.47 (brs, 2H), 3.60 (brs, 1H), 4.81 (s, 1H), 5.04 (s, 1H), 5.23 (s, 1H), 5.52 (s, 1H), 5.77 (td, J=2.2, 12.2 Hz, 1H), 6.24 (m, 1H), 6.69-6.85 (m, 1H), 7.16 (brs, 1H), 7.46-7.56 (m, 2H), 7.99 (t, J=8.5 Hz, 1H), 8.04-8.10 (m, 2H), 8.14-8.22 (m, 2H), 9.26 (dd, J=3.3, 8.8 Hz, 1H). MS m/z (M+H): 455.5.

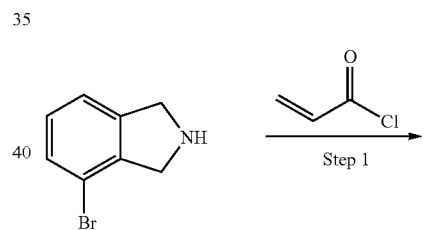

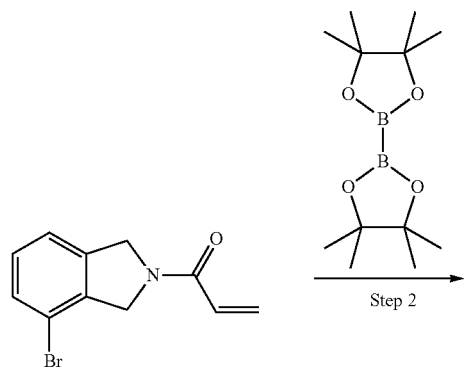

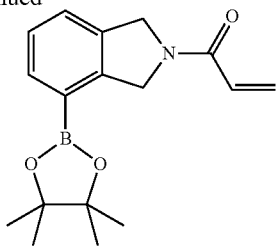

Step 1:

1-(4-bromnoisoindolin-2-yl)prop-2-en-1-one (1)

To a solution of 4-bromoisoindoline (600 mg, 2.5 mmol) in dichloromethane (12.0 mL), diisopropylethylamine (2 g, 15.4 mmol) and acryloyl chloride (278 mg, 3.0 mmol) were added at −78° C. and stirred at the same temperature for 30 min. After completion of the reaction, the reaction mixture was concentrated under reduced pressure. The resulting residue was diluted with water and extracted with dichloromethane. The organic layer was dried over anhydrous sodium sulfate and concentrated under reduce pressure. The crude obtained was triturated with pentane to afford 1 (600 mg, 78%) as a off white solid. $^1$H NMR (400 MHz, CDCl$_3$): δ 4.87 (d, J=9.8 Hz, 2H), 4.99 (d, J=16.5 Hz, 2H), 5.77-5.81 (m, 1H), 6.46-6.52 (m, 1H), 6.60 (dd, J=9.9, 16.7 Hz, 1H), 7.19-7.25 (m, 2H), 7.42-7.45 (m, 1H). MS n/z (M+H): 252.4

Step 2:

1-(4-(4,4,5,5-tetramethyl-1,3,2-dioxaborolan-2-yl)isoindolin-2-yl)prop-2-en-1-one (2)

A solution of 1-(4-bromoisoindolin-2-yl)prop-2-en-1-one (600 mg, 2.4 mmol) in 1,4-dioxane (10 mL) was treated with bis-pinacolatodiborane (728 mg, 2.8 mmol), potassium acetate (703 mg, 7.1 mmol), and [1,1'-bis(diphenylphosphino)ferrocene]dichloropalladium(II) complex with dichloromethane (97 mg, 0.1 mmol) at 100° C. for 12 h. After completion of the reaction, the solvent was removed under reduced pressure. The resulting residue was diluted with ethyl acetate and filtered through celite. The filtrate was concentrated under reduced pressure and purified by silica gel column chromatography to afford 2 (300 mg, 42%) as a pale yellow liquid. MS m/z (M+H): 300.5

Compound III-64

(R)—N-(2-(3-methyl-5-oxo-2,3,4,5-tetrahydro-1H-benzo[4,5]thieno[3,2-e][1,4]diazepin-9-yl)benzo[d]oxazol-5-yl)acrylamide

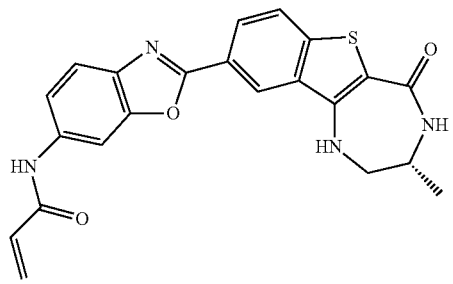 [SMILES: C=CC(=O)Nc1ccc2nc(-c3ccc4sc5c(c4c3)NC[C@@H](C)NC5=O)oc2c1]

Compound III-64 was prepared as described for compound III-61 by substituting 2-amino-3-nitrophenol used in step 1 of the synthesis of compound III-61 with 2-amino-5-nitrophenol to afford the desired product (20 mg, 25%) as a yellow solid. 1H NMR (400 MHz, DMSO-d$_6$): δ 1.16 (d, J=6.6 Hz, 3H), 3.39 (s, 2H), 3.59 (m, 1H), 5.80 (d, J=10.3 Hz, 1H), 6.30 (d, J=17.0 Hz, 1H), 6.47 (dd, J=10.3, 17.0 Hz, 1H), 7.48 (d, J=8.6 Hz, 1H), 7.74 (d, J=8.6 Hz, 1H), 7.87 (d, J=3.7 Hz, 1H), 7.94 (m, 2H), 8.17 (d, J=8.5 Hz, 1H), 8.38 (s, 1H), 8.86 (s, 1H), 10.47 (s, 1H). MS m/z (M+H): 419.6

Compound III-65

(R)—N-(3-methyl-5-(10-methyl-8-oxo-9,10,11,12-tetrahydro-8H-[1,4]diazepino[5',6':4,5]thieno[3,2-f]quinolin-3-yl)phenyl)acrylamide

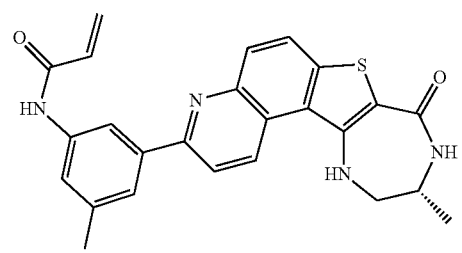 [SMILES: C=CC(=O)Nc1cc(C)cc(-c2ccc3c(ccc4sc5c(c43)NC[C@@H](C)NC5=O)n2)c1]

Compound III-65 was prepared in a similar manner to III-8 as described in Example 51 by substituting INT-3 in step 12 of Example 51 with N-(3-methyl-5-(4,4,5,5-tetramethyl-1,3,2-dioxaborolan-2-yl)phenyl) acrylamide (3), depicted below, to afford the desired product (23 mg, 28%) as a yellow solid. $^1$H NMR (400 MHz, DMSO-d$_6$): δ 1.19 (d, J=6.7 Hz, 3H), 2.43 (s, 3H), 3.47 (m, 2H), 3.59-3.61 (m, 1H), 5.78 (dd, J=1.8, 10.0 Hz, 1H), 6.29 (dd, J=1.9, 17.0 Hz, 1H), 6.49 (dd, J=10.0, 17.0 Hz, 1H), 7.13 (t, J=4.7 Hz, 1H), 7.74 (s, 1H), 7.79 (s, 1H), 7.99 (d, J=9.0 Hz, 1H), 8.06 (d, J=4.0 Hz, 1H), 8.11 (m, 2H), 8.32 (s, 1H), 9.23 (d, J=8.9 Hz, 1H), 10.28 (s, 1H). MS m/z (M+H): 443.6

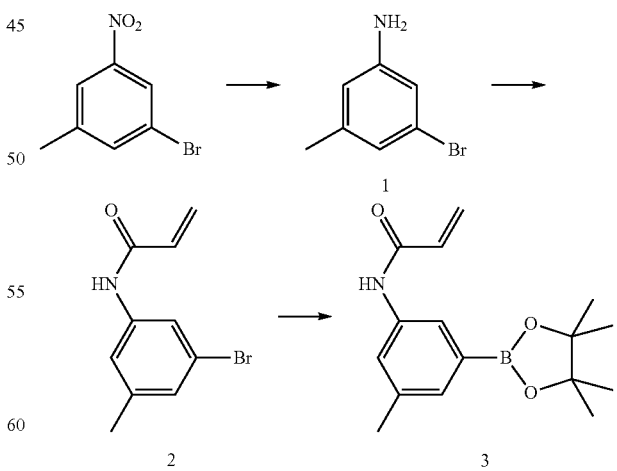

Step 1:

3-bromo-5-methylaniline (1): To a solution of 1-bromo-3-methyl-5-nitrobenzene (5 g, 23.1 mmol) in dioxane/water (3:1; 40 mL), zinc dust (15 g, 231 mmol) was added followed by the addition of ammonium chloride (12.3 g, 231 mmol). The reaction mixture was stirred at room temperature for 4 h. After completion of the reaction, the reaction mixture was diluted with water and extracted with ethyl acetate. The organic layer was dried over anhydrous sodium sulfate and concentrated under reduced pressure to afford 1 (4.0 g, 93%) as a brown solid. MS m/z (M+H): 186.2

Step 2:

N-(3-bromo-5-methylphenyl)acrylamide (2)

To a solution of 3-bromo-5-methylaniline (1.0 g, 5.4 mmol) in dichloromethane (10.0 mL), diisopropylethylamine (2.0 g, 16.2 mmol) and acryloyl chloride (450 mg, 4.9 mmol) were added at 0° C. The resulting mixture was warmed to room temperature and stirred for I h. After completion of the reaction, the solvent was removed under reduced pressure. The resulting residue was diluted with water and extracted with dichloromethane. The organic layer was dried over anhydrous sodium sulfate and concentrated under reduced pressure. The resulting residue was purified by silica gel column chromatography to afford 2 (800 mg, 62%) as an off-white solid. MS m/z (M+H): 240.4

Step 3:

N-(3-methyl-5-(4,4,5,5-tetramethyl-1,3,2-dioxaborolan-2-yl)phenyl)acrylamide (3)

A solution of N-(3-bromo-5-methylphenyl)acrylamide (500 mg, 2.1 mmol) in 1,4-dioxane (6.0 mL) was treated with bis-pinacolatodiborane (800 mg, 3.1 mmol), potassium acetate (602 mg, 6.3 mmol), and [1,1'-bis(diphenylphosphino)ferrocene]dichloropalladium(II) complex with dichloromethane (86 mg, 0.1 mmol) at 100° C. for 16 h. After completion of the reaction, solvent was removed under reduced pressure. The resulting residue was diluted with ethyl acetate and filtered through celite. The filtrate was concentrated under reduced pressure and the resulting residue was purified by silica gel column chromatography to afford 3 (250 mg, 42%) as an oily liquid. MS m/z (M+H): 288.4

Compound III-66

(R)—N-(5-methyl-2-(10-methyl-8-oxo-9,10,11,12-tetrahydro-8H-[1,4]diazepino[5',6':4,5]thieno[3,2-f]quinolin-3-yl)phenyl)acrylamide

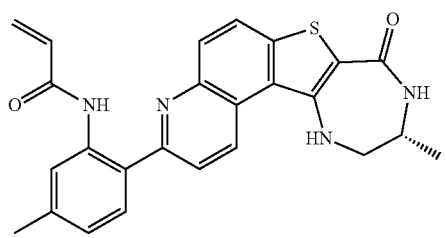

Compound III-66 was prepared according to the schemes, steps, and intermediates below utilizing intermediate 11 from step 11 of Example 51 for step 3 of this example.

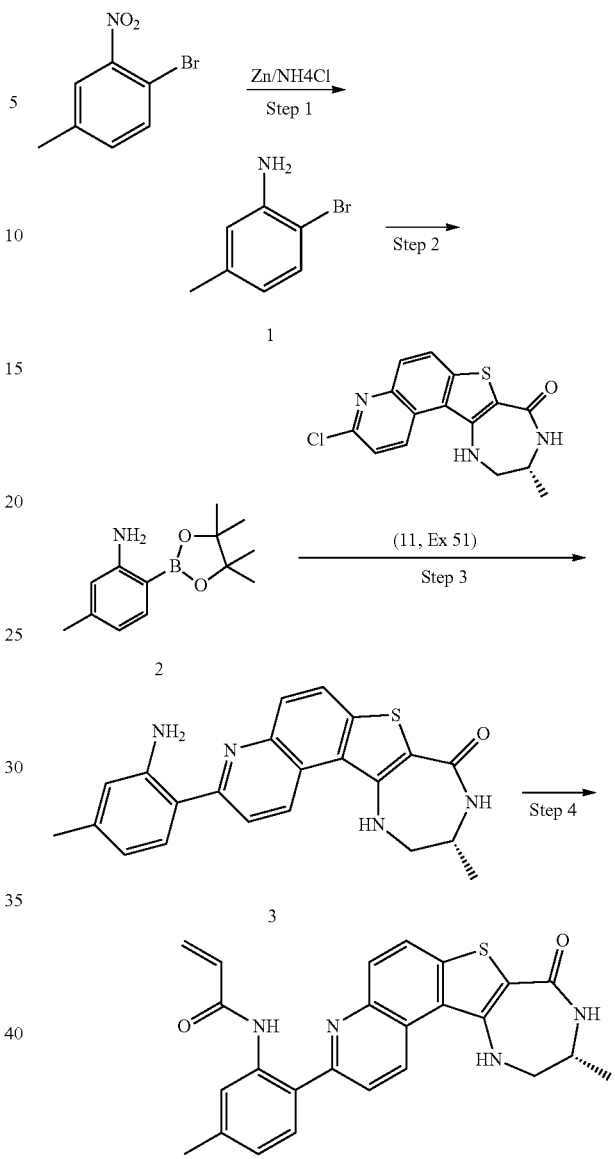

Step 1:

2-bromo-5-methylaniline (1)

To a solution of 1-bromo-4-methyl-2-nitrobenzene (3.0 g, 13.8 mmol) in dioxane/water (1:1; 60 mL), zinc dust (9 g, 138.8 mmol) was added followed by the addition of ammonium chloride (7.3 g, 138.8 mmol). The reaction mixture was stirred at room temperature for 3 h. After completion of the reaction, the reaction mixture was diluted with water and extracted with ethyl acetate. The organic layer was dried over anhydrous sodium sulfate and concentrated under reduced pressure to afford 2 (2 g, 77%) as a pale yellow liquid. $^1$H NMR (400 MHz, DMSO-$d_6$): δ 2.12 (s, 3H), 5.14 (s, 2H), 6.28 (dd, J=1.7, 8.0 Hz, 1H), 6.58 (s, 1H), 7.16 (d, J=8.0 Hz, 1H). MS m/z (M+H): 186.3

Step 2:

5-methyl-2-(4,4,5,5-tetramethyl-1,3,2-dioxaborolan-2-yl)aniline (2)

A solution of 2-bromo-5-methylaniline (1.5 g, 8.0 mmol) in dimethyl sulfoxide (20.0 mL) was treated with bis-pinacolatodiborane(2.4 g, 9.7 mmol), potassium acetate (2.4 g, 24 mmol), and [1,1'Bis(diphenylphosphino)ferrocene] dichloropalladium(II) complex with dichloromethane (329 mg, 0.04 mmol) at 110° C. for 6 h. After completion of the reaction, the reaction mixture was filtered through celite and washed with ethyl acetate. The filtrate was concentrated under reduced pressure and purified by silica gel column chromatography to afford 2 (320 mg, 17%) as a pale yellow liquid. $^1$H NMR (400 MHz, DMSO-d$_6$): δ 1.26 (s, 12H), 2.13 (s, 3H), 5.37 (s, 2H), 6.29 (d, J=7.5 Hz, 1H), 6.37 (s, 1H), 7.23 (d, J=7.5 Hz, 1H). MS m/z (M+H): 234.2

Step 3:

Compound 3:

(R)-3-chloro-10-methyl-9,10,11,12-tetrahydro-8H-[1,4] diazepino [5',6':4,5]thieno[3,2-f]quinolin-8-one (intermediate 11, Ex 51; 100 mg, 0.3 mmol) in dioxane (10.0 mL) was treated with 5-methyl-2-(4,4,5,5-tetramethyl-1,3,2-dioxaborolan-2-yl)aniline (320 mg, 0.9 mmol), sodium carbonate (100 mg, 0.9 mmol) and tetrakis (triphenylphosphine) palladium (75 mg, 0.06 mmol). The resulting mixture was heated at 100° C. for 6 h. After completion of the reaction, the solvent was removed under reduced pressure. The resulting residue was filtered through celite and washed with ethyl acetate. The filtrate was concentrated under reduced pressure and triturated with diethyl ether to afford 3 (101 mg, 83%) as a yellow solid. MS m/z (M+H): 389.6

Step 4:

To a solution of 3 (75 mg, 0.2 mmol) in acetone (10.0 mL), diisopropylethylamine (37.4 mg, 0.3 mmol) and acryloyl chloride (15.6 mg, 0.2 mmol) were added at 0° C. and stirred for 1 h at room temperature. After completion of the reaction, the solvent was removed under reduced pressure. The residue was diluted with water and the resulting solid suspension was filtered. The solid obtained was triturated with diethyl ether to afford the desired product (36 mg, 42%) as a yellow solid. $^1$H NMR (400 MHz, DMSO-d$_6$): δ 1.19 (d, J=6.7 Hz, 3H), 2.39 (s, 3H), 3.47 (m, 2H), 3.60 (m, 1H), 5.84 (d, J=11.1 Hz, 1H), 6.28 (d, J=16.8 Hz, 1H), 6.51 (dd, J=10.1, 16.9 Hz, 1H), 7.14 (m, 2H), 7.98 (d, J=8.1 Hz, 1H), 8.05 (m, 2H), 8.18 (m, 2H), 8.34 (s, 1H), 9.27 (d, J=9.0 Hz, 1H), 12.83 (s, 1H). MS m/z (M+H): 443.2

Compound III-67

(R)—N-(5-(10-methyl-8-oxo-9,10,11,12-tetrahydro-8H-[1,4]diazepino[5',6':4,5]thieno[3,2-f]quinolin-3-yl)-2-(piperidin-4-yl)phenyl)acrylamide

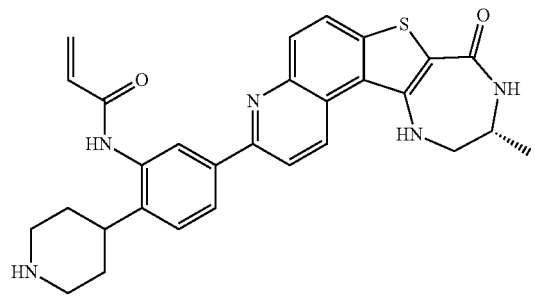 [SMILES: C=CC(=O)Nc1cc(-c2ccc3c(ccc4sc5c(c43)NC[C@@H](C)NC5=O)n2)ccc1C1CCNCC1]

Compound III-67 was prepared according to the schemes, steps, and intermediates below utilizing intermediate 11 from step 11 of Example 51 for step 7, below.

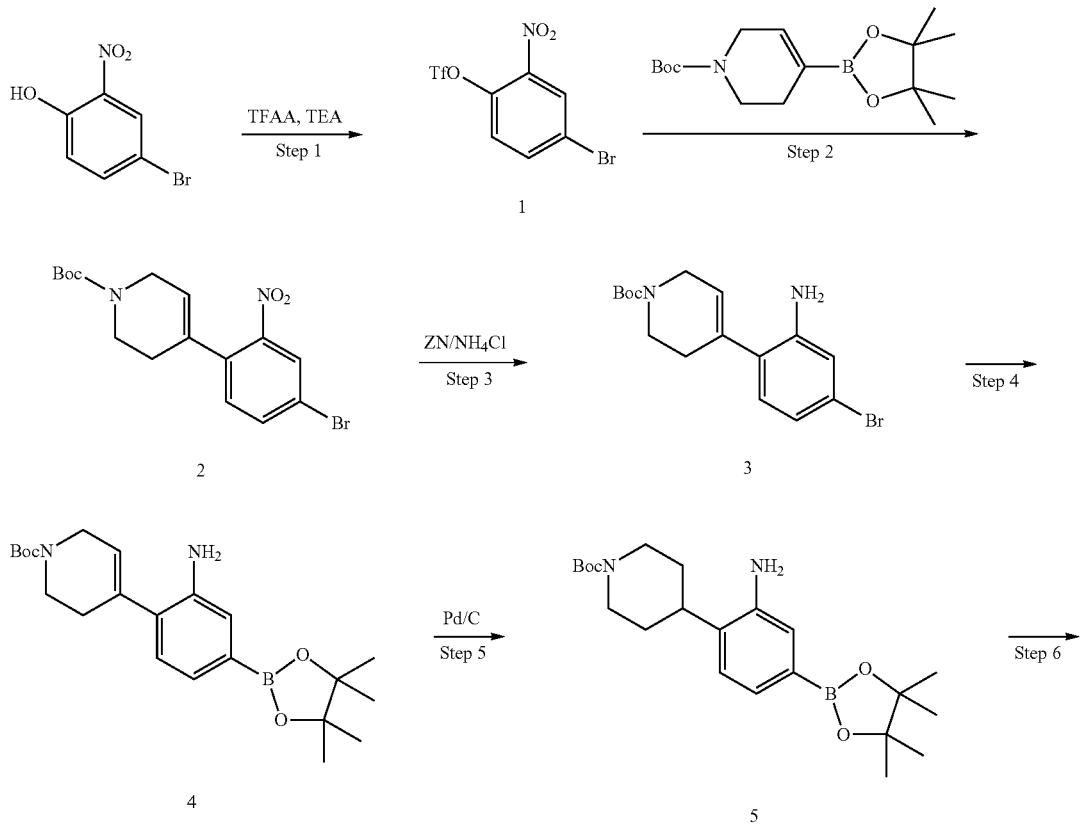

-continued

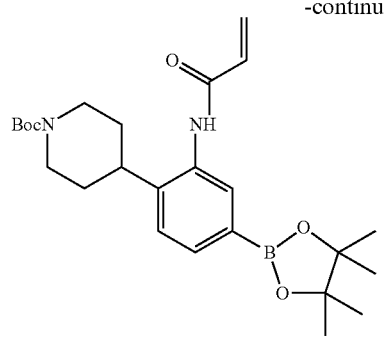

6

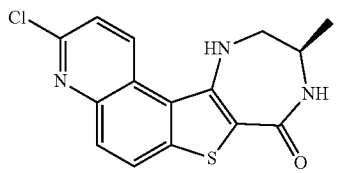

(11, Ex 51)

Step 7

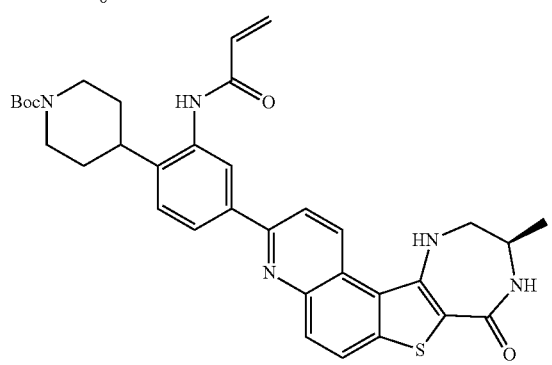

7

TFA

Step 8

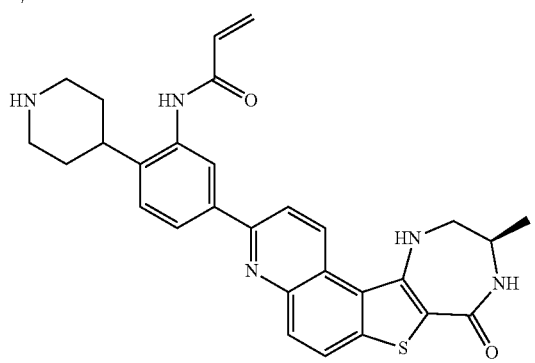

Step 1:

4-bromo-2-nitrophenyltrifluoromethanesulfonate (1)

To a solution of 4-bromo-2-nitrophenol (5.0 g, 22.9 mmol) in dichloromethane (100 mL), triethylamine (2.8 g, 27.5 mmol), 4-dimethylaminopyridine (280 mg, 2.3 mmol) and trifluoromethanesulfonic anhydride (7.8 g, 27.5 mmol) were added dropwise at 0° C. The resulting mixture was stirred at room temperature for 1 h. After completion of the reaction, the reaction mixture was partitioned between dichloromethane and water. The organic phase was washed with saturated sodium bicarbonate solution followed by brine solution. The organic layer was then dried over anhydrous sodium sulfate and concentrated under reduced pressure. The residue obtained was purified by silica gel column chromatography to afford 1 (7.2 g, 90%) as an oily liquid. $^1$H NMR (400 MHz, CDCl$_3$): δ 7.35 (d, J=8.8 Hz, 1H), 7.85-7.87 (dd, J=2.4, 8.8 Hz, 1H), 8.29 (d, J=2.4 Hz, 1H).

Step 2:

tert-butyl-4-(4-bromo-2-nitrophenyl)-5,6-dihydro-pyridine-1(2H) carboxylate (2)

To a solution of 4-bromo-2-nitrophenyltrifluoromethanesulfonate (2.0 g, 5.7 mmol) in dimethylformamide/water (3:1, 20 mL), tert-butyl-4-(4,4,5,5-tetramethyl-1,3,2-dioxaborolan-2-yl)-5,6-dihydropyridine-1(2H)-carboxylate (1.8 g, 5.7 mmol), sodium carbonate (3.0 g, 28.0 mmol) were added. The resulting mixture was degassed under nitrogen for 10 min followed by the addition of [1,1'-bis(diphenylphosphino)ferrocene]dichloropalladium(II) complex with dichloromethane (140 mg, 0.17 mmol). The resulting mixture was heated at 100° C. for 4 h. After completion of the reaction, the reaction mixture was diluted with ethyl acetate and washed with water. The organic layer was dried over anhydrous sodium sulfate and concentrated under reduced pressure. The residue obtained was purified by silica gel column chromatography to afford 2 (1.1 g, 50%) as a pale yellow solid. $^1$H NMR (400 MHz, CDCl$_3$): δ 1.49 (s, 9H), 2.30 (brs, 2H), 3.62 (t, J=5.4 Hz, 2H), 4.02 (brs, 2H), 5.60 (brs, 1H), 7.17 (d, J=8.2 Hz, 1H), 7.66-7.69 (dd, J=2.0, 8.2 Hz, 1H), 8.04 (d, J=2.0 Hz, 1H). MS m/z (M+H): 382.0.

Step 3:

tert-butyl-4-(2-amino-4-bromophenyl)-5,6-dihydro-pyridine-1(2H)-carboxylate (3)

To a solution of tert-butyl-4-(4-bromo-2-nitrophenyl)-5,6-dihydropyridine-1(2H)-carboxylate (1.1 g, 2.9 mmol) in dioxane/water (1:1; 40 mL), zinc dust (1.5 g, 23.0 mmol) was added followed by the addition of ammonium chloride (1.25 g, 23.0 mmol). The resulting mixture was stirred at room temperature for 16 h. After completion of the reaction, the reaction mixture was diluted with water and extracted with ethyl acetate. The organic layer was dried over anhydrous sodium sulfate and concentrated under reduced pressure to afford 3 (1.0 g, 99%) as a thick liquid. 1H NMR (400 MHz, DMSO-d$_6$): δ 1.41 (s, 9H), 2.23 (d, J=1.5 Hz, 2H), 3.51 (t, J=5.3 Hz, 2H), 3.55 (s, 2H), 3.91 (s, 2H), 5.09 (s, 2H), 5.64 (s, 1H), 6.61 (dd, J=2.0, 8.0 Hz, 1H), 6.77 (d, J=8.0 Hz, 1H), 6.81 (d, J=2.0 Hz, 1H).

Step 4:

tert-butyl 4-(2-amino-4-(4,4,5,5-tetramethyl-1,3,2-dioxaborolan-2-yl)phenyl)-5,6-dihydropyridine-1(2H)-carboxylate (4)

Solution of tert-butyl 4-(2-amino-4-bromophenyl)-5,6-dihydropyridine-1(2H)-carboxylate (1.0 g, 2.8 mmol) in 1,4-dioxane (30 mL) was treated with bis-pinacolatodiborane (860 mg, 3.4 mmol), potassium acetate (836 mg, 8.5 mmol), [1,1'-bis(diphenylphosphino)ferrocene]dichloropalladium (II) complex with dichloromethane (115 mg, 0.1 mmol) at 100° C. for 4 h. After completion of the reaction, the solvent was removed under reduced pressure. The resulting residue was diluted with ethyl acetate and filtered through celite. The filtrate was concentrated under reduced pressure and purified by silica gel column chromatography to afford 4 (800 mg, 71%) as a brown solid. MS m/z (M+H): 401.2.

Step 5:

tert-butyl-4-(2-amino-4-(4,4,5,5-tetramethyl-1,3,2-dioxaborolan-2-yl)phenyl)piperidine-1-carboxylate (5)

To a solution of tert-butyl-4-(2-amino-4-(4,4,5,5-tetramethyl-1,3,2-dioxaborolan-2-yl)phenyl)-5,6-dihydropyridine-1(2H)-carboxylate (800 mg, 2.0 mmol) in methanol (20.0 mL), 10% palladium/carbon (200 mg) was added and the resulting reaction mixture was stirred under hydrogen pressure at 100 psi for 12 h. After completion of the reaction, the reaction mixture was filtered through celite and washed with methanol. The filtrate was concentrated under reduced pressure to afford 5 (800 mg, 99%) as an oily liquid. MS m/z (M+H): 403.1.

Step 6:

tert-butyl 4-(2-acrylamido-4-(4,4,5,5-tetramethyl-1,3,2-dioxaborolan-2yl)phenyl) piperidine-1-carboxylate (6)

To a tert-butyl 4-(2-amino-4-(4,4,5,5-tetramethyl-1,3,2-dioxaborolan-2-yl)phenyl)piperidine-1-carboxylate (800 mg, 2.0 mmol) in dichloromethane (40 mL), diisopropylethylamine (770 mg, 6.0 mmol) and acryloyl chloride (180 mg, 2.0 mmol) were added at −78° C. The resulting mixture was stirred at room temperature for 30 min. After completion of the reaction, the reaction mixture was diluted with dichloromethane and washed with water. The organic layer was dried over anhydrous sodium sulfate and concentrated under reduced pressure. The residue obtained was triturated with n-pentane to afford 6 (750 mg, 82%) as a pale brown solid. MS m/z (M−H): 455.4.

Step 7:

Compound 7:

(R)-3-chloro-10-methyl-9,10,11,12-tetrahydro-8H-[1,4]diazepino [5',6':4,5]thieno[3,2-f]quinolin-8-one (intermediate 11, Example 51; 150 mg, 0.5 mmol) in 1,4-dioxane/water (3:1, 8 mL) was treated with tert-butyl-4-(2-acrylamido-4-(4,4,5,5-tetramethyl-1,3,2-dioxaborolan-2-yl) phenyl)piperidine-1-carboxylate (640 mg, 1.4 mmol), sodium carbonate (150 mg, 1.4 mmol), and tetrakis (triphenylphosphine) palladium (27 mg, 0.02 mmol). The resulting mixture was heated at 100° C. for 12 h. After completion of the reaction, the reaction mixture was diluted with ethyl acetate and washed with water. The organic layer was dried over anhydrous sodium sulfate and concentrated under reduced pressure. The residue obtained was purified by silica gel column chromatography using chloroform/methanol to afford 7 (220 mg, 76%) as an off white solid. 1H NMR (400 MHz, DMSO-d$_6$): $^1$H NMR (400 MHz, DMSO-d$_6$): δ 1.19 (d, J=6.7 Hz, 3H), 1.42 (s, 9H), 1.50-1.53 (m, 2H), 1.72 (d, J=12.5 Hz, 2H), 2.76 (m, 2H), 2.96 (t, J=12.1 Hz, 1H), 3.46 (m, 2H), 3.59-3.61 (m, 1H), 4.08 (m, 2H), 5.79 (d, J=10.5 Hz, 1H), 6.28 (dd, J=1.8, 17.0 Hz, 1H), 6.53-6.60 (m, 1H), 7.13 (t, J=5.2 Hz, 1H), 7.48 (d, J=8.3 Hz, 1H), 7.99 (d, J=9.0 Hz, 1H), 8.06 (d, J=4.1 Hz, 1H), 8.11 (m, 2H), 8.18 (d, J=9.0 Hz, 1H), 8.24 (s, 1H), 9.21 (d, J=9.1 Hz, 1H), 9.79 (s, 1H). MS m/z (M−H): 610.4.

Step 8:

Compound 7 (30 mg, 0.04 mmol) was treated with excess trifluoroacetic acid in dichloromethane (5.0 mL) at 0° C. The reaction mixture was stirred at room temperature for 4 h. After completion of the reaction, solvent was removed under reduced pressure and co-distilled with dichloromethane. The residue obtained was triturated with diethyl ether and dried under vacuum to afford the desired product (25 mg, quantitative) as a pale yellow solid. $^1$H NMR (400 MHz, DMSO-d$_6$): δ 1.19 (d, J=6.6 Hz, 3H), 1.81-1.93 (m, 4H), 2.94-3.06 (m, 3H), 3.34-3.49 (m, 5H), 3.59 (t, J=6.0 Hz, 1H), 5.81 (d, J=10.3 Hz, 1H), 6.29 (dd, J=1.8, 17.0 Hz, 1H), 6.57 (dd, J=10.0, 16.9 Hz, 1H), 7.13 (brs, 1H), 7.44 (d, J=8.2 Hz, 1H), 7.99 (d, J=8.9 Hz, 1H), 8.06 (d, J=3.9 Hz, 1H), 8.13 (d, J=8.9 Hz, 1H), 8.19 (m, 2H), 8.25 (s, 1H), 9.23 (d, J=9.0 Hz, 1H), 9.82 (s, 1H). MS m/z (M−H): 510.4

Compound III-68

(R)—N-(2-(1-acetylpiperidin-4-yl)-5-(10-methyl-8-oxo-9,10,11,12-tetrahydro-8H-[1,4]diazepino[5',6':4,5]thieno[3,2-f]quinolin-3-yl)phenyl)acrylamide

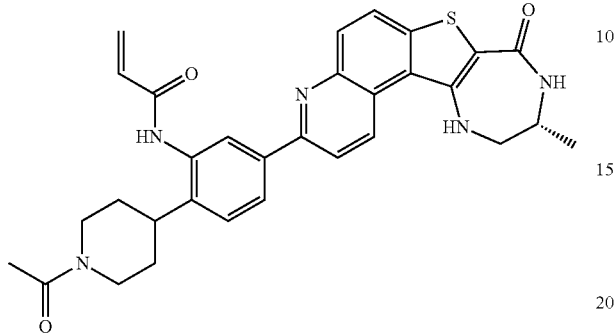

Compound III-68 was prepared from compound III-67 according to the schemes and steps described below.

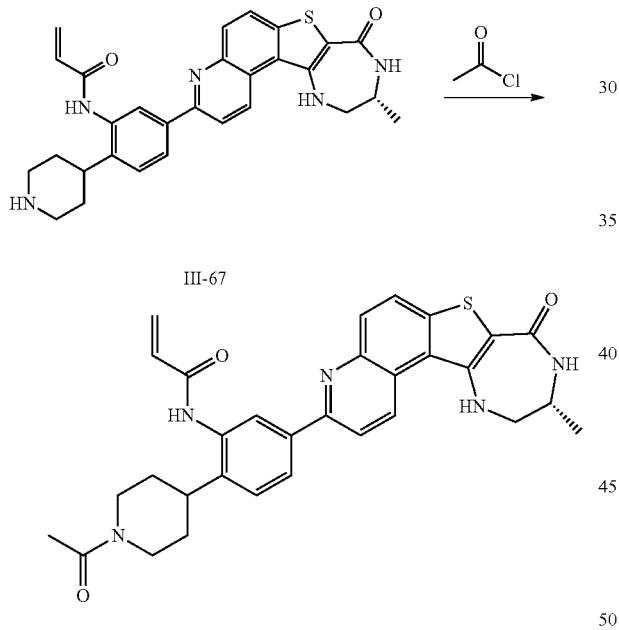

To a solution of III-67 (70 mg, 0.1 mmol) in dry dichloromethane (10 ml), triethylamine (41 mg, 0.4 mmol) and acetyl chloride (9 mg, 0.1 mmol) were added at 0° C. The resulting mixture was stirred at room temperature for 30 min. After completion of the reaction, the reaction mixture was diluted with dichloromethane and washed with water. The organic layer was dried over anhydrous sodium sulfate and concentrated under reduced pressure. The crude obtained was purified by preparative HPLC to afford the desired product (23 mg, 30%) as a pale yellow solid. $^1$H NMR (400 MHz, DMSO-$d_6$): δ 1.19 (d, J=6.7 Hz, 3H), 1.43-1.48 (m, 1H), 1.60-1.63 (m, 1H), 1.72-1.78 (m, 2H), 2.03 (s, 3H), 2.55 (m, 1H), 3.00-3.11 (m, 2H), 3.46 (brs, 2H), 3.59-3.61 (m, 1H), 3.94 (d, J=12.7 Hz, 1H), 4.55 (d, J=12.6 Hz, 1H), 5.79 (d, J=10.4 Hz, 1H), 6.28 (dd, J=1.8, 17.0 Hz, 1H), 6.58 (dd, J=10.0, 16.7 Hz, 1H), 7.13 (t, J=5.1 Hz, 1H), 7.48 (d, J=8.2 Hz, 1H), 7.99 (d, J=8.9 Hz, 1H), 8.05 (d, J=4.0 Hz, 1H), 8.10 (m, 2H), 8.18 (d, J=9.0 Hz, 1H), 8.25 (s, 1H), 9.22 (d, J=9.0 Hz, 1H), 9.79 (s, 1H). MS m/z (M−H): 552.5

Compound III-69

(R)—N-methyl-N-(2-methyl-5-(10-methyl-8-oxo-9,10,11,12-tetrahydro-8H-[1,4]diazepino[5',6':4,5]thieno[3,2-f]quinolin-3-yl)phenyl)acrylamide

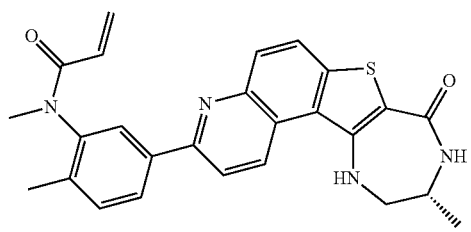

Compound III-69 was prepared according to the schemes, steps, and intermediates below utilizing intermediate 11 from step 11 of Example 51 for step 6, below.

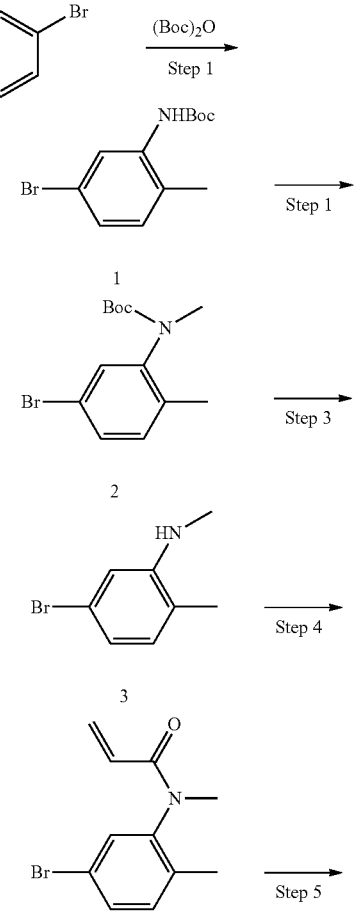

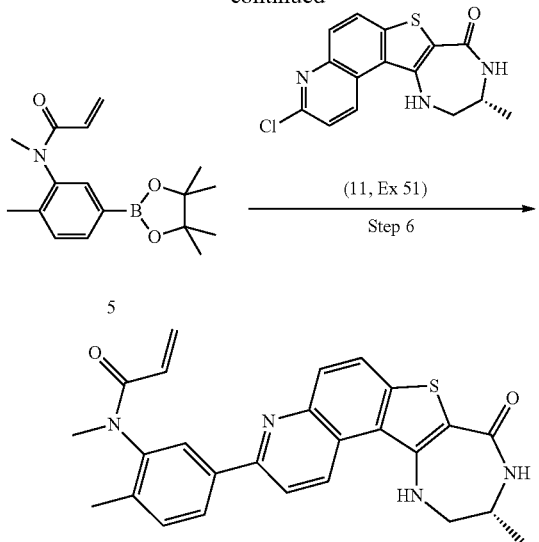

Step 1 tert-butyl 5-bromo-2-methylphenylcarbamate (1)

To a solution of 5-bromo-2-methylaniline (2.0 g, 10.7 mmol) in dichloromethane (15.0 mL), diisopropylethylamine (5.6 g, 43.0 mmol) and boc-anhydride (11.8 g, 53.5 mmol) were added. The reaction mixture was stirred at room temperature for 24 h. After completion of the reaction, solvent was removed under reduced pressure. The resulting residue was diluted with dichloromethane and extracted with water. The organic layer was dried over anhydrous sodium sulfate and concentrated under reduced pressure. The resulting residue was triturated with pentane to afford 1 (3.0 g, 98%) as an off white solid. $^1$H NMR (400 MHz, DMSO-d$_6$): δ 1.45 (s, 12H), 7.10 (d, J=8.2 Hz, 1H), 7.18 (dd, J=1.9, 8.1 Hz, 1H), 7.58 (s, 1H), 8.64 (s, 1H). MS m/z (M+H): 286.0

Step 2:

tert-butyl 5-bromo-2-methylphenyl(methyl)carbamate (2)

A solution of sodium hydride (400 mg, 5.2 mmol) in tetrahydrofuran (10.0 mL) at 0° C. was treated with tert-butyl 5-bromo-2-methylphenylcarbamate (1.0 g, 3.5 mmol) followed by the addition of methyl iodide (1.08 g, 3.8 mmol) at room temperature. The resulting mixture was heated at 75° C. for 3 h. After completion of the reaction, the reaction mixture was diluted with water and extracted with ethyl acetate. The organic layer was dried over anhydrous sodium sulfate and concentrated under reduced pressure to afford 2 (800 mg, 77%) as a grey liquid. MS m/z (M+H): 300.9

Step 3:

5-bromo-N, 2-dimethylaniline (3)

Tert-butyl 5-bromo-2-methylphenyl(methyl)carbamate (800 mg, 2.6 mmol) was treated with excess trifluoroacetic acid in dichloromethane (5.0 mL) at 0° C. The reaction mixture was stirred at room temperature for 4 h. After completion of the reaction, the reaction mixture was concentrated under reduced pressure and co-distilled with dichloromethane. The residue obtained was purified by silica gel column chromatography to afford to afford 3 (800 mg, 95%) as an off white solid. MS m/z (M+H): 200.0

Step 4:

N-(5-bromo-2-methylphenyl)

N-methylacrylamide (4): To a solution of 5-bromo-N,2-dimethylaniline (800 mg, 4.0 mmol) in dichloromethane (8.0 mL), diisopropylethylamine (1.5 g, 12 mmol) and acryloyl chloride (330 mg, 3.6 mmol) were added at room temperature and stirred for 1 h. After completion of the reaction, the solvent was removed under reduced pressure. The resulting residue was diluted with water and extracted with dichloromethane. The organic layer was dried over anhydrous sodium sulfate and concentrated under reduced pressure. The residue obtained was purified by silica gel column chromatography to afford 4 (600 mg, 93%) as a oily liquid. MS m/z (M+H): 254.5

Step 5:

N-methyl-N-(2-methyl-5-(4,4,5,5-tetramethyl-1,3,2-dioxaborolan-2-yl)phenyl)acrylamide (5)

A solution of N-(5-bromo-2-methylphenyl)-N-methyl-acrylamide (500 mg, 2.0 mmol) in 1,4-dioxane (6.0 mL) was treated with bis-pinacolatodiborane (753 mg, 3.0 mmol), potassium acetate (570 mg, 5.9 mmol) and [1,1'-bis(diphenylphosphino)ferrocene]dichloropalladium(II) complex with dichloromethane (81 mg, 0.1 mmol) at 100° C. for 6 h. After completion of the reaction, the solvent was removed under reduced pressure. The resulting residue was diluted with ethyl acetate and filtered through celite. The filtrate was concentrated under reduced pressure to afford 5 (600 mg, 59%) as a brown solid. MS m/z (M+H): 302.5

Step 6:

(R)-3-chloro-10-methyl-9,10,11,12-tetrahydro-8H-[1,4]diazepino[5',6':4,5]thieno[3,2-f]quinolin-8-one (intermediate 11, Example 51; 75 mg, 0.2 mmol) in 1,4-dioxane/water (3:1; 8 mL) was treated with N-methyl-N-(2-methyl-5-(4,4,5,5-tetramethyl-1,3,2-dioxaborolan-2-yl)phenyl)acrylamide 5 (285 mg, 0.9 mmol), sodium carbonate (75 mg, 0.7 mmol) and tetrakis (triphenylphosphine) palladium (55 mg, 0.04 mmol). The resulting mixture was stirred at 100° C. for 8 h. After completion of the reaction, the solvent was removed under reduced pressure. The residue obtained was diluted with ethyl acetate and filtered through celite. The filtrate was concentrated under reduced pressure and purified by preparative HPLC to afford the desired product (20 mg, 18%) as a yellow solid. $^1$H NMR (400 MHz, DMSO-d$_6$): δ 1.19 (d, J=6.6 Hz, 3H), 2.21 (s, 3H), 3.25 (s, 3H), 3.46 (m, 2H), 3.60 (m, 1H), 5.55 (dd, J=2.0, 10.3 Hz, 1H), 5.95 (dd, J=10.2, 16.7 Hz, 1H), 6.20 (dd, J=2.0, 16.8 Hz, 1H), 7.13 (t, J=4.8 Hz, 1H), 7.55 (d, J=8.0 Hz, 1H), 8.01 (d, J=8.9 Hz, 1H), 8.05 (d, J=3.8 Hz, 1H), 8.12 (d, J=8.9 Hz, 1H), 8.20 (s, 1H), 8.28 (m, 2H), 9.21 (d, J=8.9 Hz, 1H). MS m/z (M+H): 457.6

533

Compound III-70

(R)-2-acrylamido-N,N-dimethyl-4-(10-methyl-8-oxo-9,10,11,12-tetrahydro-8H-[1,4]diazepino[5',6':4,5]thieno[3,2-f]quinolin-3-yl)benzamide

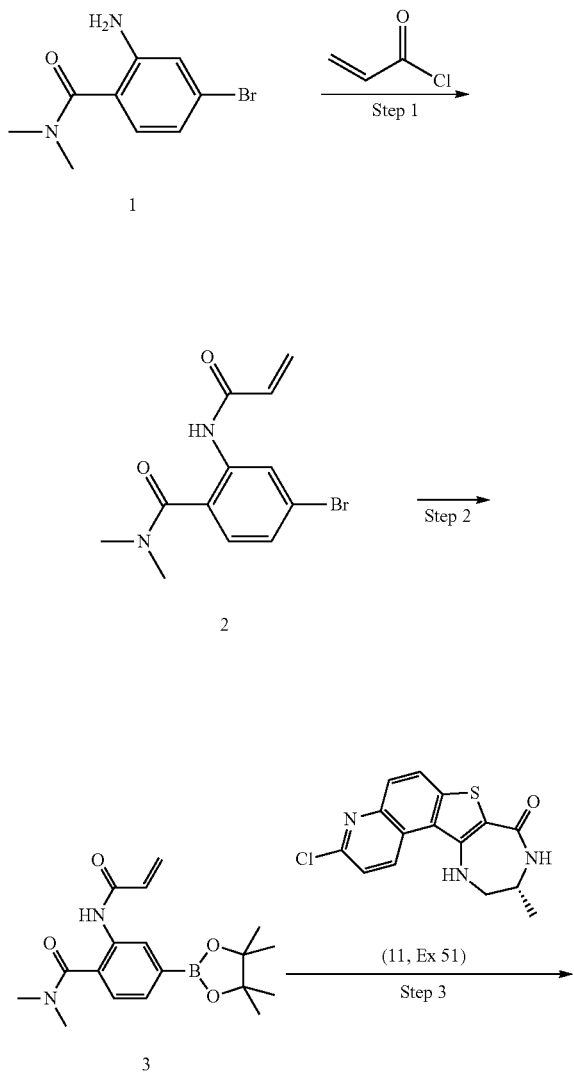

Compound III-70 was prepared according to the schemes, steps, and intermediates below utilizing intermediate 11 from step 11 of Example 51 for step 3, below.

534

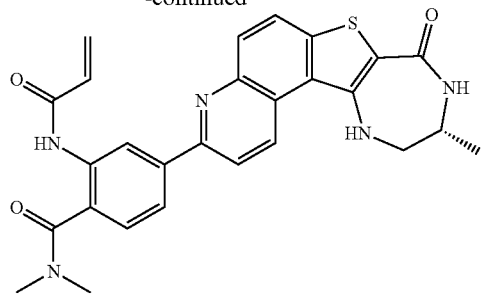

Step 1:

2-acrylamido-4-bromo-N,N-dimethylbenzamide (2)

To a solution of 2-amino-4-bromo-N,N-dimethylbenzamide 1 (400 mg, 1.6 mmol) in dichloromethane (5.0 mL), diisopropylethylamine (843 mg, 5.7 mmol) and acryloyl chloride (169 mg, 1.6 mmol) were added at −78° C. The resulting mixture was warmed to room temperature and stirred for 1 h. After completion of the reaction, the solvent was removed under reduced pressure. The resulting residue was diluted with water and extracted with ethyl acetate. The organic layer was dried over anhydrous sodium sulfate and concentrated under reduced pressure to afford 2 (450 mg, 92%) as an off white solid. $^1$H NMR (400 MHz, DMSO-$d_6$): δ 2.78 (s, 3H), 2.93 (s, 3H), 5.76 (dd, J=1.4, 10.0 Hz, 1H), 6.23 (dd, J=1.4, 16.9 Hz, 1H), 6.47 (dd, J=10.1, 17.0 Hz, 1H), 7.24 (d, J=8.2 Hz, 1H), 7.40 (dd, J=1.8, 8.2 Hz, 1H), 7.93 (d, J=1.5 Hz, 1H), 9.83 (s, 1H). MS m/z (M+H): 297.27

Step 2.

2-acrylamido-N,N-dimethyl-4-(4,4,5,5-tetramethyl-1,3,2-dioxaborolan-2-yl)benzamide (3)

A solution of 2-acrylamido-4-bromo-N,N-dimethylbenzamide 2 (400 mg, 1.3 mmol) in 1,4-dioxane (4 mL) was treated with bis-pinacolatodiborane (410 mg, 1.6 mmol), potassium acetate (399 mg, 3.9 mmol) and [1,1'-bis(diphenylphosphino)ferrocene]dichloropalladium(II) complex with dichloromethane (55 mg, 0.06 mmol) at 110° C. for 8 h. After completion of the reaction, the solvent was removed under reduced pressure. The resulting residue was diluted with ethyl acetate and filtered through celite. The filtrate was concentrated under reduced pressure and the resulting residue was purified by silica gel column chromatography to afford 3 (450 mg, 97%) as a white solid. MS m/z (M+H): 345.2

Step 3:

(R)-3-chloro-10-methyl-9,10,11,12-tetrahydro-8H-[1,4]diazepino[5',6':4,5]thieno[3,2-f]quinolin-8-one (intermediate 11, Example 51; 100 mg, 0.7 mmol) in 1,4-dioxane/water (3:1; 8 mL) was treated with 2-acrylamido-N,N-dimethyl-4-(4,4,5,5-tetramethyl-1,3,2-dioxaborolan-2-yl)benzamide 3 (80 mg, 0.2 mmol), sodium carbonate (80 mg, 0.7 mmol) and tetrakis (triphenylphosphine) palladium (58 mg, 0.05 mmol). The resulting mixture was stirred at 110° C. for 6 h. After completion of the reaction, solvent was removed under reduced pressure. The residue obtained was diluted with dioxane and filtered through celite. The filtrate was concentrated under reduced pressure and triturated with diethyl ether. The resulting solid was purified by silica gel column chromatography to afford the desired product (22 mg, 14%) as a pale yellow solid. $^1$H NMR (400 MHz, DMSO-$d_6$): δ

1.19 (d, J=6.7 Hz, 3H), 2.88 (s, 3H), 2.97 (s, 3H), 3.47 (m, 2H), 3.60-3.61 (m, 1H), 5.78 (d, J=10.2 Hz, 1H), 6.26 (d, J=17.2 Hz, 1H), 6.52 (dd, J=10.2, 17.0 Hz, 1H), 7.15 (t, J=4.9 Hz, 1H), 7.47 (d, J=8.0 Hz, 1H), 8.01 (d, J=9.0 Hz, 1H), 8.07 (d, J=4.5 Hz, 1H), 8.12-8.15 (m, 2H), 8.22 (d, J=9.0 Hz, 1H), 8.53 (s, 1H), 9.26 (d, J=9.0 Hz, 1H), 9.96 (s, 1H). MS m/z (M+H): 500.5

Compound III-71

(R)-3-(1-acryloylindolin-7-yl)-10-methyl-9,10,11,12-tetrahydro-8H-[1,4]diazepino[5',6':4,5]thieno[3,2-f]quinolin-8-one Compound III-71 was prepared according to the schemes, steps, and intermediates below utilizing intermediate 11 from step 11 of Example 51 for step 2, below.

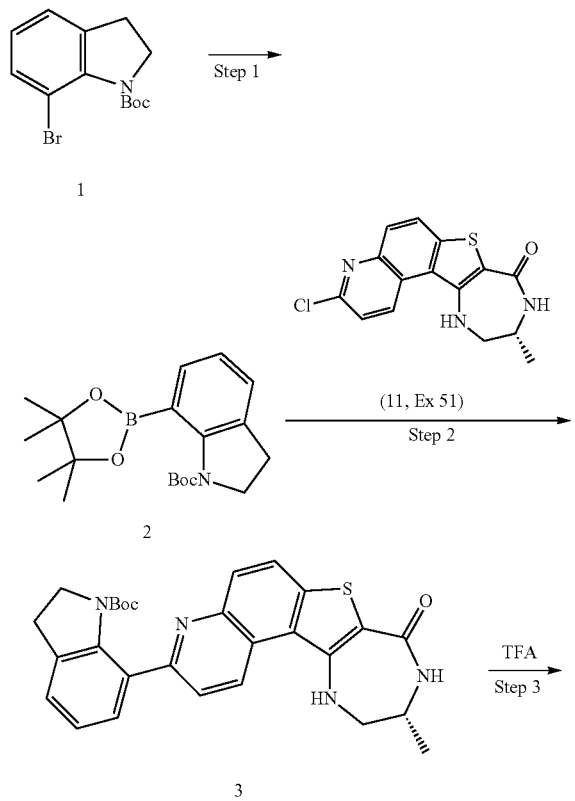

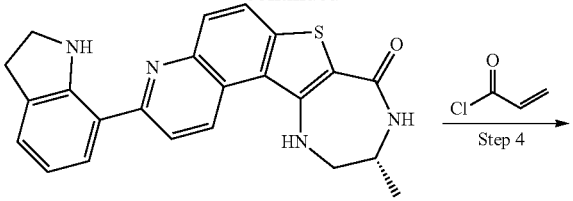

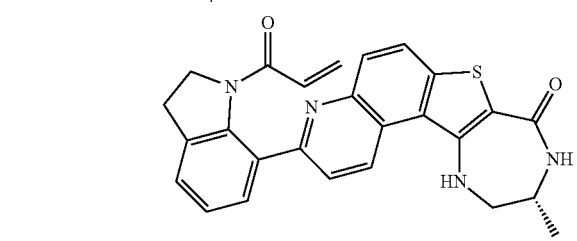

Step 1:

tert-butyl 7-(4,4,5,5-tetramethyl-1,3,2-dioxaborolan-2-yl)indoline-1-carboxylate (2)

A solution of tert-butyl 7-bromoindoline-1-carboxylate (300 mg, 1.0 mmol) in 1,4-dioxane (6.0 mL) was treated with bis-pinacolatodiborane (307 mg, 1.2 mmol), potassium acetate (297 mg, 3.0 mmol), and [1,1'-bis(diphenylphosphino)ferrocene]dichloropalladium(II) complex with dichloromethane (41 mg, 0.05 mmol) at 100° C. for 6 h. After completion of the reaction, the solvent was removed under reduced pressure. The resulting residue was diluted with ethyl acetate and filtered through celite. The filtrate was concentrated under reduced pressure and the residue obtained purified by silica gel column chromatography to afford 2 (260 mg, 75%) as a pale yellow liquid. MS m/z (M+H): 346.2.

Step 2:

Compound 3:

(R)-3-chloro-10-methyl-9,10,11,12-tetrahydro-8H-[1,4]diazepino [5',6':4,5]thieno[3,2-f]quinolin-8-one (intermediate 11, Example 51; 90 mg, 0.3 mmol) in 1,4-dioxane/water (3:1; 8 mL) was treated with tert-butyl 7-(4,4,5,5-tetramethyl-1,3,2-dioxaborolan-2-yl)indoline-1-carboxylate 2 (244 mg, 0.7 mmol), sodium carbonate (105 mg, 0.8 mmol), and tetrakis (triphenylphosphine) palladium (65 mg, 0.05 mmol). The resulting mixture was stirred at 100° C. for 6 h. After completion of the reaction, the solvent was removed under reduced pressure. The residue obtained was diluted with 10% methanol/chloroform and filtered through celite. The filtrate was concentrated under reduced pressure and the residue was purified by preparative TLC to afford 3 (150 mg, quantitative yield) as a yellow solid. MS m/z (M+H): 501.1.

Step 3:

Compound 4:

Compound 3 (150 mg, 0.3 mmol) was treated with excess trifluoroacetic acid in dichloromethane (3.0 mL) at 0° C. The reaction mixture was stirred at room temperature for 1 h. After completion of the reaction, the reaction mixture was concentrated under reduced pressure and co-distilled with dichloromethane. The residue obtained was triturated with pentane and diethyl ether to afford 4 (60 mg, 39%) as a brown solid. MS m/z (M+H): 401.1.

Step 4:

To a solution of Compound 4 (60 mg, 0.1 mmol) in acetone (6.0 mL), diisopropylethylamine (116 mg, 0.9 mmol) and acryloyl chloride (16 mg, 1.2 mmol) were added at room temperature and stirred for 30 min. After completion of the reaction, the solvent was removed under reduced pressure. The resulting residue was diluted with water and extracted with dichloromethane. The organic layer was dried over anhydrous sodium sulfate and concentrated in vacuo. The residue obtained was purified by preparative HPLC to afford the desired product (10 mg, 19%) as a yellow solid. $^1$H NMR (400 MHz, DMSO-$d_6$): δ 1.18 (d, J=5.9 Hz, 3H), 3.15 (m, 2H), 3.44 (m, 2H), 3.58 (m, 1H), 4.29 (brs, 2H), 5.68 (brs, 1H), 6.53 (brs, 1H), 7.06 (brs, 1H), 7.27 (t, J=7.5 Hz, 1H), 7.40 (d, J=6.6 Hz, 1H), 7.66 (m, 2H), 7.90 (d, J=9.1 Hz, 1H), 8.04 (d, J=7.0 Hz, 1H), 8.07 (s, 1H), 9.03 (d, J=8.5 Hz, 1H). MS m/z (M+H): 455.2

Compound III-72

(R)—N-(5-(10-methyl-8-oxo-9,10,11,12-tetrahydro-8H-[1,4]diazepino[5',6':4,5]thieno[3,2-f]quinolin-3-yl)-2-(1-(methylsulfonyl)piperidin-4-yl)phenyl)acrylamide

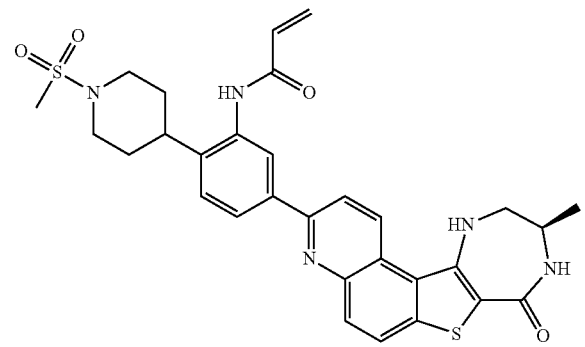 [SMILES: C=CC(=O)Nc1cc(-c2ccc3c(ccc4sc5c(c43)NC[C@@H](C)NC5=O)n2)ccc1C1CCN(S(C)(=O)=O)CC1]

Compound III-72 was prepared from compound III-67 according to the schemes and steps described below.

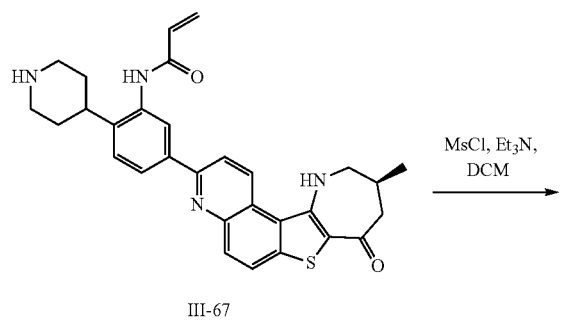

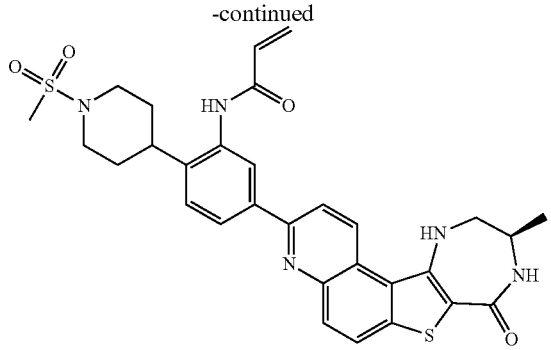

To a solution of III-67 (55 mg, 0.1 mmol) in dry dichloromethane (10 ml), triethylamine (27 mg, 0.3 mmol) and methanesulfonyl chloride (31 mg, 0.3 mmol) were added at 0° C. The resulting mixture was stirred at room temperature for 12 h. After completion of the reaction, the reaction mixture was diluted with dichloromethane and washed with water. The organic layer was dried over anhydrous sodium sulfate and concentrated under reduced pressure. The residue obtained was purified by preparative HPLC to afford the desired product (7.0 mg, 11%) as a pale yellow solid. $^1$H NMR (400 MHz, DMSO-$d_6$): δ 1.18 (d, J=6.7 Hz, 3H), 1.74 (m, 2H), 1.85 (m, 2H), 2.77 (t, J=11.7 Hz, 2H), 2.90 (brs, 4H), 3.46 (m, 2H), 3.60 (m, 1H), 3.70 (m, 2H), 5.80 (d, J=10.5 Hz, 1H), 6.28 (d, J=17.1 Hz, 1H), 6.57 (dd, J=10.3, 16.7 Hz, 1H), 7.14 (t, J=5.0 Hz, 1H), 7.55 (d, J=8.0 Hz, 1H), 8.00 (d, J=8.9 Hz, 1H), 8.05 (d, J=4.0 Hz, 1H), 8.12 (m, 2H), 8.18 (m, 2H), 9.22 (d, J=8.77 Hz, 1H), 9.84 (s, 1H). MS m/z (M+H): 590.2

Compound III-73

(R)-3-((5-fluoro-2-nitrophenyl)amino)-10-methyl-9,10,11,12-tetrahydro-8H-[1,4]diazepino[5',6':4,5]thieno[3,2-f]quinolin-8-one

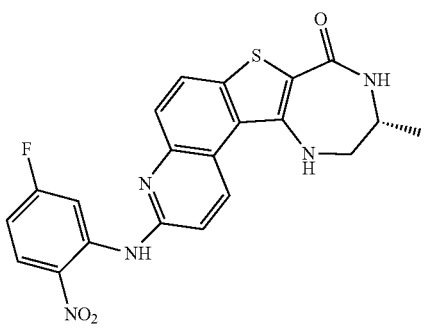 [SMILES: C[C@@H]1CNc2c(sc3ccc4nc(Nc5cc(F)ccc5[N+](=O)[O-])ccc4c23)C(=O)N1]

Compound III-73 can be prepared according to the schemes, steps, and intermediates below using intermediate 11 from step 11 of Example 51 as the starting material.

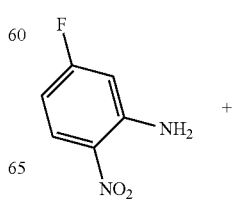

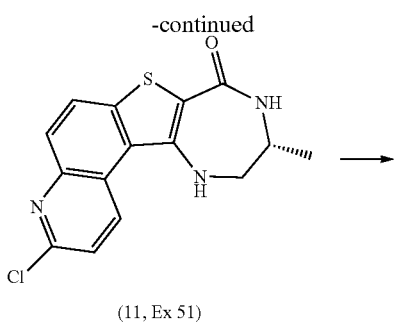

(11, Ex 51)

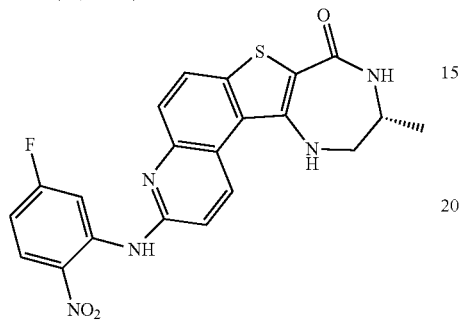

Intermediate 11 from Example 51 (120 mg, 0.4 mmol) in 1,4-dioxane (5 mL) was treated with 5-fluoro-2-nitroaniline (70 mg, 0.4 mmol), cesium carbonate (246 mg, 0.7 mmol), tris(dibenzylide-neacetone)dipalladium(0) (17 mg, 0.01 mmol) and xantphos (43 mg, 0.07 mmol). The reaction mixture was heated under microwave conditions at 130° C. for 1 h. After completion of the reaction, the reaction mixture was filtered through celite and the filtrate was concentrated under reduced pressure. The resulting residue was triturated with diethyl ether and further purified by preparative HPLC to afford the desired product (15 mg, 9%) as a pale brown solid. $^1$H NMR (400 MHz, DMSO-d$_6$): δ 1.18 (d, J=6.7 Hz, 3H), 3.44 (m, 2H), 3.57-3.59 (m, 1H), 7.00-7.04 (m, 2H), 7.47 (d, J=9.1 Hz, 1H), 7.73 (d, J=8.9 Hz, 1H), 8.02 (m, 2H), 8.24 (dd, J=6.0, 9.2 Hz, 1H), 8.73 (dd, J=2.6, 12.1 Hz, 1H), 9.07 (d, J=9.1 Hz, 1H), 10.26 (s, 1H). MS m/z (M+H): 438.2

Compound V-45

N-(1-acryloylindolin-6-yl)-1'-oxo-2',3'-dihydro-1'H-spiro[cyclobutane-1,4'-pyrazino[1,2-a]indole]-7'-carboxamide

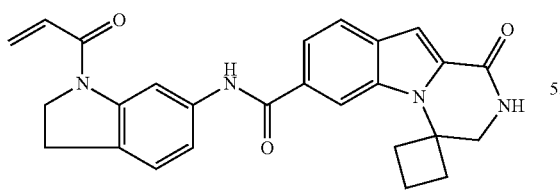

Compound V-45 was prepared as described in Example 78 by substituting INT-11 in step 8 of Example 78 with 1-(4-aminoisoindolin-2-yl)prop-2-en-1-one to give the desired product (24 mg, 18%) as an off white solid. $^1$H NMR (400 MHz, DMSO-d$_6$): δ 2.06 (m, 1H), 2.20 (m, 1H), 2.32 (m, 2H), 3.08 (m, 2H), 3.14 (t, J=8.4 Hz, 2H), 3.73 (s, 2H), 3.23 (t, J=8.4 Hz, 2H), 5.75-5.84 (dd, J=2.0 Hz, 10.4 Hz, 1H), 6.29-6.33 (dd, J=2.0 Hz, 16.8 Hz, 1H), 7.80-6.74 (dd, J=10.4 Hz, 16.8 Hz, 1H), 7.17 (s, 1H), 7.22 (d, J=8.0 Hz, 1H), 7.55 (d, J=8.0 Hz, 1H), 7.79 (m, 2H), 8.30 (s, 1H), 8.47 (s, 1H), 8.59 (s, 1H), 10.35 (s, 1H). MS m/z (M+H): 441.4.

Compound V-46

Cis-N-(2-acrylamidocyclohexyl)-1'-oxo-2',3'-dihydro-1'H-spiro[cyclobutane-1,4'-pyrazino[1,2-a]indole]-7'-carboxamide (racemic)

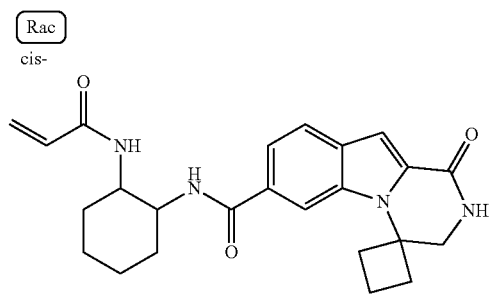 [SMILES: C=CC(=O)NC1CCCCC1NC(=O)c1ccc2cc3n(c2c1)C1(CCC1)CNC3=O]

Compound V-46 was prepared according to the schemes, steps, and intermediates described below using intermediate 7 from step 7 of Example 78 and racemic cis-cyclohexane-1,2-diamine as the starting materials.

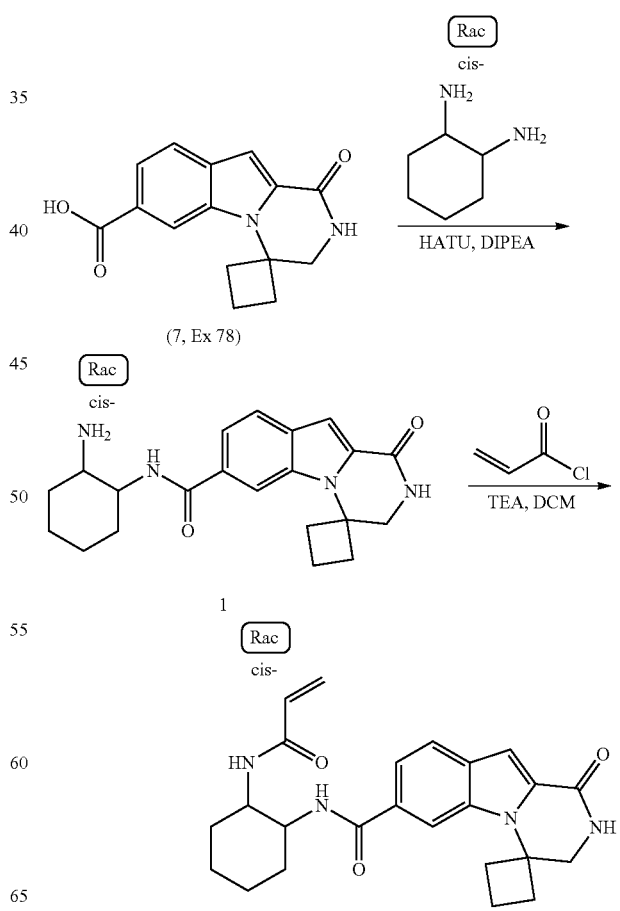

Cis-N-(2-aminocyclohexyl)-1'-oxo-2',3'-dihydro-1'H-spiro[cyclobutane-1,4'-pyrazino[1,2-a]indole]-7'-carboxamide (1): To a mixture of 1'-oxo-2',3'-dihydro-1'H-spiro[cyclobutane-1,4'-pyrazino[1,2-a]indole]-7'-carboxylic acid (intermediate 7, Example 78; 200 mg, 0.74 mmol), HATU (578 mg, 1.48 mmol) and DIPEA (287 mg, 2.2 mmol) in DCM (25.0 mL) was added (1R,2S)-cyclohexane-1,2-diamine (cis isomer, 84.4 mg, 0.74 mmol) and the resulting reaction mixture was stirred for 5 h at room temperature under nitrogen atmosphere. The reaction mixture was diluted with water (20 mL), the organic layer was separated and the aqueous layer was extracted with 10% MeOH/DCM (3×25 mL). Combined organic layers were dried over anhydrous sodium sulfate and concentrated under reduced pressure. The residue was purified by silica gel column chromatography to obtain impure 1 (220 mg, 60% pure). This material was taken to next step without any further purification. MS m/z (M+H): 367.4

To a stirred solution of crude N-((1S,2R)-2-aminocyclohexyl)-1'-oxo-2',3'-dihydro-1'H-spiro[cyclobutane-1,4'-pyrazino[1,2-a]indole]-7'-carboxamide (1) (220 mg, 0.6 mmol) in DCM (14 mL) was added acryloyl chloride (0.07 mL, 0.9 mmol) dropwise at 0° C. under nitrogen atmosphere. The resultant reaction mixture was brought to room temperature and stirred for 1 h. As no progress of the reaction was observed by TLC, Et$_3$N (1.37 mL, 1.49 mmol) was dropwise added at 0° C. and stirred at room temperature for 1 h. After consumption of the starting material, the reaction mixture was diluted with water (30 mL) and extracted with DCM (3×30 mL). The combined organic layers were dried over anhydrous sodium sulfate and concentrated under reduced pressure. The residue was purified by silica gel column chromatography to obtain the desired product (35 mg, 23%) as an off white solid. $^1$H NMR (400 MHz, CD$_3$OD): δ 1.58 (m, 2H), 1.82 (m, 6H), 2.04 (m, 1H), 2.33 (m, 2H), 2.49 (m, 1H), 3.18 (m, 2H), 3.80 (s, 2H), 4.22 (m, 1H), 4.42 (m, 1H), 5.63-5.66 (dd, J=2.0, 10.4 Hz, 1H), 6.20-6.24 (dd, J=2.0, 16.8 Hz, 1H), 6.38-6.44 (dd, J=10.4, 16.8 Hz, 1H), 7.25 (s, 1H), 7.54 (d, J=7.6 Hz, 1H), 7.73 (d, J=8.4 Hz, 1H), 8.41 (s, 1H). MS m/z (M+H): 421.3

Compound V-47

(S)—N-(1-acryloylpiperidin-3-yl)-1'-oxo-2',3'-dihydro-1'H-spiro[cyclobutane-1,4'-pyrazino[1,2-a]indole]-7'-carboxamide

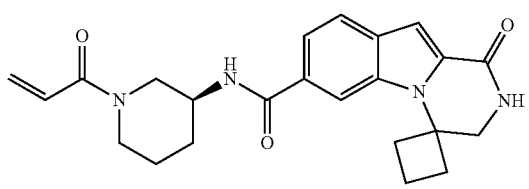 [SMILES: C=CC(=O)N1CCC[C@H](NC(=O)c2ccc3cc4n(c3c2)C2(CCC2)CNC4=O)C1]

Compound V-47 was prepared according to the schemes, steps, and intermediates described below using intermediate 7 from step 7 of Example 78 and (S)-tert-butyl 3-aminopiperidine-1-carboxylate as the starting materials.

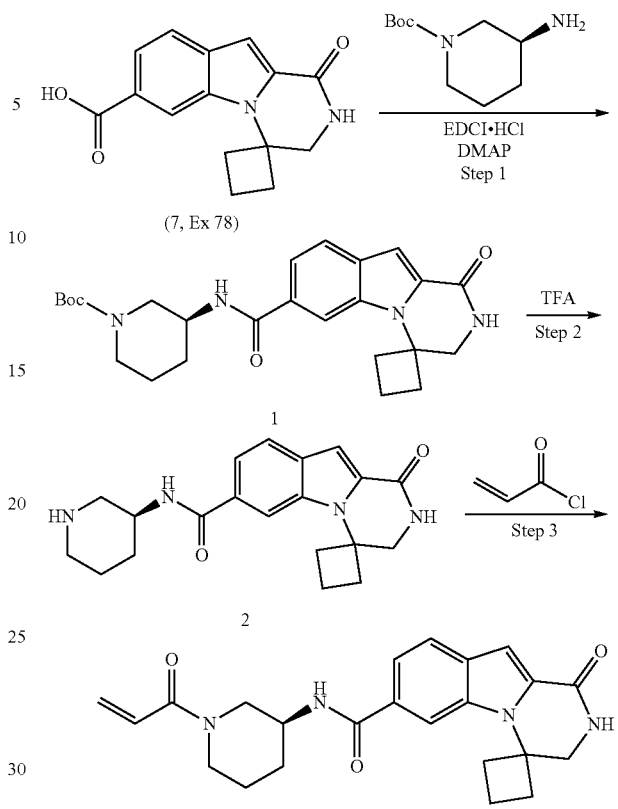

Step 1:

(S)-tert-butyl 3-(1'-oxo-2',3'-dihydro-1'H-spiro[cyclobutane-1,4'-pyrazino[1,2-a]indol]-7'-ylcarboxamido)piperidine-1-carboxylate (1)

To a mixture of 1'-oxo-2',3'-dihydro-1'H-spiro[cyclobutane-1,4'-pyrazino[1,2-a]indole]-7'-carboxylic acid (intermediate 7, Example 78; 150 mg, 0.55 mmol) and (S)-tert-butyl 3-aminopiperidine-1-carboxylate (111 mg, 0.55 mmol) in dry DMF (5.0 mL) were added DMAP (169 mg, 1.38 mmol) followed by EDCI. HCl (213 mg, 1.11 mmol). The resultant reaction mixture was stirred at room temperature under nitrogen atmosphere for 14 h. The reaction mixture was diluted with ice water (50 mL) and extracted with EtOAc (2×50 mL). The combined organic layers were further washed with brine solution (20 mL), dried over anhydrous sodium sulfate, and concentrated under reduced pressure. The residue was purified by silica gel column chromatography to obtain 1 (190 mg, 76%) as white solid. $^1$H NMR (500 MHz, DMSO-d$_6$): δ 1.37 (s, 9H), 1.45 (m, 2H), 1.60 (m, 1H), 1.73 (m, 1H), 1.90 (m, 1H), 2.07 (m, 3H), 2.30 (m, 2H), 2.98 (m, 2H), 3.70 (m, 3H), 3.81 (m, 2H), 7.13 (s, 1H), 7.63 (d, J=8.0 Hz, 1H), 7.74 (d, J=8.5 Hz, 1H), 8.30 (m, 2H), 8.35 (s, 1H). MS m/z (M+H): 453.0

Step 2:

(S)-1'-oxo-N-(piperidin-3-yl)-2',3'-dihydro-1'H-spiro[cyclobutane-1,4'-pyrazino[1,2-a]indole]-7'-carboxamide (2)

A solution of (S)-tert-butyl 3-(1'-oxo-2',3'-dihydro-1'H-spiro[cyclobutane-1,4'-pyrazino [1,2-a]indol]-7'-ylcarboxamido)piperidine-1-carboxylate (1) (190 mg, 0.42 mmol) in DCM (4 mL) was added TFA (0.64 mL, 8.4 mmol) dropwise at 0° C. under nitrogen atmosphere. After the addition, the resultant reaction mixture was brought to room temperature and stirred for 4 h. Volatiles were evaporated under reduced pressure. The obtained crude compound was washed with ether (2×10 mL) and dried under vacuum. The resultant material was further diluted with ice cold water (10 mL), adjusted pH to 8.0 using saturated NaHCO$_3$, and extracted with 10% n-BuOH/DCM (3×25 mL). The combined organic layers were dried over anhydrous sodium sulfate and concentrated under reduced pressure to obtain 2 (100 mg, 68%) as white solid. $^1$H NMR (400 MHz, DMSO-d$_6$): δ 1.49 (m, 2H), 1.67 (m, 1H), 1.89 (m, 1H), 2.06 (m, 1H), 2.16 (m, 1H), 2.32 (m, 2H), 2.46 (m, 1H), 2.87 (m, 1H), 3.00 (m, 3H), 3.36 (m, 2H), 3.71 (m, 2H), 3.90 (m, 1H), 7.14 (s, 1H), 7.63 (d, J=8.0 Hz, 1H), 7.71 (m, 1H), 8.23 (d, J=7.6 Hz, 1H), 8.28 (s, 1H), 8.36 (s, 1H). MS m/z (M+H): 353.2

Step 3:

To a stirred solution of (S)-1'-oxo-N-(piperidin-3-yl)-2', 3'-dihydro-1'H-spiro[cyclobutane-1,4'-pyrazino[1,2-a]indole]-7'-carboxamide (2) (100 mg, 0.28 mmol) in THF (4 mL) was added acryloyl chloride (0.04 mL, 0.56 mmol) in THF (2 mL) at −78° C. under argon atmosphere and stirred at −78° C. to room temperature and for 7 h. The resultant mixture was concentrated under reduced pressure, obtained crude was diluted 10% MeOH/DCM (3×10 mL) and purified by silica gel column chromatography to obtain the desired product (35 mg, 30%) as white solid. $^1$H NMR (400 MHz, DMSO-d$_6$): δ 1.45 (m, 1H), 1.72 (m, 2H), 2.03 (m, 2H), 2.18 (m, 1H), 2.31 (m, 2H), 2.50-3.15 (m, 4H), 3.47 (m, 2H), 3.85 (m, 1H), 3.96-4.40 (m, 2H), 5.66 (m, 1H), 6.09 (m, 1H), 6.74 (m, 1H), 7.14 (s, 1H), 7.62 (d, J=8.4 Hz, 1H), 7.75 (d, J=8.4 Hz, 1H), 8.32 (m, 2H), 8.36 (s, 1H). MS m/z (M+H): 407.3

Compound V-48

N-(2-acryloylisoindolin-4-yl)-1'-oxo-2',3'-dihydro-1'H-spiro[cyclobutane-1,4'-pyrazino [1,2-a]indole]-7'-carboxamide

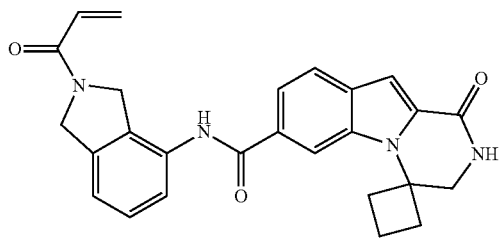 [SMILES: C=CC(=O)N1Cc2cccc(NC(=O)c3ccc4cc5n(c4c3)C3(CCC3)CNC5=O)c2C1]

Compound V-48 was prepared as described in Example 78 by substituting INT-11 in step 8 of Example 78 with 1-(4-aminoisoindolin-2-yl)prop-2-en-1-one (3, below) to obtain the desired product (100 mg, 51%) as white solid. $^1$H NMR (400 MHz, DMSO-d$_6$): δ 2.06 (m, 1H), 2.19 (m, 1H), 2.32 (m, 2H), 3.05 (m, 2H), 3.74 (m, 2H), 4.78 (m, 2H), 5.02 (m, 2H), 5.73 (m, 1H), 6.22 (m, 1H), 6.67 (m, 1H), 7.24 (m, 2H), 7.37 (m, 1H), 7.47 (m, 1H), 7.75 (d, J=8.0 Hz, 1H), 7.83 (d, J=8.4 Hz, 1H), 8.32 (s, 1H), 8.49 (s, 1H), 10.27 (s, 1H). MS m/z (M+H): 441.4.

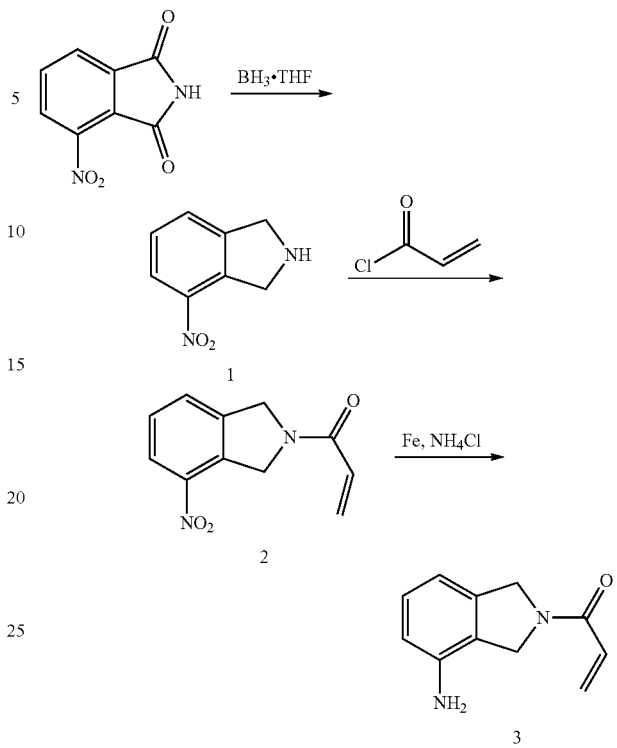

Step 1:

4-Nitroisoindoline (1)

To a solution of 4-nitroisoindoline-1,3-dione (1.0 g, 5.2 mmol) in dry THF (20 mL) was added 1M borane solution in THF (21.0 mL, 20.8 mmol) at 0° C. and then heated to 80-85° C. for 12 h. The reaction mixture was treated with MeOH (2 mL) and 6N HCl (5 mL) and refluxed for 1 h. The reaction mass was brought to room temperature and volatiles were removed under reduced pressure. The residue was dissolved in EtOAc (50 mL) and basified with saturated NaHCO$_3$ (10 mL). Organic layer was dried over anhydrous sodium sulfate and concentrated under reduced pressure. The residue was purified by silica gel column chromatography to obtain 1 (500 mg, 59%) as white solid. $^1$H NMR (500 MHz, DMSO-d$_6$): δ 4.15 (s, 2H), 4.45 (s, 2H), 7.49 (t, J=8.0 Hz, 1H), 7.71 (d, J=8.0 Hz, 2H), 8.02 (d, J=7.5 Hz, 1H).

Step 2:

1-(4-Nitroisoindolin-2-yl)prop-2-en-1-one (2)

A solution of 4-nitroisoindoline (1) (400 mg, 2.4 mmol) in DCM (10 mL) was cooled to 0° C. and acryloyl chloride (0.19 mL, 2.4 mmol) was added dropwise and stirred for 30 minutes. After completion of the reaction, saturated NaHCO$_3$ (10 mL) was added and extracted with DCM (2×10 mL). The combined organic layers were dried over anhydrous sodium sulfate and concentrated under reduced pressure. The residue was purified by silica gel column chromatography to obtain 2 (320 mg, 60%) as off white solid. $^1$H NMR (400 MHz, DMSO-d$_6$): δ 4.83 (s, 1H), 5.07 (s, 1H), 5.12 (s, 1H), 5.36 (s, 1H), 5.75-5.77 (dd, J=10.0, 12.4 Hz, 1H), 6.24 (m, 1H), 6.72 (m, 1H), 7.64 (t, J=8.4 Hz, 1H), 7.82 (m, 1H), 8.17 (d, J=8.4 Hz, 1H). MS m/z (M+H): 219.1

545

Step 3:

1-(4-aminoisoindolin-2-yl)prop-2-en-1-one (3): To a stirred solution of 1-(4-nitroisoindolin-2-yl)prop-2-en-1-one (2) (320 mg, 1.46 mmol) in EtOH:H$_2$O (8 mL:2 mL) were added iron powder (410 mg, 7.3 mmol) and ammonium chloride (785 mg, 1.46 mmol) and then heated to 100° C. for 5 h. The reaction mixture was filtered through a celite pad and volatiles were evaporated under reduced pressure. The residue was purified by silica gel column chromatography to obtain 3 (220 mg, 82%) as off white solid. $^1$H NMR (500 MHz, DMSO-d$_6$): δ 4.50 (s, 1H), 4.61 (s, 1H), 4.69 (s, 1H), 4.82 (s, 1H), 5.16 (s, 2H), 5.73 (m, 1H), 6.19-6.23 (dd, J=1.5, 17.5 Hz, 1H), 6.48 (m, 2H), 6.65 (m, 1H), 6.96 (m, 1H). MS m/z (M+H): 189.2

Compound V-49

Cis-N-(4-acrylamidotetrahydrofuran-3-yl)-1'-oxo-2',3'-dihydro-1'H-spiro[cyclobutane-1,4'-pyrazino[1,2-a]indole]-7'-carboxamide (racemic)

Compound V-49 was prepared according to the schemes, steps, and intermediates described below using intermediate 7 from step 7 of Example 78 and racemic tert-butyl cis-(4-aminotetrahydrofuran-3-yl)carbamate as starting materials.

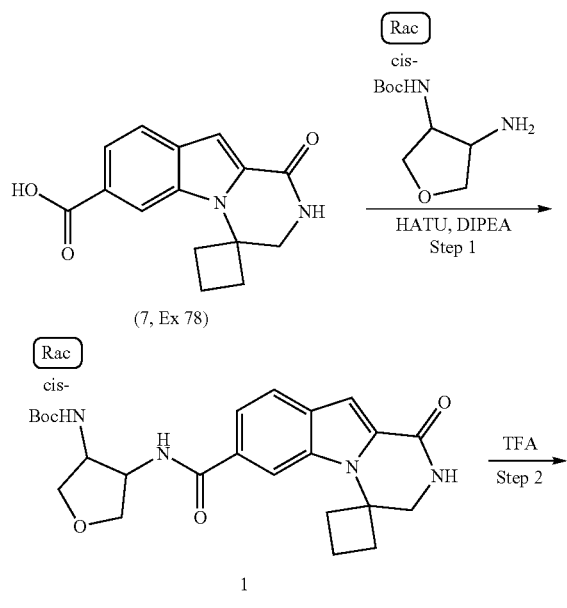

546

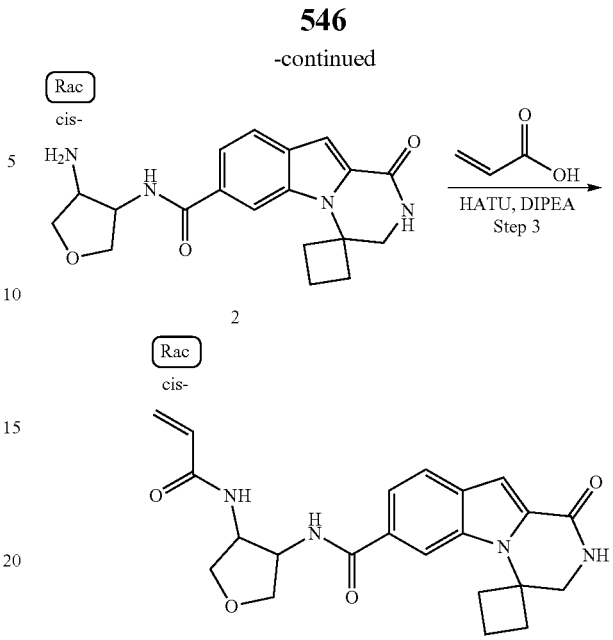

Step 1:

tert-butyl cis-4-(1'-oxo-2',3'-dihydro-1'H-spiro[cyclobutane-1,4'-pyrazino[1,2-a]indole]-7'-ylcarboxamido)tetrahydrofuran-3-ylcarbamate (1)

To a mixture of 1'-oxo-2',3'-dihydro-1'H-spiro[cyclobutane-1,4'-pyrazino[1,2-a]indole]-7'-carboxylic acid (intermediate 7, Example 78; 66 mg, 0.25 mmol) and tert-butyl cis-4-aminotetrahydrofuran-3-ylcarbamate (50 mg, 0.25 mmol) in dry DMF (4.0 mL) were added HATU (140 mg, 0.36 mmol) followed by DIPEA (0.13 mL, 0.75 mmol). The resultant reaction mixture was stirred at room temperature under nitrogen atmosphere for 14 h. The reaction mixture was diluted with ice water (50 mL) and extracted with EtOAc (2×50 mL). The combined organic layers were further washed with brine solution (20 mL), dried over anhydrous sodium sulfate, and concentrated under reduced pressure. The residue was purified by silica gel column chromatography (eluted with 0-15% MeOH in dichloromethane) to obtain 1 (80 mg, 70%) as white solid. MS m/z (M+H): 455.1

Step 2:

N-(cis-4-aminotetrahydrofuran-3-yl)-1'-oxo-2',3'-dihydro-1'H-spiro[cyclobutane-1,4'-pyrazino[1,2-a]indole]-7'-carboxamide (2)

A solution of Int-A (80 mg, 0.18 mmol) in DCM (4 mL) was added TFA (0.18 mL, 2.3 mmol) dropwise at 0° C. under nitrogen atmosphere. After the addition, the resultant reaction mixture was brought to room temperature and stirred for 4 h. Volatiles were evaporated under reduced pressure to obtain 2 as white solid which was used without further purification. MS m/z (M+H): 355.2

Step 3:

To a stirred solution of crude 2 in DMF (4 mL) was added HATU (68 mg, 0.18 mmol) and DIPEA (0.4 mL, 0.54 mmol), followed by the addition of 1 mL DMF solution of acrylic acid (13 mg, 0.18 mmol). The final mixture was stirred at rt overnight. The resultant mixture was concentrated under reduced pressure, and the obtained crude was purified by HPLC (10-90% CH$_3$CN in water modified with 4% TFA) to obtain the desired product (8 mg, 12% over two steps) as a white powder. $^1$H NMR (400 MHz, DMSO-d$_6$): δ 2.06 (m, 1H), 2.15 (m, 1H), 2.32 (m, 2H), 2.80-3.07 (m, 2H), 3.68-3.69 (m, 2H), 3.95-4.05 (m, 2H), 4.55 (m, 1H), 4.70 (m, 1H), 5.52 (d, 1H), 6.07 (d, 1H), 6.25 (dd, 1H), 7.11 (s, 1H), 7.55 (d, 1H), 7.72 (d, 1H), 8.15 (d, 1H), 8.20 (d, 1H), 8.27 (s, 1H), 8.29 (s, 1H). MS m/z (M+H): 409.3

Compound V-50

N-(4-acryloyl-2-methyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide (racemic)

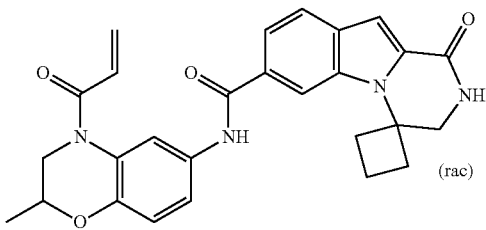 [SMILES: C=CC(=O)N1CC(C)Oc2ccc(NC(=O)c3ccc4cc5n(c4c3)C3(CCC3)CNC5=O)cc21]

Compound V-50 was prepared as described in Example 78 by substituting INT-11 in step 8 of Example 78 with racemic 1-(6-amino-2-methyl-2H-benzo[b][1,4]oxazin-4(3H)-yl)prop-2-en-1-one to give the desired product (40 mg, 42%) as an off white solid. 1H NMR (400 MHz, DMSO-d$_6$): δ 1.29 (d, 3H), 2.08 (m, 1H), 2.19 (m, 1H), 2.32 (m, 2H), 3.07 (m, 2H), 3.35 (m, 2H), 3.71 (s, 2H), 3.75 (m, 1H), 4.30 (m, 1H), 5.85 (d, 1H), 6.31 (d, 1H), 6.84-6.86 (m, 2H), 7.17 (s, 1H), 7.50 (d, 1H), 7.71 (m, 1H), 7.78 (d, 1H), 7.91 (bs, 1H), 8.28 (s, 1H), 8.43 (s, 1H), 10.29 (s, 1H). MS m/z (M+H): 471.1

Compound V-51

N-(4-acryloyl-2,2-dimethyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide

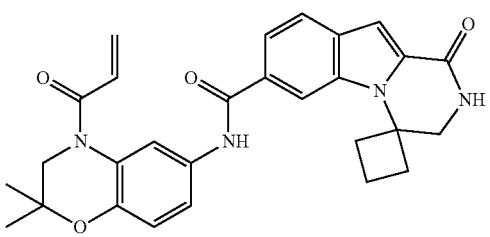 [SMILES: C=CC(=O)N1CC(C)(C)Oc2ccc(NC(=O)c3ccc4cc5n(c4c3)C3(CCC3)CNC5=O)cc21]

Compound V-51 was prepared as described in Example 78 by substituting INT-11 in step 8 of Example 78 with 1-(6-amino-2,2-dimethyl-2H-benzo[b][1,4]oxazin-4(3H)-yl)prop-2-en-1-one to give the desired product (30 mg, 31%) as an off white solid. $^1$H NMR (400 MHz, DMSO-d$_6$): δ 1,25 (s, 6H), 2.18 (m, 1H), 2.20 (m, 1H), 2.32 (m, 2H), 3.07 (m, 2H), 3.71 (s, 2H), 3.76 (m, 2H), 5.86 (d, 1H), 6.33 (d, 1H), 6.84-6.87 (m, 2H), 7.15 (s, 1H), 7.49 (d, 1H), 7.72 (d, 1H), 7.78 (d, 1H), 7.91 (bs, 1H), 8.28 (s, 1H), 8.43 (s, 1H), 10.28 (s, 1H). MS m/z (M+H): 485.3

Compound V-52

(R)—N-(1-(1'-oxo-2',3'-dihydro-1'H-spiro[cyclobutane-1,4'-pyrazino[1,2-a]indol]-7'-ylcarbonyl)piperidin-3-yl)acrylamide

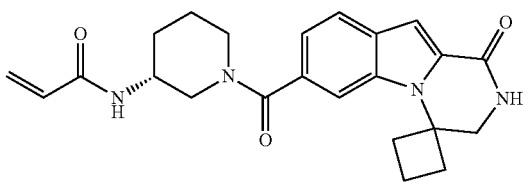 [SMILES: C=CC(=O)N[C@@H]1CCCN(C(=O)c2ccc3cc4n(c3c2)C2(CCC2)CNC4=O)C1]

Compound V-52 was prepared according to the schemes, steps, and intermediates described below using intermediate 7 from step 7 of Example 78 and (R)-tert-butyl piperidin-3-ylcarbamate as starting materials.

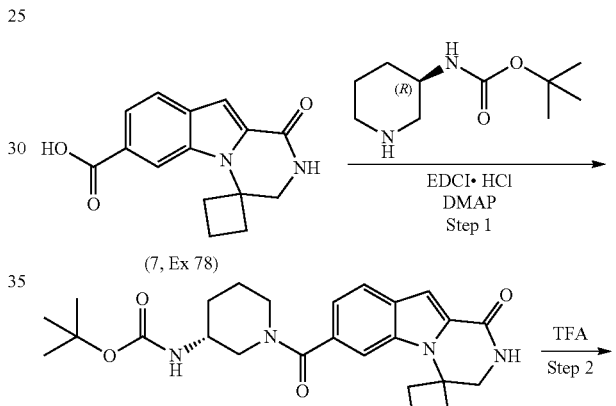

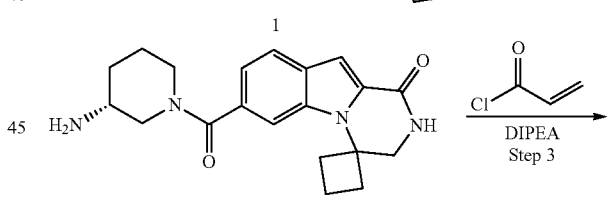

Step 1:

(R)-tert-Butyl (1-(1'-oxo-2',3'-dihydro-1'H-spiro[cyclobutane-1,4'-pyrazino[1,2-a]indol]-7'-ylcarbonyl)piperidin-3-yl)carbamate (1)

To a solution of 1'-oxo-2',3'-dihydro-1'H-spiro[cyclobutane-1,4'-pyrazino[1,2-a]indole]-7'-carboxylic acid (intermediate 7, Example 78; 74 mg, 0.27 mmol) in DCM (10 mL) were added EDCI.HCl (104 mg, 0.54 mmol) and DMAP (83 mg, 0.68 mmol) and stirred for 10 minutes. Then (R)-tertbutyl piperidin-3-ylcarbamate (54 mg, 0.27 mmol) was added and the reaction mixture was stirred at room temperature for 12 h. The reaction mixture was diluted with DCM (10 mL) and washed with citric acid (2×20 mL). The combined organic layers were dried over anhydrous sodium sulfate and concentrated under reduced pressure. The residue was purified by silica gel column chromatography to obtain 1 (50 mg, 40%) as an off white solid. 1H NMR (400 MHz, DMSO-$d_6$): δ 1.25 (s, 9H), 1.88 (m, 2H), 2.02 (m, 2H), 2.18 (m, 2H), 2.27 (m, 2H), 2.64 (m, 2H), 2.95 (m, 4H), 3.45 (m, 1H), 3.69 (s, 2H), 6.93 (s, 1H), 7.13 (s, 1H), 7.16 (d, J=8.0 Hz, 1H), 7.73 (d, J=8.0 Hz, 1H), 7.94 (s, 1H), 8.25 (s, 1H). MS m/z (M+H): 453.5

Step 2:

(R)-7'-(3-aminopiperidine-1-carbonyl)-2',3'-dihydro-1'H-spiro[cyclobutane-1,4'-pyrazino[1,2-a]indol]-1'-one (2)

A solution of ((R)-tert-butyl (1-(1'-oxo-2',3'-dihydro-1'H-spiro[cyclobutane-1,4'-pyrazino[1,2-a]indol]-7'-ylcarbonyl)piperidin-3-yl)carbamate (2) (180 mg, 0.39 mmol) in DCM (10 mL) was added TFA (1.0 mL, 7.96 mmol) dropwise at 0° C. After the addition, the resultant reaction mixture was brought to room temperature and stirred for 3 h. Volatiles were evaporated under reduced pressure. The obtained crude compound was triturated with $Et_2O$ to obtain 2 (150 mg) which was taken to next step without any purification. MS m/z (M+H): 353.2

Step 3:

A solution of (R)-7'-(3-aminopiperidine-1-carbonyl)-2',3'-dihydro-1'H-spiro[cyclobutane-1,4'-pyrazino[1,2-a]indol]-1'-one (Int-B) (130 mg, 0.36 mmol) in DCM (20 mL) was added DIPEA (0.2 mL, 1.1 mmol) at 0° C. and stirred for 5 minutes. Then acryloyl chloride (0.03 mL, 0.4 mmol) was added and stirred for 1 h. The reaction mixture was diluted with DCM (10 mL) and washed with saturated $NaHCO_3$ (2×30 mL). The organic layer was dried over anhydrous sodium sulfate and concentrated under reduced pressure. The obtained residue was purified by preparative HPLC purification to obtain the desired product (15 mg, 10%) as an off white solid. 1H NMR (400 MHz, DMSO-$d_6$): δ 1.53 (m, 2H), 1.76 (m, 1H), 2.01 (m, 1H), 2.04 (m, 1H), 2.14 (m, 1H), 2.27 (m, 2H), 2.93 (m, 4H), 3.69 (m, 3H), 3.83 (s, 2H), 5.55 (m, 1H), 6.03 (m, 1H), 6.23 (m, 1H), 7.13 (s, 2H), 7.71 (d, J=8.0 Hz, 1H), 7.95 (s, 1H), 8.08 (m, 1H), 8.23 (s, 1H). MS m/z (M+H): 407.5

Compound V-53

N-(3-acrylamido-4-methylphenyl)-1'-oxo-2',3'-dihydro-1'H-spiro[cyclobutane-1,4'-pyrazino[1,2-a]indole]-7'-carboxamide

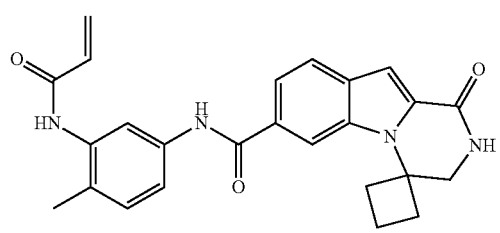 [SMILES: C=CC(=O)Nc1cc(NC(=O)c2ccc3cc4n(c3c2)C2(CCC2)CNC4=O)ccc1C]

Compound V-53 was prepared as described in Example 78 by substituting INT-11 in step 8 of Example 78 with N-(5-amino-2-methylphenyl)acrylamide to give the desired product (35 mg, 22%) as light green solid. $^1$H NMR (500 MHz, DMSO-$d_6$): δ 2.05 (m, 2H), 2.18 (s, 3H), 2.31 (m, 2H), 3.02 (m, 2H), 3.72 (s, 2H), 5.74 (m, 1H), 6.24 (m, 1H), 6.52 (m, 1H), 7.16 (s, 1H), 7.20 (m, 1H), 7.56 (m, 1H), 7.75 (m, 2H), 7.95 (s, 1H), 8.30 (s, 1H), 8.45 (s, 1H), 9.50 (s, 1H), 10.30 (s, 1H). MS m/z (M+H): 429.4

Compound V-54

N-(3-acrylamido-4-fluorophenyl)-1'-oxo-2',3'-dihydro-1'H-spiro[cyclobutane-1,4'-pyrazino[1,2-a]indole]-7'-carboxamide

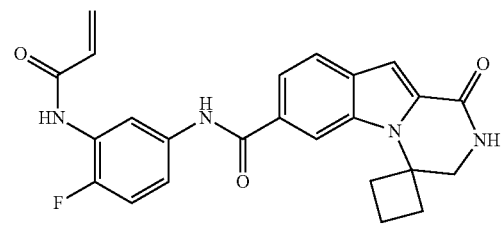 [SMILES: C=CC(=O)Nc1cc(NC(=O)c2ccc3cc4n(c3c2)C2(CCC2)CNC4=O)ccc1F]

Compound V-54 was prepared according to the schemes, steps, and intermediates described below using intermediate 7 from step 7 of Example 78 and 4-fluoro-3-nitroaniline as the starting materials.

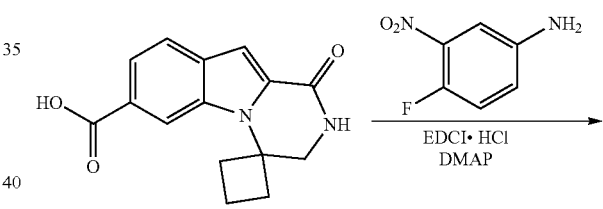

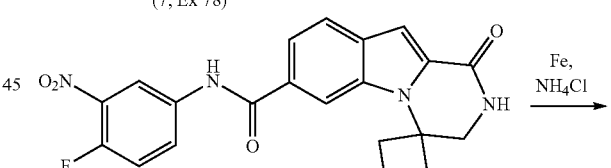

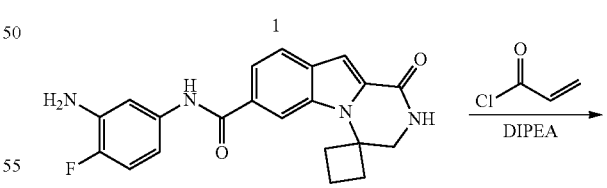

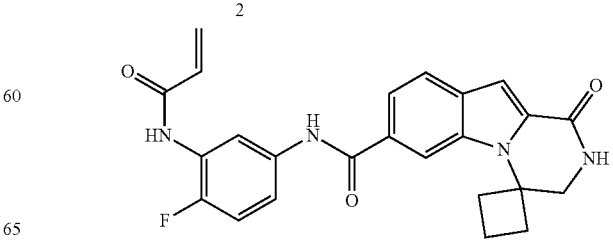

Step 1:

N-(4-Fluoro-3-nitrophenyl)-1'-oxo-2',3'-dihydro-1'H-spiro[cyclobutane-1,4'-pyrazino[1,2-a]indole]-7'-carboxamide (1)

To a solution of 1'-oxo-2',3'-dihydro-1'H-spiro[cyclobutane-1,4'-pyrazino[1,2-a]indole]-7'-carboxylic acid (intermediate 7, Example 78; 100 mg, 0.37 mmol) in DCM (10 mL) were added EDCI. HCl (142 mg, 0.74 mmol) and DMAP (114 mg, 0.92 mmol) at room temperature and stirred for 30 minutes. Then 4-fluoro-3-nitroaniline (58 mg, 0.37 mmol) was added and the reaction mixture was stirred at room temperature for 16 h. The reaction mixture was diluted with cold water (10 mL) and extracted with DCM (2×50 mL). The combined organic layers were washed with 10% citric acid, brine solution, dried over anhydrous sodium sulfate, and concentrated under reduced pressure. The residue was purified by silica gel column chromatography to obtain 1 (100 mg, 66%) as an off white solid. $^1$H NMR (400 MHz, DMSO-$d_6$): δ 2.04 (m, 1H), 2.22 (m, 1H), 2.33 (m, 2H), 3.02 (m, 2H), 3.74 (d, J=2.4 Hz, 2H), 7.19 (s, 1H), 7.63 (m, 1H), 7.77 (d, J=8.8 Hz, 1H), 7.85 (d, J=8.4 Hz, 1H), 8.17 (m, 1H), 8.34 (s, 1H), 8.50 (s, 1H), 8.73 (m, 1H), 10.75 (s, 1H). MS m/z (M+H): 409.2

Step 2:

N-(3-Amino-4-fluorophenyl)-1'-oxo-2',3'-dihydro-1'H-spiro[cyclobutane-1,4'-pyrazino[1,2-a]indole]-7'-carboxamide (2)

To a stirred solution of N-(4-fluoro-3-nitrophenyl)-1'-oxo-2',3'-dihydro-1'H-spiro[cyclobutane-1,4'-pyrazino[1,2-a]indole]-7'-carboxamide (1) (100 mg, 0.24 mmol) in EtOH:H$_2$O (8 mL:2 mL) were added iron powder (68 mg, 1.22 mmol) and ammonium chloride (131 mg, 2.45 mmol) and then heated to reflux for 5 h. The reaction mixture was diluted with 10% MeOH/DCM, filtered through a celite pad, and volatiles were evaporated under reduced pressure. The residue was taken into water, stirred for 10 minutes and filtered the solid to obtain 2 (70 mg, 76%) as an off white solid. $^1$H NMR (400 MHz, DMSO-$d_6$): δ 2.04 (m, 2H), 2.30 (m, 2H), 3.03 (m, 2H), 3.72 (s, 2H), 5.51 (s, 2H), 6.91 (m, 2H), 7.15 (s, 1H), 7.29 (m, 1H), 7.71 (m, 2H), 8.29 (s, 1H), 8.42 (s, 1H), 10.10 (s, 1H). MS m/z (M+H): 379.2

Step 3:

A solution of N-(3-amino-4-fluorophenyl)-1'-oxo-2',3'-dihydro-1'H-spiro[cyclobutane-1,4'-pyrazino[1,2-a]indole]-7'-carboxamide (2) (70 mg, 0.18 mmol) in dry THF (5 mL) was added acryloyl chloride (0.19 mL, 2.4 mmol) at −78° C. under inert atmosphere. The resultant reaction mixture was allowed to 0° C. and stirred for 1 h. The reaction mixture was diluted with water (10 mL) and extracted with EtOAc (2×20 mL). The combined organic layers were further washed with saturated NaHCO$_3$ (10 mL), dried over anhydrous sodium sulfate, and concentrated under reduced pressure. The obtained residue was suspended in THF (3 mL) and treated with DBU (0.1 mL) for 3 h. Volatiles were evaporated and the residue was purified by silica gel column chromatography to obtain the desired product (50 mg, 63%) as an off white solid. $^1$H NMR (400 MHz, DMSO-$d_6$): δ 2.06 (m, 1H), 2.19 (m, 1H), 2.32 (m, 2H), 3.03 (m, 2H), 3.74 (d, J=2.4 Hz, 2H), 5.77-5.80 (dd, J=1.6, 10.4 Hz, 1H), 6.27-6.31 (dd, J=1.6, 16.8 Hz, 1H), 6.59-6.66 (dd, J=10.0, 16.8 Hz, 1H), 7.18 (s, 1H), 7.27 (m, 1H), 7.62 (m, 1H), 7.76 (m, 2H), 8.29 (s, 1H), 8.45 (m, 2H), 9.93 (s, 1H), 10.40 (s, 1H). MS m/z (M+H): 433.4

Compound V-55

N-cis-(2-acrylamidocyclopentyl)-1'-oxo-2',3'-dihydro-1'H-spiro[cyclobutane-1,4'-pyrazino[1,2-a]indole]-7'-carboxamide (racemic)

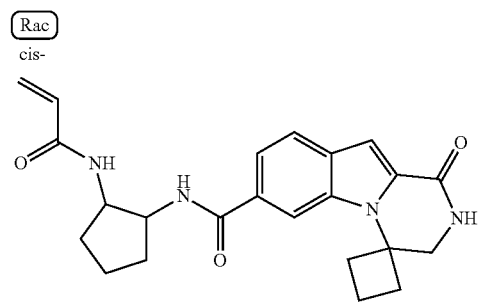 [SMILES: C=CC(=O)NC1CCCC1NC(=O)c1ccc2cc3n(c2c1)C1(CCC1)CNC3=O]

Compound V-55 was prepared according to the schemes, steps, and intermediates described below using intermediate 7 from step 7 of Example 78 in step 6, below.

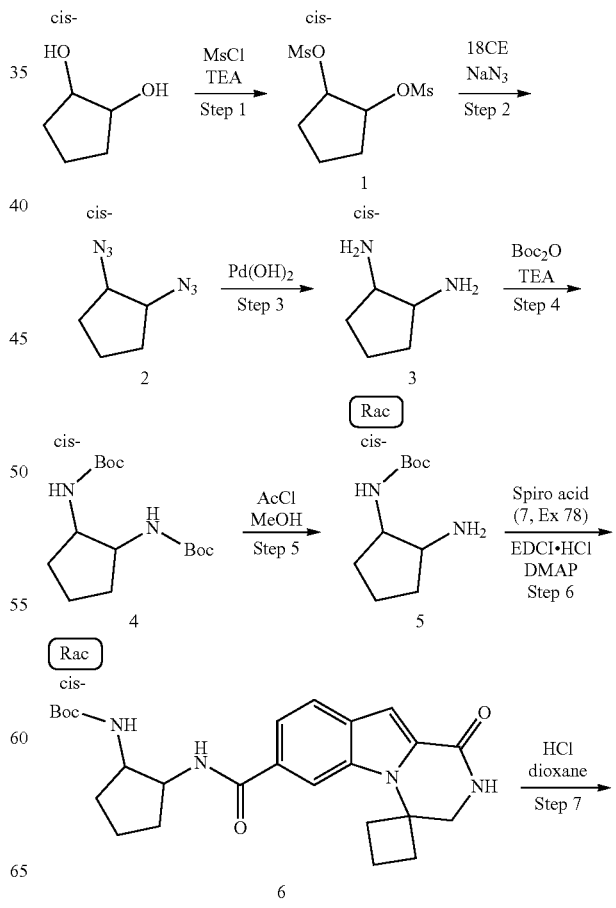

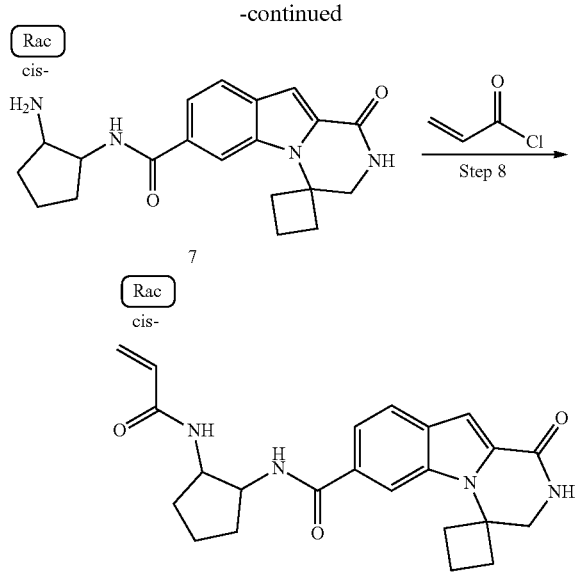

Step 1:

cis-Cyclopentane-1, 2-diyl dimethanesulfonate (1)

To a stirred solution of cis-cyclopentane-1, 2-diol (3 g, 29.41 mmol) in $CH_2Cl_2$ (100 mL) under argon atmosphere was added triethyl amine (14.85 g, 147 mmol) at 0° C. and stirred for 15 min. Then mesyl chloride (10.14 g, 88.23 mmol) was added to the reaction mass dropwise over 15 min and stirred for 3 h. The reaction was monitored by TLC; after completion of the reaction, the reaction mixture was diluted with water (150 mL) and extracted with $CH_2Cl_2$ (2×50 mL). The combined organic extracts were washed with brine solution (50 mL), dried over sodium sulfate, filtered and concentrated in vacuo to obtain the crude compound 1 (6.2 g) as brown solid. The crude was carried to the next step without any further purification. 1H NMR (400 MHz, CDCl3): δ 1.69 (m, 1H), 2.03 (m, 5H), 3.11 (s, 6H), 5.01 (m, 2H).

Step 2:

cis-1, 2-Diazidocyclopentane (2)

To a stirred solution of cis-cyclopentane-1, 2-diyl dimethanesulfonate (1) (6 g, 23.25 mmol) in DMF (60 mL) under argon atmosphere were added sodium azide (3.02 g, 46.51 mmol) and 15-crown-5-ether (513 mg, 2.32 mmol) at RT and then heated to 80° C. and stirred for 16 h. The reaction was monitored by TLC; after completion of the reaction, the reaction mixture was diluted with ice cold water (100 mL) and extracted with ether (3×100 mL). The combined organic extracts were washed with brine solution (50 mL), dried over sodium sulfate, filtered, and concentrated in vacuo to obtain the crude. The crude was purified through silica gel column chromatography to afford 2 (2.5 mg, 71%) as colorless liquid. $^1$H NMR (500 MHz, CDCl$_3$): δ 1.65 (m, 1H), 1.87 (m, 2H), 1.93 (s, 3H), 3.82 (m, 2H).

Step 3:

cis-Cyclopentane-1,2-diamine dihydrochloride (3)

To a stirred solution of (1R, 2S)-1,2-diazidocyclopentane (2) (2.5 g, 16.44 mmol) in methanol: 2 N HCl (1:1, 100 mL) under argon atmosphere was added 20% palladium hydroxide (1.5 g) at RT and stirred under hydrogen atmosphere (balloon pressure) for 16 h. The reaction was monitored by TLC; after completion of the reaction, the reaction mixture was filtered through celite and the filtrate was concentrated in vacuo. The residue was diluted with methanol and precipitated by adding EtOAc. The residue was filtered to obtain 3 (900 mg, 32%) as an off white solid. $^1$H NMR (500 MHz, D20): δ 1.94 (m, 4H), 2.30 (m, 2H), 3.94 (m, 2H), MS m/z (M+H): 101.5

Step 4:

Di-tert-butyl cis-cyclopentane-1,2-diyldicarbamate (4)

To a stirred solution of compound cis-cyclopentane-1,2-diamine dihydrochloride (3) (500 mg, 2.89 mmol) in $CH_2Cl_2$ (20 mL) under argon atmosphere was added triethyl amine (1.62 mL, 11.56 mmol) at 0° C. and stirred for 15 min. Then boc-anhydride (1.51 g, 6.93 mmol) was added to the reaction mass; warmed to RT and stirred for 16 h. The reaction was monitored by TLC; after completion of the reaction, the reaction mixture was diluted with water (20 mL) and extracted with $CH_2Cl_2$ (2×25 mL). The combined organic extracts were washed with 10% citric acid solution (20 mL), brine solution (15 mL), dried over sodium sulfate, filtered, and concentrated in vacuo to obtain the crude. The crude was triturated with n-hexane (2×10 mL) to afford 4 (600 mg, 69%) as an off white solid. $^1$H NMR (500 MHz, DMSO-d$_6$): δ 1.36 (s, 18H), 1.47 (m, 3H), 1.57 (m, 1H), 1.73 (m, 2H), 3.76 (m, 2H), 6.18 (br s, 1H), 6.30 (d, J=4.0 Hz, 1H).

Step 5:

tert-Butyl cis-(2-aminocyclopentyl) carbamate hydrochloride (5)

To a stirred solution of di-tert-butyl cis-cyclopentane-1, 2-diyldicarbamate (4) (300 mg, 1.00 mmol) in methanol (10 mL) under argon atmosphere was added acetyl chloride (94 mg, 1.20 mmol) at 0° C. and stirred for 1 h. The reaction was monitored by TLC; after completion of the reaction, the volatiles were removed in vacuo to obtain the crude. The crude was triturated with diethyl ether (4×10 mL) and dried in vacuo to afford 5 (100 mg, 50%) as white solid. 1H NMR (400 MHz, DMSO-d$_6$): δ 1.40 (s, 9H), 1.72 (m, 1H), 1.78 (m, 3H), 1.92 (m, 2H), 3.39 (m, 1H), 3.92 (m, 1H), 6.91 (d, J=8.0 Hz, 1H), 7.30 (m, 1H), MS m/z (M+H): 201.1.

Step 6:

tert-Butyl cis-2-(1'-oxo-2',3'-dihydro-1'H-spiro[cyclobutane-1, 4'-pyrazino [1, 2-a]indol]-7'-ylcarboxamido) cyclopentyl) carbamate (6)

To a stirred solution of tert-butyl cis-2-aminocyclopentyl) carbamate hydrochloride (5) (114 mg, 0.42 mmol) in DMF (5 mL) under argon atmosphere were added 1'-oxo-2',3'-dihydro-1'H-spiro[cyclobutane-1, 4'-pyrazino [1, 2-a]indole]-7'-carboxylic acid (7, Ex 78; 100 mg, 0.42 mmol), and HATU (193 mg, 0.50 mmol) at RT and stirred for 15 min. Then DIPEA (0.23 mL, 1.27 mmol) was added to the reaction mass and stirred for 16 h. The reaction was monitored by TLC; after completion of the reaction, the reaction mixture was diluted with water (20 mL) and extracted with EtOAc (2×25 mL). The combined organic extracts were washed with brine solution (20 mL), dried over sodium sulfate, filtered, and concentrated in vacuo to obtain the crude. The crude was purified through silica gel column chromatography afford 6 (100 mg, 52%) as white solid. $^1$H NMR (400 MHz, DMSO-$d_6$): δ 1.31 (s, 9H), 1.37 (m, 2H), 1.62 (m, 1H), 1.68 (m, 2H), 1.90 (m, 2H), 2.04 (m, 1H), 2.19 (m, 1H), 2.32 (m, 2H), 2.94 (m, 3H), 3.71 (s, 1H), 3.93 (m, 1H), 4.32 (m, 1H), 7.15 (s, 1H), 7.59 (d, J=8.0 Hz, 1H), 7.56 (d, J=8.0 Hz, 1H), 7.90 (m, 1H), 8.28 (s, 1H), 8.35 (s, 1H), MS m/z (M+H): 453.6.

Step 7:

N-cis-(2-Aminocyclopentyl)-1'-oxo-2',3'-dihydro-1'H-spiro[cyclobutane-1, 4'-pyrazino [1, 2-a]indole]-7'-carboxamide (7)

A stirred solution of tert-butyl cis-2-(1'-oxo-2', 3'-dihydro-1'H-spiro[cyclobutane-1, 4'-pyrazino [1, 2-a]indol]-7'-ylcarboxamido) cyclopentyl) carbamate (6) (100 mg, 0.22 mmol) in 3 N HCl in dioxane (5 mL) under argon atmosphere was stirred at RT for 2 h. The reaction was monitored by TLC; after completion of the reaction, the volatiles were removed in vacuo. The residue was triturated with diethyl ether (2×10 mL) to afford 7 (80 mg, 93% as HCl salt) as an off white solid. 1H NMR (400 MHz, DMSO-$d_6$): δ 1.29 (m, 1H), 1.80 (m, 3H), 1.97 (m, 2H), 2.19 (m, 2H), 3.04 (m, 2H), 3.56 (m, 2H), 3.37 (m, 1H), 3.66 (m, 2H), 4.48 (m, 1H), 7.15 (s, 1H), 7.75 (m, 2H), 7.98 (br s, 2H), 8.30 (s, 1H), 8.47 (m, 1H), 8.56 (m, 1H), MS m/z (M+H): 353.4.

Step 8:

To a stirred solution of N-cis-2-aminocyclopentyl)-1'-oxo-2',3'-dihydro-1'H-spiro [cyclobutane-1, 4'-pyrazino [1, 2-a]indole]-7'-carboxamide (7) (80 mg, 0.20 mmol) in THF (4 mL) under argon atmosphere was added DIPEA (110 μL, 0.61 mmol) and stirred for 15 min. Then acryloyl chloride (22 mg, 0.24 mmol) in THF (1 mL) was added to the reaction mass at -78° C. and stirred for 3 h. The reaction was monitored by TLC; after completion of the reaction, the reaction mixture was quenched with saturated NaHCO$_3$ solution (15 mL) and extracted with EtOAc (3×20 mL). The combined organic extracts were dried over sodium sulfate, filtered, and concentrated in vacuo to obtain the crude. The crude was suspended in CH$_2$Cl$_2$ (15 mL) and filtered. The obtained solid was triturated with hexanes (2×5 mL) and dried in vacuo to afford the desired product (40 mg, 48%) as white solid. $^1$H NMR (500 MHz, DMSO-$d_6$): δ 1.58 (m, 1H), 1.71 (m, 2H), 1.78 (m, 1H), 1.98 (m, 3H), 2.16 (m, 1H), 2.29 (m, 2H), 2.96 (m, 2H), 3.71 (m, 2H), 4.31 (m, 2H), 5.55 (m, 1H), 6.04 (m, 1H), 6.25 (m, 1H), 7.13 (s, 1H), 7.56 (d, J=8.0 Hz, 1H), 7.73 (d, J=8.0 Hz, 1H), 7.88 (d, J=8.0 Hz, 1H), 8.05 (d, J=7.5 Hz, 1H), 8.27 (m, 2H), MS m/z (M+H): 407.3

Compound V-56

N-trans-(2-acrylamidocyclopentyl)-1'-oxo-2',3'-dihydro-1'H-spiro[cyclobutane-1,4'-pyrazino[1,2-a]indole]-7'-carboxamide (racemic)

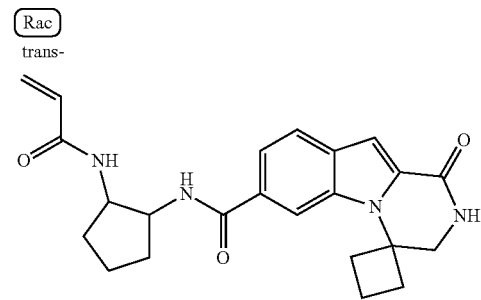 [SMILES: C=CC(=O)NC1CCCC1NC(=O)c1ccc2cc3n(c2c1)C1(CCC1)CNC3=O]

Compound V-56 was prepared according to the schemes, steps, and intermediates described below using intermediate 7 from step 7 of Example 78 in step 7, below.

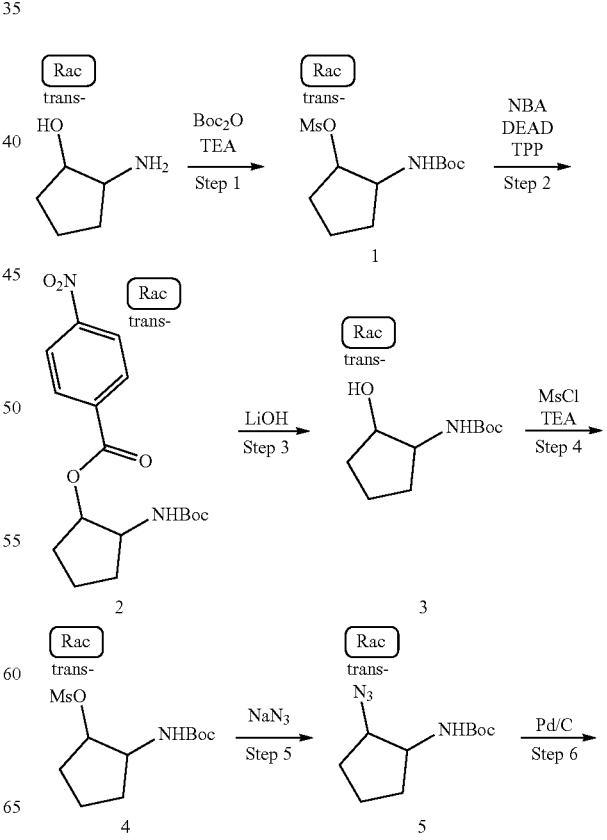

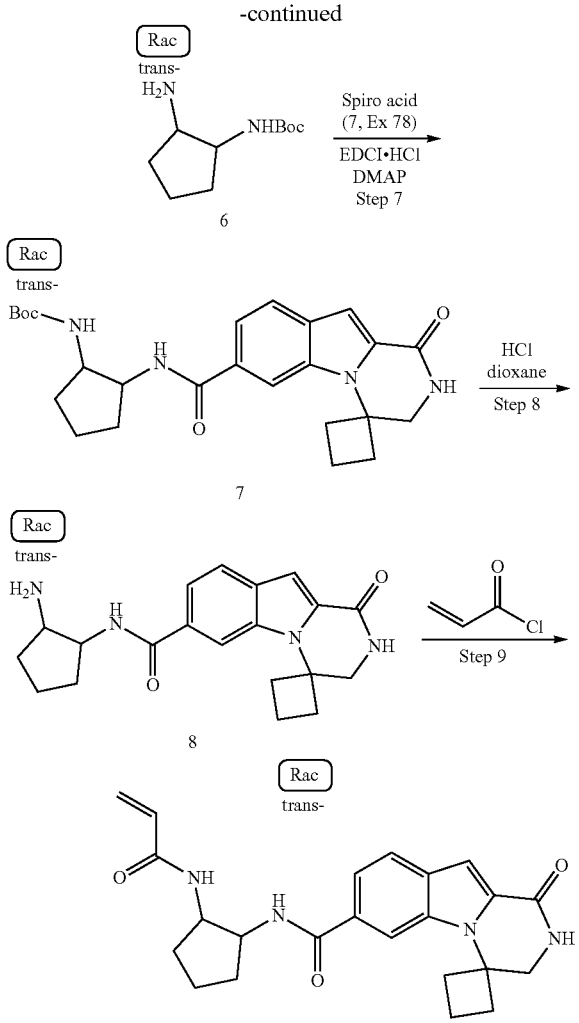

Step 1:

tert-Butyl trans-(2-hydroxycyclopentyl) carbamate (1)

To a stirred solution of trans-2-aminocyclopentanol (1 g, 7.26 mmol) in $CH_2Cl_2$:THF (9:1, 10 mL) under argon atmosphere were added boc-anhydride (1.9 g, 8.72 mmol) and triethyl amine (1.1 g, 10.90 mmol) at 0° C.; warmed to RT and stirred for 2 h. The reaction was monitored by TLC; after completion of the reaction, the solvents were removed in vacuo. The residue was diluted with saturated $NaHCO_3$ solution (15 mL) and extracted with $CH_2Cl_2$ (2×20 mL). The combined organic extracts were dried over anhydrous sodium sulfate, filtered, and concentrated in vacuo to obtain the crude. The crude was purified by silica gel column chromatography to obtain 1 (1.2 g, 82%) as colorless oil. $^1$H NMR (400 MHz, DMSO-$d_6$): δ 1.32 (s, 9H), 1.37 (m, 3H), 1.55 (m, 2H), 1.75 (m, 1H), 1.87 (m, 1H), 3.48 (m, 1H), 3.76 (m, 1H), 4.56 (d, J=4.0 Hz, 1H).

Step 2:

trans-(2-((tert-Butoxycarbonyl) amino) cyclopentyl 4-nitrobenzoate (2)

To a stirred solution of tert-butyl trans-(2-hydroxycyclopentyl) carbamate (1) (100 mg, 0.49 mmol) in dry THF (10 mL) under argon atmosphere were added TPP (200 mg, 0.79 mmol), p-nitro benzoic acid (133 mg, 0.79 mmol), and DEAD (137 mg, 0.79 mmol) at 0° C. The reaction was warmed to RT and stirred for 16 h. The reaction was monitored by TLC; after completion of the reaction, the reaction mass was quenched with saturated $NH_4Cl$ solution (10 mL) and extracted with EtOAc (2×15 mL). The combined organic extracts were dried over anhydrous sodium sulfate, filtered and concentrated in vacuo to obtain the crude. The crude was purified through silica gel column chromatography to obtain 2 (70 mg, 40%) as white solid. 1H NMR (500 MHz, CDCl3): δ 1.40 (s, 9H), 1.67 (m, 2H), 1.88 (m, 2H), 2.12 (m, 2H), 4.15 (m, 1H), 4.64 (m, 1H), 5.42 (m, 1H), 8.18 (d, J=9.0 Hz, 2H), 8.29 (d, J=9.0 Hz, 2H).

Step 3:

tert-Butyl trans-2-hydroxycyclopentyl) carbamate (3)

To a stirred solution of trans-2-((tert-butoxycarbonyl) amino) cyclopentyl 4-nitrobenzoate (2) (70 mg, 0.19 mmol) in THF:$H_2O$ (1:1, 5 mL) was added lithium hydroxide monohydrate (25 mg, 0.59 mmol) at 0° C.; warmed to RT and stirred for 2 h. The reaction was monitored by TLC; after completion of the reaction, the solvent was removed in vacuo. The residue was neutralized with saturated a $NaHCO_3$ solution (10 mL) and extracted with $CH_2Cl_2$ (3×20 mL). The combined organic extracts were dried over sodium sulfate, filtered, and concentrated in vacuo to obtain the crude. The crude was purified through silica gel column chromatography to obtain 3 (30 mg, 75%) as pale yellow solid. $^1$H NMR (400 MHz, DMSO-$d_6$): δ 1.23 (s, 9H), 1.47 (m, 3H), 1.67 (m, 3H), 3.55 (m, 1H), 3.87 (m, 1H), 4.52 (m, 1H), 6.06 (m, 1H).

Step 4:

trans-2-((tert-Butoxycarbonyl) amino) cyclopentyl methanesulfonate (4)

To a stirred solution of tert-butyl trans-2-hydroxycyclopentyl) carbamate (3) (200 mg, 0.99 mmol) in $CH_2Cl_2$ (7 mL) under argon atmosphere was added triethylamine (0.42 mL, 2.97 mmol) at 0° C. Then methanesulfonyl chloride (0.15 mL, 1.98 mmol) in $CH_2Cl_2$ (3 mL) was added to the reaction mass. The reaction was warmed to RT and stirred for 3 h. The reaction was monitored by TLC; after completion of the reaction, the reaction mixture was diluted with water (20 mL) and extracted with $CH_2Cl_2$ (2×25 mL). The combined organic extracts were washed with brine solution (15 mL), dried over sodium sulfate, filtered, and concentrated in vacuo to obtain the crude. The crude was purified through silica gel column chromatography to obtain 4 (256 mg, 90%) as white solid. $^1$H NMR (500 MHz, DMSO-$d_6$): δ 1.37 (s, 9H); 1.54 (m, 2H), 1.65 (m, 1H), 1.88 (m, 3H), 3.06 (s, 3H), 3.78 (m, 1H), 4.86 (m, 1H), 7.01 (d, J=7.0 Hz, 1H), MS m/z ([M-Boc+H]+: 180.2.

Step 5:

tert-Butyl trans-(2-azidocyclopentyl) carbamate (5)

To a stirred solution of trans-2-((tert-butoxycarbonyl) amino) cyclopentyl methanesulfonate (4) (250 mg, 0.89 mmol) in DMF (6 mL) under argon atmosphere was added sodium azide (175 mg, 2.68 mmol) at RT. The reaction was warmed to 90° C. and stirred for 4 h. The reaction was monitored by TLC; after completion of the reaction, the reaction mixture was cooled to RT, diluted with water (20 mL) and extracted with EtOAc (2×25 mL). The combined organic extracts were washed with brine solution (15 mL), dried over sodium sulfate, filtered and concentrated in vacuo to obtain the crude compound 5 (250 mg) as colorless sticky solid. The crude was carried to the next step without any further purification. 1H NMR (400 MHz, DMSO-$d_6$): δ 1.33 (s, 9H), 1.43 (m, 2H), 1.58 (m, 2H), 1.88 (m, 2H), 3.69 (m, 2H), 7.03 (m, 1H).

Step 6:

tert-Butyl trans-(2-aminocyclopentyl) carbamate (6)

To a stirred solution of tert-butyl trans-(2-azidocyclopentyl) carbamate (5) (150 mg, 0.66 mmol) in EtOH (10 mL) under argon atmosphere was added 10% Pd/C (30 mg) at RT and stirred under hydrogen atmosphere (balloon pressure) for 16 h. The reaction was monitored by TLC; after completion of the reaction, the reaction mixture was filtered through celite and the filtrate was extracted with EtOAc (2×20 mL). The combined organic extracts were dried over sodium sulfate, filtered, and concentrated in vacuo to obtain the crude compound 6 (80 mg) as colorless oil. The crude was carried to the next step without any further purification. 1H NMR (400 MHz, DMSO-$d_6$): δ 1.23 (m, 3H), 1.40 (s, 9H), 1.56 (m, 2H), 1.83 (m, 2H), 2.27 (m, 1H), 2.90 (m, 1H), 6.73 (m, 1H).

Step 7:

tert-Butyl trans-2-(1'-oxo-2',3'-dihydro-1'H-spiro [cyclobutane-1, 4'-pyrazino [1, 2-a]indol]-7'-ylcarboxamido) cyclopentyl) carbamate (7)

To a stirred solution of 1'-oxo-2',3'-dihydro-1'H-spiro [cyclobutane-1, 4'-pyrazino [1, 2-a]indole]-7'-carboxylic acid (7, Example 78; 122 mg, 0.45 mmol) in DMF (6 mL) under argon atmosphere were added HATU (342 mg, 0.90 mmol), tert-butyl trans-(2-aminocyclopentyl) carbamate 6 (90 mg, 0.45 mmol) and DIPEA (0.25 mL, 1.35 mmol) at RT and stirred for 4 h. The reaction was monitored by TLC; after completion of the reaction, the reaction mixture was diluted with water (15 mL) and extracted with EtOAc (2×20 mL). The combined organic extracts were dried over sodium sulfate, filtered, and concentrated in vacuo to obtain the crude. The crude was purified through silica gel column chromatography to obtain 7 (150 mg, 74%) as an off white solid. $^1$H NMR (500 MHz, DMSO-$d_6$): δ 1.33 (s, 9H), 1.53 (m, 2H), 1.65 (m, 2H), 2.03 (m, 3H), 2.30 (m, 3H), 3.01 (m, 2H), 3.72 (m, 2H), 3.90 (t, J=8.5 Hz, 1H), 4.11 (t, J=8.5 Hz, 1H), 6.88 (d, J=8.0 Hz, 1H), 7.13 (s, 1H), 7.57 (d, J=8.0 Hz, 1H), 7.72 (d, J=8.0 Hz, 1H), 8.31 (m, 3H); MS m/z (M+H): 453.5.

Step 8:

N-trans-2-Aminocyclopentyl)-1'-oxo-2',3'-dihydro-1'H-spiro[cyclobutane-1, 4'-pyrazino [1, 2-a]indole]-7'-carboxamide (8)

A solution of tert-butyl trans-2-(1'-oxo-2',3'-dihydro-1'H-spiro[cyclobutane-1, 4'-pyrazino [1, 2-a]indol]-7'-ylcarboxamido) cyclopentyl) carbamate (7) (140 mg, 0.31 mmol) in 1, 4-dioxane. HCl (8 mL) under argon atmosphere was stirred at RT for 4 h. The reaction was monitored by TLC; after completion of the reaction, the volatiles were removed in vacuo. The residue was triturated with diethyl ether (2×10 mL) to obtain the crude compound 8 (100 mg, 83% as HCl salt) as an off white solid. The crude was carried to the next step without any further purification. 1H NMR (500 MHz, DMSO-$d_6$): δ 1.70 (m, 3H), 2.11 (m, 3H), 2.33 (m, 2H), 2.99 (m, 2H), 3.56 (m, 2H), 3.72 (s, 2H), 4.29 (m, 1H), 7.15 (s, 1H), 7.69 (d, J=8.5 Hz, 1H), 7.77 (d, J=8.5 Hz, 1H), 8.13 (m, 3H), 8.31 (s, 1H), 8.43 (s, 1H), 8.72 (d, J=7.0 Hz, 1H); MS m/z (M+H): 353.4.

Step 9:

To a stirred solution of N-trans-2-aminocyclopentyl)-1'-oxo-2',3'-dihydro-1'H-spiro [cyclobutane-1, 4'-pyrazino [1, 2-a]indole]-7'-carboxamide (8) (90 mg, 0.23 mmol) in THF (15 mL) under argon atmosphere were added DIPEA (0.12 mL, 0.69 mmol) and acryloyl chloride (25 mg, 0.28 mmol) at −78° C. and stirred for 30 min. The reaction was monitored by TLC; after completion of the reaction, the reaction mixture was diluted with saturated NaHCO$_3$ solution (15 mL) and extracted with EtOAc (2×20 mL). The combined organic extracts were dried over sodium sulfate, filtered, and concentrated in vacuo to obtain the crude. The crude was suspended in CH$_2$Cl$_2$ (15 mL) and filtered. The obtained solid was triturated with hexanes (2×5 mL), n-pentane (2×5 mL) and dried in vacuo to afford the desired product (60 mg, 64%) as white solid. $^1$H NMR (400 MHz, DMSO-$d_6$): δ 1.52 (m, 2H), 1.67 (m, 2H), 2.05 (m, 3H), 2.27 (m, 3H), 3.16 (m, 2H), 3.71 (s, 2H), 4.16 (m, 1H), 4.27 (m, 1H), 5.54 (m, 1H), 6.04 (m, 1H), 6.22 (m, 1H), 7.13 (s, 1H), 7.58 (d, J=8.8 Hz, 1H), 7.73 (d, J=8.4 Hz, 1H), 8.25 (m, 2H), 8.32 (s, 1H), 8.48 (d, J=7.6 Hz, 1H); MS m/z (M+H): 407.5

Compound V-57

N-(2-acrylamidopyridin-3-yl)-1'-oxo-2',3'-dihydro-1'H-spiro[cyclobutane-1,4'-pyrazino[1,2-a]indole]-7'-carboxamide

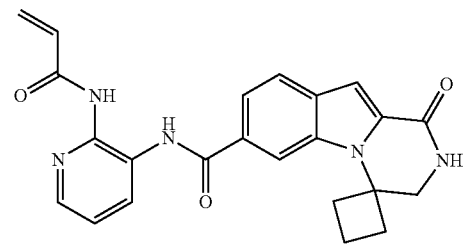 [SMILES: C=CC(=O)Nc1ncccc1NC(=O)c1ccc2cc3n(c2c1)C1(CCC1)CNC3=O]

Compound V-57 was prepared as described in Example 78, by substituting INT-11 in step 8 of Example 78 with N-(3-aminopyridin-2-yl)acrylamide, depicted as compound 3 below, to give the desired product (10 mg, 5%) as a white solid. $^1$H NMR (400 MHz, DMSO-$d_6$): δ 2.07 (m, 1H), 2.31 (m, 3H), 3.07 (m, 2H), 3.74 (s, 2H), 5.84 (m, 1H), 6.32 (m, 1H), 6.65 (m, 1H), 7.18 (s, 1H), 7.42 (m, 1H), 7.68 (m, 1H), 7.84 (m, 1H), 8.34 (m, 3H), 8.48 (s, 1H), 10.38 (s, 1H), 11.04 (s, 1H). MS m/z (M+H): 416.3.

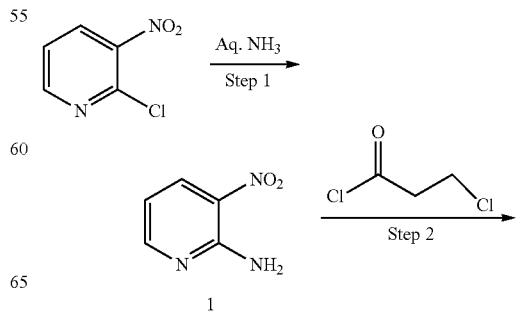

561

-continued

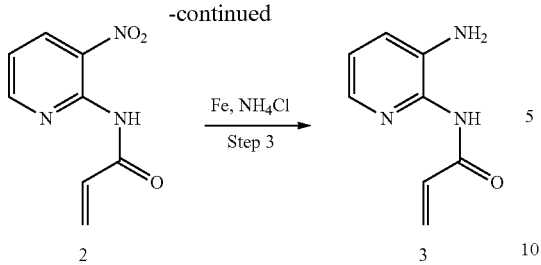

Step 1:

3-Nitropyridin-2-amine (1)

2-chloro-3-nitropyridine (4 g, 25.23 mmol) was taken in a sealed tube and aqueous $NH_3$ (8.57 g, 504.6 mmol) was added. The reaction mixture was heated to 90° C. and stirred for 16 h. The reaction mass was then cooled to 0° C. and filtered to obtain 1 (3.4 g, 97%) as a yellow solid. $^1$HNMR (400 MHz, DMSO-$d_6$): δ 6.74 (m, 1H), 7.87 (s, 2H), 8.38 (m, 2H). MS m/z (M+H): 140.3

Step 2:

N-(3-Nitropyridin-2-yl)acrylamide (2)

To a solution of 3-nitropyridin-2-amine (1) (3.4 g, 24.46 mmol) in dry THF (50 mL) was added DIPEA (17.5 mL, 97.84 mmol) at 0° C. and stirred for 15 minutes. Then 3-chloropropanoyl chloride (5.4 mL, 48.92 mmol) was added dropwise at 0° C. over a period of 20 minutes. The reaction mixture was allowed to stir at room temperature for 24 h. Reaction mixture was diluted with water (50 mL) and extracted with 10% MeOH-DCM (3×100 mL). Combined organic layers were washed with saturated brine solution, dried over anhydrous sodium sulfate and concentrated under reduced pressure. The residue was purified by silica gel column chromatography to obtain 2 (1 g, 21%) as a yellow solid. $^1$H NMR (400 MHz, DMSO-$d_6$): δ 5.86 (m, 1H), 6.30 (m, 1H), 6.54 (m, 2H), 7.47 (m, 1H), 8.39 (m, 1H), 8.70 (m, 1H). MS m/z (M+H): 194.2

Step 3:

N-(3-Aminopyridin-2-yl)acrylamide (3)

To a stirred solution of N-(3-nitropyridin-2-yl)acrylamide (2) (200 mg, 1.03 mmol) in EtOH:$H_2O$ (8 mL:2 mL) were added iron powder (285 mg, 5.18 mmol) and ammonium chloride (549 mg, 10.36 mmol) and then heated to 90° C. for 1 h. The reaction mixture was cooled to room temperature, filtered through a celite pad, and volatiles were evaporated under reduced pressure. The crude compound was diluted with EtOAc (10 mL), washed with water (2×10 mL), dried over anhydrous sodium sulfate, and concentrated under reduced pressure. The residue was purified by silica gel column chromatography to obtain 3 (20 mg, 12%) as a yellow solid. $^1$H NMR (400 MHz, $CDCl_3$): δ 4.47 (s, 2H), 5.81 (m, 1H), 6.44 (m, 2H), 7.01 (m, 1H), 7.12 (m, 1H), 7.83 (m, 1H), 8.90 (s, 1H). MS m/z (M+H): 164.3

562

Compound V-58

N-(4-acryloyl-3,3-dimethyl-3,4-dihydro-2H-benzo[b][1,4]oxazin-6-yl)-1'-oxo-2',3'-dihydro-1'H-spiro[cyclobutane-1,4'-pyrazino [1,2-a]indole]-7'-carboxamide

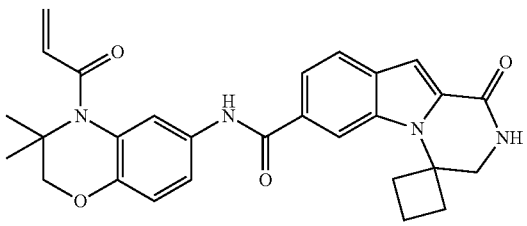 [SMILES: C=CC(=O)N1c2cc(NC(=O)c3ccc4cc5n(c4c3)C3(CCC3)CNC5=O)ccc2OCC1(C)C]

Compound V-58 was prepared according to the schemes, steps, and intermediates described below using intermediate 7 from step 7 of Example 78 in step 8, below.

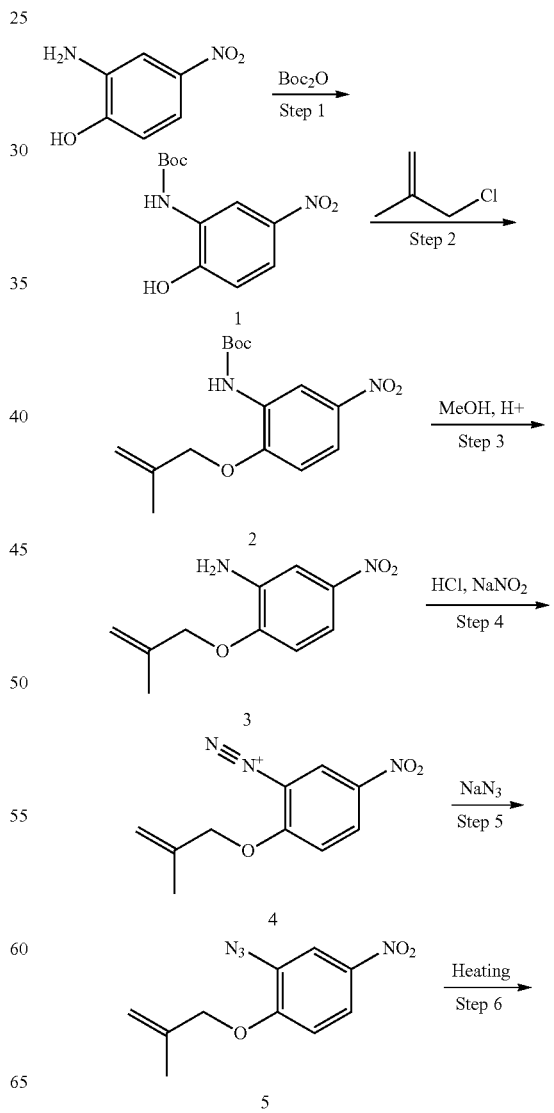

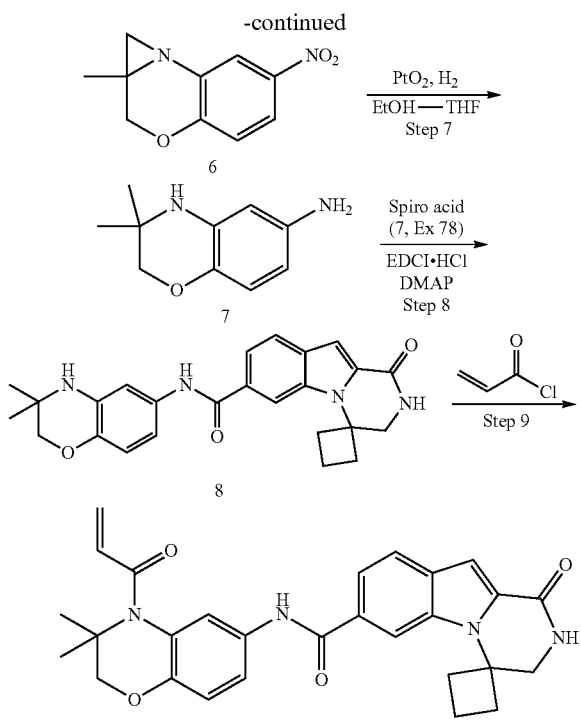

Step 3-5:

2-Azido-1-((2-methylallyl)oxy)-4-nitrobenzene (5)

A solution of methanolic. HCl solution (5 mL) was dropwise added to tert-butyl (2-((2-methylallyl)oxy)-5-nitrophenyl)carbamate (2) (100 mg, 0.32 mmol) at room temperature under a nitrogen atmosphere and stirred for 4 h. Volatiles were removed under reduced pressure. The obtained crude compound was dissolved in 4N HCl (2 mL) and cooled to −5° C., then NaNO$_2$ (50 mg, 0.72 mmol) in water (0.5 mL) was added dropwise over 3 minutes. After stirring for 30 minutes, the reaction mixture was neutralized with NaHCO$_3$ (pH=7.0) at 0° C. Then a solution of NaN$_3$ (42 mg, 0.64 mmol) in water (0.5 mL) was added dropwise to this mixture and stirred for 30 minutes at room temperature. The desired compound was extracted with EtOAc (2×20 mL). Combined organic layers were washed with brine solution (30 mL), dried over anhydrous sodium sulfate, and concentrated under reduced pressure to obtain 5 (70 mg, 92%) as brown thick liquid. $^1$H NMR (500 MHz, DMSO-d$_6$): δ 1.79 (s, 3H), 4.72 (s, 2H), 5.03 (s, 1H), 5.11 (s, 1H), 7.30 (d, J=9.0 Hz, 1H), 7.82 (s, 1H), 8.04 (m, 1H). MS m/z (M−H): 233.0

Step 6:

1a-Methyl-6-nitro-1a,2-dihydro-1H-azirino[1,2-d]benzo[b][1,4]oxazine (6)

A solution of 2-azido-1-((2-methylallyl)oxy)-4-nitrobenzene (5) (70 mg, 0.3 mmol) in benzene (10 mL) was refluxed for 12 h. The solution was cooled to room temperature and solvent was evaporated. The residue was washed with pentane (3×5 mL) and dried under vacuum to obtain 6 (40 mg, 65%) as a yellow solid. $^1$H NMR (400 MHz, DMSO-d$_6$): δ 1.32 (s, 3H), 3.30 (s, 2H), 4.22 (m, 2H), 7.09 (d, J=9.2 Hz, 1H), 7.90 (m, 1H), 8.02 (d, J=2.8 Hz, 1H). MS m/z (M+H): 207.1

Step 7:

3,3-Dimethyl-3,4-dihydro-2H-benzo[b][1,4]oxazin-6-amine (7)

A solution of 1a-methyl-6-nitro-1a,2-dihydro-1H-azirino[1,2-d]benzo[b][1,4]oxazine (6) (200 mg, 0.97 mmol) in EtOH:H$_2$O (14 mL, 1:1) was added PtO$_2$ (50 mg) and stirred at room temperature for 1 h under H$_2$ atmosphere. The reaction mixture was filtered through a celite pad and washed with EtOAc (20 mL). The combined organic layers were evaporated to obtain 7 (170 mg, 98%) as brown thick liquid. $^1$H NMR (500 MHz, DMSO-d$_6$): δ 1.08 (s, 6H), 3.59 (s, 2H), 4.30 (bs, 2H), 5.30 (s, 1H), 5.72 (m, 1H), 5.79 (s, 1H), 6.34 (d, J=8.5 Hz, 1H). MS m/z (M+H): 179.2

Step 8:

N-(3,3-dimethyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide (8)

To a solution of 1'-oxo-2',3'-dihydro-1'H-spiro[cyclobutane-1,4'-pyrazino[1,2-a]indole]-7'-carboxylic acid (50 mg, 0.18 mmol) in DCM (10 mL) were added DMAP (68 mg, 0.54 mmol), EDCI. HCl (89 mg, 0.45 mmol) and 3,3-dimethyl-3,4-dihydro-2H-benzo[b][1,4]oxazin-6-amine (7) (66 mg, 0.36 mmol) at room temperature. The resultant reaction mixture was stirred for 12 h. The reaction mixture was diluted with water (20 mL) and extracted with 10%

Step 1:

tert-Butyl (2-hydroxy-5-nitrophenyl)carbamate (1)

To a solution of 2-amino-4-nitrophenol (10 g, 65.0 mmol) in DCM (200 mL) were added triethylamine (13.8 mL, 97.3 mmol) and boc-anhydride (15.6 g, 71.4 mmol) at 0° C. and stirred for 10 minutes. Then DMAP (3.96 g, 32.4 mmol) was added portion wise and stirred for 1 h. The reaction mixture was diluted with water (50 mL) neutralized with citric acid (200 mL) and extracted with DCM (2×100 mL). The combined organic layers were dried over anhydrous sodium sulfate and concentrated under reduced pressure. The residue was purified by silica gel column chromatography to obtain 1 (13 g, 79%) as a yellow solid. $^1$H NMR (400 MHz, DMSO-d$_6$): δ 1.48 (s, 9H), 6.97 (d, J=8.8 Hz, 1H), 7.86 (m, 1H), 8.21 (s, 1H), 8.64 (d, J=2.4 Hz, 1H), 11.56 (s, 1H). MS m/z (M−H): 253.2

Step 2:

tert-Butyl (2-((2-methylallyl)oxy)-5-nitrophenyl)carbamate (2)

To a mixture of tert-butyl (2-hydroxy-5-nitrophenyl)carbamate (1) (100 mg, 0.39 mmol), K$_2$CO$_3$ (163 mg, 1.18 mmol) and KI (13 mg, 0.07 mmol) in acetone (10 mL) was added 3-chloro-2-methylprop-1-ene (0.08 mL, 0.78 mmol) in a sealed tube and then heated to 65° C. and stirred for 3 h. The reaction mixture was cooled to room temperature and filtered through a celite pad using EtOAc (10 mL). The obtained organic filtrate was dried over anhydrous sodium sulfate and concentrated under reduced pressure. The residue was washed with pentane (3×5 mL) and dried under vacuum to obtain 2 (100 mg, 83%) as a pale yellow solid. 1H NMR (400 MHz, DMSO-d$_6$): δ 1.48 (s, 9H), 1.79 (s, 3H), 4.69 (s, 2H), 5.00 (s, 1H), 5.07 (s, 1H), 7.18 (d, J=9.2 Hz, 1H), 7.95 (m, 1H), 8.42 (s, 1H), 8.62 (d, J=2.8 Hz, 1H). MS m/z (M−H): 307.8

MeOH/DCM (2×10 mL). The combined organic layers were dried over anhydrous sodium sulfate and concentrated under reduced pressure. The residue was washed with pentane and ether to obtain 8 (70 mg, 48%) as a yellow solid. $^1$H NMR (500 MHz, DMSO-d$_6$): δ 1.17 (s, 6H), 2.03 (m, 1H), 2.17 (m, 1H), 2.32 (m, 2H), 3.07 (m, 2H), 3.73 (s, 4H), 5.75 (s, 1H), 6.65 (d, J=8.5 Hz, 1H), 6.83 (d, J=7.0 Hz, 1H), 7.07 (s, 1H), 7.16 (s, 1H), 7.70 (d, J=8.5 Hz, 1H), 7.79 (d, J=8.5 Hz, 1H), 8.30 (s, 1H), 8.41 (s, 1H), 10.01 (s, 1H). MS m/z (M+H): 431.4

Step 9:

A solution of N-(3,3-dimethyl-3,4-dihydro-2H-benzo[b][1,4]oxazin-6-yl)-1'-oxo-2',3'-dihydro-1'H-spiro[cyclobutane-1,4'-pyrazino[1,2-a]indole]-7'-carboxamide (8) (70 mg, 0.16 mmol) in DCM (10 mL) was added triethylamine (0.04 mL, 0.32 mmol) and cooled to 0° C. under nitrogen atmosphere. Then acryloyl chloride (0.04 mL, 0.48 mmol) was added dropwise under nitrogen atmosphere. The resultant reaction mixture was allowed to warm to room temperature and stirred for 4 h. The reaction mixture was then diluted with water (10 mL) and extracted with DCM (2×10 mL). The combined organic layers were dried over anhydrous sodium sulfate and concentrated under reduced pressure. The obtained residue was purified by silica gel column chromatography followed by preparative TLC to obtain the desired product (10 mg, 13%) as yellow solid. 1H NMR (500 MHz, DMSO-d$_6$): δ 1.47 (s, 6H), 2.05 (m, 1H), 2.17 (m, 1H), 2.31 (m, 2H), 3.03 (m, 2H), 3.72 (d, J=2.0 Hz, 2H), 3.93 (s, 2H), 5.73 (m, 1H), 6.23 (m, 1H), 6.49 (m, 1H), 6.94 (d, J=9.0 Hz, 1H), 7.16 (s, 1H), 7.42 (m, 1H), 7.51 (s, 1H), 7.68 (d, J=8.0 Hz, 1H), 7.79 (d, J=8.5 Hz, 1H), 8.30 (s, 1H), 8.40 (s, 1H), 10.23 (s, 1H). MS m/z (M+H): 485.5

Compound V-59

N-(2-(1'-oxo-2',3'-dihydro-1'H-spiro[cyclobutane-1,4'-pyrazino[1,2-a]indol]-7'-yl)-1H-benzo[d]imidazol-5-yl)acrylamide

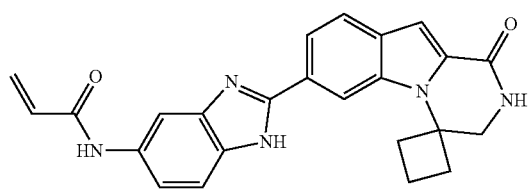 [SMILES: C=CC(=O)Nc1ccc2[nH]c(-c3ccc4cc5n(c4c3)C3(CCC3)CNC5=O)nc2c1]

Compound V-59 was prepared according to the schemes, steps, and intermediates described below using intermediate 7 from step 7 of Example 78 in step 2, below.

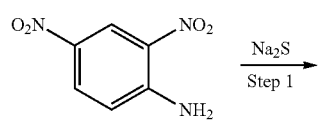

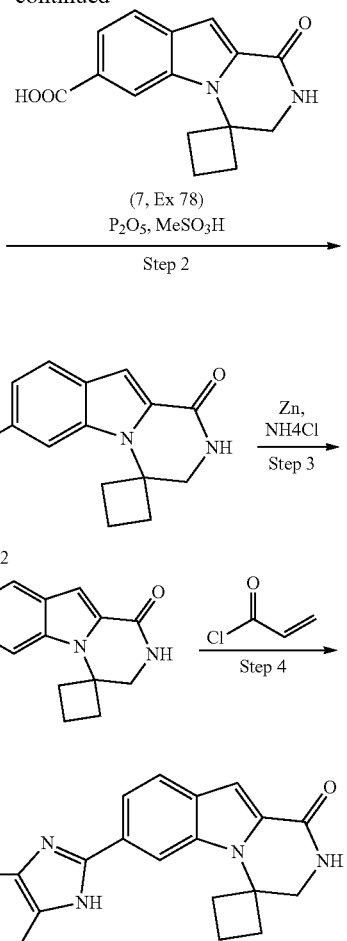

Step 1:

4-nitrobenzene-1,2-diamine (1)

To a solution of 2,4-dinitroaniline (1 g, 10.3 mmol) in ethanol/water (3:1; 26 mL), sodium sulfide (1.2 g, 15.4 mmol) was added. The resulting mixture was stirred for 12 h at room temperature. After completion of the reaction, solvent was removed under reduced pressure. The resulting residue was diluted with water and extracted with ethyl acetate. The organic layer was dried over anhydrous sodium sulphate and concentrated under reduced pressure. The residue obtained was purified by silica gel column chromatography to afford 1 (200 mg, 24%) as a brown solid. $^1$H NMR (400 MHz, DMSO-d$_6$): δ 5.03 (s, 2H), 6.00 (s, 2H), 6.51 (d, J=8.5 Hz, 1H), 7.38 (dd, J=2.6, 5.9 Hz, 1H), 7.40 (d, J=2.7 Hz, 1H).MS m/z (M+H): 154.13

Step 2:

7'-(5-nitro-1H-benzo[d]imidazol-2-yl)-2',3'-dihydro-1'H-spiro[cyclobutane-1,4'-pyrazino[1,2-a]indol]-1'-one (2)

A solution of phosphoruspentoxide (361 mg, 2.5 mmol) in methanesulfonic acid (0.6 mL) at 0° C. was treated with 1'-oxo-2',3'-dihydro-1'H-spiro[cyclobutane-1,4'-pyrazino[1,2-a]indole]-7'-carboxylic acid (intermediate 7, Example 78; 229 mg, 0.8 mmol) followed by the addition of 4-nitrobenzene-1,2-diamine (1, 130 mg, 0.8 mmol). The reaction mixture was heated at 120° C. for 2 h. After completion of the reaction, the reaction mixture was diluted with saturated sodium bicarbonate solution and extracted with ethyl acetate. The organic layer was dried over anhydrous sodium sulfate and concentrated under reduce pressure to afford 2 (150 mg, 45%) as a brown solid. MS m/z (M+H): 388.61

Step 3:

7'-(5-amino-1H-benzo[d]imidazol-2-yl)-2',3'-dihydro-1'H-spiro[cyclobutane-1,4'-pyrazino [1,2-a]indol]-1'-one (3)

To a solution of 7'-(5-nitro-1H-benzo[d]imidazol-2-yl)-2',3'-dihydro-1'H-spiro[cyclobutane-1,4'-pyrazino[1,2-a]indol]-1'-one (150 mg, 0.3 mmol) in dioxane/H$_2$O (1:1; 10 mL), zinc dust (200 mg, 3.1 mmol) was added followed by the addition of ammonium chloride (16 mg, 3.1 mmol) at room temperature. The reaction mixture was stirred at room temperature for 16 h. After completion of the reaction, the reaction mixture was diluted with water and extracted with ethyl acetate. The organic layer was dried over anhydrous sodium sulfate and concentrated under reduce pressure to afford 3 (70 mg, 50%) as a brown solid. MS m/z (M+H): 358.2

Step 4:

To a solution of 7'-(5-amino-1H-benzo[d]imidazol-2-yl)-2',3'-dihydro-1'H-spiro[cyclobutane-1,4'-pyrazino[1,2-a]indol]-1'-one (3, 70 mg, 0.2 mmol) in DCM/THF (1:1, 10.0 mL), diisopropylethylamine (75 mg, 0.6 mmol) and acryloyl chloride (9 mg, 0.2 mmol) were added at −78° C. The resulting mixture was warmed to room temperature and stirred for 1 h. After completion of the reaction, the reaction mixture was concentrated under reduced pressure. The residue obtained was diluted with water and extracted with ethyl acetate. The organic layer was dried over anhydrous sodium sulphate and concentrated under reduced pressure. The residue obtained was purified by preparative HPLC to afford the desired product (4.0 mg, 5%) as an off-white solid. 1H NMR (400 MHz, DMSO-d$_6$): δ 2.03-2.08 (m, 1H), 2.25-2.35 (m, 3H), 3.05-3.13 (m, 2H), 3.74 (s, 2H), 5.74 (dd, J=9.8, 11.8 Hz, 1H), 6.25 (d, J=17.1 Hz, 1H), 6.44-6.51 (m, 1H), 7.15 (s, 1H), 7.24 (dd, J=1.5, 8.6 Hz, 1H), 7.59 (d, J=8.6 Hz, 1H), 7.82 (d, J=8.5 Hz, 1H), 7.96 (d, J=8.2 Hz, 1H), 8.29 (m, 2H), 8.63 (d, J=10.0 Hz, 1H), 10.21 (s, 1H), 12.92 (s, 1H). MS m/z (M-+H): 412.2

Compound V-60

N-(2-(1'-oxo-2',3'-dihydro-1'H-spiro[cyclobutane-1,4'-pyrazino [1,2-a]indol-7'-yl)benzo[d]oxazol-5-yl)acrylamide

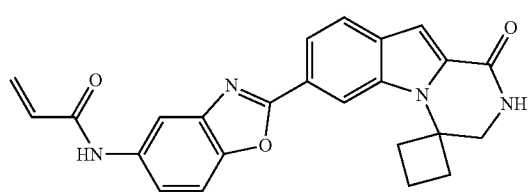 [SMILES: C=CC(=O)Nc1ccc2oc(-c3ccc4cc5n(c4c3)C3(CCC3)CNC5=O)nc2c1]

Compound V-60 was prepared according to the schemes, steps, and intermediates described below using intermediate 7 from Example 78 as the starting material.

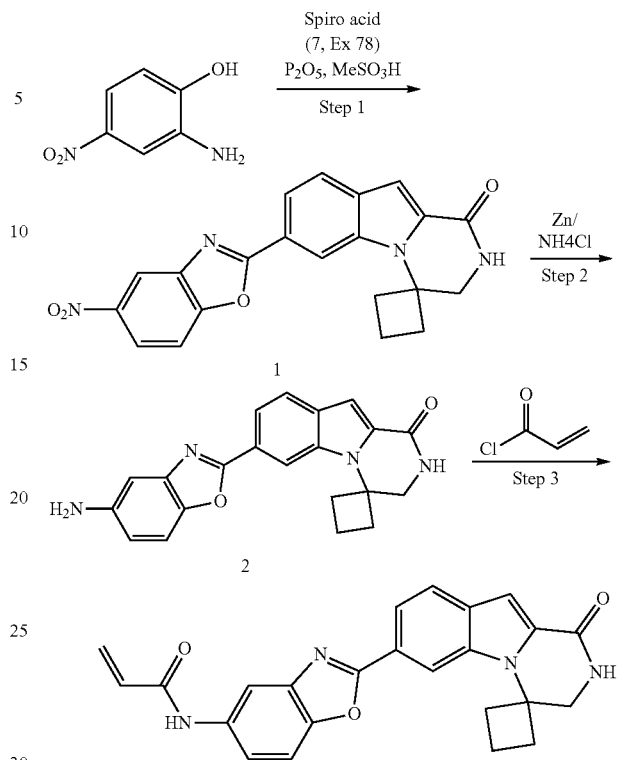

Step 1:

7'-(5-nitrobenzo[d]oxazol-2-yl)-2',3'-dihydro-1'H-spiro[cyclobutane-1,4'-pyrazino[1,2-a]indol]-1'-one (1)

Solution of phosphorus pentoxide (328 mg, 2.3 mmol) in methane sulfonic acid (3.5 mL) at 0° C. was treated with 1'-oxo-2',3'-dihydro-1'H-spiro[cyclobutane-1,4'-pyrazino[1,2-a]indole]-7'-carboxylic acid (intermediate 7, Example 78; 250 mg, 0.9 mmol) followed by the addition of 2-amino-3-nitrophenol (143 mg, 0.9 mmol). The reaction mixture was stirred at 120° C. for 5 h. After completion of the reaction, ice-cold water was added to the reaction mixture. The resulting solid suspension was filtered to afford 1 (320 mg, 89%) as a brown solid. MS m/z (M+H): 389.56.

Step 2:

7'-(5-aminobenzo[d]oxazol-2-yl)-2',3'-dihydro-1'H-spiro[cyclobutane-1,4'-pyrazino[1,2-a]indol]-1'-one (2)

To a solution of 7'-(5-nitrobenzo[d]oxazol-2-yl)-2',3'-dihydro-1'H-spiro[cyclobutane-1,4'-pyrazino[1,2-a]indol]-1'-one 1 (300 mg, 0.8 mmol) in dioxane/water (1:1; 20 mL), zinc dust (536 mg, 8.2 mmol) was added followed by the addition of ammonium chloride (445 mg, 8.2 mmol). The reaction mixture was stirred at room temperature for 3 h. After completion of the reaction, the reaction mixture was diluted with water and extracted with ethyl acetate. The organic layer was dried over anhydrous sodium sulfate and concentrated under reduced pressure to afford 2 (220 mg, 80%) as a brown solid. $^1$H NMR (400 MHz, DMSO-d$_6$): δ 2.05-2.13 (m, 1H), 2.22-2.28 (m, 1H), 2.36 (t, J=9.8 Hz, 2H), 2.97-3.05 (m, 2H), 3.73 (d, J=2.2 Hz, 2H), 5.09 (s, 2H), 6.65 (dd, J=2.0, 8.6 Hz, 1H), 6.88 (d, J=2.0 Hz, 1H), 7.19 (s, 1H), 7.43 (d, J=8.6 Hz, 1H), 7.85-7.92 (m, 2H), 8.34 (s, 1H), 8.66 (s, 1H). MS m/z (M+H): 359.58.

Step 3:

To a solution of 7'-(5-aminobenzo[d]oxazol-2-yl)-2',3'-dihydro-1'H-spiro[cyclobutane-1,4'-pyrazino[1,2-a]indol]-1'-one 2 (200 mg, 0.5 mmol) in DCM/THF (1:1, 20.0 mL), diisopropylethylamine (216 mg, 1.6 mmol), acryloyl chloride (41 mg, 0.4 mmol) were added at room temperature and stirred for 30 min. After completion of the reaction, solvent was removed under reduced pressure. The resulting residue was diluted with saturated sodium bicarbonate solution. The solid suspension obtained was filtered. The solid was purified by preparative HPLC to afford the desired product (66 mg, 28%) as an off white solid. 1H NMR (400 MHz, DMSO-d$_6$): δ 2.06-2.14 (m, 1H), 2.24-2.27 (m, 1H), 2.37 (t, J=9.3 Hz, 2H), 2.98-3.06 (m, 2H), 3.75 (d, J=2.0 Hz, 2H), 5.78 (dd, J=1.8, 10.0 Hz, 1H), 6.29 (dd, J=1.8, 16.9 Hz, 1H), 6.46 (dd, J=10.0, 16.9 Hz, 1H), 7.21 (s, 1H), 7.58 (dd, J=1.8, 8.8 Hz, 1H), 7.76 (d, J=8.8 Hz, 1H), 7.90 (d, J=8.4 Hz, 1H), 7.97 (dd, J=1.0, 8.4 Hz, 1H), 8.24 (d, J=1.5 Hz, 1H), 8.35 (s, 1H), 8.73 (s, 1H), 10.32 (s, 1H). MS m/z (M+H): 413.2

Compound V-61

N-(6-(1-methylpiperidin-4-yl)-2-(1'-oxo-2',3'-dihydro-1'H-spiro[cyclobutane-1,4'-pyrazino [1,2-a]indol]-7'-yl)benzo[d]oxazol-4-yl)acrylamide

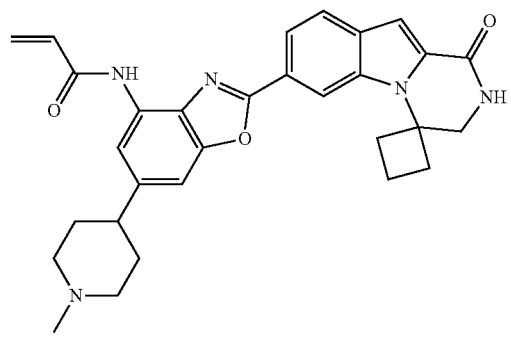 [SMILES: C=CC(=O)Nc1cc(C2CCN(C)CC2)cc2oc(-c3ccc4cc5n(c4c3)C3(CCC3)CNC5=O)nc12]

Compound V-61 was prepared according to the schemes, steps, and intermediates described below using intermediate 7 from step 7 of Example 78 in step 2, below.

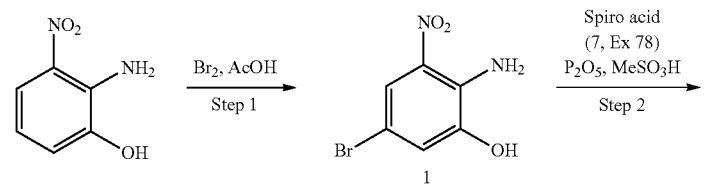

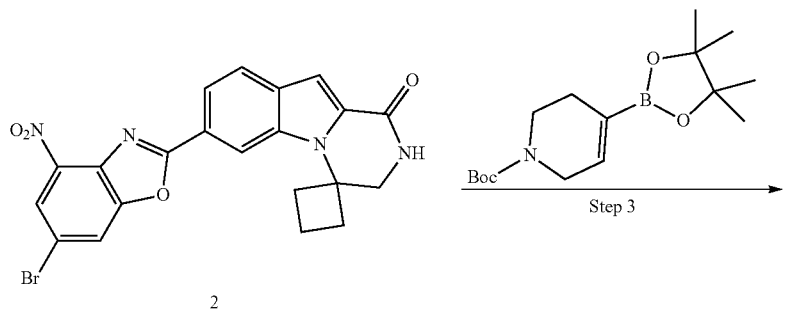

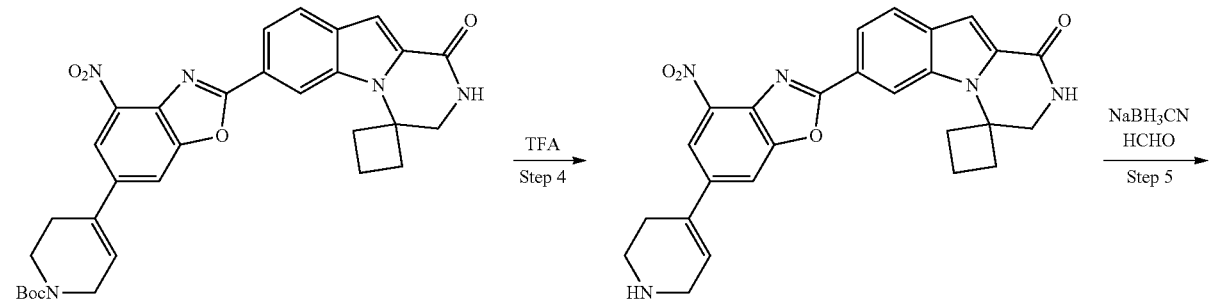

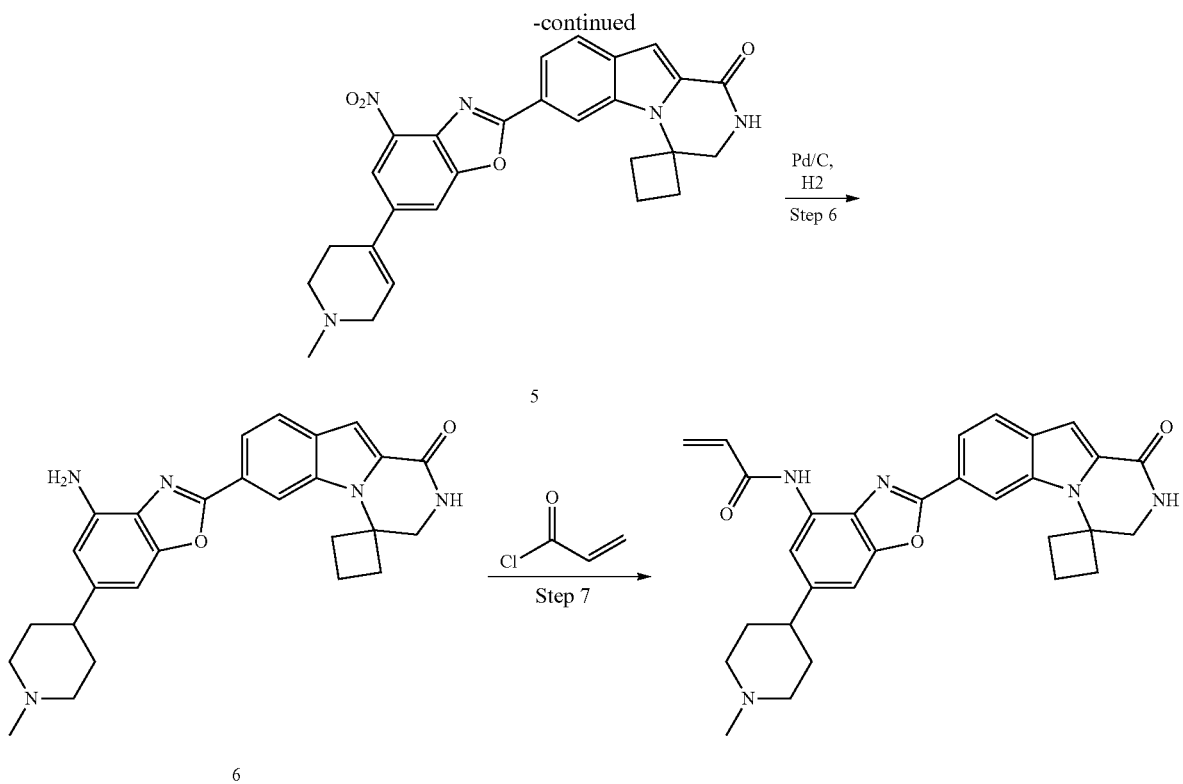

Step 1:

2-amino-5-bromo-3-nitrophenol (1)

To a solution of 2-amino-3-nitrophenol (1.0 g, 6.5 mmol) in acetic acid (8.0 mL), bromine (1.5 g, 18.7 mmol) was added at 0° C. The resulting mixture was refluxed overnight. After completion of the reaction, the reaction mixture was diluted with water and extracted with ethyl acetate. The organic layer was dried over anhydrous sodium sulfate and concentrated under reduced pressure to afford 1 (900 mg, 60%) as a brown solid. $^1$H NMR (400 MHz, DMSO-$d_6$): δ 6.94 (d, J=2.2 Hz, 1H), 7.03 (s, 2H), 7.58 (d, J=2.2 Hz, 1H), 11.00 (s, 1H).

Step 2:

7'-(6-bromo-4-nitrobenzo[d]oxazol-2-yl)-2',3'-dihydro-1'H-spiro[cyclobutane-1,4'-pyrazino [1,2-a]indol]-1'-one (2)

A solution of phosphorus pentoxide (393 mg, 2.7 mmol) in methane sulfonic acid (4.2 mL) at 0° C. was treated with 1'-oxo-2',3'-dihydro-1'H-spiro[cyclobutane-1,4'-pyrazino[1,2-a]indole]-7'-carboxylic acid (intermediate 7, Example 78; 300 mg, 1.1 mmol) followed by the addition of 2-amino-5-bromo-3-nitrophenol 1 (257 mg, 1.1 mmol). The reaction mixture was stirred at 120° C. for 3 h. After completion of the reaction, the reaction mixture was quenched with saturated sodium bicarbonate solution and extracted with ethyl acetate. The organic layer was dried over anhydrous sodium sulfate and concentrated under reduced pressure to afford 2 (460 mg, 90%) as a brown solid. MS m/z (M+H): 467.65.

Step 3:

tert-butyl-4-(4-nitro-2-(1'-oxo-2',3'-dihydro-1'H-spiro[cyclobutane-1,4'-pyrazino[1,2-a]indole]-7'-yl) benzo[d]oxazol-6-yl)-5,6-dihydropyridine-1(2H)-carboxylate (6)

Compound 2 (300 mg, 0.6 mmol) in 1,4-dioxane/water (3:1; 15 mL) was treated with 7'-(6-bromo-4-nitrobenzo[d] oxazol-2-yl)-2',3'-dihydro-1'H-spiro[cyclobutane-1,4'-pyrazino[1,2-a]indol]-1'-one (300 mg, 1.0 mmol), sodium carbonate (204 mg, 1.8 mmol) and tetrakis (triphenylphosphine) palladium (37 mg, 0.03 mmol). The resulting mixture was stirred at 110° C. for 6 h. After completion of the reaction, the solvent was removed under reduced pressure. The residue obtained was diluted with water and extracted with ethyl acetate. The organic layer was dried over anhydrous sodium sulfate and concentrated under reduced pressure. The obtained residue was triturated with diethyl ether to afford 3 (350 mg, 63%) as a brown solid. MS m/z (M+H): 570.5.

Step 4:

7'-(4-nitro-6-(1,2,3,6-tetrahydropyridin-4-yl)benzo[d]oxazol-2-yl)-2',3'-dihydro-1'H-spiro[cylobutane-1,4'-pyrazino[1,2-a]indol]-1'-one (7)

tert-butyl 4-(4-nitro-2-(1'-oxo-2',3'-dihy-dro-1'H-spiro [cyclobutane-1,4'-pyrazino[1,2-a]indole]-7'-yl)benzo[d] oxazol-6-yl)-5,6-dihydropyridine-1(2H)-carboxylate (350 mg, 0.6 mmol) was treated with excess trifluoroacetic acid in dichloromethane (6.0 mL) at 0° C. The reaction mixture was stirred at room temperature for 1 h. After completion of the reaction, the reaction mixture was concentrated under reduced pressure and co-distilled with dichloromethane. The residue obtained was triturated with diethyl ether to afford 4 (350 mg, 98%) as a pale green solid. MS m/z (M+H): 470.2.

Step 5:

7'-(4-nitro-6-(1,2,3,6-tetrahydropyridin-4-yl)benzo[d]oxazol-2-yl)-2',3'-dihydro-1'H-spiro[cyclobutane-1,4'-pyrazino[1,2-a]indol]-1'-one (8)

Solution of 7'-(4-nitro-6-(1,2,3,6-tetrahydropyridin-4-yl)benzo[d]oxazol-2-yl)-2',3'-dihydro-1'H-spiro[cyclobutane-1,4'-pyrazino[1,2-a]indol]-1'-one (350 mg, 0.7 mmol) in methanol (10 mL) was treated with formaldehyde (223 mg, 7.4 mmol), sodium cyanoborohydride (46 mg, 0.7 mmol) and acetic acid (catalytic) at 0° C. The resulting mixture was warmed to room temperature and stirred for 12 h. After completion of the reaction, the solvent was removed under reduced pressure. The resulting residue was diluted with water and extracted with ethyl acetate. The organic layer was dried over anhydrous sodium sulfate and concentrated under reduced pressure to afford 5 (180 mg, 64%) as a yellow solid. MS m/z (M+H): 484.2.

Step 6:

7'-(4-amino-6-(1-methylpiperidin-4-yl)benzo[d]oxazol-2-yl)-2',3'-dihydro-1'H-spiro[cyclobutane-1,4'-pyrazino[1,2-a]indol]-1'-one (9)

To a solution of 7'-(4-nitro-6-(1,2,3,6-tetrahydropyridin-4-yl)benzo[d]oxazol-2-yl)-2',3'-dihydro-1'H-spiro[cyclobutane-1,4'-pyrazino[1,2-a]indol]-1'-one (180 mg, 0.4 mmol) in methanol (10.0 mL), 10% palladium/carbon (40 mg) was added and the resulting reaction mixture was stirred under hydrogen pressure at 100 psi for 12 h. After completion of the reaction, the reaction mixture was filtered through celite and washed with methanol. The filtrate was concentrated under reduced pressure to afford 6 (90 mg, 52%) as a brown solid. MS m/z (M+H): 456.3.

Step 7:

To a solution of 7'-(4-amino-6-(1-methylpiperidin-4-yl)benzo[d]oxazol-2-yl)-2',3'-dihydro-1'H-spiro[cyclobutane-1,4'-pyrazino[1,2-a]indol]-1'-one (90 mg, 0.2 mmol) in dimethylacetamide (2.0 mL), diisopropylethylamine (38 mg, 0.3 mmol) and acryloyl chloride (53.5 mg, 0.6 mmol) were added at 0° C. The resulting mixture was warmed to room temperature and stirred for 2 h. After completion of the reaction, the solvent was removed under reduced pressure. The resulting residue was diluted with water and extracted with ethyl acetate. The organic layer was concentrated under reduced pressure and the crude obtained was purified by preparative HPLC to afford the desired product (4 mg, 4%) as an off white solid. 1H NMR (400 MHz, CD₃OD): δ 1.97-2.05 (m, 7H), 2.41-2.52 (m, 4H), 2.63 (s, 3H), 2.73 (m, 2H), 2.89-2.95 (m, 1H), 3.21-3.26 (m, 2H), 3.40 (m, 1H), 5.89 (d, J=11.6 Hz, 1H), 6.49 (dd, J=1.4, 17.0 Hz, 1H), 6.70 (dd, J=10.2, 17.0 Hz, 1H), 7.35 (s, 1H), 7.45 (s, 1H), 7.91 (d, J=8.4 Hz, 1H), 8.08 (d, J=8.5 Hz, 1H), 8.18 (s, 1H), 8.88 (s, 1H). MS m/z (M+H): 510.3

Compound V-62

N-(6-chloro-2-(1'-oxo-2',3'-dihydro-1'H-spiro[cyclobutane-1,4'-pyrazino[1,2-a]indol]-7'-yl)benzo[d]oxazol-4-yl)acrylamide

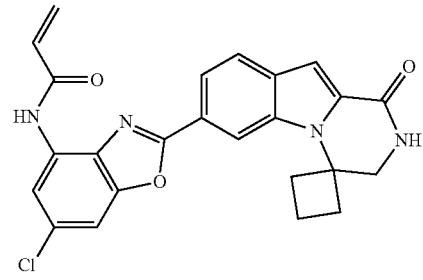 [SMILES: C=CC(=O)Nc1cc(Cl)cc2oc(-c3ccc4cc5n(c4c3)C3(CCC3)CNC5=O)nc12]

Compound V-62 was prepared similarly to Compound V-39 by substituting 2-amino-3-nitrophenol used in step 1 of the synthesis of Compound V-39 with 2-amino-5-chloro-3-nitrophenol, depicted below as compound 1, to give the desired product (33 mg, 21%) as a yellow solid. ¹H NMR (400 MHz, DMSO-d₆): δ 2.12 (m, 1H), 2.25 (m, 1H), 2.37 (t, J=9.9 Hz, 2H), 2.99-3.07 (m, 2H), 3.76 (d, J=2.1 Hz, 2H), 5.84 (dd, J=1.7, 10.1 Hz, 1H), 6.35 (dd, J=1.7, 16.9 Hz, 1H), 6.88 (dd, J=10.2, 16.9 Hz, 1H), 7.22 (s, 1H), 7.74 (d, J=1.8 Hz, 1H), 7.93 (d, J=8.4 Hz, 1H), 8.01 (dd, J=0.9, 8.5 Hz, 1H), 8.32 (d, J=2.0 Hz, 1H), 8.36 (s, 1H), 8.74 (s, 1H), 10.66 (s, 1H). MS m/z (M+H): 447.1

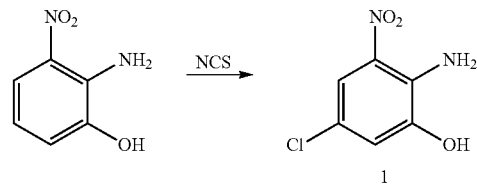 [SMILES: Nc1c(O)cccc1[N+](=O)[O-] ; "NCS" ; Nc1c(O)cc(Cl)cc1[N+](=O)[O-]]

2-amino-5-chloro-3-nitrophenol (1)

A solution of 2-amino-3-nitrophenol (3.0 g, 19.4 mmol) was treated with N-chlorosuccinamide (3.1 g, 23.3 mmol) in acetonitrile (100 mL). The resulting solution was refluxed for 3 h. After completion of the reaction, the solvent was removed under reduced pressure. The resulting residue was diluted with water and extracted with ethyl acetate. The organic layer was dried over anhydrous sodium sulfate and concentrated under reduced pressure to afford 1 (3.5 g, 95%) as a brown solid. 1H NMR (400 MHz, DMSO-d₆): δ 6.85 (d, J=2.3 Hz, 1H), 7.02 (br s, 2H), 7.45 (d, J=2.4 Hz, 1H), 11.02 (s, 1H). MS m/z (M+H): 189.2

Compound V-63

N-(2-(1'-oxo-2',3'-dihydro-1'H-spiro[cyclobutane-1,4'-pyrazino [1,2-a]indol]-7'-yl)-1H-benzo[d]imidazol-4-yl)acrylamide

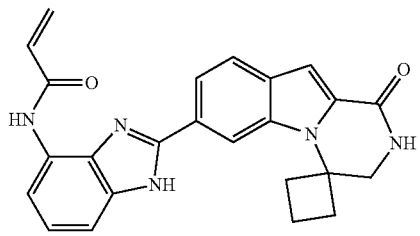 [SMILES: C=CC(=O)Nc1cccc2[nH]c(-c3ccc4cc5n(c4c3)C3(CCC3)CNC5=O)nc12]

Compound V-63 was prepared similarly to Compound V-39 by substituting 2-amino-3-nitrophenol used in step 1 of the synthesis of Compound V-39 with 3-nitrobenzene-1,2-diamine to give the desired product (13.5 mg, 15%) as an off white solid. 1H NMR (400 MHz, DMSO-$d_6$): δ 2.06-2.10 (m, 1H), 2.28-2.35 (m, 3H), 3.09-3.17 (m, 2H), 3.74 (d, J=1.7 Hz, 2H), 5.76 (dd, J=1.6, 10.0 Hz, 1H), 6.29 (dd, J=1.8, 17.0 Hz, 1H), 6.90 (dd, J=10.3, 16.9 Hz, 1H), 7.17 (dd, J=8.0, 13.8 Hz, 2H), 7.30 (d, J=7.9 Hz, 1H), 7.85 (d, J=8.4 Hz, 1H), 8.01 (d, J=7.7 Hz, 1H), 8.11 (d, J=8.5 Hz, 1H), 8.28 (s, 1H), 8.66 (s, 1H), 10.05 (s, 1H), 13.09 (s, 1H). MS m/z (M+H): 412.2

Compound V-64 trans-(2-acrylamidocyclohexyl)-1'-oxo-2',3'-dihydro-1'H-spiro[cyclobutane-1,4'-pyrazino[1,2-a]indole]-7'-carboxamide (racemic)

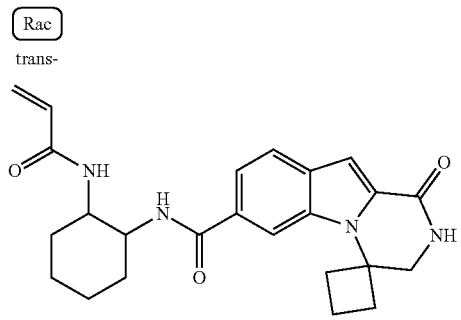 [SMILES: C=CC(=O)NC1CCCCC1NC(=O)c1ccc2cc3n(c2c1)C1(CCC1)CNC3=O]

Compound V-64 was prepared as described in Example 78, by substituting INT-11 in step 8 of Example 78 with trans-(2-aminocyclohexyl)acrylamide (racemic), depicted below as compound 3, to afford the desired product (10 mg, 11%) as an off white solid. $^1$H NMR (400 MHz, DMSO-$d_6$): δ 1.22-1.44 (m, 6H), 1.72 (m, 2H), 1.86 (m, 1H), 1.94-2.01 (m, 2H), 2.27 (m, 3H), 2.93-2.98 (m, 1H), 3.04-3.09 (m, 1H), 3.77 (m, 1H), 3.86 (m, 1H), 5.47 (d, J=10.0 Hz, 1H), 5.99 (d, J=15.4 Hz, 1H), 6.16 (dd, J=10.1, 17.1 Hz, 1H), 7.09 (s, 1H), 7.49 (d, J=8.2 Hz, 1H), 7.68 (d, J=8.4 Hz, 1H), 8.07 (d, J=8.0 Hz, 1H), 8.20-8.25 (m, 3H). MS m/z (M+H): 421.3.

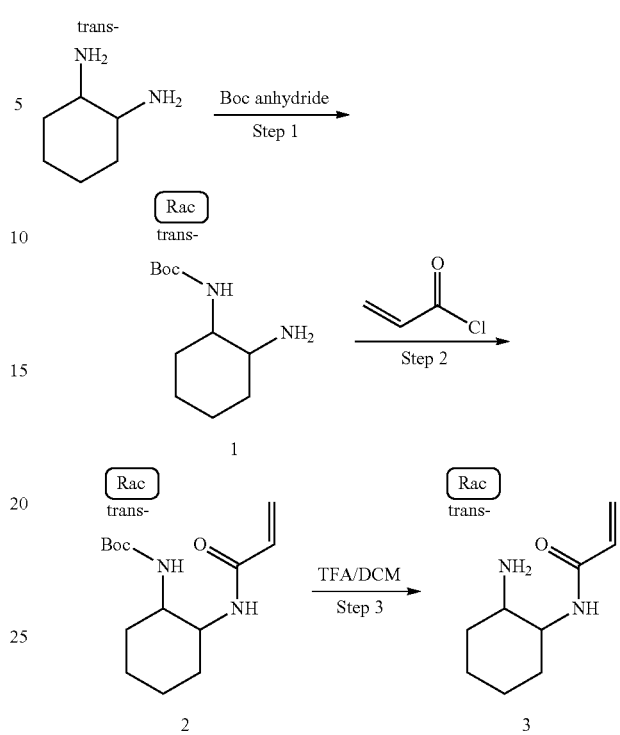

Step 1:

Tert-butyl trans-2-aminocyclohexylcarbamate (1)

A solution of trans-cyclohexane-1,2-di-amine (1.0 g, 8.7 mmol) in dioxane (20.0 ml) was treated with Boc anhydride (569 mg, 2.6 mmol) at room temperature and stirred for 6 h. After completion of the reaction, the solvent was removed under reduced pressure. The resulting residue was diluted with water and extracted with ethyl acetate. The organic layer was concentrated under reduced pressure and the crude obtained was triturated with pentane to afford 1 (300 mg, 16%) as a white solid. $^1$H NMR (400 MHz, DMSO-$d_6$): δ 0.99-1.07 (m, 2H), 1.10-1.15 (m, 2H), 1.29 (s, 2H), 1.36 (s, 9H), 1.56-1.58 (m, 2H), 1.73-1.76 (m, 2H), 2.26-2.32 (m, 1H), 2.85-2.87 (m, 1H), 6.60 (d, J=7.5 Hz, 1H).

Step 2:

Tert-butyl trans-2-acrylamidocyclohexylcarbamate (2)

To a solution of tert-butyl trans-2-aminocyclohexylcarbamate (300 mg, 2.6 mmol) in dichloromethane (6.0 mL), diisopropylethylamine (129 mg, 5.2 mmol) and acryloyl chloride (235 mg, 2.6 mmol) were added at −78° C. The resulting mixture was warmed to room temperature and stirred for 30 min. After completion of the reaction, the solvent was removed under reduced pressure. The resulting residue was diluted with water and extracted with dichloromethane. The organic layer was concentrated under reduced pressure and the crude obtained was purified by silica gel column chromatography to afford 2 (200 mg, 53%) as an off white solid. $^1$H NMR (400 MHz, DMSO-$d_6$): δ 1.16-1.24 (m, 4H), 1.31 (s, 9H), 1.61 (m, 2H), 1.75-1.77 (m, 2H), 3.18-3.20 (m, 1H), 3.52-3.54 (m, 1H), 5.51 (dd, J=2.0, 10.0 Hz, 1H), 6.01 (dd, J=2.0, 17.0 Hz, 1H), 6.16 (dd, J=10.0, 17.0 Hz, 1H), 6.53 (d, J=8.8 Hz, 1H), 7.80 (d, J=8.5 Hz, 1H).

Step 3:

trans-(2-aminocyclohexyl)acrylamide (3, Racemic)

tert-butyl trans-2-acrylamidocyclohexyl-carbamate (200 mg, 0.7 mmol) was treated with excess trifluoro acetic acid in dichloromethane (2.0 mL) at 0° C. The reaction mixture was stirred at room temperature for 2 h. After completion of the reaction, the reaction mixture was concentrated under reduced pressure and co-distilled with dichloromethane. The residue obtained was triturated with pentane to afford 3 (150 mg, 71%) as an oily liquid. MS m/z (M+H): 169.2

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

---

We claim:

1. A compound of formula V-a or V-b:

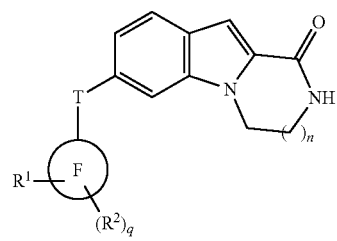

V-a

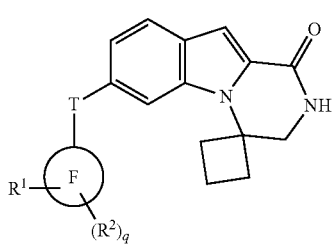

V-b or a pharmaceutically acceptable salt thereof, wherein:
Ring F is an optionally substituted group selected from phenyl, a 3-8 membered saturated or partially unsaturated carbocyclic ring, a 4-7 membered heterocyclic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;

$R^1$ is a warhead group L-Y-, wherein:

L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; or L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; or L is a bivalent $C_{2-8}$ straight or branched, hydrocarbon chain wherein L has at least one triple bond and one or two additional methylene units of L are optionally and independently replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and Y is hydrogen or $C_{1-6}$ aliphatic optionally substituted with oxo, halogen, NO$_2$, or CN; or L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—; and Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; or L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, or —SO$_2$NH—; and Y is selected from:

(i) $C_{1-6}$ alkyl substituted with oxo, halogen, NO$_2$, or CN; or (ii) $C_{2-6}$ alkenyl substituted with oxo, halogen, NO$_2$, or CN; or (iii) $C_{2-6}$ alkynyl optionally substituted with oxo, halogen, NO$_2$, or CN; or (iv) a saturated 3-4 membered heterocyclic ring having 1 heteroatom selected from oxygen or nitrogen wherein said ring is substituted with 1-2 $R^e$ groups; or (v) a saturated 5-6 membered heterocyclic ring having 1-2 heteroatom selected from oxygen or nitrogen wherein said ring is substituted with 1-4 $R^e$ groups; or

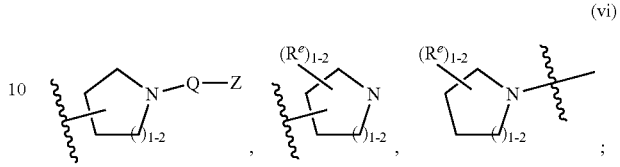

(vi)

or (vii) a saturated 3-6 membered carbocyclic ring, wherein said ring is substituted with 1-4 $R^e$ groups; or (viii) a partially unsaturated 3-6 membered monocyclic ring having 0-3 heteroatoms independently selected from nitrogen, oxygen, or sulfur, wherein said ring is substituted with 1-4 $R^e$ groups; or (ix) a partially unsaturated 3-6 membered carbocyclic ring, wherein said ring is substituted with 1-4 $R^e$ groups; or

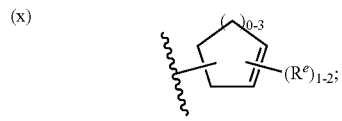

(x)

or (xi) a partially unsaturated 4-6 membered heterocyclic ring having 1-2 heteroatoms independently selected from nitrogen, oxygen, or sulfur, wherein said ring is substituted with 1-4 $R^e$ groups; or

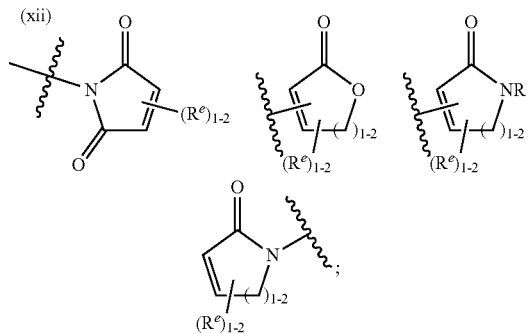

(xii)

or (xiii) a 6-membered aromatic ring having 0-2 nitrogens wherein said ring is substituted with 1-4 $R^e$ groups; or (xiv)

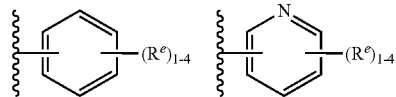

-continued

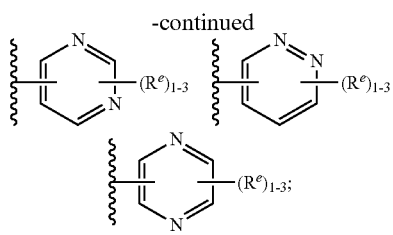

or
(xv) a 5-membered heteroaryl ring having 1-3 heteroatoms independently selected from nitrogen, oxygen, or sulfur, wherein said ring is substituted with 1-3 $R^e$ groups; or (xvi)
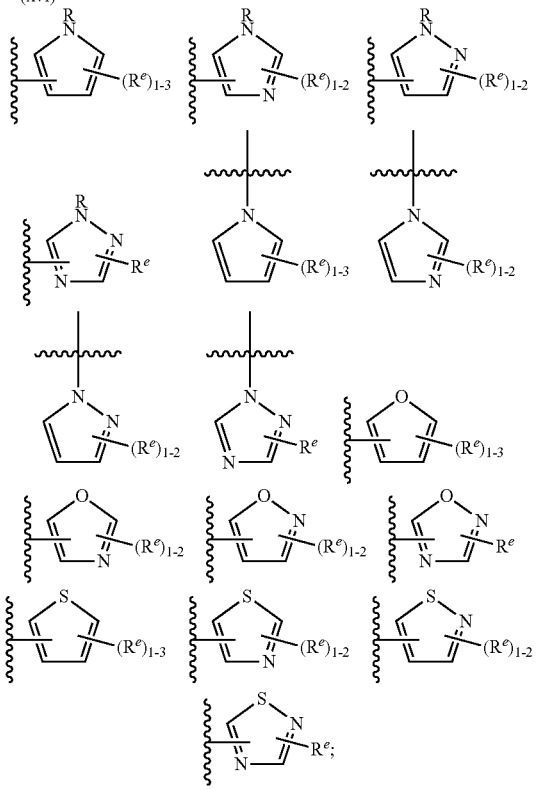

or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups; or L is a covalent bond, —C(O)—, —N(R)C(O)—, or a bivalent $C_{1-8}$ saturated or unsaturated, straight or branched, hydrocarbon chain; and Y is selected from:
  (i) $C_{1-6}$ alkyl substituted with oxo, halogen, $NO_2$, or CN; or
  (ii) $C_{2-6}$ alkenyl optionally substituted with oxo, halogen, $NO_2$, or CN; or
  (iii) $C_{2-6}$ alkynyl optionally substituted with oxo, halogen, $NO_2$, or CN; or
  (iv) a saturated 3-4 membered heterocyclic ring having 1 heteroatom selected from oxygen or nitrogen wherein said ring is substituted with 1-2 $R^e$ groups; or
  (v) a saturated 5-6 membered heterocyclic ring having 1-2 heteroatom selected from oxygen or nitrogen wherein said ring is substituted with 1-4 $R^e$ groups; or (vi)
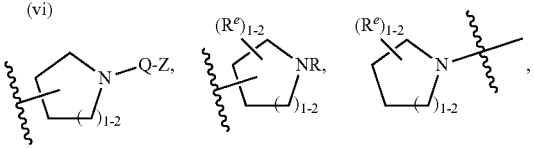

or
(vii) a saturated 3-6 membered carbocyclic ring, wherein said ring is substituted with 1-4 $R^e$ groups; or
(viii) a partially unsaturated 3-6 membered monocyclic ring having 0-3 heteroatoms independently selected from nitrogen, oxygen, or sulfur, wherein said ring is substituted with 1-4 $R^e$ groups; or
(ix) a partially unsaturated 3-6 membered carbocyclic ring, wherein said ring is substituted with 1-4 $R^e$ groups; or (x)
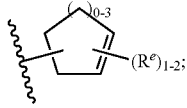

or
(xi) a partially unsaturated 4-6 membered heterocyclic ring having 1-2 heteroatoms independently selected from nitrogen, oxygen, or sulfur, wherein said ring is substituted with 1-4 $R^e$ groups; or (xii)
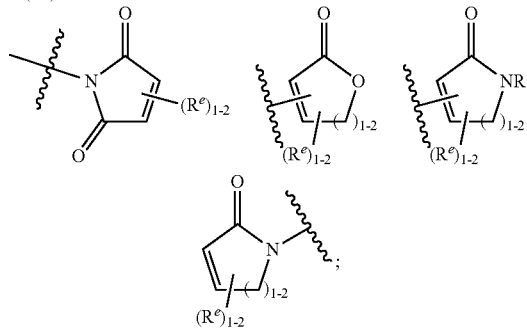

or
(xiii) a 6-membered aromatic ring having 0-2 nitrogens wherein said ring is substituted with 1-4 $R^e$ groups; or (xiv)

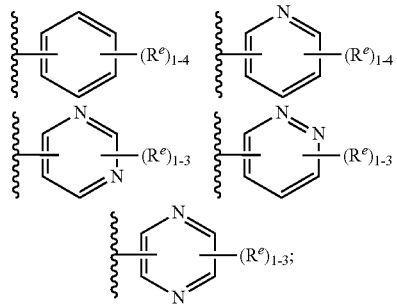

or (xv) a 5-membered heteroaryl ring having 1-3 heteroatoms independently selected from nitrogen, oxygen, or sulfur, wherein said ring is substituted with 1-3 $R^e$ groups; or (xvi)

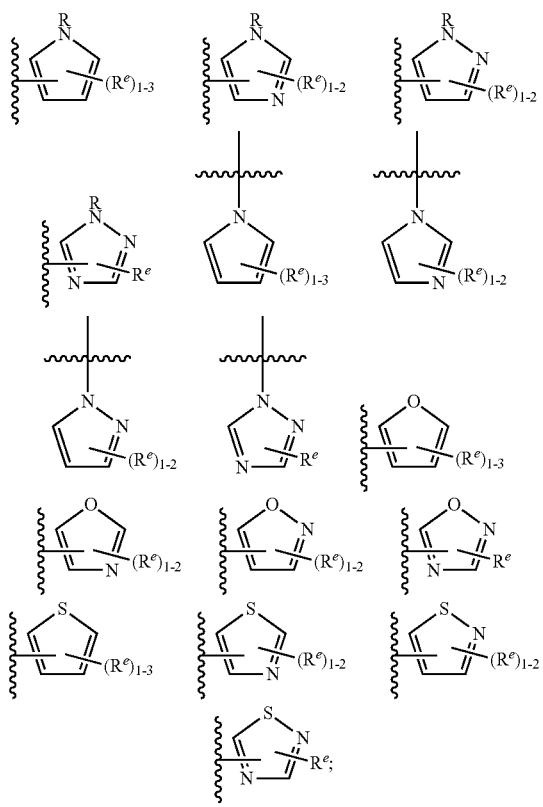

or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups;

each $R^e$ is independently selected from -Q-Z, oxo, $NO_2$, halogen, CN, a suitable leaving group, or a $C_{1-6}$ aliphatic optionally substituted with oxo, halogen, $NO_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN;

q is 0-6;

each $R^2$ is independently —R, halogen, —OR, —SR, —CN, —$NO_2$, —$SO_2$NR, —$SO_2$R, —SOR, —C(O)R, —$CO_2$R, —C(O)N(R)$_2$, —NRC(O)R, —NRC(O)OR, —NRC(O)N(R)$_2$, —NR$SO_2$R, or —N(R)$_2$;

each R is independently hydrogen or an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocyclic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

n is 1 or 2;

and

T is a covalent bond, —C(O)—, or —C(O)NH—.

2. The compound according to claim 1, wherein:
L is a bivalent $C_{2-8}$ straight or branched, hydrocarbon chain wherein L has at least one double bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, or —C(O)—.

3. The compound according to claim 1, wherein:
L is a bivalent $C_{2-8}$ straight or branched, hydrocarbon chain wherein L has at least one triple bond and one or two additional methylene units of L are optionally and independently replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—.

4. A composition comprising a compound according to claim 1, and a pharmaceutically acceptable adjuvant, carrier, or vehicle.

5. The compound of claim 1, wherein Ring F is

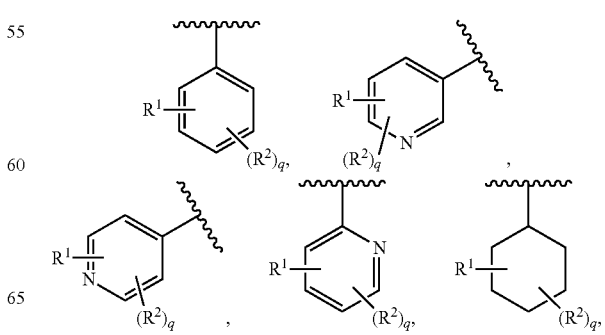

587
-continued
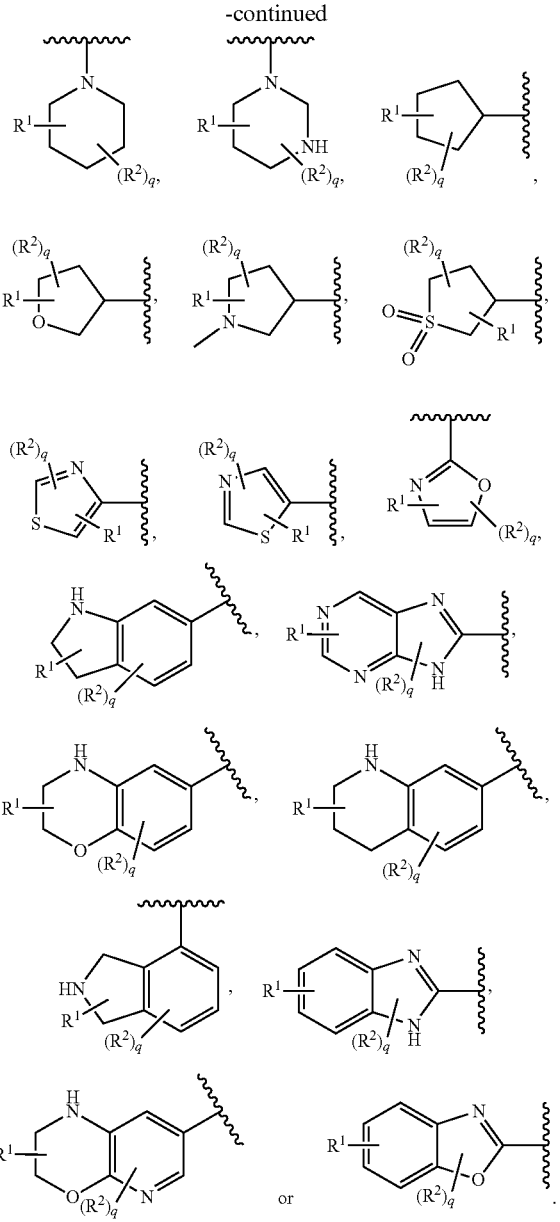
6. The compound of claim 1, wherein the compound is selected from the group consisting of:
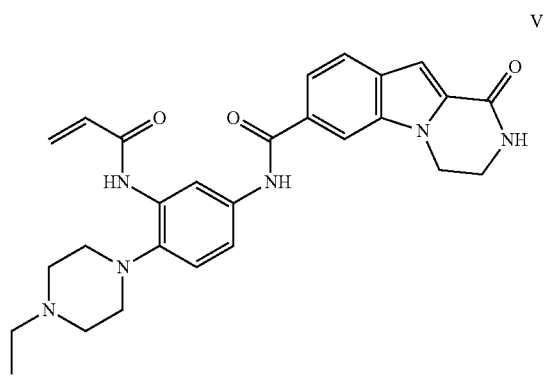
588
-continued
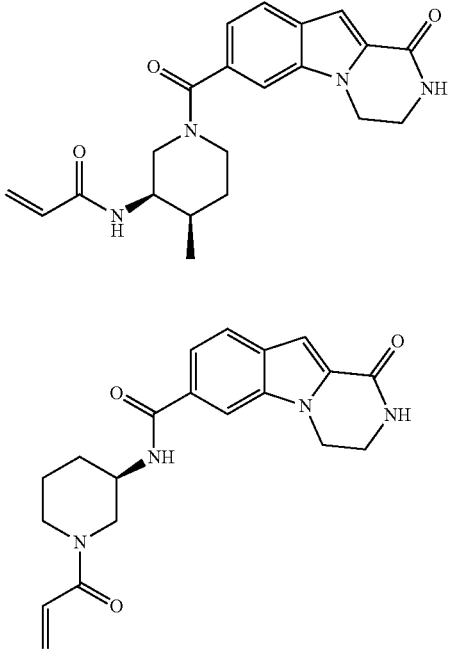
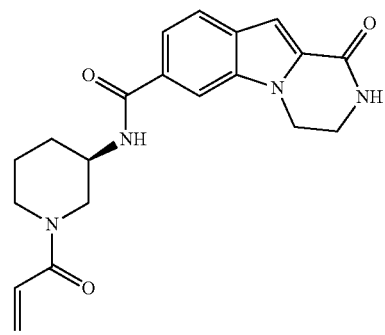
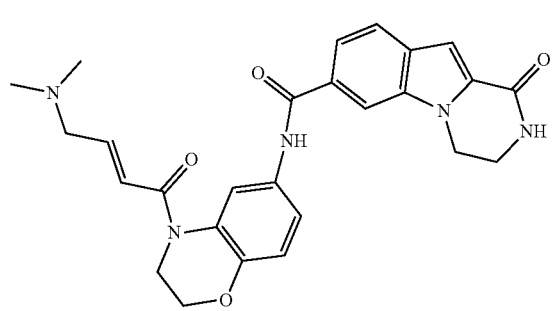
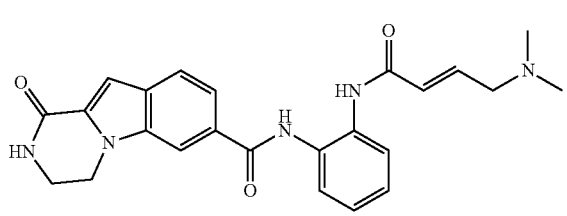
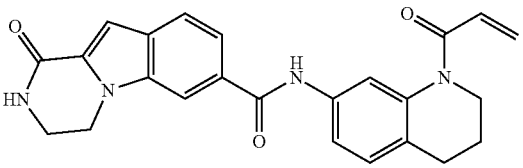
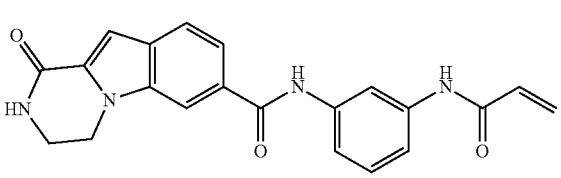

-continued
V-8
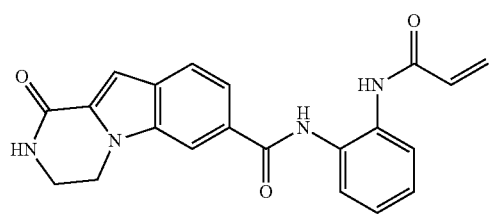
V-9
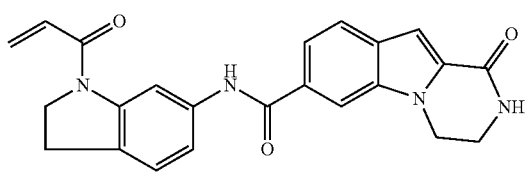
V-10
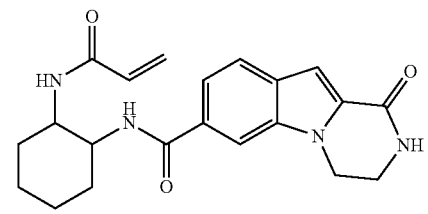
V-11
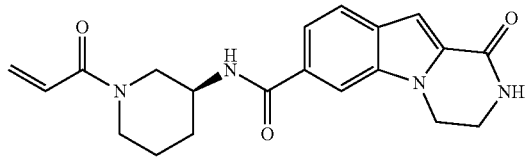
V-12
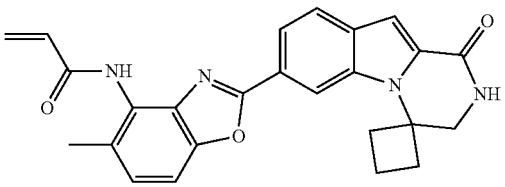
V-13
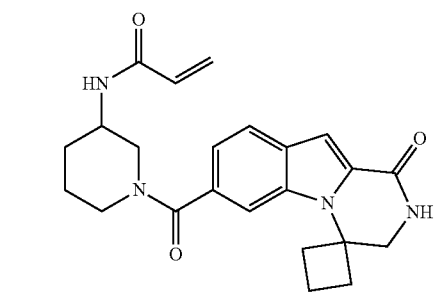
V-14
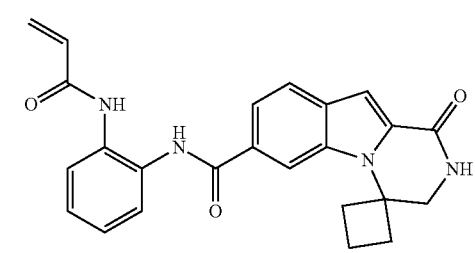
-continued
V-15
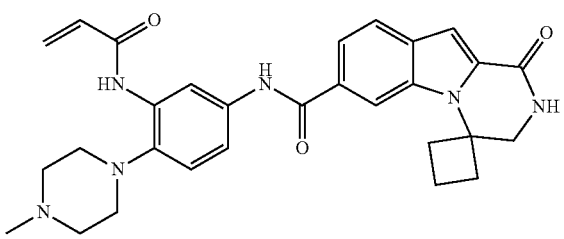
V-16
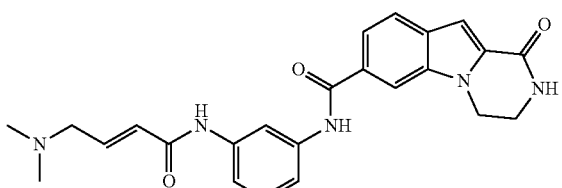
V-17
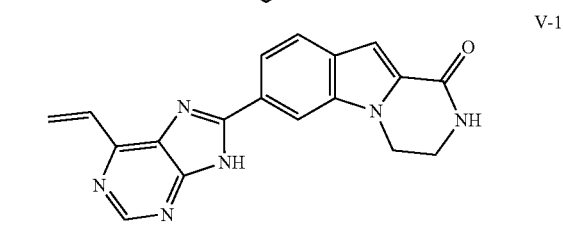
V-19
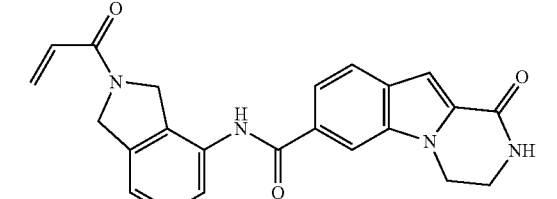
V-20
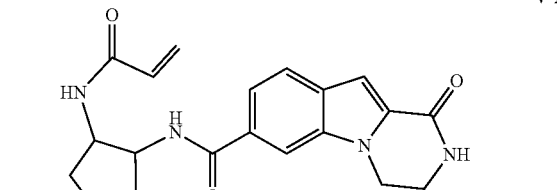
V-21
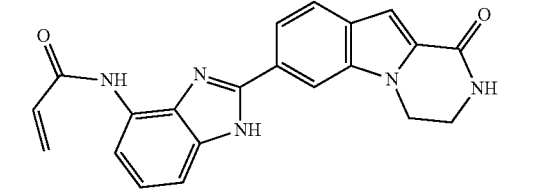
V-22
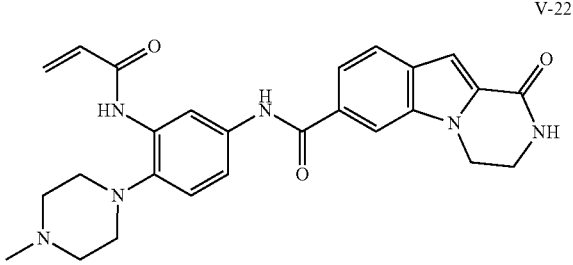

-continued
V-23
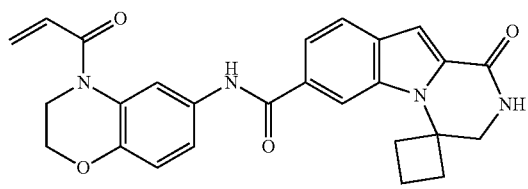
V-24
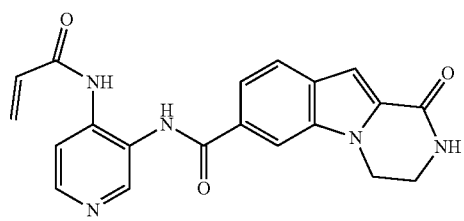
V-25
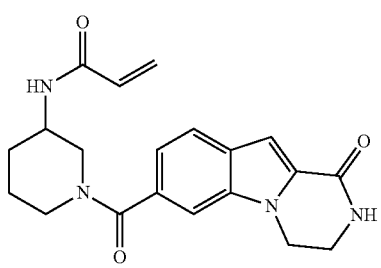
V-26
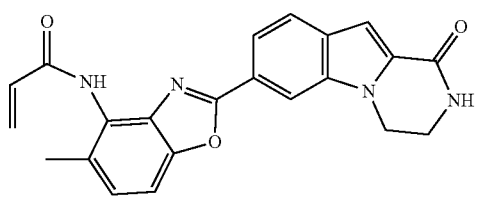
V-27
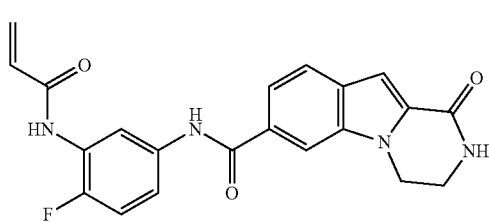
V-28
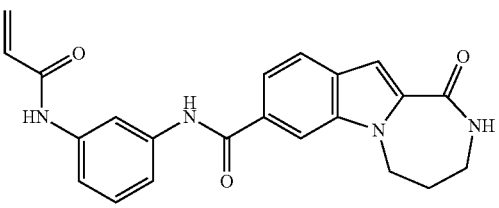
-continued
V-29
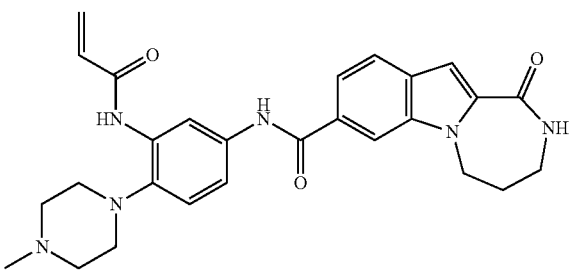
V-30
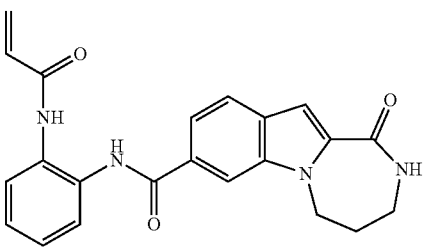
V-31
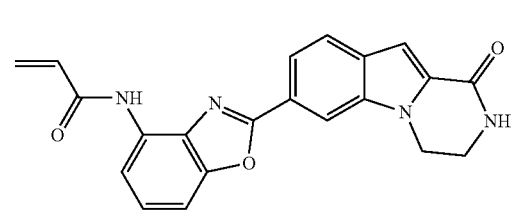
V-32
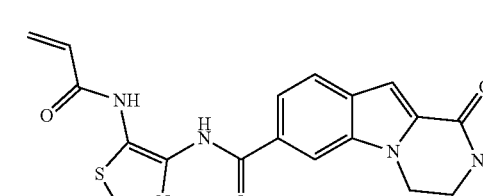
V-33
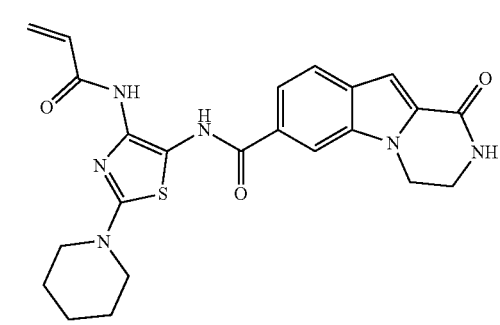

593
-continued
V-34
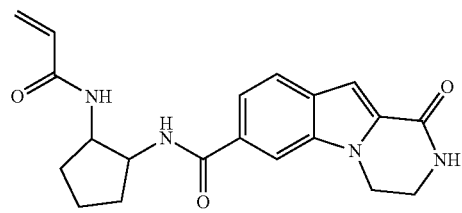
V-35
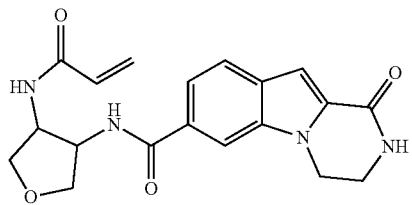
V-36
V-37
V-38
V-39
V-40
594
-continued
V-41
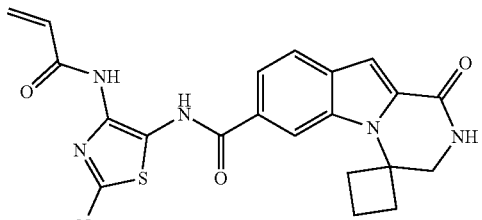
V-42
V-43
V-44
V-45
V-46 (cis)
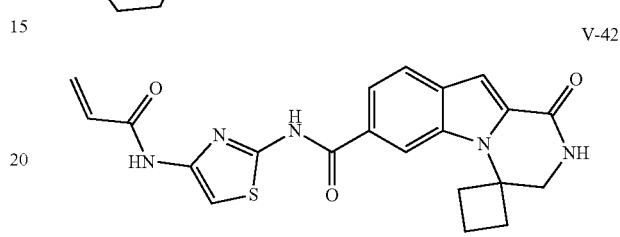
V-47

-continued
V-48
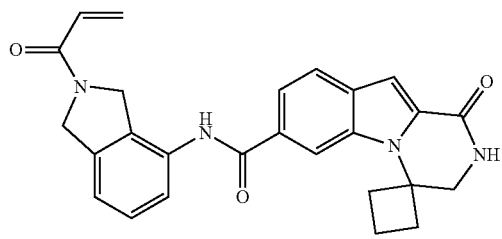
V-49
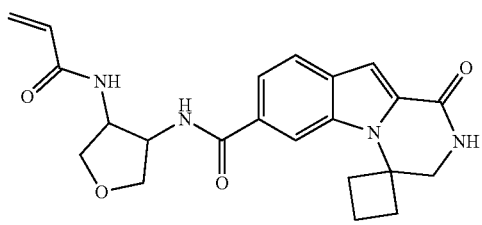
V-50
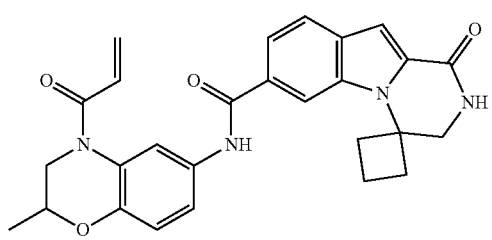
V-51
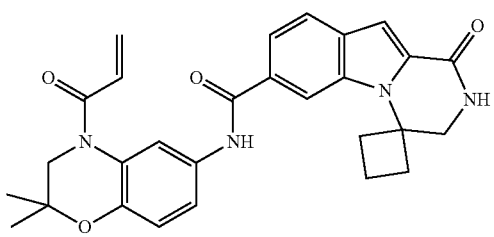
V-52
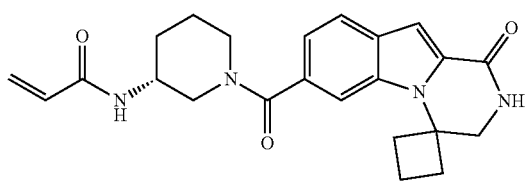
V-53
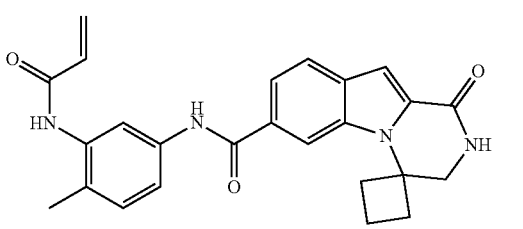
-continued
V-54
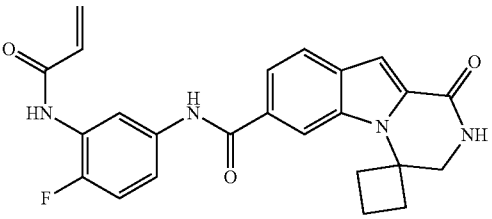
V-55 (cis)
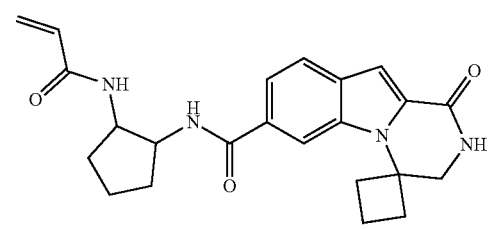
V-56 (trans)
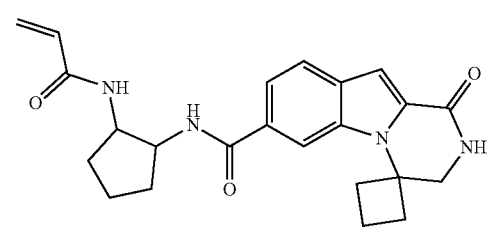
V-57
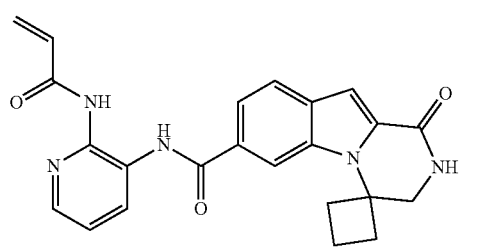
V-58
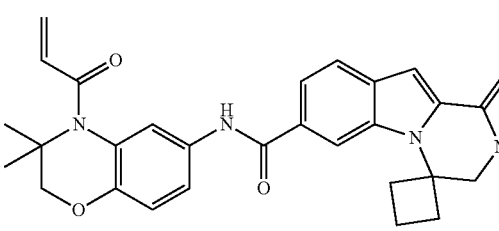
V-59
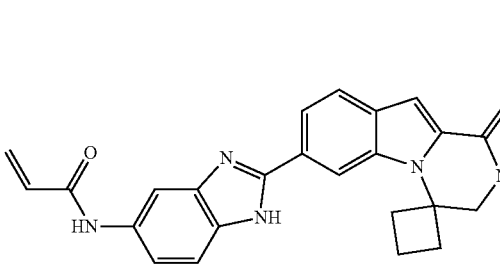

-continued
V-60
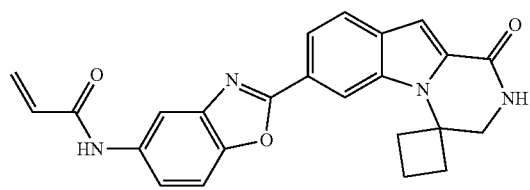
V-61
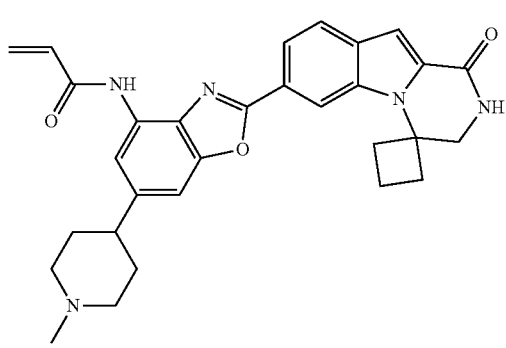
V-62
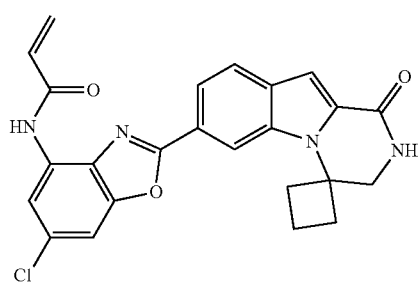
V-63
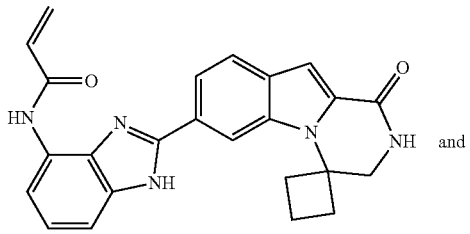 and
V-64 (trans)
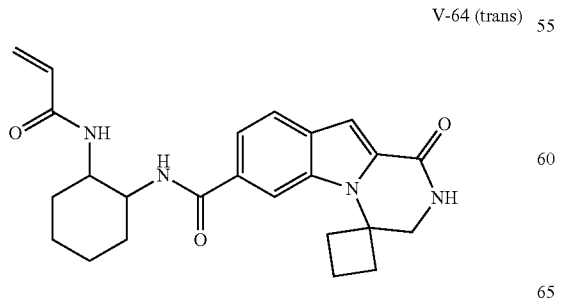
or a pharmaceutically acceptable salt thereof.
7. The compound of claim 1, wherein Ring F is:
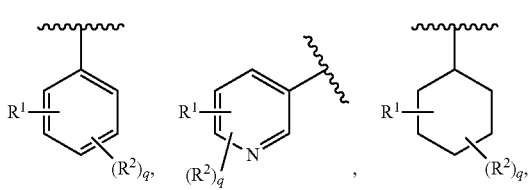
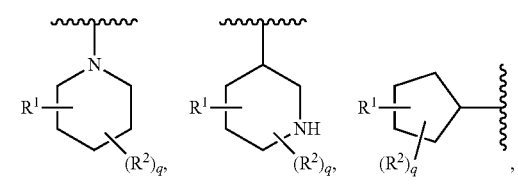
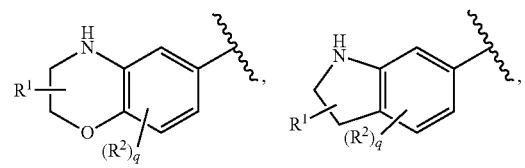
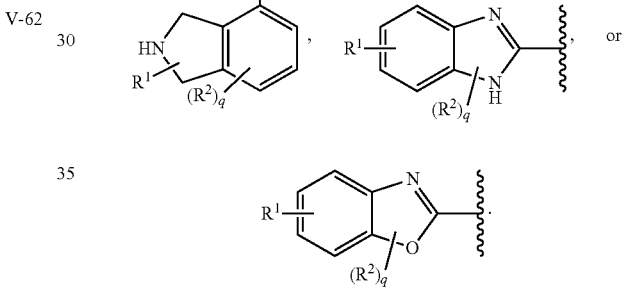
8. The compound of claim 1, wherein each $R^2$ is independently:
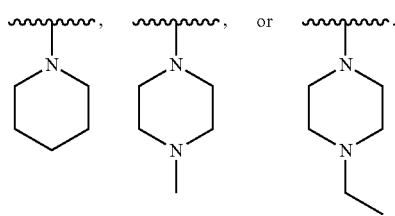
9. The compound of claim 1, wherein the moiety
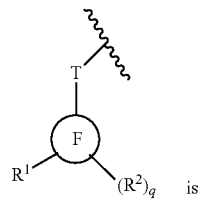
is selected from the group consisting of:
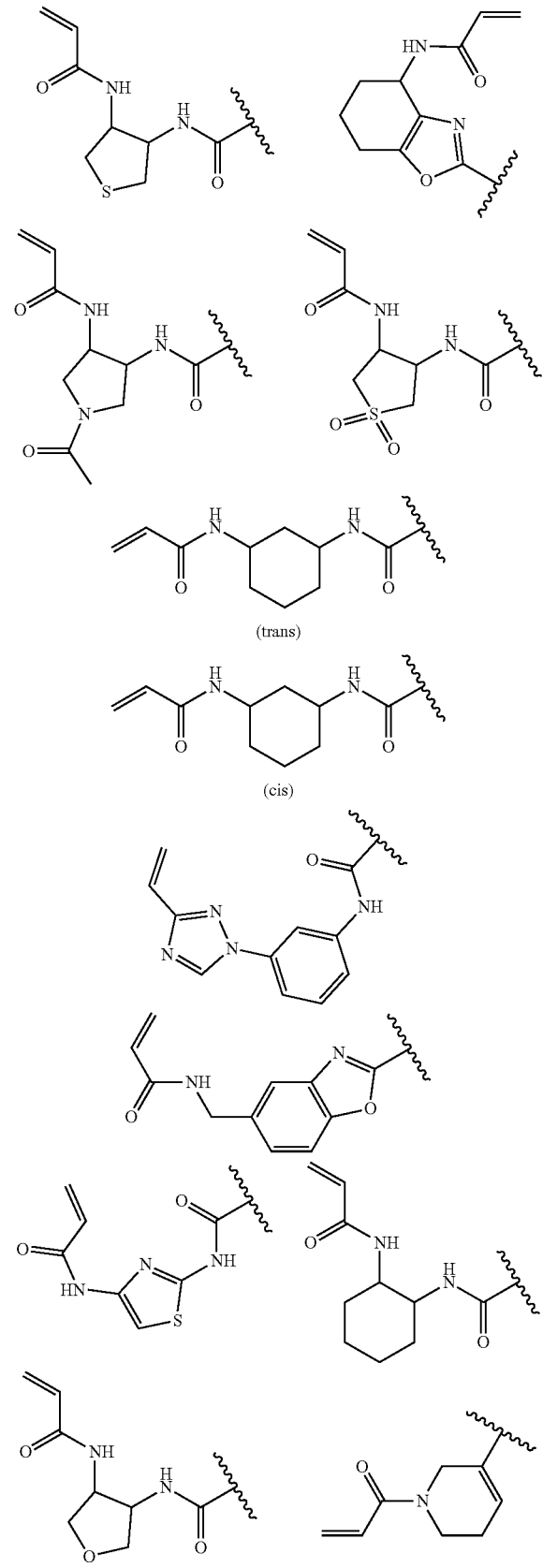
(trans)
(cis)
-continued
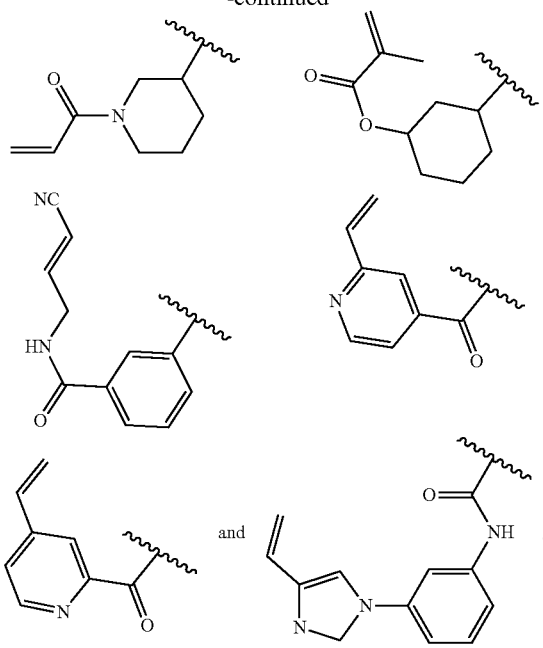
and
10. The compound of claim 2, wherein Ring F is:
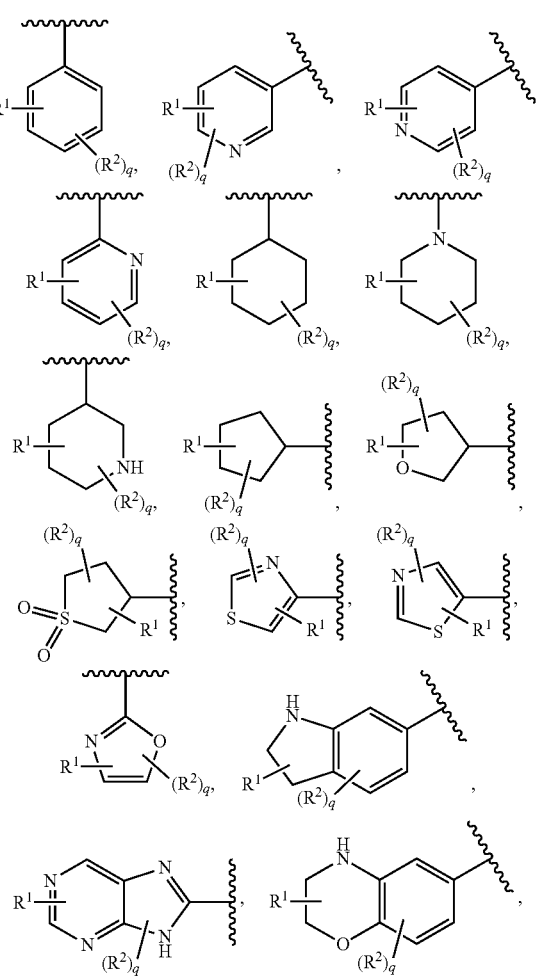

-continued
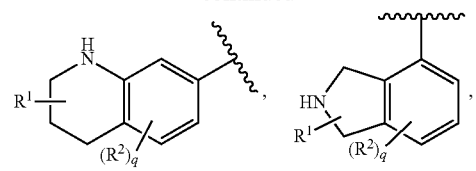
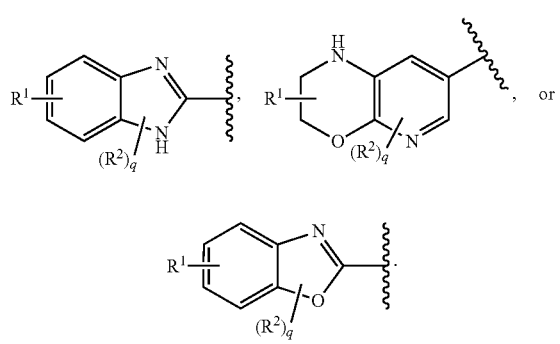
11. The compound of claim 2, wherein Ring F is:
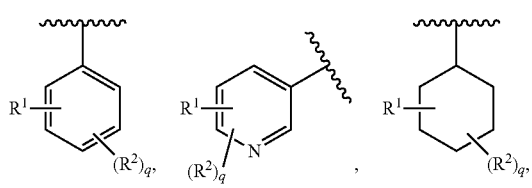
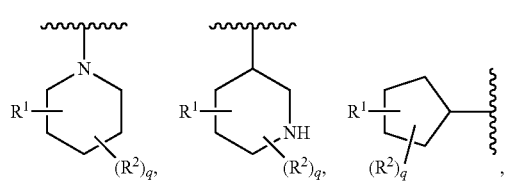
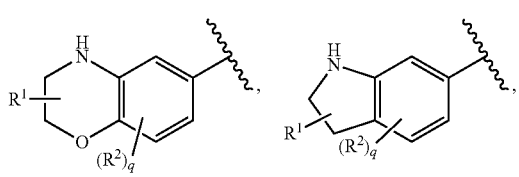
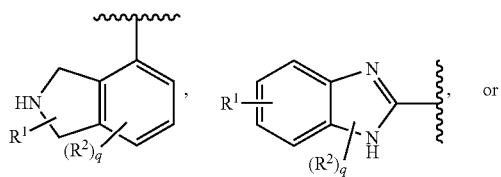
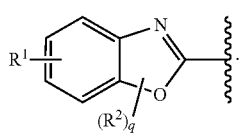
12. The compound of claim 2, wherein each $R^2$ is independently:
13. The compound of claim 2, wherein the moiety
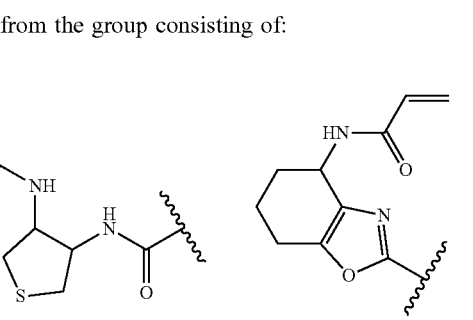 is
selected from the group consisting of:
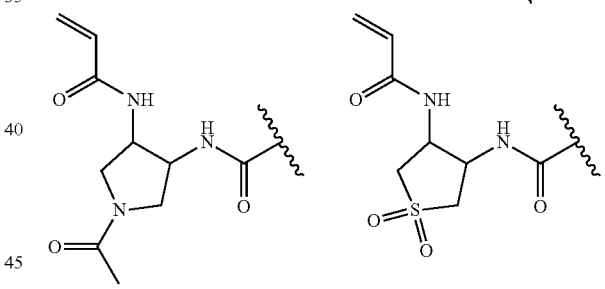
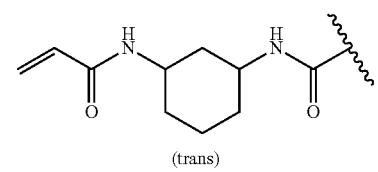
(trans)
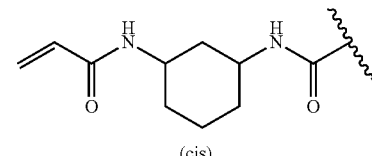
(cis)
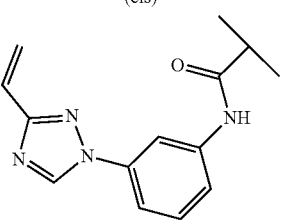

603
-continued
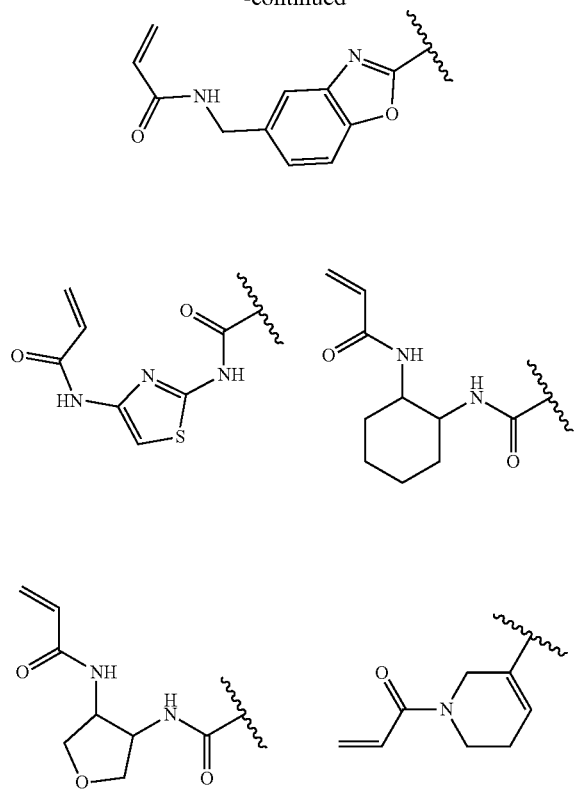
604
-continued
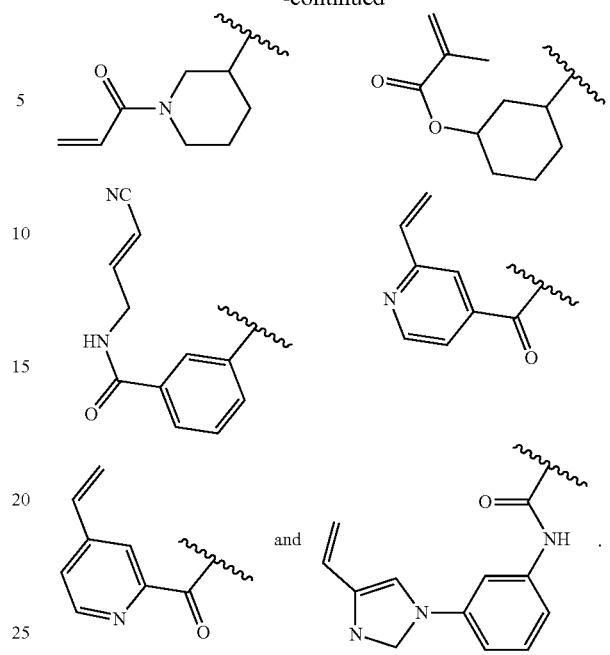
14. A composition comprising a compound according to claim 6, and a pharmaceutically acceptable adjuvant, carrier, or vehicle.
* * * * *